(12) United States Patent
Pujala et al.

(10) Patent No.: US 10,189,826 B2
(45) Date of Patent: Jan. 29, 2019

(54) HETEROCYCLIC COMPOUNDS AND METHODS OF USE

(71) Applicant: Medivation Technologies LLC, San Francisco, CA (US)

(72) Inventors: Brahmam Pujala, Noida (IN); Ramniwas Jangir, Noida (IN); Rambabu Guguloth, Noida (IN); Bharat Uttam Shinde, Noida (IN); Roopa Rai, San Francisco, CA (US); Son Minh Pham, San Francisco, CA (US); Sebastian Bernales, San Francisco, CA (US); Jeffrey Lindquist, Redwood City, CA (US); Mausumee Guha, Trabuco Canyon, CA (US); Satyanarayana Kallem, Noida (IN); Bhawana Bhatt, Noida (IN); Vikas Ramdas Bhagwat, Noida (IN)

(73) Assignee: Medivation Technologies LLC, San Francisco, CA (US)

( * ) Notice: Subject to any disclaimer, the term of this patent is extended or adjusted under 35 U.S.C. 154(b) by 0 days.

(21) Appl. No.: 15/553,622

(22) PCT Filed: Mar. 4, 2016

(86) PCT No.: PCT/US2016/020802
§ 371 (c)(1),
(2) Date: Aug. 25, 2017

(87) PCT Pub. No.: WO2016/141258
PCT Pub. Date: Sep. 9, 2016

(65) Prior Publication Data
US 2018/0051013 A1   Feb. 22, 2018

(30) Foreign Application Priority Data

Mar. 4, 2015  (IN) .............................. 615/DEL/2015
Mar. 9, 2015  (IN) .............................. 640/DEL/2015

(51) Int. Cl.
| | | |
|---|---|---|
| *C07D 409/14* | (2006.01) | |
| *A61K 31/4436* | (2006.01) | |
| *C07D 401/14* | (2006.01) | |
| *C07D 413/14* | (2006.01) | |
| *C07D 409/04* | (2006.01) | |
| *C07D 417/04* | (2006.01) | |
| *C07D 417/14* | (2006.01) | |
| *C07D 471/04* | (2006.01) | |
| *C07D 471/10* | (2006.01) | |
| *C07D 487/04* | (2006.01) | |
| *C07D 491/107* | (2006.01) | |

(52) U.S. Cl.
CPC ......... *C07D 409/14* (2013.01); *C07D 401/14* (2013.01); *C07D 409/04* (2013.01); *C07D 413/14* (2013.01); *C07D 417/04* (2013.01); *C07D 417/14* (2013.01); *C07D 471/04* (2013.01); *C07D 471/10* (2013.01); *C07D 487/04* (2013.01); *C07D 491/107* (2013.01)

(58) Field of Classification Search
CPC .. C07D 409/14; C07D 417/14; C07D 471/02; A61K 31/4436
See application file for complete search history.

(56) References Cited

U.S. PATENT DOCUMENTS

| | | | |
|---|---|---|---|
| 6,444,687 | B1 | 9/2002 | Stamford et al. |
| 6,924,298 | B2 | 8/2005 | Tisdell et al. |
| 7,244,739 | B2 | 7/2007 | Cheng et al. |
| 8,063,080 | B2 | 11/2011 | Fulp et al. |
| 8,207,196 | B2 | 6/2012 | Uesugi et al. |
| 8,229,106 | B2 | 7/2012 | Greiss et al. |
| 8,822,513 | B2 | 9/2014 | Lu et al. |
| 8,907,099 | B2 | 12/2014 | Learmonth et al. |
| 9,670,172 | B2 | 6/2017 | Chakravarty et al. |
| 2001/0031781 | A1 | 10/2001 | Illig et al. |
| 2013/0165472 | A1 | 6/2013 | Chau et al. |
| 2014/0045854 | A1 | 2/2014 | Uesugi et al. |
| 2014/0303213 | A1 | 10/2014 | Uesugi et al. |

FOREIGN PATENT DOCUMENTS

| | | |
|---|---|---|
| EP | 0438230 A2 | 7/1991 |
| WO | 199940088 A1 | 8/1999 |
| WO | 2006131336 A1 | 12/2006 |
| WO | 2008097835 A2 | 8/2008 |
| WO | 2008114157 A1 | 9/2008 |
| WO | 2009080663 A1 | 7/2009 |
| WO | 2011085269 A1 | 7/2011 |
| WO | 2012084678 A1 | 6/2012 |
| WO | 2012099200 A1 | 7/2012 |
| WO | 2013038136 A1 | 3/2013 |
| WO | 2014199164 A1 | 12/2014 |

(Continued)

OTHER PUBLICATIONS

Patani, Bioisosterism: A Rational Approach in Drug Design, Chem Review, 1996, vol. 96, p. 3147-3176. (Year: 1996).*
Bellale et al., "Diarylthiazole: an Antimycobacterial Scaffold Potentially Targeting PrrB-PrrA Two-Component System," Journal of Medicinal Chemistry, 2014, vol. 57, pp. 6572-6582.
Bernales et al., U.S. Appl. No. 15/553,589, amended claims filed Aug. 25, 2017, 26 pages.
International Search Report and Written Opinion for PCT/US2014/053215 dated Jan. 29, 2015, 11 pages.
International Preliminary Report on Patentability for PCT/US2016/020644 dated Sep. 5, 2017, 7 pages.
International Search Report for PCT/US2016/020644 dated Jun. 9, 2016, 6 pages.

(Continued)

Primary Examiner — Rebecca L Anderson
Assistant Examiner — Karen Cheng
(74) Attorney, Agent, or Firm — Banner & Witcoff, Ltd.

(57) ABSTRACT

This disclosure provides compounds and methods of using those compounds to treat metabolic disorders and hyperproliferative disorders, including administration of the compounds in conjunction with hormone receptor antagonists.

14 Claims, No Drawings

(56) References Cited

FOREIGN PATENT DOCUMENTS

| | | |
|---|---|---|
| WO | 2014210389 A1 | 12/2014 |
| WO | 2015031650 A1 | 3/2015 |
| WO | 2016141159 A1 | 9/2016 |

OTHER PUBLICATIONS

International Search Report and Written Opinion for PCT/US2016/020802, dated Apr. 29, 2016, 17 pages.

Kamisuki et al., "Synthesis and Evaluation of Diarylthiazole Derivatives That Inhibit Activation of Sterol Regulatory Element-Binding Proteins," Journal of Medivinal Chemistry, American Chemical Society, vol. 54, No. 13, Jul. 14, 2011, pp. 4923-4927.

Li et al., "Synthesis and biological evaluation of 1,2,4-trisubstituted imidazoles and 1,3,5-trisubstituted pyrazoles as inhibitors of transforming growth factor beta type receptor (ALK5)," Bioorganic & Medicinal Chemistry Letters, vol. 19, No. 16, Aug. 2009, pp. 4868-4872.

Rice et al., "An Improved Synthesis of 1,2,4-Oxadiazoles on Solid Support," Bioorganic & Medicinal Chemistry Letters, vol. 11, No. 6, Jan. 2011, pp. 753-755.

Shahlaei & Nazari, "Prediction of glucagon receptor antagonist activities of some substituted imidazoles using combined radial basis function neural network and density functional theory," Medicinal Chemistry Research, 2014, vol. 23, pp. 2744-2756.

Tani et al., "Programmed synthesis of arylthiazoles through sequential C—H couplings," Chemical Science, 2014, vol. 5, pp. 123-135.

\* cited by examiner

HETEROCYCLIC COMPOUNDS AND METHODS OF USE

This application claims priority to and incorporates by reference Indian applications 615/DEL/2015 filed on Mar. 4, 2015 and 640/DEL/2015 filed on Mar. 9, 2015. Each reference cited in this disclosure is incorporated herein by reference in its entirety.

TECHNICAL FIELD

This disclosure relates generally to therapeutics for treatment of hyperproliferative disorders, metabolic disorders, and pancreatitis.

BACKGROUND

Sterol regulatory element-binding proteins (SREBPs) are major transcription factors regulating the biosynthesis of cholesterol, fatty acid, and triglyceride. They control the expression of crucial genes involved in lipogenesis and uptake. Inhibition of the SREBP pathway can reduce lipid biosynthesis and thus can be a strategy to treat metabolic diseases, such as type II diabetes, insulin resistance, fatty liver and atherosclerosis [Xiao et al. *Acta Biochim. Biophys. Sin* (2013) 45:1, pp 2-10]. In mammals, three SREBP isoforms are known, designated SREBP-1a, SREBP-1c, and SREBP-2. SREBP-1a controls a broad range of SREBP targets including production of fatty acids, triglycerides, phospholipids and cholesterol. SREBP-1c preferentially activates genes of fatty acid and triglyceride metabolism, whereas SREBP-2 preferentially activates genes of cholesterol metabolism, both of which have been studied in human and mice models [Horton et al. *J. Clin. Invest.* (2002) 109:9, pp 1125-1131], as well as *Drosophila* [Rawson. *Nature Rev. Mol. Cell Biol.* (2003) 4:8, pp 631-640].

Recent studies have also presented a link between upregulation of lipid synthesis and prostate cancer [Suburu et al. *Prostaglandins Other Lipid Mediat.* (2012) 98:0, pp 1-10]. The metabolic shift from catabolic to anabolic metabolism is a hallmark of cancer cells. Many cancers require synthesis of fatty acids, and other lipids such as cholesterol and androgens are implicated in prostate cancer. SREBP-1c is the major transcriptional regulator of enzymes in the fatty acid synthesis pathway, and its expression can be stimulated by androgens and epidermal growth factor (EGF) in prostate cancer cells. Overexpression of SREBP-1c is sufficient to cause tumorigenicity and invasion of prostate cancer cells. SREBP-1 can also increase expression of NOX5, a prominent producer of reactive oxygen species (ROS) and regulator of prostate cancer cell growth [Brar et al. *Am. J. Physiol. Cell Physiol.* (2003) 285:2, pp C353-369; Huang et al. *Mol. Cancer Res.* (2012) 10:1, pp 133-142; Huang et al. *Cancer Research* (2012) 72:8, SUPPL. 1; Huang et al. *Mol. Cancer Res.* (2014) 13:4, pp 855-866].

SREBP-2, a regulator of androgen synthesis, is also itself regulated by androgens, demonstrating a direct feedback circuit for regulation of androgen production. SREBP-2 expression increases during disease progression and is significantly higher after castration. This transcription factor also lacks its feedback inhibition in prostate cancer cells, implicating a role for cholesterol and androgen synthesis in prostate cancer [Eberle et al. *Biochimie* (2004) 86:11, pp 839-848; Ettinger et al. *Cancer Res.* (2004), 64:6, pp 2212-2221; Chen et al. *Int. J. Cancer* (2001), 91:1, pp 41-45].

Blocking SREBP functions linked to disease states therefore represents an important therapeutic approach for limiting lipid/cholesterol synthesis in membrane production which occurs in metabolic diseases and in cancer progression, as well as in viral pathogenesis [Naar et al. *Clin. Lipidol.* (2012) 7:1, pp 27-36]. Small molecule therapeutics affecting metabolic regulators such as mTOR, AMPK or SIRT1, including Rapamycin, Metformin, or Resveratrol, respectively, may impinge on the transcriptional activity of SREBPs. Recently, two non-sterol small molecules, fatostatin and betulin have been found to inhibit SREBP processing [Kamisuki et al. *Chem. Biol.* (2009) 16:8, pp 882-892; Tang et al. *Cell. Metab.* (2011) 13:1, pp 44-56]. Methods for the treatment of cancers having a p53 mutation, such as breast cancer cells, using SREBP inhibitors have been presented [Freed-Pastor et al. PCT Publication WO2013-110007A1].

Fatostatin analogs have recently been described as potential therapeutics for the treatment of metabolic disorders [Uesugi et al. U.S. Pat. No. 8,207,196]. Key compounds presented therein are based around Formula X:

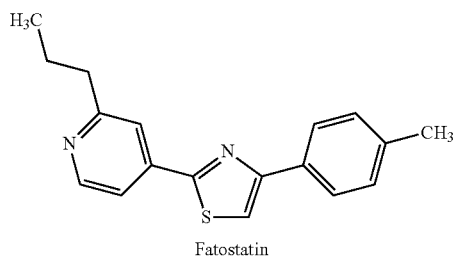

Fatostatin

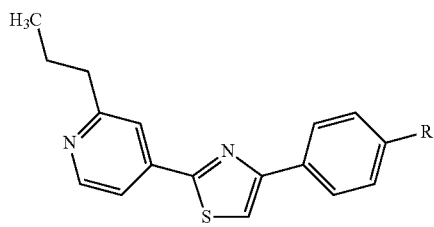

Formula X wherein R is H, F, Cl, Br, OBz, OH, OCH$_3$, OCH$_2$CO$_2$Me, OCH$_2$CO$_2$H, NH$_2$, NHiPr, NHCOCH$_3$, NHSO$_2$Me, NH[benzyl], NH[cyclopropyl], NH[tertbutyloxycarbonyl], NH[cyclohexyl], NH[tosyl], NH[quinolin-8-yl], and NH[thiophen-2-yl]. In particular, one compound (FGH10019), the methanesulfonamide derivative of fatostatin above wherein R is NHSO$_2$Me, has been described as a lead candidate [Kamisuki et al. *J. Med. Chem.* (2011) 54:13, pp 4923-4927]. Further examples of Fatostatin analogs have been presented [Chakravarty et al. PCT Publication WO2015/031650A1].

BRIEF SUMMARY

This disclosure relates generally to therapeutics for treatment of hyperproliferative disorders, metabolic disorders, and pancreatitis. This disclosure provides compounds and methods of using those compounds to treat benign and malignant hyperproliferative disorders, as well as metabolic disorders and pancreatitis, as described below. The disclosed compounds may also find use in treating cancer.

Compounds disclosed herein fall within Formulae (Ia) or (Ib):

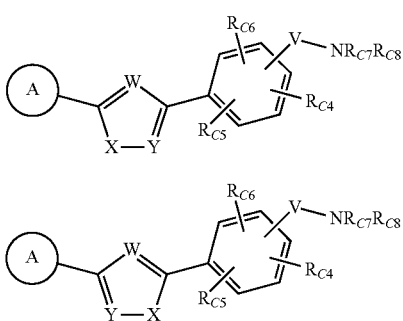

or a pharmaceutically acceptable salt thereof, wherein:
A is either:
  i. a heteroaryl having only one ring, substituted with one or more R1 or R2; or
  ii. an aryl or heteroaryl, each having more than one ring, optionally substituted with one or more R1 or R3;
R1 is C1-C6 linear or branched alkyl, C2-C6 linear or branched alkenyl, C2-C6 linear or branched alkynyl, C3-C6 cycloalkyl, C3-C6 cycloalkylmethyl, C3-C6 cycloalkenyl, aryl, or heteroaryl; each optionally substituted with one or more R3;
R2 is halogen, —CN, —OH, —O(Alkyl), —NO$_2$, —SH, —S(Alkyl), —S(O)(Alkyl), —S(O)$_2$(Alkyl), —CH$_2$OCH$_3$, —OBn, —CO$_2$H, —CO$_2$(Alkyl), —NR10R11, —CONR10R11, and —S(O)$_2$NR10R11;
R3 is halogen, —CN, —OH, —O(Alkyl), =O, —NO$_2$, —SH, —S(Alkyl), —S(O)(Alkyl), —S(O)$_2$(Alkyl), —CH$_2$OCH$_3$, —OBn, —CO$_2$H, —CO$_2$(Alkyl), —NR10R11, —CONR10R11, and —S(O)$_2$NR10R11;
Each $R_{C4}$, $R_{C5}$, and $R_{C6}$, is independently hydrogen, R1, or R2; or $R_{C4}$ is taken with $R_{C7}$ to form a heterocyclyl optionally substituted with one or more R3;
Each $R_{C7}$ and $R_{C8}$ is independently hydrogen, R1, or —SO$_2$R$_{C12}$; or $R_{C7}$ and $R_{C8}$ are taken together with the N to which they are attached to form a C3-C8 heterocycle optionally substituted with one or more R1 or R3; or $R_{C7}$ is taken with $R_{C4}$ to form a heterocyclyl optionally substituted with one or more R3;
R10 and R11 are independently hydrogen, C1-C6 linear or branched alkyl, —C(O)R$_{C12}$, —C(O)$_2$R$_{C12}$, —C(O)N(R$_{C12}$)$_2$, —SO$_2$R$_{C12}$, or are taken together with the N to which they are attached to form a C3-C8 heterocyclyl;
$R_{C12}$ is hydrogen, a linear or branched C1-C6 alkyl, a linear or branched C2-C6 alkenyl, a linear or branched C2-C6 alkynyl, or aryl; wherein each alkyl, alkenyl, alkynyl, or aryl group is optionally substituted with one or more halogen atoms, one or more —NH$_2$ groups, or one or more —OH groups;
V is the moiety —C(=O)— or —S(=O)$_2$—; and
The ring comprising W, X, and Y is a 5-membered heteroaromatic, wherein W and Y are independently selected from the group consisting of CR$_A$, N, NR$_B$, O and S; X is selected from the group consisting of NR$_B$, O and S; wherein R$_A$ is hydrogen, R1 or R2; and R$_B$ is hydrogen or R1;
With the proviso that when W is N, X is S, and Y is C, then one of $R_{C4}$, $R_{C5}$ and $R_{C6}$ is other than H.

Examples of some of the disclosed compounds are described in Table 1, such as a compound selected from the group consisting of Compound Nos. 1 to 104; or a pharmaceutically acceptable salt, solvate, prodrug, or N-oxide thereof.

Examples of other of the disclosed compounds are described in Table 2, such as a compound selected from the group consisting of Compound Nos. 2.1 to 2.152; or a pharmaceutically acceptable salt, solvate, prodrug, or N-oxide thereof.

Further provided is a pharmaceutical composition, comprising a compound of Formulae (Ia) or (Ib), or any variations described herein, or a salt thereof, and a pharmaceutically acceptable carrier or excipient.

Further provided is a kit, comprising a compound of Formulae (Ia) or (Ib), or any variations described herein, or a salt thereof and instructions for use.

Further provided are methods of treating one or more of the following: hyperproliferative disorders, metabolic disorders and/or pancreatitis in individuals in need thereof, such as humans, comprising administering to an individual in need thereof a therapeutically effective amount of a compound of Formulae (Ia) or (Ib), or any variations described herein, or a pharmaceutically acceptable salt thereof.

Further provided are methods of treating any diseases or conditions for which the modulation of SREBP is believed to be or is beneficial, comprising administering to an individual in need thereof a therapeutically effective amount of a compound of Formulae (Ia) or (Ib), or any variations described herein, or a pharmaceutically acceptable salt thereof.

DETAILED DESCRIPTION

Definitions

For use herein, unless clearly indicated otherwise, use of the terms "a," "an" and the like refers to one or more.

As used herein, reference to "about" a value or parameter herein includes (and describes) embodiments that are directed to that value or parameter per se. For example, description referring to "about X" includes description of "X."

"Alkyl" refers to and includes saturated linear or branched univalent hydrocarbon structures and combinations thereof. Particular alkyl groups are those having 1 to 6 carbon atoms (a "C1-C6 alkyl"). Unless otherwise defined, "C1-C6 linear or branched alkyl" means methyl, ethyl, and C1-C6, C1-C5, C1-C4, C1-C3, C1-C2, C2-C6, C2-C5, C2-C4, C2-C3, C3-C6, C3-C5, C3-C4, C4-C6, C4-C5, C5-C6, C3, C4, C5, and C6 linear or branched alkyl. When an alkyl residue having a specific number of carbons is named, unless otherwise defined, all geometric isomers having that number of carbons are intended to be encompassed and described; thus, for example, "butyl" is meant to include n-butyl, sec-butyl, iso-butyl, and tert-butyl; "propyl" includes n-propyl and iso-propyl. Examples of alkyl include methyl, t-butyl, n-heptyl, octyl, and the like.

"Alkenyl" refers to an unsaturated hydrocarbon group having at least one site of olefinic unsaturation (i.e., having at least one moiety of the formula C=C). Unless otherwise defined, "C2-C6 linear or branched alkenyl" means ethenyl and C2-C6, C2-C5, C2-C4, C2-C3, C3-C6, C3-C5, C3-C4, C4-C6, C4-C5, C5-C6, C3, C4, C5, and C6 linear or branched alkenyl. Examples of alkenyl include but are not limited to ethenyl "—CH=CH$_2$," —CH$_2$—CH=CH—CH$_3$ and —CH=CH—CH=CH$_2$.

"Alkynyl" refers to an unsaturated hydrocarbon group having at least one site of acetylenic unsaturation (i.e., having at least one moiety of the formula C≡C). Unless otherwise defined, "C2-C6 linear or branched alkynyl" means ethynyl and C2-C6, C2-C5, C2-C4, C2-C3, C3-C6, C3-C5, C3-C4, C4-C6, C4-C5, C5-C6, C3, C4, C5, and C6 linear or branched alkynyl. Examples of alkynyl include but are not limited to ethynyl "—C≡CH," —CH$_2$—C≡C—CH$_3$ and —C≡C—C≡CH.

"Cycloalkyl" refers to and includes cyclic univalent hydrocarbon structures. Cycloalkyl can consist of one ring, such as cyclohexyl, or multiple rings, such as adamantyl. A cycloalkyl comprising more than one ring may be fused, spiro or bridged, or combinations thereof. A preferred cycloalkyl is a saturated cyclic hydrocarbon having from 3 to 13 annular carbon atoms. A more preferred cycloalkyl is a saturated cyclic hydrocarbon having from 3 to 6 annular carbon atoms (a "C3-C6 cycloalkyl"). Examples of cycloalkyl groups include adamantyl, decahydronaphthalenyl, cyclopropyl, cyclobutyl, cyclopentyl, cyclohexyl, and the like. Unless otherwise defined, "C3-C6 cycloalkyl" means C3-C6, C3-C5, C3-C4, C4-C6, C4-C5, C5-C6, C3, C4, C5, and C6 cycloalkyl.

"Cycloalkenyl" refers to an unsaturated hydrocarbon group within a cycloalkyl having at least one site of olefinic unsaturation (i.e., having at least one moiety of the formula C=C). Cycloalkenyl can consist of one ring, such as cyclohexyl, or multiple rings, such as norbornenyl. A more preferred cycloalkenyl is an unsaturated cyclic hydrocarbon having from 3 to 8 annular carbon atoms (e.g., "C3-C8 cycloalkenyl," "C3-C6 cycloalkenyl"). Unless otherwise defined, "C3-C6 cycloalkenyl" means C3-C6, C3-C5, C3-C4, C4-C6, C4-C5, C5-C6, C3, C4, C5, and C6 cycloalkenyl. Examples of cycloalkenyl groups include cyclopropenyl, cyclobutenyl, cyclopentenyl, cyclohexenyl, and the like.

"Heterocycle," "heterocyclic," or "heterocyclyl" refers to a saturated or an unsaturated non-aromatic group having a single ring or multiple condensed rings, and having from 1 to 10 annular carbon atoms and from 1 to 4 annular heteroatoms, such as nitrogen, sulfur or oxygen, and the like. A heterocycle comprising more than one ring may be fused, spiro or bridged, or any combination thereof. In fused ring systems, one or more of the rings can be aryl or heteroaryl. A heterocycle having more than one ring where at least one ring is aromatic may be connected to the parent structure at either a non-aromatic ring position or at an aromatic ring position. In one variation, a heterocycle having more than one ring where at least one ring is aromatic is connected to the parent structure at a non-aromatic ring position. Unless otherwise defined, "C3-C8 heterocycle" (or "heterocyclyl" or "heterocyclic") means C3-C8, C3-C7, C3-C6, C3-C4, C3-C5, C4-C8 C4-C7, C4-C6, C4-C5, C5-C8, C5-C7, C5-C6, C6-C8, C6-C7, C7-C8, C3, C4, C5, C6, C7, and C8 heterocycle (or heterocyclyl or heterocyclic)

"Aryl" as used herein refers to an unsaturated aromatic carbocyclic group having a single ring (e.g., phenyl) or multiple condensed rings (e.g., naphthyl or anthryl) which condensed rings mayor may not be aromatic. The aryl group may be optionally substituted independently with one or more substituents described herein. Particular aryl groups are those having from 6 to 14 annular (i.e., ring) carbon atoms (a "C6-C14 aryl"). An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Heteroaryl" as used herein refers to an unsaturated aromatic cyclic group having from 1 to 14 annular (i.e., ring) carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl) which condensed rings mayor may not be aromatic. The heteroaryl group may be optionally substituted independently with one or more substituents described herein. Particular heteroaryl groups are 5- to 14-membered rings having 1 to 12 annular (i.e., ring) carbon atoms and 1 to 6 annular (i.e., ring) heteroatoms independently selected from nitrogen, oxygen and sulfur; 5- to 10-membered rings having 1 to 8 annular carbon atoms and 1 to 4 annular heteroatoms independently selected from nitrogen, oxygen and sulfur; and 5-, 6- or 7-membered rings having 1 to 5 annular carbon atoms and 1 to 4 annular heteroatoms independently selected from nitrogen, oxygen and sulfur. In one variation, heteroaryl includes monocyclic aromatic 5-, 6- or 7-membered rings having from 1 to 6 annular carbon atoms and 1 to 4 annular heteroatoms independently selected from nitrogen, oxygen and sulfur. In another variation, heteroaryl includes polycyclic aromatic rings having from 1 to 12 annular carbon atoms and 1 to 6 annular heteroatoms independently selected from nitrogen, oxygen and sulfur. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position.

"Alkoxy" refers to the group alkyl-O—, which includes, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Hydroxyalkyl" refers to the group alkyl-OH, which includes, by way of example, hydroxymethyl, 1-hydroxyethyl, 2-hydroxyethyl, 1-hydroxyprop-1-yl, 2-hydroxyprop-2-yl, 3-hydroxypropyl, 4-hydroxybutyl, 5-hydroxypentyl, 6-hydroxyhexyl, and the like.

"Halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each H is replaced with a halo group is referred to as a "perhaloalkyl." An alkenyl group in which each H is replaced with a halo group is referred to as a "perhaloalkenyl." An alkynyl group in which each H is replaced with a halo group is referred to as a "perhaloalkynyl." A preferred perhaloalkyl group is trifluoroalkyl (—CF$_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—OCF$_3$).

Any and all stereoisomers, including geometric isomers (cis/trans or E/Z isomers), tautomers, salts, N-oxides, and solvates of the compounds described herein can be used in the disclosed methods. This disclosure also provides methods of making such compounds.

Compounds

Compounds disclosed herein fall within Formulae (Ia) or (Ib):

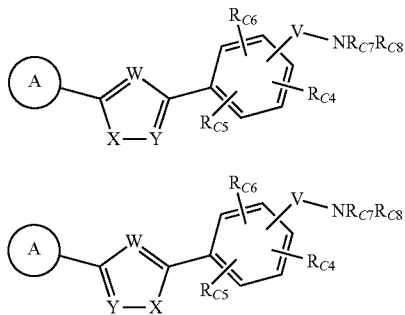

or a pharmaceutically acceptable salt thereof, wherein:
A is either:
  i. a heteroaryl having only one ring, substituted with one or more R1 or R2; or
  ii. an aryl or heteroaryl, each having more than one ring, optionally substituted with one or more R1 or R3;
R1 is C1-C6 linear or branched alkyl, C2-C6 linear or branched alkenyl, C2-C6 linear or branched alkynyl, C3-C6 cycloalkyl, C3-C6 cycloalkylmethyl, C3-C6 cycloalkenyl, aryl, or heteroaryl; each optionally substituted with one or more R3;
R2 is halogen, —CN, —OH, —O(Alkyl), —NO$_2$, —SH, —S(Alkyl), —S(O)(Alkyl), —S(O)$_2$(Alkyl), —CH$_2$OCH$_3$, —OBn, —CO$_2$H, —CO$_2$(Alkyl), —NR10R11, —CONR10R11, and —S(O)$_2$NR10R11;
R3 is halogen, —CN, —OH, —O(Alkyl), =O, —NO$_2$, —SH, —S(Alkyl), —S(O)(Alkyl), —S(O)$_2$(Alkyl), —CH$_2$OCH$_3$, —OBn, —CO$_2$H, —CO$_2$(Alkyl), —NR10R11, —CONR10R11, and —S(O)$_2$NR10R11;
Each $R_{C4}$, $R_{C5}$, and $R_{C6}$, is independently hydrogen, R1, or R2; or $R_{C4}$ is taken with $R_{C7}$ to form a heterocyclyl optionally substituted with one or more R3;
Each $R_{C7}$ and $R_{C8}$ is independently hydrogen, R1, or —SO$_2$R$_{C12}$; or $R_{C7}$ and $R_{C8}$ are taken together with the N to which they are attached to form a C3-C8 heterocycle optionally substituted with one or more R1 or R3; or $R_{C7}$ is taken with $R_{C4}$ to form a heterocyclyl optionally substituted with one or more R3;
R10 and R11 are independently hydrogen, C1-C6 linear or branched alkyl, —C(O)R$_{C12}$, —C(O)$_2$R$_{C12}$, —C(O)N(R$_{C12}$)$_2$, —SO$_2$R$_{C12}$, or are taken together with the N to which they are attached to form a C3-C8 heterocyclyl;
$R_{C12}$ is hydrogen, a linear or branched C1-C6 alkyl, a linear or branched C2-C6 alkenyl, a linear or branched C2-C6 alkynyl, or aryl; wherein each alkyl, alkenyl, alkynyl, or aryl group is optionally substituted with one or more halogen atoms, one or more —NH$_2$ groups, or one or more —OH group;
V is the moiety —C(=O)— or —S(=O)$_2$—; and
The ring comprising W, X, and Y is a 5-membered heteroaromatic, wherein W and Y are independently selected from the group consisting of CR$_A$, N, NR$_B$, O and S; X is selected from the group consisting of NR$_B$, O and S; wherein R$_A$ is hydrogen, R1 or R2; and R$_B$ is hydrogen or R1;
With the proviso that when W is N, X is S, and Y is C, then one of R$_{C4}$, R$_{C5}$ and R$_{C6}$ is other than H.

Variations in which a is a Heteroaryl Having Only One Ring

In some variations of Formulae (Ia) or (Ib), A is a heteroaryl having only one ring, substituted with one R1 (i.e., there is a first R1). In some variations, A is a heteroaryl having only one ring, substituted with two R1 (i.e., there is a first R1 and a second R1). In some variations, A is a heteroaryl having only one ring, substituted with three R1 (i.e., there is a first R1, a second R1, and a third R1).

In some variations, the first R1 is unsubstituted C1-C6 linear or branched alkyl. In some variations, the first R1 is unsubstituted C2-C6 linear or branched alkenyl. In some variations, the first R1 is unsubstituted C2-C6 linear or branched alkynyl. In some variations, the first R1 is unsubstituted C3-C6 cycloalkyl. In some variations, the first R1 is unsubstituted C3-C6 cycloalkylmethyl. In some variations, the first R1 is unsubstituted C3-C6 cycloalkenyl. In some variations, the first R1 is unsubstituted aryl. In some variations, the first R1 is unsubstituted heteroaryl. In some variations, the first R1 is C1-C6 linear or branched alkyl substituted with one or more R3. In some variations, the first R1 is C2-C6 linear or branched alkenyl substituted with one or more R3. In some variations, the first R1 is C2-C6 linear or branched alkynyl substituted with one or more R3. In some variations, the first R1 is C3-C6 cycloalkyl substituted with one or more R3. In some variations, the first R1 is C3-C6 cycloalkylmethyl substituted with one or more R3. In some variations, the first R1 is C3-C6 cycloalkenyl substituted with one or more R3. In some variations, the first R1 is aryl substituted with one or more R3. In some variations, the first R1 is heteroaryl substituted with one or more R3.

In some variations, the second R1 is unsubstituted C1-C6 linear or branched alkyl. In some variations, the second R1 is unsubstituted C2-C6 linear or branched alkenyl. In some variations, the second R1 is unsubstituted C2-C6 linear or branched alkynyl. In some variations, the second R1 is unsubstituted C3-C6 cycloalkyl. In some variations, the second R1 is unsubstituted C3-C6 cycloalkylmethyl. In some variations, the second R1 is unsubstituted C3-C6 cycloalkenyl. In some variations, the second R1 is unsubstituted aryl. In some variations, the second R1 is unsubstituted heteroaryl. In some variations, the second R1 is C1-C6 linear or branched alkyl substituted with one or more R3. In some variations, the second R1 is C2-C6 linear or branched alkenyl substituted with one or more R3. In some variations, the second R1 is C2-C6 linear or branched alkynyl substituted with one or more R3. In some variations, the second R1 is C3-C6 cycloalkyl substituted with one or more R3. In some variations, the second R1 is C3-C6 cycloalkylmethyl substituted with one or more R3. In some variations, the second R1 is C3-C6 cycloalkenyl substituted with one or more R3. In some variations, the second R1 is aryl substituted with one or more R3. In some variations, the second R1 is heteroaryl substituted with one or more R3.

In some variations, the third R1 is unsubstituted C1-C6 linear or branched alkyl. In some variations, the third R1 is unsubstituted C2-C6 linear or branched alkenyl. In some variations, the third R1 is unsubstituted C2-C6 linear or branched alkynyl. In some variations, the third R1 is unsubstituted C3-C6 cycloalkyl. In some variations, the third R1 is unsubstituted C3-C6 cycloalkylmethyl. In some variations, the third R1 is unsubstituted C3-C6 cycloalkenyl. In some variations, the third R1 is unsubstituted aryl. In some variations, the third R1 is unsubstituted heteroaryl. In some variations, the third R1 is C1-C6 linear or branched alkyl substituted with one or more R3. In some variations, the third R1 is C2-C6 linear or branched alkenyl substituted with one or more R3. In some variations, the third R1 is C2-C6 linear or branched alkynyl substituted with one or more R3. In some variations, the third R1 is C3-C6 cycloalkyl substituted with one or more R3. In some variations, the third R1 is C3-C6 cycloalkylmethyl substituted with one or more R3. In some variations, the third R1 is C3-C6 cycloalkenyl substituted with one or more R3. In some variations, the third R1 is aryl substituted with one or more R3. In some variations, the third R1 is heteroaryl substituted with one or more R3.

In some variations, at least one R3 is halogen. In some variations, at least one R3 is —CN. In some variations, at least one R3 is —O(R12). In some variations, at least one R3 is =O. In some variations, at least one R3 is —NO$_2$. In some variations, at least one R3 is —S(R12). In some variations, at least one R3 is —S(O)(R12). In some variations, at least one R3 is —S(O)$_2$(R12). In some variations, at least one R3 is —CH$_2$OCH$_3$. In some variations, at least one R3 is —OBn. In some variations, at least one R3 is —CO$_2$H. In some variations, at least one R3 is —CO$_2$(R12). In some variations, at least one R3 is —NR10R11. In some variations, at least one R3 is —CONR10R11. In some variations, at least one R3 is —S(O)$_2$NR10R11.

In some variations of Formulae (Ia) or (Ib), A is a heteroaryl having only one ring, substituted with one R2 (a first R2). In some variations, A is a heteroaryl having only one ring, substituted with two R2 (a first R2 and a second R2). In some variations, A is a heteroaryl having only one ring, substituted with three R2 (a first R2, a second R2, and a third R2). In some of these variations, the first R2 is halogen. In some of these variations, the first R2 is —CN. In some of these variations, the first R2 is —OH. In some of these variations, the first R2 is —O(Alkyl). In some of these variations, the first R2 is —NO$_2$. In some of these variations, the first R2 is —SH. In some of these variations, the first R2 is —S(Alkyl). In some of these variations, the first R2 is —S(O)(Alkyl). In some of these variations, the first R2 is —S(O)$_2$(Alkyl). In some of these variations, the first R2 is —CH$_2$—OCH$_3$. In some of these variations, the first R2 is —OBn. In some of these variations, the first R2 is —CO$_2$H. In some of these variations, the first R2 is —CO$_2$(Alkyl). In some of these variations, the first R2 is —NR10R11. In some of these variations, the first R2 is —CONR10R11. In some of these variations, the first R2 is —S(O)$_2$NR10R11. In some of these variations, the second R2 is halogen. In some of these variations, the second R2 is —CN. In some of these variations, the second R2 is —OH. In some of these variations, the second R2 is —O(Alkyl). In some of these variations, the second R2 is —NO$_2$. In some of these variations, the second 12 is —SH. In some of these variations, the second R2 is —S(Alkyl). In some of these variations, the second R2 is —S(O)(Alkyl). In some of these variations, the second R2 is —S(O)$_2$(Alkyl). In some of these variations, the second R2 is —CH$_2$OCH$_3$. In some of these variations, the second R2 is —OBn. In some of these variations, the second R2 is —CO$_2$H. In some of these variations, the second R2 is —CO$_2$(Alkyl). In some of these variations, the second R2 is —NR10R11. In some of these variations, the second R2 is —CONR10R11. In some of these variations, the second R2 is —S(O)$_2$NR10R11. In some of these variations, the third R2 is halogen. In some of these variations, the third R2 is —CN. In some of these variations, the third R2 is —OH. In some of these variations, the third R2 is —O(Alkyl). In some of these variations, the third R2 is —NO$_2$. In some of these variations, the third R2 is —SH. In some of these variations, the third R2 is —S(Alkyl). In some of these variations, the third R2 is —S(O)(Alkyl). In some of these variations, the third R2 is —S(O)$_2$(Alkyl). In some of these variations, the third R2 is —CH$_2$OCH$_3$. In some of these variations, the third R2 is —OBn. In some of these variations, the third R2 is —CO$_2$H. In some of these variations, the third R2 is —CO$_2$(Alkyl). In some of these variations, the third R2 is —NR10R11. In some of these variations, the third R2 is —CONR10R11. In some of these variations, the third R2 is —S(O)$_2$NR10R11.

Variations in which a is an Aryl or Heteroaryl, Each Having More than One Ring

In some variations of Formulae (Ia) or (Ib), A is an aryl or heteroaryl, each having more than one ring.

Variations in which a is an Aryl Having More than One Ring

In some variations of Formulae (Ia) or (Ib), A is an aryl having more than one ring, substituted with one R1 (a first R1). In some variations, A is an aryl having more than one ring, substituted with two R1 (a first R1 and a second R1). In some variations, A is an aryl having more than one ring, substituted with three R1 (a first R1, a second R1, and a third R1). In some of these variations, the first R1 is unsubstituted C1-C6 linear or branched alkyl. In some of these variations, the first R1 is unsubstituted C2-C6 linear or branched alkenyl. In some of these variations, the first R1 is unsubstituted C2-C6 linear or branched alkynyl. In some of these variations, the first R1 is unsubstituted C3-C6 cycloalkyl. In some of these variations, the first R1 is unsubstituted C3-C6 cycloalkylmethyl. In some of these variations, the first R1 is unsubstituted C3-C6 cycloalkenyl. In some variations, the second R1 is unsubstituted aryl. In some variations, the second R1 is unsubstituted heteroaryl. In some of these variations, the first R1 is C1-C6 linear or branched alkyl substituted with one or more 13. In some of these variations, the first R1 is C2-C6 linear or branched alkenyl substituted with one or more R3. In some of these variations, the first R1 is C2-C6 linear or branched alkynyl substituted with one or more R3. In some of these variations, the first R1 is C3-C6 cycloalkyl substituted with one or more R3. In some of these variations, the first R1 is C3-C6 cycloalkylmethyl substituted with one or more R3. In some of these variations, the first R1 is C3-C6 cycloalkenyl substituted with one or more R3. In some variations, the first R1 is aryl substituted with one or more R3. In some variations, the first R1 is heteroaryl substituted with one or more R3. In some of these variations, the second R1 is unsubstituted C1-C6 linear or branched alkyl. In some of these variations, the second R1 is unsubstituted C2-C6 linear or branched alkenyl. In some of these variations, the second R1 is unsubstituted C2-C6 linear or branched alkynyl. In some of these variations, the second R1 is unsubstituted C3-C6 cycloalkyl. In some of these variations, the second R1 is unsubstituted C3-C6 cycloalkylmethyl. In some of these variations, the second R1 is unsubstituted C3-C6 cycloalkenyl. In some variations, the second R1 is unsubstituted aryl. In some variations, the second R1 is unsubstituted heteroaryl. In some of these variations, the second R1 is C1-C6 linear or branched alkyl substituted with one or more R3. In some of these variations, the second R1 is C2-C6 linear or branched alkenyl substituted with one or more R3. In some of these variations, the second R1 is C2-C6 linear or branched alkynyl substituted with one or more R3. In some of these variations, the second R1 is C3-C6 cycloalkyl substituted with one or more R3. In some of these variations, the second R1 is C3-C6 cycloalkylmethyl substituted with one or more R3. In some of these variations, the second R1 is C3-C6 cycloalkenyl substituted with one or more R3. In some variations, the second R1 is aryl substituted with one or more R3. In some variations, the second R1 is heteroaryl substituted with one or more R3. In some of these variations, the third R1 is unsubstituted C1-C6 linear or branched alkyl. In some of these variations, the third R1 is unsubstituted C2-C6 linear or branched alkenyl. In some of these variations, the third R1 is unsubstituted C2-C6 linear or branched alkynyl. In some of these variations, the third R1 is unsubstituted C3-C6 cycloalkyl. In some of these variations, the third R1 is unsubstituted C3-C6 cycloalkylmethyl. In some of these variations, the third R1 is unsubstituted C3-C6 cycloalkenyl. In some variations, the third R1 is unsubstituted aryl. In some variations, the third R1 is unsubstituted heteroaryl. In some of these variations, the third R1 is C1-C6 linear or branched alkyl substituted with one or more R3. In some of these variations, the third R1 is C2-C6 linear or branched alkenyl substituted with one or more R3. In some of these variations, the third R1 is C2-C6 linear or branched alkynyl substituted with one or more R3. In some of these variations, the third R1 is C3-C6 cycloalkyl substituted with one or more R3. In some of these variations, the third R1 is C3-C6 cycloalkylmethyl substituted with one or more R3. In some of these variations, the third R1 is C3-C6 cycloalkenyl substituted with one or more R3. In some variations, the third R1 is aryl substituted with one or more R3. In some variations, the third R1 is heteroaryl substituted with one or more R3. In some of these variations, at least one R3 is halogen. In some of these variations, at least one R3 is —CN. In some of these variations, at least one R3 is —OH. In some of these variations, at least one R3 is —O(Alkyl). In some of these variations, at least one R3 is =O. In some of these variations, at least one R3 is —NO$_2$. In some of these variations, at least one R3 is —SH. In some of these variations, at least one R3 is —S(Alkyl). In some of these variations, at least one R3 is —S(O)(Alkyl). In some of these variations, at least one R3 is —S(O)$_2$(Alkyl). In some of these variations, at least one R3 is —CH$_2$OCH$_3$. In some of these variations, at least one R3 is —OBn. In some of these variations, at least one R3 is —CO$_2$H. In some of these variations, at least one R3 is —CO$_2$(Alkyl). In some of these variations, at least one R3 is —NR10R11. In some of these variations, at least one R3 is —CONR10R11. In some of these variations, at least one R3 is —S(O)$_2$NR10R11.

In some variations of Formulae (Ia) or (Ib), A is an aryl having more than one ring, substituted with one R3 (a first R3). In some variations, A is an aryl having more than one ring, substituted with two R3 (a first R3 and a second R3). In some variations, A is an aryl having more than one ring, substituted with three R3 (a first R3, a second R3, and a third R3). In some of these variations, the first R3 is halogen. In some of these variations, the first R3 is —CN. In some of these variations, the first R3 is —OH. In some of these variations, the first R3 is —O(Alkyl). In some of these variations, the first R3 is =O. In some of these variations, the first R3 is —NO$_2$. In some of these variations, the first R3 is —SH. In some of these variations, the first R3 is —S(Alkyl). In some of these variations, the first R3 is —S(O)(Alkyl). In some of these variations, the first R3 is —S(O)$_2$(Alkyl). In some of these variations, the first R3 is —CH$_2$OCH$_3$. In some of these variations, the first R3 is —OBn. In some of these variations, the first R3 is —CO$_2$H. In some of these variations, the first R3 is —CO$_2$(Alkyl). In some of these variations, the first R3 is —NR10R11. In some of these variations, the first R3 is —CONR10R11. In some of these variations, the first R3 is —S(O)$_2$NR10R11. In some of these variations, the second R3 is halogen. In some of these variations, the second R3 is —CN. In some of these variations, the second R3 is —OH. In some of these variations, the second R3 is —O(Alkyl). In some of these variations, the second R3 is =O. In some of these variations, the second R3 is —NO$_2$. In some of these variations, the second R3 is —SH. In some of these variations, the second R3 is —S(Alkyl). In some of these variations, the second R3 is —S(O)(Alkyl). In some of these variations, the second R3 is —S(O)$_2$(Alkyl). In some of these variations, the second R3 is —CH$_2$OCH$_3$. In some of these variations, the second R3 is —OBn. In some of these variations, the second R3 is —CO$_2$H. In some of these variations, the second R3 is —CO$_2$(Alkyl). In some of these variations, the second R3 is —NR10R11. In some of these variations, the second R3 is —CONR10R11. In some of these variations, the second R3 is —S(O)$_2$NR10R11. In some of these variations, the third R3 is halogen. In some of these variations, the third R3 is —CN. In some of these variations, the third R3 is =OH. In some of these variations, the third R3 is —O(Alkyl). In some of these variations, the third R3 is =O. In some of these variations, the third R3 is —NO$_2$. In some of these variations, the third R3 is —SH. In some of these variations, the third R3 is —S(Alkyl). In some of these variations, the third R3 is —S(O)(Alkyl). In some of these variations, the third R3 is —S(O)$_2$(Alkyl). In some of these variations, the third R3 is —CH$_2$OCH$_3$. In some of these variations, the third R3 is —OBn. In some of these variations, the third R3 is —CO$_2$H. In some of these variations, the third R3 is —CO$_2$(Alkyl). In some of these variations, the third R3 is —NR10R11. In some of these variations, the third R3 is —CONR10R11. In some of these variations, the third R3 is —S(O)$_2$NR10R11.

Variations in which a is a Heteroaryl Having More than One Ring

In some variations of Formulae (Ia) or (Ib), A is a heteroaryl having more than one ring, substituted with one R1 (a first R11). In some variations, A is a heteroaryl having more than one ring, substituted with two R1 (a first R1 and a second R1). In some variations, A is a heteroaryl having more than one ring, substituted with three R1 (a first R1, a second R1, and a third R1). In some of these variations, the first R1 is unsubstituted C1-C6 linear or branched alkyl. In some of these variations, the first R1 is unsubstituted C2-C6 linear or branched alkenyl. In some of these variations, the first R1 is unsubstituted C2-C6 linear or branched alkynyl. In some of these variations, the first R1 is unsubstituted C3-C6 cycloalkyl. In some of these variations, the first R1 is unsubstituted C3-C6 cycloalkylmethyl. In some of these variations, the first R1 is unsubstituted C3-C6 cycloalkenyl. In some variations, the first R1 is unsubstituted aryl. In some variations, the first R1 is unsubstituted heteroaryl. In some of these variations, the first R1 is C1-C6 linear or branched alkyl substituted with one or more R3. In some of these variations, the first R1 is C2-C6 linear or branched alkenyl substituted with one or more R3. In some of these variations, the first R1 is C2-C6 linear or branched alkynyl substituted with one or more R3. In some of these variations, the first R1 is C3-C6 cycloalkyl substituted with one or more R3. In some of these variations, the first R1 is C3-C6 cycloalkylmethyl substituted with one or more R3. In some of these variations, the first R1 is C3-C6 cycloalkenyl substituted with one or more R3. In some variations, the first R1 is aryl substituted with one or more R3. In some variations, the first R1 is heteroaryl substituted with one or more R3. In some of these variations, the second R1 is unsubstituted C1-C6 linear or branched alkyl. In some of these variations, the second R1 is unsubstituted C2-C6 linear or branched alkenyl. In some of these variations, the second R1 is unsubstituted C2-C6 linear or branched alkynyl. In some of these variations, the second R1 is unsubstituted C3-C6 cycloalkyl. In some of these variations, the second R1 is unsubstituted C3-(6 cycloalkylmethyl. In some of these variations, the second R1 is unsubstituted C3-C6 cycloalkenyl. In some variations, the second R1 is unsubstituted aryl. In some variations, the second R1 is unsubstituted heteroaryl. In some of these variations, the second R1 is C1-C6 linear or branched alkyl substituted with one or more R3. In some of these variations, the second R1 is C2-C6 linear or branched alkenyl substituted with one or more R3. In some of these variations, the second R1 is C2-C6 linear or branched alkynyl substituted with one or more R3. In some of these variations, the second R1 is C3-C6 cycloalkyl substituted with one or more R3. In some of these variations, the second R1 is C3-C6 cycloalkylmethyl substituted with one or more R3. In some of these variations, the second R1 is C3-C6 cycloalkenyl substituted with one or more R3. In some variations, the second R1 is aryl substituted with one or more R3. In some variations, the second R1 is heteroaryl substituted with one or more R3. In some of these variations, the third R1 is unsubstituted C1-C6 linear or branched alkyl. In some of these variations, the third R1 is unsubstituted C2-C6 linear or branched alkenyl. In some of these variations, the third R1 is unsubstituted C2-C6 linear or branched alkynyl. In some of these variations, the third R1 is unsubstituted C3-C6 cycloalkyl. In some of these variations, the third R1 is unsubstituted C3-C6 cycloalkylmethyl. In some of these variations, the third R1 is unsubstituted C3-C6 cycloalkenyl. In some variations, the third R1 is unsubstituted aryl. In some variations, the third R1 is unsubstituted heteroaryl. In some of these variations, the third R1 is C1-C6 linear or branched alkyl substituted with one or more R3. In some of these variations, the third R1 is C2-C6 linear or branched alkenyl substituted with one or more R3. In some of these variations, the third R1 is C2-C6 linear or branched alkynyl substituted with one or more R3. In some of these variations, the third R1 is C3-C6 cycloalkyl substituted with one or more R3. In some of these variations, the third R1 is C3-C6 cycloalkylmethyl substituted with one or more R3. In some of these variations, the third R1 is C3-C6 cycloalkenyl substituted with one or more R3. In some variations, the third R1 is aryl substituted with one or more R3. In some variations, the third R1 is heteroaryl substituted with one or more R3. In some of these variations, at least one R3 is halogen. In some of these variations, at least one R3 is —CN. In some of these variations, at least one R3 is —OH. In some of these variations, at least one R3 is —O(Alkyl). In some of these variations, at least one R3 is =O. In some of these variations, at least one R3 is —NO$_2$. In some of these variations, at least one R3 is —SH. In some of these variations, at least one R3 is —S(Alkyl). In some of these variations, at least one R3 is —S(O)(Alkyl). In some of these variations, at least one R3 is —S(O)-(Alkyl). In some of these variations, at least one R3 is —CH$_2$OCH$_3$. In some of these variations, at least one R3 is —OBn. In some of these variations, at least one R3 is —CO$_2$H. In some of these variations, at least one R3 is —CO$_2$(Alkyl). In some of these variations, at least one R3 is —NR10R11. In some of these variations, at least one R3 is —CONR10R11. In some of these variations, at least one R3 is —S(O)$_2$NR10R11.

In some variations of Formulae (Ia) or (Ib), A is a heteroaryl having more than one ring, substituted with one R3 (a first R3). In some variations, A is a heteroaryl having more than one ring, substituted with two R3 (a first R3 and a second R3). In some variations, A is a heteroaryl having more than one ring, substituted with three R3 (a first R3, a second R3, and a third R3). In some of these variations, the first R3 is halogen. In some of these variations, the first R3 is —CN. In some of these variations, the first R3 is —OH. In some of these variations, the first R3 is —O(Alkyl). In some of these variations, the first R3 is =O. In some of these variations, the first R3 is —NO$_2$. In some of these variations, the first R3 is —SH. In some of these variations, the first R3 is —S(Alkyl). In some of these variations, the first R3 is —S(O)(Alkyl). In some of these variations, the first R3 is —S(O)$_2$(Alkyl). In some of these variations, the first R3 is —CH$_2$OCH$_3$. In some of these variations, the first R3 is —OBn. In some of these variations, the first R3 is —CO$_2$H. In some of these variations, the first R3 is —CO$_2$(Alkyl). In some of these variations, the first R3 is —NR10R11. In some of these variations, the first R3 is —CONR10R11. In some of these variations, the first R3 is —S(O)$_2$NR10R11. In some of these variations, the second R3 is halogen. In some of these variations, the second R3 is —CN. In some of these variations, the second R3 is —OH. In some of these variations, the second R3 is —O(Alkyl). In some of these variations, the second R3 is =O. In some of these variations, the second R3 is —NO$_2$. In some of these variations, the second R3 is —SH. In some of these variations, the second R3 is —S(Alkyl). In some of these variations, the second R3 is —S(O)(Alkyl). In some of these variations, the second R3 is —S(O)$_2$(Alkyl). In some of these variations, the second R3 is —CH$_2$OCH$_3$. In some of these variations, the second R3 is —OBn. In some of these variations, the second R3 is —CO$_2$Hi. In some of these variations, the second R3 is —CO$_2$(Alkyl). In some of these variations, the second R3 is —NR10R11. In some of these variations, the second R3 is —CONR10R11. In some of these variations, the second R3 is —S(O)$_2$NR10R11. In some of these variations, the third R3 is halogen. In some of these variations, the third R3 is —CN. In some of these variations, the third R3 is —OH. In some of these variations, the third R3 is —O(Alkyl). In some of these variations, the third R3 is =O. In some of these variations, the third R3 is —NO$_2$. In some of these variations, the third R3 is —SH. In some of these variations, the third R3 is —S(Alkyl). In some of these variations, the third R3 is —S(O)(Alkyl). In some of these variations, the third R3 is —S(O)$_2$(Alkyl). In some of these variations, the third R3 is —CH$_2$OCH$_3$. In some of these variations, the third R3 is —OBn. In some of these variations, the third R3 is —CO$_2$H. In some of these variations, the third R3 is —CO$_2$(Alkyl). In some of these variations, the third R3 is —NR10R11. In some of these variations, the third R3 is —CONR10R11. In some of these variations, the third R3 is —S(O)$_2$NR10R11.

In some variations of Formulae (Ia) or (Ib), A is a moiety selected from the group consisting of:

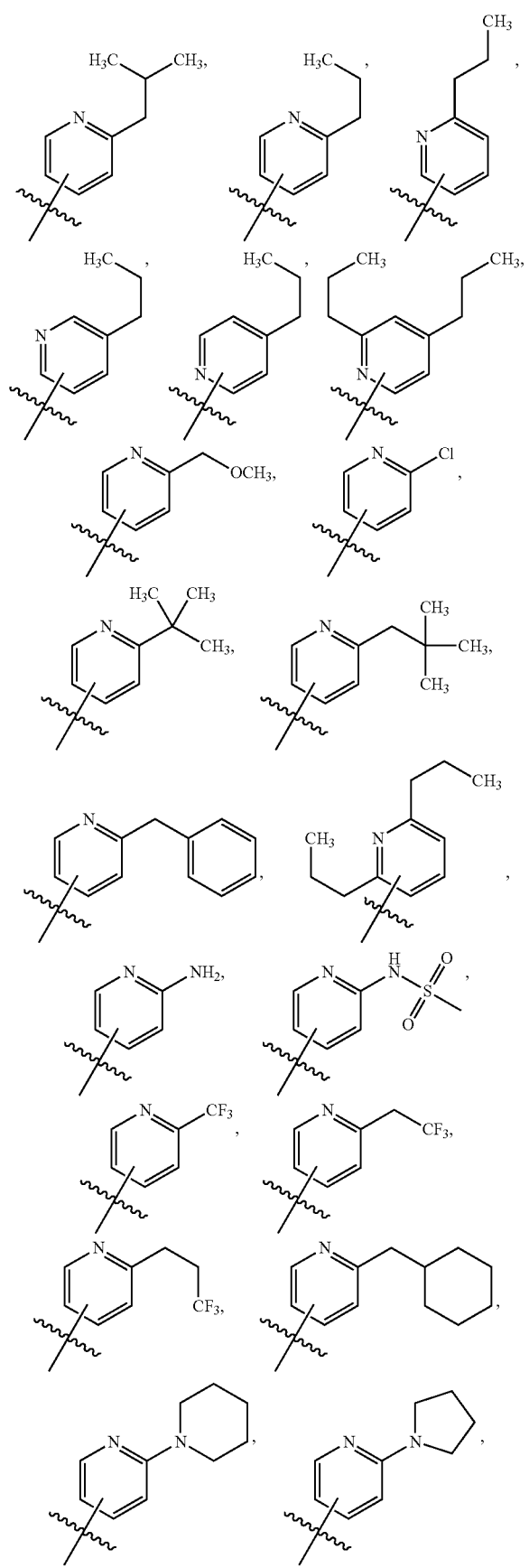
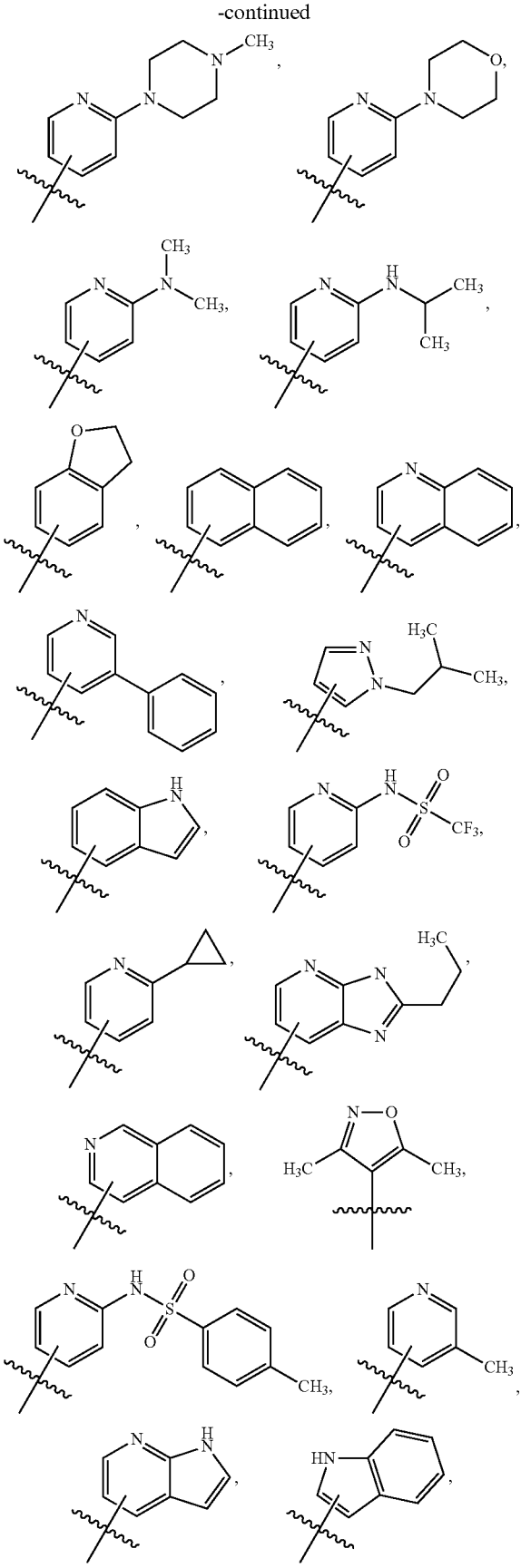

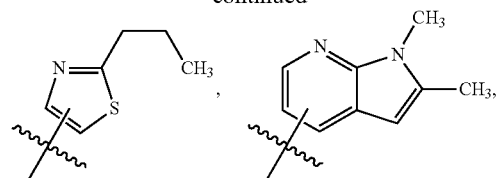
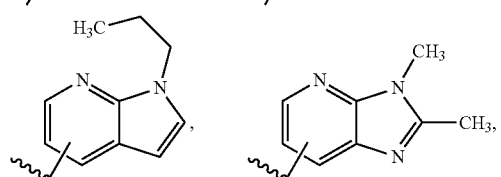
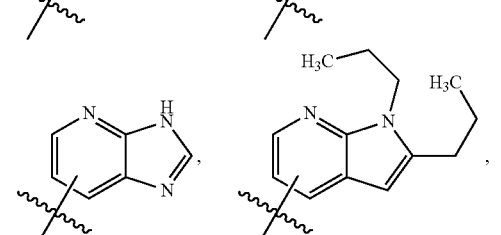
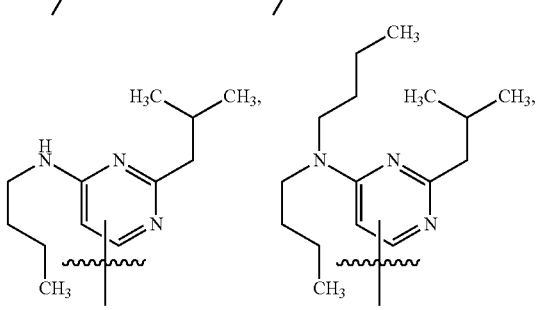
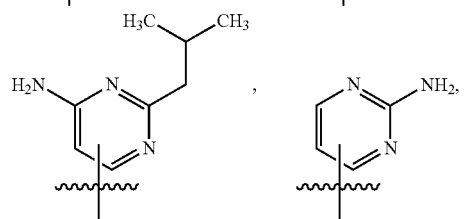
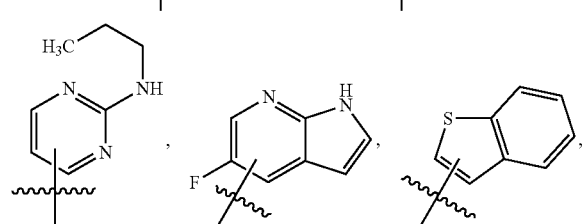
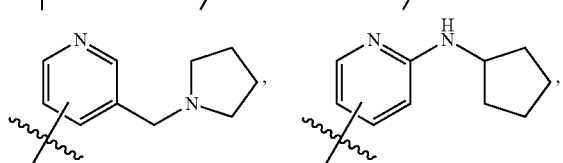
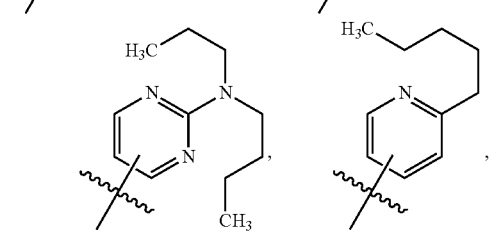
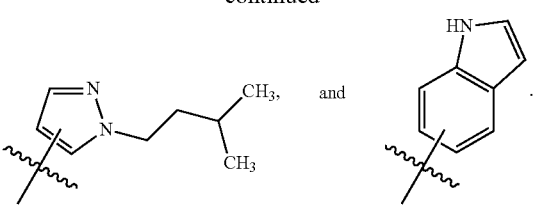
In some variations of Formulae (Ia) or (Ib), A is a moiety selected from the group consisting of:
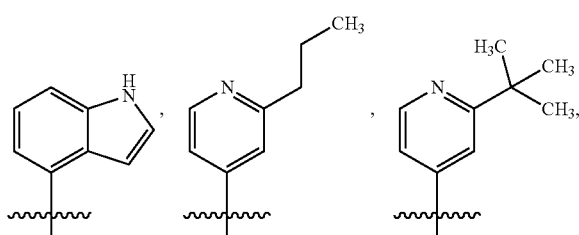
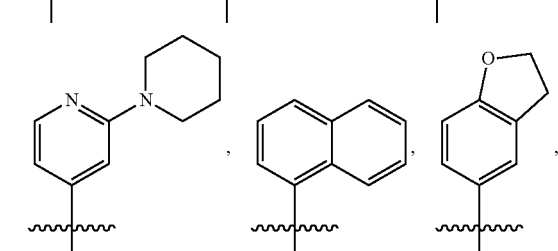
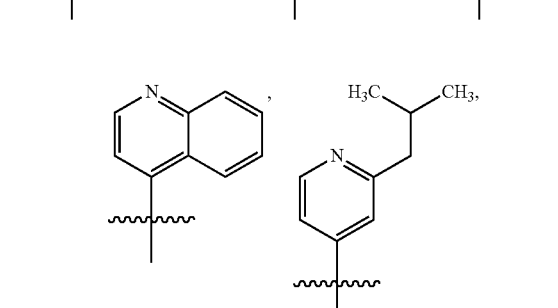
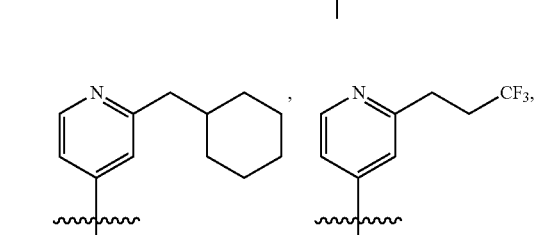
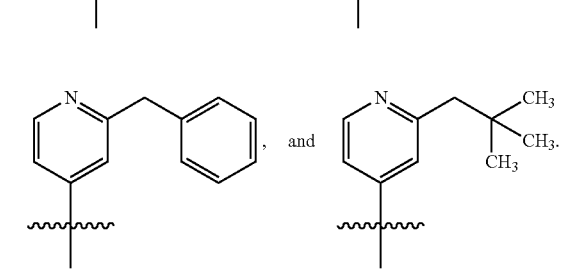
In some variations of Formulae (Ia) or (Ib), A is a moiety selected from the group consisting of:

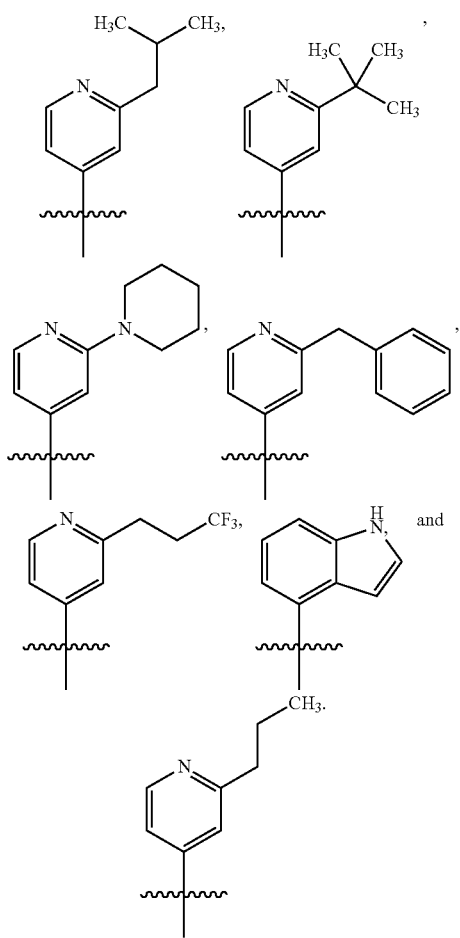

In some variations of Formulae (Ia) or (Ib), V is the moiety —C(=O)—.

In some variations of Formulae (Ia) or (Ib), V is the moiety —S(=O)$_2$—.

In some variations of Formulae (Ia) or (Ib), the ring comprising W, X, and Y, and the carbon atoms to which they are attached, is a 5-membered heteroaromatic group selected from the group consisting of:

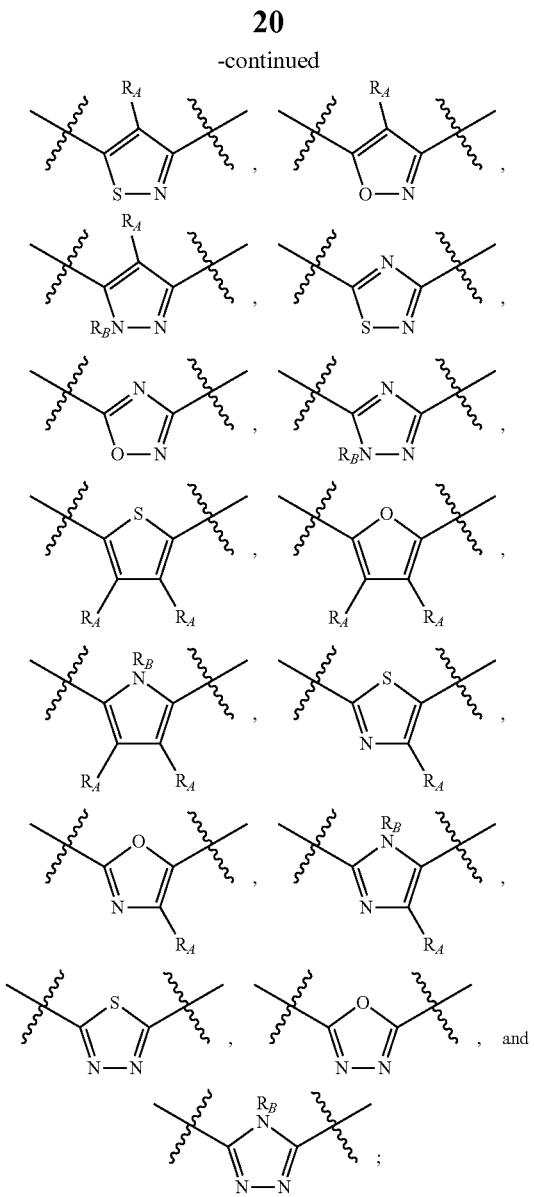

wherein $R_A$ is hydrogen, R1, or R2; and $R_B$ is hydrogen or R1. In some variations, the 5-membered group is In particular variations, the 5-membered group is

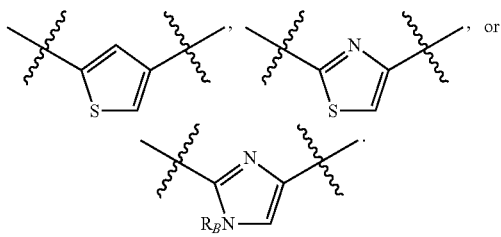

In some of these embodiments, $R_A$ is hydrogen and $R_B$ is hydrogen. In some of these embodiments, $R_A$ is hydrogen and $R_B$ is a first R1. In some of these embodiments, $R_A$ is a first R1 and $R_B$ is hydrogen. In some of these embodiments, $R_A$ is a first R1 and $R_B$ is a second R1. In some of these embodiments, $R_A$ is R2 and $R_B$ is hydrogen. In some of these embodiments, $R_A$ is a R2 and $R_B$ is a first R1. In some of these variations, the first R1 is unsubstituted C1-C6 linear or branched alkyl. In some of these variations, the first R1 is unsubstituted C2-C6 linear or branched alkenyl. In some of these variations, the first R1 is unsubstituted C2-C6 linear or branched alkynyl. In some of these variations, the first R1 is unsubstituted C3-C6 cycloalkyl. In some of these variations, the first R1 is unsubstituted C3-C6 cycloalkylmethyl. In some of these variations, the first R1 is unsubstituted or C3-C6 cycloalkenyl. In some of these variations, the first R1 is C1-C6 linear or branched alkyl substituted with one or more R3. In some of these variations, the first R1 is C2-C6 linear or branched alkenyl substituted with one or more R3. In some of these variations, the first R1 is C2-C6 linear or branched alkynyl substituted with one or more R3. In some of these variations, the first R1 is C3-C6 cycloalkyl substituted with one or more R3. In some of these variations, the first R1 is C3-C6 cycloalkylmethyl substituted with one or more R3. In some of these variations, the first R1 is or C3-C6 cycloalkenyl substituted with one or more R3. In some of these variations, the second R1 is unsubstituted C1-C6 linear or branched alkyl. In some of these variations, the second R1 is unsubstituted C2-C6 linear or branched alkenyl. In some of these variations, the second R1 is unsubstituted C2-C6 linear or branched alkynyl. In some of these variations, the second R1 is unsubstituted C3-C6 cycloalkyl. In some of these variations, the second R1 is unsubstituted C3-C6 cycloalkylmethyl. In some of these variations, the second R1 is unsubstituted or C3-C6 cycloalkenyl. In some of these variations, the second R1 is C1-C6 linear or branched alkyl substituted with one or more R3. In some of these variations, the second R1 is C2-C6 linear or branched alkenyl substituted with one or more R3. In some of these variations, the second R1 is C2-C6 linear or branched alkynyl substituted with one or more R3. In some of these variations, the second R1 is C3-C6 cycloalkyl substituted with one or more R3. In some of these variations, the second R1 is C3-C6 cycloalkylmethyl substituted with one or more R3. In some of these variations, the second R1 is or C3-C6 cycloalkenyl substituted with one or more R3. In some of these variations, at least one R3 is halogen. In some of these variations, at least one R3 is —CN. In some of these variations, at least one R3 is —OH. In some of these variations, at least one R3 is —O(Alkyl). In some of these variations, at least one R3 is =O. In some of these variations, at least one R3 is —NO$_2$. In some of these variations, at least one R3 is —SH. In some of these variations, at least one R3 is —S(Alkyl). In some of these variations, at least one R3 is —S(O)(Alkyl). In some of these variations, at least one R3 is —S(O)$_2$(Alkyl). In some of these variations, at least one R3 is —CH$_2$OCH$_3$. In some of these variations, at least one R3 is —OBn. In some of these variations, at least one R3 is —CO$_2$H. In some of these variations, at least one R3 is —CO$_2$(Alkyl). In some of these variations, at least one R3 is —NR10R11. In some of these variations, at least one R3 is —CONR10R11. In some of these variations, at least one R3 is —S(O)$_2$NR10R11. In some of these variations, R2 is halogen. In some of these variations, R2 is —CN. In some of these variations, R2 is —OH. In some of these variations, R2 is —O(Alkyl). In some of these variations, R2 is —NO$_2$. In some of these variations, R2 is —SH. In some of these variations, R2 is —S(Alkyl). In some of these variations, R2 is —S(O)(Alkyl). In some of these variations, R2 is —S(O)$_2$(Alkyl). In some of these variations, R2 is —CH$_2$OCH$_3$. In some of these variations, R2 is —OBn. In some of these variations, R2 is —CO$_2$H. In some of these variations, R2 is —CO$_2$(Alkyl). In some of these variations, R2 is —NR10R11. In some of these variations, R2 is —CONR10R11. In some of these variations, R2 is —S(O)$_2$NR10R11.

In some variations of Formulae (Ia) or (Ib), the phenyl ring containing the groups $R_{C4}$, $R_{C5}$, $R_{C6}$, and —C(=O)NR$_{C7}$R$_{C8}$, is a moiety selected from the group consisting of:

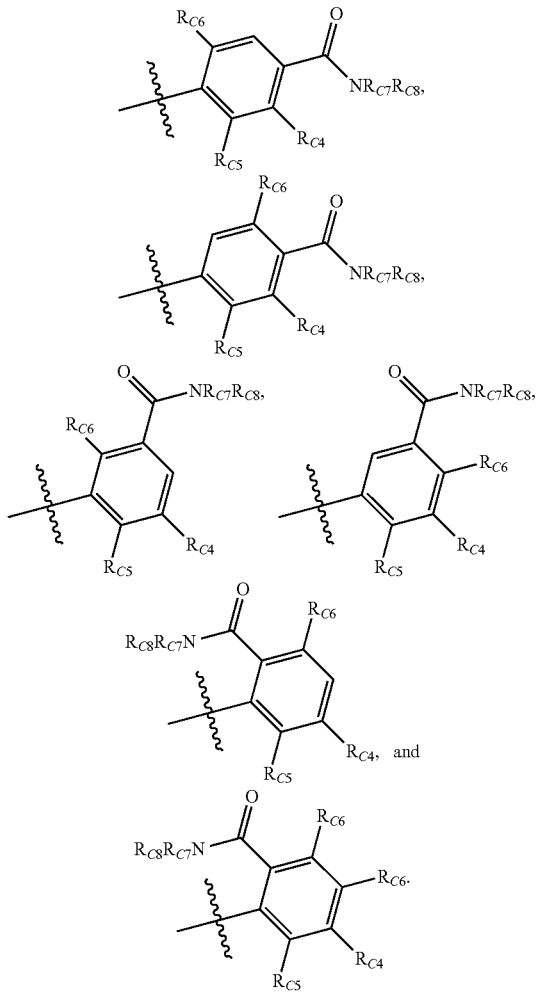

In particular variations of Formulae (Ia) or (Ib), the phenyl ring containing the groups $R_{C4}$, $R_{C5}$, $R_{C6}$, and —C(=O)$NR_{C7}R_{C8}$, is a moiety selected from:

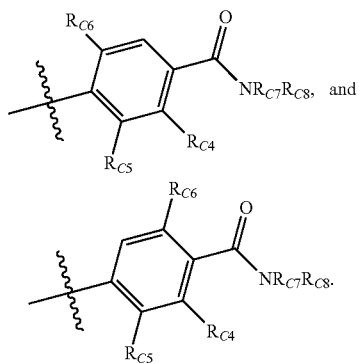

In some variations of Formulae (Ia) or (Ib), one of $R_{C4}$, $R_{C5}$ and $R_{C6}$ is hydrogen. In some variations, two of $R_{C4}$, $R_{C5}$ and $R_{C6}$ are hydrogen. In some variations, each $R_{C4}$, $R_{C5}$ and $R_{C6}$ is hydrogen.

In some variations of Formulae (Ia) or (Ib), one of $R_{C4}$, $R_{C5}$ and $R_{C6}$ is R1. In some of these variations, $R_{C4}$ is R1. In some of these variations, $R_{C5}$ is R1. In some of these variations, $R_{C6}$ is R1. In some of these variations, R1 is unsubstituted C1-C6 linear or branched alkyl. In some of these variations, R1 is unsubstituted C2-C6 linear or branched alkenyl. In some of these variations, R1 is unsubstituted C2-C6 linear or branched alkynyl. In some of these variations, R1 is unsubstituted C3-C6 cycloalkyl. In some of these variations, R1 is unsubstituted C3-C6 cycloalkylmethyl. In some of these variations, R1 is unsubstituted C3-C6 cycloalkenyl. In some variations, R1 is unsubstituted aryl. In some variations, R1 is unsubstituted heteroaryl. In some of these variations, R1 is C1-C6 linear or branched alkyl substituted with one or more R3. In some of these variations, R1 is C2-C6 linear or branched alkenyl substituted with one or more R3. In some of these variations. R1 is C2-C6 linear or branched alkynyl substituted with one or more R3. In some of these variations, R1 is C3-C6 cycloalkyl substituted with one or more R3. In some of these variations, R1 is C3-C6 cycloalkylmethyl substituted with one or more R3. In some of these variations, R1 is C3-C6 cycloalkenyl substituted with one or more R3. In some variations, R1 is aryl substituted with one or more R3. In some variations R1 is heteroaryl substituted with one or more R3. In some of these variations, at least one R3 is halogen. In some of these variations, at least one R3 is —CN. In some of these variations, at least one R3 is —OH. In some of these variations, at least one R3 is —O(Alkyl). In some of these variations, at least one R3 is =O. In some of these variations, at least one R3 is —NO$_2$. In some of these variations, at least one R3 is —SH. In some of these variations, at least one R3 is —S(Alkyl). In some of these variations, at least one R3 is —S(O)(Alkyl). In some of these variations, at least one R3 is —S(O)$_2$(Alkyl). In some of these variations, at least one R3 is —CH$_2$OCH$_3$. In some of these variations, at least one R3 is —OBn. In some of these variations, at least one R3 is —CO$_2$H. In some of these variations, at least one R3 is —CO$_2$(Alkyl). In some of these variations, at least one R3 is —NR10R11. In some of these variations, at least one R3 is —CONR10R11. In some of these variations, at least one R3 is —S(O)$_2$NR10R11.

In some variations of Formulae (Ia) or (Ib), two of $R_{C4}$, $R_{C5}$ and $R_{C6}$ are R11. In some of these variations, $R_{C4}$ is a first R1 and $R_{C5}$ is a second R1. In some of these variations, $R_{C4}$ is a first R1 and $R_{C6}$ is a second R1. In some of these variations, $R_{C5}$ is a first R1 and $R_{C5}$ is a second R1. In some of these variations, the first R1 is unsubstituted C1-C6 linear or branched alkyl. In some of these variations, the first R1 is unsubstituted C2-C6 linear or branched alkenyl. In some of these variations, the first R1 is unsubstituted C2-C6 linear or branched alkynyl. In some of these variations, the first R1 is unsubstituted C3-C6 cycloalkyl. In some of these variations, the first R1 is unsubstituted C3-C6 cycloalkylmethyl. In some of these variations, the first R1 is unsubstituted C3-C6 cycloalkenyl. In some variations, the first R1 is unsubstituted aryl. In some variations, the first R1 is unsubstituted heteroaryl. In some of these variations, the first R1 is C1-C6 linear or branched alkyl substituted with one or more R3. In some of these variations, the first R1 is C2-C6 linear or branched alkenyl substituted with one or more R3. In some of these variations, the first R1 is C2-C6 linear or branched alkynyl substituted with one or more R3. In some of these variations, the first R1 is C3-C6 cycloalkyl substituted with one or more R3. In some of these variations, the first R1 is C3-C6 cycloalkylmethyl substituted with one or more R3. In some of these variations, the first R1 is C3-C6 cycloalkenyl substituted with one or more R3. In some variations, the first R1 is aryl substituted with one or more R3. In some variations, the first R1 is heteroaryl substituted with one or more R3. In some of these variations, the second R1 is unsubstituted C1-C6 linear or branched alkyl. In some of these variations, the second R1 is unsubstituted C2-C6 linear or branched alkenyl. In some of these variations, the second R1 is unsubstituted C2-C6 linear or branched alkynyl. In some of these variations, the second R1 is unsubstituted C3-C6 cycloalkyl. In some of these variations, the second R1 is unsubstituted C3-C6 cycloalkylmethyl. In some of these variations, the second R1 is unsubstituted C3-C6 cycloalkenyl. In some variations, the second R1 is unsubstituted aryl. In some variations, the second R1 is unsubstituted heteroaryl. In some of these variations, the second R1 is C1-C6 linear or branched alkyl substituted with one or more R3. In some of these variations, the second R1 is C2-C6 linear or branched alkenyl substituted with one or more R3. In some of these variations, the second R1 is C2-C6 linear or branched alkynyl substituted with one or more R3. In some of these variations, the second R1 is C3-C6 cycloalkyl substituted with one or more R3. In some of these variations, the second R1 is C3-C6 cycloalkylmethyl substituted with one or more R3. In some of these variations, the second R1 is C3-C6 cycloalkenyl substituted with one or more R3. In some variations, the second R1 is aryl substituted with one or more R3. In some variations, the second R1 is heteroaryl substituted with one or more R3. In some of these variations, at least one R3 is halogen. In some of these variations, at least one R3 is —CN. In some of these variations, at least one R3 is —OH. In some of these variations, at least one R3 is —O(Alkyl). In some of these variations, at least one R3 is =O. In some of these variations, at least one R3 is —NO$_2$. In some of these variations, at least one R3 is —SH. In some of these variations, at least one R3 is —S(Alkyl). In some of these variations, at least one R3 is —S(O)(Alkyl). In some of these variations, at least one R3 is —S(O)$_2$(Alkyl). In some of these variations, at least one R3 is —CH$_2$OCH$_3$. In some of these variations, at least one R3 is —OBn. In some of these variations, at least one R3 is —CO$_2$H. In some of these variations, at least one R3 is —CO$_2$(Alkyl). In some of these variations, at least one R3 is —NR10R11. In some of these variations, at least one R3 is —CONR10R11. In some of these variations, at least one R3 is —S(O)$_2$NR10R11.

In some variations of Formulae (Ia) or (Ib), each $R_{C4}$, $R_{C5}$ and $R_{C6}$ is R1 (i.e., $R_{C4}$ is a first R1, $R_{C5}$ is a second R1, and $R_{C6}$ is a third R1). In some of these variations, the first R1 is unsubstituted C1-C6 linear or branched alkyl. In some of these variations, the first R1 is unsubstituted C2-C6 linear or branched alkenyl. In some of these variations, the first R1 is unsubstituted C2-C6 linear or branched alkynyl. In some of these variations, the first R1 is unsubstituted C3-C6 cycloalkyl. In some of these variations, the first R1 is unsubstituted C3-C6 cycloalkylmethyl. In some of these variations, the first R1 is unsubstituted C3-C6 cycloalkenyl. In some variations, the first R1 is unsubstituted aryl. In some variations, the first R1 is unsubstituted heteroaryl. In some of these variations, the first R1 is C1-C6 linear or branched alkyl substituted with one or more R3. In some of these variations, the first R1 is C2-C6 linear or branched alkenyl substituted with one or more R3. In some of these variations, the first R1 is C2-C6 linear or branched alkynyl substituted with one or more R3. In some of these variations, the first R1 is C3-C6 cycloalkyl substituted with one or more R3. In some of these variations, the first R1 is C3-C6 cycloalkylmethyl substituted with one or more R3. In some of these variations, the first R1 is C3-C6 cycloalkenyl substituted with one or more R3. In some variations, the first R1 is aryl substituted with one or more R3. In some variations, the first R1 is heteroaryl substituted with one or more R3. In some of these variations, the second R1 is unsubstituted C1-C6 linear or branched alkyl. In some of these variations, the second R1 is unsubstituted C2-C6 linear or branched alkenyl. In some of these variations, the second R1 is unsubstituted C2-C6 linear or branched alkynyl. In some of these variations, the second R1 is unsubstituted C3-C6 cycloalkyl. In some of these variations, the second R1 is unsubstituted C3-C6 cycloalkylmethyl. In some of these variations, the second R1 is unsubstituted C3-C6 cycloalkenyl. In some variations, the second R1 is unsubstituted aryl. In some variations, the second R1 is unsubstituted heteroaryl. In some of these variations, the second R1 is C1-C6 linear or branched alkyl substituted with one or more R3. In some of these variations, the second R1 is C2-C6 linear or branched alkenyl substituted with one or more R3. In some of these variations, the second R1 is C2-C6 linear or branched alkynyl substituted with one or more R3. In some of these variations, the second R1 is C3-C6 cycloalkyl substituted with one or more R3. In some of these variations, the second R1 is C3-C6 cycloalkylmethyl substituted with one or more R3. In some of these variations, the second R1 is C3-C6 cycloalkenyl substituted with one or more R3. In some variations, the second R1 is aryl substituted with one or more R3. In some variations, the second R1 is heteroaryl substituted with one or more R3. In some of these variations, the third R1 is unsubstituted C1-C6 linear or branched alkyl. In some of these variations, the third R11 is unsubstituted C2-C6 linear or branched alkenyl. In some of these variations, the third R1 is unsubstituted C2-C6 linear or branched alkynyl. In some of these variations, the third R1 is unsubstituted C3-C6 cycloalkyl. In some of these variations, the third R1 is unsubstituted C3-C6 cycloalkylmethyl. In some of these variations, the third R1 is unsubstituted C3-C6 cycloalkenyl. In some variations, the third R1 is unsubstituted aryl. In some variations, the third R1 is unsubstituted heteroaryl. In some of these variations, the third R1 is C1-C6 linear or branched alkyl substituted with one or more R3. In some of these variations, the third R1 is C2-C6 linear or branched alkenyl substituted with one or more R3. In some of these variations, the third R1 is C2-C6 linear or branched alkynyl substituted with one or more R3. In some of these variations, the third R1 is C3-C6 cycloalkyl substituted with one or more R3. In some of these variations, the third R1 is C3-C6 cycloalkylmethyl substituted with one or more R3. In some of these variations, the third R1 is C3-C6 cycloalkenyl substituted with one or more R3. In some variations, the third R1 is aryl substituted with one or more R3. In some variations, the third R1 is heteroaryl substituted with one or more R3. In some of these variations, at least one R3 is halogen. In some of these variations, at least one R3 is —CN. In some of these variations, at least one R3 is —OH. In some of these variations, at least one R3 is —O(Alkyl). In some of these variations, at least one R3 is =O. In some of these variations, at least one R3 is —NO$_2$. In some of these variations, at least one R3 is —SH. In some of these variations, at least one R3 is —S(Alkyl). In some of these variations, at least one R3 is —S(O)(Alkyl). In some of these variations, at least one R3 is —S(O)$_2$(Alkyl). In some of these variations, at least one R3 is —CH$_2$OCH$_3$. In some of these variations, at least one R3 is —OBn. In some of these variations, at least one R3 is —CO$_2$H. In some of these variations, at least one R3 is —CO$_2$(Alkyl). In some of these variations, at least one R3 is —NR10R11. In some of these variations, at least one R3 is —CONR10R11. In some of these variations, at least one R3 is —S(O)$_2$NR10R11.

In some variations of Formulae (Ia) or (Ib), one or more of $R_{C4}$, $R_{C5}$ and $R_{C6}$ is C1-C6 linear or branched alkyl substituted with one or more R3. In some variations, one or more of $R_{C4}$, $R_{C5}$ and $R_{C6}$ is C2-C6 linear or branched alkenyl substituted with one or more R3. In some variations, one or more of $R_{C4}$, $R_{C5}$ and $R_{C6}$ is C2-C6 linear or branched alkynyl substituted with one or more R3. In some variations, one or more of $R_{C4}$, $R_{C5}$ and $R_{C6}$ is C3-C6 cycloalkyl substituted with one or more R3. In some variations, one or more of $R_{C4}$, $R_{C5}$ and $R_{C6}$ is C3-C6 cycloalkylmethyl substituted with one or more R3. In some variations, one or more of $R_{C4}$, $R_{C5}$ and $R_{C6}$ is C3-C6 cycloalkenyl substituted with one or more R3. In some of these variations, at least one R3 is halogen. In some of these variations, at least one R3 is —CN. In some of these variations, at least one R3 is —OH. In some of these variations, at least one R3 is —O(Alkyl). In some of these variations, at least one R3 is =O. In some of these variations, at least one R3 is —NO$_2$. In some of these variations, at least one R3 is —SH. In some of these variations, at least one R3 is —S(Alkyl). In some of these variations, at least one R3 is —S(O)(Alkyl). In some of these variations, at least one R3 is —S(O)$_2$(Alkyl). In some of these variations, at least one R3 is —CH$_2$OCH$_3$. In some of these variations, at least one R3 is —OBn. In some of these variations, at least one R3 is —CO$_2$H. In some of these variations, at least one R3 is —CO$_2$(Alkyl). In some of these variations, at least one R3 is —NR10R11. In some of these variations, at least one R3 is —CONR10R11.

In some variations of Formulae (Ia) or (Ib), one of $R_{C4}$, $R_{C5}$ and $R_{C6}$ is R2. In some of these variations, R2 is halogen. In some of these variations, R2 is —CN. In some of these variations, R2 is —OH. In some of these variations, R2 is —O(Alkyl). In some of these variations, R2 is —NO$_2$. In some of these variations, R2 is —SH. In some of these variations, R2 is —S(Alkyl). In some of these variations, R2 is —S(O)(Alkyl). In some of these variations, R2 is —S(O)$_2$(Alkyl). In some of these variations, R2 is —CH$_2$OCH$_3$. In some of these variations, R2 is —OBn. In some of these variations, R2 is —CO$_2$H. In some of these variations, R2 is —CO$_2$(Alkyl). In some of these variations, R2 is —NR10R11. In some of these variations, R2 is —CONR10R11. In some of these variations, R2 is —S(O)₂NR10R11.

In some variations of Formulae (Ia) or (Ib), two of $R_{C4}$, $R_{C5}$ and $R_{C6}$ are R2. In some variations, $R_4$ is a first R2 and $R_{C5}$ is a second R2. In some variations, $R_{C4}$ is a first R2 and $R_{C6}$ is a second R2. In some variations, $R_{C5}$ is a first R2 and $R_{C6}$ is a second R2. In some of these variations, the first R2 is halogen. In some of these variations, the first R2 is —CN. In some of these variations, the first R2 is —OH. In some of these variations, the first R2 is —O(Alkyl). In some of these variations, the first R2 is —NO₂. In some of these variations, the first R2 is —SH. In some of these variations, the first R2 is —S(Alkyl). In some of these variations, the first R2 is —S(O)(Alkyl). In some of these variations, the first R2 is —S(O)₂(Alkyl). In some of these variations, the first R2 is —CH₂OCH₃. In some of these variations, the first R2 is —OBn. In some of these variations, the first R2 is —CO₂H. In some of these variations, the first R2 is —CO₂(Alkyl). In some of these variations, the first R2 is —NR10R11. In some of these variations, the first R2 is —CONR10R11. In some of these variations, the first R2 is —S(O)₂NR10R11. In some of these variations, the second R2 is halogen. In some of these variations, the second R2 is —CN. In some of these variations, the second R2 is —OH. In some of these variations, the second R2 is —O(Alkyl). In some of these variations, the second R2 is —NO₂. In some of these variations, the second R2 is —SH. In some of these variations, the second R2 is —S(Alkyl). In some of these variations, the second R2 is —S(O)(Alkyl). In some of these variations, the second R2 is —S(O)₂(Alkyl). In some of these variations, the second R2 is —CH₂OCH₃. In some of these variations, the second R2 is —OBn. In some of these variations, the second R2 is —CO₂H. In some of these variations, the second R2 is —CO₂(Alkyl). In some of these variations, the second R2 is —NR10R11. In some of these variations, the second R2 is —CONR10R11.

In some variations of Formulae (Ia) or (Ib), each $R_{C4}$, $R_{C5}$ and $R_{C6}$ is R2 (i.e., there is a first R2, a second R2, and a third R2). In some of these variations, the first R2 is halogen. In some of these variations, the first R2 is —CN. In some of these variations, the first R2 is —OH. In some of these variations, the first R2 is —O(Alkyl). In some of these variations, the first R2 is —NO₂. In some of these variations, the first R2 is —SH. In some of these variations, the first R2 is —S(Alkyl). In some of these variations, the first R2 is —S(O)(Alkyl). In some of these variations, the first R2 is —S(O)₂(Alkyl). In some of these variations, the first R2 is —CH₂OCH₃. In some of these variations, the first R2 is —OBn. In some of these variations, the first R2 is —CO₂H. In some of these variations, the first R2 is —CO₂(Alkyl). In some of these variations, the first R2 is —NR10R11. In some of these variations, the first R2 is —CONR10R11. In some of these variations, the first R2 is —S(O)₂NR10R11. In some of these variations, the second R2 is halogen. In some of these variations, the second R2 is —CN. In some of these variations, the second R2 is —OH. In some of these variations, the second R2 is —O(Alkyl). In some of these variations, the second R2 is —NO₂. In some of these variations, the second R2 is —SH. In some of these variations, the second R2 is —S(Alkyl). In some of these variations, the second R2 is —S(O)(Alkyl). In some of these variations, the second R2 is —S(O)₂(Alkyl). In some of these variations, the second R2 is —CH₂OCH₃. In some of these variations, the second R2 is —OBn. In some of these variations, the second R2 is —CO₂H. In some of these variations, the second R2 is —CO₂(Alkyl). In some of these variations, the second R2 is —NR10R11. In some of these variations, the second R2 is —CONR10R11. In some of these variations, the second R2 is —S(O)₂NR10R11. In some of these variations, the third R2 is halogen. In some of these variations, the third R2 is —CN. In some of these variations, the third R2 is —OH. In some of these variations, the third R2 is —O(Alkyl). In some of these variations, the third R2 is —NO₂. In some of these variations, the third R2 is —SH. In some of these variations, the third R2 is —S(Alkyl). In some of these variations, the third R2 is —S(O)(Alkyl). In some of these variations, the third R2 is —S(O)₂(Alkyl). In some of these variations, the third R2 is —CH₂OCH₃. In some of these variations, the third R2 is —OBn. In some of these variations, the third R2 is —CO₂H. In some of these variations, the third R2 is —CO₂(Alkyl). In some of these variations, the third R2 is —NR10R11. In some of these variations, the third R2 is —CONR10R11. In some of these variations, the third R2 is —S(O)₂NR10R11.

In some variations of Formulae (Ia) or (Ib), one or more of $R_{C4}$, $R_{C5}$ and $R_{C6}$ is halogen. In some variations, one or more of $R_{C4}$, $R_{C5}$ and $R_{C6}$ is —CN. In some variations, one or more of $R_{C4}$, $R_{C5}$ and $R_{C6}$ is —OH. In some variations, one or more of $R_{C4}$, $R_{C5}$ and $R_{C6}$ is —O(Alkyl). In some variations, one or more of $R_{C4}$, $R_{C5}$ and $R_{C6}$ is —NO₂. In some variations, one or more of $R_{C4}$, $R_{C5}$ and $R_{C6}$ is —SH. In some variations, one or more of $R_{C4}$, $R_{C5}$ and $R_{C6}$ is —S(Alkyl). In some variations, one or more of $R_{C4}$, $R_{C5}$ and $R_{C6}$ is —S(O)(Alkyl). In some variations, one or more of $R_{C4}$, $R_{C5}$ and $R_{C6}$ is —S(O)₂(Alkyl). In some variations, one or more of $R_{C4}$, $R_{C5}$ and $R_{C6}$ is —CH₂OCH₃. In some variations, one or more of $R_{C4}$, $R_{C5}$ and $R_{C6}$ is —OBn. In some variations, one or more of $R_{C4}$, $R_{C5}$ and $R_{C6}$ is —CO₂H. In some variations, one or more of $R_{C4}$, $R_{C5}$ and $R_{C6}$ is —CO₂(Alkyl). In some variations, one or more of $R_{C4}$, $R_{C5}$ and $R_{C6}$ is —NR10R11. In some variations, one or more of $R_{C4}$, $R_{C5}$ and $R_{C6}$ is —CONR10R11. In some variations, one or more of $R_{C4}$, $R_{C5}$ and $R_{C6}$ is —S(O)₂NR10R11.

In some variations of Formulae (Ia) or (Ib), one of $R_{C4}$, $R_{C5}$ and $R_{C6}$ is halogen. In some variations, two of $R_{C4}$, $R_{C5}$ and $R_{C6}$ are halogen. In some variations each $R_{C4}$, $R_{C5}$ and $R_{C6}$ is halogen. In some variations, one of $R_{C4}$, $R_{C5}$ and $R_{C6}$ is hydrogen, and the remaining two of $R_{C4}$, $R_{C5}$ and $R_{C6}$ are halogen. In some variations, two of $R_{C4}$, $R_{C5}$ and $R_{C6}$ are hydrogen, and the remaining one of $R_{C4}$, $R_{C5}$ and $R_{C6}$ is halogen. In some variations, $R_{C4}$, $R_{C5}$ and $R_{C6}$ are each halogen. In some embodiments, one of $R_{C4}$, $R_{C5}$ and $R_{C6}$ is fluoro, chloro or bromo. In some embodiments, two of $R_{C4}$, $R_{C5}$ and $R_{C6}$ are fluoro, chloro or bromo. In some embodiments, one of $R_{C4}$, $R_{C5}$ and $R_{C6}$ is chloro. In some embodiments, one of $R_{C4}$, $R_{C5}$ and $R_{C6}$ is chloro and one of $R_{C4}$, $R_{C5}$ and $R_{C6}$ is bromo. In some embodiments, $R_{C4}$ is chloro. In some embodiments, $R_{C5}$ is chloro. In some embodiments, $R_{C4}$ is bromo. In some embodiments, $R_{C5}$ is bromo.

In some variations of Formulae (Ia) or (Ib), $R_{C4}$ is taken together with $R_{C7}$ to form a heterocyclyl optionally substituted with one or more R3. In some variations, $R_{C4}$ is taken together with $R_{C7}$ to form a moiety selected from:

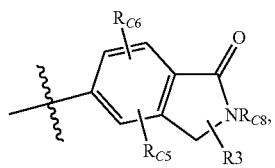

-continued

[Chemical structure showing fused bicyclic system with substituents $R_{C6}$, $R_{C5}$, $NR_{C8}$, R3, and carbonyl group]

[Chemical structure showing similar fused bicyclic system with substituents $R_{C6}$, $R_{C5}$, $NR_{C8}$, R3, and carbonyl group]

In some variations of Formulae (Ia) or (Ib), $R_{C7}$ is hydrogen. In some variations, $R_{C7}$ is R1. In some of these variations, R1 is unsubstituted C1-C6 linear or branched alkyl. In some of these variations, R1 is unsubstituted C2-C6 linear or branched alkenyl. In some of these variations, R1 is unsubstituted C2-C6 linear or branched alkynyl. In some of these variations, R1 is unsubstituted C3-C6 cycloalkyl. In some of these variations, R1 is unsubstituted C3-C6 cycloalkylmethyl. In some of these variations, R1 is unsubstituted C3-C6 cycloalkenyl. In some variations, R1 is unsubstituted aryl. In some variations, R1 is unsubstituted heteroaryl. In some variations, R1 is C1-C6 linear or branched alkyl substituted with one or more R3. In some of these variations, R1 is C2-C6 linear or branched alkenyl substituted with one or more R3. In some of these variations, R1 is C2-C6 linear or branched alkynyl substituted with one or more R3. In some of these variations, R1 is C3-C6 cycloalkyl substituted with one or more R3. In some of these variations, R1 is C3-C6 cycloalkylmethyl substituted with one or more R3. In some of these variations, R1 is C3-C6 cycloalkenyl substituted with one or more R3. In some variations, R1 is aryl substituted with one or more R3. In some variations, R1 is heteroaryl substituted with one or more R3. In some of these variations, at least one R3 is halogen. In some of these variations, at least one R3 is —CN. In some of these variations, at least one R3 is —OH. In some of these variations, at least one R3 is —O(Alkyl). In some of these variations, at least one R3 is =O. In some of these variations, at least one R3 is —NO$_2$. In some of these variations, at least one R3 is —SH. In some of these variations, at least one R3 is —S(Alkyl). In some of these variations, at least one R3 is —S(O)(Alkyl). In some of these variations, at least one R3 is —S(O)$_2$(Alkyl). In some of these variations, at least one R3 is —CH$_2$OCH$_3$. In some of these variations, at least one R3 is —OBn. In some of these variations, at least one R3 is —CO$_2$H. In some of these variations, at least one R3 is —CO$_2$(Alkyl). In some of these variations, at least one R3 is —NR10R11. In some of these variations, at least one R3 is —CONR10R11. In some of these variations, at least one R3 is —S(O)$_2$NR10R11.

In some variations of Formulae (Ia) or (Ib), $R_{C7}$ is —SO$_2$R$_{C12}$. In some of these variations, $R_{C12}$ is unsubstituted linear or branched C1-C6 alkyl. In some of these variations, $R_{C12}$ is unsubstituted linear or branched C2-C6 alkenyl. In some of these variations, $R_{C12}$ is unsubstituted linear or branched C2-C6 alkynyl. In some of these variations, $R_{C12}$ is aryl. In some of these variations, $R_{C12}$ is linear or branched C1-C6 alkyl substituted with one or more halogen atoms. In some of these variations, $R_{C12}$ is linear or branched C2-C6 alkenyl substituted with one or more halogen atoms. In some of these variations, $R_{C12}$ is linear or branched C2-C6 alkynyl substituted with one or more halogen atoms. In some of these variations, $R_{C12}$ is aryl substituted with one or more halogen atoms. In some of these variations, $R_{C12}$ is linear or branched C1-C6 alkyl substituted with one or more one or more —NH$_2$ groups. In some of these variations, $R_{C12}$ is linear or branched C2-C6 alkenyl substituted with one or more one or more —NH$_2$ groups. In some of these variations, $R_{C12}$ is linear or branched C2-C6 alkynyl substituted with one or more one or more —NH$_2$ groups. In some of these variations, $R_{C12}$ is aryl substituted with one or more one or more —NH$_2$ groups. In some of these variations, $R_{C12}$ is linear or branched C1-C6 alkyl substituted with one or more one or more —OH groups. In some of these variations, $R_{C12}$ is linear or branched C2-C6 alkenyl substituted with one or more one or more —OH groups. In some of these variations, $R_{C12}$ is linear or branched C2-C6 alkynyl substituted with one or more one or more —OH groups. In some of these variations, $R_{C12}$ is aryl substituted with one or more one or more —OH groups.

In some variations of Formulae (Ia) or (Ib), $R_{C8}$ is hydrogen. In some variations, $R_{C8}$ is R1. In some of these variations, R1 is unsubstituted C1-C6 linear or branched alkyl. In some of these variations, R1 is unsubstituted C2-C6 linear or branched alkenyl. In some of these variations, R1 is unsubstituted C2-C6 linear or branched alkynyl. In some of these variations, R1 is unsubstituted C3-C6 cycloalkyl. In some of these variations, R1 is unsubstituted C3-C6 cycloalkylmethyl. In some of these variations, R1 is unsubstituted C3-C6 cycloalkenyl. In some variations, R1 is unsubstituted aryl. In some variations, R1 is unsubstituted heteroaryl. In some variations, R1 is C1-C6 linear or branched alkyl substituted with one or more R3. In some of these variations, R1 is C2-C6 linear or branched alkenyl substituted with one or more R3. In some of these variations, R1 is C2-C6 linear or branched alkynyl substituted with one or more R3. In some of these variations, R1 is C3-C6 cycloalkyl substituted with one or more R3. In some of these variations, R1 is C3-C6 cycloalkylmethyl substituted with one or more R3. In some of these variations, R1 is C3-C6 cycloalkenyl substituted with one or more R3. In some variations, R1 is aryl substituted with one or more R3. In some variations, R1 is heteroaryl substituted with one or more R3. In some of these variations, at least one R3 is halogen. In some of these variations, at least one R3 is —CN. In some of these variations, at least one R3 is —OH. In some of these variations, at least one R3 is —O(Alkyl). In some of these variations, at least one R3 is =O. In some of these variations, at least one R3 is —NO$_2$. In some of these variations, at least one R3 is —SH. In some of these variations, at least one R3 is —S(Alkyl). In some of these variations, at least one R3 is —S(O)(Alkyl). In some of these variations, at least one R3 is —S(O)$_2$(Alkyl). In some of these variations, at least one R3 is —CH$_2$OCH$_3$. In some of these variations, at least one R3 is —OBn. In some of these variations, at least one R3 is —CO$_2$H. In some of these variations, at least one R3 is —CO$_2$(Alkyl). In some of these variations, at least one R3 is —NR10R11. In some of these variations, at least one R3 is —CONR10R11. In some of these variations, at least one R3 is —S(O)$_2$NR10R11.

In some variations of Formulae (Ia) or (Ib), $R_{C8}$ is —SO$_2$R$_{C12}$. In some of these variations, $R_{C12}$ is unsubstituted linear or branched C1-C6 alkyl. In some of these variations, $R_{C12}$ is unsubstituted linear or branched C2-C6 alkenyl. In some of these variations, $R_{C12}$ is unsubstituted linear or branched C2-C6 alkynyl. In some of these variations, $R_{C12}$ is aryl. In some of these variations, $R_{C12}$ is linear or branched C1-C6 alkyl substituted with one or more halogen atoms. In some of these variations, $R_{C12}$ is linear or branched C2-C6 alkenyl substituted with one or more halogen atoms. In some of these variations, $R_{C12}$ is linear or branched C2-C6 alkynyl substituted with one or more halogen atoms. In some of these variations, $R_{C12}$ is aryl substituted with one or more halogen atoms. In some of these variations, $R_{C12}$ is linear or branched C1-C6 alkyl substituted with one or more one or more —NH$_2$ groups. In some of these variations, $R_{C12}$ is linear or branched C2-C6 alkenyl substituted with one or more one or more —NH$_2$ groups. In some of these variations, $R_{C12}$ is linear or branched C2-C6 alkynyl substituted with one or more one or more —NH$_2$ groups. In some of these variations, $R_{C12}$ is aryl substituted with one or more one or more —NH$_2$ groups. In some of these variations, $R_{C12}$ is linear or branched C1-C6 alkyl substituted with one or more one or more —OH groups. In some of these variations, $R_{C12}$ is linear or branched C2-C6 alkenyl substituted with one or more one or more —OH groups. In some of these variations, $R_{C12}$ is linear or branched C2-C6 alkynyl substituted with one or more one or more —OH groups. In some of these variations, $R_{C12}$ is aryl substituted with one or more one or more —OH groups.

In some variations of Formulae (Ia) or (Ib), $R_{C7}$ and $R_{C8}$ are taken together with the N to which they are attached to form a C3-C8 heterocycle optionally substituted with one or more R1. In some of these variations, R1 is unsubstituted C1-C6 linear or branched alkyl. In some of these variations, R1 is unsubstituted C2-C6 linear or branched alkenyl. In some of these variations, R1 is unsubstituted C2-C6 linear or branched alkynyl. In some of these variations, R1 is unsubstituted C3-C6 cycloalkyl. In some of these variations, R1 is unsubstituted C3-C6 cycloalkylmethyl. In some of these variations, R1 is unsubstituted C3-C6 cycloalkenyl. In some variations, R1 is unsubstituted aryl. In some variations, R1 is unsubstituted heteroaryl. In some of these variations, R1 is C1-C6 linear or branched alkyl substituted with one or more R3. In some of these variations, R1 is C2-C6 linear or branched alkenyl substituted with one or more R3. In some of these variations, R1 is C2-C6 linear or branched alkynyl substituted with one or more R3. In some of these variations, R1 is C3-C6 cycloalkyl substituted with one or more R3. In some of these variations, R1 is C3-C6 cycloalkylmethyl substituted with one or more R3. In some of these variations, R1 is C3-C6 cycloalkenyl substituted with one or more R3. In some variations, R1 is aryl substituted with one or more R3. In some variations, R1 is heteroaryl substituted with one or more R3. In some of these variations, at least one R3 is halogen. In some of these variations, at least one R3 is —CN. In some of these variations, at least one R3 is —OH. In some of these variations, at least one R3 is —O(Alkyl). In some of these variations, at least one R3 is =O. In some of these variations, at least one R3 is —NO$_2$. In some of these variations, at least one R3 is —SH. In some of these variations, at least one R3 is —S(Alkyl). In some of these variations, at least one R3 is —S(O)(Alkyl). In some of these variations, at least one R3 is —S(O)$_2$(Alkyl). In some of these variations, at least one R3 is —CH$_2$OCH$_3$. In some of these variations, at least one R3 is —OBn. In some of these variations, at least one R3 is —CO$_2$H. In some of these variations, at least one R3 is —CO$_2$(Alkyl). In some of these variations, at least one R3 is —NR10R11. In some of these variations, at least one R3 is —CONR10R11. In some of these variations, at least one R3 is —S(O)$_2$NR10R11.

In some of these variations, $R_{C7}$ and $R_{C8}$ are taken together with the N to which they are attached to form a C3-C8 heterocycle optionally substituted with one or more R3. In some of these variations, at least one R3 is halogen. In some of these variations, at least one R3 is —CN. In some of these variations, at least one R3 is —OH. In some of these variations, at least one R3 is —O(Alkyl). In some of these variations, at least one R3 is =O. In some of these variations, at least one R3 is —NO$_2$. In some of these variations, at least one R3 is —SH. In some of these variations, at least one R3 is —S(Alkyl). In some of these variations, at least one R3 is —S(O)(Alkyl). In some of these variations, at least one R3 is —S(O)$_2$(Alkyl). In some of these variations, at least one R3 is —CH$_2$OCH$_3$. In some of these variations, at least one R3 is —OBn. In some of these variations, at least one R3 is —CO$_2$H. In some of these variations, at least one R3 is —CO$_2$(Alkyl). In some of these variations, at least one R3 is —NR10R11. In some of these variations, at least one R3 is —CONR10R11. In some of these variations, at least one R3 is —S(O)$_2$NR10R11.

In some variations of Formulae (Ia) or (Ib), one or both of R10 and R11 are hydrogen. In some variations, one or both of R10 and R11 are C1-C6 linear or branched alkyl. In some variations, one or both of R10 and R11 are —C(O)$R_{C12}$. In some variations, one or both of R10 and R11 are —C(O)$_2R_{C12}$. In some variations, one or both of R10 and R11 are —C(O)N($R_{C12}$)$_2$. In some variations, one or both of R10 and R11 are —SO$_2R_{C12}$. In some variations, R10 and R11 are taken together with the N to which they are attached to form a C3-C8 heterocycle.

In some variations of Formulae (Ia) or (Ib), $R_{C12}$ is hydrogen. In some variations, $R_{C12}$ is a linear or branched C1-C6 alkyl. In some variations, $R_{C12}$ is a linear or branched C2-C6 alkenyl. In some variations, $R_{C12}$ is a linear or branched C2-C6 alkynyl. In some variations, $R_{C12}$ is aryl.

In some variations of Formulae (Ia) or (Ib), $R_{C12}$ is a linear or branched C1-C6 alkyl having at least two halogen atoms. In some variations, $R_{C12}$ is a linear or branched C2-C6 alkenyl having at least two halogen atoms. In some variations, $R_{C12}$ is a linear or branched C2-C6 alkynyl having at least two halogen atoms.

In some variations of Formulae (Ia) or (Ib), $R_{C12}$ is selected from:

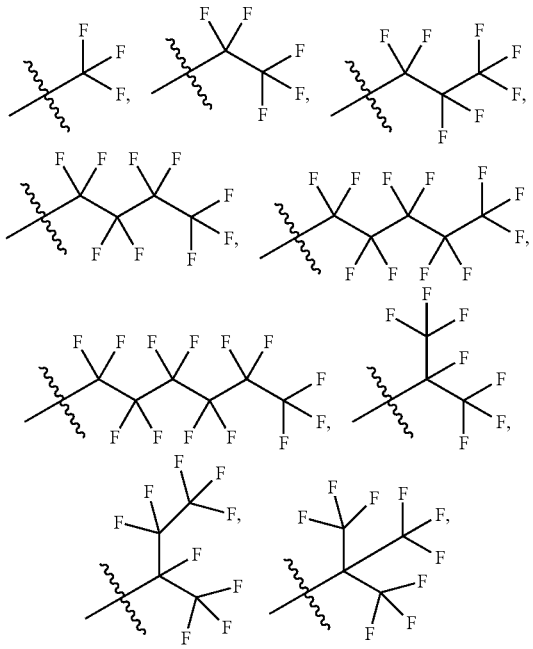

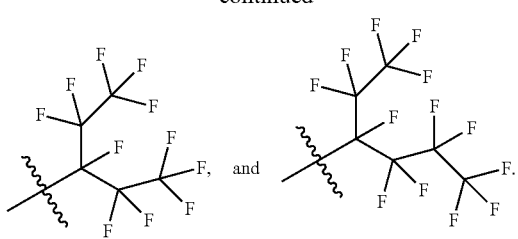, and
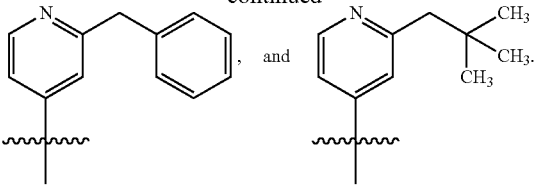, and
In some variations, $R_{C12}$ is selected from:
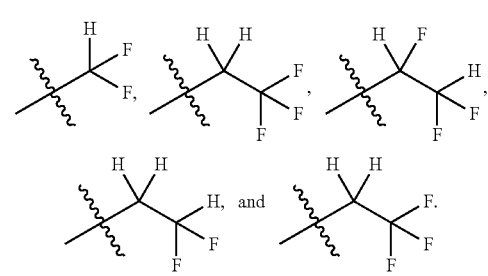
In some variations of Formulae (Ia) or (Ib), A is a moiety selected from
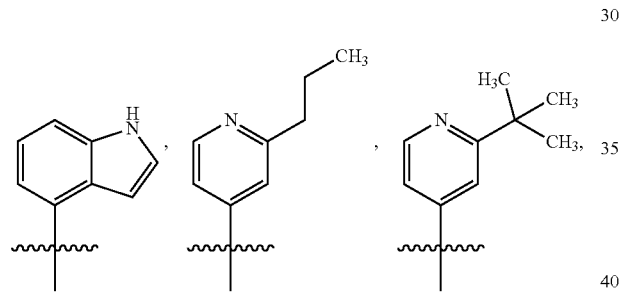
the 5-membered heteroaromatic group comprising W, X and Y is selected from:
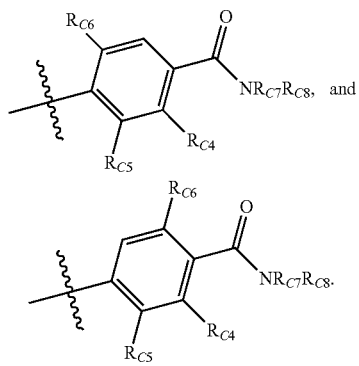
and the phenyl ring containing the groups $R_{C4}$, $R_{C5}$, $R_{C6}$, and —C(=O)$NR_{C7}R_{C8}$, is a moiety selected from:
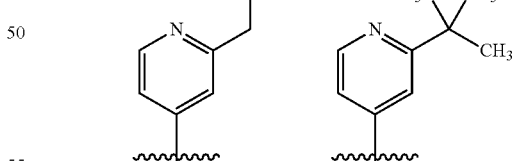
In some variations of Formulae (Ia) or (Ib), A is a moiety selected from
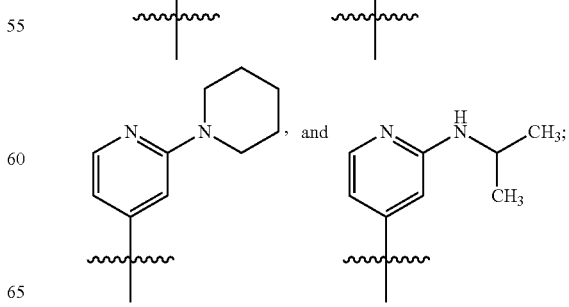
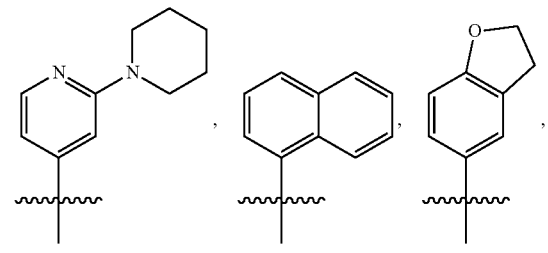
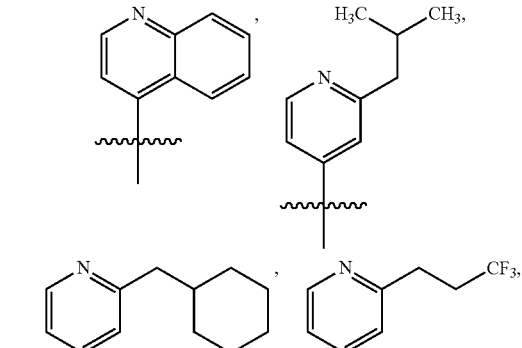
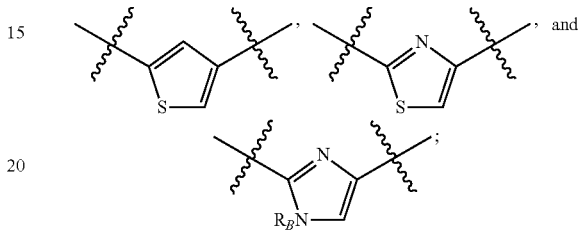

the 5-membered heteroaromatic group comprising W, X and V is selected from:

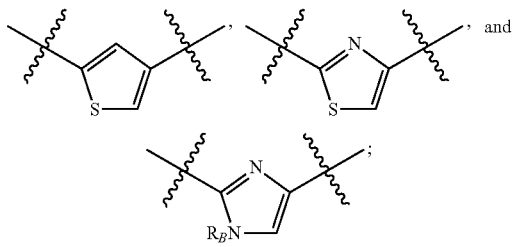

and the phenyl ring containing the groups $R_{C4}$, $R_{C5}$, $R_{C6}$, and —C(=O)$NR_{C7}R_{C8}$, is a moiety selected from:

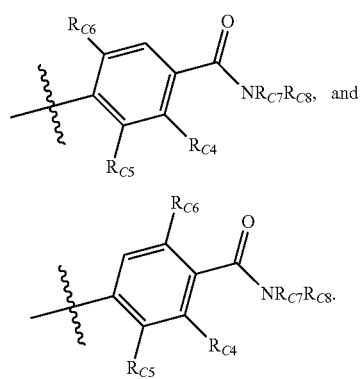

In some variations of Formulae (Ia) or (Ib), A is

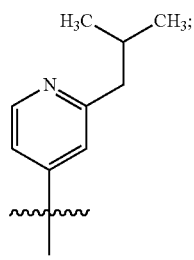 [SMILES: *c1ccnc(CC(C)C)c1]

the 5-membered heteroaromatic group comprising W, X and Y is selected from:

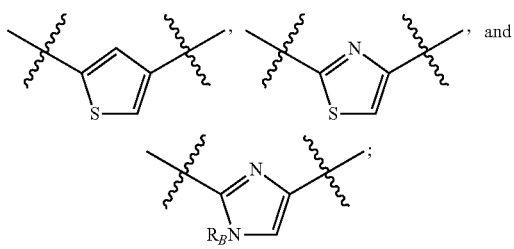

and the phenyl ring containing the groups $R_{C4}$, $R_{C5}$, $R_{C6}$, and —C(=O)$NR_{C7}R_{C8}$, is:

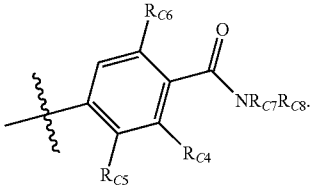

In some variations, the compound is of Formulae (Ia), wherein A is a moiety selected from

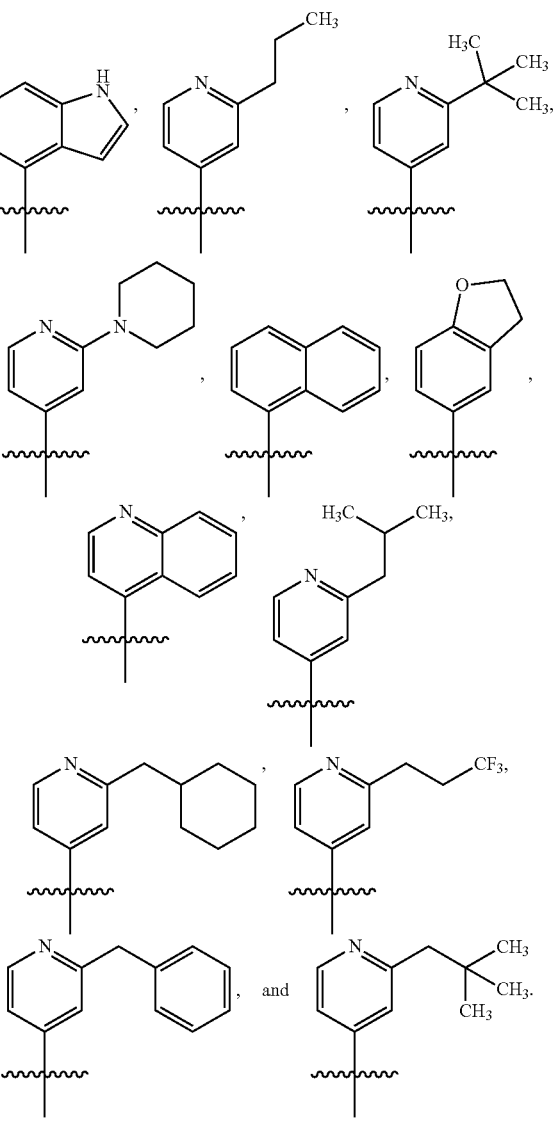

the 5-membered heteroaromatic group comprising W, X and Y is selected from:

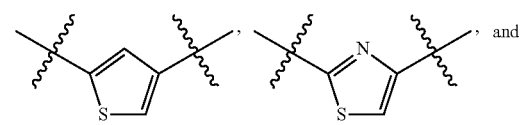

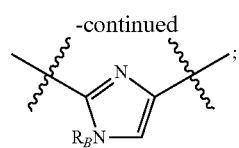

and the phenyl ring containing the groups $R_{C4}$, $R_{C5}$, $R_{C6}$, and —C(=O)$NR_{C7}R_{C8}$, is a moiety selected from:

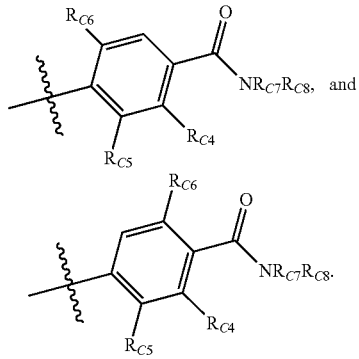

In some variations, the compound is of Formulae (Ia), wherein A is

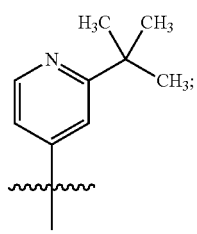 [SMILES: *c1ccnc(C(C)(C)C)c1]

the 5-membered heteroaromatic group comprising W, X and Y is selected from:

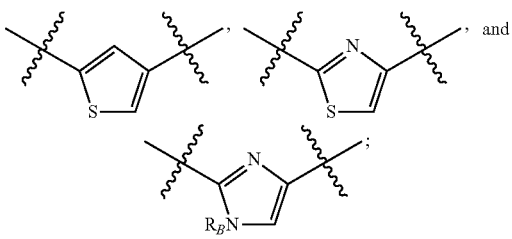

and the phenyl ring containing the groups $R_{C4}$, $R_{C5}$, $R_{C6}$, and —C(=O)$NR_{C7}R_{C8}$, is:

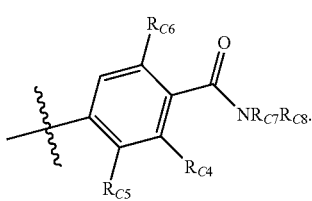

In some of these variations, $R_{C4}$, $R_{C5}$, $R_{C6}$ are each independently H or halogen. In some of these variations, $R_{C4}$ and $R_{C6}$ are each H, and $R_{C5}$ is halogen.

In some variations, the compound of Formula (Ia) is a compound of Formula (IIa):

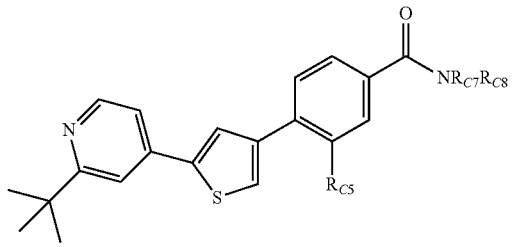

IIa wherein $R_{C5}$ is halogen, and each $R_{C7}$ and $R_{C8}$ is independently hydrogen, R1, or —SO$_2$R$_{C12}$; or $R_{C7}$ and $R_{C8}$ are taken together with the N to which they are attached to form a C3-C8 heterocycle optionally substituted with one or more R1 or R3. In some variations, $R_{C5}$ is chloro. In some variations, $R_{C7}$ and $R_{C8}$ are taken together with the N to which they are attached to form a pyrrolidinyl, piperidinyl, piperazinyl, or morpholinyl, each optionally substituted with one or more R1 or R3.

In some variations, the compound of Formula (Ib) is a compound of Formula (IIb):

IIb wherein $R_{C5}$ is halogen, and each $R_{C7}$ and $R_{C8}$ is independently hydrogen, R1, or —SO$_2$R$_{C12}$; or $R_{C7}$ and $R_{C8}$ are taken together with the N to which they are attached to form a C3-C8 heterocycle optionally substituted with one or more R1 or R3. In some variations, $R_{C5}$ is chloro. In some variations, $R_{C7}$ and $R_{C8}$ are taken together with the N to which they are attached to form a pyrrolidinyl, piperidinyl, piperazinyl, or morpholinyl, each optionally substituted with one or more R1 or R3.

Variations of Formula (IIa) or (IIb) in which $R_{C7}$ and $R_{C8}$ are Taken Together with the N to which they are Attached to Form an Optionally Substituted C3-C8 Heterocycle In some variations of Formula (IIa) or (IIb), $R_{C7}$ and $R_{C8}$ are taken together with the N to which they are attached to form a C3-C8 heterocycle optionally substituted with one or more R1. In some of these variations, the (C3-C8 heterocycle is unsubstituted. In some of these variations, the C3-C8 heterocycle is substituted with a first R1. In some of these variations, the C3-C8 heterocycle is substituted with a first R1 and a second R1. In some of these variations, the C3-C8 heterocycle is substituted with a first R1, a second R1, and a third R1. In some of these variations, the C3-C8 heterocycle is substituted with a first R31. In some of these variations, the C3-C8 heterocycle is substituted with a first R3 and a second R3. In some of these variations, the C3-C8 heterocycle is substituted with a first R3, a second R3, and a third R3. In some of these variations, the C3-(C8 heterocycle is substituted with a first R1 and a first R3. In some of these variations, the C3-C8 heterocycle is substituted with a first R1, a second R1, and a first R3. In some of these variations, the C3-C8 heterocycle is substituted with a first R1, a first R3, and a second R3.

In some variations, the first R1 is unsubstituted C1-C6 linear or branched alkyl. In some variations, the first R1 is unsubstituted C2-C6 linear or branched alkenyl. In some variations, the first R1 is unsubstituted C2-C6 linear or branched alkynyl. In some variations, the first R1 is unsubstituted C3-C6 cycloalkyl. In some variations, the first R1 is unsubstituted C3-C6 cycloalkylmethyl. In some variations, the first R1 is unsubstituted C3-C6 cycloalkenyl. In some variations, the first R1 is unsubstituted aryl. In some variations, the first R1 is unsubstituted heteroaryl. In some variations, the first R1 is C1-C6 linear or branched alkyl substituted with one or more R3. In some variations, the first R1 is C2-C6 linear or branched alkenyl substituted with one or more R3. In some variations, the first R1 is C2-C6 linear or branched alkynyl substituted with one or more R3. In some variations, the first R1 is C3-C6 cycloalkyl substituted with one or more R3. In some variations, the first R1 is C3-C6 cycloalkylmethyl substituted with one or more R3. In some variations, the first R1 is C3-C6 cycloalkenyl substituted with one or more R3. In some variations, the first R1 is aryl substituted with one or more R3. In some variations, the first R1 is heteroaryl substituted with one or more R3. In some variations, the first R1 is substituted with at least one halogen. In some variations, the first R1 is substituted with at least one —CN. In some variations, the first R1 is substituted with at least one —OH. In some variations, the first R1 is substituted with at least one —O(Alkyl). In some variations, the first R1 is substituted with at least one =O. In some variations, the first R1 is substituted with at least one —NO$_2$. In some variations, the first R1 is substituted with at least one —SH. In some variations, the first R1 is substituted with at least one —S(Alkyl). In some variations, the first R1 is substituted with at least one —S(O)(Alkyl). In some variations, the first R1 is substituted with at least one —S(O)$_2$(Alkyl). In some variations, the first R1 is substituted with at least one —CH$_2$OCH$_3$. In some variations, the first R1 is substituted with at least one —OBn. In some variations, the first R1 is substituted with at least one —CO$_2$H. In some variations, the first R1 is substituted with at least one —CO$_2$(Alkyl). In some variations, the first R1 is substituted with at least one —NR10R11. In some variations, the first R1 is substituted with at least one —CONR10R11. In some variations, the first R1 is substituted with at least one —S(O)$_2$NR10R11.

In some variations, the second R1 is unsubstituted C1-C6 linear or branched alkyl. In some variations, the second R1 is unsubstituted C2-C6 linear or branched alkenyl. In some variations, the second R1 is unsubstituted C2-C6 linear or branched alkynyl. In some variations, the second R11 is unsubstituted C3-C6 cycloalkyl. In some variations, the second R1 is unsubstituted C3-C6 cycloalkylmethyl. In some variations, the second R1 is unsubstituted C3-C6 cycloalkenyl. In some variations, the second R1 is unsubstituted aryl. In some variations, the second R1 is unsubstituted heteroaryl. In some variations, the second R1 is C1-C6 linear or branched alkyl substituted with one or more R3. In some variations, the second R1 is C2-C6 linear or branched alkenyl substituted with one or more R3. In some variations, the second R1 is C2-C6 linear or branched alkynyl substituted with one or more R3. In some variations, the second R1 is C3-C6 cycloalkyl substituted with one or more R3. In some variations, the second R1 is C3-C6 cycloalkylmethyl substituted with one or more R3. In some variations, the second R1 is C3-C6 cycloalkenyl substituted with one or more R3. In some variations, the second R1 is aryl substituted with one or more R3. In some variations, the second R1 is heteroaryl substituted with one or more R3. In some variations, the second R1 is substituted with at least one halogen. In some variations, the second R1 is substituted with at least one —CN. In some variations, the second R1 is substituted with at least one —OH. In some variations, the second R1 is substituted with at least one —O(Alkyl). In some variations, the second R1 is substituted with at least one =O. In some variations, the second R1 is substituted with at least one —NO$_2$. In some variations, the second R1 is substituted with at least one —SH. In some variations, the second R1 is substituted with at least one —S(Alkyl). In some variations, the second R1 is substituted with at least one —S(O)(Alkyl). In some variations, the second R1 is substituted with at least one —S(O)$_2$(Alkyl). In some variations, the second R1 is substituted with at least one —CH$_2$OCH$_3$. In some variations, the second R1 is substituted with at least one —OBn. In some variations, the second R1 is substituted with at least one —CO$_2$H. In some variations, the second R1 is substituted with at least one —CO$_2$(Alkyl). In some variations, the second R1 is substituted with at least one —NR10R11. In some variations, the second R1 is substituted with at least one —CONR10R11. In some variations, the second R1 is substituted with at least one —S(O)$_2$NR10R11.

In some variations, the third R1 is unsubstituted C1-C6 linear or branched alkyl. In some variations, the third R1 is unsubstituted C2-C6 linear or branched alkenyl. In some variations, the third R1 is unsubstituted C2-C6 linear or branched alkynyl. In some variations, the third R1 is unsubstituted C3-C6 cycloalkyl. In some variations, the third R1 is unsubstituted C3-C6 cycloalkylmethyl. In some variations, the third R1 is unsubstituted C3-C6 cycloalkenyl. In some variations, the third R1 is unsubstituted aryl. In some variations, the third R1 is unsubstituted heteroaryl. In some variations, the third R1 is C1-C6 linear or branched alkyl substituted with one or more R3. In some variations, the third R1 is C2-C6 linear or branched alkenyl substituted with one or more R3. In some variations, the third R1 is C2-C6 linear or branched alkynyl substituted with one or more R3. In some variations, the third R1 is C3-C6 cycloalkyl substituted with one or more R3. In some variations, the third R1 is C3-C6 cycloalkylmethyl substituted with one or more R3. In some variations, the third R1 is C3-C6 cycloalkenyl substituted with one or more R3. In some variations, the third R1 is aryl substituted with one or more R3. In some variations, the third R1 is heteroaryl substituted with one or more R3. In some variations, the third R1 is substituted with at least one halogen. In some variations, the third R1 is substituted with at least one —CN. In some variations, the third R1 is substituted with at least one —OH. In some variations, the third R1 is substituted with at least one —O(Alkyl). In some variations, the third R1 is substituted with at least one =O. In some variations, the third R1 is substituted with at least one —NO$_2$. In some variations, the third R1 is substituted with at least one —SH. In some variations, the third R1 is substituted with at least one —S(Alkyl). In some variations, the third R1 is substituted with at least one —S(O)(Alkyl). In some variations, the third R1 is substituted with at least one —S(O)$_2$(Alkyl). In some variations, the third R1 is substituted with at least one —CH$_2$OCH$_3$. In some variations, the third R1 is substituted with at least one —OBn. In some variations, the third R1 is substituted with at least one —CO$_2$H. In some variations, the third R1 is substituted with at least one —CO$_2$(Alkyl). In some variations, the third R1 is substituted with at least one —NR10R11. In some variations, the third R1 is substituted with at least one —CONR10R11. In some variations, the third R1 is substituted with at least one —S(O)$_2$NR10R11.

In some of these variations, the first R3 is halogen. In some of these variations, the first R3 is —CN. In some of these variations, the first R3 is —OH. In some of these variations, the first R3 is —O(Alkyl). In some of these variations, the first R3 is =O. In some of these variations, the first R3 is —NO$_2$. In some of these variations, the first R3 is —SH. In some of these variations, the first R3 is —S(Alkyl). In some of these variations, the first R3 is —S(O)(Alkyl). In some of these variations, the first R3 is —S(O)$_2$(Alkyl). In some of these variations, the first R3 is —CH$_2$OCH$_3$. In some of these variations, the first R3 is —OBn. In some of these variations, the first R3 is —CO$_2$H. In some of these variations, the first R3 is —CO$_2$(Alkyl). In some of these variations, the first R3 is —NR10R11. In some of these variations, the first R3 is —CONR10R11. In some of these variations, the first R3 is —S(O)$_2$NR10R11.

In some of these variations, the second R3 is halogen. In some of these variations, the second R3 is —CN. In some of these variations, the second R3 is —OH. In some of these variations, the second R3 is —O(Alkyl). In some of these variations, the second R3 is =O. In some of these variations, the second R3 is —NO$_2$. In some of these variations, the second R3 is —SH. In some of these variations, the second R3 is —S(Alkyl). In some of these variations, the second R3 is —S(O)(Alkyl). In some of these variations, the second R3 is —S(O)$_2$(Alkyl). In some of these variations, the second R3 is —CH$_2$OCH$_3$. In some of these variations, the second R3 is —OBn. In some of these variations, the second R3 is —CO$_2$H. In some of these variations, the second R3 is —CO$_2$(Alkyl). In some of these variations, the second R3 is —NR10R11. In some of these variations, the second R3 is —CONR10R11. In some of these variations, the second R3 is —S(O)$_2$NR10R11.

In some of these variations, the third R3 is halogen. In some of these variations, the third R3 is —CN. In some of these variations, the third R3 is —OH. In some of these variations, the third R3 is —O(Alkyl). In some of these variations, the third R3 is =O. In some of these variations, the third R3 is —NO$_2$. In some of these variations, the third 13 is —SH. In some of these variations, the third R3 is —S(Alkyl). In some of these variations, the third R3 is —S(O)(Alkyl). In some of these variations, the third R3 is —S(O)$_2$(Alkyl). In some of these variations, the third R3 is —CH$_2$OCH$_3$. In some of these variations, the third R3 is —OBn. In some of these variations, the third R3 is —CO$_2$H. In some of these variations, the third R3 is —CO$_2$(Alkyl). In some of these variations, the third R3 is —NR10R11. In some of these variations, the third R3 is —CONR10R11. In some of these variations, the third R3 is —S(O)$_2$NR10R11.

It is intended and understood that each and every variation of A, R1, R2, R3, R$_{C4}$, R$_{C5}$, R$_{C6}$, R$_{C7}$, R$_{C8}$, R10, R11, R$_{C12}$, W, X, Y, R$_A$, and R$_B$, where present, described for formulae (Ia) or (Ib) may be combined with each and every variation of A, R1, R2, R3, R$_{C4}$, R$_{C5}$, R$_{C6}$, R$_{C7}$, R$_{C8}$, R10, R11, R$_{C12}$, W, X, Y, R$_A$, and R$_B$, as if each and every combination is individually described.

In some embodiments, the compound is selected from the group consisting of:
N-methyl-4-[2-(2-propylpyridin-4-yl)-1,3-thiazol-4-yl]benzamide;
N,N-dimethyl-4-[2-(2-propylpyridin-4-yl)-1,3-thiazol-4-yl]benzamide;
4-[2-(2-propylpyridin-4-yl)-1,3-thiazol-4-yl]benzamide;
4-{4-[2-chloro-4-(piperidine-1-carbonyl)phenyl]-1,3-thiazol-2-yl}-1H-indole;
2-tert-butyl-4-{4-[2-chloro-4-(piperidine-1-carbonyl)phenyl]-1,3-thiazol-2-yl}pyridine;
3-chloro-4-[2-(1H-indol-4-yl)-1,3-thiazol-4-yl]-N,N-dimethylbenzamide;
4-{4-[5-(2-tert-butylpyridin-4-yl)thiophen-3-yl]-3-chlorobenzoyl}piperazin-2-one;
4-[5-(2-tert-butylpyridin-4-yl)thiophen-3-yl]-3-chloro-N-cyclobutylbenzamide;
3-chloro-N,N-dimethyl-4-{2-[2-(piperidin-1-yl)pyridin-4-yl]-1,3-thiazol-4-yl}benzamide;
1-{4-[5-(2-tert-butylpyridin-4-yl)thiophen-3-yl]-3-chlorobenzoyl}-4-methylpiperazine;
2-tert-butyl-4-{4-[2-chloro-4-(piperidine-1-carbonyl)phenyl]thiophen-2-yl}pyridine;
2-tert-butyl-4-{4-[2-chloro-4-(3,3-difluoropyrrolidine-1-carbonyl)phenyl]thiophen-2-yl}pyridine;
2-tert-butyl-4-{4-[2-chloro-4-(4,4-difluoropiperidine-1-carbonyl)phenyl]thiophen-2-yl}pyridine;
4-[5-(2-tert-butylpyridin-4-yl)thiophen-3-yl]-3-chloro-N-cyclopropylbenzamide;
N-tert-butyl-4-[5-(2-tert-butylpyridin-4-yl)thiophen-3-yl]-3-chlorobenzamide;
2-tert-butyl-4-{4-[2-chloro-4-(piperidine-1-carbonyl)phenyl]-5-methylthiophen-2-yl}pyridine,
4-(3-chloro-4-{2-[2-(piperidin-1-yl)pyridin-4-yl]-1,3-thiazol-4-yl}benzoyl)morpholine;
3-chloro-N-(2-hydroxypropyl)-4-{2-[2-(piperidin-1-yl)pyridin-4-yl]-1,3-thiazol-4-yl}benzamide;
tert-butyl N-(1-{4-[5-(2-tert-butylpyridin-4-yl)thiophen-3-yl]-3-chlorobenzoyl}piperidin-3-yl)carbonate;
tert-butyl N-[(3R)-1-{4-[5-(2-tert-butylpyridin-4-yl)thiophen-3-yl]-3-chlorobenzoyl}piperidin-3-yl]carbamate;
tert-butyl N-[(3S)-1-{4-[5-(2-tert-butylpyridin-4-yl)thiophen-3-yl]-3-chlorobenzoyl}piperidin-3-yl]carbamate;
4-{4-[5-(2-tert-butylpyridin-4-yl)thiophen-3-yl]-3-chlorobenzoyl}-1λ$^6$,4-thiomorpholine-1,1-dione;
1-{4-[5-(2-tert-butylpyridin-4-yl)thiophen-3-yl]-3-chlorobenzoyl}piperidin-3-amine;
(3R)-1-{4-[5-(2-tert-butylpyridin-4-yl)thiophen-3-yl]-3-chlorobenzoyl}piperidin-3-amine;
(3S)-1-{4-[5-(2-tert-butylpyridin-4-yl)thiophen-3-yl]-3-chlorobenzoyl}piperidin-3-amine;
4-{4-[5-(2-tert-butylpyridin-4-yl)thiophen-3-yl]-3-chlorobenzoyl}morpholine;
4-[5-(2-tert-butylpyridin-4-yl)thiophen-3-yl]-3-chloro-N-phenylbenzamide;
2-tert-butyl-4-{4-[2-chloro-4-(4,4-difluoropiperidine-1-carbonyl)phenyl]-1H-imidazol-2-yl}pyridine;
2-tert-butyl-4-{4-[2-chloro-4-(piperidine-1-carbonyl)phenyl]-1H-imidazol-2-yl}pyridine;
6-[5-(2-tert-butylpyridin-4-yl)thiophen-3-yl]-2-methyl-1,2,3,4-tetrahydroisoquinolin-1-one;
tert-butyl 4-{4-[5-(2-tert-butylpyridin-4-yl)thiophen-3-yl]-3-chlorobenzoyl}piperazine-1-carboxylate;

1-{4-[5-(2-tert-butylpyridin-4-yl)thiophen-3-yl]-3-chlorobenzoyl}piperazine;
1-(4-{4-[5-(2-tert-butylpyridin-4-yl)thiophen-3-yl]-3-chlorobenzoyl}piperazin-1-yl)ethan-1-one;
1-{4-[5-(2-tert-butylpyridin-4-yl)thiophen-3-yl]-3-chlorobenzoyl}-4-methanesulfonylpiperazine;
N-(1-{4-[5-(2-tert-butylpyridin-4-yl)thiophen-3-yl]-3-chlorobenzoyl}piperidin-3-yl)methanesulfonamide;
N-(1-{4-[5-(2-tert-butylpyridin-4-yl)thiophen-3-yl]-3-chlorobenzoyl}piperidin-3-yl)acetamide;
4-[5-(2-tert-butylpyridin-4-yl)thiophen-3-yl]-3-chloro-N,N-bis(propan-2-yl)benzamide;
1-(1-{4-[5-(2-tert-butylpyridin-4-yl)thiophen-3-yl]-3-chlorobenzoyl}piperidin-3-yl)pyrrolidin-2-one;
6-[5-(2-tert-butylpyridin-4-yl)thiophen-3-yl]-2-(propan-2-yl)-1,2,3,4-tetrahydroisoquinolin-1-one,
2-(1-{4-[5-(2-tert-butylpyridin-4-yl)thiophen-3-yl]-3-chlorobenzoyl}piperidin-3-yl)-1$\lambda^6$,2-thiazolidine-1,1-dione;
tert-butyl N-(1-{4-[5-(2-tert-butylpyridin-4-yl)thiophen-3-yl]-3-chlorobenzoyl}piperidin-4-yl)carbamate,
N-(1-{4-[5-(2-tert-butylpyridin-4-yl)thiophen-3-yl]-3-chlorobenzoyl}piperidin-4-yl)acetamide;
4-{4-[5-(2-tert-butylpyridin-4-yl)thiophen-3-yl]-3-chlorobenzoyl}-1-ethylpiperazin-2-one;
2-tert-butyl-4-{5-[2-chloro-4-(4,4-difluoropiperidine-1-carbonyl)phenyl]thiophen-3-yl}pyridine;
4-[5-(2-tert-butylpyridin-4-yl)thiophen-3-yl]-3-chloro-N-methyl-N-phenylbenzamide;
4-{4-[4-(azetidine-1-carbonyl)-2-chlorophenyl]thiophen-2-yl}-2-tert-butylpyridine;
6-{4-[5-(2-tert-butylpyridin-4-yl)thiophen-3-yl]-3-chlorobenzoyl}-2-oxa-6-azaspiro[3.3]heptane;
ethyl N-(1-{4-[5-(2-tert-butylpyridin-4-yl)thiophen-3-yl]-3-chlorobenzoyl}piperidin-3-yl)carbamate;
ethyl 4-{4-[5-(2-tert-butylpyridin-4-yl)thiophen-3-yl]-3-chlorobenzoyl}piperazine-1-carboxylate;
1-(4-{4-[5-(2-tert-butylpyridin-4-yl)thiophen-3-yl]-3-chlorobenzoyl}piperazin-1-yl)-2,2-dimethylpropan-1-one;
N-[2-(1-{4-[5-(2-tert-butylpyridin-4-yl)thiophen-3-yl]-3-chlorophenyl}-N-ethylformamido)ethyl]acetamide;
1-{4-[5-(2-tert-butylpyridin-4-yl)thiophen-3-yl]-3-chlorobenzoyl}piperidin-3-ol;
(3R)-1-{4-[5-(2-tert-butylpyridin-4-yl)thiophen-3-yl]-3-chlorobenzoyl}piperidin-3-ol,
(3S)-1-{4-[5-(2-tert-butylpyridin-4-yl)thiophen-3-yl]-3-chlorobenzoyl}piperidin-3-ol;
4-[5-(2-tert-butylpyridin-4-yl)thiophen-3-yl]-3-chloro-N-(3-hydroxyphenyl)benzamide;
(2S,6R)-4-{4-[5-(2-tert-butylpyridin-4-yl)thiophen-3-yl]-3-chlorobenzoyl}-2,6-dimethylmorpholine;
1-{4-[4-(2-tert-butylpyridin-4-yl)thiophen-2-yl]-3-chlorobenzoyl}-1,2,3,4-tetrahydro-1,8-naphthyridine;
6-[5-(2-tert-butylpyridin-4-yl)thiophen-3-yl]-7-chloro-2-(propan-2-yl)-1,2,3,4-tetrahydroisoquinolin-1-one;
4-[5-(2-tert-butylpyridin-4-yl)thiophen-3-yl]-3-chloro-N-[(4,6-dimethyl-2-oxo-1,2-dihydropyridin-3-yl)methyl]benzamide;
4-[5-(2-tert-butyl pyridin-4-vi)thiophen-3-yl]-3-chloro-N-(4-fluorophenyl)benzamide
N-(1-{4-[5-(2-tert-butylpyridin-4-yl)thiophen-3-yl]-3-chlorobenzoyl}piperidin-3-yl)-2,2-dimethylpropanamide;
1-(1-{4-[5-(2-tert-butylpyridin-4-yl)thiophen-3-yl]-3-chlorobenzoyl}piperidin-3-yl)-3-cyclopropylurea;
1-{4-[5-(2-tert-butylpyridin-4-yl)thiophen-3-yl]-3-chlorobenzoyl}piperidin-4-ol;
4-[5-(2-tert-butylpyridin-4-yl)thiophen-3-yl]-3-chloro-N-(pyridin-3-yl)benzamide;
N-(1-{4-[5-(2-tert-butylpyridin-4-yl)thiophen-3-yl]-3-chlorobenzoyl}piperidin-4-yl)methanesulfonamide;
4-[5-(2-tert-butylpyridin-4-yl)thiophen-3-yl]-3-chloro-N-methyl-N-(1,3-oxazol-2-yl)benzamide;
4-[5-(2-tert-butylpyridin-4-yl)thiophen-3-yl]-3-chloro-N-[2-(morpholin-4-yl)-2-oxoethyl]benzamide;
4-[5-(2-tert-butylpyridin-4-yl)thiophen-3-yl]-3-chloro-N-{8-methyl-8-azabicyclo[3.2.1]octan-3-yl}benzamide;
ethyl N-(1-{4-[5-(2-tert-butylpyridin-4-yl)thiophen-3-yl]-3-chlorobenzoyl}piperidin-4-yl)carbamate;
tert-butyl N-[1-(3-chloro-4-{5-[2-(morpholin-4-yl)pyridin-4-yl]thiophen-3-yl}benzoyl)piperidin-3-yl]carbamate;
1-(3-chloro-4-{5-[2-(morpholin-4-yl)pyridin-4-yl]thiophen-3-yl}benzoyl)piperidin-3-amine;
1-{4-[5-(2-tert-butylpyridin-4-yl)-2-methylthiophen-3-yl]-3-chlorobenzoyl}piperidin-3-amine;
4-[5-(2-tert-butylpyridin-4-yl)-2-methylthiophen-3-yl]-chloro-N-phenylbenzamide;
(3S)-1-{4-[4-(2-tert-butylpyridin-4-yl)thiophen-2-yl]-3-chlorobenzoyl}pyrrolidin-3-ol;
(3R)-1-{4-[4-(2-tert-butylpyridin-4-yl)thiophen-2-yl]-3-chlorobenzoyl}pyrrolidin-3-ol;
tert-butyl N-[(3R)-1-{4-[4-(2-tert-butylpyridin-4-yl)thiophen-2-yl]-3-chlorobenzoyl}piperidin-3-yl]carbamate;
tert-butyl N-(1-{4-[5-(2-tert-butylpyridin-4-yl)thiophen-3-yl]-3-chlorobenzoyl}piperidin-3-yl)-N-methylcarbamate;
tert-butyl 3-{4-[5-(2-tert-butylpyridin-4-yl)thiophen-3-yl]-3-chlorobenzamido}piperidine-1-carboxylate;
1-{4-[5-(2-tert-butylpyridin-4-yl)thiophen-3-yl]-3-chlorobenzoyl}piperidin-4-amine;
6-[5-(2-tert-butylpyridin-4-yl)thiophen-3-yl]-5-chloro-N-phenylpyridine-3-carboxamide;
(3R)-1-{4-[4-(2-tert-butylpyridin-4-yl)thiophen-2-yl]-3-chlorobenzoyl}piperidin-3-amine;
(3S)-1-{4-[4-(2-tert-butylpyridin-4-yl)thiophen-2-yl]-3-chlorobenzoyl}piperidin-3-amine;
1-{4-[5-(2-tert-butylpyridin-4-yl)thiophen-3-yl]-3-chlorobenzoyl}-N-methylpiperidin-3-amine;
N-(1-{4-[5-(2-tert-butylpyridin-4-yl)thiophen-3-yl]-3-chlorobenzoyl}piperidin-4-yl)-2,2-dimethylpropanamide;
4-{4-[4-(2-tert-butylpyridin-4-yl)-5-methyl thiophen-2-yl]-3-chlorobenzoyl}piperazin-2-one;
tert-butyl 4-{4-[5-(2-tert-butylpyridin-4-yl)thiophen-3-yl]-3-chlorobenzamido}piperidine-1-carboxylate;
tert-butyl N-[(3R)-1-{4-[4-(2-tert-butylpyridin-4-yl)-5-methylthiophen-2-yl]-3-chlorobenzoyl}piperidin-3-yl]carbamate;
tert-butyl N-[(3S)-1-{4-[4-(2-tert-butyl pyridin-4-yl)-5-methylthiophen-2-yl]-3-chlorobenzoyl}piperidin-3-yl]carbamate;
1-{4-[5-(2-tert-butylpyridin-4-yl)thiophen-3-yl]-3-chlorobenzoyl}-N-[(4 chlorophenyl)methyl]piperidin-3-amine;
(3R)-1-{4-[5-(2-tert-butylpyridin-4-yl)thiophen-3-yl]-3-chlorobenzoyl}-N-[(4 chlorophenyl)methyl]piperidin-3-amine;
(3R)-1-{4-[4-(2-tert-butylpyridin-4-yl)thiophen-2-yl]-3-chlorobenzoyl}-N-[(4-chlorophenyl)methyl]piperidin-3-amine;
1-{4-[5-(2-tert-butylpyridin-4-yl)thiophen-3-yl]-3-chlorobenzoyl}-N-[(3 chlorophenyl)methyl]piperidin-3-amine;

(3R)-1-{4-[5-(2-tert-butylpyridin-4-yl)thiophen-3-yl]-3-chlorobenzoyl}pyrrolidin-3-ol;
7-{4-[5-(2-tert-butylpyridin-4-yl)thiophen-3-yl]-3-chlorobenzoyl}-2,7-diazaspiro[4.5]decan-1-one;
2-tert-butyl-4-[4-(2-chloro-4-{octahydropyrrolo[1,2-a]piperazine-2-carbonyl}phenyl)thiophen-2-yl]pyridine;
1-{4-[2-(2-tert-butylpyridin-4-yl)-1H-imidazol-4-yl]-3-chlorobenzoyl}piperidin-3-amine;
1-{4-[4-(2-tert-butylpyridin-4-yl)thiophen-2-yl]-3-chlorobenzoyl}piperidin-4-ol;
(3S)-1-{4-[4-(2-tert-butyl pyridin-4-yl)-5-methylthiophen-2-yl]-3-chlorobenzoyl}piperidin-3-amine;
(3R)-1-{4-[4-(2-tert-butylpyridin-4-yl)-5-methylthiophen-2-yl]-3-chlorobenzoyl}piperidin-3-amine;
1-{4-[4-(2-tert-butylpyridin-4-yl)thiophen-2-yl]-3-chlorobenzoyl}piperidine-4-carboxylic acid;
1-{4-[4-(2-tert-butylpyridin-4-yl)thiophen-2-yl]-3-chlorobenzoyl}piperidin-3-ol;
(3R)-1-{4-[4-(2-tert-butylpyridin-4-yl)thiophen-2-yl]-3-chlorobenzoyl}piperidin-3-ol;
(3S)-1-{4-[4-(2-tert-butylpyridin-4-yl)thiophen-2-yl]-3-chlorobenzoyl}piperidin-3-ol;
tert-butyl N-[(3R)-1-{4-[5-(2-tert-butylpyridin-4-yl)thiophen-3-yl]-3-chlorobenzoyl}pyrrolidin-3-yl]carbamate;
(3R)-1-{4-[4-(2-tert-butylpyridin-4-yl)thiophen-2-yl]-3-chlorobenzoyl}piperidine-3-carboxylic acid;
2-tert-butyl-4-[5-(2-chloro-4-{3H,4H,5H,6H,7H-imidazo[4,5-c]pyridine-5-carbonyl}phenyl)thiophen-3-yl]pyridine;
4-{4-[4-(2-tert-butylpyridin-4-yl)thiophen-2-yl]-3-chlorobenzoyl}piperazin-2-one;
1-[(3R)-1-{4-[4-(2-tert-butylpyridin-4-yl)thiophen-2-yl]-3-chlorobenzoyl}piperidin-3-yl]imidazolidin-2-one;
1-{4-[4-(2-tert-butylpyridin-4-yl)thiophen-2-yl]-3-chlorobenzoyl}-3-methylpiperidin-3-amine;
(3R)-1-{4-[4-(2-tert-butylpyridin-4-yl)thiophen-2-yl]-3-chlorobenzoyl}-3-methylpiperidin-3-amine;
(3S)-1-{4-[4-(2-tert-butylpyridin-4-yl)thiophen-2-yl]-3-chlorobenzoyl}-3-methylpiperidin-3-amine;
(3R)-1-{4-[4-(2-tert-butylpyridin-4-yl)thiophen-2-yl]-3-chlorobenzoyl}pyrrolidin-3-amine;
(3S)-1-{4-[4-(2-tert-butylpyridin-4-yl)thiophen-2-yl]-3-chlorobenzoyl}pyrrolidin-3-amine;
1-{4-[4-(2-tert-butylpyridin-4-yl)thiophen-2-yl]-3-chlorobenzoyl}-1,2,3,4-tetrahydro-1,5-naphthyridine;
1-{4-[2-(2-tert-butylpyridin-4-yl)-1H-imidazol-4-yl]-3-chlorobenzoyl}piperidin-4-ol;
2-tert-butyl-4-{5-[2-chloro-4-(3-methoxypiperidine-1-carbonyl)phenyl]thiophen-3-yl}pyridine;
1-{4-[4-(2-tert-butylpyridin-4-yl)thiophen-2-yl]-3-chlorobenzoyl}-4-methylpiperidin-4-ol;
(3R)-1-{4-[4-(2-tert-butylpyridin-4-yl)thiophen-2-yl]-3-chlorobenzoyl}-3-methylpiperidin-3-ol;
(3S)-1-{4-[4-(2-tert-butylpyridin-4-yl)thiophen-2-yl]-3-chlorobenzoyl}-3-methylpiperidin-3-ol;
4-(3-chloro-4-{5-[1-(3-methylbutyl)-1H-pyrazol-5-yl]thiophen-3-yl}benzoyl)morpholine;
1-(3-chloro-4-{5-[1-(3-methylbutyl)-1H-pyrazol-5-yl]thiophen-3-yl}benzoyl)-4,4-difluoropiperidine;
1-(3-chloro-4-{4-[1-(3-methylbutyl)-1H-pyrazol-5-yl]thiophen-2-yl}benzoyl)piperidin-3-ol; and
3-(1-{4-[4-(2-tert-butylpyridin-4-yl)thiophen-2-yl]-3-chlorophenyl}-N-(4-fluorophenyl)formamido)propanoic acid.

In some embodiments, the compound is selected from the group consisting of:
piperidin-1-yl(4-(5-(2-propylpyridin-4-yl)thiophen-3-yl)phenyl)methanone;
piperidin-1-yl(3-(5-(2-propylpyridin-4-yl)thiophen-3-yl)phenyl)methanone;
(4-(5-(1-isobutyl-1H-pyrazol-5-yl)thiophen-3-yl)phenyl)(piperidin-1-yl)methanone;
(3-chloro-4-(5-(2-propylpyridin-4-yl)thiophen-3-yl)phenyl)(piperidin-1-yl)methanone;
(4-(4-(2-tert-butylpyridin-4-yl)thiophen-2-yl)-3-chlorophenyl)(piperidin-1-yl)methanone;
(3-chloro-4-(5-(1,2-dimethyl-1H-pyrrolo[2,3-b]pyridin-4-yl)thiophen-3-yl)phenyl) (piperidin-1-yl)methanone;
(3-chloro-4-(5-(1-propyl-1H-pyrrolo[2,3-b]pyridin-4-yl)thiophen-3-yl)phenyl)(piperidin-1-yl)methanone;
(3-chloro-4-(5-(2,3-dimethyl-3H-imidazo[4,5-b]pyridin-7-yl)thiophen-3-yl)phenyl) (piperidin-1-yl)methanone;
(3-chloro-4-(5-(3-propyl-3H-imidazo[4,5-b]pyridin-7-yl)thiophen-3-yl)phenyl)(piperidin-1-yl)methanone;
(4-(5-(3H-imidazo[4,5-b]pyridin-7-yl)thiophen-3-yl)-3-chlorophenyl)(piperidin-1-yl)methanone;
(3-chloro-4-(5-(1,2-dipropyl-1H-pyrrolo[2,3-b]pyridin-4-yl)thiophen-3-yl)phenyl) (piperidin-1-yl)methanone;
(4-(5-(6-(butylamino)-2-isobutylpyrimidin-4-yl)thiophen-3-yl)-3-chlorophenyl) (piperidin-1-yl)methanone;
(3-chloro-4-(5-(6-(dibutylamino)-2-isobutylpyrimidin-4-yl)thiophen-3-yl)phenyl) (piperidin-1-yl)methanone;
(4-(5-(6-amino-2-isobutylpyrimidin-4-yl)thiophen-3-yl)-3-chlorophenyl)(piperidin-1-yl)methanone;
(4-(5-(2-aminopyrimidin-4-yl)thiophen-3-yl)-3-chlorophenyl)(piperidin-1-yl)methanone;
(3-chloro-4-(5-(2-(propylamino)pyrimidin-4-yl)thiophen-3-yl)phenyl)(piperidin-1-yl) methanone;
(4-(5-(2-(butyl(propyl)amino)pyrimidin-4-yl)thiophen-3-yl)-3-chlorophenyl)(piperidin-1-yl)methanone;
(3-chloro-4-(5-(2-propylthiazol-4-yl)thiophen-3-yl)phenyl) (piperidin-1-yl)methanone;
(3-chloro-4-(5-(5-propyl-1,2,4-thiadiazol-3-yl)thiophen-3-yl)phenyl)(piperidin-1-yl) methanone;
(3-chloro-4-(5-(5-propyl-1,2,4-oxadiazol-3-yl)thiophen-3-yl)phenyl)(piperidin-1-yl) methanone;
(3-chloro-4-(5-(2-propylthiazol-5-yl)thiophen-3-yl)phenyl) (piperidin-1-yl)methanone;
(3-chloro-4-(5-(5-propyl-1,3,4-thiadiazol-2-yl)thiophen-3-yl)phenyl)(piperidin-1-yl) methanone;
(3-chloro-4-(5-(5-propyl-1,3,4-oxadiazol-2-yl)thiophen-3-yl)phenyl)(piperidin-1-yl) methanone;
5-(4-(2-chloro-4-(piperidine-1-carbonyl)phenyl)thiophen-2-yl)-1-isobutylpyridin-2(1H)-one;
(3-chloro-4-(5-(2-morpholinopyridin-4-yl)thiophen-3-yl)phenyl)(4,4-difluoropiperidin-1-yl)methanone;
(2-bromo-3-chloro-4-(5-(2-isobutylpyridin-4-yl)thiophen-3-yl)phenyl)(piperidin-1-yl) methanone;
(3,5-dichloro-4-(5-(2-isobutylpyridin-4-yl)thiophen-3-yl)phenyl)(piperidin-1-yl) methanone;
(4-(5-(2-isobutylpyridin-4-yl)thiophen-3-yl)-2-(trifluoromethyl)phenyl)(piperidin-1-yl) methanone;
(2-cyclopropyl-4-(5-(2-isobutyl pyridin-4-yl)thiophen-3-yl)phenyl)(piperidin-1-yl) methanone;
(4-(5-(2-isobutylpyridin-4-yl)thiophen-3-yl)-2-methylphenyl)(piperidin-1-yl)methanone;
(4-(5-(2-isobutylpyridin-4-yl)thiophen-3-yl)-2-isopropylphenyl)(piperidin-1-yl) methanone;
(2-ethynyl-4-(5-(2-isobutylpyridin-4-yl)thiophen-3-yl)phenyl)(piperidin-1-yl)methanone;
(2-bromo-3-ethynyl-4-(5-(2-isobutylpyridin-4-yl)thiophen-3-yl)phenyl)(piperidin-1-yl) methanone;
(2-bromo-6-chloro-4-(5-(2-isobutylpyridin-4-yl)thiophen-3-yl)phenyl)(piperidin-1-yl) methanone;

(2-chloro-4-(5-(2-isobutylpyridin-4-yl)thiophen-3-yl)-6-methylphenyl)(piperidin-1-yl) methanone;
(4-(4-(2-tert-butylpyridin-4-yl)-1-methyl-1H-imidazol-2-yl)-3-chlorophenyl)(piperidin-1-yl)methanone;
(3-chloro-4-(5-(2-isobutylpyridin-4-yl)thiophen-3-yl)phenyl)(piperidin-1-yl)methanone;
(2-bromo-4-(2-(2-isobutylpyridin-4-yl)-1-methyl-1H-imidazol-4-yl)phenyl)(piperidin-1-yl)methanone;
(2-bromo-3-chloro-4-(2-(2-isobutylpyridin-4-yl)-1H-imidazol-4-yl)phenyl)(piperidin-1-yl)methanone;
(2-bromo-5-chloro-4-(2-(2-isobutylpyridin-4-yl)-1-methyl-1H-imidazol-4-yl)phenyl) (piperidin-1-yl)methanone;
(4-(4-(2-tert-butylpyridin-4-yl)oxazol-2-yl)-3-chlorophenyl)(piperidin-1-yl)methanone;
(4-(2-(2-tert-butylpyridin-4-yl)oxazol-4-yl)-3-chlorophenyl)(piperidin-1-yl)methanone;
(3-chloro-4-(5-(2-(dimethylamino)pyridin-4-yl)thiophen-3-yl)phenyl)(piperidin-1-yl) methanone;
(3,5-dichloro-4-(5-(2-propylpyridin-4-yl)thiophen-3-yl)phenyl)(piperidin-1-yl) methanone;
N-(4-(4-(2-chloro-4-(piperidine-1-carbonyl)phenyl)thiophen-2-yl)pyridin-2-yl) methanesulfonamide;
(3-chloro-4-(5-(2-(3,3,3-trifluoropropyl)pyridin-4-yl)thiophen-3-yl)phenyl)(piperidin-1-yl)methanone;
(3-chloro-4-(1-methyl-2-(2-(3,3,3-trifluoropropyl)pyridin-4-yl)-1H-imidazol-4-yl)phenyl) (piperidin-1-yl)methanone;
(2-hydroxy-4-(5-(2-propylpyridin-4-yl)thiophen-3-yl)phenyl)(piperidin-1-yl)methanone;
(4-(5-(2-tert-butylpyridin-4-yl)thiophen-3-yl)-2-hydroxyphenyl)(piperidin-1-yl) methanone;
(2-methoxy-4-(5-(2-propylpyridin-4-yl)thiophen-3-yl)phenyl)(piperidin-1-yl)methanone;
(4-(5-(2-isobutylpyridin-4-yl)thiophen-3-yl)-2-methoxyphenyl)(piperidin-1-yl) methanone;
(4-(5-(2-tert-butylpyridin-4-yl)thiophen-3-yl)-2-methoxyphenyl)(piperidin-1-yl) methanone;
(4-(5-(2-isobutylpyridin-4-yl)thiophen-3-yl)-3-(trifluoromethyl)phenyl)(piperidin-1-yl) methanone;
(3-chloro-4-(5-(2-neopentylpyridin-4-yl)thiophen-3-yl)phenyl)(piperidin-1-yl) methanone;
(3-chloro-4-(5-(2-isobutylpyridin-4-yl)thiophen-3-yl)-5-(trifluoromethyl)phenyl) (piperidin-1-yl)methanone;
(2,3-dichloro-4-(5-(2-isobutylpyridin-4-yl)thiophen-3-yl)phenyl)(piperidin-1-yl) methanone;
(4-(2-(2-isobutylpyridin-4-yl)-1-methyl-1H-imidazol-4-yl)-2-methoxyphenyl)(piperidin-1-yl)methanone;
(2-methoxy-4-(1-methyl-2-(2-propylpyridin-4-yl)-1H-imidazol-4-yl)phenyl)(piperidin-1-yl)methanone;
(4-(2-(2-tert-butylpyridin-4-yl)-1-methyl-1H-imidazol-4-yl)-2-methoxyphenyl)(piperidin-1-yl)methan one;
(4-(5-(2-benzyl pyridin-4-yl)thiophen-3-yl)-3-chlorophenyl)(piperidin-1-yl)methanone;
(4-(5-(2-aminopyridin-4-yl)thiophen-3-yl)-3-chlorophenyl)(piperidin-1-yl)methanone;
N-(4-(4-(2-chloro-4-(piperidine-1-carbonyl)phenyl)-1-methyl-1H-imidazol-2-yl)pyridin-2-yl)methanesulfonamide;
(2-hydroxy-4-(5-(2-isobutyl pyridin-4-yl)thiophen-3-yl)phenyl)(piperidin-1-yl) methanone;
(3-chloro-4-(5-(2-(3,3,3-trifluoropropyl)pyridin-4-yl)furan-3-yl)phenyl)(piperidin-1-yl) methanone;
(2-methoxy-4-(5-(2-neopentylpyridin-4-yl)thiophen-3-yl)phenyl)(piperidin-1-yl) methanone;
N-(4-(4-(2-chloro-4-(piperidine-1-carbonyl)phenyl)thiophen-2-yl)pyridin-2-yl)-1,1,1-trifluoromethanesulfonamide;
1-(4-(4-(4-(2-chloro-4-(4,4-difluoropiperidine-1-carbonyl)phenyl)thiophen-2-yl)pyridin-2-yl)piperazin-1-yl)ethanone;
(3-chloro-4-(5-(1-isopentyl-1H-pyrazol-5-yl)thiophen-3-yl)phenyl)(piperidin-1-yl) methanone;
(3-chloro-4-(5-(1-isopentyl-1H-pyrazol-5-yl)furan-3-yl)phenyl)(piperidin-1-yl) methanone;
(3-chloro-4-(5-(2-(cyclohexylmethyl)pyridin-4-yl)thiophen-3-yl)phenyl)(piperidin-1-yl)methanone;
(3-chloro-4-(5-(naphthalen-1-yl)thiophen-3-yl)phenyl)(piperidin-1-yl)methanone;
(4-(5-(1H-indol-6-yl)thiophen-3-yl)-3-chlorophenyl)(piperidin-1-yl)methanone;
(4-(5-(1H-indol-4-yl)thiophen-3-yl)-3-chlorophenyl)(4,4-difluoropiperidin-1-yl) methanone;
(4-(5-(1H-benzo[d]imidazol-4-yl)thiophen-3-yl)-3-chlorophenyl)(4,4-difluoropiperidin-1-yl)methanone;
(3-chloro-4-(5-(isoquinolin-4-yl)thiophen-3-yl)phenyl)(piperidin-1-yl)methanone;
(3-chloro-4-(5-(2-(4-methylpiperazin-1-yl)pyridin-4-yl)thiophen-3-yl)phenyl)(piperidin-1-yl)methanone;
(3-chloro-4-(5-(3,5-dimethylisoxazol-4-yl)thiophen-3-yl)phenyl)(piperidin-1-yl) methanone;
(3-chloro-4-(5-(1-isopentyl-1H-pyrazol-5-yl)thiophen-3-yl)phenyl)(4,4-difluoropiperidin-1-yl)methanone;
(3-chloro-4-(5-(1-ethyl-1H-indol-4-yl)thiophen-3-yl)phenyl)(4,4-difluoropiperidin-1-yl) methanone;
(4-(5-(1H-indol-4-yl)thiophen-3-yl)-3-chlorophenyl)(piperidin-1-yl)methanone;
(3-chloro-4-(5-(1-ethyl-1H-benzo[d]imidazol-4-yl)thiophen-3-yl)phenyl)(4,4-difluoropiperidin-1-yl)methanone;
(3-chloro-4-(5-(2,3-dihydrobenzofuran-5-yl)thiophen-3-yl)phenyl)piperidin-1-yl) methanone;
(3-chloro-4-(5-(2-(hydroxymethyl)pyridin-4-yl)thiophen-3-yl)phenyl)(piperidin-1-yl) methanone;
(3-chloro-4-(5-(3-(hydroxymethyl)pyridin-4-yl)thiophen-3-yl)phenyl)piperidin-1-yl) methanone;
(3-chloro-4-(5-(2-(piperidin-1-yl)pyridin-4-yl)thiophen-3-yl)phenyl)(piperidin-1-yl) methanone;
(3-chloro-4-(5-(3-methylpyridin-4-yl)thiophen-3-yl)phenyl)(piperidin-1-yl)methanone;
(4-(5-(1H-pyrrolo[2,3-b]pyridin-4-yl)thiophen-3-yl)-3-chlorophenyl)(piperidin-1-yl) methanone;
(3-chloro-4-(5-(2-(piperidin-1-yl)pyridin-4-yl)thiophen-3-yl)phenyl)(4,4-difluoropiperidin-1-yl)methanone;
(3-chloro-4-(5-(5-fluoro-1H-pyrrolo[2,3-b]pyridin-4-yl)thiophen-3-yl)phenyl)(piperidin-1-yl)methanone;
(4-(5-(benzo[b]thiophen-3-yl)thiophen-3-yl)-3-chlorophenyl)(piperidin-1-yl)methanone;
(3-chloro-4-(5-(3-(pyrrolidin-1-ylmethyl)pyridin-4-yl)thiophen-3-yl)phenyl)(piperidin-1-yl)methanone;
(3-chloro-4-(5-(2-(cyclopentylamino)pyridin-4-yl)thiophen-3-yl)phenyl)(piperidin-1-yl) methanone;
(4-(5-(1H-indol-3-yl)thiophen-3-yl)-3-chlorophenyl)(piperidin-1-yl)methanone;
(3-chloro-4-(5-(quinolin-4-yl)thiophen-3-yl)phenyl)(piperidin-1-yl)methanone;
(3-chloro-4-(5-(2-chloropyridin-4-yl)thiophen-3-yl)phenyl) (piperidin-1-yl)methanone;
(2-bromo-4-(5-(2-tert-butylpyridin-4-yl)thiophen-3-yl)-3-chlorophenyl)(piperidin-1-yl) methanone;
(2-bromo-4-(2-(2-propylpyridin-4-yl)-1H-imidazol-4-yl)phenyl)(piperidin-1-yl)methanone;
(2-bromo-4-(5-(2-tert-butylpyridin-4-yl)furan-3-yl)-3-chlorophenyl)(piperidin-1-yl) methanone;
(2-bromo-4-(5-(2-tert-butylpyridin-4-yl)-1H-pyrrol-3-yl)-3-chlorophenyl)(piperidin-1-yl) methanone;

(4-(2-(2-tert-butyl pyridin-4-yl)-1H-imidazol-4-yl)-3-fluorophenyl)(piperidin-1-yl) methanone;
(4-(4-(2-tert-butylpyridin-4-yl)-1H-imidazol-2-yl)-3-chlorophenyl)(piperidin-1-yl) methanone;
(2-bromo-4-(2-(2-(piperidin-1-yl)pyridin-4-yl)-1H-imidazol-4-yl)phenyl)(piperidin-1-yl) methanone;
(4-(2-(2-tert-butylpyridin-4-yl)-1-methyl-1H-imidazol-4-yl)-3-chlorophenyl)(piperidin-1-yl)methanone;
(4-(5-(2-tert-butylpyridin-4-yl)-1H-pyrrol-3-yl)-3-chlorophenyl)(piperidin-1-yl) methanone;
(4-(4-(2-tert-butylpyridin-4-yl)furan-2-yl)-3-chlorophenyl)(piperidin-1-yl)methanone;
(4-(4-(2-tert-butylpyridin-4-yl)-1H-pyrrol-2-yl)-3-chlorophenyl)(piperidin-1-yl) methanone;
(4-(4-(2-tert-butyl pyridin-4-yl)-1-methyl-1H-pyrrol-2-yl)-3-chlorophenyl)(piperidin-1-yl) methanone;
(4-(4-(2-tert-butylpyridin-4-yl)thiazol-2-yl)-3-chlorophenyl)(piperidin-1-yl)methanone;
(4-(5-(2-tert-butylpyridin-4-yl)isothiazol-3-yl)-3-chlorophenyl)(piperidin-1-yl) methanone;
(4-(5-(2-tert-butylpyridin-4-yl)isoxazol-3-yl)-3-chlorophenyl)(piperidin-1-yl)methanone;
(4-(5-(2-tert-butylpyridin-4-yl)-1H-pyrazol-3-yl)-3-chlorophenyl)(piperidin-1-yl) methanone;
(4-(3-(2-tert-butylpyridin-4-yl)isothiazol-5-yl)-3-chlorophenyl)(piperidin-1-yl) methanone;
(4-(3-(2-tert-butylpyridin-4-yl)isoxazol-5-yl)-3-chlorophenyl)(piperidin-1-yl)methanone;
(4-(3-(2-tert-butyl pyridin-4-yl)-1H-pyrazol-5-yl)-3-chlorophenyl)(piperidin-1-yl) methanone;
(4-(3-(2-tert-butylpyridin-4-yl)-1-methyl-1H-pyrazol-5-yl)-3-chlorophenyl)(piperidin-1-yl)methanone;
(3-chloro-4-(5-(2-isobutylpyridin-4-yl)-1H-pyrrol-3-yl)phenyl)(piperidin-1-yl) methanone;
(3-fluoro-4-(5-(2-propylpyridin-4-yl)thiophen-3-yl)phenyl)(piperidin-1-yl)methanone;
(3-chloro-4-(2-(2-isobutylpyridin-4-yl)-1H-imidazol-4-yl)phenyl)(piperidin-1-yl) methanone;
(3-chloro-4-(2-(2-isobutylpyridin-4-yl)oxazol-4-yl)phenyl)(piperidin-1-yl)methanone;
(3-chloro-4-(2-(2-isobutylpyridin-4-yl)thiazol-4-yl)phenyl)(piperidin-1-yl)methanone;
(3-(5-(2-isobutylpyridin-4-yl)thiophen-3-yl)phenyl)(piperidin-1-yl)methanone;
(2-bromo-4-(5-(2-isobutylpyridin-4-yl)thiophen-3-yl)phenyl)(piperidin-1-yl)methanone;
(2-bromo-4-(2-(2-isobutylpyridin-4-yl)-1H-imidazol-4-yl)phenyl)(piperidin-1-yl) methanone;
(4-(5-(2-butylpyridin-4-yl)thiophen-3-yl)-3-chlorophenyl)(piperidin-1-yl)methanone;
(3-chloro-4-(5-(2-(methoxymethyl)pyridin-4-yl)thiophen-3-yl)phenyl)(piperidin-1-yl) methanone;
(3-chloro-4-(5-(4,6-di propyl pyridin-2-yl)thiophen-3-yl)phenyl)(piperidin-1-yl) methanone;
piperidin-1-yl(4-(5-(4-propylpyridin-2-yl)thiophen-3-yl)phenyl)methanone;
(4-(5-(2,6-dipropylpyridin-3-yl)thiophen-3-yl)phenyl)(piperidin-1-yl)methanone;
(4-(5-(2-(cyclohexylmethyl)pyridin-4-yl)thiophen-3-yl)phenyl)(piperidin-1-yl) methanone;
(4-(5-(2-isobutylpyridin-4-yl)thiophen-3-yl)-3-methoxyphenyl)(piperidin-1-yl) methanone;
(3-chloro-4-(5-(2-(((trifluoromethylsulfonyl)methyl)pyridin-4-yl)thiophen-3-yl)phenyl) (piperidin-1-yl)methanone;
(3-chloro-4-(1-methyl-2-(1H-pyrrolo[2,3-b]pyridin-4-yl)-1H-imidazol-4-yl)phenyl) (piperidin-1-yl)methanone;
(3-chloro-4-(5-(2-propyl-3H-imidazo[4,5-b]pyridin-7-yl) thiophen-3-yl)phenyl)(piperidin-1-yl)methanone;
4-(4-(2-chloro-4-(piperidine-1-carbonyl)phenyl)thiophen-2-yl)-N-cyclopropyl picolinamide;
4-(4-(2-chloro-4-(piperidine-1-carbonyl)phenyl)thiophen-2-yl)-N-cyclohexyl picolinamide;
(4-(2-(1H-indol-4-yl)-1-methyl-1H-imidazol-4-yl)-3-chlorophenyl)(piperidin-1-yl) methanone;
(3-chloro-4-(4-(2-(piperidin-1-yl)pyridin-4-yl)thiophen-2-yl)phenyl)(4,4-difluoro piperidin-1-yl)methanone;
(3-chloro-4-(4-(2-(piperidin-1-yl)pyridin-4-yl)thiophen-2-yl)phenyl)(piperidin-1-yl) methanone;
(2-bromo-4-(2-(2-tert-butylpyridin-4-yl)-1H-imidazol-4-yl) phenyl)(piperidin-1-yl) methanone;
(2-chloro-4-(2-(2-propylpyridin-4-yl)-1H-imidazol-4-yl) phenyl)(piperidin-1-yl) methanone;
(2-bromo-5-chloro-4-(2-(2-propylpyridin-4-yl)-1H-imidazol-4-yl)phenyl)(piperidin-1-yl) methanone;
(3-chloro-4-(5-(2-isobutylpyridin-4-yl)thiophen-3-yl)phenyl)(4,4-difluoropiperidin-1-yl) methanone;
(3-chloro-4-(5-(2-cyclopropylpyridin-4-yl)thiophen-3-yl) phenyl)(piperidin-1-yl) methanone;
piperidin-1-yl(4-(5-(2-propylpyridin-4-yl)thiophen-3-yl)-3-(trifluoromethyl)phenyl) methanone;
(3-chloro-4-(5-(2-propylpyridin-4-yl)thiophen-3-yl)phenyl) (3,3-difluoropyrrolidin-1-yl) methanone;
(3-chloro-4-(2-(2-propylpyridin-4-yl)-1H-imidazol-4-yl) phenyl)(piperidin-1-yl) methanone;
(2-bromo-4-(5-(2-propylpyridin-4-yl)thiophen-3-yl)phenyl) (piperidin-1-yl)methanone;
(4-(5-(2-isobutylpyridin-4-yl)thiophen-3-yl)phenyl)(piperidin-1-yl)methanone;
5-(5-(2-isobutylpyridin-4-yl)thiophen-3-yl)-2-(piperidine-1-carbonyl)benzonitrile;
piperidin-1-yl(4-(5-(6-propylpyridin-3-yl)thiophen-3-yl) phenyl)methanone;
(4-(5-(2-pentylpyridin-4-yl)thiophen-3-yl)phenyl)(piperidin-1-yl)methanone; and
(2-bromo-4-(1-methyl-2-(2-propylpyridin-4-yl)-1H-imidazol-4-yl)phenyl)(piperidin-1-yl) methanone.

In some embodiments, the compound is selected from the group consisting of:
(4-(2-(1H-indol-4-yl)thiazol-4-yl)-3-chlorophenyl)(piperidin-1-yl)methanone;
(4-(2-(2-tert-butylpyridin-4-yl)thiazol-4-yl)-3-chlorophenyl)(piperidin-1-yl)methanone;
4-(2-(1H-indol-4-yl)thiazol-4-yl)-3-chloro-N,N-dimethylbenzamide;
3-chloro-N,N-dimethyl-4-(2-(2-(piperidin-1-yl)pyridin-4-yl)thiazol-4-yl)benzamide;
(4-(5-(2-tert-butylpyridin-4-yl)thiophen-3-yl)-3-chlorophenyl)(piperidin-1-yl)methanone;
(4-(5-(2-tert-butylpyridin-4-yl)thiophen-3-yl)-3-chlorophenyl)(3,3-difluoropyrrolidin-1-yl)methanone;
(4-(5-(2-tert-butylpyridin-4-yl)thiophen-3-yl)-3-chlorophenyl)(4,4-difluoropiperidin-1-yl) methanone;
4-(5-(2-tert-butylpyridin-4-yl)thiophen-3-yl)-3-chloro-N-cyclopropylbenzamide; and
N-tert-butyl-4-(5-(2-tert-butylpyridin-4-yl)thiophen-3-yl)-3-chlorobenzamide.

The compounds described below are not intended to be limiting; rather, these embodiments and variations are intended to provide examples of compounds within the scope of Formulae (Ia) or (Ib).

Representative compounds are presented in Table 1 and Table 2.

TABLE 1
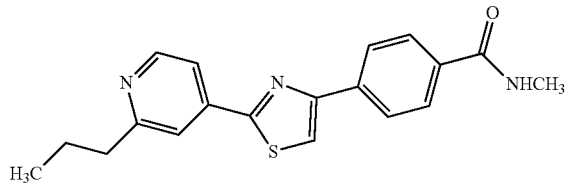 [SMILES: CCCc1cc(-c2nc(-c3ccc(C(=O)NC)cc3)cs2)ccn1] 1
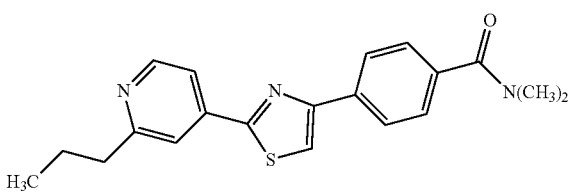 [SMILES: CCCc1cc(-c2nc(-c3ccc(C(=O)N(C)C)cc3)cs2)ccn1] 2
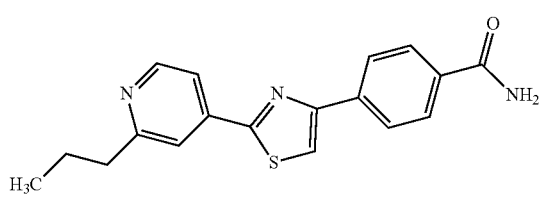 [SMILES: CCCc1cc(-c2nc(-c3ccc(C(N)=O)cc3)cs2)ccn1] 3
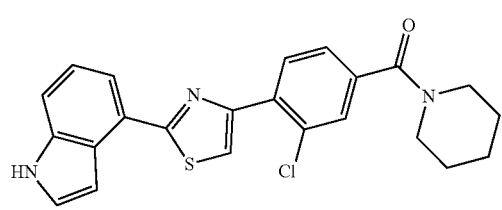 [SMILES: O=C(c1ccc(-c2csc(-c3cccc4[nH]ccc34)n2)c(Cl)c1)N1CCCCC1] 4
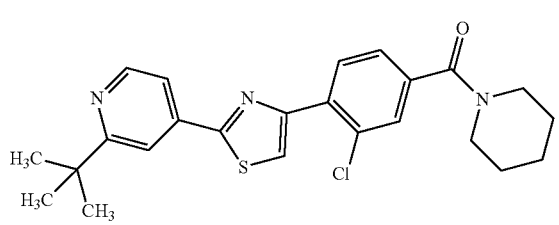 [SMILES: CC(C)(C)c1cc(-c2nc(-c3ccc(C(=O)N4CCCCC4)cc3Cl)cs2)ccn1] 5
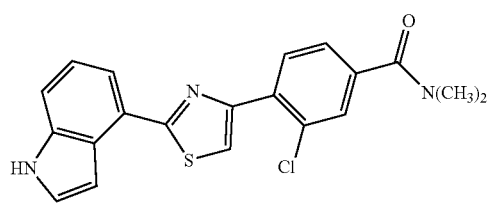 [SMILES: CN(C)C(=O)c1ccc(-c2csc(-c3cccc4[nH]ccc34)n2)c(Cl)c1] 6
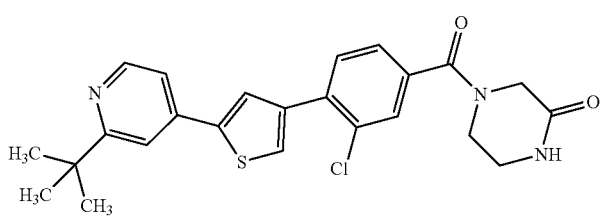 [SMILES: CC(C)(C)c1cc(-c2cc(-c3ccc(C(=O)N4CCNC(=O)C4)cc3Cl)cs2)ccn1] 7

TABLE 1-continued
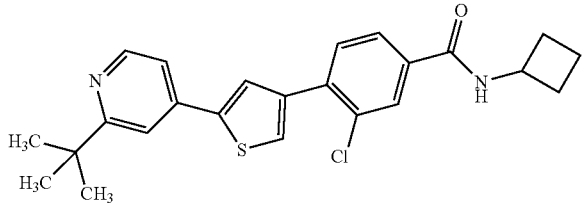 [SMILES: CC(C)(C)c1cc(-c2cc(-c3ccc(C(=O)NC4CCC4)cc3Cl)cs2)ccn1] 8
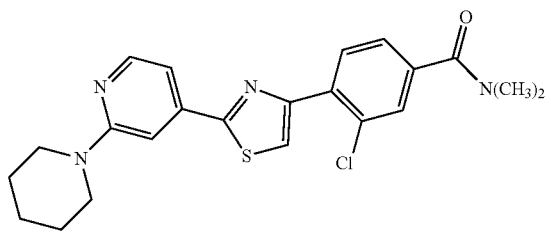 [SMILES: CN(C)C(=O)c1ccc(-c2csc(-c3ccnc(N4CCCCC4)c3)n2)c(Cl)c1] 9
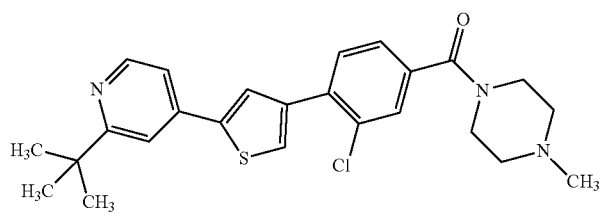 [SMILES: CN1CCN(C(=O)c2ccc(-c3csc(-c4ccnc(C(C)(C)C)c4)c3)c(Cl)c2)CC1] 10
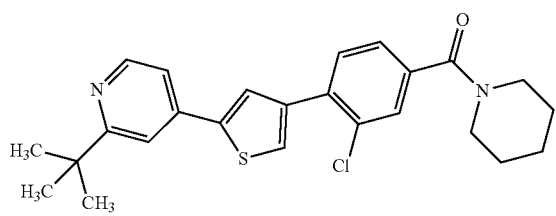 [SMILES: CC(C)(C)c1cc(-c2cc(-c3ccc(C(=O)N4CCCCC4)cc3Cl)cs2)ccn1] 11
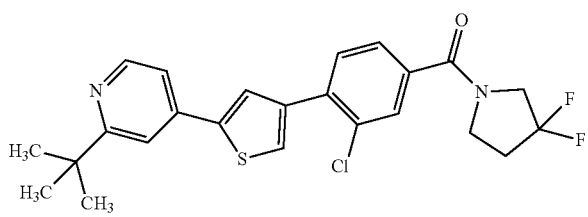 [SMILES: CC(C)(C)c1cc(-c2cc(-c3ccc(C(=O)N4CCC(F)(F)C4)cc3Cl)cs2)ccn1] 12
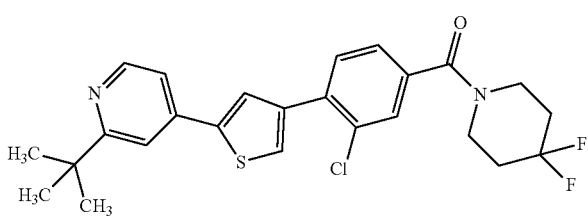 [SMILES: CC(C)(C)c1cc(-c2cc(-c3ccc(C(=O)N4CCC(F)(F)CC4)cc3Cl)cs2)ccn1] 13
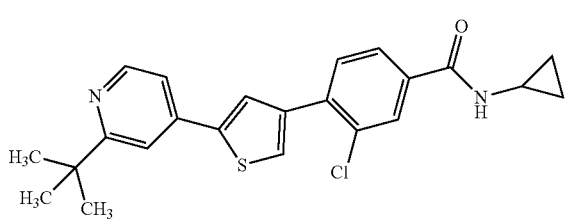 [SMILES: CC(C)(C)c1cc(-c2cc(-c3ccc(C(=O)NC4CC4)cc3Cl)cs2)ccn1] 14

TABLE 1-continued
| | |
|---|---|
| 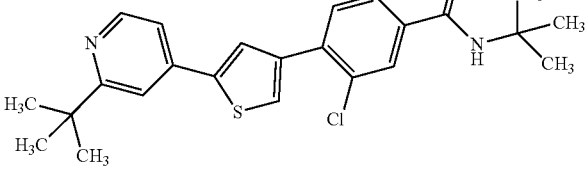 | 15 |
| 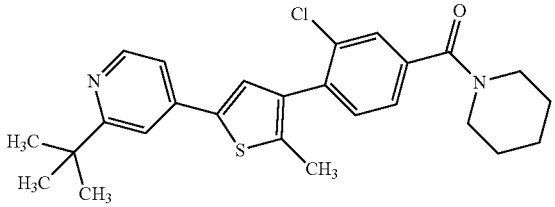 [SMILES: Cc1sc(-c2ccnc(C(C)(C)C)c2)cc1-c1ccc(C(=O)N2CCCCC2)cc1Cl] | 16 |
| 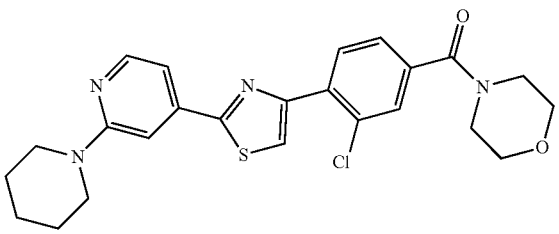 [SMILES: O=C(c1ccc(-c2csc(-c3ccnc(N4CCCCC4)c3)n2)c(Cl)c1)N1CCOCC1] | 17 |
| 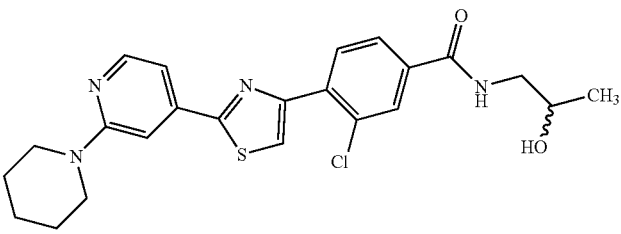 [SMILES: CC(O)CNC(=O)c1ccc(-c2csc(-c3ccnc(N4CCCCC4)c3)n2)c(Cl)c1] | 18 18a, 18b |
| 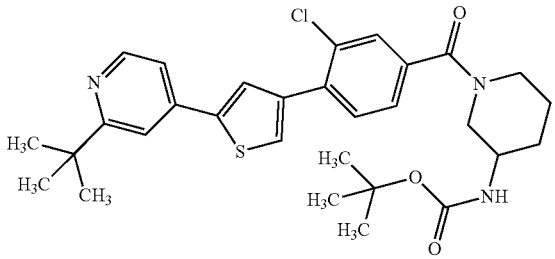 [SMILES: CC(C)(C)OC(=O)NC1CCCN(C(=O)c2ccc(-c3csc(-c4ccnc(C(C)(C)C)c4)c3)c(Cl)c2)C1] | 19 19a, 19b |
| 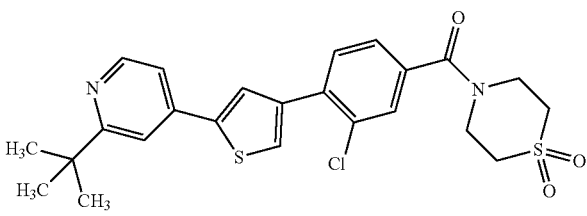 [SMILES: CC(C)(C)c1cc(-c2cc(-c3ccc(C(=O)N4CCS(=O)(=O)CC4)cc3Cl)cs2)ccn1] | 20 |
| 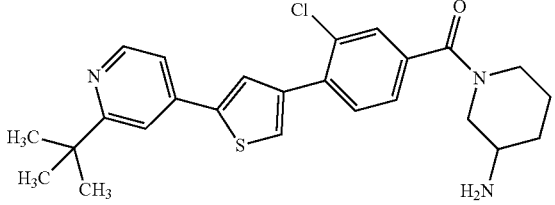 [SMILES: CC(C)(C)c1cc(-c2cc(-c3ccc(C(=O)N4CCCC(N)C4)cc3Cl)cs2)ccn1] | 21 21, 21b |

TABLE 1-continued
| | |
|---|---|
| 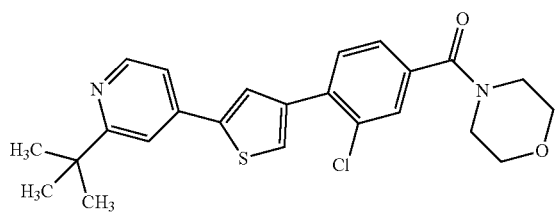 | 22 |
| 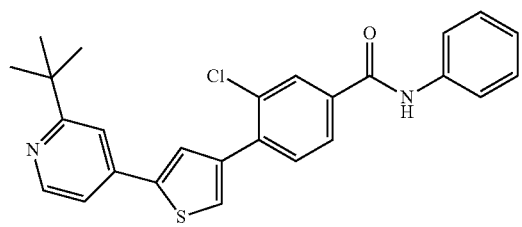 [SMILES: CC(C)(C)c1cc(-c2cc(-c3ccc(C(=O)Nc4ccccc4)cc3Cl)cs2)ccn1] | 23 |
| 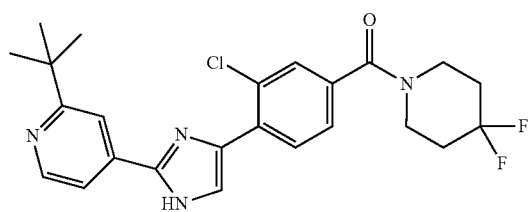 [SMILES: CC(C)(C)c1cc(-c2nc(-c3ccc(C(=O)N4CCC(F)(F)CC4)cc3Cl)c[nH]2)ccn1] | 24 |
| 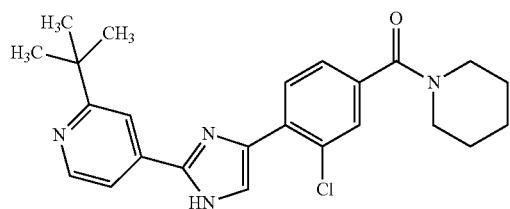 | 25 |
| 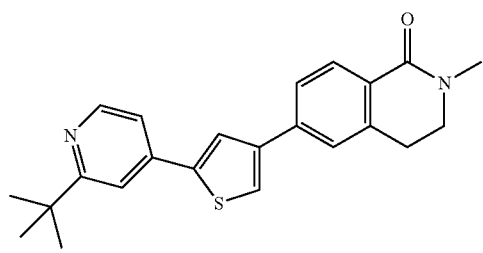 [SMILES: CN1CCc2cc(-c3csc(-c4ccnc(C(C)(C)C)c4)c3)ccc2C1=O] | 26 |
| 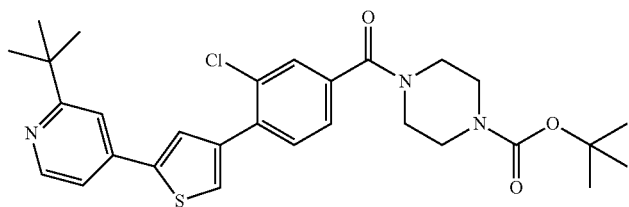 [SMILES: CC(C)(C)OC(=O)N1CCN(C(=O)c2ccc(-c3csc(-c4ccnc(C(C)(C)C)c4)c3)c(Cl)c2)CC1] | 27 |
|  | 28 |

TABLE 1-continued
| | |
|---|---|
| 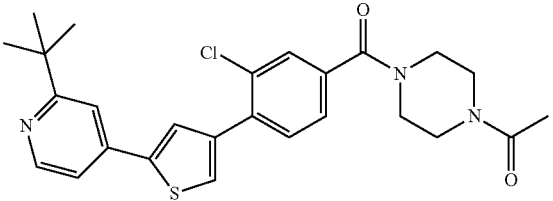 [SMILES: CC(=O)N1CCN(C(=O)c2ccc(-c3csc(-c4ccnc(C(C)(C)C)c4)c3)c(Cl)c2)CC1] | 29 |
| 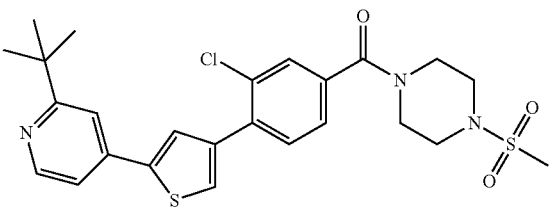 [SMILES: CC(C)(C)c1cc(-c2cc(-c3ccc(C(=O)N4CCN(S(C)(=O)=O)CC4)cc3Cl)cs2)ccn1] | 30 |
| 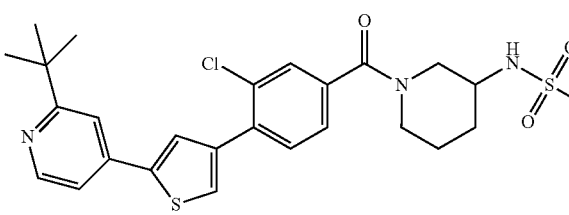 | 31 31a, 31b |
| 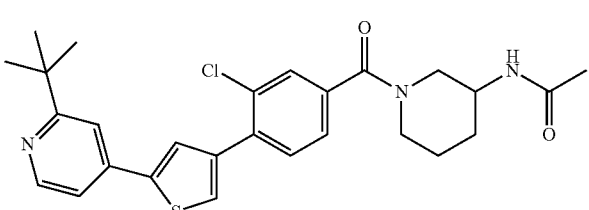 | 32 32a, 32b |
| 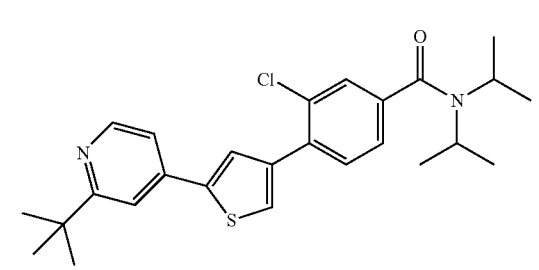 [SMILES: CC(C)N(C(=O)c1ccc(-c2csc(-c3ccnc(C(C)(C)C)c3)c2)c(Cl)c1)C(C)C] | 33 |
| 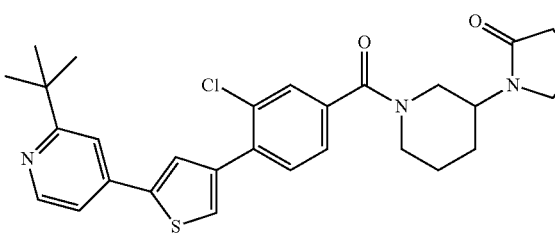 | 34 34a, 34b |
| 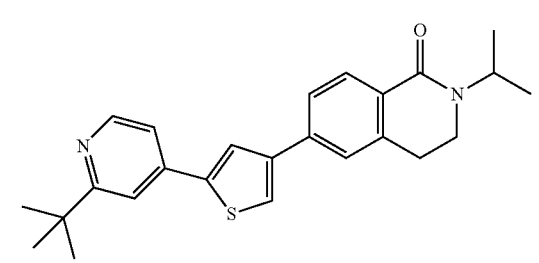 [SMILES: CC(C)N1CCc2cc(-c3csc(-c4ccnc(C(C)(C)C)c4)c3)ccc2C1=O] | 35 |

TABLE 1-continued
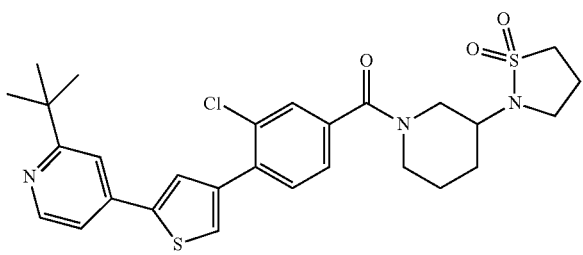 [SMILES: CC(C)(C)c1cc(-c2cc(-c3ccc(C(=O)N4CCCC(N5CCCS5(=O)=O)C4)cc3Cl)cs2)ccn1] 36 36a, 36b
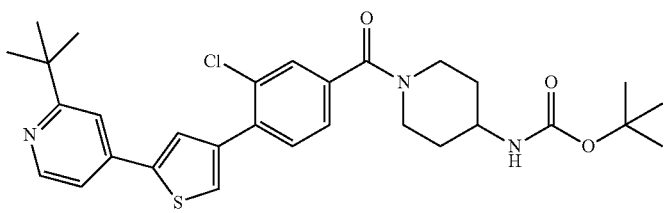 [SMILES: CC(C)(C)OC(=O)NC1CCN(C(=O)c2ccc(-c3csc(-c4ccnc(C(C)(C)C)c4)c3)c(Cl)c2)CC1] 37
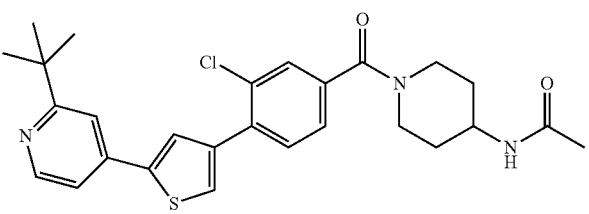 [SMILES: CC(=O)NC1CCN(C(=O)c2ccc(-c3csc(-c4ccnc(C(C)(C)C)c4)c3)c(Cl)c2)CC1] 38
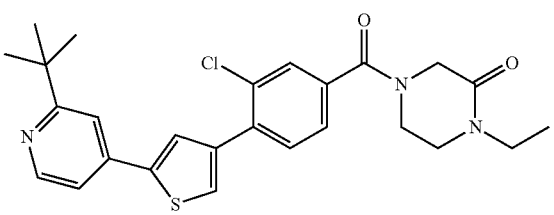 [SMILES: CCN1CCN(C(=O)c2ccc(-c3csc(-c4ccnc(C(C)(C)C)c4)c3)c(Cl)c2)CC1=O] 39
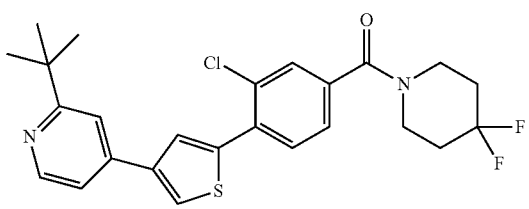 [SMILES: CC(C)(C)c1cc(-c2csc(-c3ccc(C(=O)N4CCC(F)(F)CC4)cc3Cl)c2)ccn1] 40
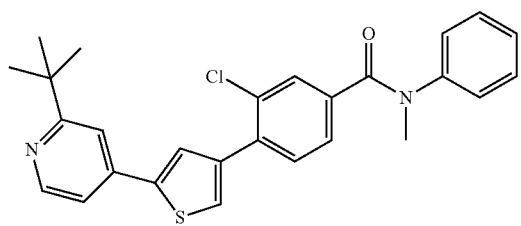 [SMILES: CN(C(=O)c1ccc(-c2csc(-c3ccnc(C(C)(C)C)c3)c2)c(Cl)c1)c1ccccc1] 41
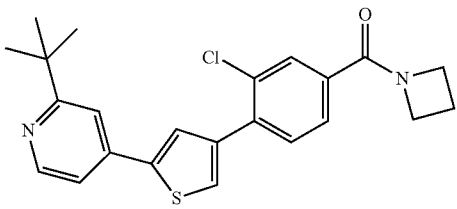 [SMILES: CC(C)(C)c1cc(-c2cc(-c3ccc(C(=O)N4CCC4)cc3Cl)cs2)ccn1] 42

TABLE 1-continued
| | |
|---|---|
| 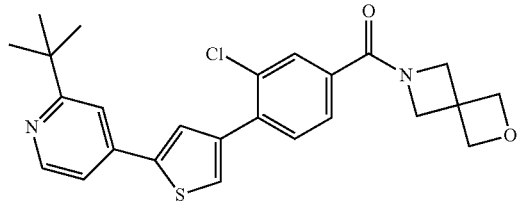 [SMILES: CC(C)(C)c1cc(-c2cc(-c3ccc(C(=O)N4CC5(COC5)C4)cc3Cl)cs2)ccn1] | 43 |
| 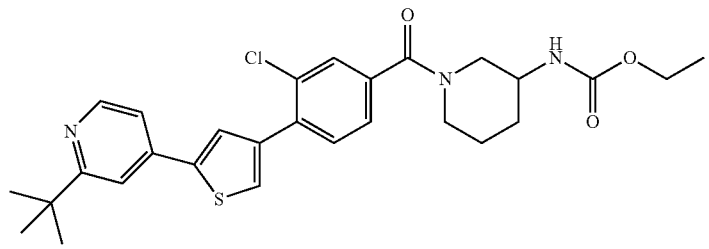 [SMILES: CCOC(=O)NC1CCCN(C(=O)c2ccc(-c3csc(-c4ccnc(C(C)(C)C)c4)c3)c(Cl)c2)C1] | 44 44a, 44b |
| 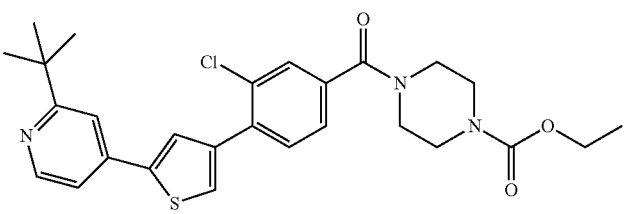 [SMILES: CCOC(=O)N1CCN(C(=O)c2ccc(-c3csc(-c4ccnc(C(C)(C)C)c4)c3)c(Cl)c2)CC1] | 45 |
| 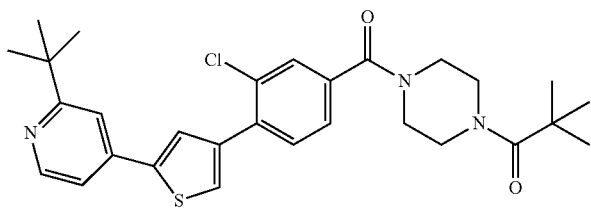 [SMILES: CC(C)(C)C(=O)N1CCN(C(=O)c2ccc(-c3csc(-c4ccnc(C(C)(C)C)c4)c3)c(Cl)c2)CC1] | 46 |
| 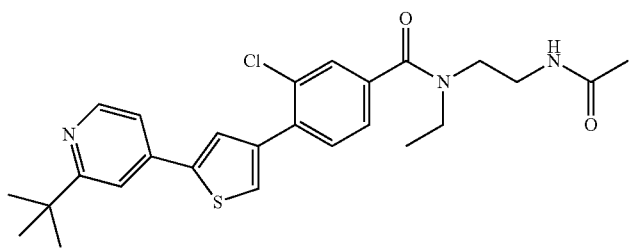 [SMILES: CCN(CCNC(C)=O)C(=O)c1ccc(-c2csc(-c3ccnc(C(C)(C)C)c3)c2)c(Cl)c1] | 47 |
| 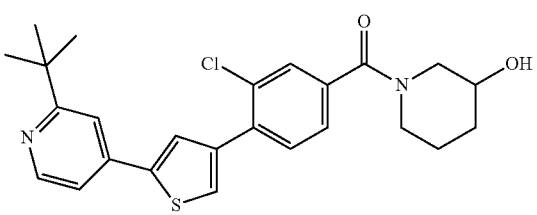 [SMILES: CC(C)(C)c1cc(-c2cc(-c3ccc(C(=O)N4CCCC(O)C4)cc3Cl)cs2)ccn1] | 48 48a, 48b |
| 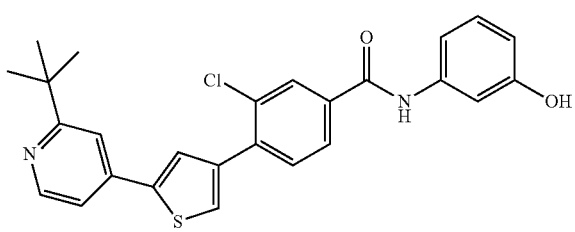 [SMILES: CC(C)(C)c1cc(-c2cc(-c3ccc(C(=O)Nc4cccc(O)c4)cc3Cl)cs2)ccn1] | 49 |

TABLE 1-continued

| | |
|---|---|
| (structure) | 50 50a, 50b, 50c |
| (structure) | 51 |
| (structure) | 52 |
| (structure) | 53 |
| (structure) | 54 |
| (structure) | 55 55a, 55b |

TABLE 1-continued
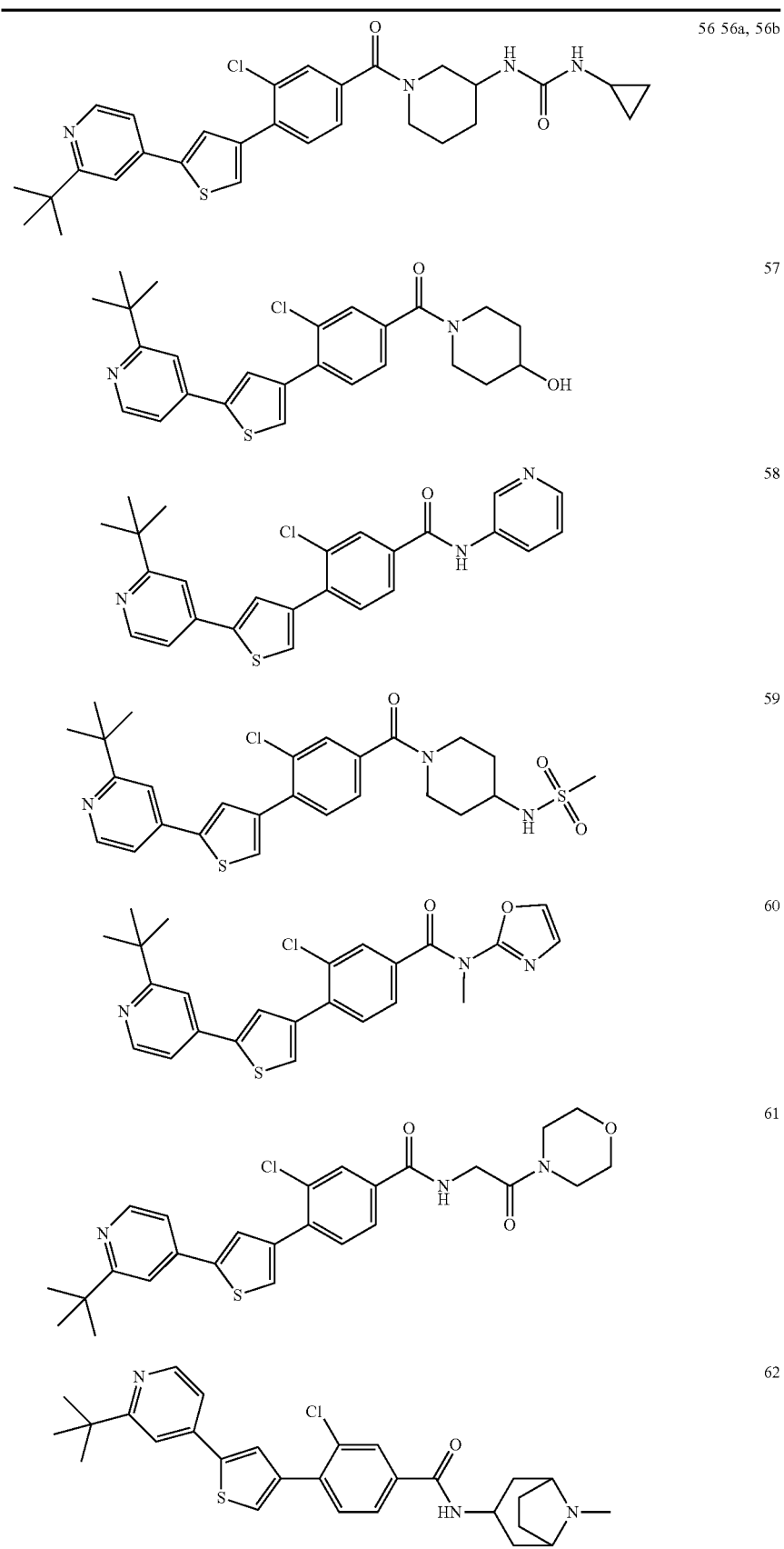
56 56a, 56b
57
58
59
60
61
62

TABLE 1-continued
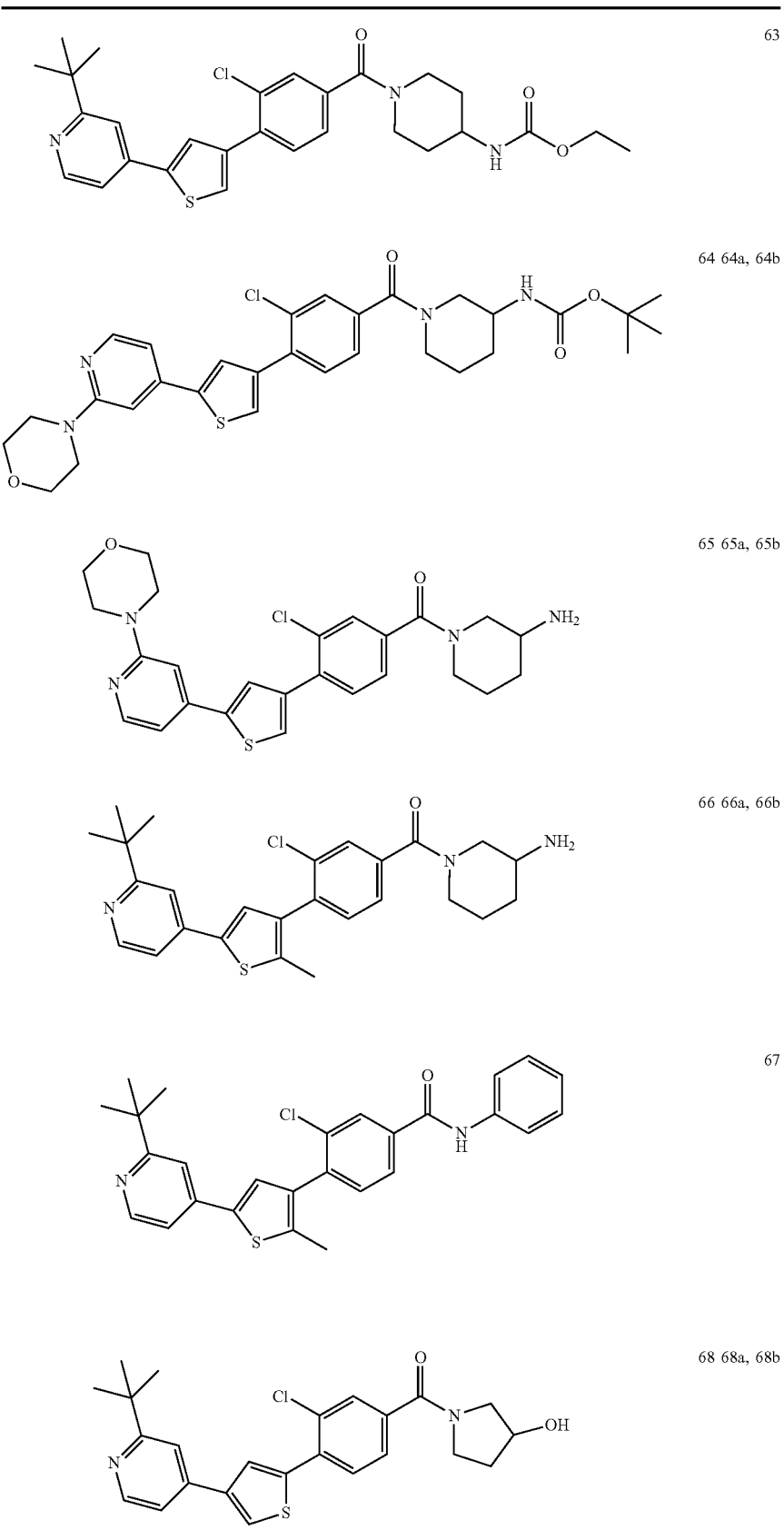
63
64 64a, 64b
65 65a, 65b
66 66a, 66b
67
68 68a, 68b TABLE 1-continued
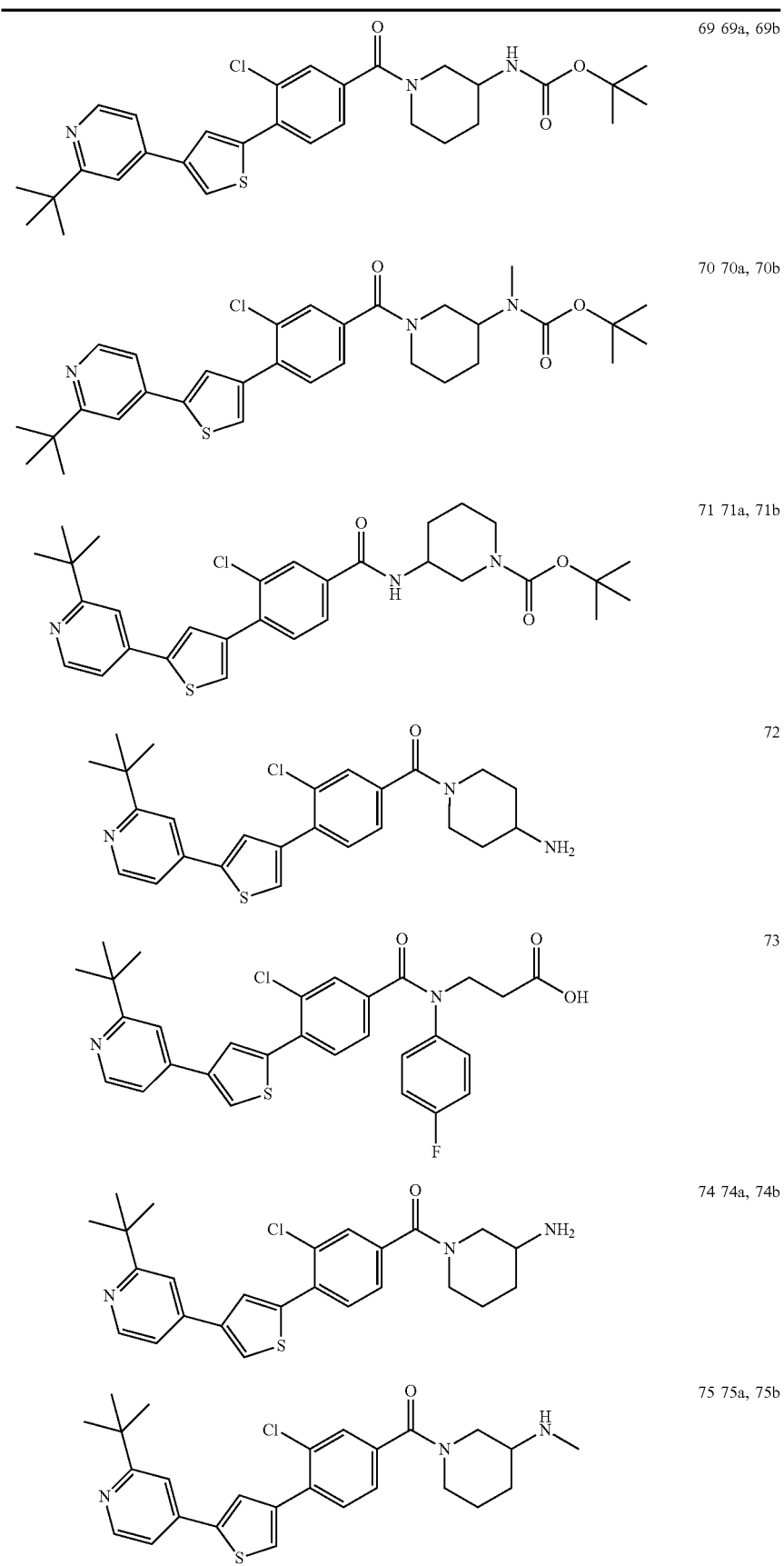
| | |
|---|---|
| 69 | 69a, 69b |
| 70 | 70a, 70b |
| 71 | 71a, 71b |
| 72 | |
| 73 | |
| 74 | 74a, 74b |
| 75 | 75a, 75b |

TABLE 1-continued
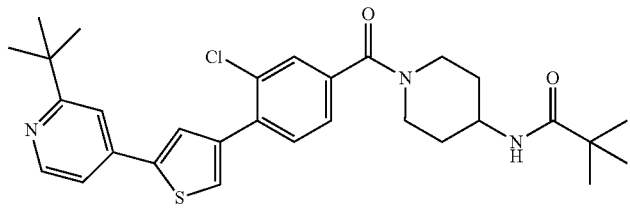 [SMILES: CC(C)(C)C(=O)NC1CCN(C(=O)c2ccc(-c3csc(-c4ccnc(C(C)(C)C)c4)c3)c(Cl)c2)CC1] 76
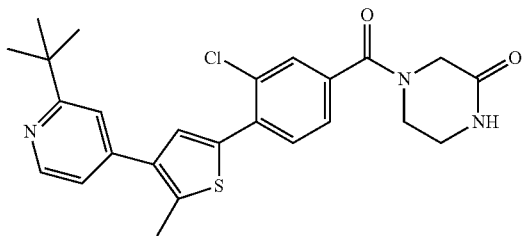 [SMILES: Cc1sc(-c2ccc(C(=O)N3CCNC(=O)C3)cc2Cl)cc1-c1ccnc(C(C)(C)C)c1] 77
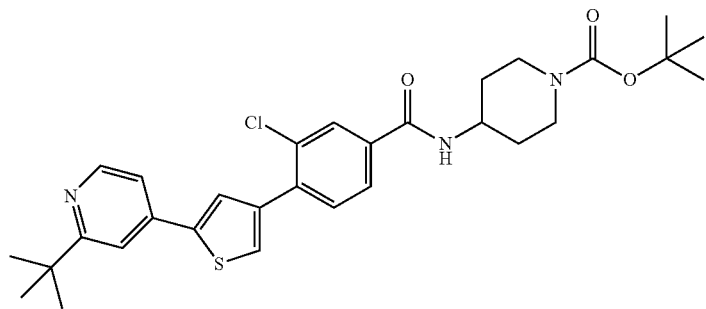 [SMILES: CC(C)(C)OC(=O)N1CCC(NC(=O)c2ccc(-c3csc(-c4ccnc(C(C)(C)C)c4)c3)c(Cl)c2)CC1] 78
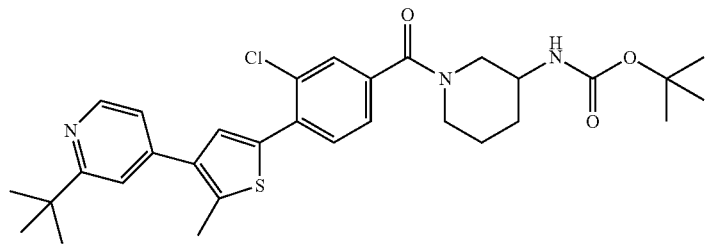 [SMILES: Cc1sc(-c2ccc(C(=O)N3CCCC(NC(=O)OC(C)(C)C)C3)cc2Cl)cc1-c1ccnc(C(C)(C)C)c1] 79 79a, 79b
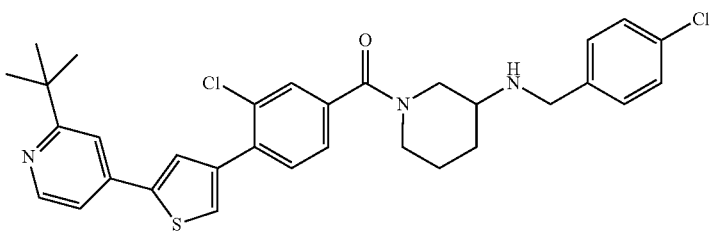 [SMILES: CC(C)(C)c1cc(-c2cc(-c3ccc(C(=O)N4CCCC(NCc5ccc(Cl)cc5)C4)cc3Cl)cs2)ccn1] 80 80a, 80b
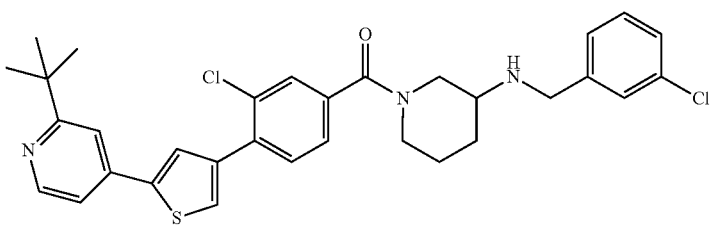 [SMILES: CC(C)(C)c1cc(-c2cc(-c3ccc(C(=O)N4CCCC(NCc5cccc(Cl)c5)C4)cc3Cl)cs2)ccn1] 81 81a, 81b TABLE 1-continued
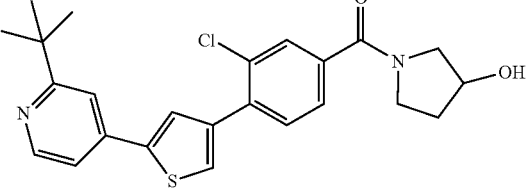
82 82a, 82b
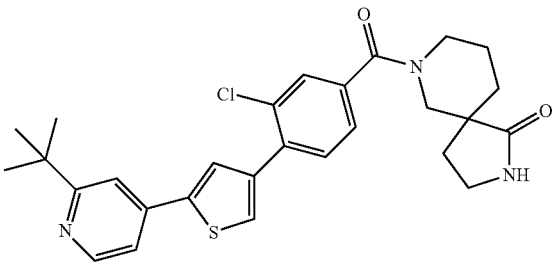 [SMILES: CC(C)(C)c1cc(-c2cc(-c3ccc(C(=O)N4CCCC5(CCNC5=O)C4)cc3Cl)cs2)ccn1]
83 83a, 83b
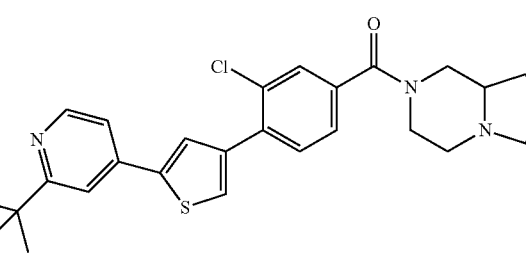
84 84a, 84b
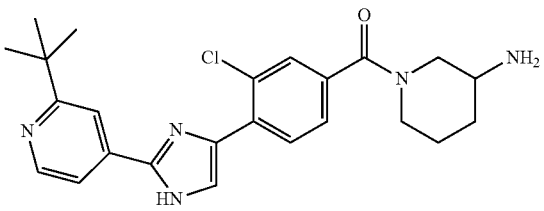 [SMILES: CC(C)(C)c1cc(-c2nc(-c3ccc(C(=O)N4CCCC(N)C4)cc3Cl)c[nH]2)ccn1]
85 85a, 85b
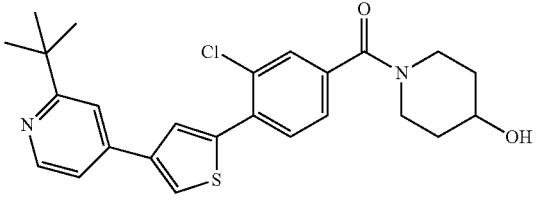 [SMILES: CC(C)(C)c1cc(-c2csc(-c3ccc(C(=O)N4CCC(O)CC4)cc3Cl)c2)ccn1]
86
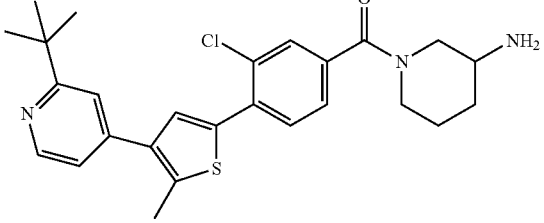
87 87a, 87b
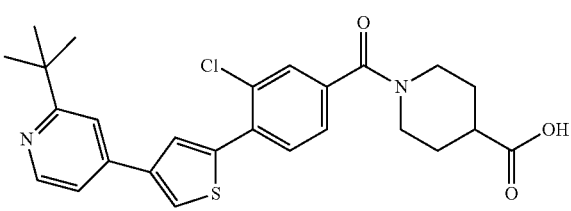 [SMILES: CC(C)(C)c1cc(-c2csc(-c3ccc(C(=O)N4CCC(C(=O)O)CC4)cc3Cl)c2)ccn1]
88

TABLE 1-continued
| | |
|---|---|
| 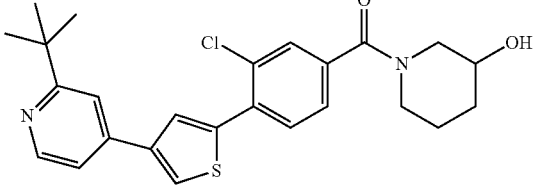 | 89 89a, 89b |
| 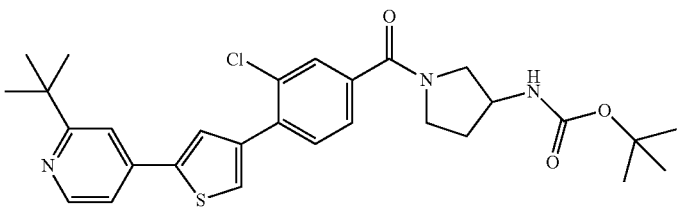 [SMILES: CC(C)(C)OC(=O)NC1CCN(C(=O)c2ccc(-c3csc(-c4ccnc(C(C)(C)C)c4)c3)c(Cl)c2)C1] | 90 90a, 90b |
| 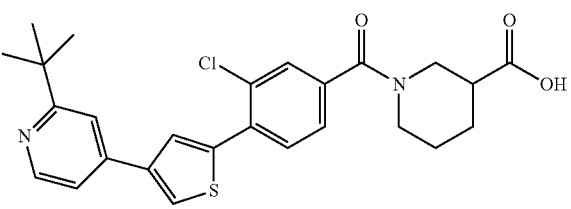 [SMILES: CC(C)(C)c1cc(-c2csc(-c3ccc(C(=O)N4CCCC(C(=O)O)C4)cc3Cl)c2)ccn1] | 91 91a, 91b |
| 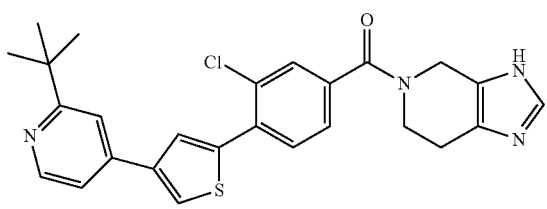 [SMILES: CC(C)(C)c1cc(-c2csc(-c3ccc(C(=O)N4CCc5nc[nH]c5C4)cc3Cl)c2)ccn1] | 92 |
| 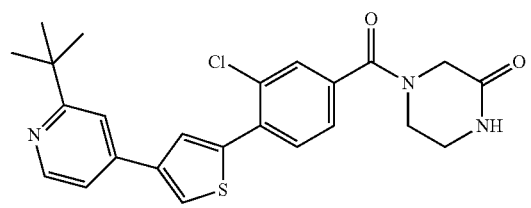 [SMILES: CC(C)(C)c1cc(-c2csc(-c3ccc(C(=O)N4CCNC(=O)C4)cc3Cl)c2)ccn1] | 93 |
| 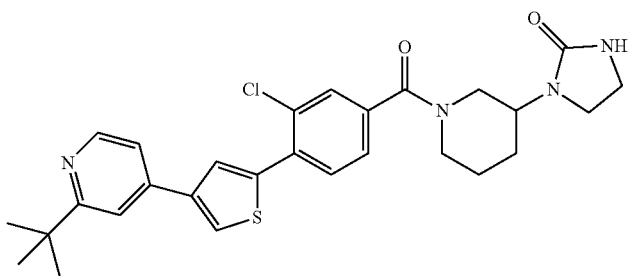 [SMILES: CC(C)(C)c1cc(-c2csc(-c3ccc(C(=O)N4CCCC(N5CCNC5=O)C4)cc3Cl)c2)ccn1] | 94 94a, 94b |
| 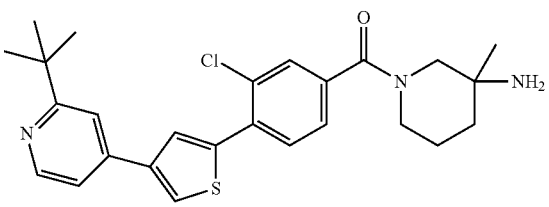 [SMILES: CC1(N)CCCN(C(=O)c2ccc(-c3cc(-c4ccnc(C(C)(C)C)c4)cs3)c(Cl)c2)C1] | 95 95a, 95b |

TABLE 1-continued
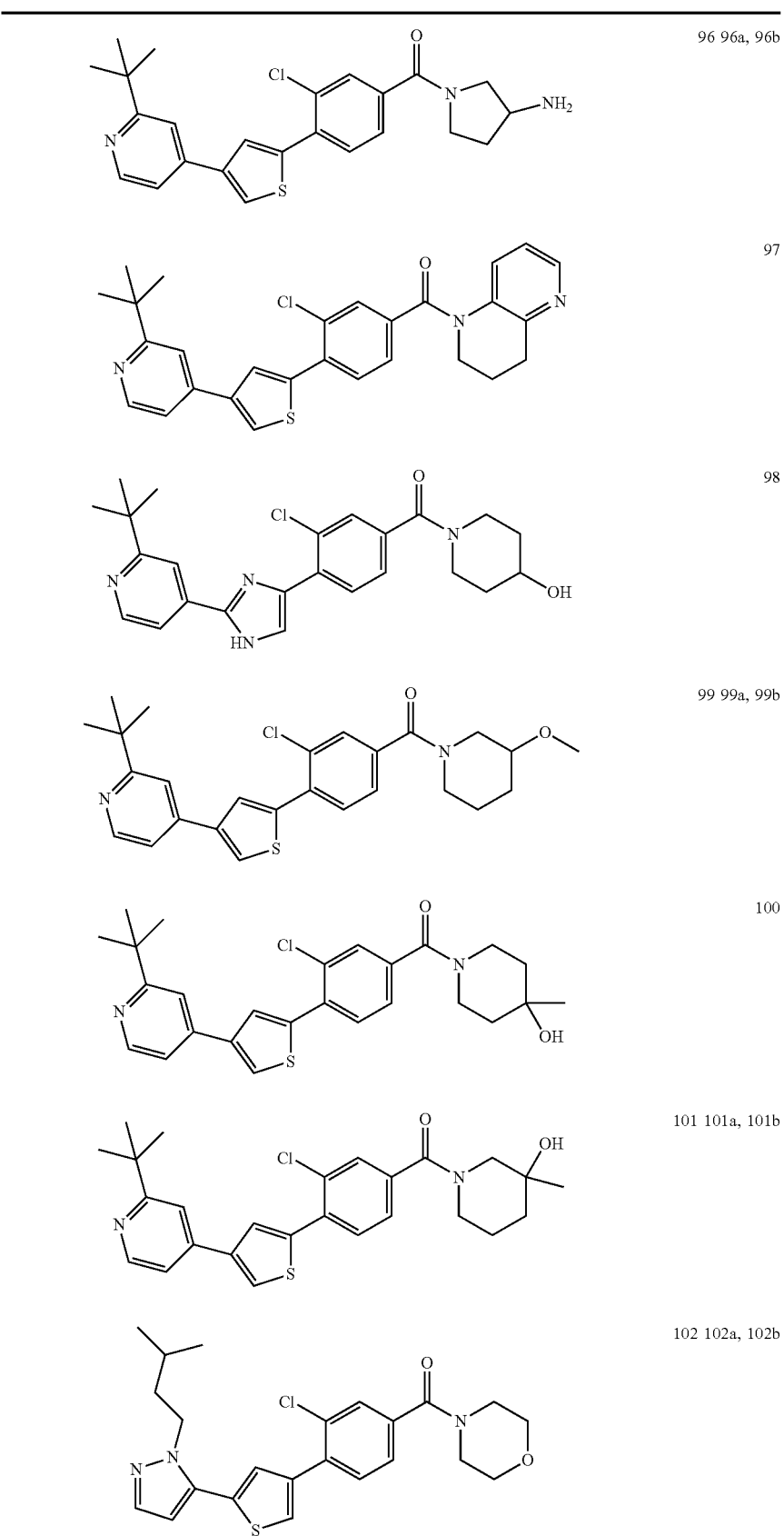

TABLE 1-continued
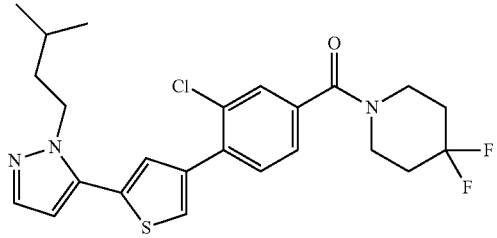 [SMILES: CC(C)CCn1nccc1-c1cc(-c2ccc(C(=O)N3CCC(F)(F)CC3)cc2Cl)cs1]
103
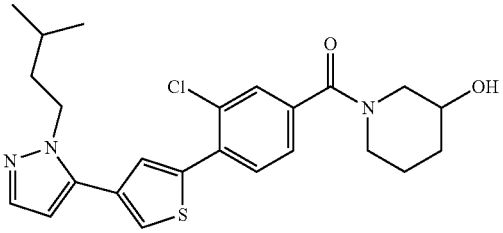 [SMILES: CC(C)CCn1nccc1-c1csc(-c2ccc(C(=O)N3CCCC(O)C3)cc2Cl)c1]
104 104, 104b
TABLE 2
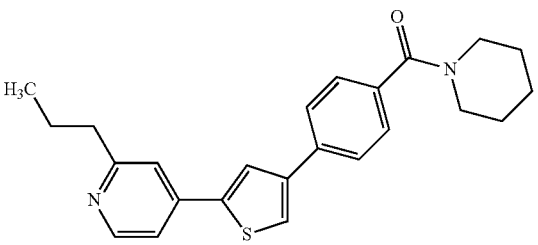 [SMILES: CCCc1cc(-c2cc(-c3ccc(C(=O)N4CCCCC4)cc3)cs2)ccn1]
2.1
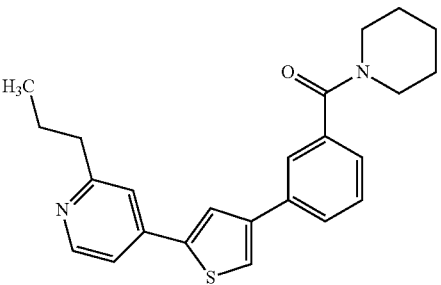 [SMILES: CCCc1cc(-c2cc(-c3cccc(C(=O)N4CCCCC4)c3)cs2)ccn1]
2.2
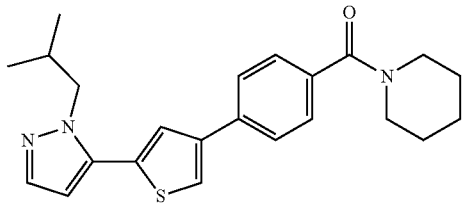 [SMILES: CC(C)Cn1nccc1-c1cc(-c2ccc(C(=O)N3CCCCC3)cc2)cs1]
2.3
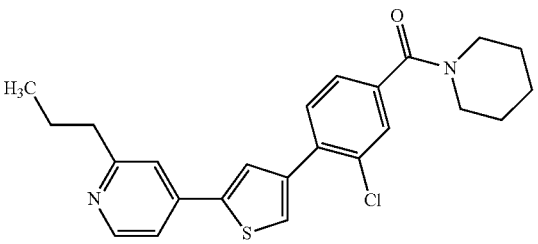 [SMILES: CCCc1cc(-c2cc(-c3ccc(C(=O)N4CCCCC4)cc3Cl)cs2)ccn1]
2.4

TABLE 2-continued
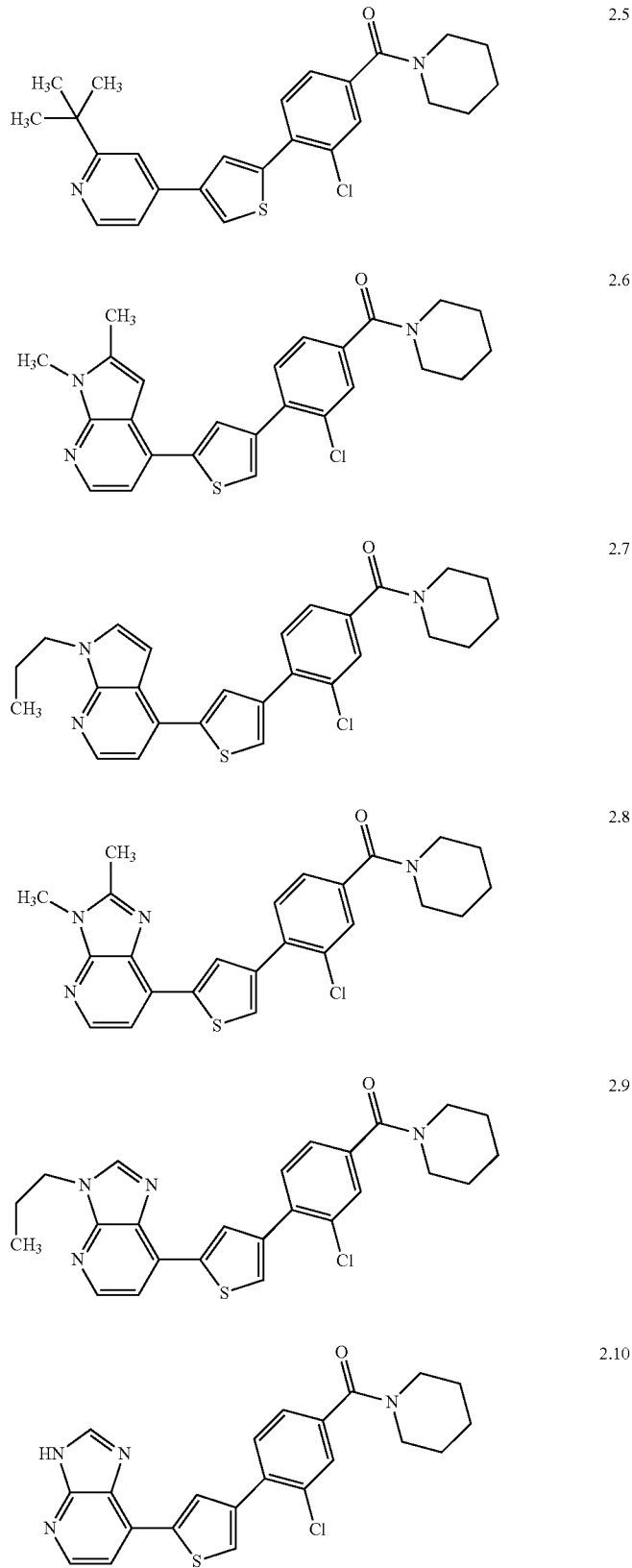

TABLE 2-continued
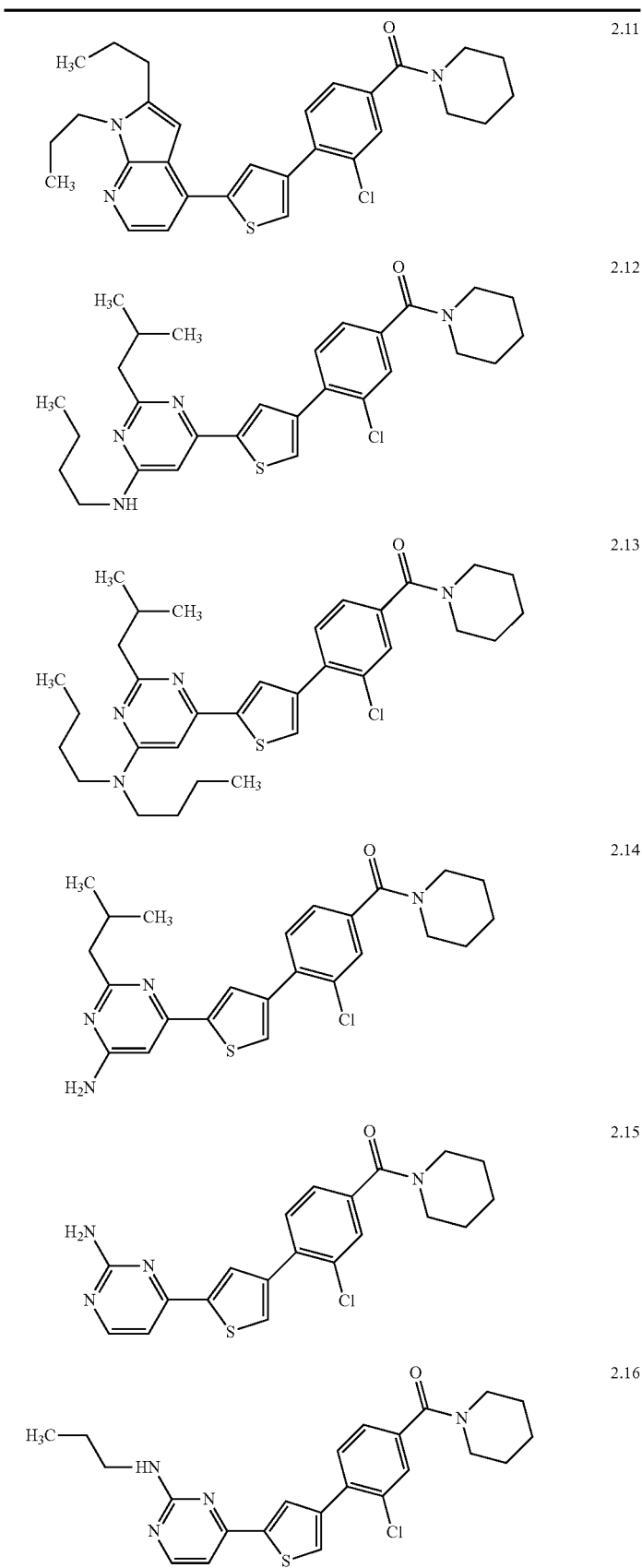

TABLE 2-continued
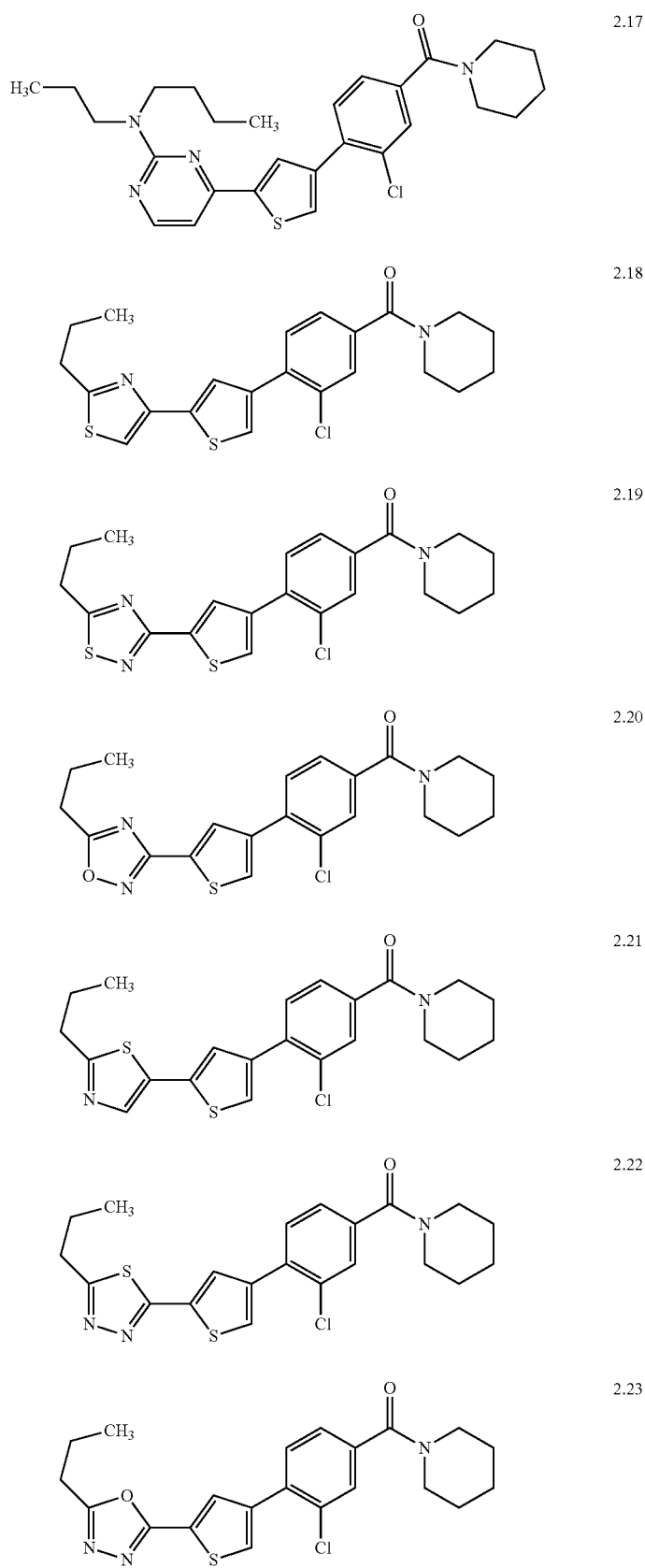

TABLE 2-continued
| | |
|---|---|
| 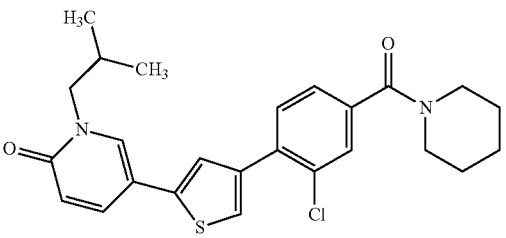 [SMILES: CC(C)Cn1cc(-c2cc(-c3ccc(C(=O)N4CCCCC4)cc3Cl)cs2)ccc1=O] | 2.24 |
| 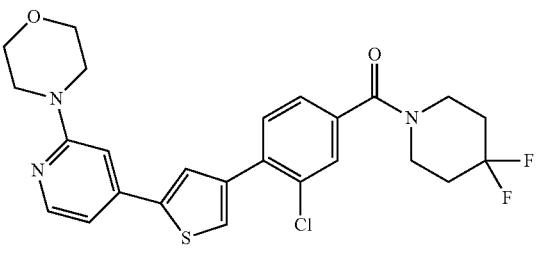 [SMILES: O=C(c1ccc(-c2csc(-c3ccnc(N4CCOCC4)c3)c2)c(Cl)c1)N1CCC(F)(F)CC1] | 2.25 |
| 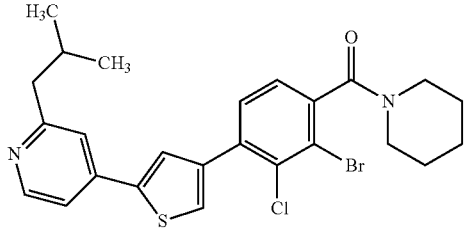 [SMILES: CC(C)Cc1cc(-c2cc(-c3ccc(C(=O)N4CCCCC4)c(Br)c3Cl)cs2)ccn1] | 2.26 |
| 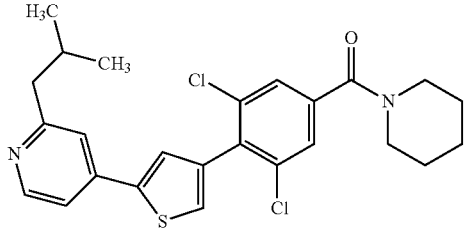 [SMILES: CC(C)Cc1cc(-c2cc(-c3c(Cl)cc(C(=O)N4CCCCC4)cc3Cl)cs2)ccn1] | 2.27 |
| 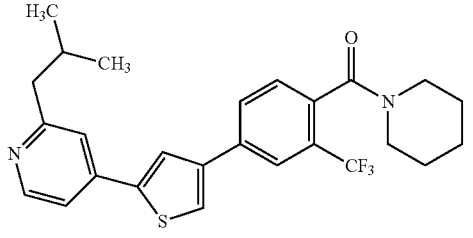 [SMILES: CC(C)Cc1cc(-c2cc(-c3ccc(C(=O)N4CCCCC4)c(C(F)(F)F)c3)cs2)ccn1] | 2.28 |
| 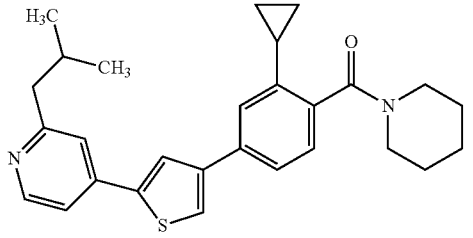 [SMILES: CC(C)Cc1cc(-c2cc(-c3ccc(C(=O)N4CCCCC4)c(C4CC4)c3)cs2)ccn1] | 2.29 |

TABLE 2-continued

| (structure) | 2.30 |
| (structure) | 2.31 |
| (structure) | 2.32 |
| (structure) | 2.33 |
| (structure) | 2.34 |
| (structure) | 2.35 |

TABLE 2-continued
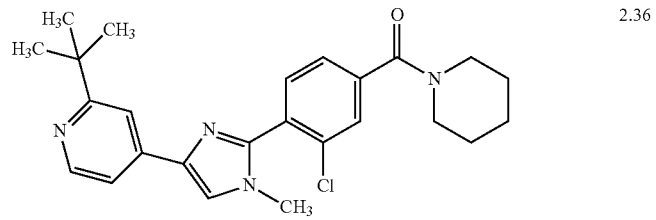 2.36
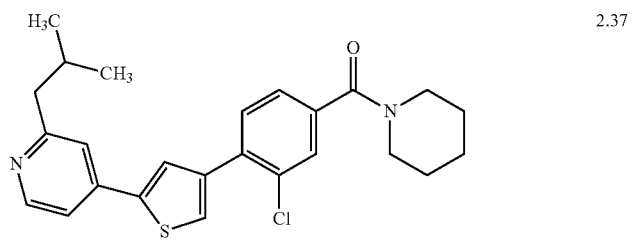 2.37
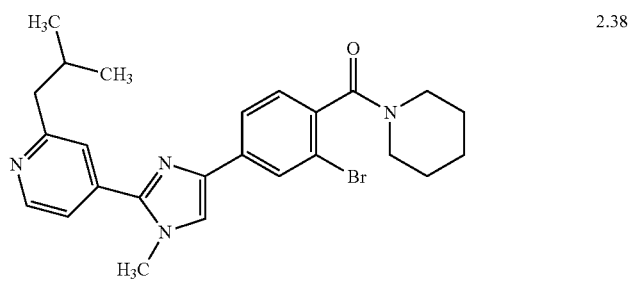 2.38
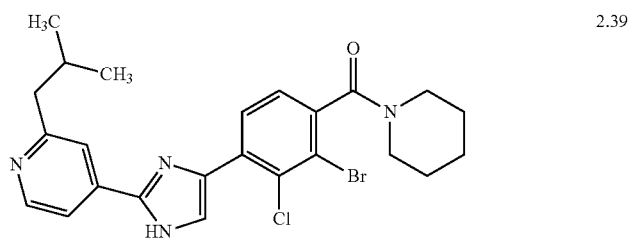 2.39
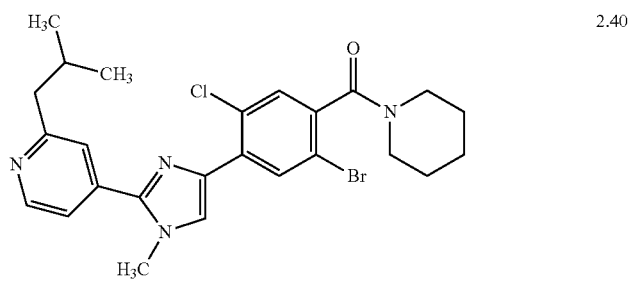 2.40
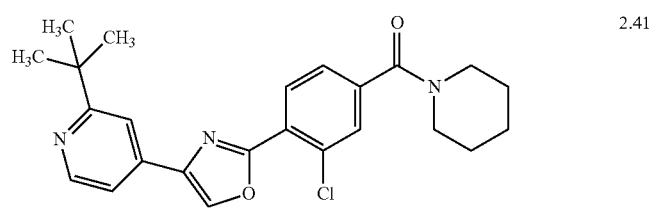 2.41

TABLE 2-continued
| | |
|---|---|
| 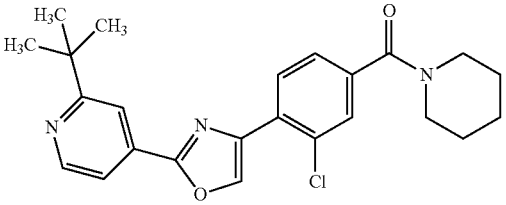 [SMILES: CC(C)(C)c1cc(-c2nc(-c3ccc(C(=O)N4CCCCC4)cc3Cl)co2)ccn1] | 2.42 |
| 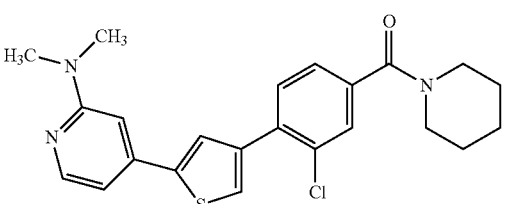 | 2.43 |
| 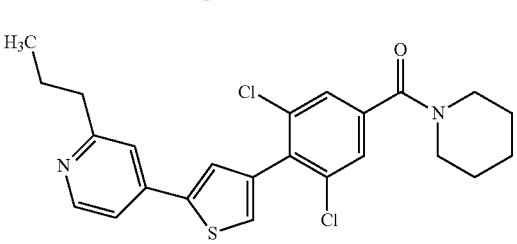 | 2.44 |
| 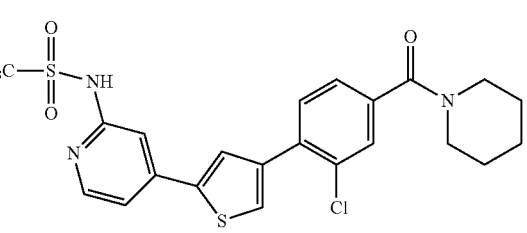 | 2.45 |
| 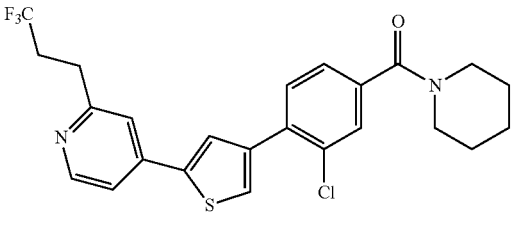 [SMILES: O=C(c1ccc(-c2csc(-c3ccnc(CCC(F)(F)F)c3)c2)c(Cl)c1)N1CCCCC1] | 2.46 |
| 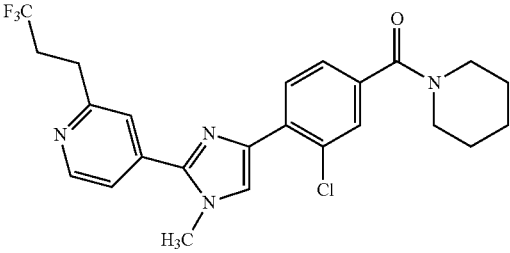 [SMILES: Cn1cc(-c2ccc(C(=O)N3CCCCC3)cc2Cl)nc1-c1ccnc(CCC(F)(F)F)c1] | 2.47 |
| 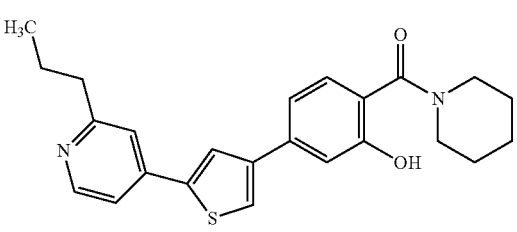 | 2.48 |

TABLE 2-continued
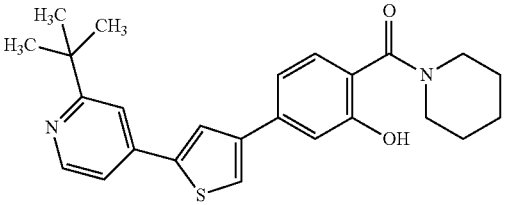 [SMILES: CC(C)(C)c1cc(-c2cc(-c3ccc(C(=O)N4CCCCC4)c(O)c3)cs2)ccn1] 2.49
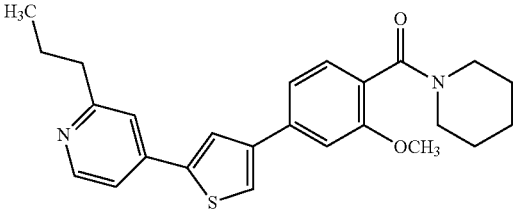 2.50
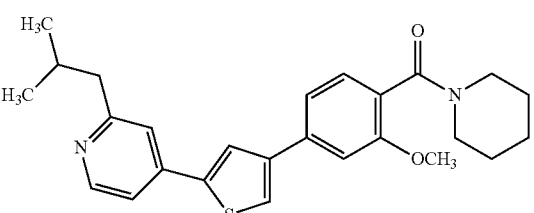 2.51
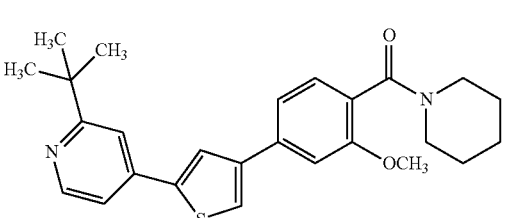 2.52
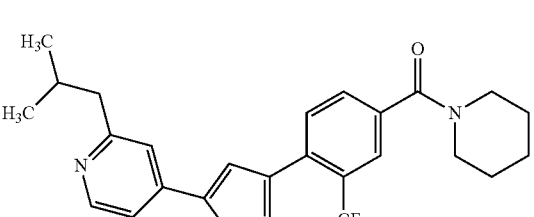 2.53
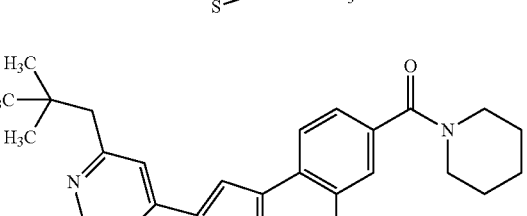 2.54
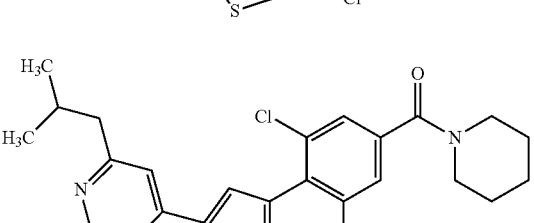 2.55

TABLE 2-continued
| 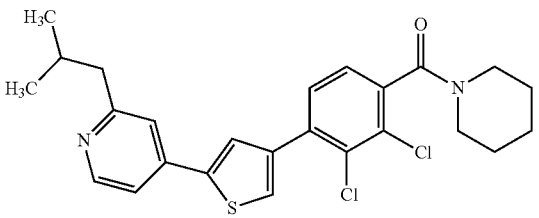 [SMILES: CC(C)Cc1cc(-c2cc(-c3ccc(C(=O)N4CCCCC4)c(Cl)c3Cl)cs2)ccn1] | 2.56 |
| 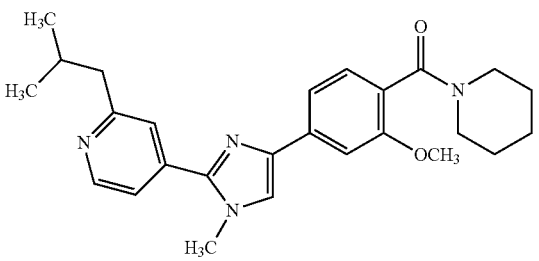 [SMILES: COc1cc(-c2cn(C)c(-c3ccnc(CC(C)C)c3)n2)ccc1C(=O)N1CCCCC1] | 2.57 |
| 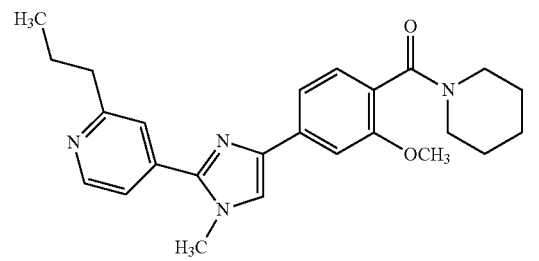 [SMILES: CCCc1cc(-c2nc(-c3ccc(C(=O)N4CCCCC4)c(OC)c3)cn2C)ccn1] | 2.58 |
| 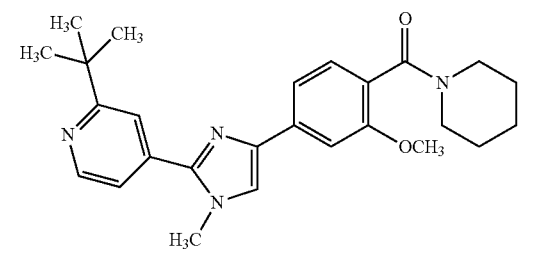 [SMILES: COc1cc(-c2cn(C)c(-c3ccnc(C(C)(C)C)c3)n2)ccc1C(=O)N1CCCCC1] | 2.59 |
| 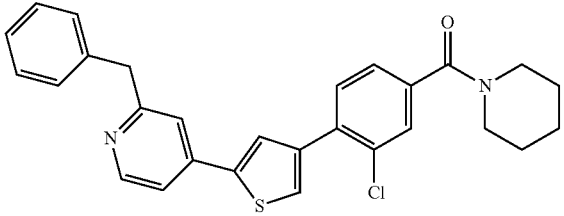 [SMILES: O=C(c1ccc(-c2csc(-c3ccnc(Cc4ccccc4)c3)c2)c(Cl)c1)N1CCCCC1] | 2.60 |
| 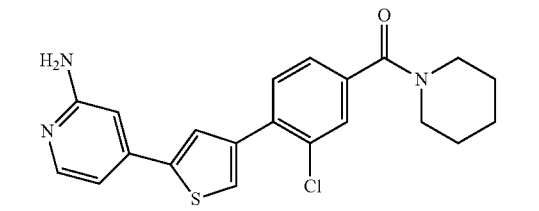 | 2.61 |

TABLE 2-continued
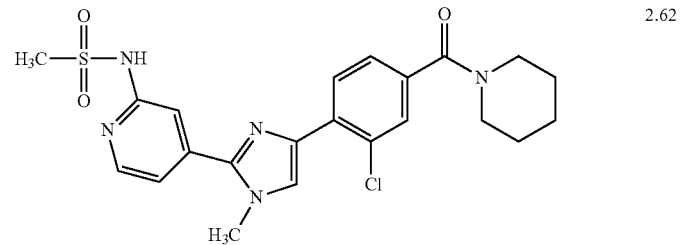 2.62
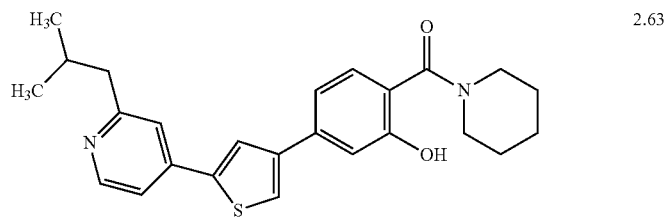 2.63
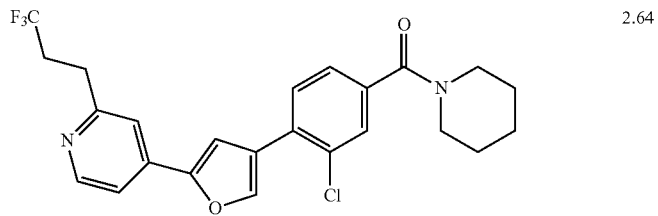 2.64
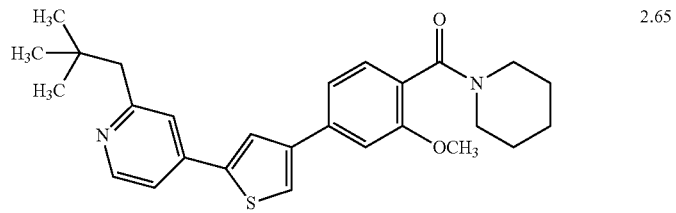 2.65
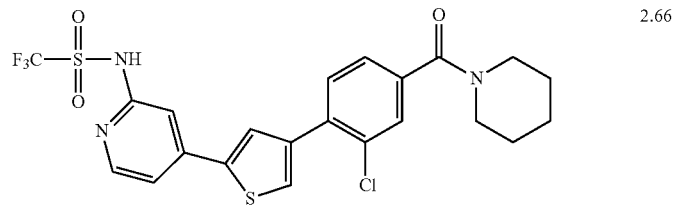 2.66
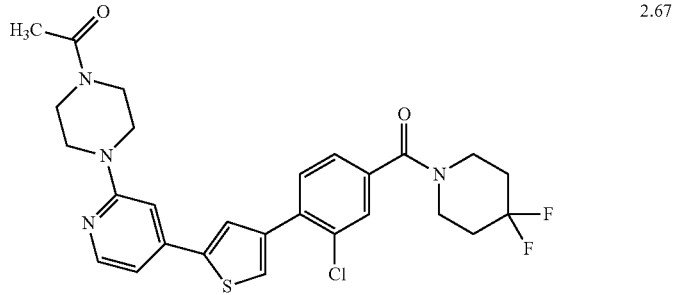 2.67

TABLE 2-continued

| Structure | # |
|---|---|
| (structure) | 2.68 |
| (structure) | 2.69 |
| (structure) | 2.70 |
| (structure) | 2.71 |
| (structure) | 2.72 |
| (structure) | 2.73 |
| (structure) | 2.74 |

TABLE 2-continued
| | |
|---|---|
| 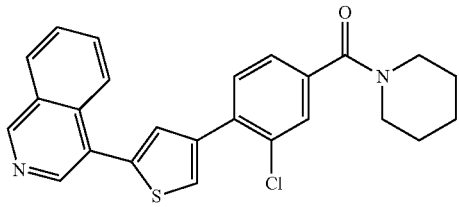 [SMILES: O=C(c1ccc(-c2csc(-c3cncc4ccccc34)c2)c(Cl)c1)N1CCCCC1] | 2.75 |
| 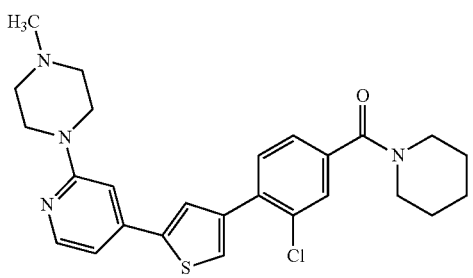 [SMILES: CN1CCN(c2cc(-c3cc(-c4ccc(C(=O)N5CCCCC5)cc4Cl)cs3)ccn2)CC1] | 2.76 |
| 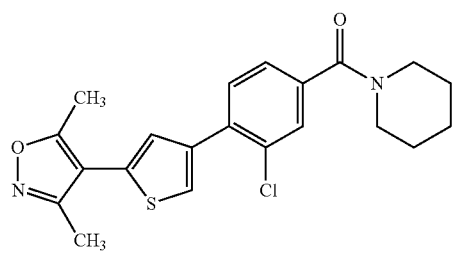 [SMILES: Cc1noc(C)c1-c1cc(-c2ccc(C(=O)N3CCCCC3)cc2Cl)cs1] | 2.77 |
| 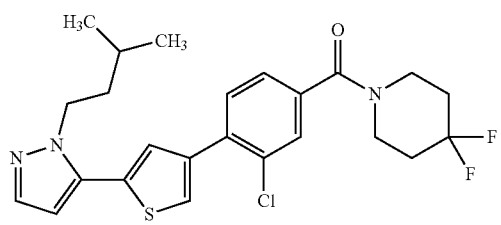 [SMILES: CC(C)CCn1nccc1-c1cc(-c2ccc(C(=O)N3CCC(F)(F)CC3)cc2Cl)cs1] | 2.78 |
| 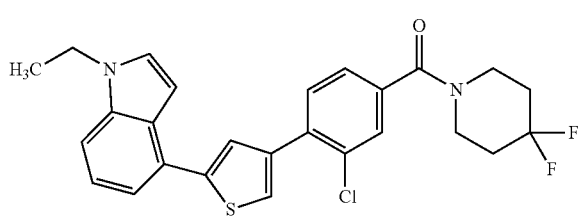 [SMILES: CCn1ccc2c(-c3cc(-c4ccc(C(=O)N5CCC(F)(F)CC5)cc4Cl)cs3)cccc21] | 2.79 |
| 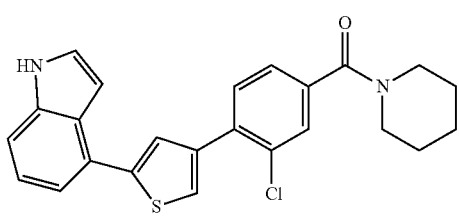 [SMILES: O=C(c1ccc(-c2csc(-c3cccc4[nH]ccc34)c2)c(Cl)c1)N1CCCCC1] | 2.80 |
| 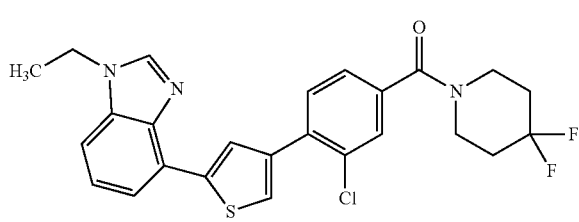 [SMILES: CCn1cnc2c(-c3cc(-c4ccc(C(=O)N5CCC(F)(F)CC5)cc4Cl)cs3)cccc21] | 2.81 |

TABLE 2-continued
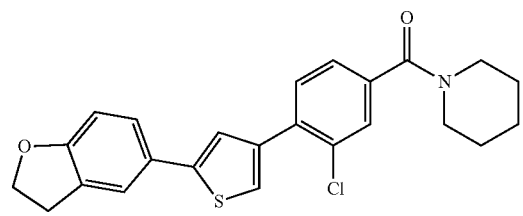 [SMILES: O=C(c1ccc(-c2csc(-c3ccc4c(c3)CCO4)c2)c(Cl)c1)N1CCCCC1] 2.82
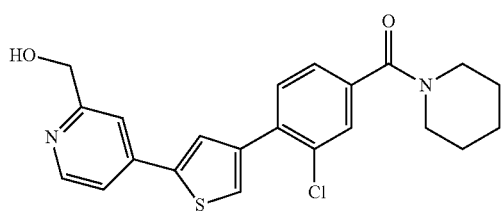 [SMILES: O=C(c1ccc(-c2csc(-c3ccnc(CO)c3)c2)c(Cl)c1)N1CCCCC1] 2.83
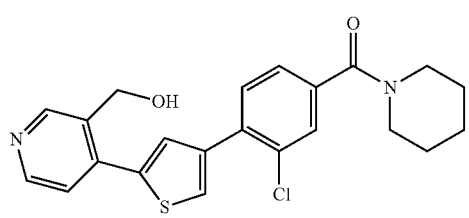 [SMILES: O=C(c1ccc(-c2csc(-c3ccncc3CO)c2)c(Cl)c1)N1CCCCC1] 2.84
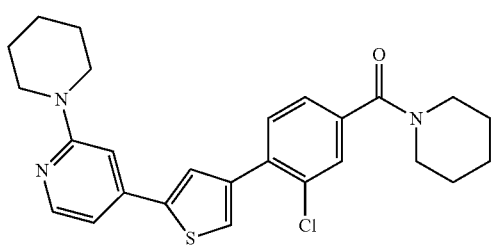 [SMILES: O=C(c1ccc(-c2csc(-c3ccnc(N4CCCCC4)c3)c2)c(Cl)c1)N1CCCCC1] 2.85
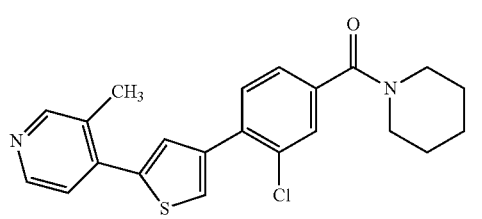 [SMILES: Cc1cnccc1-c1cc(-c2ccc(C(=O)N3CCCCC3)cc2Cl)cs1] 2.86
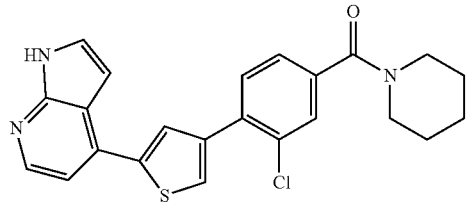 [SMILES: O=C(c1ccc(-c2csc(-c3ccnc4[nH]ccc34)c2)c(Cl)c1)N1CCCCC1] 2.87
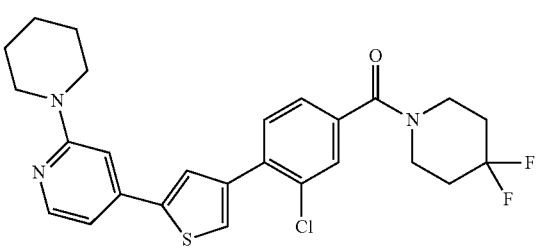 [SMILES: O=C(c1ccc(-c2csc(-c3ccnc(N4CCCCC4)c3)c2)c(Cl)c1)N1CCC(F)(F)CC1] 2.88

TABLE 2-continued
| | |
|---|---|
| 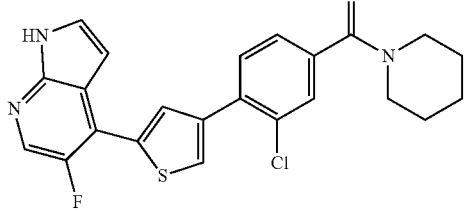 | 2.89 |
| | 2.90 |
| | 2.91 |
| | 2.92 |
| | 2.93 |
| | 2.94 |
| | 2.95 |

TABLE 2-continued

| Structure | # |
|---|---|
| (2-tert-butylpyridin-4-yl)-thiophene-phenyl(Cl,Br)-C(O)-piperidine | 2.96 |
| (6-propylpyridin-4-yl)-1H-imidazole-phenyl(Br)-C(O)-piperidine | 2.97 |
| (2-tert-butylpyridin-4-yl)-furan-phenyl(Cl,Br)-C(O)-piperidine | 2.98 |
| (2-tert-butylpyridin-4-yl)-1H-pyrrole-phenyl(Cl,Br)-C(O)-piperidine | 2.99 |
| (2-tert-butylpyridin-4-yl)-1H-imidazole-phenyl(F)-C(O)-piperidine | 2.100 |
| (2-tert-butylpyridin-4-yl)-1H-imidazole-phenyl(Cl)-C(O)-piperidine | 2.101 |
| (2-piperidin-1-yl-pyridin-4-yl)-1H-imidazole-phenyl(Br)-C(O)-piperidine | 2.102 |

TABLE 2-continued
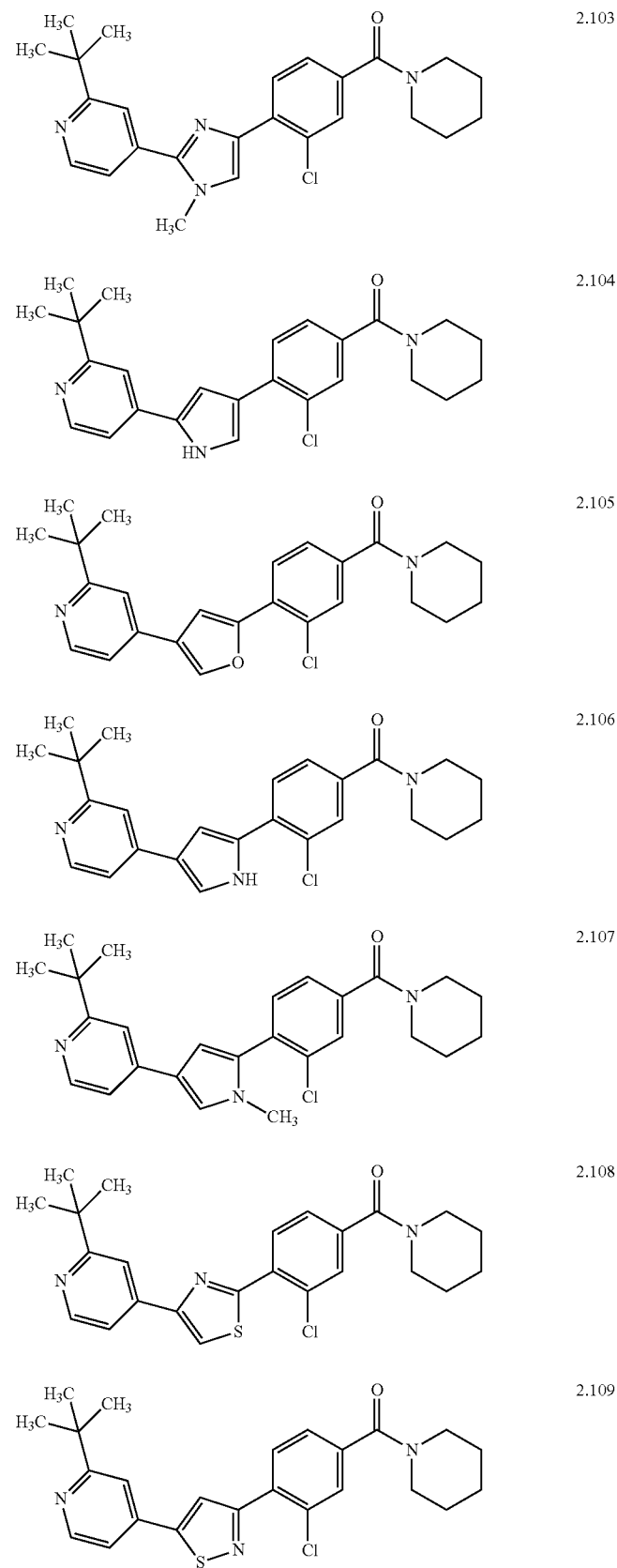

TABLE 2-continued
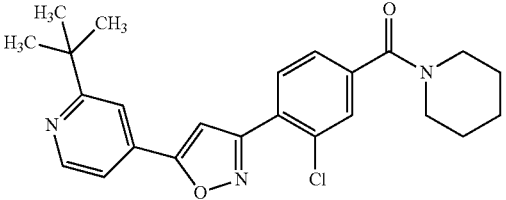 [SMILES: CC(C)(C)c1cc(-c2cc(-c3ccc(C(=O)N4CCCCC4)cc3Cl)no2)ccn1] 2.110
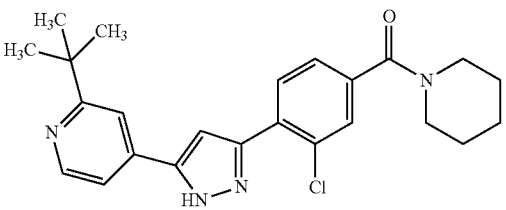 [SMILES: CC(C)(C)c1cc(-c2cc(-c3ccc(C(=O)N4CCCCC4)cc3Cl)n[nH]2)ccn1] 2.111
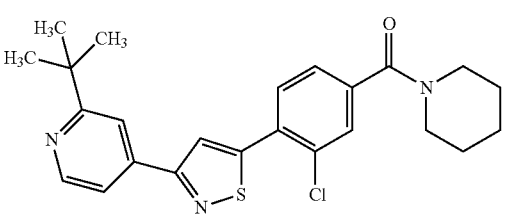 [SMILES: CC(C)(C)c1cc(-c2cc(-c3ccc(C(=O)N4CCCCC4)cc3Cl)on2)ccn1] 2.112
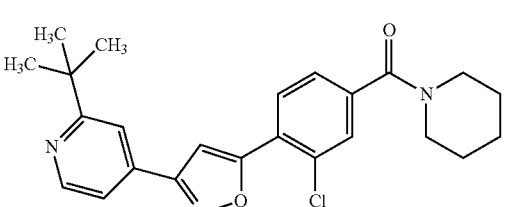 2.113
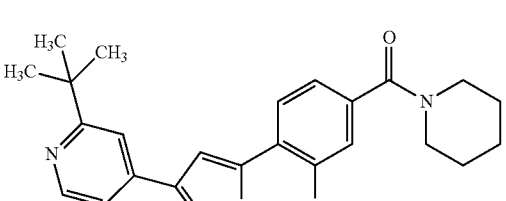 2.114
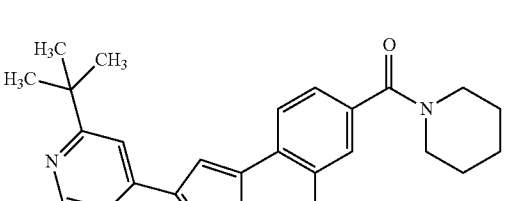 2.115
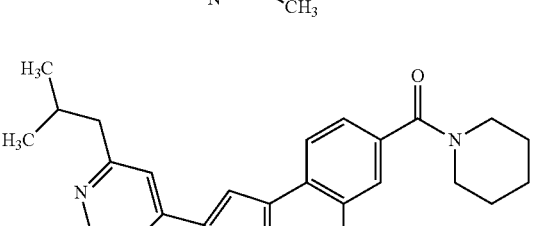 2.116

TABLE 2-continued
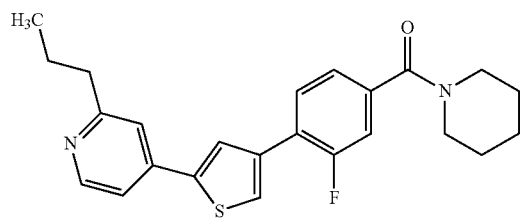 [SMILES: CCCc1cc(-c2cc(-c3ccc(C(=O)N4CCCCC4)cc3F)cs2)ccn1] 2.117
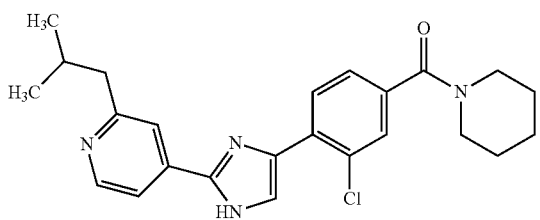 [SMILES: CC(C)Cc1cc(-c2nc(-c3ccc(C(=O)N4CCCCC4)cc3Cl)c[nH]2)ccn1] 2.118
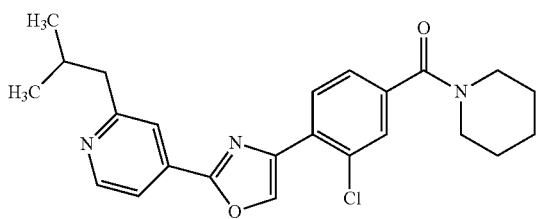 [SMILES: CC(C)Cc1cc(-c2nc(-c3ccc(C(=O)N4CCCCC4)cc3Cl)cs2)ccn1] 2.119
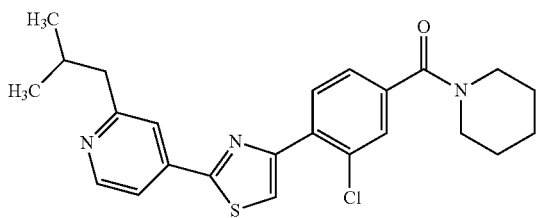 2.120
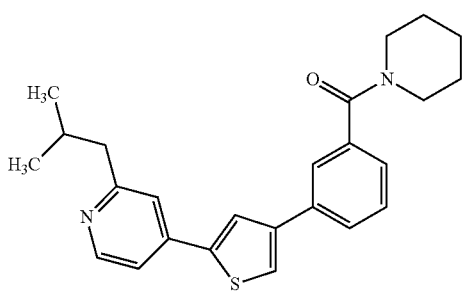 [SMILES: CC(C)Cc1cc(-c2cc(-c3cccc(C(=O)N4CCCCC4)c3)cs2)ccn1] 2.121
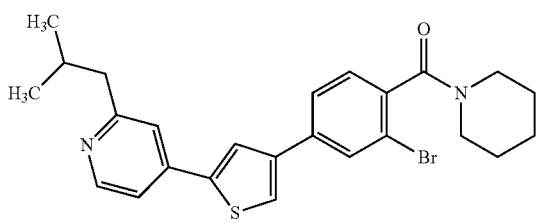 [SMILES: CC(C)Cc1cc(-c2cc(-c3ccc(C(=O)N4CCCCC4)c(Br)c3)cs2)ccn1] 2.122
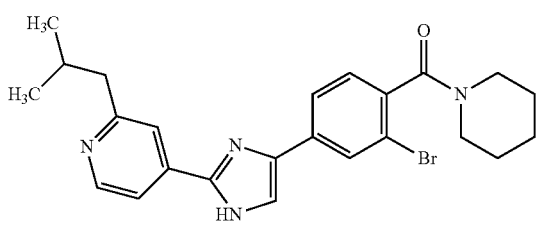 2.123

TABLE 2-continued
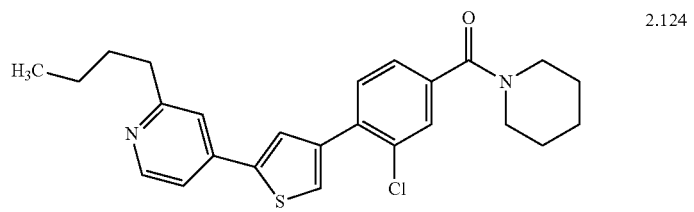 2.124
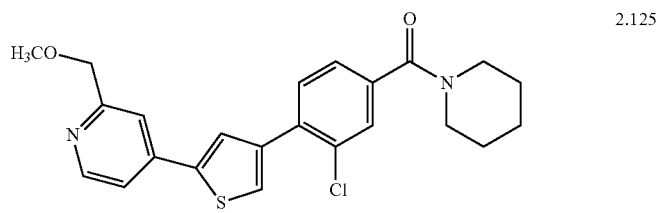 2.125
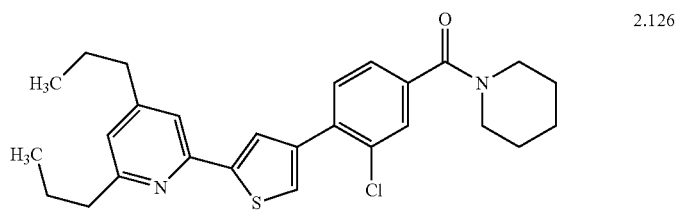 2.126
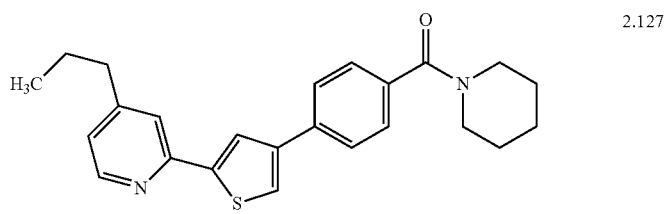 2.127
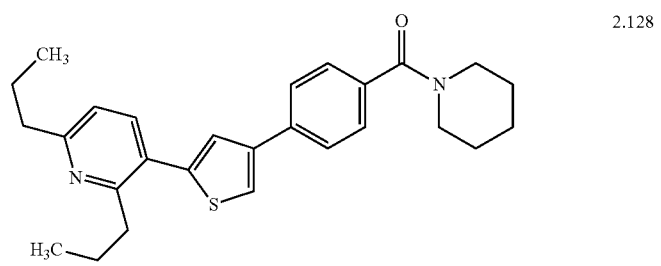 2.128
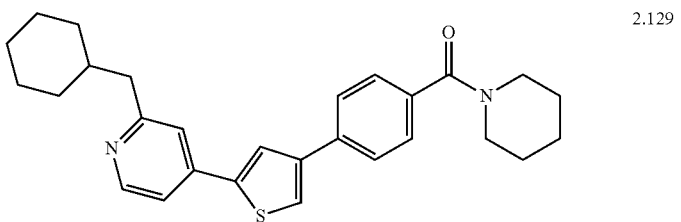 2.129
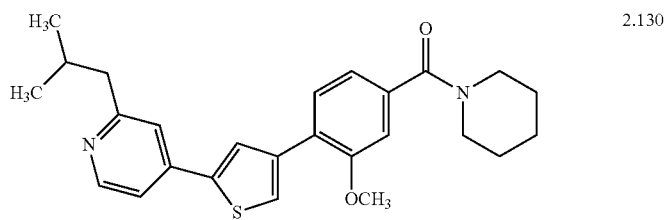 2.130

TABLE 2-continued
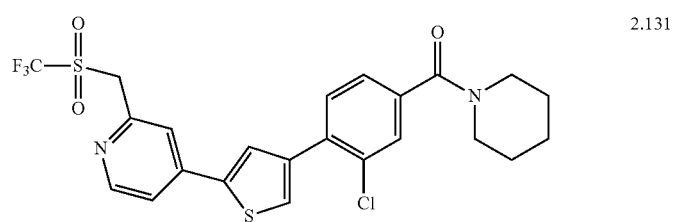
2.131
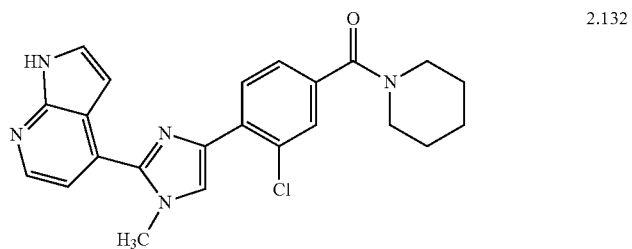
2.132
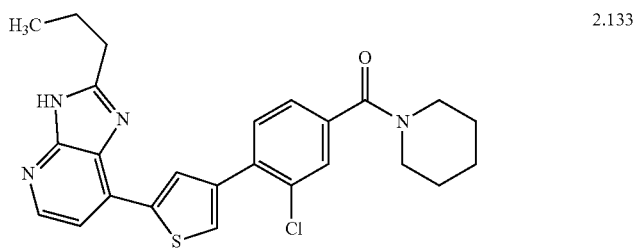
2.133
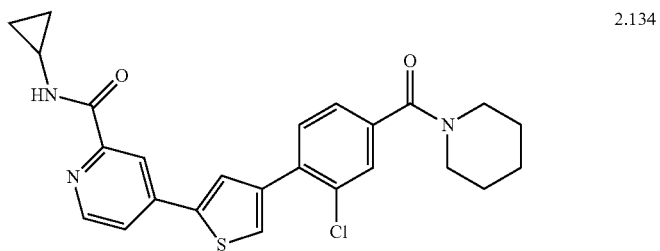
2.134
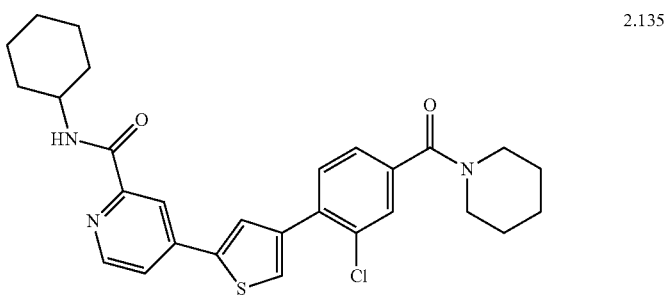
2.135
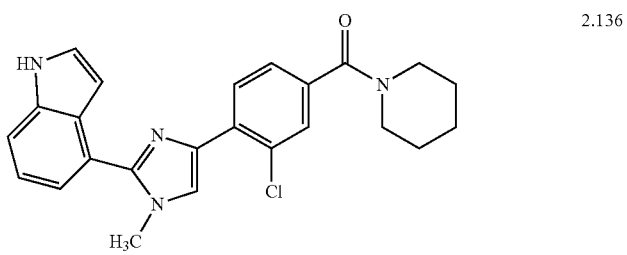
2.136

TABLE 2-continued
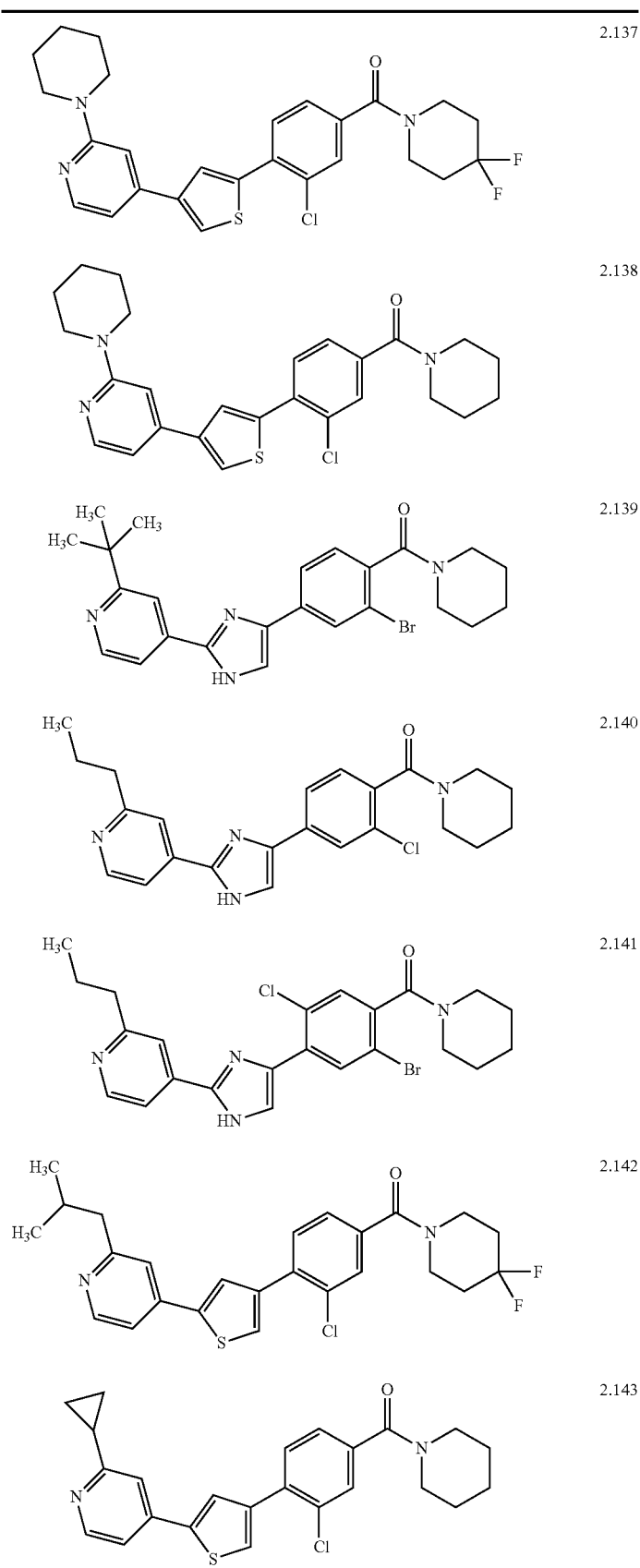

TABLE 2-continued
| 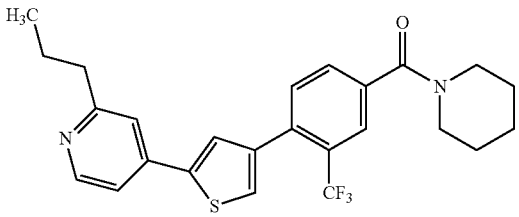 [SMILES: CCCc1cc(-c2cc(-c3ccc(C(=O)N4CCCCC4)cc3C(F)(F)F)cs2)ccn1] | 2.144 |
| 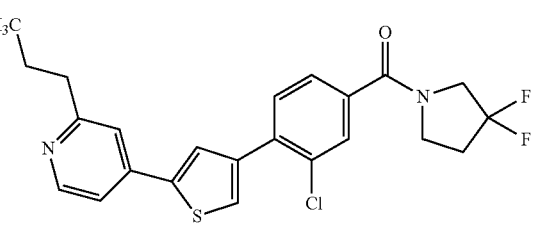 | 2.145 |
| 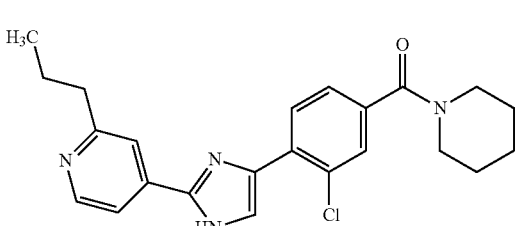 | 2.146 |
| 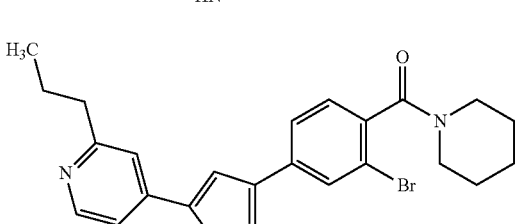 | 2.147 |
| 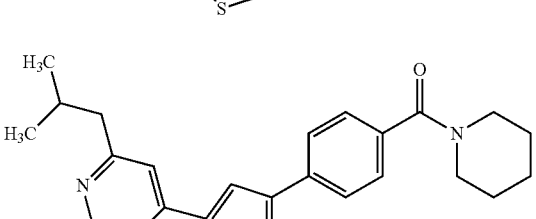 | 2.148 |
| 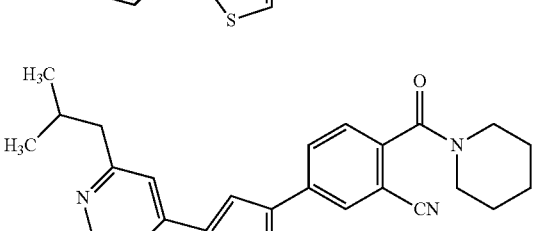 | 2.149 |
| 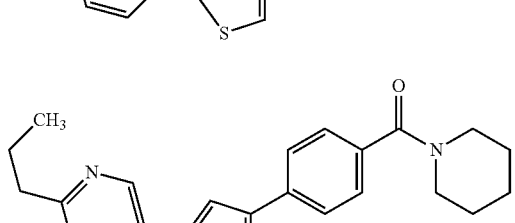 | 2.150 |

TABLE 2-continued

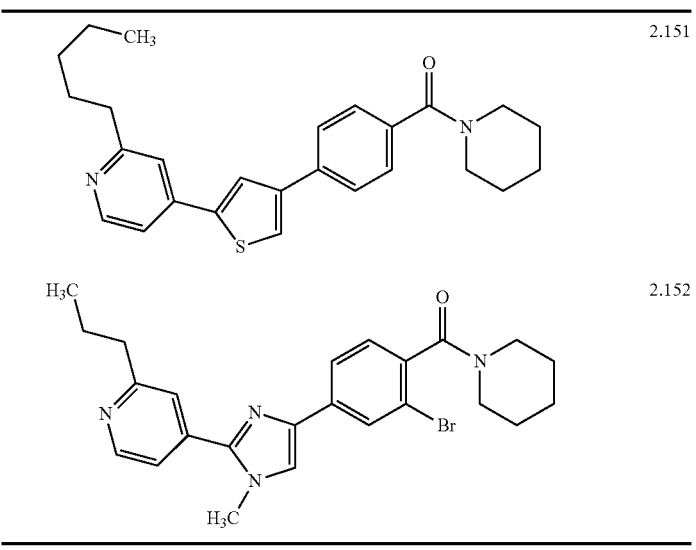

In some embodiments, the compound is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, or 104, or stereoisomers thereof.

In some embodiments, the compound is 2.1, 2.2, 2.3, 2.4, 2.5, 2.6, 2.7, 2.8, 2.9, 2.10, 2.11, 2.12, 2.13, 2.14, 2.15, 2.16, 2.17, 2.18, 2.19, 2.20, 2.21, 2.22, 2.23, 2.24, 2.25, 2.26, 2.27, 2.28, 2.29, 2.30, 2.31, 2.32, 2.33, 2.34, 2.35, 2.36, 2.37, 2.38, 2.39, 2.40, 2.41, 2.42, 2.43, 2.44, 2.45, 2.46, 2.47, 2.48, 2.49, 2.50, 2.51, 2.52, 2.53, 2.54, 2.55, 2.56, 2.57, 2.58, 2.59, 2.60, 2.61, 2.62, 2.63, 2.64, 2.65, 2.66, 2.67, 2.68, 2.69, 2.70, 2.71, 2.72, 2.73, 2.74, 2.75, 2.76, 2.77, 2.78, 2.79, 2.80, 2.81, 2.82, 2.83, 2.84, 2.85, 2.86, 2.87, 2.88, 2.89, 2.90, 2.91, 2.92, 2.93, 2.94, 2.95, 2.96, 2.97, 2.98, 2.99, 2.100, 2.101, 2.102, 2.103, 2.104, 2.105, 2.106, 2.107, 2.108, 2.109, 2.110, 2.111, 2.112, 2.113, 2.114, 2.115, 2.116, 2.117, 2.118, 2.119, 2.120, 2.121, 2.122, 2.123, 2.124, 2.125, 2.126, 2.127, 2.128, 2.129, 2.130, 2.131, 2.132, 2.133, 2.134, 2.135, 2.136, 2.137, 2.138, 2.139, 2.140, 2.141, 2.142, 2.143, 2.144, 2.145, 2.146, 2.147, 2.148, 2.149, 2.150, 2.151, or 2.152.

Representative examples of compounds detailed herein, including intermediates and final compounds, are depicted in Table 1 and elsewhere herein. It is understood that in one aspect, any of the compounds may be used in the methods detailed herein, including, where applicable, intermediate compounds that may be isolated and administered to an individual.

This disclosure also includes any or all of the stereochemical forms, including any enantiomeric or diastereomeric forms of the compounds described. The structure or name is intended to embrace all possible stereoisomers of a compound depicted, and each unique stereoisomer has a compound number bearing a suffix "a," "b," etc. All forms of the compounds are also embraced by this disclosure, such as crystalline or non-crystalline forms of the compounds. Compositions comprising one or more disclosed compounds are also intended, such as a composition of substantially pure compound, including a specific stereochemical form thereof, or a composition comprising mixtures of compounds in any ratio, including two or more stereochemical forms, such as in a racemic or non-racemic mixture.

The compounds depicted herein may be present as salts even if salts are not depicted, and it is understood that the compositions and methods provided herein embrace all salts and solvates of the compounds depicted here, as well as the non-salt and non-solvate form of the compound, as is well understood by the skilled artisan. In some embodiments, the salts of the compounds provided herein are pharmaceutically acceptable salts.

In one embodiment, the compound is a pharmaceutically acceptable salt of a compound of Formulae (Ia) or (Ib), or any variation presented herein, or a pharmaceutically acceptable salt thereof.

The disclosed compounds may include isotopically-labeled and/or isotopically-enriched forms of the compounds. The compounds herein may contain unnatural proportions of atomic isotopes at one or more of the atoms that constitute such compounds. In some embodiments, the compound is isotopically-labeled, such as an isotopically-labeled compound of the Formulae (Ia) or (Ib), or variations thereof described herein, where a fraction of one or more atoms are replaced by an isotope of the same element. Examples of isotopes that can be incorporated into the disclosed compounds include isotopes of hydrogen, carbon, nitrogen, oxygen, phosphorus, sulfur, chlorine, such as $^{2}H$, $^{3}H$, $^{11}C$, $^{13}C$, $^{14}C$, $^{13}N$, $^{15}O$, $^{17}O$, $^{32}P$, $^{35}S$, $^{18}F$, $^{36}Cl$. Certain isotope labeled compounds (e.g. $^{3}H$ and $^{14}C$) are useful in compound or substrate tissue distribution study. Incorporation of heavier isotopes such as deuterium ($^{2}H$) can afford certain therapeutic advantages resulting from greater metabolic stability, for example, increased in vivo half-life, or reduced dosage requirements, hence may be preferred in some instances.

Isotopically-labeled compounds can generally be prepared by standard methods and techniques known to those skilled in the art or by procedures similar to those described in the accompanying Examples substituting appropriate isotopically-labeled reagents in place of the corresponding non-labeled reagent.

This disclosure also includes any or all metabolites of any of the compounds described. The metabolites may include any chemical species generated by a biotransformation of any of the compounds described, such as intermediates and products of metabolism of the compound.

In some embodiments, certain compounds presented herein are considered to be "prodrug" forms of other compounds herein. Prodrugs are precursor derivatives that, upon administration to a patient, undergo metabolism in-vivo such as, for example, hydrolysis to release the active form of the compound—the 'parent' compound. The prodrug form itself is either inactive or less active than the parent. Prodrugs are designed to improve bioavailability or to improve selective administration to particular organs, such as the liver [see, for example, Erion et al. *PNAS* (2007) 104:39, pp 15490-15495; Erion et al. *J. Pharmacol. Exp. Ther.* (2005) 312:2, pp 554-560; Meyer et al. Patent Publication US 2006-0281695A1]. In some embodiments, prodrug forms of compounds presented herein are provided. Conventional procedures for the selection and preparation of suitable prodrug derivatives are described, for example, in "*Design of Prodrugs*," ed. H. Bundgaard, Elsevier, 1985; Beaumont; K. et al. *Curr. Drug Metab.* (2003) 4, pp 461-485; Mizen, L et al. *Pharm. Biotechnol.* (1998) 11, pp 345-365. In addition to prodrugs, this disclosure provides salts, esters, amides, and other protected or derivatized forms of the described compounds.

Pharmaceutically Acceptable Salts

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth metal ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Further examples of pharmaceutically acceptable salts include those listed in Berge et al., Pharmaceutical Salts, *J. Pharm. Sci.* 1977 January; 66(1):1-19. Pharmaceutically acceptable salts can be prepared in situ in the manufacturing process, or by separately reacting a purified compound disclosed herein in its free acid or base form with a suitable organic or inorganic base or acid, respectively, and isolating the salt thus formed during subsequent purification. In one embodiment, a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

Pharmaceutical Compositions

A compound of Formulae (Ia) or (Ib), or any variation presented herein, typically is provided in a pharmaceutical composition comprising a pharmaceutically acceptable carrier and/or excipient. A "pharmaceutically acceptable" carrier or excipient is a material that is not biologically or otherwise undesirable, e.g., the material may be incorporated into a pharmaceutical composition administered to an individual without causing significant undesirable biological effects or interacting in a deleterious manner with any of the other components of the composition, wherein it is contained. Pharmaceutically acceptable carriers or excipients meet the required standards of toxicological and manufacturing testing and/or are included on the Inactive Ingredient Guide prepared by the U.S. Food and Drug administration.

A pharmaceutical composition can comprise one or more compounds of Formulae (Ia) or (Ib), or any variation presented herein. In some embodiments, a pharmaceutical composition further comprises chemotherapeutic agent, as described below.

Preferably a compound of Formulae (Ia) or (Ib), or any variation presented herein, is bioavailable orally. However, the compounds may also be formulated for parenteral (e.g., intravenous) administration.

A compound of Formulae (Ia) or (Ib), or any variation presented herein, can be used in the preparation of a medicament by combining the compound or compounds as an active ingredient with a pharmacologically acceptable carrier, which is known in the art. Depending on the therapeutic form of the medication, the carrier may be in various forms. In one variation, the manufacture of a medicament is for use in any of the methods disclosed herein.

Methods as provided herein may comprise administering to an individual a pharmacological composition that contains an effective amount of a compound of Formulae (Ia) or (Ib), or any variation presented herein, and a pharmaceutically acceptable carrier. The effective amount of the compound may in one aspect be a dose of between about 0.01 and about 100 mg.

The compound may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

A compound of Formulae (Ia) or (Ib), or any variation presented herein, can be used in the preparation of a formulation, such as a pharmaceutical formulation, by combining the compound or compounds as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulators, sweeteners, dyes, adjusters, salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington's Pharmaceutical Sciences*, Mack Publishing Company, Philadelphia, Pa., 20<sup>th</sup> ed. (2000), which is incorporated herein by reference.

A compound of Formulae (Ia) or (Ib), or any variation presented herein, may be administered to individuals in a form of generally accepted oral compositions, such as tablets, coated tablets, gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulators, sweeteners, dyes, adjusters, salts for the adjustment of osmotic pressure, buffers, coating agents or antioxidants.

A compound of Formulae (Ia) or (Ib), or any variation presented herein, can be formulated in a tablet in any dosage form described, for example, a compound as described herein or a pharmaceutically acceptable salt thereof can be formulated as a 10 mg tablet.

A compound of Formulae (Ia) or (Ib), or any variation presented herein, may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, a compound of Formulae (Ia) or (Ib), or any variation presented herein, is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

In some embodiments, a pharmaceutical composition is provided as a unit dosage form, such as a tablet, capsule, or individually packaged container (e.g., an ampoule, syringe, or vial).

In some embodiments, the unit dosage form contains a daily dose of a compound of Formulae (Ia) or (Ib), or any variation presented herein. In some embodiments, the unit dosage form contains a daily sub-dose of the compound.

In some embodiments, the unit dosage form contains a daily dose of each of two or more compounds of Formulae (Ia) or (Ib), or any variation presented herein. In some embodiments, the unit dosage form contains a daily sub-dose of each of two or more compounds.

In some embodiments, the unit dosage form contains a daily dose of compound of Formulae (Ia) or (Ib), or any variation presented herein, and a daily dose of each of one or more chemotherapeutic agents. In some embodiments, the unit dosage form contains a daily sub-dose of the compound and a daily sub-dose of each of one or more chemotherapeutic agents.

In some embodiments, the unit dosage form contains a daily dose of each of two or more compounds of Formulae (Ia) or (Ib), or any variation presented herein, and a daily dose of each of one or more chemotherapeutic agents. In some embodiments, the unit dosage form contains a daily sub-dose of each of two or more compounds and a daily dose of each of one or more chemotherapeutic agents.

Kits and Articles of Manufacture

This disclosure also provides kits and articles of manufacture comprising one or more compounds of Formulae (Ia) or (Ib), or any variation presented herein, or a pharmacological composition comprising a compound of Formulae (Ia) or (Ib), or any variation presented herein. The kits may employ any of the compounds disclosed herein. In one variation, the kit employs a compound described herein or a pharmaceutically acceptable salt thereof.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound as disclosed herein and/or a second pharmaceutically active compound useful for a disease detailed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the disclosed methods. The instructions included with the kit generally include information as to the components and their administration to an individual.

Therapeutic Uses

Unless otherwise defined, "treat," as used herein, refers to the reduction of one or more symptoms associated with a disorder or to slowing the progression of one or more such symptoms.

Compounds of Formulae (Ia) or (Ib), or any variation presented herein, can be used to treat hyperproliferative disorders. A "hyperproliferative disorder" is a disorder associated with some degree of abnormal cell proliferation. A hyperproliferative disorder can be benign (including pre-cancerous disorders) or malignant.

In some embodiments, the hyperproliferative disorder is benign, such as benign prostatic hyperplasia, neurofibromatosis, actinic keratosis, hypertrophic actinic keratosis, Bowenoid actinic keratosis, arsenical keratosis, hydrocarbon keratosis, thermal keratosis, radiation keratosis, chronic scar keratosis, viral keratosis, actinic cheilitis, Bowen's disease, erythroplaquia of queyrat, oral erythroplaquia, leukoplakia, intraepidermal epithelioma, psoriasis, polyps, Barrett's esophagus, atrophic gastritis, cervical dysplasia, benign meningioma, and benign ovarian epithelial tumors (e.g., serous adenomas, mucinous adenomas, Brenner tumors).

In some embodiments, the hyperproliferative disorder is malignant, e.g., adenocarcinoma, bladder cancer, breast cancer, cervical cancer, cholangiocarcinoma, CNS cancer (e.g., astrocytoma, dendroma, ependymoma, glioma, malignant meningioma, medulloblastoma, neuroblastoma, neuroglioma, oligodendroglioma), gastrointestinal cancer (e.g., gastrointestinal stromal carcinoma, colorectal cancer), kidney cancer, leukemia (e.g., acute lymphocytic leukemia; acute myelogenous leukemia; chronic lymphocytic leukemia; chronic myelogenous leukemia), liver cancer (e.g., hepatic cancer, hepatocellular carcinoma), lung cancer (e.g., lung squamous carcinoma, small-cell lung carcinoma, non-small-cell lung carcinoma, mesothelioma), lymphoma (e.g., Hodgkin lymphoma and non-Hodgkin lymphoma), melanoma, myeloma (e.g., multiple myeloma, plasmacytoma), ovarian cancer, pancreatic cancer, prostate cancer, renal cancer, thyroid cancer, and uterine cancer.

In some embodiments, the breast cancer is AR+, ER+, and Her2+. In some embodiments, the breast cancer is AR+, ER+, and PR+. In some embodiments, the breast cancer is AR+, ER+, Her2+, and PR+. In some embodiments, the breast cancer is AR−, ER+, and Her2+. In some embodiments, the breast cancer is AR−, ER+, and PR+. In some embodiments, the breast cancer is AR−, ER+, Her2+, and PR+.

In some embodiments, the breast cancer is ductal carcinoma in situ. In some embodiments, the breast cancer is invasive ductal carcinoma. In some embodiments, the breast cancer is triple negative breast cancer (e.g., basal-like type 1 (BL1), basal-like type 2 (BL2), immunomodulatory (IM), mesenchymal (M), mesenchymal stem-like (MSL), and luminal androgen receptor (LAR) subtypes). In some embodiments, the breast cancer is inflammatory breast cancer. In some embodiments, the breast cancer is BRCA1-related breast cancer. In some embodiments, the breast cancer is medullary breast cancer, metaplastic breast cancer. In some embodiments, the breast cancer is special histologic type of breast cancer. In some embodiments, the breast cancer is resistant to endocrine therapy.

In some embodiments, the prostate cancer is hormone-sensitive prostate cancer. In some embodiments, the prostate cancer is castration-resistant prostate cancer.

In some embodiments, the ovarian cancer is an epithelial carcinoma. In some embodiments, the ovarian cancer is a germ cell tumor. In some embodiments, the ovarian cancer is an ovarian stromal tumor (e.g., granulosa-theca tumors and Sertoli-Leydig cell tumors).

Compounds disclosed herein also can be used to treat a variety of metabolic disorders, including metabolic disorders that are mediated by genetic factors (e.g., Niemann-Pick disease, Fabry disease, Gaucher disease, Forbe's disease, Tangier disease) and environmental factors (e.g., diets rich in fat and/or sugar). Compounds also may be useful in the treatment of complications of metabolic diseases, such as cardiovascular disease, non-alcoholic hepatic steatosis, hyperlipemia, and obesity.

Compounds disclosed herein also can be used to treat pancreatitis.

Compounds can be used to treat liver fibrosis, elevated cholesterol levels, and insulin resistance.

a. Liver Fibrosis

Compounds disclosed herein can be administered to an individual to treat liver fibrosis. In some embodiments, the liver fibrosis is secondary to chronic hepatitis C virus infection. In some embodiments, the liver fibrosis is secondary to alcohol abuse. In some embodiments, the liver fibrosis is secondary to nonalcoholic steatohepatitis (NASH).

In some embodiments in which the liver fibrosis is secondary to NASH, the individual has been diagnosed with NASH following a liver biopsy in which one or more of steatosis, hepatocyte ballooning, lobular inflammation, Mallory hyaline bodies, mixed inflammatory infiltrate, pericellular fibrosis, and perisinusoidal fibrosis is detected.

In other embodiments in which the liver fibrosis is secondary to NASH, the individual is suspected of having NASH based on one or more symptoms such as such as elevated serum levels of liver enzymes (e.g., alanine aminotransferase (ALT), aspartate aminotransferase (AST), γ-glutamyltransferase, alkaline phosphatase); focal or diffuse accumulation of lipid as detected by imaging techniques such as magnetic resonance spectroscopy, ultrasonography, computed tomography; abdominal discomfort, acanthosis nigricans, bowel dismotility, coma, constipation, disseminated intravascular coagulopathy, epigastric pain, fatigue, fluid retention, hepatomegaly, hypoglycemia, intestinal bleeding, jaundice, lipomatosis, lipoatrophy, lipodystrophy, muscle wasting, nausea, neurological defects, Palmer erythema, panniculitis, periumbilical pain, small bowel bacterial overgrowth, spider angiomata, splenomegaly, subacute liver failure, or vomiting.

In some embodiments, the individual is overweight or obese. In some embodiments, the individual has symptoms of insulin resistance, as described below; i.e., the individual is pre-diabetic or has type II diabetes.

In some embodiments, administration of one or more disclosed compounds prevents or slows the histologic progression of liver fibrosis and the clinical progression to cirrhosis in patients with NASH.

Treatment can be assessed by one or more of the following:
  reduction in average liver fat concentration (measured, e.g., by NMRS or MRI);
  reduction of serum ALT;
  reduction of serum AST;
  reduction of serum γ-glutamyltransferase;
  reduction of serum alkaline phosphatase;
  increased in plasma concentrations of the cholesterol synthesis intermediate lathosterol; improved NASH activity index or NAFLD activity score (NAS) (Kleiner et al., Hepatology 41, 1313-21, 2005);
  improved SAF score (Bedossa et al., Hepatology 56, 1751-59, 2012;
  changes in insulin resistance (measured, e.g., by Homeostatis Model Assessment of Insulin Resistance (HOMA-IR);
  reduced hemoglobin A1c levels;
  adiponectin level;
  leptin:adiponectin ratio (LAR);
  reduction in one or more markers of inflammation or fibrosis such as fibrinogen, CK-18, C-reactive protein (CRP), TNFα, IL-6;
  reduction in body weight; or
  reduced histological features such as cholestosis, fat cysts, fibrosis, granular iron, hepatocellular ballooning, increased numbers of eosinophils, inflammation, lobular disarray, lobular inflammation, macrovesicular steatosis, Mallory bodies, megamitochondria, necrosis, periodic acid-Schiff stained globulines, portal inflammation, microvesicular steatosis, or steatosis.

b. Elevated Cholesterol Levels

Compounds disclosed herein can be administered to an individual to treat elevated cholesterol levels, e.g., cholesterol levels above 200 mg/dL (5.2 mmol/L), such as 200-239 mg/dL (5.2-6.2 mmol/L) or 240 mg/dL (6.2 mmol/L) and above. In some embodiments, the individual has LDL cholesterol levels in the range of 130-159 mg/dL (3.4-4.1 mmol/L). In some embodiments, the individual has LDL cholesterol levels in the range of 160-189 mg/dL (4.1-4.9 mmol/L). In some embodiments, the individual has LDL cholesterol levels in the range of 190 mg/dL (4.9 mmol/L) and above. In some embodiments, the individual has HDL cholesterol levels below 40 mg/dL (1 mmol/L; men) or below 50 mg/dL (1.3 mmol/L; women). In some embodiments, the individual has HDL cholesterol levels in the range of 50-59 mg/dL (1.3-1.5 mmol/L). In some embodiments, the individual has triglyceride levels in the range of 150-199 mg/dL (1.7-2.2 mmol/L). In some embodiments, the individual has triglyceride levels in the range of 200-499 mg/dL (2.3-5.6 mmol/L). In some embodiments, the individual has triglyceride levels in the range of 500 mg/dL (5.6 mmol/L) and above.

In some embodiments, the individual has NASH or is suspected of having NASH, as described above.

In some embodiments, the individual has symptoms of insulin resistance, as described below.

c. Insulin Resistance

Compounds disclosed herein can be administered to an individual to treat insulin resistance. In some embodiments, the individual has pre-diabetes, e.g., the individual has a hemoglobin A1C level between 5.7 and 6.4 percent and/or a fasting blood sugar level from 100-125 mg/dL (5.6-6.9 mmol/L). In some embodiments, the individual has type II diabetes e.g., the individual has a hemoglobin A1C level of 6.5 percent or higher and/or a fasting blood sugar level of 126 mg/dL (7 mmol/L) or higher.

In some embodiments, the individual has one or more of the following symptoms, which may improve upon treatment with one or more compounds disclosed herein: increased thirst and frequent urination, increased hunger; weight loss; fatigue; blurred vision; slow-healing sores or frequent infections; and acanthosis nigricans.

In some embodiments, the individual has NASH or is suspected of having NASH, as described above.

d. Combination Therapies

Compounds disclosed herein can be administered in combination with other therapeutic interventions for treating elevated cholesterol levels, liver fibrosis, or insulin resistance. Unless otherwise defined, "in combination" includes any coordinated administration of such therapeutic interventions with one or more therapeutic compounds disclosed herein, including sequential administration, alternating administration, and substantially simultaneous administration.

Therapeutic interventions for treating elevated cholesterol levels include, but are not limited to, statins, such as atorvastatin (e.g., LIPITOR®), fluvastatin (e.g., LESCOL®), lovastatin (e.g., ALTOPREV®, MEVACOR®), pitavastatin (E.G., LIVALO®), pravastatin (e.g., PRAVACHOL®), rosuvastatin (e.g., CRESTOR®), and SIMVASTATIN (e.g, ZOCOR®); bile acid binding resins, such as cholestyramine (e.g., PREVALITE®), colesevelam (e.g., WELCHOL®), and colestipol (e.g., COLESTID®); and cholesterol absorption inhibitors such as ezetimibe (e.g., ZETIA®).

Therapeutic interventions for treating liver fibrosis include, but are not limited to, angiotensin inhibitors, colchicine, corticosteroids, endothelin inhibitors, interferon-α, interleukin 10, pentoxifylline or oxpentifylline (e.g., TRENTAL®), phosphatidylcholine, PPAR antagonists, S-adenosyl-methionine, TGF-β inhibitors, and tocopherol.

Therapeutic interventions for treating insulin resistance include, but are not limited to, insulin-sensitizing agents such as metformin (e.g., GLUCOPHAGE®), thiazolidinediones such as pioglitazone (e.g., ACTOS®) and rosiglitazone (e.g., AVANDIA®); and leptin); α-glucosidase inhibitors such as miglitol (e.g., GIYSET®); insulin; meglitinides such as repaglinide (e.g., PRANDIN®) and nateglinide (e.g., STARLIX®); sulfonylureas such as glyburide (e.g., ORINASE®, TOLINASE®, MICRONASE®, GLYNASE®, DIABETA®, AMARYL®) and chlorpropamide (e.g., DIABINASE®, GLUTROL®, GLUCOTROL XL®; and combinations such as AVANDAMET® (metformin and rosiglitazone).

Treatment Regimens

Compounds can be administered alone or in conjunction with other therapeutic interventions. The disclosed compounds decrease the synthesis of cholesterol and fatty acids, which are essential components of cell membranes and cell division; accordingly, administration of a compound should decrease the rate of cell division. These effects, coupled with alterations in lipid-mediated cell signaling pathways, induce cell death.

Administration of a compound of Formulae (Ia) or (Ib), or any variation presented herein, "in conjunction with" another therapeutic intervention may include any of the following regimens.

Dosing and Method of Administration

The dose of a compound administered to an individual (such as a human) may vary with the particular compound or salt thereof, the method of administration, and the particular stage of hyperproliferative or metabolic disorder being treated. For therapeutic purposes, "effective dose" or "effective amount" refers to that amount of each active compound or pharmaceutical agent, alone or in combination, that elicits the biological or medicinal response in a tissue system, animal, or human that is being sought by a researcher, veterinarian, medical doctor, or other clinician, which includes alleviation of the symptoms of the disease or disorder being treated. For prophylactic purposes (i.e., preventing or inhibiting the onset or progression of a disorder), the term "effective dose" or "effective amount" refers to that amount of each active compound or pharmaceutical agent, alone or in combination, that inhibits in a subject the onset or progression of a disorder as being sought by a researcher, veterinarian, medical doctor, or other clinician, the delaying of which disorder is mediated, at least in part, by blocking of SREBP function. The amount should be sufficient to produce a desirable response, such as a therapeutic or prophylactic response against the disorder. In some embodiments, the amount of the compound or salt thereof is a therapeutically effective amount. In some embodiments, the amount of the compound or salt thereof is a prophylactically effective amount. In some embodiments, the amount of compound or salt thereof is below the level that induces a toxicological effect (e.g., an effect above a clinically acceptable level of toxicity) or is at a level where a potential side effect can be controlled or tolerated when the composition is administered to the individual.

In some embodiments, the amount of compound or salt thereof is an amount sufficient to inhibit cancer cell growth and/or proliferation or increase apoptosis of cancer cells.

The effective amount of the compound may in one aspect be a dose of between about 0.01 and about 100 mg/kg.

Any of the methods provided herein may in one aspect comprise administering to an individual a pharmaceutical composition that contains an effective amount of a compound provided herein or a salt thereof and a pharmaceutically acceptable excipient.

A compound or composition provided herein may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

The compounds provided herein or a salt thereof may be administered to an individual via various routes, including, e.g., intravenous, intramuscular, subcutaneous, oral and transdermal.

In one aspect, provided is a method of treating cancer in an individual by parenterally administering to the individual (e.g., a human) an effective amount of a compound or salt thereof. In some embodiments, the route of administration is intravenous, intra-arterial, intramuscular, or subcutaneous. In some embodiments, the route of administration is oral. In still other embodiments, the route of administration is transdermal. In one aspect are provided compositions (including pharmaceutical compositions) as described herein for the use in treating a hyperproliferative or metabolic disorder, such as cancer (e.g., prostate cancer).

Also provided are compositions (including pharmaceutical compositions) as described herein for the use in treating, preventing, and/or delaying the onset and/or development of cancer and other methods described herein. In certain embodiments, the composition comprises a pharmaceutical formulation which is present in a unit dosage form.

Also provided are articles of manufacture, comprising a compound provided herein or a salt thereof, composition, and unit dosages described herein in suitable packaging for use in the methods described herein. Suitable packaging is known in the art and includes, for example, vials, vessels, ampules, bottles, jars, flexible packaging and the like. An article of manufacture may further be sterilized and/or sealed.

Anti-Proliferative Agents

An "anti-proliferative agent" is an intervention that increases apoptosis of hyperproliferating cells. In some embodiments, a compound of Formulae (Ia) or (Ib), or any variation presented herein, is used in conjunction with an anti-proliferative agent which is a chemotherapeutic agent. Chemotherapeutic agents include any pharmacological agent which is currently approved by the FDA in the U.S. (or elsewhere by any other regulatory body) for use as pharmacological treatment for hyperproliferative disorders, including cancer, or which is currently being used experimentally as part of a clinical trial program.

General Synthetic Methods

The compounds may be prepared by a number of processes as generally described below in the General Synthetic Schemes and more specifically in the Examples hereinafter. In the following process descriptions, the symbols when used in the formulae depicted are to be understood to represent those groups described above in relation to the formulae herein.

Chromatography, recrystallization and other conventional separation procedures may also be used with intermediates or final products where it is desired to obtain a particular isomer of a compound or to otherwise purify a product of a reaction.

The following abbreviations are used herein: thin layer chromatography (TLC); h (h); minute (min); second (sec); ethanol (EtOH); dimethylsulfoxide (DMSO); N,N-dimethylformamide (DMF); trifluoroacetic acid (TFA); tetrahydrofuran (THF); Normal (N); aqueous (aq.); methanol (MeOH); dichloromethane (DCM); ethyl acetate (EtOAc); Retention factor (Rf); room temperature (RT).

The following General Synthetic Schemes and Examples are provided to illustrate but not to limit the scope of this disclosure. Those skilled in the art will be familiar with many of the reaction steps described. See also WO2015/031650, which is incorporated herein by reference in its entirety.

General Synthetic Scheme 1

General Synthetic Scheme 1 provides methods to prepare compounds with a thiazole or imidazole B-ring as presented herein. Substituents $R_1$-$R_6$ are as exemplified in the Examples below. Syntheses of tricyclic substituted thiazoles, oxazoles and imidazoles, such as those presented herein, will be familiar to those skilled in the art. An example to illustrate a synthesis of a substituted thiazole is presented below. Complete details for syntheses of the compounds presented herein are provided in the Examples.

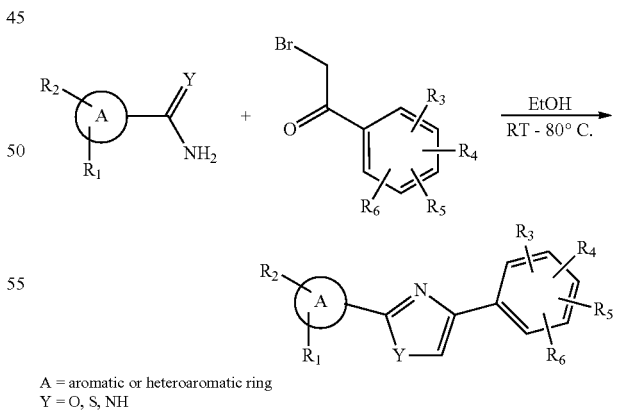

A = aromatic or heteroaromatic ring
Y = O, S, NH

General Procedure:

The corresponding substituted pyridine-4-carbothioamide or isonicotinamide and the corresponding substituted 2-bromoacetylbenzene are dissolved in EtOH. The resultant reaction mixture is stirred at between RT and 70° C. for between 30 min and 2 h. The progress of the reaction is monitored by TLC and LCMS. The reaction mixture is cooled to RT, basified with aq. sodium bicarbonate solution and the mixture extracted with EtOAc. The organic layer is dried over sodium sulfate and concentrated to obtain the crude product, which is purified by silica gel (100-200 mesh) column chromatography or by HPLC to obtain the desired product.

EXAMPLES

Example 1. Preparation of Compound No. 1

Synthesis of N-methyl-4-[2-(2-propylpyridin-4-yl)-1,3-thiazol-4-yl]benzamide

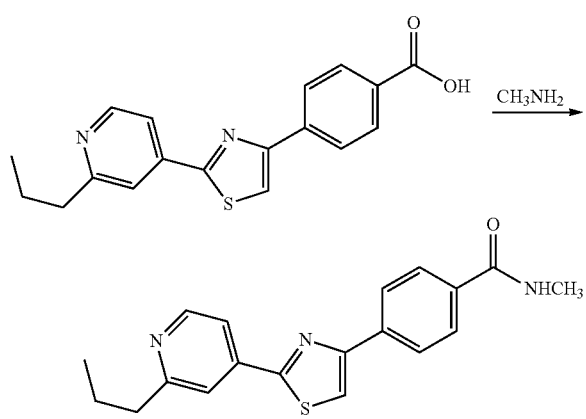

To DCM (2 mL) was added oxalyl chloride (0.04 mL, 0.462 mmol) and DMF (0.01 mL) dropwise respectively at 0° C. The resultant mixture was stirred at 0° C. for 10 min. To the reaction mixture was added 4-(2-(2-propylpyridin-4-yl)thiazol-4-yl)benzoic acid (50 mg, 0.154 mmol), and the reaction mixture was allowed to come to RT. The reaction mixture was stirred at RT for 30 min. To the reaction mixture was added methyl amine (2M in THF) (0.23 mL, 0.462 mmol) dropwise at 0° C. and the mixture stirred for 10 min. To this reaction mixture was added water (2 mL) and then the reaction mixture was diluted with DCM (10 mL). The DCM layer was separated and the aqueous layer was extracted with DCM (2×5 mL). The combined organic layer was dried over anhydrous sodium sulfate and concentrated to obtain the crude product. The crude product was purified by HPLC to obtain N-methyl-4-[2-(2-propylpyridin-4-yl)-1,3-thiazol-4-yl]benzamide (10 mg).

$^1$H NMR (methanol-d4): δ (ppm): 8.75 (d, J=6.1 Hz, 1H), 8.42 (m, 3H), 8.20 (d, J=8.0 Hz, 2H), 7.95 (d, J=8.0 Hz, 2H), 3.02 (t, 2H), 2.95 (s, 3H), 1.91 (h, 2H), 1.09 (t, 3H).

Example 2. Preparation of Compound No. 2

Synthesis of N,N-dimethyl-4-[2-(2-propylpyridin-4-yl)-1,3-thiazol-4-yl]benzamide

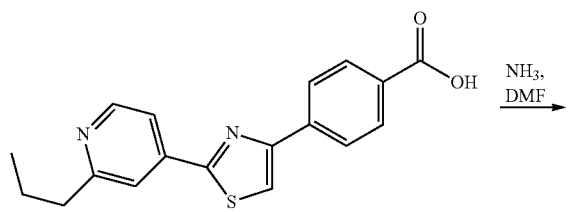

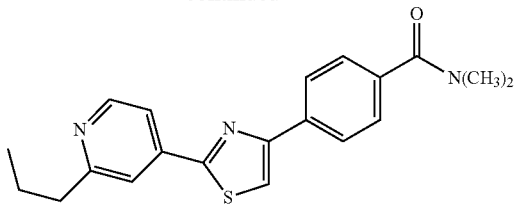

To DCM (2 mL) was added oxalyl chloride (0.04 mL, 0.462 mmol) and DMF (0.01 mL) dropwise respectively at 0° C. The resultant mixture was stirred at 0° C. for 10 min. To this reaction mixture was added 4-(2-(2-propylpyridin-4-yl)thiazol-4-yl)benzoic acid (50 mg, 0.154 mmol) and the reaction mixture was allowed to come to RT. The reaction mixture was then stirred at RT for 30 min. To this reaction mixture was added liquid ammonia (till pH became basic) dropwise at 0° C. and the mixture stirred for 10 min at the same temperature. Then, to the reaction mixture was added water (2 mL) and the reaction mixture was diluted with DCM (10 mL). The DCM layer was separated and the aqueous layer was extracted with DCM (2×5 mL). The combined organic layer was dried over anhydrous sodium sulfate and concentrated to obtain the crude product, as a mixture with Compound No. 3. The crude product was purified by HPLC to get N,N-dimethyl-4-[2-(2-propylpyridin-4-yl)-1,3-thiazol-4-yl]benzamide (11 mg).

$^1$H NMR (methanol-d4): δ (ppm): 8.78 (d, J=6.3 Hz, 1H), 8.55 (S, 1H), 8.47 (m, 2H), 8.21 (d, J=8.0, 2H), 7.57 (d, J=7.8 Hz, 2H), 3.13-3.08 (m, 8H), 1.91 (m, 2H), 1.10 (t, J=7.3 Hz 3H).

Example 3. Preparation of Compound No. 3

Synthesis of 4-[2-(2-propylpyridin-4-yl)-1,3-thiazol-4-yl]benzamide

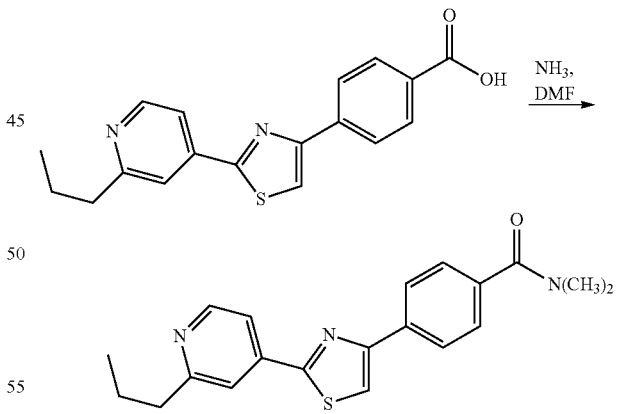

To DCM (2 mL) was added oxalyl chloride (0.04 mL, 0.462 mmol) and DMF (0.01 mL) dropwise respectively at 0° C. The resultant mixture was stirred at the same temperature for 10 min. To this stirred reaction mixture was added 4-(2-(2-propylpyridin-4-yl)thiazol-4-yl)benzoic acid (50 mg, 0.154 mmol) and the reaction mixture was allowed to come to RT. The mixture was stirred at RT for 30 min. To this reaction mixture was added liquid ammonia (till pH became basic) dropwise at 0° C. and the mixture stirred for 10 min. Water (2 mL) was added to the reaction mixture and then the reaction mixture was diluted with DCM (10 mL). The DCM layer was separated and the aqueous layer was extracted with DCM (2×5 mL). The combined organic layer was dried over anhydrous sodium sulfate and concentrated to obtain the crude product, as a mixture with Compound No. 2. The crude product was purified by HPLC to obtain get 4-[2-(2-propylpyridin-4-yl)-1,3-thiazol-4-yl]benzamide (12 mg).

$^1$H NMR (methanol-d4): δ (ppm): 8.78 (d, J=6.0 Hz, 1H), 8.53 (s, 1H), 8.47 (d. J=4.8, 1H), 8.22 (d, J=8.0 Hz, 2H), 8.01 (d, J=7.9 Hz, 2H), 3.18-2.77 (m, 3H), 1.92 (m, 2H), 1.10 (t, J=7.3, 3H).

Example 4. Preparation of Compound No. 4

Synthesis of 4-{4-[2-chloro-4-(piperidine-1-carbonyl)phenyl]-1,3-thiazol-2-yl}-1H-indole

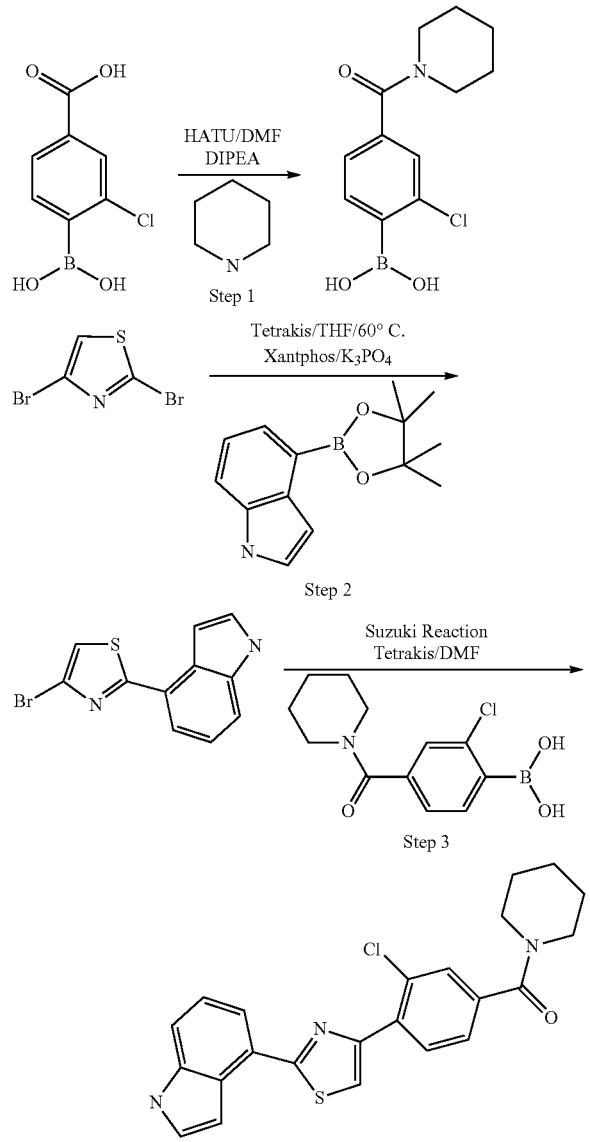

Step-1: Synthesis of [2-chloro-4-(piperidine-1-carbonyl)phenyl]boronic acid

In a 250 mL flask was placed 4-bromo-3-chloro-benzoic acid (1.0 g, 5 mmol, 1 eq.) in DMF (25 mL), followed by addition of DIPEA (3.6 mL, 20 mmol, 4 eq.) and the mixture was stirred for 5 min at RT. Then HATU (3.8 g, 10 mmol, 2 eq.) and piperidine (1.7 mL, 17.5 mmol, 3.5 eq.) were added and the mixture stirred at RT overnight. After completion of reaction (monitored by TLC and 1H-NMR/LCMS), the mixture was diluted with 1N aq. HCl (100 mL) and extracted with EtOAc (2×100 mL) then dried over anhydrous sodium sulfate and the combined organic layer was concentrated under reduced pressure to give a viscous compound, which was purified by silica gel (60-120) column chromatography using acetone: hexane (0-35%) to elute pure compound as a semisolid which solidified in a refrigerator overnight (1.0 g).

Step 2: Synthesis of 4-bromo-2-(1H-indol-4-yl)thiazole

In a 100 mL glass bottle was placed 2,4 dibromothiazole (1 g, 4.11 mmol, 1 eq.) along with 4-(4,4,5,5-tetramethyl-1,3,2-dioxaborolan-2-yl)-1H-indole (1 g, 4.11 mmol, 1 eq.) and potassium phosphate (2.18 g, 2.5 eq.) in (30 mL) of THF. Then it was purged with nitrogen for 15 min then Xantphos (167 mg, 0.07 eq.) and tetrakis (333 mg, 0.07 eq.) were added; repurged for 5 min more and the mixture stirred at 60° C. overnight. After completion of reaction (monitored by TLC & LCMS), the mixture was allowed to cool to RT and then diluted with water (100 mL) and extracted with EtOAc (3×150 mL). The combined organic layer was washed with (50 mL) brine then dried over anhydrous sodium sulfate, and concentrated under reduced pressure to give a viscous compound which was purified by silica gel (60-120) column chromatography using EtOAc/Hexane (0-20%) as eluent system to afford 4-bromo-2-(1H-indol-4-yl)thiazole pure compound as a yellow colored solid (950 mg).

Step-3: Synthesis of [3-chloro-4-[2-(1H-indol-4-yl)thiazol-4-yl]phenyl]-(1-piperidyl)methanone In a 25 mL glass bottle were placed 4-bromo-2-(1H-indol-4-yl)thiazole (250 mg, 0.89 mmol, 1 eq.) and [2-chloro-4-(piperidine-1-carbonyl)phenyl]boronic acid (313 mg, 1.16 mmol, 1.3 eq.), and sodium carbonate (238 mg, 2.5 eq. dissolved in water (1.0 mL) in DMF (7 mL) and purged with nitrogen gas for 5 min. After adding tetrakis (103 mg, 0.089 mmol, 0.1 eq.), the mixture was repurged for 2 min and heated to 70° C. for 4 h. The reaction was monitored by TLC and LCMS. After completion of reaction, the mixture was allowed to come to RT and diluted with water (50 mL) and extracted with EtOAc (3×100 mL). The combined organic layer was washed with water (4×50 mL), dried over anhydrous sodium sulfate and concentrated under reduced pressure to obtain the crude viscous compound, which was purified by reverse phase HPLC to afford [3-chloro-4-[2-(1H-indol-4-yl)thiazol-4-yl]phenyl]-(1-piperidyl)methanon (53 mg) as a white solid, the free base.

$^1$H NMR (400 MHz, DMSO-d6) δ (ppm): 11.49 (s, 1H), 8.24 (s, 1H), 8.13 (d, J=7.9 Hz, 1H), 7.75-7.61 (m, 1H), 7.60 (d, J=5.1 Hz, 1H), 7.60-7.47 (m, 3H), 7.24 (s, 2H), 3.61 (s, 2H), 1.63 (s, 4H), 1.53 (s, 4H). LCMS: (M+1) 422.1.

Example 5. Preparation of Compound No. 5

Synthesis of 2-tert-butyl-4-{4-[2-chloro-4-(piperidine-1-carbonyl)phenyl]-1,3-thiazol-2-yl}pyridine

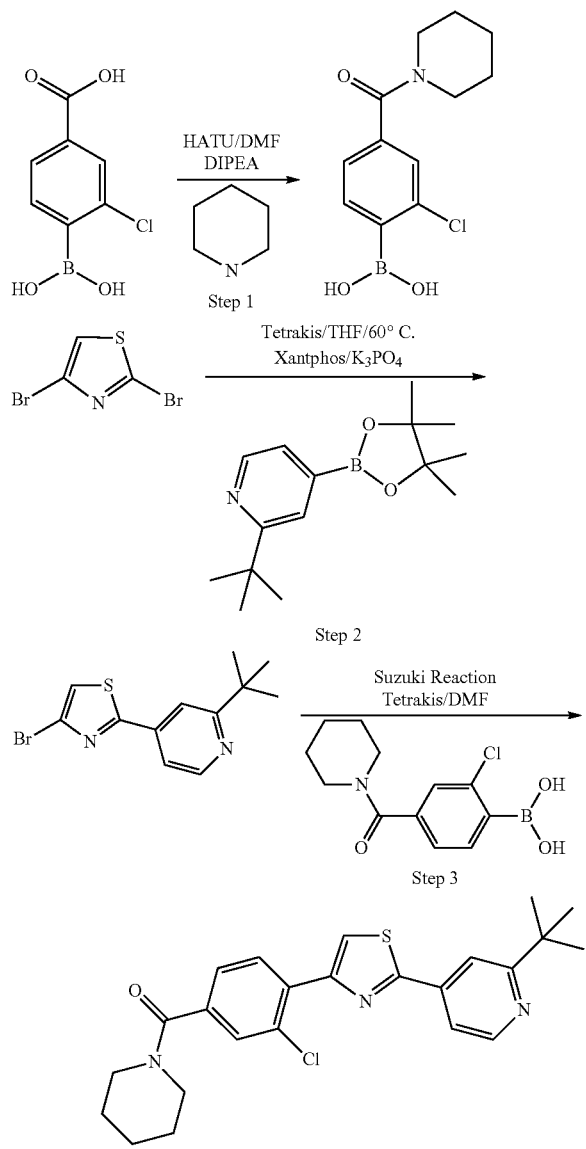

Step-1: Synthesis of
[2-chloro-4-(piperidine-1-carbonyl) phenyl] boronic acid

In a 250 mL flask was placed 4-borono-3-chloro-benzoic acid (1.0 g, 5 mmol, 1 eq.) dissolved in DMF (25 mL), followed by addition of DIPEA (3.6 mL, 20 mmol, 4 eq.) and the mixture was stirred for 5 min. Then HATU (3.8 g, 10 mmol, 2 eq.) and piperidine (1.7 mL, 17.5 mmol, 3.5 eq.) were added and the mixture stirred at RT overnight. After completion of reaction (monitored by TLC and 1H-NMR/LCMS), the mixture was diluted with 1N aq. HCl (100 mL) and extracted with EtOAc (2×100 mL) then dried over anhydrous sodium sulfate and the combined organic layer was concentrated under reduced pressure to give a viscous compound, which was purified by silica gel (60-120) column chromatography using acetone: hexane (0-35%) to elute pure compound as a semisolid which solidified in a refrigerator overnight (1.0 g).

Step-2: Synthesis of
4-bromo-2-(2-tert-butyl-4-pyridyl)thiazole

In a 100 mL glass bottle were placed 2,4 dibromothiazole (200 mg, 0.82 mmol, 1 eq.) along with 2-tert-butyl-4-(4,4,5,5-tetramethyl-1,3,2-dioxaborolan-2-yl)pyridine (215, 0.82 mmol, 1 eq.) and potassium phosphate (349 mg, 2.5 eq.) dissolved in 10 mL of THF. The mixture was purged with nitrogen for 15 min, then Xantphos (47 mg, 0.1 eq.) and tetrakis (95 mg, 0.1 eq.) were added, and the mixture repurged for 5 min and the mixture stirred at 60° C. overnight. When the reaction was completed (monitored by TLC & LCMS), the mixture was cooled to RT, water (100 mL) was added and the mixture extracted with EtOAc (3×150 mL). The combined organic layer was washed with brine (50 mL) then dried over anhydrous sodium sulfate, and concentrated under reduced pressure to give a viscous compound which was purified by silica gel (60-120) column chromatography using EtOAc/Hexane (0-15%) as eluent system to afford 4-bromo-2-(1H-indol-4-yl)thiazole pure compound as a yellow colored solid (200 mg).

Step-3: Synthesis of [4-[2-(2-tert-butyl-4-pyridyl)thiazol-4-yl]-3-chloro-phenyl]-(1-piperidyl)methanone In a 25 mL glass bottle were placed 4-bromo-2-(2-tert-butyl-4-pyridyl)thiazole (200 mg, 0.67 mmol, 1 eq.), [2-chloro-4-(piperidine-1-carbonyl)phenyl]boronic acid (234 mg, 0.87 mmol, 1.3 eq.), and sodium carbonate (180 mg, 2.5 eq. dissolved in water (1.0 mL), in DMF (7 mL). The mixture was purged with nitrogen gas for 5 min. After adding tetrakis (78 mg, 0.067 mmol, 0.1 eq.), the mixture was repurged for 2 min and then heated to 70° C. for 4 h. The reaction was monitored by TLC and LCMS. The reaction mixture was allowed to come to RT, diluted with water (50 mL) and extracted with EtOAc (3×100 mL). The combined organic layer was washed with water (4×50 mL), dried over anhydrous sodium sulfate and concentrated under reduced pressure to obtain the crude product which was purified by reverse phase HPLC to afford [4-[2-(2-tert-butyl-4-pyridyl)thiazol-4-yl]-3-chloro-phenyl]-(1-piperidyl)methanone (35 mg) as an off-white solid, the free base.

$^1$H NMR (400 MHz, Methanol-d4) δ (ppm): 8.62 (d, J=5.2 Hz, 1H), 8.22 (s, 1H), 8.11 (d, J=8.0 Hz, 1H), 8.04 (s, 1H), 7.79 (d, J=5.1 Hz, 1H), 7.60 (s, 1H), 7.47 (d, J=8.0 Hz, 1H), 3.73 (m, 2H), 3.43 (m, 2H), 1.72 (s, 4H), 1.59 (m, 2H), 1.44 (s, 9H). LCMS: (M+1) 440.2.

Example 6. Preparation of Compound No. 6

Synthesis of 3-chloro-4-[2-(1H-indol-4-yl)-1,3-thiazol-4-yl]-N,N-dimethylbenzamide

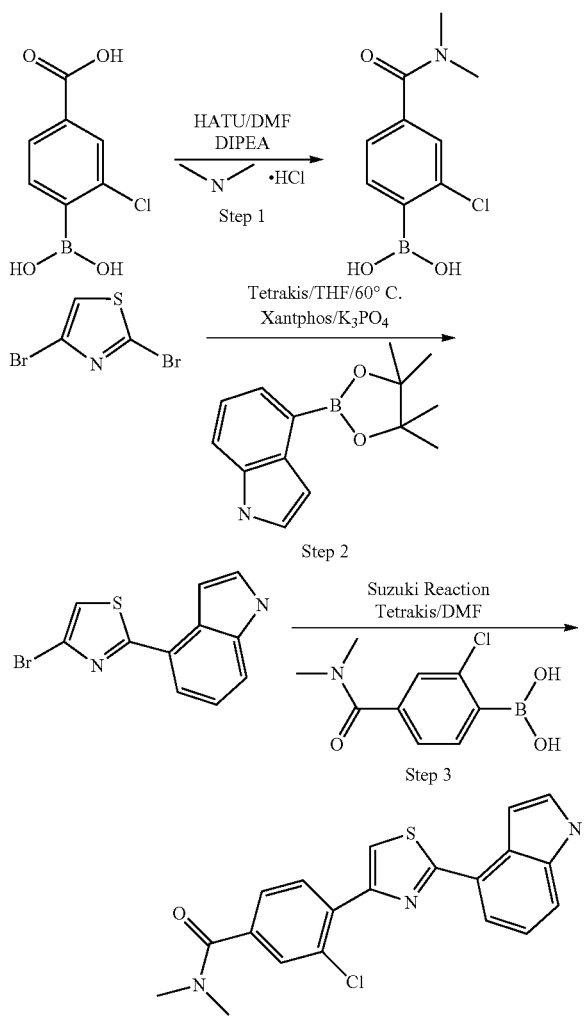

Step-1: Synthesis of [2-chloro-4-(dimethylcarbamoyl)phenyl]boronic acid

In a 250 mL flask was placed 4-borono-3-chloro-benzoic acid (1.5 g, 7.5 mmol, 1 eq.) was dissolved in DMF (25 mL), followed by addition of DIPEA (6.9 mL, 37.5 mmol, 5 eq.) and resulting mixture was stirred for 5 min then at RT. Then HATU (5.7 g, 15, mmol, 2 eq.) and dimethyl amine hydrochloride (2.43 g, 30 mmol, 4 eq.) were added and the mixture stirred at RT overnight. After completion of reaction (monitored by TLC and 1H-NMR/LCMS), the mixture was diluted with 1N aq. HCl (100 mL) and extracted with EtOAc (2×100 mL), then dried over anhydrous sodium sulfate and the combined organic layer was concentrated under reduced pressure to give a viscous compound, which was purified by silica gel (60-120) column chromatography using acetone: hexane (0-35%0) to elute pure compound as a semisolid which solidified in a refrigerator overnight (1.05 g).

Step-2: Synthesis of 4-bromo-2-(1H-indol-4-yl)thiazole

In a 100 mL glass bottle were placed 2,4 dibromothiazole (1 g, 4.11 mmol, 1 eq.) along with 4-(4,4,5,5-tetramethyl-1,3,2-dioxaborolan-2-yl)-1H-indole (1 g, 4.11 mmol, 1 eq.) and potassium phosphate (2.18 g, 2.5 eq.) in 30 mL of THF. Then the mixture was purged with nitrogen for 15 min then Xantphos (167 mg, 0.07 eq.) and tetrakis (333 mg, 0.07 eq.) were added to the mixture and repurged for 5 min. Then the reaction mixture was stirred at 60° C. overnight. After completion of reaction (monitored by TLC & LCMS), the mixture was allowed to cool to RT followed by addition of water (100 mL) and the mixture was extracted with EtOAc (3×150 mL). The combined organic layer was washed with brine (50 mL) then dried over anhydrous sodium sulfate, and concentrated under reduced pressure to give a viscous compound which was purified by silica gel (60-120) column chromatography using EtOAc/Hexane (0-20%) as eluent system to afford 4-bromo-2-(1H-indol-4-yl)thiazole pure compound as a yellow colored solid (950 mg).

Step-3: Synthesis of 3-chloro-4-[2-(1H-indol-4-yl) thiazol-4-yl]-N, N-dimethyl-benzamide In a 25 mL glass bottle were placed 4-bromo-2-(1H-indol-4-yl)thiazole (250 mg, 0.89 mmol, 1 eq.) and [2-chloro-4-(dimethylcarbamoyl)phenyl]boronic acid (265 mg, 1.16 mmol, 1.3 eq.), sodium carbonate (258 mg, 2.5 eq. dissolved in water (1.0 mL), in DMF (7 mL), and purged with nitrogen gas for 5 min. After adding tetrakis (104 mg, 0.089 mmol, 0.1 eq.), the mixture was repurged for 2 min and heated to 70° C. overnight. The reaction was monitored by TLC and LCMS. The reaction mixture was allowed to come to RT; water (50 mL) was added and the mixture extracted with EtOAc (3×100 mL). The combined organic layer was washed with water (4×50 mL), dried over anhydrous sodium sulfate and concentrated under reduced pressure to obtain the crude product which was purified by reverse phase HPLC to afford 3-chloro-4-[2-(1H-indol-4-yl)thiazol-4-yl]-N,N-dimethyl-benzamide (53 mg—as the freebase) as an off yellow solid.

$^1$H NMR (400 MHz, DMSO-d6) δ (ppm): 11.48 (s, 1H), 8.24 (s, 1H), 8.13 (d, J=8.0 Hz, 1H), 7.72 (d, J=7.4 Hz, 1H), 7.64 (s, 1H), 7.62-7.51 (m, 3H), 7.24 (s, 2H), 3.00 (m, J=13.7 Hz, 6H). LCMS: (M+1) 382.1.

Example 7. Preparation of Compound No. 7

Synthesis of 4-{4-[5-(2-tert-butylpyridin-4-yl)thiophen-3-yl]-3-chlorobenzoyl}piperazin-2-one

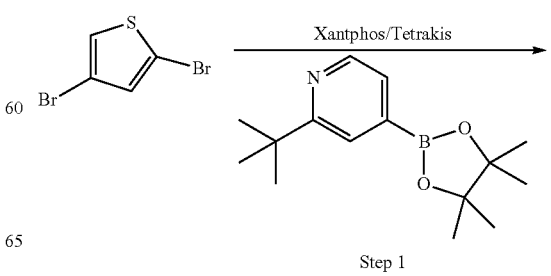

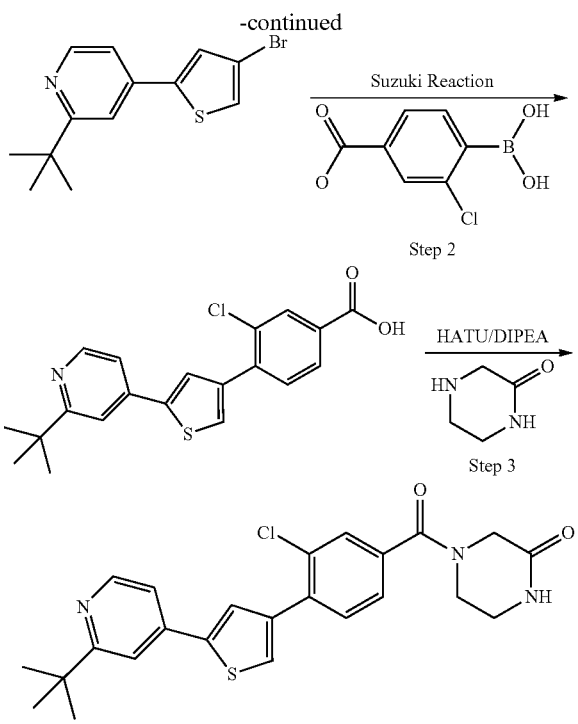

Step-1: Synthesis of 4-(4-bromo-2-thienyl)-2-tert-butyl-pyridine

In a 100 mL glass bottle was placed 2,4-dibromothiophene (600 mg, 2.5 mmol, 1 eq.) along with 2-tert-butyl-4-(4,4,5,5-tetramethyl-1,3,2-dioxaborolan-2-yl)pyridine (652 mg, 1 eq.) and potassium phosphate (1.325 g, 2.5 eq.) in 25 mL of THF. Then the mixture was purged with nitrogen for 15 min then Xantphos (145 mg, 0.1 eq.) and tetrakis (289 mg, 0.1 eq.) were added, and the mixture repurged for 5 min and the mixture stirred at 60° C. overnight. The progress of the reaction was monitored by TLC & LCMS. When the reaction was completed, the mixture was cooled to RT, water (100 mL) was added and the mixture extracted with EtOAc (3×100 mL). The combined organic layer was washed with brine (50 mL) then dried over anhydrous sodium sulfate, and concentrated under reduced pressure to give a viscous compound which was purified by silica gel (60-120) column chromatography using EtOAc/Hexane (0-20%) as eluent system to afford 4-(4-bromo-2-thienyl)-2-tert-butyl-pyridine as a colorless semi-solid (500 mg).

Step-2: Synthesis of 4-[5-(2-tert-butyl-4-pyridyl)-3-thienyl]-3-chloro-benzoic acid In a 25 mL glass bottle was placed 4-(4-bromo-2-thienyl)-2-tert-butyl-pyridine (450 mg, 1.52 mmol, 1 eq.) and 4-borono-3-chloro-benzoic acid (397 mg, 1.98 mmol, 1.3 eq.) in DMF (7 mL) followed by addition of sodium carbonate (404 mg, 2.5 equiv dissolved in water (2.0 mL) and the reaction mixture was purged with nitrogen gas for 5 min. After adding tetrakis triphenylphosphine palladium(0) (176 mg, 0.152 mmol, 0.1 eq.), the mixture was repurged for 2 min and was stirred at 90° C. overnight. The progress of the reaction was monitored by TLC and LCMS. After completion of reaction, the mixture was allowed to come to RT and diluted with water (50 mL) and extracted with EtOAc: MeOH (90:10), (3×100 mL). The combined organic layer was dried over anhydrous sodium sulfate and concentrated under reduced pressure to afford a semi-solid compound, 3-chloro-4-[5-[3-(1-piperidyl)phenyl]-3-thienyl]benzoic acid (500 mg) which was used as such for the next step of synthesis.

Step-3: Synthesis of 4-[4-[5-(2-tert-butyl-4-pyridyl)-3-thienyl]-3-chloro-benzoyl]piperazin-2-one In a 100 mL flask was placed 4-[5-(2-tert-butyl-4-pyridyl)-3-thienyl]-3-chloro-benzoic acid (125 mg, 0.34 mmol, 1 eq.) was dissolved in DMF (5 mL), followed by addition of DIPEA (0.25 mL, 1.34 mmol, 4 eq.) and HATU (255 mg, 0.68 mmol, 2 equiv), and the resulting mixture was stirred for 10 min at RT and piperazine-2-one (168 mg, 1.68 mmol, 5 eq.) were added and the mixture stirred at RT under nitrogen atmosphere overnight. The progress of the reaction was monitored by TLC and LCMS. After completion of reaction, the mixture was diluted with water (100 mL) and extracted with EtOAc (2×100 mL), washed with water (4×100 mL) then dried over anhydrous sodium sulfate and the combined organic layer was concentrated under reduced pressure to give a viscous compound, which was purified by reverse phase HPLC process to afford 4-{4-[5-(2-tert-butylpyridin-4-yl)thiophen-3-yl]-3-chlorobenzoyl}piperazin-2-one (25 mg) as an off-white solid, the free base.

$^1$H NMR (400 MHz, Methanol-d4) δ (ppm): 8.49 (d, J=5.2 Hz, 1H), 7.92 (s, 1H), 7.8 (s, 1H), 7.75-7.64 (m, 3H), 7.58-7.41 (m, 2H), 4.31 (s, 1H), 4.18 (m, 1H) 3.95 (s, 1H), 3.72 (s, 1H), 3.41 (s, 2H), 1.42 (s, 9H). LCMS: (M+1) 454.1.

Example 8. Preparation of Compound No. 8

Synthesis of 4-[5-(2-tert-butylpyridin-4-yl)thiophen-3-yl]-3-chloro-N-cyclobutylbenzamide

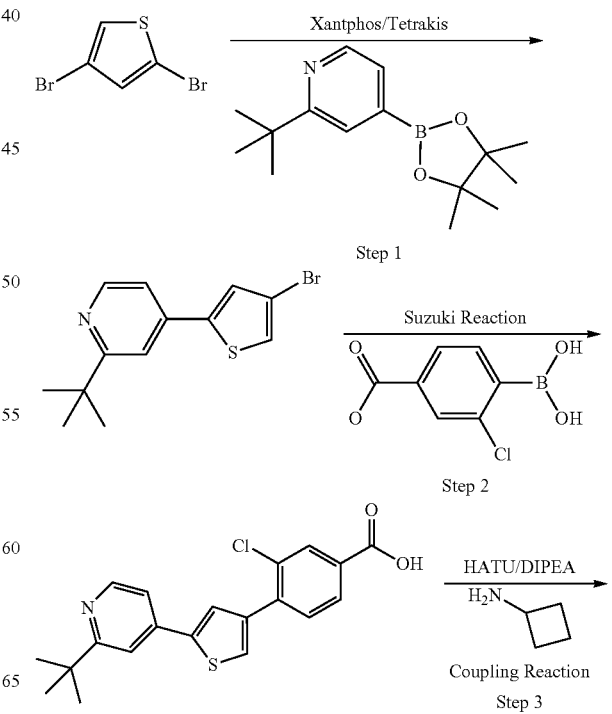

-continued

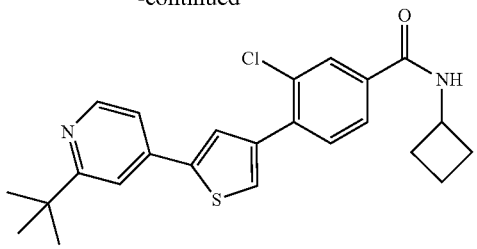

Step-1: Synthesis of 4-(4-bromo-2-thienyl)-2-tert-butyl-pyridine

In a 100 mL glass bottle was placed 2,4 dibromothiophene (600 mg, 2.5 mmol, 1 eq.) along with 2-tert-butyl-4-(4,4,5,5-tetramethyl-1,3,2-dioxaborolan-2-yl)pyridine (652 mg, 1 eq.) and potassium phosphate (1.325 g, 2.5 eq.) in 25 mL of THF. Then the mixture was purged with nitrogen for 15 min then Xantphos (145 mg, 0.1 eq.) and tetrakis (289 mg, 0.1 eq.) were added, and the mixture repurged for 5 min and the mixture stirred at 60° C. overnight. The progress of the reaction was monitored by TLC & LCMS. When the reaction was completed, the mixture was cooled to RT, water (100 mL) was added and the mixture extracted with EtOAc (3×100 mL). The combined organic layer was washed with brine (50 mL) then dried over anhydrous sodium sulfate, and concentrated under reduced pressure to give a viscous compound which was purified by silica gel (60-120) column chromatography using EtOAc/Hexane (0-20%) as eluent system to afford 4-(4-bromo-2-thienyl)-2-tert-butyl-pyridine as a colorless semi-solid (500 mg).

Step-2: Synthesis of 4-[5-(2-tert-butyl-4-pyridyl)-3-thienyl]-3-chloro-benzoic acid In a 25 mL glass bottle was placed 4-(4-bromo-2-thienyl)-2-tert-butyl-pyridine (450 mg, 1.52 mmol, 1 eq.) and 4-borono-3-chloro-benzoic acid (397 mg, 1.98 mmol, 1.3 eq.) in DMF (7 mL) followed by addition of sodium carbonate (404 mg, 2.5 equiv dissolved in water (2.0 mL) and the reaction mixture was purged with nitrogen gas for 5 min. After adding tetrakis triphenylphosphine palladium(0) (176 mg, 0.152 mmol, 0.1 eq.), the mixture was repurged for 2 min and was stirred at 90° C. overnight. The progress of the reaction was monitored by TLC and LCMS. After completion of reaction, the mixture was allowed to come to RT and diluted with water (50 mL) and extracted with EtOAc: MeOH (90:10), (3×100 mL). The combined organic layer was dried over anhydrous sodium sulfate and concentrated under reduced pressure to afford a semi-solid compound, 3-chloro-4-[5-[3-(1-piperidyl)phenyl]-3-thienyl]benzoic acid (500 mg) which was used as such for the next step of synthesis.

Step-3: Synthesis of 4-[5-(2-tert-butyl-4-pyridyl)-3-thienyl]-3-chloro-N-cyclobutyl-benzamide In a 100 mL flask was placed 4-[5-(2-tert-butyl-4-pyridyl)-3-thienyl]-3-chloro-benzoic acid (200 mg, 0.54 mmol, 1 eq.) was dissolved in DMF (7 mL), followed by addition of DIPEA (0.4 mL, 2.15 mmol, 4 eq.) and HATU (409 mg, 1.07 mmol, 2 equiv), and the resulting mixture was stirred for 10 min at RT and cyclobutyl amine (191 mg, 2.69 mmol, 5 eq.) were added and the mixture stirred at RT under nitrogen atmosphere overnight. The progress of the reaction was monitored by TLC and LCMS. After completion of reaction, the mixture was diluted with water (100 mL) and extracted with EtOAc (2×100 mL), washed with water (4×100 mL) then dried over anhydrous sodium sulfate and the combined organic layer was concentrated under reduced pressure to give a viscous compound, which was purified by reverse phase HPLC process to afford 4-[5-(2-tert-butylpyridin-4-yl)thiophen-3-yl]-3-chloro-N-cyclobutylbenzamide (13 mg) as an off-white solid, the free base.

$^1$H NMR (400 MHz, Methanol-d4) δ (ppm): 8.48 (d, J=5.3 Hz, 1H), 8.02 (s, 1H), 7.94-7.89 (m, 1H), 7.87-7.77 (m, 2H), 7.72-7.62 (m, 2H), 7.52 (d, J=4.7 Hz, 1H), 4.61-4.47 (m, 1H), 2.37 (s, 2H), 2.14 (p, J=9.6 Hz, 2H), 1.86-1.73 (m, 2H), 1.42 (s, 9H). LCMS: (M+1) 425.2.

Example 9. Preparation of Compound No. 9

Synthesis of 3-chloro-N,N-dimethyl-4-{2-[2-(piperidin-1-yl)pyridin-4-yl]-1,3-thiazol-4-yl}benzamide

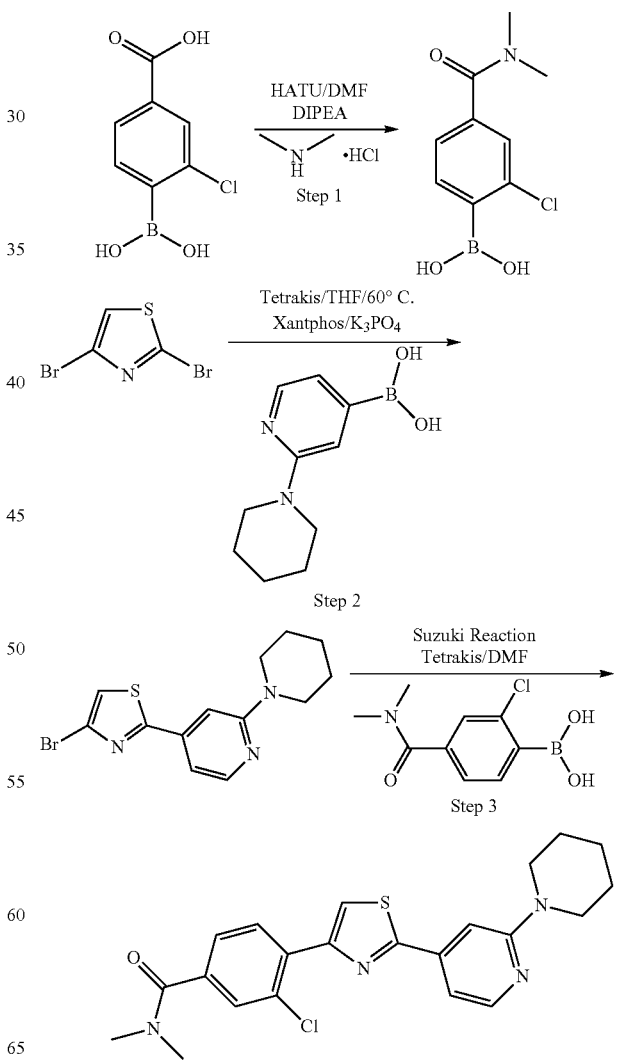

Step-1: Synthesis of [2-chloro-4-(dimethylcarbamoyl)phenyl]boronic acid

In a 250 mL flask was placed 4-borono-3-chloro-benzoic acid (1.5 g, 7.5 mmol, 1 eq.) in (25 mL) of DMF, then at RT, DIPEA (6.9 mL, 37.5 mmol, 5 eq.) was added, stirred for 5 min then at RT, HATU (5.7 g, 15 mmol, 2 eq.) and dimethyl amine hydrochloride (2.43 g, 30 mmol, 4 eq.) were added and the mixture stirred at RT overnight. When the reaction was completed (monitored by TLC and 1H-NMR/LCMS), 1N aq. HCl (100 mL) was added and the mixture extracted with EtOAc (2×100 mL) then dried over anhydrous sodium sulfate and the combined organic layer was concentrated under reduced pressure to give a viscous compound, which was purified by silica gel (60-120) column chromatography using acetone: hexane (0-35%) to elute pure compound as a semisolid which solidified in a refrigerator overnight (1.05 g).

Step-2: Synthesis of 4-bromo-2-[3-(1-piperidyl)phenyl]thiazole

In a 100 mL glass bottle were placed 2,4 dibromothiazole (400 mg, 1.64 mmol, 1 eq.) along with [2-(1-piperidyl)-4-pyridyl]boronic acid (340 mg, 1.64 mmol, 1 eq.) and potassium phosphate (697 mg, 3.29 mmol, 2.5 eq.) dissolved in 15 mL of THF. Then the mixture was purged with nitrogen for 15 min then Xantphos (95 mg, 0.1 eq.) and tetrakis (190 mg, 0.1 eq.) were added then repurged nitrogen for 5 min and the mixture stirred at 60° C. overnight. After completion of reaction (monitored by TLC & LCMS), the mixture was cooled to RT, water (100 mL) was added and the mixture extracted with EtOAc (3×100 mL), the combined organic layer was washed with brine (50 mL) then dried over anhydrous sodium sulfate, and concentrated under reduced pressure to give a viscous compound which was purified by silica gel (60-120) column chromatography using EtOAc/Hexane (0-20%) as eluent system to afford 4-bromo-2-(1H-indol-4-yl)thiazole pure compound as a yellow colored solid (325 mg).

Step-3: Synthesis of 3-chloro-N,N-dimethyl-4-[2-[2-(1-piperidyl)-4-pyridyl]thiazol-4-yl]benzamide In a 25 mL glass bottle were placed 4-bromo-2-[3-(1-piperidyl)phenyl]thiazole (300 mg, 0.92 mmol, 1 eq.) and [2-chloro-4-(dimethylcarbamoyl)phenyl]boronic acid (295 mg, 1.3 mmol, 1.4 eq.), sodium carbonate (246 mg, 2.32 mmol, 2.5 eq. dissolved in water (1.5 mL), in DMF (7 mL), and purged with nitrogen gas for 5 min. After adding tetrakis (107 mg, 0.062 mmol, 0.1 eq.), the mixture was repurged for 2 min and heated to 80° C. overnight. The reaction was monitored by TLC and LCMS. The reaction mixture was allowed to come to RT; water (50 mL) was added and the mixture extracted with EtOAc (3×100 mL). The combined organic layer was washed with water (4×50 mL), dried over anhydrous sodium sulfate and concentrated under reduced pressure to obtain the crude product which was purified by reverse phase HPLC to afford 3-chloro-N,N-dimethyl-4-[2-[2-(1-piperidyl)-4-pyridyl]thiazol-4-yl]benzamide (100 mg) as a yellow solid, the free base.

$^1$H NMR (400 MHz, DMSO-d6) δ (ppm): 8.34 (s, 1H), 8.23 (d, J=5.1 Hz, 1H), 8.05 (d, J=7.9 Hz, 1H), 7.63 (s, 1H), 7.51 (d, J=7.9 Hz, 1H), 7.28 (s, 1H), 7.12 (d, J=5.1 Hz, 1H), 3.60 (t, J=5.1 Hz, 2H), 2.98 (d, J=19.1 Hz, 6H), 1.9 (m, 2H), 1.6 (t, J=11.3 Hz, 6H). LCMS: (M+1) 427.2.

Example 10. Preparation of Compound No. 10

Synthesis of 1-{4-[5-(2-tert-butylpyridin-4-yl)thiophen-3-yl]-3-chlorobenzoyl}-4-methylpiperazine

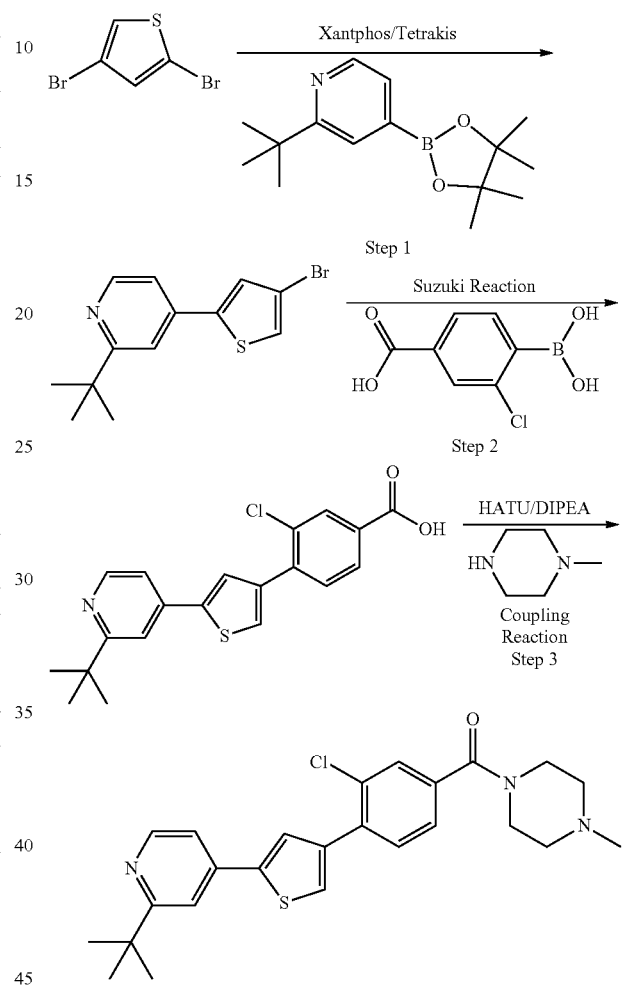

Step-1: Synthesis of 4-(4-bromo-2-thienyl)-2-tert-butyl-pyridine

In a 100 mL glass bottle was placed 2,4 dibromothiophene (600 mg, 2.5 mmol, 1 eq.) along with 2-tert-butyl-4-(4,4,5,5-tetramethyl-1,3,2-dioxaborolan-2-yl)pyridine (652 mg, 1 eq.) and potassium phosphate (1.325 g, 2.5 eq.) in 25 mL of THF. Then the mixture was purged with nitrogen for 15 min then Xantphos (145 mg, 0.1 eq.) and tetrakis (289 mg, 0.1 eq.) were added, and the mixture repurged for 5 min and the mixture stirred at 60° C. overnight. The progress of the reaction was monitored by TLC & LCMS. When the reaction was completed, the mixture was cooled to RT, water (100 mL) was added and the mixture extracted with EtOAc (3×100 mL). The combined organic layer was washed with brine (50 mL) then dried over anhydrous sodium sulfate, and concentrated under reduced pressure to give a viscous compound which was purified by silica gel (60-120) column chromatography using EtOAc/Hexane (0-20%) as eluent system to afford 4-(4-bromo-2-thienyl)-2-tert-butyl-pyridine as a colorless semi-solid (500 mg).

Step-2: Synthesis of 4-[5-(2-tert-butyl-4-pyridyl)-3-thienyl]-3-chloro-benzoic acid In a 25 mL glass bottle was placed 4-(4-bromo-2-thienyl)-2-tert-butyl-pyridine (450 mg, 1.52 mmol, 1 eq.) and 4-borono-3-chloro-benzoic acid (397 mg, 1.98 mmol, 1.3 eq.) in DMF (7 mL) followed by addition of sodium carbonate (404 mg, 2.5 equiv dissolved in water (2.0 mL) and the reaction mixture was purged with nitrogen gas for 5 min. After adding tetrakis triphenylphosphine palladium(0) (176 mg, 0.152 mmol, 0.1 eq.), the mixture was repurged for 2 min and was stirred at 90° C. overnight. The progress of the reaction was monitored by TLC and LCMS. After completion of reaction, the mixture was allowed to come to RT and diluted with water (50 mL) and extracted with EtOAc:MeOH (90:10), (3×100 mL). The combined organic layer was dried over anhydrous sodium sulfate and concentrated under reduced pressure to afford a semi-solid compound, 3-chloro-4-[5-[3-(1-piperidyl)phenyl]-3-thienyl]benzoic acid (500 mg) which was used as such for the next step of synthesis.

Step-3: Synthesis of [4-[5-(2-tert-butyl-4-pyridyl)-3-thienyl]-3-chloro-phenyl]-(4-methylpiperazin-1-yl)methanone In a 100 mL flask was placed 4-[5-(2-tert-butyl-4-pyridyl)-3-thienyl]-3-chloro-benzoic acid (200 mg, 0.54 mmol, 1 eq.) was dissolved in DMF (7 mL), followed by addition of DIPEA (0.4 mL, 2.15 mmol, 4 eq.) and HATU (409 mg, 1.07 mmol, 2 equiv), and the resulting mixture was stirred for 10 min at RT and 4-methyl piperidine (269 mg, 2.69 mmol, 5 eq.) were added and the mixture stirred at RT under nitrogen atmosphere overnight. The progress of the reaction was monitored by TLC and LCMS. After completion of reaction, the mixture was diluted with water (100 mL) and extracted with EtOAc (2×100 mL), washed with water (4×100 mL) then dried over anhydrous sodium sulfate and the combined organic layer was concentrated under reduced pressure to give a viscous compound, which was purified by reverse phase HPLC process to afford 1-{4-[5-(2-tert-butylpyridin-4-yl)thiophen-3-yl]-3-chlorobenzoyl}-4-methylpiperazine (20 mg) as an off-white solid, the free base.

$^1$H NMR (400 MHz, Methanol-d4) δ (ppm): 8.49 (d, J=5.3 Hz, 1H), 7.91 (d, J=1.4 Hz, 1H), 7.78 (d, J=1.5 Hz, 1H), 7.71-7.58 (m, 3H), 7.52 (dd, J=5.3, 1.8 Hz, 1H), 7.43 (dd, J=7.9, 1.7 Hz, 1H), 3.80 (s, 2H), 3.54 (s, 2H), 2.53 (s, 4H), 2.37 (s, 3H), 1.42 (s, 9H). LCMS: (M+1) 454.1.

Example 11. Preparation of Compound No. 11

Synthesis of 2-tert-butyl-4-{4-[2-chloro-4-(piperidine-1-carbonyl)phenyl]thiophen-2-yl}pyridine

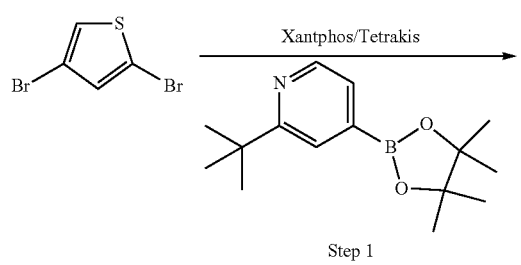

Step 1

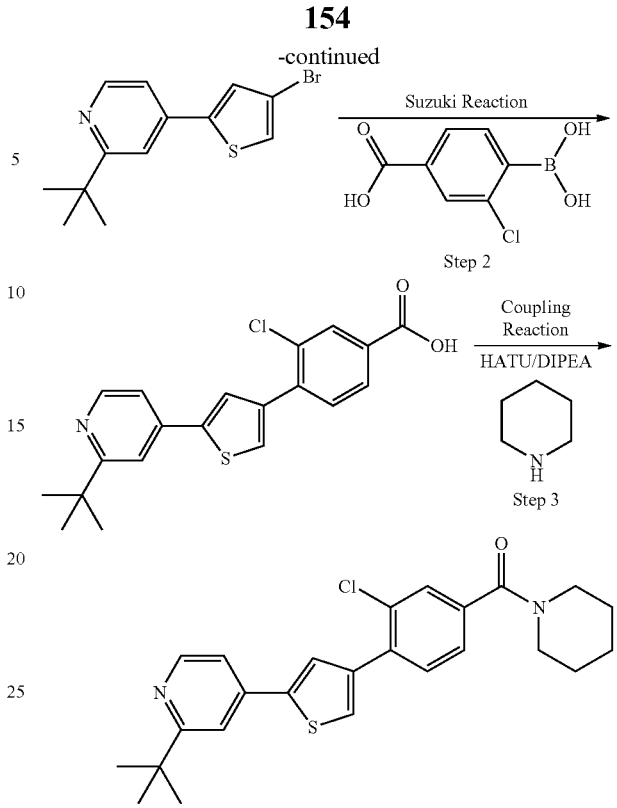

Step-1: Synthesis of 4-(4-bromo-2-thienyl)-2-tert-butyl-pyridine

In a 100 mL glass bottle was placed 2,4 dibromothiophene (600 mg, 2.5 mmol, 1 eq.), 2-tert-butyl-4-(4,4,5,5-tetramethyl-1,3,2-dioxaborolan-2-yl)pyridine (652 mg, 1 eq.) and potassium phosphate (1.325 g, 2.5 eq.) in 25 mL of THF. Then the mixture was purged with nitrogen for 15 min then Xantphos (145 mg, 0.1 eq.) and tetrakis (289 mg, 0.1 eq.) were added, and the mixture repurged for 5 min and the mixture stirred at 60° C. overnight. The progress of the reaction was monitored by TLC & LCMS. When the reaction was completed, the mixture was cooled to RT, water (100 mL) was added and the mixture extracted with EtOAc (3×100 mL). The combined organic layer was washed with brine (50 mL) then dried over anhydrous sodium sulfate, and concentrated under reduced pressure to give a viscous compound that was purified by silica gel (60-120) column chromatography using EtOAc/Hexane (0-20%) as eluent system to afford 4-(4-bromo-2-thienyl)-2-tert-butyl-pyridine as a colorless semi-solid (500 mg).

Step-2: Synthesis of 4-[5-(2-tert-butyl-4-pyridyl)-3-thienyl]-3-chloro-benzoic acid In a 25 mL glass bottle was placed 4-(4-bromo-2-thienyl)-2-tert-butyl-pyridine (450 mg, 1.52 mmol, 1 eq.) and 4-borono-3-chloro-benzoic acid (397 mg, 1.98 mmol, 1.3 eq.) in DMF (7 mL) followed by addition of sodium carbonate (404 mg, 2.5 equiv dissolved in water (2.0 mL), and the reaction mixture was purged with nitrogen gas for 5 min. After adding tetrakis (176 mg, 0.152 mmol, 0.1 eq.), the mixture was repurged for 2 min and was stirred at 90° C. overnight. The progress of the reaction was monitored by TLC and LCMS. After completion of reaction, the mixture was allowed to come to RT and diluted with water (50 mL) and extracted with EtOAc:MeOH (90:10) (3×100 mL). The combined organic layer was dried over anhydrous sodium sulfate and concentrated under reduced pressure to afford a semi-solid compound, 3-chloro-4-[5-[3-(1-piperidyl)phenyl]-3-thienyl]benzoic acid (500 mg) which was used as such for the next step of synthesis.

Step-3: Synthesis of [4-[5-(2-tert-butyl-4-pyridyl)-3-thienyl]-3-chloro-phenyl]-(1-piperidyl)methanone In a 100 mL flask was placed 4-[5-(2-tert-butyl-4-pyridyl)-3-thienyl]-3-chloro-benzoic acid (150 mg, 0.40 mmol, 1 eq.) dissolved in DMF (10 mL), followed by addition of DIPEA (0.37 mL, 1.61 mmol, 5 eq.) and HATU (307 mg, 0.80 mmol, 2 equiv), and the resulting mixture was stirred for 5 min at RT. Piperidine (137 mg, 1.61 mmol, 4 eq.) was added and the mixture was stirred at RT under nitrogen atmosphere overnight. The progress of the reaction was monitored by TLC and LCMS. After completion of reaction, the mixture was diluted with water (100 mL) and extracted with EtOAc (2×100 mL), washed with water (4×100 mL) then dried over anhydrous sodium sulfate and the combined organic layer was concentrated under reduced pressure to give a viscous compound, which was purified by reverse phase HPLC process to afford [4-[5-(2-tert-butyl-4-pyridyl)-3-thienyl]-3-chloro-phenyl]-(1-piperidyl)methanone (40 mg) as an off-white solid, the free base.

$^1$H NMR (400 MHz, Methanol-d4) δ (ppm): 8.49 (d, J=5.2 Hz, 1H), 7.91 (s, 1H), 7.77 (s, 1H), 7.71-7.61 (m, 2H), 7.59-7.45 (m, 2H), 7.41 (d, J=8.0 Hz, 1H), 3.73 (m, 2H), 3.44 (m, 2H), 1.73 (m, 4H), 1.59 (m, 2H), 1.42 (s, 9H). LCMS: (M+1) 439.2.

Example 12. Preparation of Compound No. 12

Synthesis of 2-tert-butyl-4-{4-[2-chloro-4-(3,3-difluoropyrrolidine-1-carbonyl)phenyl] thiophen-2-yl}pyridine

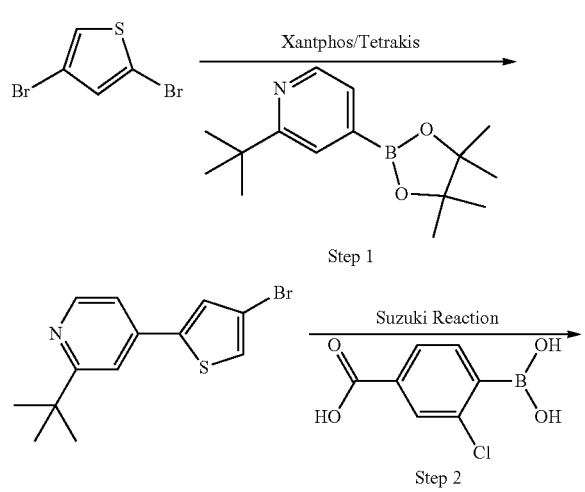

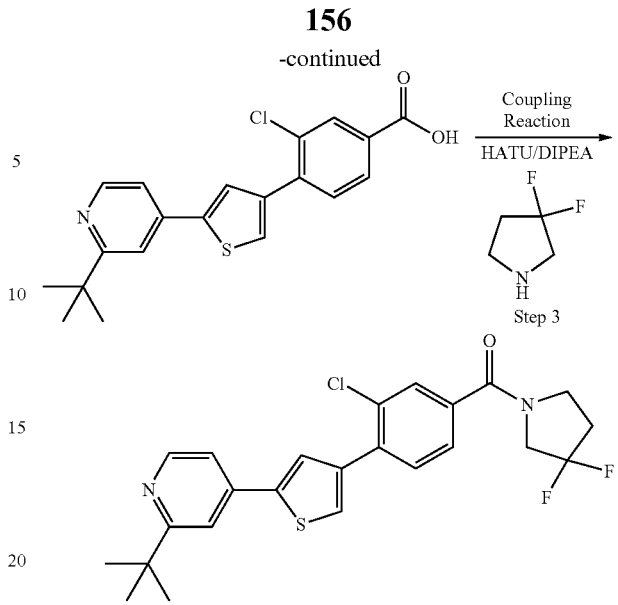

Step-1: Synthesis of 4-(4-bromo-2-thienyl)-2-tert-butyl-pyridine

In a 100 mL glass bottle was placed 2,4 dibromothiophene (600 mg, 2.5 mmol, 1 eq.) along with 2-tert-butyl-4-(4,4,5,5-tetramethyl-1,3,2-dioxaborolan-2-yl)pyridine (652 mg, 1 eq.) and potassium phosphate (1.325 g, 2.5 eq.) in 25 mL of THF. Then the mixture was purged with nitrogen for 15 min then Xantphos (145 mg, 0.1 eq.) and tetrakis (289 mg, 0.1 eq.) were added, and the mixture repurged for 5 min and the mixture stirred at 60° C. overnight. The progress of the reaction was monitored by TLC & LCMS. When the reaction was completed, the mixture was cooled to RT, water (100 mL) was added and the mixture extracted with EtOAc (3×100 mL). The combined organic layer was washed with brine (50 mL) then dried over anhydrous sodium sulfate, and concentrated under reduced pressure to give a viscous compound which was purified by silica gel (60-120) column chromatography using EtOAc/Hexane (0-20%) as eluent system to afford 4-(4-bromo-2-thienyl)-2-tert-butyl-pyridine as a colorless semi-solid (500 mg).

Step-2: Synthesis of 4-[5-(2-tert-butyl-4-pyridyl)-3-thienyl]-3-chloro-benzoic acid In a 25 mL glass bottle was placed 4-(4-bromo-2-thienyl)-2-tert-butyl-pyridine (450 mg, 1.52 mmol, 1 eq.) and 4-borono-3-chloro-benzoic acid (397 mg, 1.98 mmol, 1.3 eq.), in DMF (7 mL) followed by addition of sodium carbonate (404 mg, 2.5 equiv dissolved in water (2.0 mL) and the reaction mixture was purged with nitrogen gas for 5 min. After adding tetrakis triphenylphosphine palladium(0) (176 mg, 0.152 mmol, 0.1 eq.), the mixture was repurged for 2 min and was stirred at 90° C. overnight. The progress of the reaction was monitored by TLC and LCMS. After completion of reaction, the mixture was allowed to come to RT and diluted with water (50 mL) and extracted with EtOAc:MeOH (90:10), (3×100 mL). The combined organic layer was dried over anhydrous sodium sulfate and concentrated under reduced pressure to afford a semi-solid compound, 3-chloro-4-[5-[3-(1-piperidyl)phenyl]-3-thienyl]benzoic acid (500 mg) which was used as such for the next step of synthesis.

Step-3: Synthesis of [4-[5-(2-tert-butyl-4-pyridyl)-3-thienyl]-3-chloro-phenyl]-(3,3-difluoropyrrolidin-1-yl)methanone In a 100 mL flask was placed 4-[5-(2-tert-butyl-4-pyridyl)-3-thienyl]-3-chloro-benzoic acid (150 mg, 0.40 mmol, 1 eq.) in DMF (10 mL), followed by addition of DIPEA (0.37 mL, 1.61 mmol, 5 eq.) and HATU (307 mg, 0.80 mmol, 2 equiv), and the resulting mixture was stirred for 5 min at RT and 3,3-difluoropyrrolidine (173 mg, 1.61 mmol, 4 eq.) were added and the mixture stirred at RT under nitrogen atmosphere overnight. The progress of the reaction was monitored by TLC and LCMS. After completion of reaction, the mixture was diluted with water (100 mL) and extracted with EtOAc (2×100 mL), washed with water (4×100 mL) then dried over anhydrous sodium sulfate and the combined organic layer was concentrated under reduced pressure to give a viscous compound, which was purified by reverse phase HPLC process to afford [4-[5-(2-tert-butyl-4-pyridyl)-3-thienyl]-3-chloro-phenyl]-(3,3-difluoropyrrolidin-1-yl) methanone (33 mg) as an off-white solid, the free base.

$^1$H NMR (400 MHz, Methanol-d4) δ (ppm): 8.49 (d, J=5.3 Hz, 1H), 7.91 (s, 1H), 7.79 (s, 1H), 7.73 (s, 1H), 7.68 (d, J=10.2 Hz, 2H), 7.54 (dd, J=16.3, 6.5 Hz, 2H), 3.97 (t, J=14.1 Hz, 2H), 3.81 (d, J=7.4 Hz, 2H), 2.49 (s, 2H), 1.42 (s, 9H). LCMS: (M+1) 461.1.

Example 13. Preparation of Compound No. 13

Synthesis of 2-tert-butyl-4-{4-[2-chloro-4-(4,4-difluoropiperidine-1-carbonyl)phenyl] thiophen-2-yl}pyridine

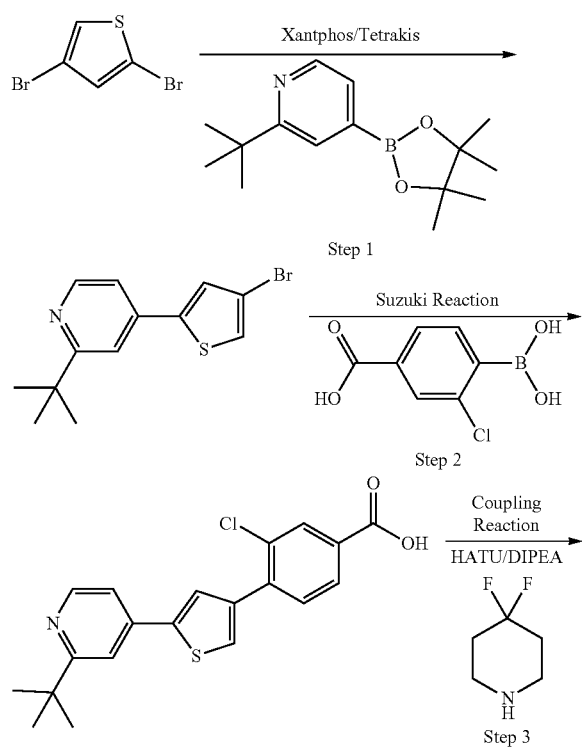

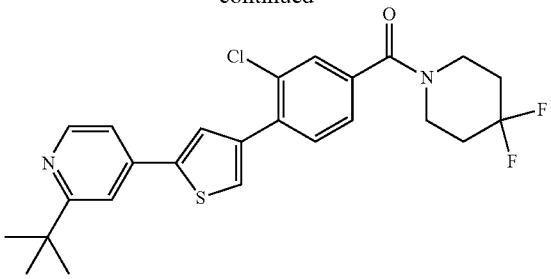

Step-1: Synthesis of 4-(4-bromo-2-thienyl)-2-tert-butyl-pyridine

In a 100 mL glass bottle was place 2,4 dibromothiophene (600 mg, 2.5 mmol, 1 eq.) along with 2-tert-butyl-4-(4,4,5,5-tetraethyl-1,3,2-dioxaborolan-2-yl)pyridine (652 mg, 1 eq.) and potassium phosphate (1.325 g, 2.5 eq.) in 25 mL of THF. Then the mixture was purged with nitrogen for 15 min then Xantphos (145 mg, 0.1 eq.) and tetrakis (289 mg, 0.1 eq.) were added, and the mixture repurged for 5 min and the mixture stirred at 60° C. overnight. The progress of the reaction was monitored by TLC & LCMS. When the reaction was completed, the mixture was cooled to RT, water (100 mL) was added and the mixture extracted with EtOAc (3×100 mL). The combined organic layer was washed with brine (50 mL) then dried over anhydrous sodium sulfate, and concentrated under reduced pressure to give a viscous compound which was purified by silica gel (60-120) column chromatography using EtOAc/Hexane (0-20%) as eluent system to afford 4-(4-bromo-2-thienyl)-2-tert-butyl-pyridine as a colorless semi-solid (500 mg).

Step-2: Synthesis of 4-[5-(2-tert-butyl-4-pyridyl)-3-thienyl]-3-chloro-benzoic acid In a 25 mL glass bottle was placed 4-(4-bromo-2-thienyl)-2-tert-butyl-pyridine (450 mg, 1.52 mmol, 1 eq.) and 4-borono-3-chloro-benzoic acid (397 mg, 1.98 mmol, 1.3 eq.) in DMF (7 mL) followed by addition of sodium carbonate (404 mg, 2.5 equiv dissolved in water (2.0 mL) and the reaction mixture was purged with nitrogen gas for 5 min. After adding tetrakis triphenylphosphine palladium(0) (176 mg, 0.152 mmol, 0.1 eq.), the mixture was repurged for 2 min and was stirred at 90° C. overnight. The progress of the reaction was monitored by TLC and LCMS. After completion of reaction, the mixture was allowed to come to RT and diluted with water (50 mL) and extracted with EtOAc: MeOH (90:10), (3×100 mL). The combined organic layer was dried over anhydrous sodium sulfate and concentrated under reduced pressure to afford a semi-solid compound, 3-chloro-4-[5-[3-(1-piperidyl)phenyl]-3-thienyl]benzoic acid (500 mg) which was used as such for the next step of synthesis.

Step-3: Synthesis of [4-[5-(2-tert-butyl-4-pyridyl)-3-thienyl]-3-chloro-phenyl]-(4,4-difluoro-1-piperidyl)methanone In a 100 mL flask was placed 4-[5-(2-tert-butyl-4-pyridyl)-3-thienyl]-3-chloro-benzoic acid (150 mg, 0.40 mmol, 1 eq.) in DMF (10 mL), followed by addition of DIPEA (0.37 mL, 1.61 mmol, 5 eq.) and HATU (307 mg, 0.80 mmol, 2 equiv), and the resulting mixture was stirred for 5 min at RT and 3,3-difluoropiperidine (196 mg, 1.61 mmol, 4 eq.) were added and the mixture stirred at RT under nitrogen atmosphere overnight. The progress of the reaction was monitored by TLC and LCMS. After completion of reaction, the mixture was diluted with water (100 mL) and extracted with EtOAc (2×100 mL), washed with water (4×100 mL) then dried over anhydrous sodium sulfate and the combined organic layer was concentrated under reduced pressure to give a viscous compound, which was purified by reverse phase HPLC process to afford [4-[5-(2-tert-butyl-4-pyridyl)-3-thienyl]-3-chloro-phenyl]-(4,4-difluoro-1-piperidyl) methanone (50 mg) as an off-white solid, the free base.

$^1$H NMR (400 MHz, Methanol-d4) δ (ppm): 8.49 (d, J=5.2 Hz, 1H), 7.91 (s, 1H), 7.78 (s, 1H), 7.71-7.61 (m, 3H), 7.52 (d, J=5.2 Hz, 1H), 7.47 (d, J=7.9 Hz, 1H), 3.87 (t, 2H), 3.62 (t, 2H), 2.08 (t, 4H), 1.42 (s, 9H). LCMS: (M+1) 475.2.

Example 14. Preparation of Compound No. 14

Synthesis of 4-[5-(2-tert-butylpyridin-4-yl)thiophen-3-yl]-3-chloro-N-cyclopropylbenzamide

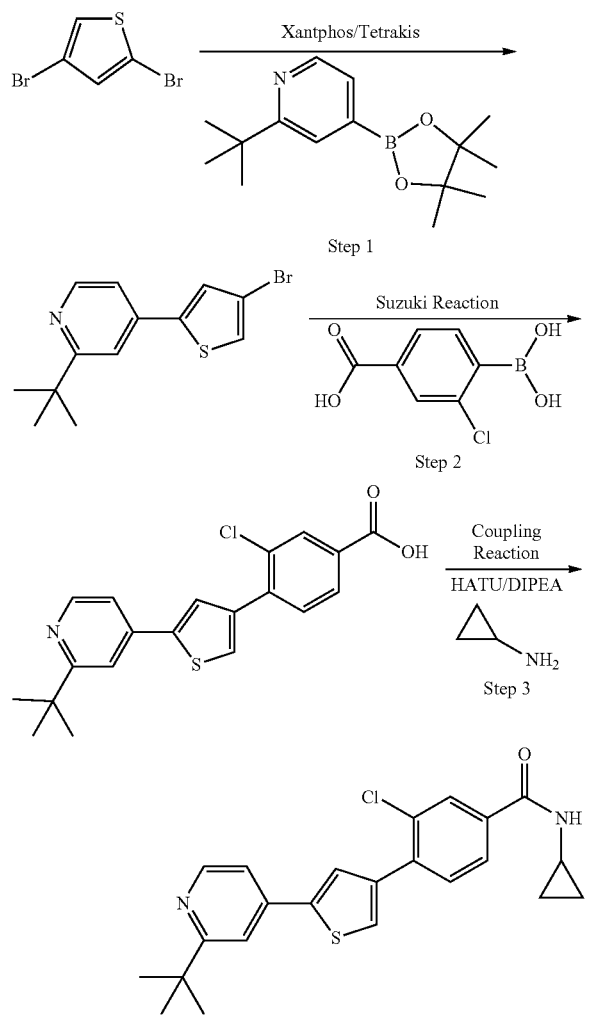

Step-1: Synthesis of 4-(4-bromo-2-thienyl)-2-tert-butyl-pyridine

In a 100 mL glass bottle was placed 2,4 dibromothiophene (600 mg, 2.5 mmol, 1 eq.) along with 2-tert-butyl-4-(4,4,5,5-tetramethyl-1,3,2-dioxaborolan-2-yl)pyridine (652 mg, 1 eq.) and potassium phosphate (1.325 g, 2.5 eq.) in 25 mL of THF. Then the mixture was purged with nitrogen for 15 min then Xantphos (145 mg, 0.1 eq.) and tetrakis (289 mg, 0.1 eq.) were added, and the mixture repurged for 5 min and the mixture stirred at 60° C. overnight. The progress of the reaction was monitored by TLC & LCMS. When the reaction was completed, the mixture was cooled to RT, water (100 mL) was added and the mixture extracted with EtOAc (3×100 mL). The combined organic layer was washed with brine (50 mL) then dried over anhydrous sodium sulfate, and concentrated under reduced pressure to give a viscous compound which was purified by silica gel (60-120) column chromatography using EtOAc/Hexane (0-20%) as eluent system to afford 4-(4-bromo-2-thienyl)-2-tert-butyl-pyridine as a colorless semi-solid (500 mg).

Step-2: Synthesis of 4-[5-(2-tert-butyl-4-pyridyl)-3-thienyl]-3-chloro-benzoic acid In a 25 mL glass bottle was placed 4-(4-bromo-2-thienyl)-2-tert-butyl-pyridine (450 mg, 1.52 mmol, 1 eq.) and 4-borono-3-chloro-benzoic acid (397 mg, 1.98 mmol, 1.3 eq.) in DMF (7 mL) followed by addition of sodium carbonate (404 mg, 2.5 equiv dissolved in water (2.0 mL) and the reaction mixture was purged with nitrogen gas for 5 min. After adding tetrakis triphenylphosphine palladium(0) (176 mg, 0.152 mmol, 0.1 eq.), the mixture was repurged for 2 min and was stirred at 90° C. overnight. The progress of the reaction was monitored by TLC and LCMS. After completion of reaction, the mixture was allowed to come to RT and diluted with water (50 mL) and extracted with EtOAc: MeOH (90:10), (3×100 mL). The combined organic layer was dried over anhydrous sodium sulfate and concentrated under reduced pressure to afford a semi-solid compound, 3-chloro-4-[5-[3-(1-piperidyl)phenyl]-3-thienyl]benzoic acid (500 mg) which was used as such for the next step of synthesis.

Step-3: Synthesis of 4-[5-(2-tert-butyl-4-pyridyl)-3-thienyl]-3-chloro-N-cyclopropyl-benzamide In a 100 mL flask was placed 4-[5-(2-tert-butyl-4-pyridyl)-3-thienyl]-3-chloro-benzoic acid (160 mg, 0.43 mmol, 1 eq.) in DMF (10 mL), followed by addition of DIPEA (0.40 mL, 2.15 mmol, 5 eq.) and HATU (327 mg, 0.86 mmol, 2 equiv), and the resulting mixture was stirred for 5 min at RT and cyclopropyl amine (98 mg, 1.72 mmol, 5 eq.) were added and the mixture stirred at RT under nitrogen atmosphere overnight. The progress of the reaction was monitored by TLC and LCMS. After completion of reaction, the mixture was diluted with water (100 mL) and extracted with EtOAc (2×100 mL), washed with water (4×100 mL) then dried over anhydrous sodium sulfate and the combined organic layer was concentrated under reduced pressure to give a viscous compound, which was purified by reverse phase HPLC process to afford 4-[5-(2-tert-butyl-4-pyridyl)-3-thienyl]-3-chloro-N-cyclopropyl-benzamide (18 mg) as an off-white solid, the free base.

$^1$H NMR (400 MHz, Methanol-d4) δ (ppm): 8.48 (d, J=5.3 Hz, 1H), 7.97 (s, 1H), 7.91 (s, 1H), 7.81 (d, J=9.7 Hz, 2H), 7.71-7.61 (m, 2H), 7.55-7.49 (m, 1H), 2.91-2.84 (m, 1H), 1.42 (s, 9H), 0.83 (t, J=6.7 Hz, 2H), 0.67 (t, 2H). LCMS: (M+1) 411.1.

Example 15. Preparation of Compound No. 15

Synthesis of N-tert-butyl-4-[5-(2-tert-butylpyridin-4-yl)thiophen-3-yl]-3-chlorobenzamide

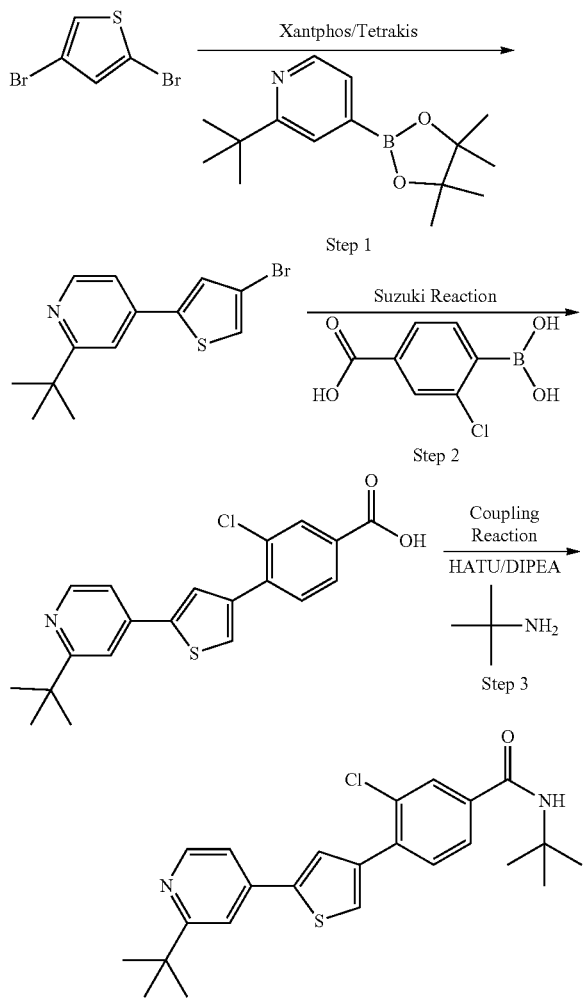

Step-1: Synthesis of 4-(4-bromo-2-thienyl)-2-tert-butyl-pyridine

In a 100 mL glass bottle was placed 2,4 dibromothiophene (600 mg, 2.5 mmol, 1 eq.) along with 2-tert-butyl-4-(4,4,5,5-tetramethyl-1,3,2-dioxaborolan-2-yl)pyridine (652 mg, 1 eq.) and potassium phosphate (1.325 g, 2.5 eq.) in 25 mL of THF. Then the mixture was purged with nitrogen for 15 min then Xantphos (145 mg, 0.1 eq.) and tetrakis (289 mg, 0.1 eq.) were added, and the mixture repurged for 5 min and the mixture stirred at 60° C. overnight. The progress of the reaction was monitored by TLC & LCMS. When the reaction was completed, the mixture was cooled to RT, water (100 mL) was added and the mixture extracted with EtOAc (3×100 mL). The combined organic layer was washed with brine (50 mL) then dried over anhydrous sodium sulfate, and concentrated under reduced pressure to give a viscous compound which was purified by silica gel (60-120) column chromatography using EtOAc/Hexane (0-20%) as eluent system to afford 4-(4-bromo-2-thienyl)-2-tert-butyl-pyridine as a colorless semi-solid (500 mg).

Step-2: Synthesis of 4-[5-(2-tert-butyl-4-pyridyl)-3-thienyl]-3-chloro-benzoic acid In a 25 mL glass bottle was placed 4-(4-bromo-2-thienyl)-2-tert-butyl-pyridine (450 mg, 1.52 mmol, 1 eq.) and 4-borono-3-chloro-benzoic acid (397 mg, 1.98 mmol, 1.3 eq.) in DMF (7 mL) followed by addition of sodium carbonate (404 mg, 2.5 equiv dissolved in water (2.0 mL) and the reaction mixture was purged with nitrogen gas for 5 min. After adding tetrakis triphenylphosphine palladium(0) (176 mg, 0.152 mmol, 0.1 eq.), the mixture was repurged for 2 min and was stirred at 90° C. overnight. The progress of the reaction was monitored by TLC and LCMS. After completion of reaction, the mixture was allowed to come to RT and diluted with water (50 mL) and extracted with EtOAc: MeOH (90:10), (3×100 mL). The combined organic layer was dried over anhydrous sodium sulfate and concentrated under reduced pressure to afford a semi-solid compound, 3-chloro-4-[5-[3-(1-piperidyl)phenyl]-3-thienyl]benzoic acid (500 mg) which was used as such for the next step of synthesis.

Step-3: Synthesis of N-tert-butyl-4-[5-(2-tert-butyl-4-pyridyl)-3-thienyl]-3-chloro-benzamide In a 100 mL flask was placed 4-[5-(2-tert-butyl-4-pyridyl)-3-thienyl]-3-chloro-benzoic acid (160 mg, 0.43 mmol, 1 eq.) was dissolved in DMF (10 mL), followed by addition of DIPEA (0.40 mL, 2.15 mmol, 5 eq.) and HATU (327 mg, 0.86 mmol, 2 equiv), and the resulting mixture was stirred for 5 min at RT and isobutyl amine (127 mg, 1.72 mmol, 4 eq.) were added and the mixture stirred at RT under nitrogen atmosphere overnight. The progress of the reaction was monitored by TLC and LCMS. After completion of reaction, the mixture was diluted with water (100 mL) and extracted with EtOAc (2×100 mL), washed with water (4×100 mL) then dried over anhydrous sodium sulfate and the combined organic layer was concentrated under reduced pressure to give a viscous compound, which was purified by reverse phase HPLC process to afford N-tert-butyl-4-[5-(2-tert-butyl-4-pyridyl)-3-thienyl]-3-chloro-benzamide (16 mg) as an off-white solid, the free base.

$^1$H NMR (400 MHz, Methanol-d4) δ (ppm): 8.48 (d, J=5.2 Hz, 1H), 7.91 (m, 2H), 7.82-7.73 (m, 2H), 7.72-7.67 (m, 1H), 7.63 (d, J=8.0 Hz, 1H), 7.55-7.47 (m, 1H), 1.47 (s, 9H), 1.42 (s, 9H). LCMS: (M+1) 427.2.

Example 16. Preparation of Compound No. 16

Synthesis of 2-tert-butyl-4-{4-[2-chloro-4-(piperidine-1-carbonyl)phenyl]-5-methylthiophen-2-yl}pyridine

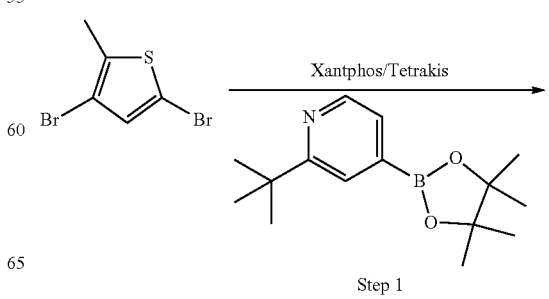

Step 1

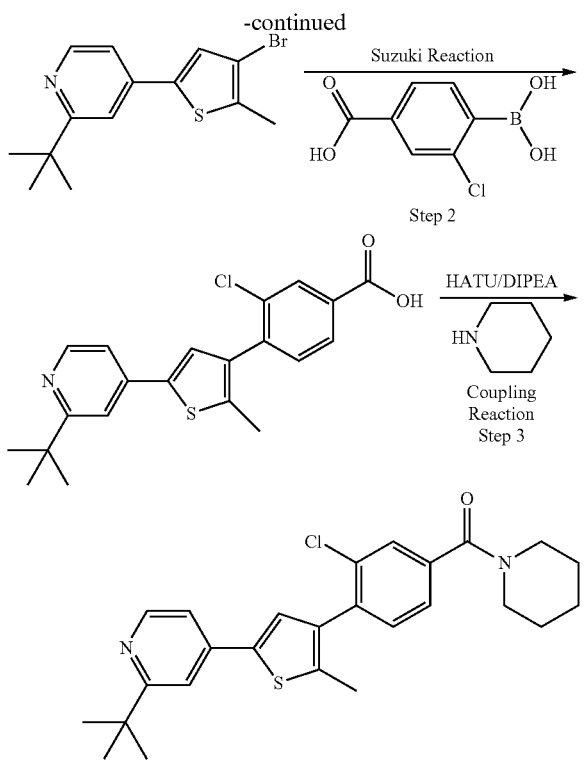

Step-1: Synthesis of 4-(4-bromo-5-methyl-2-thienyl)-2-tert-butyl-pyridine

In a 100 mL glass bottle was placed 3,5-dibromo-2-methyl-thiophene (500 mg, 1.95 mmol, 1 eq.) along with (2-tert-butyl-4-pyridyl)boronic acid (350 mg, 1 eq.) and potassium phosphate (1.03 g, 2.5 eq.) in 15 mL of THF. Then the mixture was purged with nitrogen for 15 min then Xantphos (90 mg, 0.08 eq.) and tetrakis (180 mg, 0.08 eq.) were added, and the mixture repurged for 5 min and the mixture stirred at 60° C. overnight. The progress of the reaction was monitored by TLC & LCMS. When the reaction was completed, the mixture was cooled to RT, water (100 mL) was added and the mixture extracted with EtOAc (3×100 mL). The combined organic layer was washed with brine (50 mL) then dried over anhydrous sodium sulfate, and concentrated under reduced pressure to give a viscous compound which was purified by silica gel (60-120) column chromatography using EtOAc/Hexane (0-20%) as eluent system to afford 4-(4-bromo-5-methyl-2-thienyl)-2-tert-butyl-pyridine as a colorless semi-solid (500 mg).

Step-2: Synthesis of 4-[5-(2-tert-butyl-4-pyridyl)-2-methyl-3-thienyl]-3-chloro-benzoic acid In a 25 mL glass bottle was placed 4-(4-bromo-5-methyl-2-thienyl)-2-tert-butyl-pyridine (350 mg, 1.13 mmol, 1 eq.) and 4-borono-3-chloro-benzoic acid (292 mg, 1.46 mmol, 1.3 eq.) in DMF (7 mL) followed by addition of sodium carbonate (298 mg, 2.5 equiv dissolved in water (1.5 mL) and the reaction mixture was purged with nitrogen gas for 5 min. After adding tetrakis triphenylphosphine palladium(0) (130 mg, 0.113 mmol, 0.1 eq.), the mixture was repurged for 2 min and was stirred at 90° C. overnight. The progress of the reaction was monitored by TLC and LCMS. After completion of reaction, the mixture was allowed to come to RT and diluted with water (50 mL) and extracted with EtOAc:MeOH (90:10), (3×100 mL). The combined organic layer was dried over anhydrous sodium sulfate and concentrated under reduced pressure to afford a semi-solid compound, 4-[5-(2-tert-butyl-4-pyridyl)-2-methyl-3-thienyl]-3-chloro-benzoic acid (350 mg) which was used as such for the next step of synthesis.

Step-3: Synthesis of [4-[5-(2-tert-butyl-4-pyridyl)-2-methyl-3-thienyl]-3-chloro-phenyl]-(1-piperidyl)methanone In a 100 mL flask was placed 4-[5-(2-tert-butyl-4-pyridyl)-2-methyl-3-thienyl]-3-chloro-benzoic acid (200 mg, 0.52 mmol, 1 eq.) was dissolved in DMF (15 mL), followed by addition of DIPEA (0.38 mL, 2.07 mmol, 4 eq.) and HATU (394 mg, 1.03 mmol, 2 equiv), and the resulting mixture was stirred for 10 min at RT and piperidine (221 mg, 2.59 mmol, 5 eq.) were added and the mixture stirred at RT under nitrogen atmosphere overnight. The progress of the reaction was monitored by TLC and LCMS. After completion of reaction, the mixture was diluted with water (100 mL) and extracted with EtOAc (2×100 mL), washed with water (4×100 mL) then dried over anhydrous sodium sulfate and the combined organic layer was concentrated under reduced pressure to give a viscous compound, which was purified by reverse phase HPLC process to afford 2-tert-butyl-4-{4-[2-chloro-4-(piperidine-1-carbonyl)phenyl]-5-methylthiophen-2-yl}pyridine (34 mg) as an off-white solid, the free base.

$^1$H NMR (400 MHz, DMSO-d6) δ (ppm): 8.49 (d, J=5.2 Hz, 1H), 7.76 (s, 1H), 7.59 (dd, J=5.2, 1.6 Hz, 2H), 7.49 (d, J=7.8 Hz, 1H), 7.45-7.35 (m, 2H), 3.60 (s, 2H), 2.34 (s, 3H), 1.71-1.22 (m, 8H), 1.34 (s, 9H). LCMS: (M+1) 453.2.

Example 17. Preparation of Compound No. 17

Synthesis of 4-(3-chloro-4-{2-[2-(piperidin-1-yl)pyridin-4-yl]-1,3-thiazol-4-yl}benzoyl) morpholine

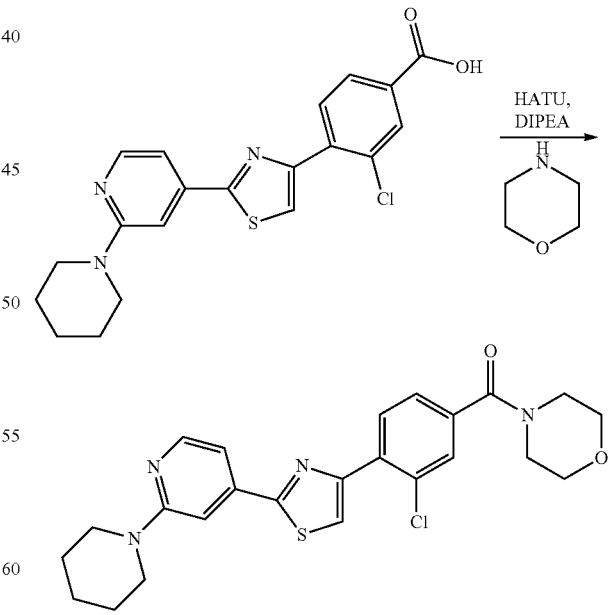

To a stirred solution of 3-chloro-4-[2-[2-(1-piperidyl)-4-pyridyl]thiazol-4-yl]benzoic acid (230 mg, 0.576 mmol) in DMF (6 mL) was added DIPEA (0.4 mL, 2.305 mmol) followed by addition of HATU (394 mg, 1.037 mmol) and the mixture stirred at RT for 30 min. Then morpholine (125 mg, 1.441 mmol) was added at the same temperature. The reaction mixture was stirred at RT overnight. The reaction was monitored by TLC and LCMS. After completion of reaction, the mixture was diluted with water (10 mL) and extracted with EtOAc (2×50 mL), the organic layer was washed with water (2×20 mL) and brine (20 mL) and dried over anhydrous sodium sulfate to obtain the crude compound which was purified by HPLC to obtain [3-chloro-4-[2-[2-(1-piperidyl)-4-pyridyl]thiazol-4-yl]phenyl]-morpholino-methanone (70 mg) freebase as a solid.

$^1$H NMR (400 MHz, Methanol-d4) δ (ppm): 8.21-8.07 (m, 3H), 7.59 (s, 1H), 7.49 (d, J=8.0 Hz, 1H), 7.37 (s, 1H), 7.15 (d, J=5.2 Hz, 1H), 3.77 (m, 4H), 3.71-3.59 (m, 4H), 3.51 (m, 2H), 3.34-3.28 (m, 4H), 1.69 (m, 4H). LCMS: −469 (M+1).

Example 18. Preparation of Compound Nos. 18, 18a and 18b

Synthesis of 3-chloro-N-(2-hydroxypropyl)-4-{2-[2-(piperidin-1-yl)pyridin-4-yl]-1,3-thiazol-4-yl}benzamide

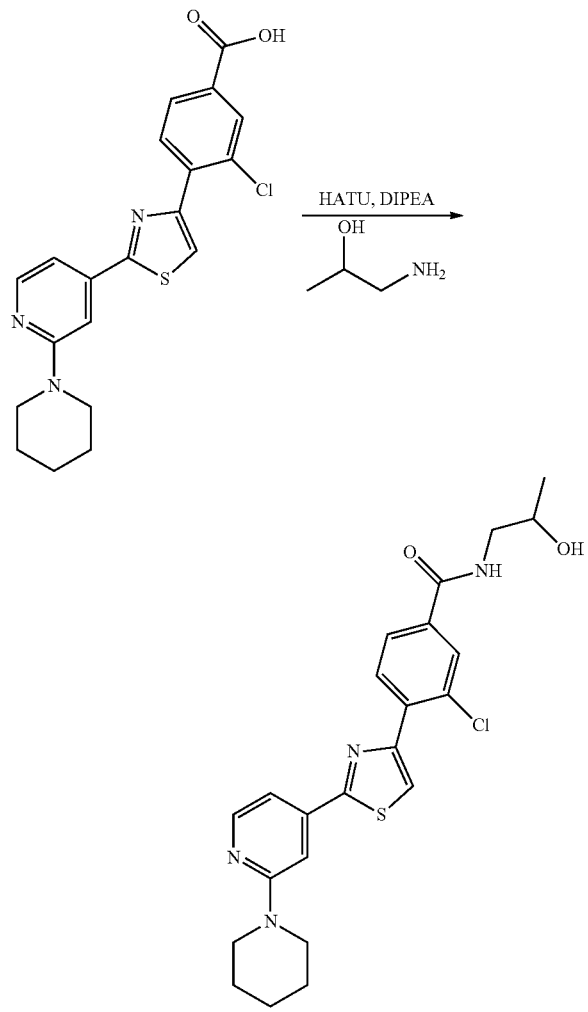

To a stirred solution of 3-chloro-4-[2-[2-(1-piperidyl)-4-pyridyl]thiazol-4-yl]benzoic acid (230 mg, 0.576 mmol) in DMF (6 mL), was added DIPEA (0.4 mL, 2.305 mmol) followed by addition of HATU (394 mg, 1.037 mmol) and the mixture stirred at RT for 30 min. Then (S)1-aminopropan-2-ol (108 mg, 1.441 mmol) was added at the same temperature. The reaction mixture was stirred at RT overnight. The reaction was monitored by TLC and LCMS. After completion of reaction, the mixture was diluted with water (10 mL) and extracted with EtOAc (2×50 mL), the organic layer was washed with water (2×20 mL) and brine (20 mL) and dried over anhydrous sodium sulfate to obtain the crude compound which was purified by HPLC to obtain 3-chloro-N-(2-hydroxypropyl)-4-[2-[2-(1-piperidyl)-4-pyridyl]thiazol-4-yl]benzamide (34 mg) freebase as a solid. The enantiomers can be prepared from chiral HPLC resolution of the racemate.

$^1$H NMR (400 MHz, Methanol-d4) δ (ppm): 8.18 (d, J=5.3 Hz, 2H), 8.11 (d, J=8.1 Hz, 1H), 8.04 (s, 1H), 7.89 (d, J=8.2 Hz, 1H), 7.37 (s, 1H), 7.15 (d, J=5.3 Hz, 1H), 3.99 (q, J=6.2 Hz, 1H), 3.62 (t, J=4.8 Hz, 4H), 3.45 (dd, J=13.6, 4.7 Hz, 1H), 3.39-3.31 (m, 1H), 1.69 (m, 6H), 1.22 (d, J=6.3 Hz, 3H). LCMS: −457 (M+1).

Example 19. Preparation of Compound Nos. 19, 19a, and 19b

Synthesis of tert-butyl N-(1-{4-[5-(2-tert-butylpyridin-4-yl)thiophen-3-yl]-3-chlorobenzoyl}piperidin-3-yl)carbamate

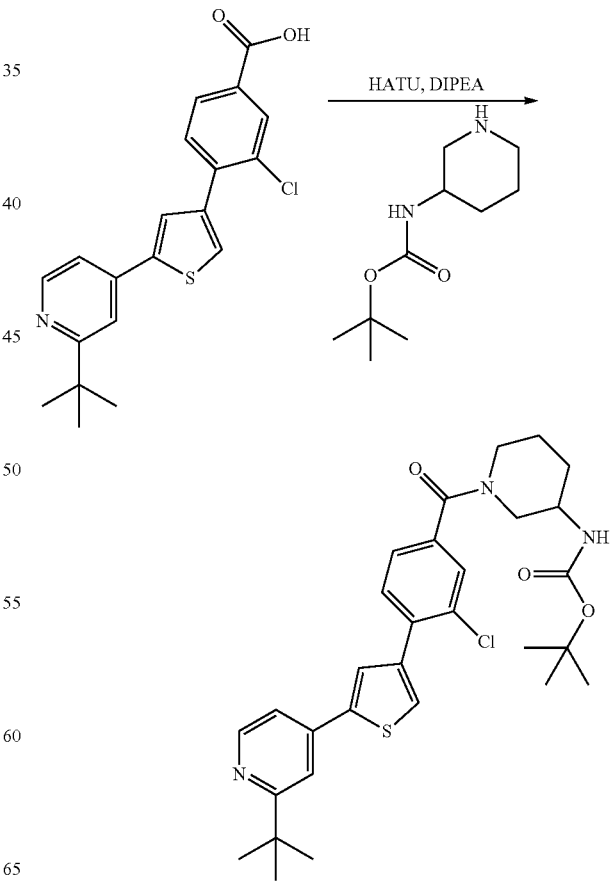

To a stirred solution of 4-[5-(2-tert-butyl-4-pyridyl)-3-thienyl]-3-chloro-benzoic acid (100 mg, 0.268 mmol) in DMF (5 mL) was added DIPEA (0.18 mL, 1.072 mmol) followed by addition of HATU (183 mg, 0.482 mmol) and the mixture stirred at RT for 30 min. Then tert-butyl N-(3-piperidyl)carbamate (134 mg, 0.670 mmol) was added at the same temperature. The reaction mixture was stirred at RT overnight. The reaction was monitored by TLC and LCMS. After completion of reaction, the mixture was diluted with water (10 mL) and extracted with EtOAc (2×50 mL), the organic layer was washed with water (2×20 mL) and brine (20 mL) and dried over anhydrous sodium sulfate to obtain the crude compound which was purified by HPLC to obtain tert-butyl N-(1-{4-[5-(2-tert-butylpyridin-4-yl)thiophen-3-yl]-3-chlorobenzoyl}piperidin-3-yl)carbamate (15 mg) freebase as a solid. Each of the enantiomers of this racemate were prepared using both the (R) and (S) forms of the carbamate reagent, to give Compound 19a [tert-butyl (R)-(1-(4-(5-(2-(tert-butyl)pyridin-4-yl)thiophen-3-yl)-3-chlorobenzoyl)piperidin-3-yl)carbamate] and Compound 19b [tert-butyl (S)-(1-(4-(5-(2-(tert-butyl)pyridin-4-yl)thiophen-3-yl)-3-chlorobenzoyl)piperidin-3-yl)carbamate].

¹H NMR (400 MHz, Methanol-d4) δ (ppm): 8.48 (d, J=5.2 Hz, 1H), 7.88 (s, 1H), 7.75 (s, 1H), 7.70-7.57 (m, 3H), 7.51 (dd, J=5.3, 1.8 Hz, 1H), 7.43 (dd, J=7.9, 1.7 Hz, 1H), 3.87 (m, 1H), 3.56 (m, 3H), 2.01 (d, J=19.4 Hz, 2H), 1.87 (m, 1H), 1.76 (m, 1H), 1.47 (m, 1H), 1.41 (s, 18H). LCMS: −554 (M+1).

Example 20. Preparation of Compound No. 20

Synthesis of 4-{4-[5-(2-tert-butylpyridin-4-yl)thiophen-3-yl]-3-chlorobenzoyl}-1λ⁶,4-thiomorpholine-1,1-dione

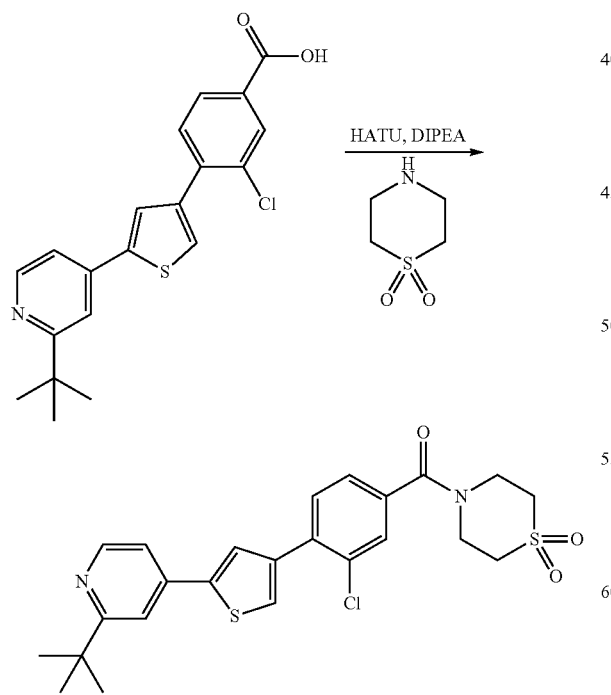

To a stirred solution of 4-[5-(2-tert-butyl-4-pyridyl)-3-thienyl]-3-chloro-benzoic acid (100 mg, 0.268 mmol) in DMF (5 mL), was added DIPEA (0.18 mL, 1.072 mmol) followed by addition of HATU (183 mg, 0.482 mmol) and the mixture stirred at RT for 30 min. Then 1,4-thiazinane 1,1-dioxide (91 mg, 0.670 mmol) was added at the same temperature. The reaction mixture was stirred at RT overnight. The reaction was monitored by TLC and LCMS. After completion of reaction, the mixture was diluted with water (10 mL) and extracted with EtOAc (2×50 mL). The organic layer was washed with water (2×20 mL) and brine (20 mL) and dried over anhydrous sodium sulfate to obtain the crude compound which was purified by HPLC to obtain 4-{4-[5-(2-tert-butylpyridin-4-yl)thiophen-3-yl]-3-chlorobenzoyl}-1λ⁶,4-thiomorpholine-1,1-dione (11.5 mg) freebase as a solid.

¹H NMR (400 MHz, Methanol-d4) δ (ppm): 8.49 (d, J=5.2 Hz, 1H), 7.90 (s, 1H), 7.79 (d, J=1.2 Hz, 1H), 7.69 (t, J=10.2 Hz, 3H), 7.52 (d, J=5.8 Hz, 2H), 4.08 (m, 4H), 3.25 (m, 4H), 1.42 (s, 9H). LCMS: −489 (M+1).

Example 21. Preparation of Compound Nos. 21, 21a, and 21b

Synthesis of 1-{4-[5-(2-tert-butylpyridin-4-yl)thiophen-3-yl]-3-chlorobenzoyl}piperidin-3-amine

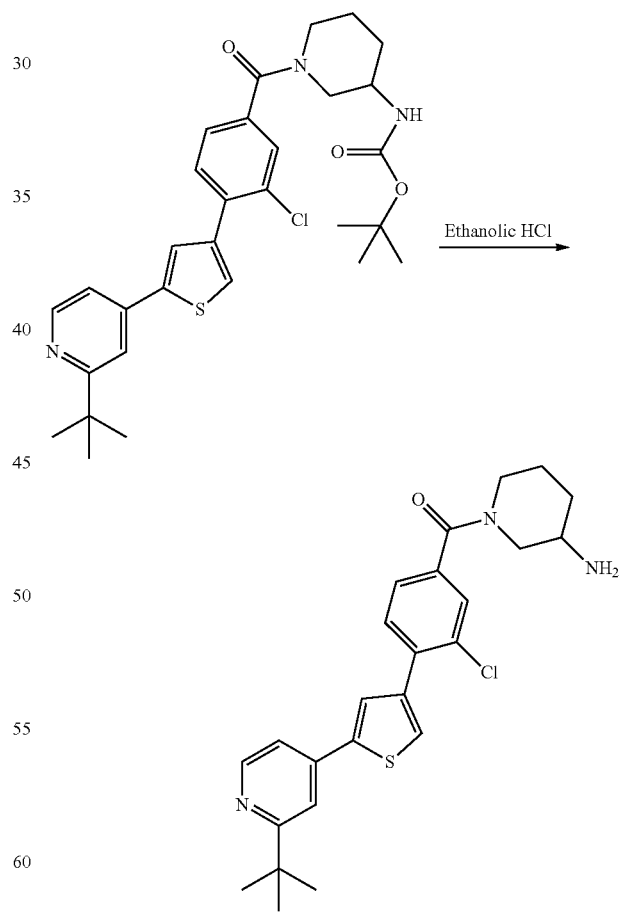

A stirred solution of tert-butyl N-[1-[4-[5-(2-tert-butyl-4-pyridyl)-3-thienyl]-3-chloro-benzoyl]-3-piperidyl]carbamate (10 mg, 0.0180 mmol) in ethanolic HCl (3 mL) was stirred at RT for 2 h. The reaction was monitored by LCMS.

After completion of reaction, the mixture was concentrated under reduced pressure to obtain 1-{4-[5-(2-tert-butylpyridin-4-yl)thiophen-3-yl]-3-chlorobenzoyl}piperidin-3-amine HCl (8 mg) as a solid. The enantiomers were prepared from chiral HPLC resolution of the racemate to give Compound 21a [(R)-(3-aminopiperidin-1-yl)(4-(5-(2-(tert-butyl)pyridin-4-yl)thiophen-3-yl)-3-chlorophenyl)methanone] and Compound 21b [(S)-(3-aminopiperidin-1-yl)(4-(5-(2-(tert-butyl)pyridin-4-yl)thiophen-3-yl)-3-chlorophenyl)methanone].

$^1$H NMR (400 MHz, Methanol-d4) δ (ppm): 8.60 (d, J=6.3 Hz, 1H), 8.36 (s, 1H), 8.15 (d, J=15.3 Hz, 3H), 7.74-7.66 (m, 2H), 7.51 (dd, J=7.8, 1.7 Hz, 1H), 4.43 (m, 2H), 3.64 (m, 1H), 3.39 (m, 2H), 3.34 (m, 2H), 2.18 (m, 1H), 1.74 (d, J=15.5 Hz, 1H), 1.56 (s, 9H). LCMS: −454 (M+1).

Example 22. Preparation of Compound No. 22

Synthesis of 4-{4-[5-(2-tert-butylpyridin-4-yl)thiophen-3-yl]-3-chlorobenzoyl}morpholine

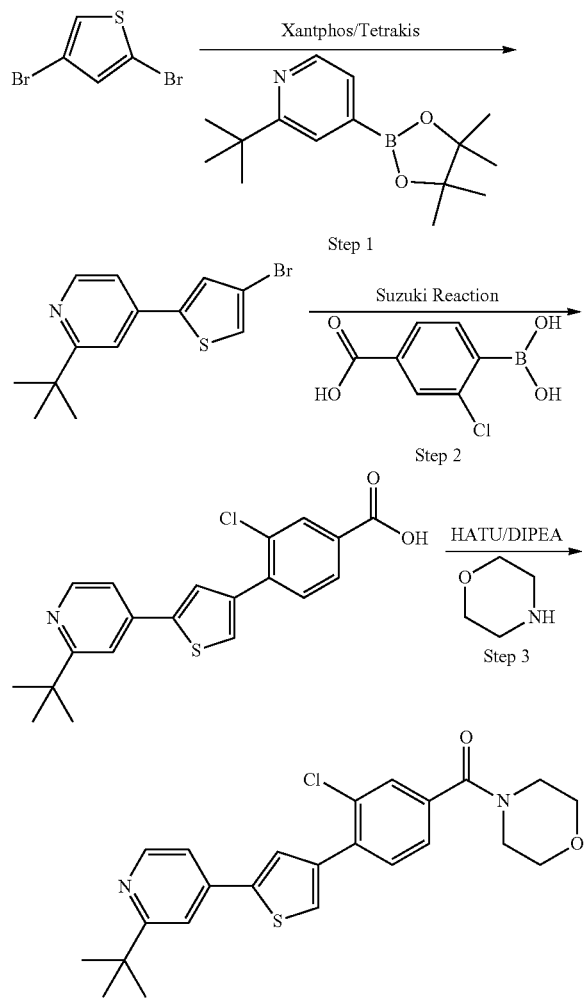

Step-1: Synthesis of 4-(4-bromo-2-thienyl)-2-tert-butyl-pyridine

In a 100 mL glass bottle was placed 2,4 dibromothiophene (600 mg, 2.5 mmol, 1 eq.) along with 2-tert-butyl-4-(4,4,5,5-tetramethyl-1,3,2-dioxaborolan-2-yl)pyridine (652 mg, 1 eq.) and potassium phosphate (1.325 g, 2.5 eq.) in 25 mL of THF. Then the mixture was purged with nitrogen for 15 min then Xantphos (145 mg, 0.1 eq.) and tetrakis (289 mg, 0.1 eq.) were added, and the mixture repurged for 5 min and the mixture stirred at 60° C. overnight. The progress of the reaction was monitored by TLC & LCMS. When the reaction was completed, the mixture was cooled to RT, water (100 mL) was added and the mixture extracted with EtOAc (3×100 mL). The combined organic layer was washed with brine (50 mL) then dried over anhydrous sodium sulfate, and concentrated under reduced pressure to give a viscous compound which was purified by silica gel (60-120) column chromatography using EtOAc/Hexane (0-20%) as eluent system to afford 4-(4-bromo-2-thienyl)-2-tert-butyl-pyridine as a colorless semi-solid (500 mg).

Step-2: Synthesis of 4-[5-(2-tert-butyl-4-pyridyl)-3-thienyl]-3-chloro-benzoic acid In a 25 mL glass bottle was placed 4-(4-bromo-2-thienyl)-2-tert-butyl-pyridine (450 mg, 1.52 mmol, 1 eq.) and 4-borono-3-chloro-benzoic acid (397 mg, 1.98 mmol, 1.3 eq.) in DMF (7 mL) followed by addition of sodium carbonate (404 mg, 2.5 equiv dissolved in water (2.0 mL) and the reaction mixture was purged with nitrogen gas for 5 min. After adding tetrakis triphenylphosphine palladium(0) (176 mg, 0.152 mmol, 0.1 eq.), the mixture was repurged for 2 min and was stirred at 90° C. overnight. The progress of the reaction was monitored by TLC and LCMS. After completion of reaction, the mixture was allowed to come to RT and diluted with water (50 mL) and extracted with EtOAc: MeOH (90:10), (3×100 mL). The combined organic layer was dried over anhydrous sodium sulfate and concentrated under reduced pressure to afford a semi-solid compound, 3-chloro-4-[5-[3-(1-piperidyl)phenyl]-3-thienyl]benzoic acid (500 mg) which was used as such for the next step of synthesis.

Step-3: Synthesis of [4-[5-(2-tert-butyl-4-pyridyl)-3-thienyl]-3-chloro-phenyl]-morpholino-methanone In a 100 mL flask was placed 4-[5-(2-tert-butyl-4-pyridyl)-3-thienyl]-3-chloro-benzoic acid (125 mg, 0.34 mmol, 1 eq.) was dissolved in DMF (5 mL), followed by addition of DIPEA (0.25 mL, 1.34 mmol, 4 eq.) and HATU (255 mg, 0.68 mmol, 2 equiv), and the resulting mixture was stirred for 10 min at RT and piperidine (146 mg, 1.68 mmol, 5 eq.) were added and the mixture stirred at RT under nitrogen atmosphere overnight. The progress of the reaction was monitored by TLC and LCMS. After completion of reaction, the mixture was diluted with water (100 mL) and extracted with EtOAc (2×100 mL), washed with water (4×100 mL) then dried over anhydrous sodium sulfate and the combined organic layer was concentrated under reduced pressure to give a viscous compound, which was purified by reverse phase HPLC process to afford 4-{4-[5-(2-tert-butylpyridin-4-yl)thiophen-3-yl]-3-chlorobenzoyl}morpholine (50 mg) as the formate salt as a yellow solid.

$^1$H NMR (400 MHz, Methanol-d4) δ (ppm): 8.49 (d, J=5.2 Hz, 1H), 7.90 (d, J=1.5 Hz, 1H), 7.78 (d, J=1.4 Hz, 1H), 7.71-7.64 (m, 2H), 7.62 (d, J=1.6 Hz, 1H), 7.52 (dd, J=5.2, 1.7 Hz, 1H), 7.44 (dd, J=7.8, 1.7 Hz, 1H), 3.76 (s, 5H), 3.52 (s, 3H), 1.42 (s, 9H). LCMS: (M+1) 441.0.

Example 23. Preparation of Compound No. 23

Synthesis of 4-[5-(2-tert-butylpyridin-4-yl)thiophen-3-yl]-3-chloro-N-phenylbenzamide

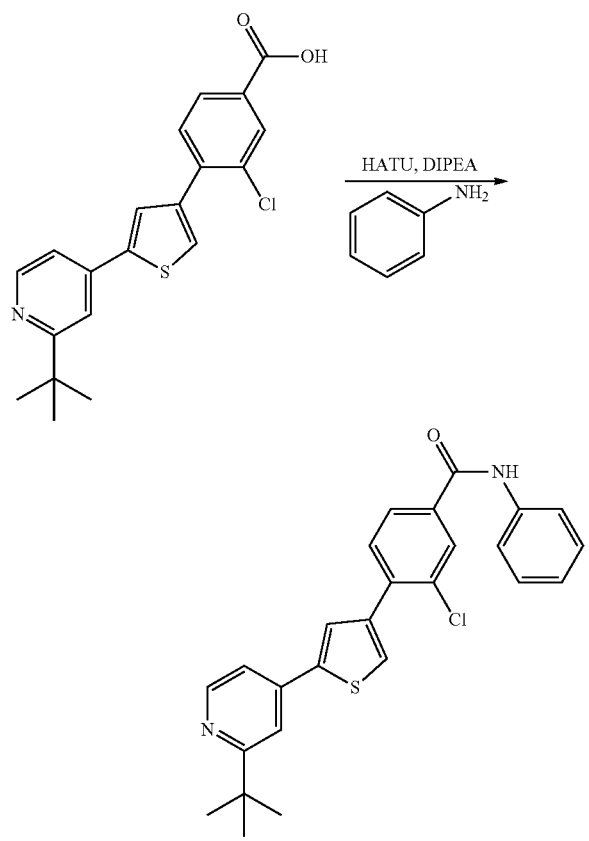

To a stirred solution of 4-[5-(2-tert-butyl-4-pyridyl)-3-thienyl]-3-chloro-benzoic acid (100 mg, 0.269 mmol) in DMF (5 mL), was added DIPEA (0.2 mL, 1.076 mmol) followed by addition of HATU (204 mg, 0.538 mmol) and stirred at RT for 30 min. Then aniline (125 mg, 1.347 mmol) was added at the same temperature. The reaction mixture was stirred at RT overnight. The reaction was monitored by TLC and LCMS. After completion of reaction, the mixture was diluted with water (50 mL) and extracted with EtOAc (2×50 mL). The organic layer was washed with water (2×20 mL) and brine (20 mL) and dried over anhydrous sodium sulfate to obtain a crude compound, which was purified by Reverse phase HPLC to obtain 4-[5-(2-tert-butyl-4-pyridyl)-3-thienyl]-3-chloro-N-phenyl-benzamide (45 mg) freebase, as a solid.

$^1$H NMR (400 MHz, Dmso-d6) δ (ppm): 10.4 (s, 1H), 8.58 (d, J=5.2 Hz, 1H), 8.20 (s, 1H), 8.10 (s, 1H), 8.00 (m, 2H), 7.8 (m, 3H), 7.65 (s, 1H), 7.5 (s, 1H), 7.38 (m, 2H), 7.10 (m, 1H), 1.41 (s, 9H). LCMS=446.9 (M+1).

Example 24. Preparation of Compound No. 24

Synthesis of 2-tert-butyl-4-{4-[2-chloro-4-(4,4-difluoropiperidine-1-carbonyl)phenyl]-1H-imidazol-2-yl}pyridine To a solution of (4-(2-(2-tert-butyl-4-pyridyl)-3-(methoxymethyl)-1H-imidazole-5-yl)-3-chloro-phenyl)-(- 4,4-difluoro-1-piperidyl) methanone (360 mg, 0.716 mmol) in THF (20 mL) was added 3M HCl solution (10 mL) and heated at 80° C. for 2 h. The reaction was monitored by LCMS and when complete, the reaction mixture was basified with saturated sodium bicarbonate solution (30 mL) (pH-7) and extracted with EtOAc (3×50 mL). The combined organic layer was washed with water (50 mL), dried over anhydrous sodium sulfate and concentrated under reduced pressure to obtain a crude product, which was purified by reverse phase HPLC to afford (40 mg) of 2-tert-butyl-4-{4-[2-chloro-4-(4,4-difluoropiperidine-1-carbonyl)phenyl]-1H-imidazol-2-yl}pyridine.

$^1$H NMR (400 MHz, DMSO-d6): 8.55 (d, J=8.5 Hz, 1H), 8.10 (s, 1H), 7.98 (s, 2H), 7.71 (d, J=8.2 Hz, 1H), 7.45 (s, 1H), 7.38 (d, J=3.5 Hz, 1H), 3.55 (s, 2H), 3.25 (s, 2H), 1.58 (s, 4H), 1.40 (s, 2H), 1.30 (s, 9H). LCMS −(M+1) 459.3.

Example 25. Preparation of Compound No. 25

Synthesis of 2-tert-butyl-4-{4-[2-chloro-4-(piperidine-1-carbonyl)phenyl]-1H-imidazol-2-yl}pyridine To a solution of (4-(2-(2-tert-butyl-4-pyridyl)-3-(methoxymethyl)-1H-imidazole-5-yl)-3-chloro-phenyl)-(1-piperidyl) methanone (400 mg, 0.854 mmol) and THF (20 mL) was added 3M HCl solution (10 mL) and the mixture heated at 80° C. for 2 h. The reaction was monitored by LCMS and when complete, the reaction mixture was basified with saturated sodium bicarbonate solution (30 mL) (pH-7) and extracted with EtOAc (3×50 mL). The combined organic layer was washed with water (50 mL), dried over anhydrous sodium sulfate and concentrated under reduced pressure to obtain a crude product, which was purified by reverse phase HPLC to afford (30 mg) of 2-tert-butyl-4-{4-[2-chloro-4-(piperidine-1-carbonyl)phenyl]-1H-imidazol-2-yl}pyridine.

$^1$H NMR (400 MHz, DMSO-d6): 8.55 (d, J=8.5 Hz, 1H), 8.10 (s, 1H), 7.98 (s, 2H), 7.71 (d, J=8.2 Hz, 1H), 7.45 (s, 1H), 7.38 (d, J=3.5 Hz, 1H), 3.55 (s, 2H), 3.25 (s, 2H), 1.58 (s, 4H), 1.40 (s, 2H), 1.30 (s, 9H). LCMS=423.2 (M+1).

Example 26. Preparation of Compound No. 26

Synthesis of 6-[5-(2-tert-butylpyridin-4-yl)thiophen-3-yl]-2-methyl-1,2,3,4-tetrahydroisoquinolin-1-one

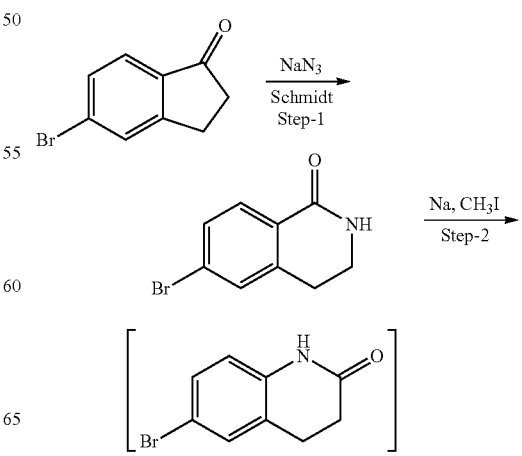

173

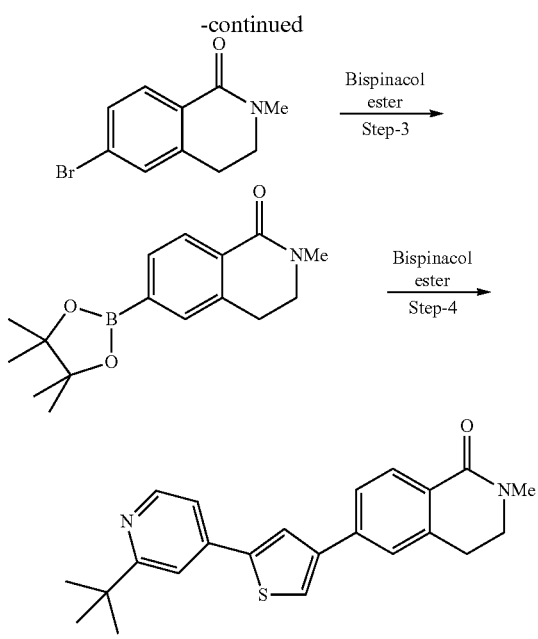

Step-1: Synthesis of 6-bromo-3,4-dihydro-2H-isoquinolin-1-one

To a stirred solution of 5-bromoindan-1-one (4 g, 0.0189 mol) in DCM (30 mL) was added methanesulfonic acid (20 mL) and stirred for 2 min at 0° C. under nitrogen atmosphere. Then sodium azide (2.46 g, 0.0379 mol) was added portionwise and stirred at the same temperature for 2 h. The reaction was monitored by TLC and LCMS. After completion of reaction, the mixture was quenched with 20% NaOH solution and extracted with DCM (2×100 mL). The combined organic layer was washed with water (2×50 mL) and brine (50 mL). The organic layer dried over anhydrous sodium sulfate and concentrated under reduced pressure to obtain a crude product, which was purified by chromatography using eluent 40% EtOAc in hexane to obtain 6-bromo-3,4-dihydro-2H-isoquinolin-1-one (3.59 g) as an off-white solid.

Step-2: Synthesis of 6-bromo-2-methyl-3,4-dihydroisoquinolin-1-one

To a stirred solution of 6-bromo-3,4-dihydro-2H-isoquinolin-1-one (3.5 g, 0.01548 mol) in DMF (20 mL) was added NaH (60% mineral oil) (1.2 g, 0.0309 mol) at 0° C. under nitrogen atmosphere and stirred for 30 min at RT. Then methyl iodide (1.5 mL, 0.023 mol) was added and the reaction mixture was stirred for 2 h. The reaction was monitored by TLC and HNMR. After completion of reaction, the mixture was quenched with ice cold water (50 mL) and extracted with EtOAc (2×100 mL). The combined organic layer was washed with water (2×50 mL) and brine (50 mL). The organic layer dried over anhydrous sodium sulfate and concentrated under reduced pressure to 6-bromo-2-methyl-3,4-dihydroisoquinolin-1-one (3.3 gm) as an off-white solid.

Step-3: Synthesis of 2-methyl-6-(4,4,5,5-tetramethyl-1,3,2-dioxaborolan-2-yl)-3,4-dihydroisoquinolin-1-one A mixture of 6-bromo-2-methyl-3,4-dihydroisoquinolin-1-one (1 g, 0.00418 mol), bis(pinacolato)diboron (1.59 g,

174

0.00627 mol) and potassium acetate (1.2 g, 0.0125 mol) were dissolved in DMF (15 mL) and the mixture was degassed with nitrogen for 15 min. Then, a catalytic amount of $PdCl_2(dppf).CH_2Cl_2$ (0.17 g, 0.0002 mol) was added and purging with nitrogen continued for 5 min. Then the mixture was heated at 80° C. for 2 h. The reaction was monitored by TLC and 1HNMR. After completion of reaction, the mixture was diluted with water (50 mL) and extracted with EtOAc (2×100 mL). The combined organic layer was washed with water (2×50 mL) and brine (50 mL). The organic layer was dried over anhydrous sodium sulfate and concentrated under reduced pressure to obtain a crude product, which was purified by chromatography using eluent 40% EtOAc in hexane to obtain 2-methyl-6-(4,4,5,5-tetramethyl-1,3,2-dioxaborolan-2-yl)-3,4-dihydroisoquinolin-1-one (890 mg) as a light yellow oil.

Step-4: Synthesis of 6-[5-(2-tert-butyl-4-pyridyl)-3-thienyl]-2-methyl-3,4-dihydroisoquinolin-1-one To a stirred solution of 4-(4-bromo-2-thienyl)-2-tert-butyl-pyridine (200 mg, 0.675 mmol) and 2-methyl-6-(4,4,5,5-tetramethyl-1,3,2-dioxaborolan-2-yl)-3,4-dihydroisoquinolin-1-one (291 mg, 1.0135 mmol) in DMF (4 mL) was added a solution of sodium carbonate (179 mg, 1.689 mmol) in water (4 mL). The mixture was degassed with nitrogen for 20 min. Then tetrakis (62.4 mg, 0.054 mmol) was added and purging with nitrogen was continued for 5 min. The reaction mixture was heated at 80° C. overnight. The reaction was monitored by TLC and LCMS. After the completion of reaction, the mixture was diluted with water (10 mL) and extracted with EtOAc (2×50 mL). The organic layer washed with brine (20 mL), dried over sodium sulfate and concentrated under reduced pressure to obtain a crude product, which was purified by chromatography using eluent 50% EtOAc in hexane to obtain the product, which was triturated with n-pentane (10 mL) and dried to obtain 6-[5-(2-tert-butyl-4-pyridyl)-3-thienyl]-2-methyl-3,4-dihydroisoquinolin-1-one (95 mg) as the freebase, an off-white solid.

$^1$H NMR (400 MHz, DMSO-d6) δ (ppm): 8.54 (d, J=5.1 Hz, 1H), 8.38 (s, 1H), 8.15 (s, 1H), 7.91 (d, J=8.1 Hz, 1H), 7.85-7.71 (m, 3H), 7.51 (dd, J=5.2, 1.7 Hz, 1H), 3.59 (t, J=6.6 Hz, 2H), 3.05 (d, J=13.6 Hz, 2H), 3.04 (s, 3H), 1.38 (s, 9H). LCMS=377 (M+1).

Example 27. Preparation of Compound No. 27

Synthesis of tert-butyl 4-{4-[5-(2-tert-butylpyridin-4-yl)thiophen-3-yl]-3-chlorobenzoyl}piperazine-1-carboxylate

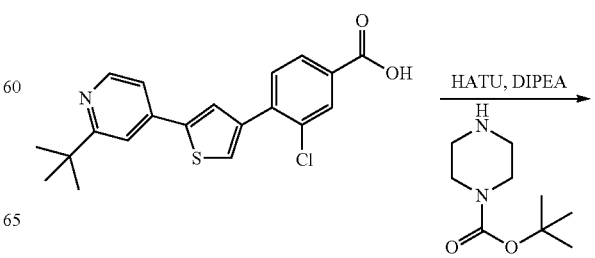

-continued

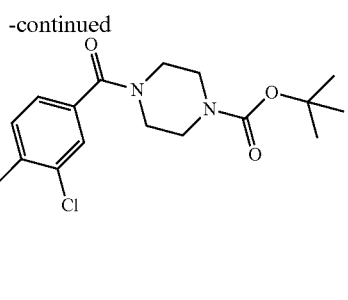

To a stirred solution of 4-[5-(2-tert-butyl-4-pyridyl)-3-thienyl]-3-chloro-benzoic acid (700 mg, 1.88 mmol) in DMF (10 mL), was added DIPEA (1.3 mL, 7.52 mmol) followed by addition of HATU (1.286 g, 3.384 mmol) and the mixture stirred at RT for 30 min. Then tert-butyl piperazine-1-carboxylate (1.75 g, 9.411 mmol) was added at the same temperature. The reaction mixture was stirred at RT overnight. The reaction was monitored by TLC and LCMS. After completion of reaction, the mixture was diluted with water (10 mL) and extracted with EtOAc (2×100 mL). The organic layer was washed with water (2×50 mL) and brine (50 mL) and dried over anhydrous sodium sulfate to obtain a crude compound (820 mg) and 80 mg of the crude compound was purified by reverse phase HPLC to obtain tert-butyl 4-[4-[5-(2-tert-butyl-4-pyridyl)-3-thienyl]-3-chloro-benzoyl]piperazine-1-carboxylate (15 mg) freebase as a solid.

$^1$H NMR (400 MHz, Methanol-d4) δ (ppm): 8.48 (d, J=5.3 Hz, 1H), 7.89 (d, J=1.5 Hz, 1H), 7.70-7.59 (m, 4H), 7.54-7.40 (m, 2H), 3.73 (m, 2H), 3.48 (m, 6H), 1.47 (s, 9H), 1.41 (s, 9H). LCMS: −540 (M+1).

Example 28. Preparation of Compound No. 28

Synthesis of 1-{4-[5-(2-tert-butylpyridin-4-yl)thiophen-3-yl]-3-chlorobenzoyl}piperazine

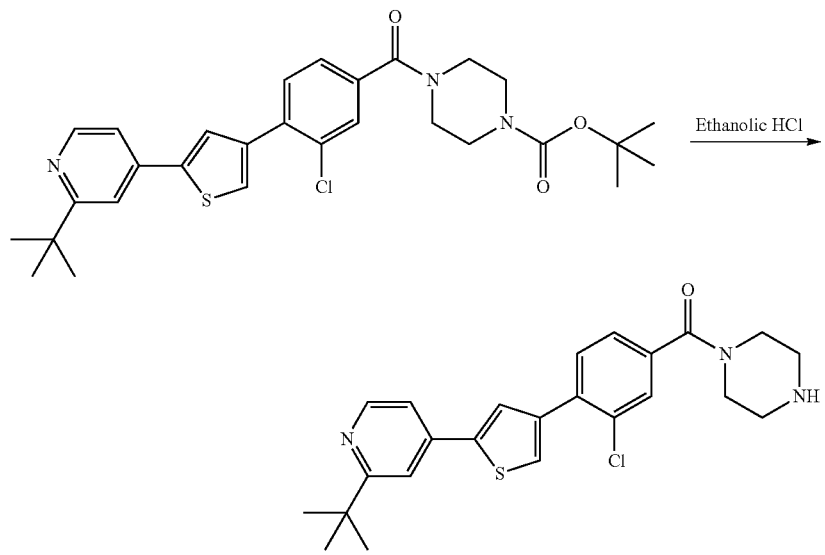

A solution of tert-butyl 4-[4-[5-(2-tert-butyl-4-pyridyl)-3-thienyl]-3-chloro-benzoyl]piperazine-1-carboxylate (700 mg, 1.296 mmol) in ethanolic HCl (30 mL) was stirred at RT for 2 h. Progress of the reaction was monitored by LCMS. After completion of reaction, the mixture was concentrated under reduced pressure to obtain 650 mg of crude compound and 100 mg crude compound was purified by reverse phase HPLC to obtain [4-[5-(2-tert-butyl-4-pyridyl)-3-thienyl]-3-chloro-phenyl]-piperazin-1-yl-methanone (28 mg) as a solid.

$^1$H NMR (400 MHz, Methanol-d4) δ (ppm): 8.49 (d, J=5.2 Hz, 1H), 7.90 (d, J=1.4 Hz, 1H), 7.71-7.60 (m, 4H), 7.55-7.41 (m, 2H), 3.77 (m, 2H), 3.61 (m, 2H), 3.00 (m, 4H), 1.42 (s, 9H). LCMS: −440 (M+1).

Example 29. Preparation of Compound No. 29

Synthesis of 1-(4-{4-[5-(2-tert-butylpyridin-4-yl)thiophen-3-yl]-3-chlorobenzoyl}piperazin-1-yl)ethan-1-one

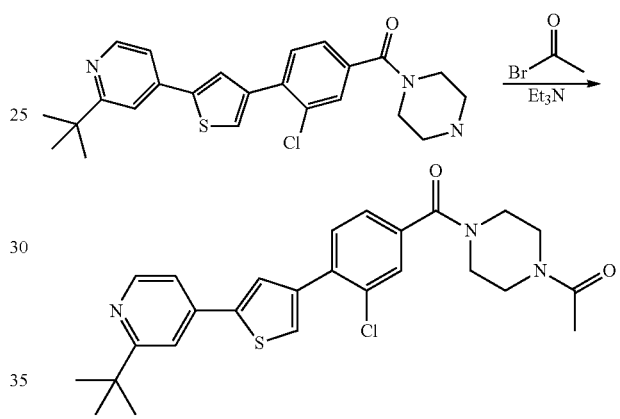

To a stirred solution of [4-[5-(2-tert-butyl-4-pyridyl)-3-thienyl]-3-chloro-phenyl]-piperazin-1-yl-methanone (150 mg, 0.3409 mmol) in DMF (5 mL) was added trimethyl amine (0.237 mL, 1.704 mmol) at 0° C. under nitrogen atmosphere. Then, acetyl bromide (76 mg, 0.613 mmol) was added at the same temperature. The reaction mixture was stirred at RT for 1 h. The reaction was monitored by TLC and LCMS. After completion of reaction, the mixture was diluted with water (10 mL) and extracted with EtOAc (2×50 mL). The combined organic layer was washed with water (2×25 mL) and brine (20 mL) and dried over anhydrous sodium sulfate and concentrated under reduced pressure to obtain a crude compound which was purified by reverse phase HPLC to obtain 1-[4-[4-[5-(2-tert-butyl-4-pyridyl)-3-thienyl]-3-chloro-benzoyl]piperazin-1-yl]ethanone (46 mg) as the freebase, a white solid.

$^1$H NMR (400 MHz, Methanol-d4) δ (ppm): 8.48 (d, J=5.2 Hz, 1H), 7.90 (d, J=1.4 Hz, 1H), 7.77 (s, 1H), 7.70-7.61 (m, 3H), 7.56-7.42 (m, 2H), 3.64 (m, 8H), 2.14 (s, 3H), 1.41 (s, 9H). LCMS: −482 (M+1).

Example 30. Preparation of Compound No. 30

Synthesis of 1-{4-[5-(2-tert-butylpyridin-4-yl)thiophen-3-yl]-3-chlorobenzoyl}-4-methane sulfonylpiperazine

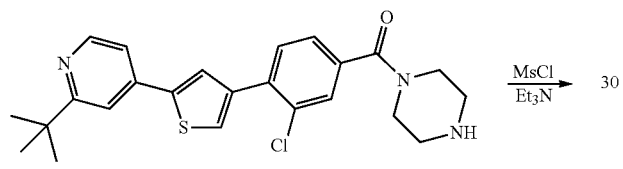

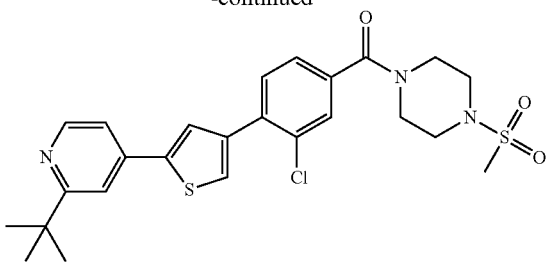

To a stirred solution of [4-[5-(2-tert-butyl-4-pyridyl)-3-thienyl]-3-chloro-phenyl]-piperazin-1-yl-methanone 150 mg, 0.3409 mmol in DMF (5 mL) was added triethylamine (0.237 mL, 1.704 mmol) at 0° C. under nitrogen atmosphere. Then methane sulphonyl chloride (69 mg, 0.613 mmol) was added at the same temperature. The reaction mixture was stirred at RT for 1 h. The reaction was monitored by TLC and LCMS. After completion of reaction, the mixture was diluted with water (10 mL) and extracted with EtOAc (2×50 mL). The combined organic layer was washed with water (2×25 mL) and brine (20 mL) and dried over anhydrous sodium sulfate and concentrated under reduced pressure to obtain a crude compound which was purified by reverse phase HPLC to obtain [4-[5-(2-tert-butyl-4-pyridyl)-3-thienyl]-3-chloro-phenyl]-(4-methylsulfonylpiperazine-1-yl) methanone (46 mg) as the freebase, a white solid.

Example 31. Preparation of Compound Nos. 31, 31a, and 31b

Synthesis of N-(1-{4-[5-(2-tert-butylpyridin-4-yl) thiophen-3-yl]-3-chlorobenzoyl}piperidin-3-yl) methanesulfonamide

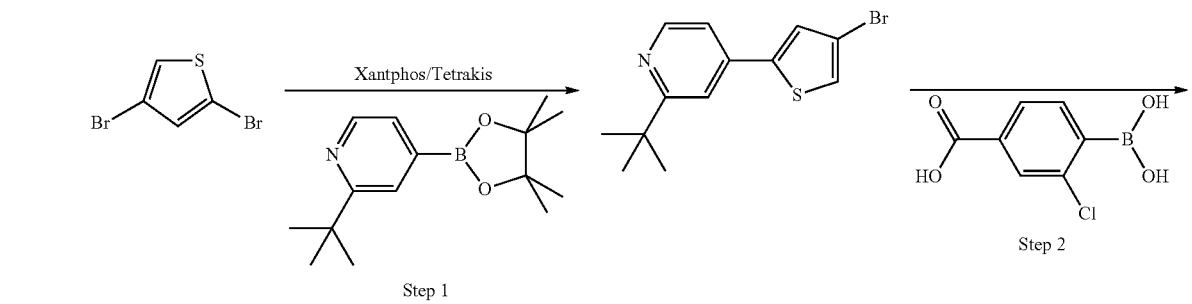

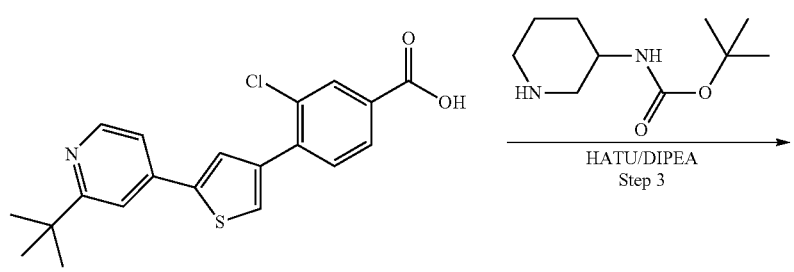

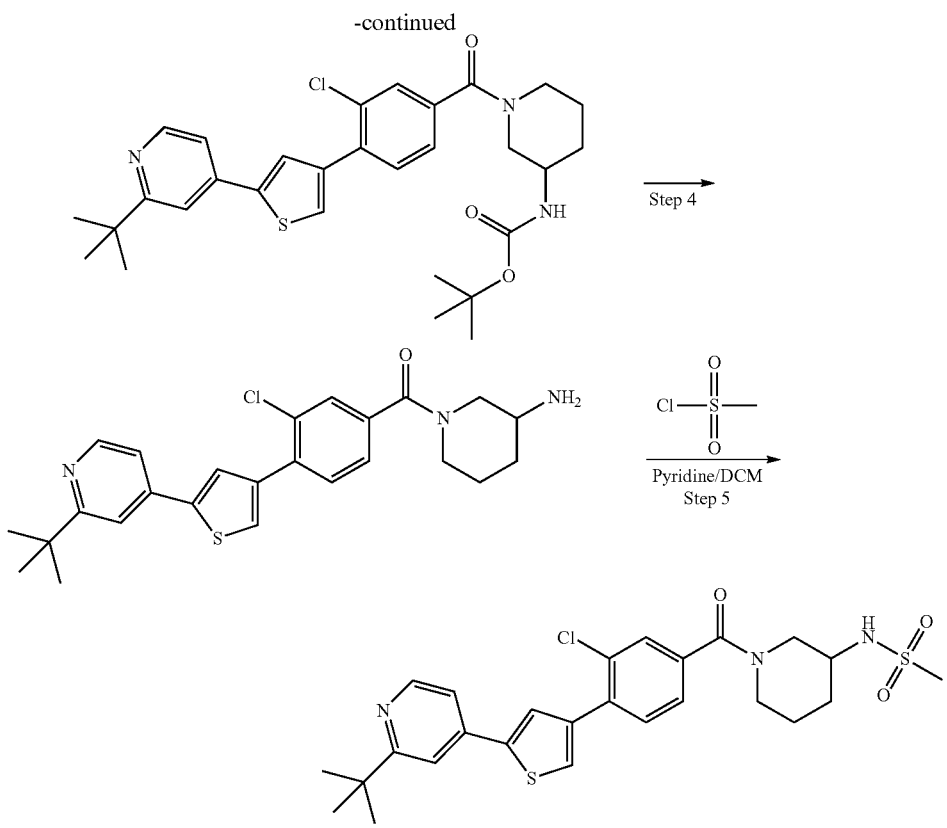

Step 1. Synthesis of 4-(4-bromo-2-thienyl)-2-tert-butyl-pyridine

In a 100 mL glass bottle, 2,4 dibromothiophene (600 mg, 2.5 mmol, 1 eq.) along with 2-tert-butyl-4-(4,4,5,5-tetramethyl-1,3,2-dioxaborolan-2-yl)pyridine (652 mg, 1 eq.) and potassium phosphate (1.325 g, 2.5 eq.) were charged in THF (25 mL). The mixture was purged with nitrogen for 15 min and then xantphos (145 mg, 0.1 eq.) and tetrakis ((289 mg, 0.1 eq.) were added, and the mixture repurged for 5 min and the resultant solution was stirred at 60° C. overnight. Progress of the reaction was monitored by TLC & LCMS. When the reaction was completed, the mixture was cooled to RT, water (100 mL) was added and the mixture extracted with EtOAc (3×100 mL). The combined organic layer was washed with brine (50 mL) then dried over anhydrous sodium sulfate, concentrated under reduced pressure to give a viscous compound which was purified by silica gel (60-120) column chromatography using EtOAc/Hexane (0-20%) as eluent system to afford 4-(4-bromo-2-thienyl)-2-tert-butyl-pyridine as a colorless semi-solid (500 mg) in pure form.

Step 2. Synthesis of 4-[5-(2-tert-butyl-4-pyridyl)-3-thienyl]-3-chloro-benzoic acid In a 25 mL glass bottle, 4-(4-bromo-2-thienyl)-2-tert-butyl-pyridine (450 mg, 1.52 mmol, 1 eq.) and 4-borono-3-chloro-benzoic acid (397 mg, 1.98 mmol, 1.3 eq.), were charged in DMF (7 mL) followed by addition of sodium carbonate (404 mg, 2.5 equiv dissolved in water (2.0 mL) and the reaction mixture was purged with nitrogen gas for 5 min. After adding tetrakis (176 mg, 0.152 mmol, 0.1 equiv) the mixture was repurged for 2 min and was stirred at 90° C. overnight. The progress of the reaction was monitored by TLC and LCMS. After completion of reaction, the mixture was allowed to come at RT and diluted with water (50 mL) and extracted with EtOAc:MeOH (90:10), (3×100 mL). The combined organic layer was dried over anhydrous sodium sulfate and concentrated under reduced pressure to afford a semi-solid compound, 3-chloro-4-[5-[3-(1-piperidyl)phenyl]-3-thienyl]benzoic acid (500 mg) which was used as such for the next step of synthesis.

Step 3. Synthesis of tert-butyl N-[1-[4-[5-(2-tert-butyl-4-pyridyl)-3-thienyl]-3-chloro-benzoyl]-3-piperidyl]carbamate In a 100 mL flask, 4-[5-(2-tert-butyl-4-pyridyl)-3-thienyl]-3-chloro-benzoic acid (700 mg, 1.88 mmol, 1 eq.) was dissolved in DMF (10 mL), followed by addition of DIPEA (1.4 mL, 7.54 mmol, 4 eq.) and HATU (1.4 mg, 3.77 mmol, 2 equiv), and the resulting mixture was stirred for 10 min at RT and tert-butyl N-(3-piperidyl)carbamate (1.5 g, 7.54 mmol, 4 eq.) was added and the mixture stirred at RT under nitrogen atmosphere overnight. The progress of the reaction was monitored by TLC and LCMS. After completion of reaction, the mixture was diluted with water (100 mL) and extracted with EtOAc (2×100 mL), washed with water (4×100 mL) then dried over anhydrous sodium sulfate and the combined organic layer was concentrated under reduced pressure to afford N-[1-[4-[5-(2-tert-butyl-4-pyridyl)-3-thienyl]-3-chloro-benzoyl]-3-piperidyl]carbamate (700 mg) as a crude viscous compound which was used as such for the next step of synthesis.

Step 4. Synthesis of (3-amino-1-piperidyl)-[4-[5-(2-tert-butyl-4-pyridyl)-3-thienyl]-3-chloro-phenyl]methanone In a 100 mL flask, tert-butyl N-[1-[4-[5-(2-tert-butyl-4-pyridyl)-3-thienyl]-3-chloro-benzoyl]-3-piperidyl]carbamate (700 mg, 1.26 mmol, 1 eq.) was charged in DCM (15 mL), the reaction mixture was maintained at 0° C. and trifluoroacetic acid (5 mL) was added dropwise and the mixture stirred at RT for 2.5 h. Progress of reaction was monitored by TLC/LCMS. After completion of reaction, the DCM was evaporated under reduced pressure, the residue basified with saturated aqueous sodium bicarbonate solution and extracted with EtOAc (2×100 mL). The organic layer was washed with brine (100 mL) and dried over anhydrous sodium sulfate. The solution was concentrated under reduced pressure to afford (3-amino-1-piperidyl)-[4-[5-(2-tert-butyl-4-pyridyl)-3-thienyl]-3-chloro-phenyl]methanone as a crude viscous compound (570 mg) which was used as such for the next step of synthesis.

Step 5. Synthesis of N-[1-[4-[5-(2-tert-butyl-4-pyridyl)-3-thienyl]-3-chloro-benzoyl]-3-piperidyl] methanesulfonamide In a 25 mL flask, (3-amino-1-piperidyl)-[4-[5-(2-tert-butyl-4-pyridyl)-3-thienyl]-3-chloro-phenyl]methanone, (150 mg, 0.33 mmol, 1 eq.) was suspended in DCM (5 mL), then pyridine (1 mL) was added and the mixture stirred for 10 min at RT. The mixture was maintained at 0° C. condition and mesyl chloride (63 mg, 0.43 mmol, 1.3 eq.) was added dropwise and the mixture stirred for 1 h at the same temperature. Progress of the reaction was monitored by TLC & 1H-NMR/LCMS. After maximum conversion of the starting material into product, the mixture was diluted with (100 mL) water and extracted with EtOAc (3×100 mL), the combined organic layer was washed with brine (50 mL) then dried over anhydrous sodium sulfate, concentrated under reduced pressure to give a viscous desired compound which was submitted for reverse phase HPLC for purification to afford N-[1-[4-[5-(2-tert-butyl-4-pyridyl)-3-thienyl]-3-chloro-benzoyl]-3-piperidyl] methanesulfonamide as the freebase (10 mg) as an off-white solid. The enantiomers can be prepared from chiral HPLC resolution of the racemate.

$^1$H NMR (400 MHz, Methanol-d4) δ (ppm): 8.48 (d, J=5.2 Hz, 1H), 7.91 (s, 1H), 7.78 (s, 1H), 7.72-7.60 (m, 3H), 7.52 (d, J=5.3 Hz, 1H), 7.45 (d, J=7.9 Hz, 1H), 3.82 (m, 1H), 3.45-3.43 (m, 2H), 3.1-3.04 (m, 1H), 2.92 (s, 3H), 2.10 (m, 1H), 1.92 (m, 2H), 1.63 (m, 2H), 1.42 (s, 9H). LCMS −(M+1) 532.1.

Example 32. Preparation of Compound Nos. 32, 32a, and 32b

Synthesis of N-[1-[4-[5-(2-tert-butyl-4-pyridyl)-3-thienyl]-3-chloro-benzoyl]-3-piperidyl]acetamide

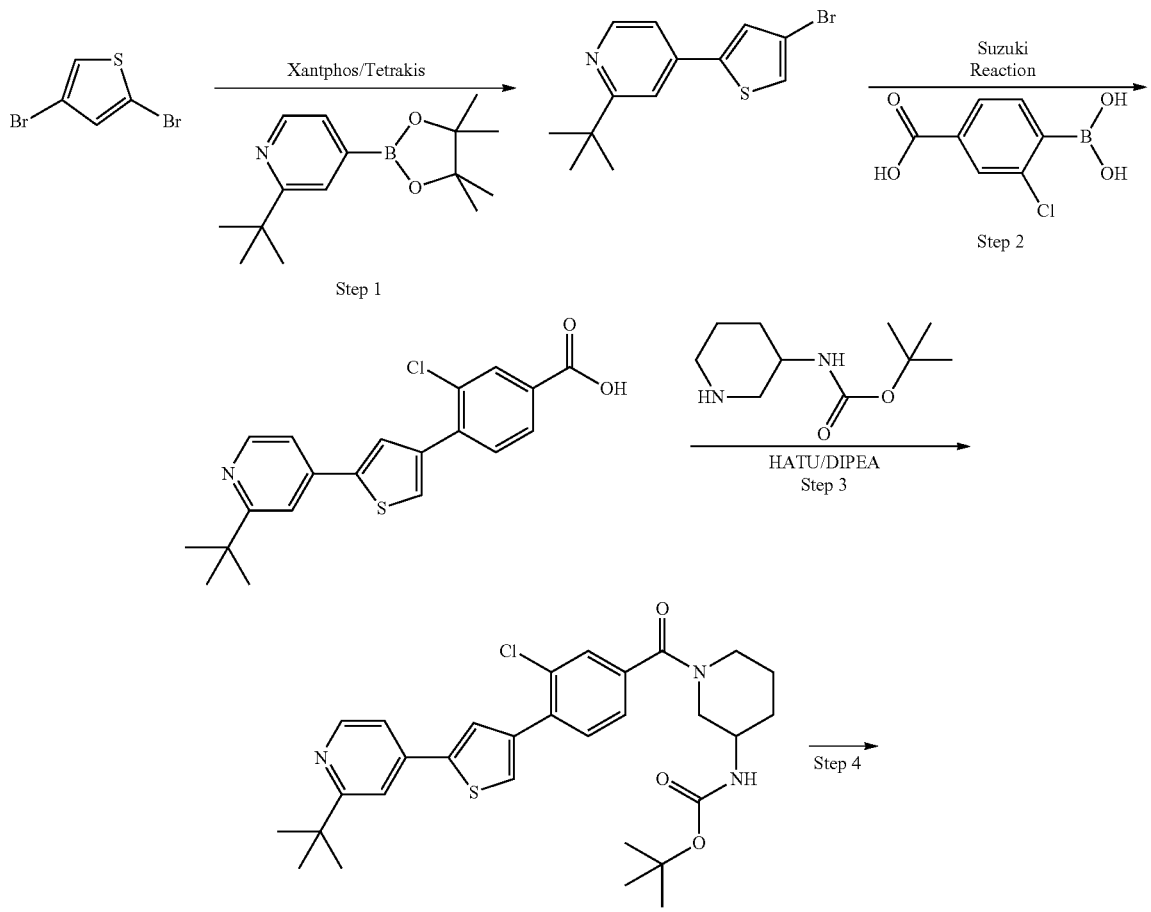

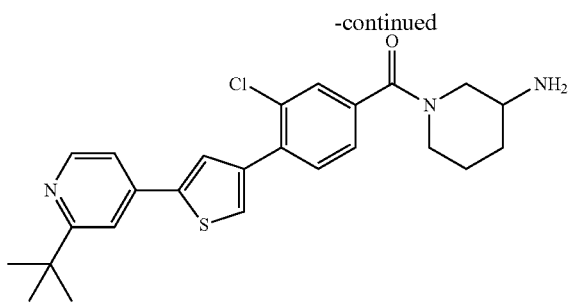
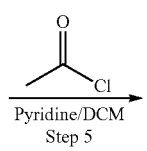

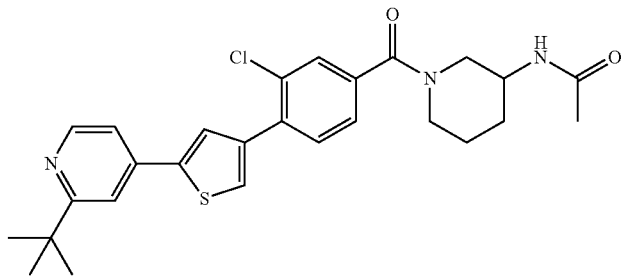

Steps 1-4: See Example 31.

Step 5: In a 25 mL flask, (3-amino-1-piperidyl)-[4-[5-(2-tert-butyl-4-pyridyl)-3-thienyl]-3-chloro-phenyl]methanone (150 mg, 0.33 mmol, 1 eq.) was suspended in DCM (5 mL), then pyridine (1 mL) was added and the mixture stirred for 10 min at RT. The mixture was maintained at 0° C. condition and acetyl chloride (26 mg, 0.33 mmol, 1 eq.) was added dropwise and the mixture stirred for 1 h at the same temperature. Progress of the reaction was monitored by TLC & 1H-NMR/LCMS. After maximum conversion of the starting material into product, the mixture was diluted with water (100 mL) and extracted with EtOAc (3×100 mL). The combined organic layer was washed with brine (50 mL) then dried over anhydrous sodium sulfate, concentrated under reduced pressure to give a viscous desired compound which was submitted for reverse phase HPLC for purification to afford N-[1-[4-[5-(2-tert-butyl-4-pyridyl)-3-thienyl]-3-chloro-benzoyl]-3-piperidyl]acetamide as the freebase (50 mg) as an off-white solid. The enantiomers can be prepared from chiral HPLC resolution of the racemate.

$^1$H NMR (400 MHz, DMSO-d6) δ (ppm): 8.50 (d, J=5.2 Hz, 1H), 8.04-7.99 (m, 1H), 7.89 (s, 1H), 7.64 (m, 2H), 7.54-7.45 (m, 2H), 7.39 (s, 1H), 4.18 (d, 1H), 3.41 (m, 2H), 3.08 (m, 2H), 2.88 (m, 1H), 1.80-1.70 (m, 3H), 1.48 (m, 2H), 1.33 (s, 9H), 1.20 (m, 2H). LCMS –(M+1) 496.2.

Example 33. Preparation of Compound No. 33

Synthesis of 4-[5-(2-tert-butylpyridin-4-yl)thiophen-3-yl]-3-chloro-N,N-bis(propan-2-yl) benzamide In a 25 mL flask, 4-(5-(2-tert-butyl-4-pyridyl)-3-thienyl)-3-chloro-benzoic acid (100 mg, 0.26 mmol, 1 eq.) was suspended in DMF (5 mL) then to it was added diisopropylethylamine (139.8 mg, 1.076 mmol) and HATU (204 mg, 0.53 mmol) and the mixture stirred for 10 min at RT. Then added N-isopropylpropan-2-amine (136 mg, 1.347 mmol) and the mixture stirred for 12 h at RT. Progress of the reaction was monitored by TLC & 1H-NMR/LCMS, the reaction mixture was diluted with water (100 mL) and extracted with EtOAc (3×100 mL), the combined organic layer was washed with brine (50 mL) then dried over anhydrous sodium sulfate, concentrated under reduced pressure to give a viscous desired compound which was submitted for reverse phase HPLC for purification to afford 4-(5-(2-tert-butyl-4-pyridyl)-3-thienyl)-3-chloro-N,N-diisopropyl-benzamide as the freebase (12 mg) as an off-white solid.

$^1$H NMR (400 MHz, DMSO-d6) δ (ppm): 8.50 (d, J=5.2 Hz, 1H), 8.04-7.99 (m, 1H), 7.89 (s, 1H), 7.64 (m, 2H), 7.54-7.45 (m, 2H), 7.39 (s, 1H), 3.61 (m, 2H), 1.35 (s, 9H), 1.21 (s, 12H). LCMS –(M+1) 455.1.

Example 34. Preparation of Compound Nos. 34, 34a, and 34b

Synthesis of 1-(1-{4-[5-(2-tert-butylpyridin-4-yl)thiophen-3-yl]-3-chlorobenzoyl}piperidin-3-yl) pyrrolidin-2-one

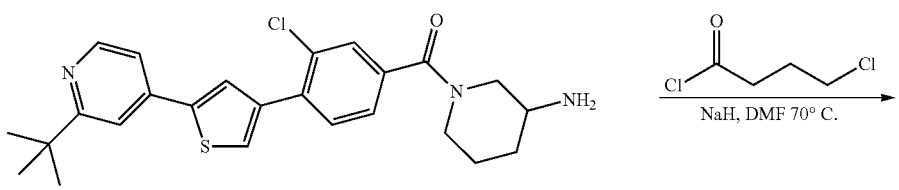

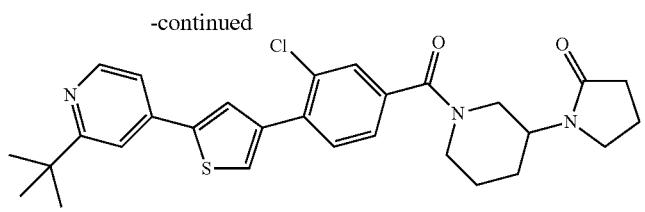

To a stirred solution of (3-amino-1-piperidyl)-[4-[5-(2-tert-butyl-4-pyridyl)-3-thienyl]-3-chloro-phenyl]methanone (100 mg, 0.204 mmol) in DMF (5 mL) was added NaH (60%) (16 mg, 0.408 mmol) at 0° C. under nitrogen atmosphere and the mixture stirred for 30 min at RT for 30 min. Then 4-chlorobutanoyl chloride (43 mg, 0.306 mmol) was added and the reaction mixture was heated at 70° C. for 2 h. The reaction was monitored by LCMS. After completion of reaction, the mixture was diluted with water (10 mL) and extracted with EtOAc (2×100 mL). The combined organic layer was dried over anhydrous sodium sulfate and concentrated under reduced pressure to obtain a crude product which was purified by reverse phase HPLC to obtain 1-[1-[4-[5-(2-tert-butyl-4-pyridyl)-3-thienyl]-3-chloro-benzoyl]-3-piperidyl]pyrrolidin-2-one (22 mg) freebase, an off-white solid. The enantiomers can be prepared from chiral HPLC resolution of the racemate.

¹H NMR (400 MHz, Methanol-d4) δ (ppm): 8.48 (d, J=5.3 Hz, 1H), 7.90 (d, J=1.5 Hz, 1H), 7.77 (d, J=1.4 Hz, 1H), 7.71-7.57 (m, 3H), 7.51 (dd, J=5.3, 1.7 Hz, 1H), 7.45 (s, 1H), 4.57 (m, 1H), 4.00 (m, 1H), 3.70 (m, 1H), 3.52 (m, 2H), 3.07 (m, 1H), 2.84 (m, 1H), 2.40 (m, 1H), 2.33 (m, 1H), 2.01 (m, 3H), 1.95-1.79 (m, 2H), 1.67 (m, 1H), 1.41 (s, 9H). LCMS: −522 (M+1).

Example 35. Preparation of Compound No. 35

Synthesis of 6-[5-(2-tert-butylpyridin-4-yl)thiophen-3-yl]-2-(propan-2-yl)-1,2,3,4-tetrahydroisoquinolin-1-one Step-1. Synthesis of 6-bromo-3,4-dihydro-2H-isoquinolin-1-one To a stirred solution of 5-bromoindan-1-one (4 g, 0.0189 mol) in DCM (30 mL) was added methane sulfonic acid (20 mL) and the mixture stirred for 2 min at 0° C. under nitrogen atmosphere. Then sodium azide (2.46 g, 0.0379 mol) was added portionwise and the mixture stirred at the same temperature for 2 h. The reaction was monitored by TLC and LCMS. After completion of reaction, the mixture was quenched with 20% NaOH solution and extracted with DCM (2×100 mL). The combined organic layer was washed with water (2×50 mL) and brine (50 mL). The organic layer was dried over anhydrous sodium sulfate and concentrated under reduced pressure to obtain a crude product which was purified by chromatography using eluent 40% EtOAc in hexane to obtain 6-bromo-3,4-dihydro-2H-isoquinolin-1-one (3.59 g) as an off-white solid.

Step-2. Synthesis of 6-bromo-2-isopropyl-3,4-dihydroisoquinolin-1-one

To a stirred solution of 6-bromo-3,4-dihydro-2H-isoquinolin-1-one (1 g, 0.0044 mol) in DMF (20 mL) was added NaH (60% mineral oil) (354 mg, 0.0088 mol) at 0° C. under nitrogen atmosphere and the mixture stirred for 30 min at RT. Then isopropyl iodide (1.12 g, 0.0066 mol) was added and The reaction mixture was stirred at 70° C. for 2 h. The reaction was monitored by TLC and HNMR. After completion of reaction, the mixture was quenched with ice cold water (50 mL) and extracted with EtOAc (2×100 mL). The

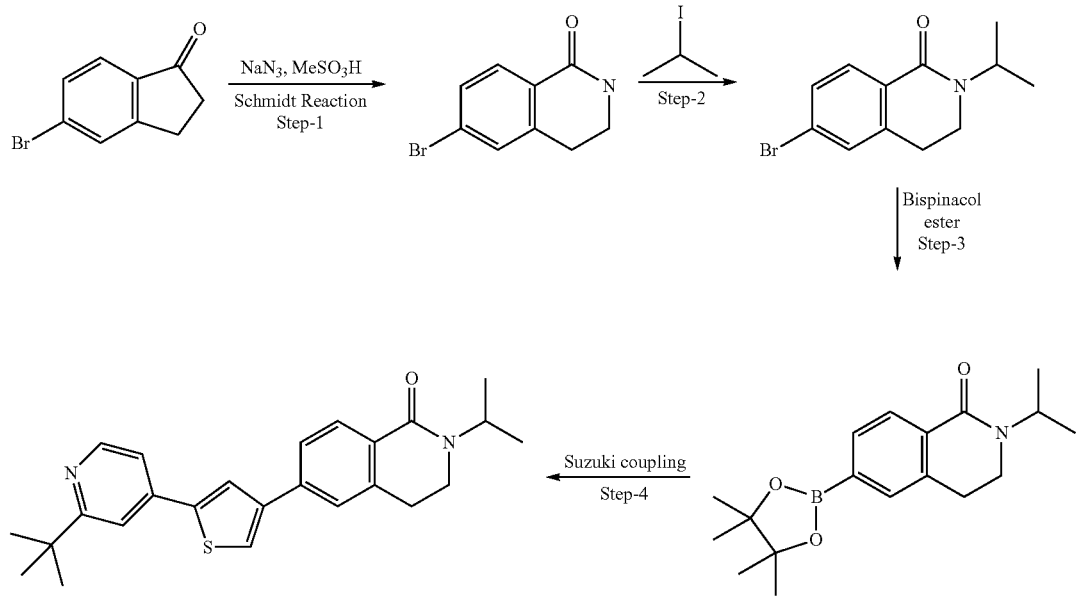

combined organic layer was washed with water (2×50 mL) and brine (50 mL). The organic layer was dried over anhydrous sodium sulfate and concentrated under reduced pressure to 66-bromo-2-isopropyl-3,4-dihydroisoquinolin-1-one (1.2 g) as a light brown solid.

Step-3. Synthesis of 2-isopropyl-6-(4,4,5,5-tetramethyl-1,3,2-dioxaborolan-2-yl)-3,4-dihydroisoquinolin-1-one A mixture of 6-bromo-2-methyl-3,4-dihydroisoquinolin-1-one (1.2 g, 0.0044 mol), bis(pinacolato)diboron (1.704 g, 0.0067 mol) and potassium acetate (1.293 g, 0.0132 mol) were dissolved in DMF (15 mL) and the mixture was degassed with nitrogen for 15 min. Then, a catalytic amount of PdCl$_2$(dppf).CH$_2$Cl$_2$ (0.179 g, 0.00022 mol) was added and the mixture purged further with nitrogen for 5 min. Then the mixture was heated at 80° C. for 2 h. The reaction was monitored by TLC and HNMR. After completion of reaction, the mixture was diluted with water (50 mL) and extracted with EtOAc (2×100 mL). The combined organic layer was washed with water (2×50 mL) and brine (50 mL).

The organic layer was dried over anhydrous sodium sulfate and concentrated under reduced pressure to obtain a crude product which was purified by chromatography using 40% EtOAc in hexane to obtain 2-isopropyl-6-(4,4,5,5-tetramethyl-1,3,2-dioxaborolan-2-yl)-3,4-dihydroisoquinolin-1-one (600 mg) as a light yellow oil.

Step-4. Synthesis of 6-[5-(2-tert-butyl-4-pyridyl)-3-thienyl]-2-isopropyl-3,4-dihydroisoquinolin-1-one To a stirred solution of 4-(4-bromo-2-thienyl)-2-tert-butyl-pyridine (281 mg, 0.996 mmol) and 2-isopropyl-6-(4,4,5,5-tetramethyl-1,3,2-dioxaborolan-2-yl)-3,4-dihydroisoquinolin-1-one (200 mg, 0644 mmol) in DMF (5 mL) was added a solution of sodium carbonate (140 mg, 1.228 mmol) in water (5 mL). The mixture was degassed nitrogen for 20 min. Then tetrakis (62.4 mg, 0.053 mmol) was added and purging with nitrogen was continued for 5 min. The reaction mixture was heated at 80° C. overnight. The reaction was monitored by TLC and LCMS. After completion of reaction, the mixture was diluted with water (10 mL) and extracted with EtOAc (2×50 mL) and organic layer washed with brine (20 mL) and dried over sodium sulfate and concentrated under reduced pressure to obtain a crude product which was purified by chromatography using 50% EtOAc in hexane to obtain the product, which was triturated n-pentane (10 mL) to obtain 6-[5-(2-tert-butyl-4-pyridyl)-3-thienyl]-2-isopropyl-3,4-dihydroisoquinolin-1-one (20 mg) as the freebase, an off-white solid.

$^1$H NMR (400 MHz, Methanol-d4) δ (ppm): 8.47 (d, J=5.3 Hz, 1H), 8.10 (s, 1H), 7.98 (d, J=7.9 Hz, 1H), 7.88 (s, 1H), 7.72 (d, J=8.8 Hz, 2H), 7.64 (s, 1H), 7.52 (d, J=5.3 Hz, 1H), 4.98 (p, J=6.7, 6.3 Hz, 1H), 3.52 (t, J=6.5 Hz, 2H), 3.02 (t, J=6.5 Hz, 2H), 1.42 (s, 9H), 1.24 (d, J=6.9 Hz, 6H). LCMS: –405 (M+1).

Example 36. Preparation of Compound Nos. 36, 36a, and 36b

Synthesis of 2-(1-{4-[5-(2-tert-butylpyridin-4-yl) thiophen-3-yl]-3-chlorobenzoyl}piperidin-3-yl)-1λ$^6$, 2-thiazolidine-1,1-dione

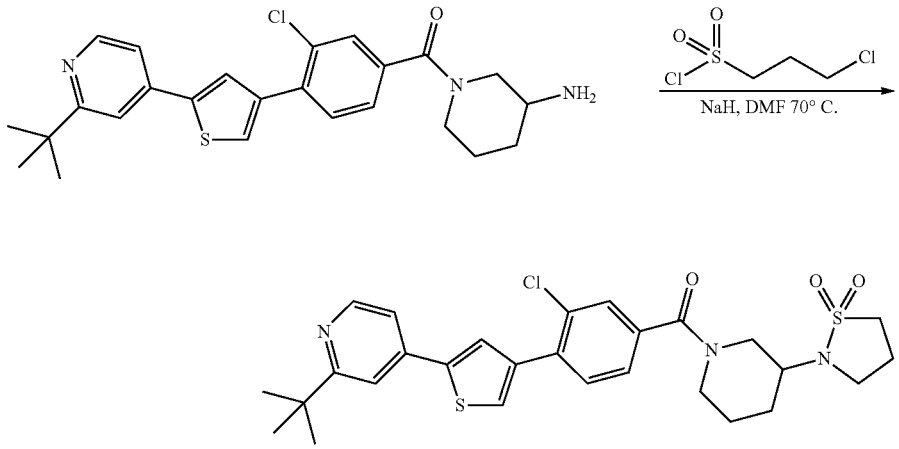

To a stirred solution of (3-amino-1-piperidyl)-[4-[5-(2-tert-butyl-4-pyridyl)-3-thienyl]-3-chloro-phenyl]methanone (100 mg, 0.204 mmol) in DMF (5 mL) was added NaH (60%) (16 mg, 0.408 mmol) at 0° C. under nitrogen atmosphere and the mixture stirred for 30 min at RT for 30 min. Then addition of 3-chloropropane-1-sulfonyl chloride (54 mg, 0.306 mmol) and the reaction mixture was heated at 70° C. for 2 h. The reaction was monitored by LCMS. After completion of reaction, the reaction mixture was diluted with water (10 mL) and extracted with EtOAc (2×100 mL) combined organic layer was dried over anhydrous sodium sulfate and concentrated under reduced pressure to obtain a crude product which was purified by reverse phase HPLC to obtain [4-[5-(2-tert-butyl-4-pyridyl)-3-thienyl]-3-chloro-phenyl]-[3-(1,1-dioxo-1,2-thiazolidin-2-yl)-1-piperidyl] methanone (12 mg) freebase, an off-white solid. The enantiomers can be prepared from chiral HPLC resolution of the racemate.

$^1$H NMR (400 MHz, Methanol-d4) δ (ppm): 8.48 (d, J=5.3 Hz, 1H), 7.91 (d, J=1.4 Hz, 1H), 7.78 (d, J=1.4 Hz, 1H), 7.72-7.57 (m, 3H), 7.52 (dd, J=5.2, 1.7 Hz, 1H), 7.44 (d, J=7.8 Hz, 1H), 4.57 (m, 1H), 3.64 (m, 3H), 3.25 (d, J=12.7 Hz, 3H), 2.84 (m, 2H), 2.09 (d, J=12.5 Hz, 2H), 1.93 (m, 2H), 1.62 (m, 2H), 1.42 (s, 9H). LCMS: –558 (M+1).

Example 37. Preparation of Compound No. 37

Synthesis of tert-butyl N-(1-{4-[5-(2-tert-butylpyridin-4-yl)thiophen-3-yl]-3-chlorobenzoyl}piperidin-4-yl)carbamate

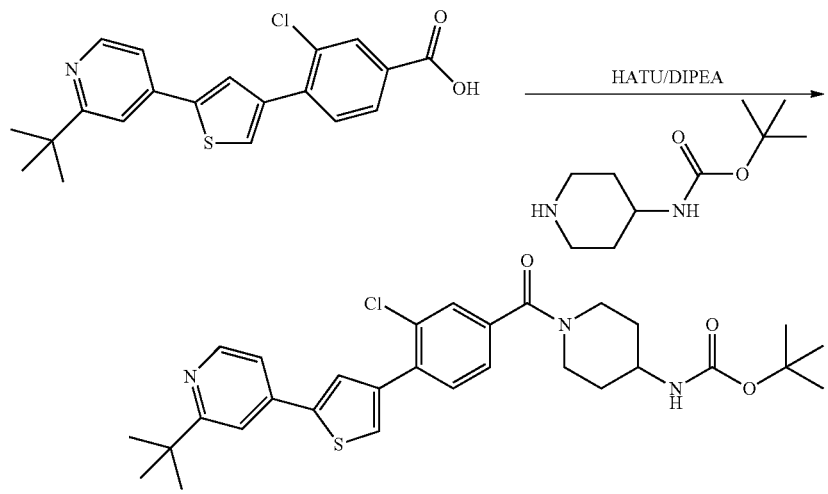

To a stirred solution of 4-[5-(2-tert-butyl-4-pyridyl)-2-thienyl]-3-chloro-benzoic acid (200 mg, 0.538 mmol) in DMF (10 mL), was added DIPEA (0.36 mL, 2.152 mmol) followed by addition of HATU (408 mg, 1.076 mmol) and the mixture stirred at RT for 30 min. Then tert-butyl N-(4-piperidyl) carbamate (409 mg, 2.04 mmol) was added at the same temperature. The reaction mixture was stirred at RT overnight. The reaction was monitored by TLC and LCMS. After completion of reaction, the mixture was diluted with water (10 mL) and extracted with EtOAc (2×50 mL), the organic layer was washed with water (2×20 mL) and brine (20 mL) and dried over anhydrous sodium sulfate to obtain a crude product which was purified by reverse phase HPLC to obtain tert-butyl N-[1-[4-[5-(2-tert-butyl-4-pyridyl)-2-thienyl]-3-chloro-benzoyl]-4-piperidyl]carbamate (15 mg) freebase as a solid.

$^{1}$H NMR (400 MHz, Methanol-d4) δ (ppm): 8.48 (d, J=5.2 Hz, 1H), 7.88 (s, 1H), 7.75 (s, 1H), 7.70-7.57 (m, 3H), 7.51 (dd, J=5.3, 1.8 Hz, 1H), 7.43 (dd, J=7.9, 1.7 Hz, 1H), 3.87 (m, 1H), 3.56 (m, 3H), 2.01 (d, J=19.4 Hz, 2H), 1.87 (m, 18H), 1.76 (m, 1H), 1.47 (m, 1H), 1.41 (s, 18H). LCMS: −554 (M+1).

Example 38. Preparation of Compound No. 38

Synthesis of N-(1-{4-[5-(2-tert-butylpyridin-4-yl)thiophen-3-yl]-3-chlorobenzoyl}piperidin-4-yl) acetamide

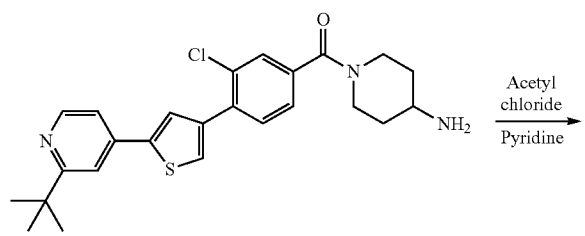

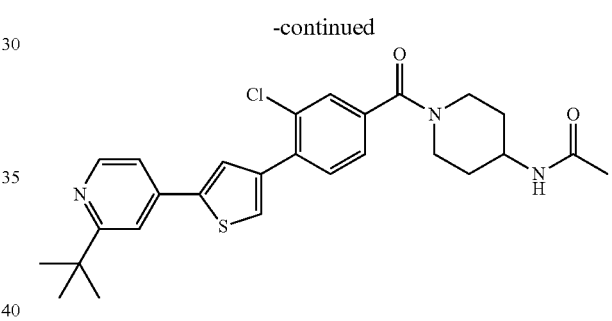

To a solution of (4-amino-1-piperidyl)-[4-[5-(2-tert-butyl-4-pyridyl)-3-thienyl)3-chloro-phenyl] methanone (100 mg, 0.2208 mmol) in DCM (5 mL), was added pyridine (1 mL) and the mixture stirred for 15 min at 0° C. Acetyl chloride (17.2 mg, 0.2208 mmol) was added and the mixture stirred for 1 h at RT. The reaction mixture was monitored by TLC and LCMS. The reaction mixture was diluted with water (20 mL) and extracted with EtOAc (3×50 mL). The combined organic layers were concentrated under reduced pressure to obtain a crude product which was purified by reverse phase HPLC to afford N-[1-[4-[5-(2-tert-butyl-4-pyridyl)-3-thienyl]-3-chloro-benzoyl]-4-piperidyl]acetamide (24 mg) as a white solid.

$^{1}$H NMR (400 MHz, DMSO-d6) δ (ppm): 8.54 (d, J=5.1 Hz, 1H), 8.07 (d, J=1.5 Hz, 1H), 7.84 (d, J=7.5 Hz, 1H), 7.71-7.64 (m, 2H), 7.57 (d, J=1.6 Hz, 1H), 7.52-7.38 (m, 2H), 4.30 (s, 1H), 3.82 (s, 3H), 3.56 (s, 1H), 3.19 (s, 2H), 3.02 (s, 2H), 1.80 (s, 3H), 1.36 (s, 9H). LCMS −(M+1) 495.

Example 39. Preparation of Compound No. 39

Synthesis of 4-{4-[5-(2-tert-butylpyridin-4-yl)thiophen-3-yl]-3-chlorobenzoyl}-1-ethylpiperazin-2-one

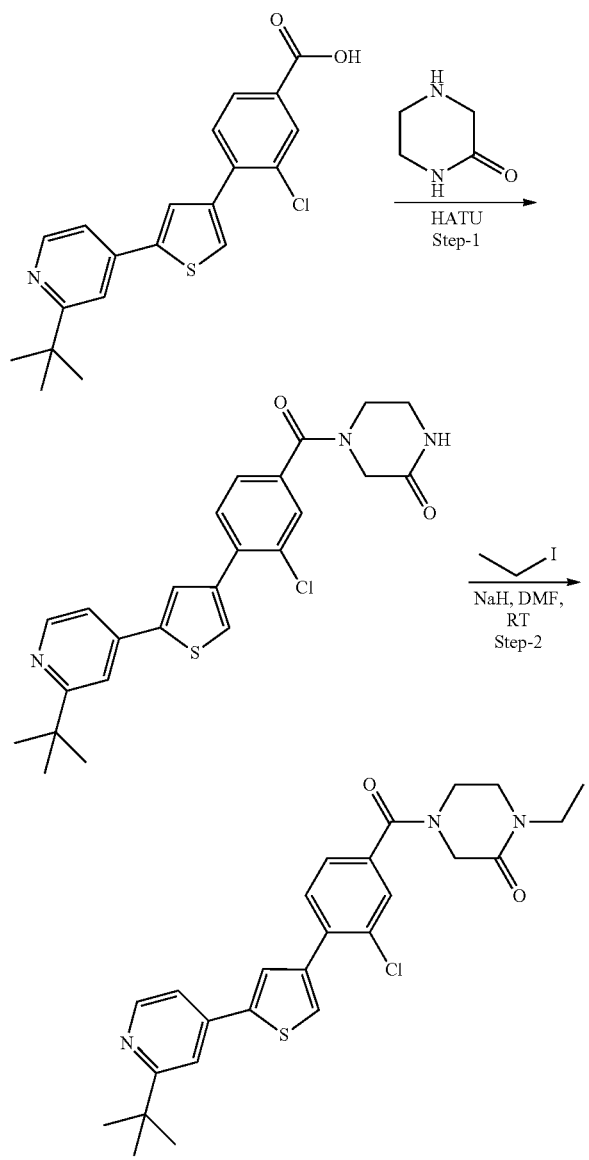

Step-1. Synthesis of 4-[4-[5-(2-tert-butyl-4-pyridyl)-3-thienyl]-3-chloro-benzoyl]piperazin-2-one 4-[5-(2-tert-Butyl-4-pyridyl)-3-thienyl]-3-chloro-benzoic acid (200 mg, 0.53 mmol) was taken in DMF (8 mL), followed by addition of DIPEA (0.37 mL, 2.15 mmol), HATU (409 mg, 1.078 mmol), DMF (8 mL), under nitrogen atmosphere. The reaction mixture was stirred at RT for 0.5 h, followed by addition of piperazin-2-one (215 mg, 2.15 mmol). The reaction mixture was stirred at RT for 16 h. After completion of reaction, water (50 mL) was added and the mixture extracted with EtOAc (3×50 mL). The combined organic layer was washed with water (50 mL), dried over anhydrous sodium sulfate and concentrated under reduced pressure to obtain 4-[4-[5-(2-tert-butyl-4-pyridyl)-3-thienyl]-3-chloro-benzoyl] piperazin-2-one crude (500 mg) as a brown oil.

Step-2. Synthesis of 4-[4-[5-(2-tert-butyl-4-pyridyl)-3-thienyl]-3-chloro-benzoyl]-1-ethyl-piperazin-2-one 4-[4-[5-(2-tert-Butyl-4-pyridyl)-3-thienyl]-3-chloro-benzoyl] piperazin-2-one (300 mg, 0.66 mmol) was taken in dry DMF (5 mL) under nitrogen atmosphere and to it was added NaH (60%) (52 mg, 1.32 mmol) at 0° C., then the reaction mixture was stirred at RT for 15 min. Ethyl iodide (0.05 mL, 0.66 mmol) was added at 0° C., then the reaction mixture was stirred at RT for 2 h. The reaction was monitored by TLC and LCMS. After completion of reaction, the mixture was quenched with ice cold water (10 mL) and extracted with EtOAc (3×50 mL). The combined organic layer was washed with water (2×25 mL) and finally brine (2×25 mL), dried over anhydrous sodium sulfate and concentrated under reduced pressure to obtain the crude product which was purified by reverse phase HPLC to obtain -[4-[5-(2-tert-butyl-4-pyridyl)-3-thienyl]-3-chloro-benzoyl]-1-ethyl-piperazin-2-one (37 mg) as the freebase, an off-white solid.

$^1$H NMR (400 MHz, DMSO-d6) δ (ppm): 8.54 (d, J=5.1 Hz, 1H), 8.08 (s, 1H), 7.97 (d, J=1.5 Hz, 1H), 7.70 (d, J=8.0 Hz, 1H), 7.68 (s, 2H), 7.55-7.46 (m, 2H), 4.14 (m, 2H), 3.62 (m, 2H), 3.42-3.32 (m, 4H), 1.36 (s, 9H), 1.06 (t, J=7.1 Hz, 3H). LCMS: −(M+1) 482.1.

Example 40. Preparation of Compound No. 40

Synthesis of 2-tert-butyl-4-{5-[2-chloro-4-(4,4-difluoropiperidine-1-carbonyl)phenyl]thiophen-3-yl}pyridine

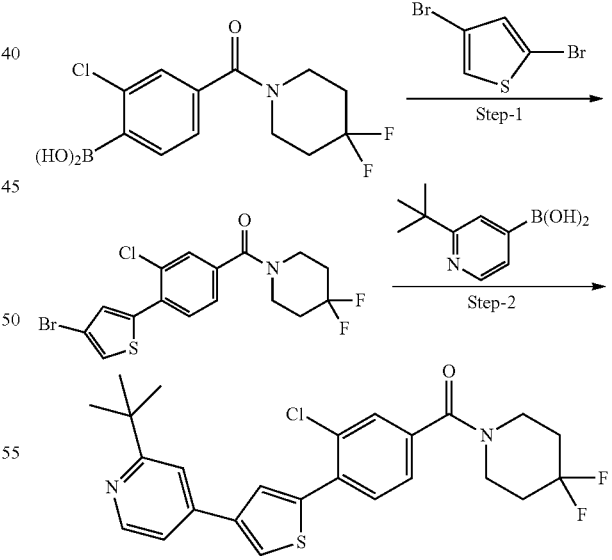

Step-1. Synthesis of (4-(4-bromothiophen-2-yl)-3-chlorophenyl)(4,4-difluoropiperidin-1-yl)methanone In a 25 mL glass bottle [2-chloro-4-(4,4-difluoropiperidine-1-carbonyl)phenyl]boronic acid (200 mg, 0.6601 mmol), 2,4-dibromothiophene (189.2 mg, 0.7921 mmol), and sodium carbonate (173 mg 1.65 mmol), DMF (7 mL), water (2 mL) were charged and purged with nitrogen gas for 5 min. After adding tetrakis (76 mg 0.066 mmol) and Xantphos (38.2 mg, 0.066 mmol), the reaction mixture was heated to 100° C. The reaction mixture was stirred overnight. The reaction was monitored by TLC and LCMS. After completion of reaction, the mixture was diluted with water (10 mL) and extracted with EtOAc (2×50 mL), the organic layer was washed with water (2×20 mL) and brine (20 mL) and dried over anhydrous sodium sulfate to obtain (4-(4-bromothiophen-2-yl)-3-chlorophenyl)(4,4-difluoropiperidin-1-yl)methanone (300 mg) as a brown colored crude product.

Step-2. Synthesis of [4-[4-(2-tert-butyl-4-pyridyl)-2-thienyl]-3-chloro-phenyl]-(4,4-difluoro-1-piperidyl) methanone (4-(4-Bromothiophen-2-yl)-3-chlorophenyl)(4,4-difluoropiperidin-1-yl)methanone (300 mg, 0.7160 mmol), (2-tert-butyl-4-pyridyl)boronic acid (153.9 mg, 0.8592 mmol), and sodium carbonate (188 mg 1.79 mmol), DMF (10 mL), water (1 mL) were charged in a 25 mL glass bottle and purged with nitrogen gas for 5 min. After adding tetrakis (82.7 mg 0.0716 mmol), the reaction mixture was heated to 100° C. The reaction mixture was stirred overnight. The reaction was monitored by TLC and LCMS. After completion of reaction, the mixture was diluted with water (10 mL) and extracted with EtOAc (2×50 mL), the organic layer was washed with water (2×20 mL) and brine (20 mL) and dried over anhydrous sodium sulfate to obtain the crude product which was purified by reverse phase HPLC to afford (4-(4-bromothiophen-2-yl)-3-chlorophenyl)(4,4-difluoropiperidin-1-yl)methanone (20 mg) as a white solid.

$^1$H NMR (400 MHz, DMSO-d6) δ (ppm): 8.51 (d, J=5.1 Hz, 1H), 7.99 (s, 1H), 7.88 (s, 1H), 7.65 (s, 1H), 7.45 (m, 2H), 7.34 (t, J=7.7 Hz, 1H), 7.25 (d, J=7.3 Hz, 1H), 3.88 (m, 4H), 1.34 (s, 9H), 1.12 (m, 4H). LCMS=475.1 (M+1).

Example 41. Preparation of Compound No. 41

Synthesis of 4-[5-(2-tert-butylpyridin-4-yl)thiophen-3-yl]-3-chloro-N-methyl-N-phenyl benzamide

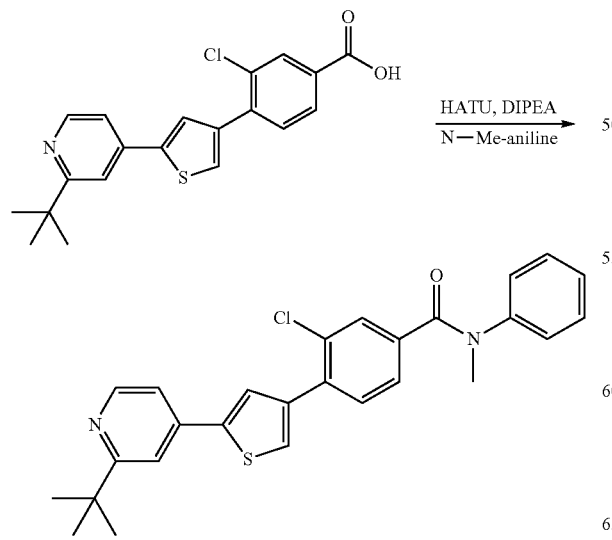

To a stirred solution of 4-[5-(2-tert-butyl-4-pyridyl)-3-thienyl]-3-chloro-benzoic acid (200 mg, 0.538 mmol) in DMF (10 mL), was added DIPEA (0.36 mL, 2.152 mmol) followed by addition of HATU (408 mg, 1.076 mmol) and the mixture stirred at RT for 30 min. Then N-methyl aniline (219 mg, 2.04 mmol) was added at the same temperature. The reaction mixture was stirred at RT overnight. The reaction was monitored by TLC and LCMS. After completion of reaction, the mixture was diluted with water (10 mL) and extracted with EtOAc (2×50 mL), the organic layer was washed with water (2×20 mL) and brine (20 mL) and dried over anhydrous sodium sulfate to obtain a crude product which was purified by reverse phase HPLC to obtain 4-[5-(2-tert-butyl-4-pyridyl)-3-thienyl]-3-chloro-N-methyl-N-phenyl-benzamide (10 mg) freebase as a solid.

$^1$H NMR (400 MHz, DMSO-d6) δ (ppm): 8.48 (d, J=5.2 Hz, 1H), 8.0 (d, J=5.2 Hz, 1H), 7.88 (s, 1H), 7.75 (m, 1H), 7.47 (m, 3H), 7.43 (dd, J=7.9, 1.7 Hz, 1H), 7.20-7.42 (m, 5H), 3.41 (s, 3H), 1.41 (s, 9H). LCMS=461.1 (M+1).

Example 42. Preparation of Compound No. 42

Synthesis of 4-{4-[4-(azetidine-1-carbonyl)-2-chlorophenyl]thiophen-2-yl}-2-tert-butylpyridine

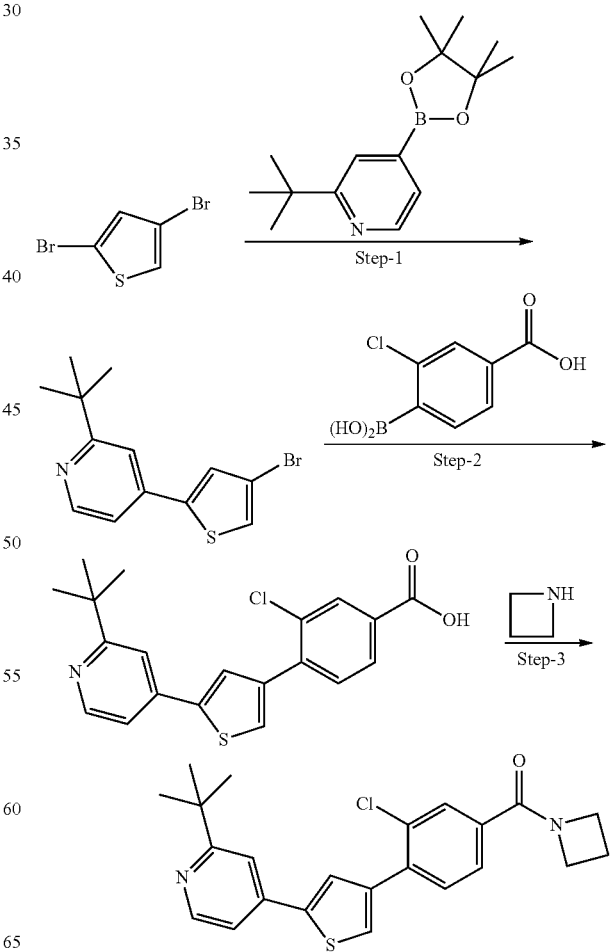

Step-1: Synthesis of 4-(4-bromo-2-thienyl)-2-tert-butyl-pyridine

In a 100 mL glass bottle, 2,4 dibromothiophene (600 mg, 2.5 mmol, 1 eq.) along with 2-tert-butyl-4-(4,4,5,5-tetramethyl-1,3,2-dioxaborolan-2-yl)pyridine (652 mg, 1 eq.) and potassium phosphate (1.325 g, 2.5 eq.) were charged in 25 mL of THF. The mixture was purged with nitrogen for 15 min then Xantphos (145 mg, 0.1 eq.) and tetrakis (289 mg, 0.1 eq.) were added, and the mixture repurged for 5 min and the mixture stirred at 60° C. overnight. Progress of the reaction was monitored by TLC & LCMS. When the reaction was completed, the mixture was cooled to RT, water (100 mL) added and the mixture extracted with EtOAc (3×100 mL). The combined organic layer was washed with brine (50 mL) then dried over anhydrous sodium sulfate, concentrated under reduced pressure to give a viscous compound which was purified by silica gel (60-120) column chromatography using EtOAc/Hexane (0-20%) as eluent system to afford 4-(4-bromo-2-thienyl)-2-tert-butyl-pyridine as a colorless semi-solid (500 mg) in pure form.

Step-2: Synthesis of 4-[5-(2-tert-butyl-4-pyridyl)-3-thienyl]-3-chloro-benzoic acid In a 25 mL glass bottle, 4-(4-bromo-2-thienyl)-2-tert-butyl-pyridine (1 g, 2.69 mmol, 1 eq.) and 4-borono-3-chloro-benzoic acid (700 mg, 3.5 mmol, 1.3 eq.), were charged in DMF (13 mL) followed by addition of sodium carbonate (898 mg, 2.5 equiv dissolved in water (2.0 mL) and the reaction mixture was purged with nitrogen gas for 5 min. After adding tetrakis (311 mg, 0.269 mmol, 0.1 eq.) the mixture was repurged for 2 min and was stirred at 80° C. overnight. The progress of the reaction was monitored by TLC and LCMS. After completion of reaction, the mixture was allowed to come to RT and diluted with water (50 mL) and extracted with EtOAc:MeOH (95:05), (3×100 mL). The combined organic layer was dried over anhydrous sodium sulfate and concentrated under reduced pressure to afford a solid compound, 3-chloro-4-[5-[3-(1-piperidyl)phenyl]-3-thienyl]benzoic acid (700 mg) which was used as such for the next step of synthesis.

Step-3: Synthesis of azetidin-1-yl-[4-[5-(2-tert-butyl-4-pyridyl)-3-thienyl]-3-chloro-phenyl]methanone In a 100 mL flask, 4-[5-(2-tert-butyl-4-pyridyl)-3-thienyl]-3-chloro-benzoic acid (200 mg, 0.54 mmol, 1 eq.) was dissolved in DMF (7 mL), followed by addition of DIPEA (0.5 mL, 2.76 mmol, 5 eq.) and HATU (410 mg, 1.08 mmol, 2 eq.), and the resulting mixture was stirred for 10 min at RT and azetidine hydrochloride (200 mg, 2.15 mmol, 4 eq.) were added and the mixture stirred at RT under nitrogen atmosphere overnight. The progress of the reaction was monitored by TLC and LCMS. After completion of reaction, the mixture was diluted with water (100 mL) and extracted with EtOAc (2×100 mL), washed with water (4×100 mL) then dried over anhydrous sodium sulfate and the combined organic layer was concentrated under reduced pressure which was submitted to reverse phase HPLC process for its purification to afford azetidin-1-yl-[4-[5-(2-tert-butyl-4-pyridyl)-3-thienyl]-3-chloro-phenyl]methanone (64 mg—as freebase) as an off-white solid.

$^1$H NMR (400 MHz, Methanol-d4) δ (ppm): 8.48 (d, J=5.3 Hz, 1H), 7.91 (d, J=1.5 Hz, 1H), 7.82-7.76 (m, 2H), 7.71-7.59 (m, 3H), 7.52 (dd, J=5.3, 1.8 Hz, 1H), 4.44 (t, J=7.8 Hz, 2H), 4.23 (t, J=7.9 Hz, 2H), 2.39 (tt, J=14.3, 7.7 Hz, 2H), 1.42 (s, 9H). LCMS=411.1 (M+1).

Example 43. Preparation of Compound No. 43

Synthesis of 6-{4-[5-(2-tert-butylpyridin-4-yl)thiophen-3-yl]-3-chlorobenzoyl}-2-oxa-6-azaspiro[3.3]heptane

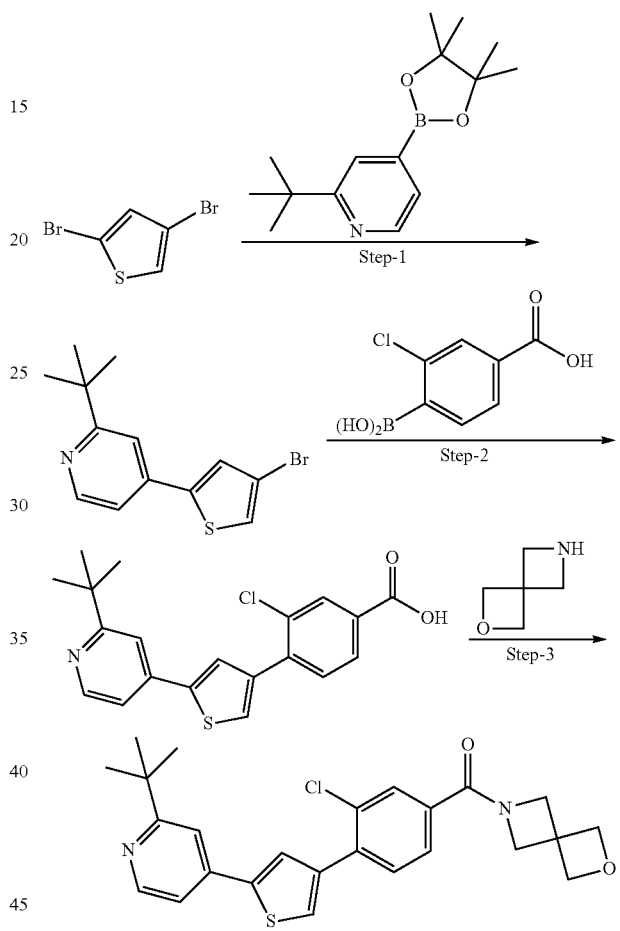

Step-1: Synthesis of 4-(4-bromo-2-thienyl)-2-tert-butyl-pyridine

In a 100 mL glass bottle 2,4 dibromothiophene (600 mg, 2.5 mmol, 1 eq.) along with 2-tert-butyl-4-(4,4,5,5-tetramethyl-1,3,2-dioxaborolan-2-yl)pyridine (652 mg, 1 eq.) and potassium phosphate (1.325 g, 2.5 eq.) were charged in 25 mL of THF. The mixture was purged with nitrogen for 15 min then Xantphos (145 mg, 0.1 eq.) and tetrakis (289 mg, 0.1 eq.) were added, and the mixture repurged for 5 min and the mixture stirred at 60° C. overnight. Progress of the reaction was monitored by TLC & LCMS. When the reaction was completed, the mixture was cooled to RT, water (100 mL) was added and the mixture extracted with EtOAc (3×100 mL). The combined organic layer was washed with brine (50 mL) then dried over anhydrous sodium sulfate, concentrated under reduced pressure to give a viscous compound which was purified by silica gel (60-120) column chromatography using EtOAc/Hexane (0-20%) as eluent system to afford 4-(4-bromo-2-thienyl)-2-tert-butyl-pyridine as a colorless semi-solid (500 mg) in pure form.

Step-2: Synthesis of 4-[5-(2-tert-butyl-4-pyridyl)-3-thienyl]-3-chloro-benzoic acid In a 25 mL glass bottle, 4-(4-bromo-2-thienyl)-2-tert-butyl-pyridine (1 g, 2.69 mmol, 1 eq.) and 4-borono-3-chloro-benzoic acid (700 mg, 3.5 mmol, 1.3 eq.), were charged in DMF (13 mL) followed by addition of sodium carbonate (898 mg, 2.5 equiv dissolved in water (2.0 mL) and the reaction mixture was purged with nitrogen gas for 5 min. After adding tetrakis (311 mg, 0.269 mmol, 0.1 eq.) the mixture was repurged for 2 min and was stirred at 80° C. overnight. The progress of the reaction was monitored by TLC and LCMS. After completion of reaction, the mixture was allowed to come to RT and diluted with water (50 mL) and extracted with EtOAc:MeOH (95:05), (3×100 mL). The combined organic layer was dried over anhydrous sodium sulfate and concentrated under reduced pressure to afford a solid compound, 3-chloro-4-[5-[3-(1-piperidyl)phenyl]-3-thienyl]benzoic acid (700 mg) which was used as such for the next step of synthesis.

Step-3: Synthesis of [4-[5-(2-tert-butyl-4-pyridyl)-3-thienyl]-3-chloro-phenyl]-(6-oxa-2-azaspiro[3.3] heptan-2-yl)methanone In a 100 mL flask, 4-[5-(2-tert-butyl-4-pyridyl)-3-thienyl]-3-chloro-benzoic acid (150 mg, 0.40 mmol, 1 eq.) was dissolved in DMF (7 mL), followed by addition of DIPEA (0.4 mL, 2.01 mmol, 5 eq.) and HATU (307 mg, 0.80 mmol, 2 eq.), and the resulting mixture was stirred for 10 min at RT and 6-oxa-2-azaspiro[3.3]heptane oxalate (305 mg, 1.61 mmol, 4 eq.) were added and the mixture stirred at RT under nitrogen atmosphere overnight. The progress of the reaction was monitored by TLC and LCMS. After completion of reaction, the mixture was diluted with water (100 mL) and extracted with EtOAc (2×100 mL), washed with water (4×100 mL) then dried over anhydrous sodium sulfate and the combined organic layer was concentrated under reduced pressure which was submitted to reverse phase HPLC process for its purification to afford [4-[5-(2-tert-butyl-4-pyridyl)-3-thienyl]-3-chloro-phenyl]-(6-oxa-2-azaspiro[3.3] heptan-2-yl)methanone (54 mg—as freebase) as an off-white solid.

$^1$H NMR (400 MHz, Methanol-d4) δ (ppm): 8.48 (d, J=5.3 Hz, 1H), 7.90 (s, 1H), 7.79 (d, J=4.3 Hz, 2H), 7.71-7.59 (m, 3H), 7.52 (dt, J=5.3, 1.3 Hz, 1H), 4.83 (d, J=2.8 Hz, 4H), 4.59 (d, 2H), 4.36 (d, 2H), 1.42 (s, 9H). LCMS: –453.1.

Example 44. Preparation of Compound Nos. 44, 44a, and 44b

Synthesis of ethyl N-(1-{4-[5-(2-tert-butylpyridin-4-yl)thiophen-3-yl]-3-chlorobenzoyl}piperidin-3-yl) carbamate

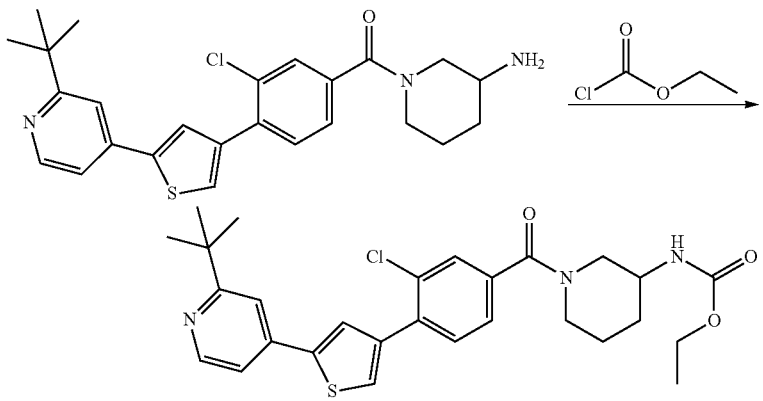

(3-Amino-1-piperidyl)-[4-[5-(2-tert-butyl-4-pyridyl)-3-thienyl]-3-chloro-phenyl]methanone (200 mg, 0.451 mmol) was taken in DCM (2 mL) under nitrogen atmosphere. Pyridine (1.0 mL) was added at 0° C. followed by addition of ethylcarbonochloride (71 mg, 0.622 mmol) then The reaction mixture was stirred at RT for 4 h. The reaction was monitored by TLC and LCMS. After completion of reaction, the mixture was quenched with water (10 mL) and extracted with EtOAc (3×50 mL). The combined organic layer was washed with water (2×25 mL) dried over anhydrous sodium sulfate and concentrated under reduced pressure to obtain the crude product which was purified by reverse phase HPLC to obtain ethyl —N-[1-[4-[5-(2-tert-butyl-4-pyridyl)-3-thienyl]-3-chloro-benzoyl]-3-piperidyl] carbamate (20 mg) as the freebase, an off-white solid. The enantiomers can be prepared from chiral HPLC resolution of the racemate.

$^1$H NMR (400 MHz, DMSO-d6) δ (ppm): 8.60 (d, J=5.5 Hz, 1H), 8.24 (s, 1H), 8.07 (s, 1H), 7.84 (s, 1H), 7.74-7.54 (m, 2H), 7.47 (d, J=9.0 Hz, 1H), 7.29 (s, 1H), 4.18-3.81 (m, 6H), 3.09-2.98 (m, 4H), 1.41 (s, 9H), 1.23 (t, 3H). LCMS: –(M+1) 526.2.

Example 45. Preparation of Compound No. 45

Synthesis of ethyl 4-{4-[5-(2-tert-butylpyridin-4-yl)thiophen-3-yl]-3-chlorobenzoyl}piperazine-1-carboxylate

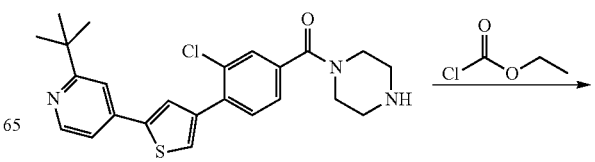

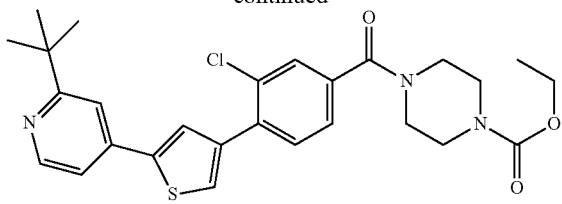

To a stirred solution of [4-[5-(2-tert-butyl-4-pyridyl)-3-thienyl]-3-chloro-phenyl]-piperazin-1-yl-methanone (150 mg, 0.3409 mmol) in DCM (4 mL) and DMF (2 mL), was added triethylamine (68.9 mg, 0.6818 mmol) at 0° C. under nitrogen atmosphere. Then ethylchloroformate (55.49 mg, 0.5113 mmol) was added at the same temperature. The reaction mixture was stirred at RT for 2 h. The reaction was monitored by TLC and LCMS. After completion of reaction, the mixture was diluted with water (25 mL) and extracted with DCM (2×80 mL). The organic layer was washed with brine solution (50 mL). The combined organic layer was dried over anhydrous sodium sulfate and concentrated under reduced pressure to obtain a crude product which was purified by reverse phase chromatography to obtain ethyl 4-[4-[5-(2-tert-butyl-4-pyridyl)-3-thienyl]-3-chloro-benzoyl]piperazine-1-carboxylate (38.87 mg). This was dissolved in ethanolic HCl and the mixture stirred at for 30 min at RT then concentrated under reduced pressure to obtain ethyl 4-[4-[5-(2-tert-butyl-4-pyridyl)-3-thienyl]-3-chloro-benzoyl]piperazine-1-carboxylate HCl (40 mg), an off-white solid.

$^1$H NMR (400 MHz, Methanol-d4) δ (ppm): 8.61 (d, J=6.4 Hz, 1H), 8.41 (d, J=1.4 Hz, 1H), 8.25-8.14 (m, 3H), 7.73-7.64 (m, 2H), 7.49 (dd, J=7.8, 1.7 Hz, 1H), 4.16 (q, J=7.1 Hz, 2H), 3.77 (m, 2H), 3.60 (m, 2H), 3.51 (m, 4H), 1.58 (s, 10H), 1.27 (dd, J=8.9, 5.1 Hz, 3H). LCMS=512 (M+1).

Example 46. Preparation of Compound No. 46

Synthesis of 1-(4-{4-[5-(2-tert-butylpyridin-4-yl)thiophen-3-yl]-3-chlorobenzoyl}piperazin-1-yl)-2,2-dimethylpropan-1-one

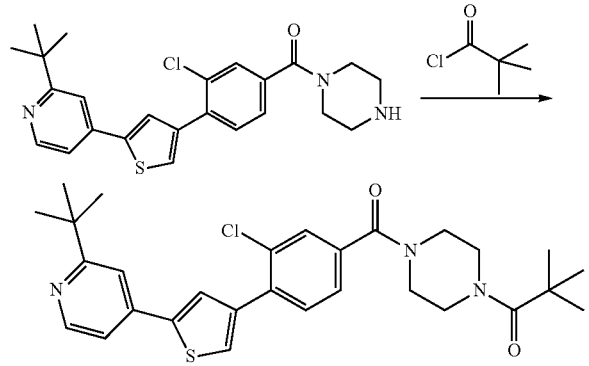

To a stirred solution of [4-[5-(2-tert-butyl-4-pyridyl)-3-thienyl]-3-chloro-phenyl]-piperazin-1-yl-methanone (150 mg, 0.3409 mmol) in DCM (4 mL) and DMF (2 mL). Triethylamine (68.9 mg, 0.6818 mmol) was added at 0° C. under nitrogen atmosphere. Then pivaloyl chloride (61.65 mg, 0.5113 mmol) was added at the same temperature. The reaction mixture was stirred at RT for 2 h. The reaction was monitored by TLC and LCMS. After completion of reaction, the mixture was diluted with water (50 mL) and extracted with DCM (2×100 mL). The organic layer was washed with brine solution (50 mL). The organic layer was dried over anhydrous sodium sulfate and concentrated under reduced pressure to obtain a crude product which was purified by reverse phase chromatography to obtain 1-[4-[4-[5-(2-tert-butyl-4-pyridyl)-3-thienyl]-3-chloro-benzoyl]piperazin-1-yl]-2,2-dimethyl-propan-1-one (36 mg). This was dissolved in ethanolic HCl and the mixture stirred at for 30 min at RT then concentrated under reduced pressure to obtain 1-[4-[4-[5-(2-tert-butyl-4-pyridyl)-3-thienyl]-3-chloro-benzoyl]piperazin-1-yl]-2,2-dimethyl-propan-1-one HCl (38 mg), an off-white solid.

$^1$H NMR (400 MHz, Methanol-d4) δ (ppm): 8.58 (d, J=6.2 Hz, 1H), 8.31 (s, 1H), 8.14-8.03 (m, 3H), 7.75-7.65 (m, 2H), 7.49 (dd, J=7.9, 1.7 Hz, 1H), 3.80 (m, 4H), 3.71 (m, 2H), 3.53 (m, 2H), 1.54 (s, 9H), 1.30 (s, 9H). LCMS=524 (M+1).

Example 47. Preparation of Compound No. 47

Synthesis of N-[2-(1-{4-[5-(2-tert-butylpyridin-4-yl)thiophen-3-yl]-3-chlorophenyl}-N-ethylformamido)ethyl]acetamide

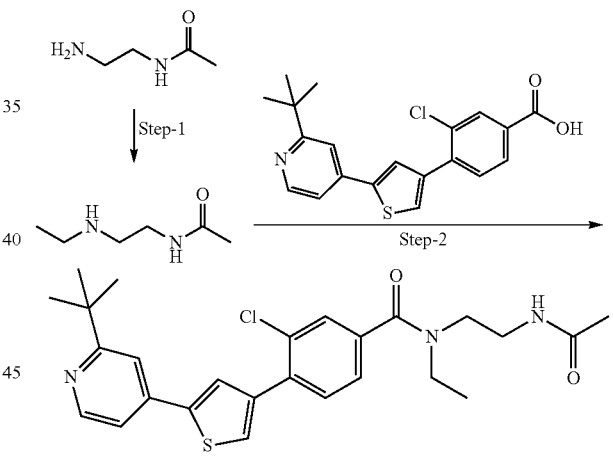

Step-1: Synthesis of N-[2-(ethyl amino) ethyl]acetamide

N-(2-Aminoethyl) acetamide (500 mg, 4.90 mmol) and dry DMF (5 mL) were charged in a 50 mL 2 neck flask under nitrogen atmosphere, and to it was added NaH (60%) (392 mg, 9.80 mmol) at 0° C. then the reaction mixture was stirred at RT for 15 min. Ethyl iodide (0.29 mL, 4.90 mmol) was added at 0° C. then the reaction mixture was stirred at RT for 2 h. The reaction was monitored by TLC. After completion of reaction, the mixture was quenched with ice cold water (10 mL) and extracted with EtOAc (3×50 mL). The combined organic layer was washed with water (2×25 mL) and brine (2×25 mL), dried over anhydrous sodium sulfate and concentrated under reduced pressure to obtain crude —N-[2-(ethyl amino)ethyl]acetamide (500 mg) as a brown oil.

Step-2: N-(2-acetamidoethyl)-4-[5-(2-tert-butyl-4-pyridyl)-3-thienyl]-3-chloro-N-ethyl-benzamide 4-[5-(2-tert-Butyl-4-pyridyl)-3-thienyl]-3-chloro-benzoic acid (150 mg, 0.40 mmol) was taken in DMF (5 mL), followed by addition of DIPEA (0.28 mL, 1.61 mmol), HATU (307 mg, 0.80 mmol), under nitrogen atmosphere. The reaction mixture was stirred at RT for 0.5 h, followed by addition of N-[2-(ethyl amino)ethyl]acetamide (210 mg, 1.61 mmol). The reaction mixture was stirred at RT for 16 h. After completion of reaction, water (50 mL) was added and the mixture extracted with EtOAc (3×50 mL). The combined organic layer was washed with water (50 mL), dried over anhydrous sodium sulfate and concentrated under reduced pressure to obtain the crude product which was purified by reverse phase HPLC to obtain N-(2-acetamido-ethyl)-4-[5-(2-tert-butyl-4-pyridyl)-3-thienyl]-3-chloro-N-ethyl-benzamide (12 mg) as the freebase, an off-white solid.

$^1$H NMR (400 MHz, DMSO-d6) δ (ppm): 8.54 (d, J=5.2 Hz, 1H), 8.06 (d, J=24.5 Hz, 1H), 7.97 (s, 1H), 7.77-7.63 (m, 2H), 7.52 (s, 2H), 7.43 (d, J=8.6 Hz, 1H), 3.66-3.44 (m, 2H), 3.33-3.22 (m, 2H), 3.25-3.12 (m, 2H), 1.84 (s, 3H), 1.44 (s, 9H), 1.19 (t, 3H). LCMS: −(M+1) 485.1.

Example 48. Preparation of Compound Nos. 48, 48a, and 48b

Synthesis of 1-{4-[5-(2-tert-butylpyridin-4-yl)thiophen-3-yl]-3-chlorobenzoyl}piperidin-3-ol

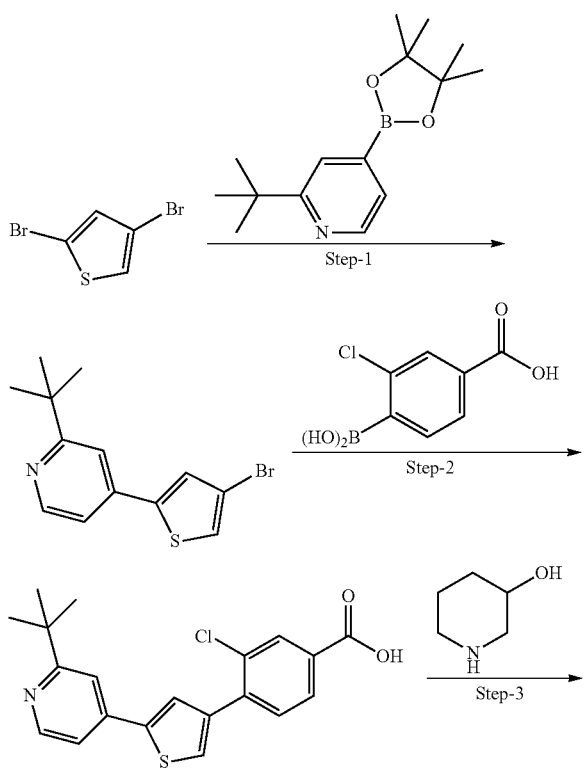

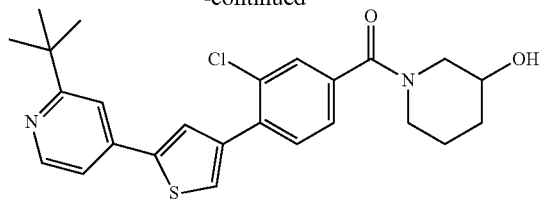

Step-1: Synthesis of 4-(4-bromo-2-thienyl)-2-tert-butyl-pyridine

In a 100 mL glass bottle 2,4 dibromothiophene (600 mg, 2.5 mmol, 1 eq.), 2-tert-butyl-4-(4,4,5,5-tetramethyl-1,3,2-dioxaborolan-2-yl)pyridine (652 mg, 1 eq.) and potassium phosphate (1.325 g, 2.5 eq.) were charged in 25 mL of THF. The mixture was purged with nitrogen for 15 min then Xantphos (145 mg, 0.1 eq.) and tetrakis (289 mg, 0.1 eq.) were added, and the mixture repurged for 5 min and the mixture stirred at 60° C. overnight. Progress of the reaction was monitored by TLC & LCMS. When the reaction was completed, the mixture was cooled to RT, water (100 mL) was added and the mixture extracted with EtOAc (3×100 mL). The combined organic layer was washed with brine (50 mL) then dried over anhydrous sodium sulfate, concentrated under reduced pressure to give a viscous compound which was purified by silica gel (60-120) column chromatography using EtOAc/Hexane (0-20%) as eluent system to afford 4-(4-bromo-2-thienyl)-2-tert-butyl-pyridine as a colorless semi-solid (500 mg) in pure form.

Step-2: Synthesis of 4-[5-(2-tert-butyl-4-pyridyl)-3-thienyl]-3-chloro-benzoic acid In a 25 mL glass bottle, 4-(4-bromo-2-thienyl)-2-tert-butyl-pyridine (1 g, 2.69 mmol, 1 eq.) and 4-borono-3-chloro-benzoic acid (700 mg, 3.5 mmol, 1.3 eq.), were charged in DMF (13 mL) followed by addition of sodium carbonate (898 mg, 2.5 equiv dissolved in water (2.0 mL) and the reaction mixture was purged with nitrogen gas for 5 min. After adding tetrakis (311 mg, 0.269 mmol, 0.1 eq.) the mixture was repurged for 2 min and was stirred at 80° C. overnight. The progress of the reaction was monitored by TLC and LCMS. After completion of reaction, the mixture was allowed to come to RT and diluted with water (50 mL) and extracted with EtOAc:MeOH (95:05), (3×100 mL). The combined organic layer was dried over anhydrous sodium sulfate and concentrated under reduced pressure to afford a solid compound, 3-chloro-4-[5-[3-(1-piperidyl)phenyl]-3-thienyl]benzoic acid (700 mg) which was used as such for the next step of synthesis.

Step-3: Synthesis of [4-[5-(2-tert-butyl-4-pyridyl)-3-thienyl]-3-chloro-phenyl]-(3-hydroxy-1-piperidyl)methanone In a 100 mL flask, 4-[5-(2-tert-butyl-4-pyridyl)-3-thienyl]-3-chloro-benzoic acid (150 mg, 0.40 mmol, 1 eq.) was dissolved in DMF (7 mL), followed by addition of DIPEA (0.4 mL, 2.01 mmol, 5 eq.) and HATU (307 mg, 0.80 mmol, 2 eq.), and the resulting mixture was stirred for 10 min at RT and 3-hydroxypiperidine (163 mg, 1.61 mmol, 4 eq.) were added and the mixture stirred at RT under nitrogen atmosphere overnight. The progress of the reaction was monitored by TLC and LCMS. After completion of reaction, the mixture was diluted with water (100 mL) and extracted with EtOAc (2×100 mL), washed with water (4×100 mL) then dried over anhydrous sodium sulfate and the combined organic layer was concentrated under reduced pressure which was submitted to reverse phase HPLC process for its purification to afford [4-[5-(2-tert-butyl-4-pyridyl)-3-thienyl]-3-chloro-phenyl]-(3-hydroxy-1-piperidyl)methanone (54 mg—as freebase) as an off-white solid then it was treated with ethanolic HCl (1.25 M) to obtain its HCl salt (55 mg) as an off-white solid. The enantiomers were prepared from chiral HPLC resolution of the racemate to give Compound 48a [(R)-(4-(5-(2-(tert-butyl)pyridin-4-yl)thiophen-3-yl)-3-chlorophenyl)(3-hydroxypiperidin-1-yl)methanone] and Compound 48b [(S)-(4-(5-(2-(tert-butyl)pyridin-4-yl)thiophen-3-yl)-3-chlorophenyl)(3-hydroxypiperidin-1-yl)methanone].

¹H NMR (400 MHz, Methanol-d4) δ (ppm): 8.61 (d, J=6.3 Hz, 1H), 8.40 (d, J=1.5 Hz, 1H), 8.24-8.13 (m, 3H), 7.66 (t, J=11.3 Hz, 2H), 7.49 (d, J=8.8 Hz, 1H), 4.11 (d, J=12.5 Hz, 1H), 3.79-3.73 (s, 2H), 3.64-3.4 (m, 2H), 3.56 (d, J=14.1 Hz, 1H), 1.99-1.92 (m, 2H), 1.81-1.61 (m, 1H), 1.58 (s, 9H). LCMS=455.1 (M+1).

Example 49. Preparation of Compound No. 49

Synthesis of 4-[5-(2-tert-butylpyridin-4-yl)thiophen-3-yl]-3-chloro-N-(3-hydroxyphenyl) benzamide

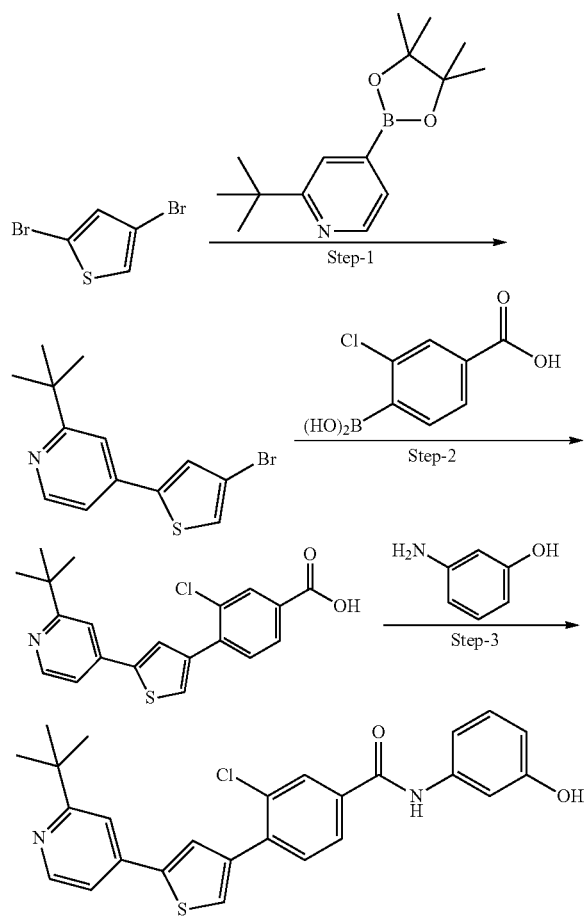

Step-1: Synthesis of 4-(4-bromo-2-thienyl)-2-tert-butyl-pyridine

In a 100 mL glass bottle 2,4 dibromothiophene (600 mg, 2.5 mmol, 1 eq.) along with 2-tert-butyl-4-(4,4,5,5-tetramethyl-1,3,2-dioxaborolan-2-yl)pyridine (652 mg, 1 eq.) and potassium phosphate (1.325 g, 2.5 eq.) were charged in 25 mL of THF. The mixture was purged with nitrogen for 15 min then Xantphos (145 mg, 0.1 eq.) and tetrakis (289 mg, 0.1 eq.) were added, and the mixture repurged for 5 min and the mixture stirred at 60° C. overnight. Progress of the reaction was monitored by TLC & LCMS. When the reaction was completed, the mixture was cooled to RT, water (100 mL) was added and the mixture extracted with EtOAc (3×100 mL). The combined organic layer was washed with brine (50 mL) then dried over anhydrous sodium sulfate, concentrated under reduced pressure to give a viscous compound which was purified by silica gel (60-120) column chromatography using EtOAc/Hexane (0-20%) as eluent system to afford 4-(4-bromo-2-thienyl)-2-tert-butyl-pyridine as a colorless semi-solid (500 mg) in pure form.

Step-2: Synthesis of 4-[5-(2-tert-butyl-4-pyridyl)-3-thienyl]-3-chloro-benzoic acid In a 25 mL glass bottle, 4-(4-bromo-2-thienyl)-2-tert-butyl-pyridine (1 g, 2.69 mmol, 1 eq.) and 4-borono-3-chloro-benzoic acid (700 mg, 3.5 mmol, 1.3 eq.), were charged in DMF (13 mL) followed by addition of sodium carbonate (898 mg, 2.5 equiv dissolved in water (2.0 mL) and the reaction mixture was purged with nitrogen gas for 5 min. After adding tetrakis (311 mg, 0.269 mmol, 0.1 eq.) the mixture was repurged for 2 min and was stirred at 80° C. overnight. The progress of the reaction was monitored by TLC and LCMS. After completion of reaction, the mixture was allowed to come to RT and diluted with water (50 mL) and extracted with EtOAc:MeOH (95:05), (3×100 mL). The combined organic layer was dried over anhydrous sodium sulfate and concentrated under reduced pressure to afford a solid compound, 3-chloro-4-[5-[3-(1-piperidyl)phenyl]-3-thienyl]benzoic acid (700 mg) which was used as such for the next step of synthesis.

Step-3: Synthesis of 4-[5-(2-tert-butyl-4-pyridyl)-3-thienyl]-3-chloro-N-(3-hydroxyphenyl)benzamide In a 100 mL flask, 4-[5-(2-tert-butyl-4-pyridyl)-3-thienyl]-3-chloro-benzoic acid (250 mg, 0.67 mmol, 1 eq.) was dissolved in DMF (7 mL), followed by addition of DIPEA (0.5 mL, 2.69 mmol, 4 eq.) and HATU (513 mg, 1.34 mmol, 2 eq.), and the resulting mixture was stirred for 10 min at RT and 3-hydroxyaniline (295 mg, 2.69 mmol, 4 eq.) were added and the mixture stirred at RT under nitrogen atmosphere overnight. The progress of the reaction was monitored by TLC and LCMS. After completion of reaction, the mixture was diluted with water (100 mL) and extracted with EtOAc (2×100 mL), washed with water (4×100 mL) then dried over anhydrous sodium sulfate and the combined organic layer was concentrated under reduced pressure which was submitted to reverse phase HPLC process for its purification to afford 4-[5-(2-tert-butyl-4-pyridyl)-3-thienyl]-3-chloro-N-(3-hydroxyphenyl)benzamide (110 mg freebase) as an off-white solid then it was treated with ethanolic HCl (1.25 M) to obtain its HCl salt (118 mg) as an off-white solid.

¹H NMR (400 MHz, DMSO-d6) δ (ppm): 10.29 (s, 1H), 9.46 (s, 1H), 8.66 (d, J=5.5 Hz, 1H), 8.44 (s, 1H), 8.25 (d, J=9.1 Hz, 1H), 8.18 (d, J=1.8 Hz, 1H), 8.06-7.98 (m, 2H), 7.96 (s, 1H), 7.79 (d, J=8.0 Hz, 1H), 7.37 (t, J=2.2 Hz, 1H), 7.16 (dt, J=15.9, 8.0 Hz, 2H), 6.58-6.50 (m, 1H), 1.46 (d, J=5.0 Hz, 9H). LCMS=463.2 (M+1).

Example 50. Preparation of Compound Nos. 50, 50a, 50b, and 50c

Synthesis of (2R,6S)-4-{4-[5-(2-tert-butylpyridin-4-yl)thiophen-3-yl]-3-chlorobenzoyl}-2,6-dimethylmorpholine

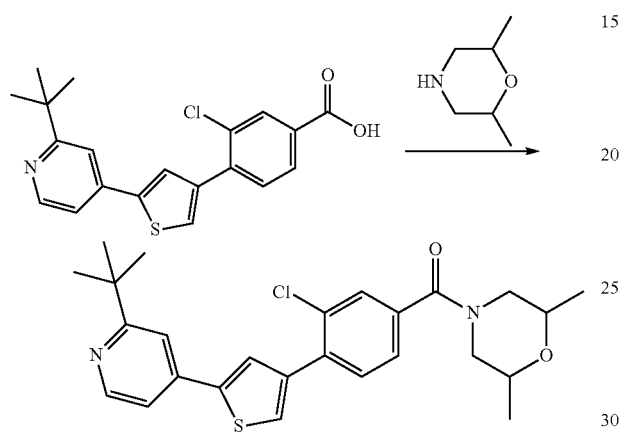

To a stirred solution of 4-[5-(2-tert-butyl-4-pyridyl)-3-thienyl]-3-chloro-benzoic acid (100 mg, 0.269 mmol) in DMF 5 mL, was added DIPEA (34.8 mg, 0.2695 mmol) followed by addition of HATU (204 mg, 0.539 mmol) and the mixture stirred at RT for 30 min. Then (2R, 6S)-2,6-dimethyl morpholine (124 mg, 1.07 mmol) was added at the same temperature. The reaction mixture was stirred at RT overnight. The reaction was monitored by TLC and LCMS. After completion of reaction, the mixture was diluted with water (10 mL) and extracted with EtOAc (2×50 mL), the organic layer was washed with water (2×20 mL) and brine (20 mL) and dried over anhydrous sodium sulfate to obtain a crude product which was purified by reverse phase HPLC to obtain 4-[5-(2-tert-butyl-4-pyridyl)-3-thienyl]-3-chlorophenyl)-((2R,6S)-2,6-dimethylmorpholin-4-yl) methanone (25 mg) as the HCl salt. The other diastereomers can be prepared using appropriate stereoisomers of the 2,6-dimethylmorpholine reagent.

¹H NMR (400 MHz, DMSO-d6) δ (ppm): 8.45 (d, J=5.2 Hz, 1H), 7.95 (s, 1H), 7.78 (s, 1H), 7.65 (m, 2H), 7.61 (s, 1H), 7.51 (d, J=5.2 Hz, 1H), 7.40 (d, J=5.2 Hz, 1H), 4.5 (s, 1H), 3.60 (s, 3H), 2.96 (s, 1H), 2.60 (s, 1H), 1.41 (s, 9H), 1.20 (s, 3H), 1.08 (s, 3H). LCMS=469.1 (M+1).

Example 51. Preparation of Compound No. 51

Synthesis of 1-{4-[4-(2-tert-butylpyridin-4-yl)thiophen-2-yl]-3-chlorobenzoyl}-1,2,3,4-tetrahydro-1,8-naphthyridine

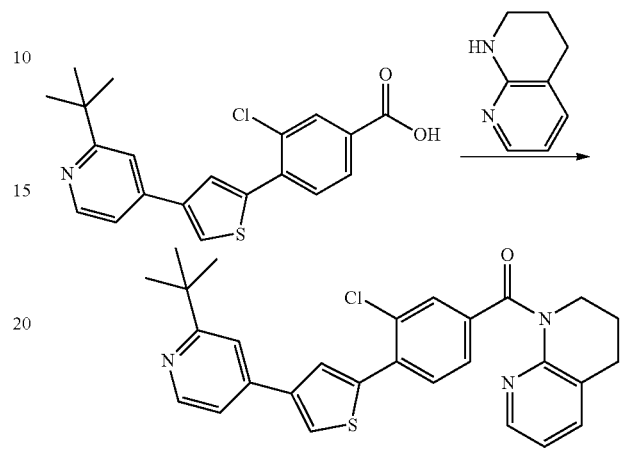

To a stirred solution of 4-[4-(2-tert-butyl-4-pyridyl)-2-thienyl]-3-chloro-benzoic acid (300 mg, 0.80 mmol) in DMF (5 mL), were added DIPEA (0.6 mL, 3.22 mmol) and HATU (612 mg, 1.61 mmol), under nitrogen atmosphere. The reaction mixture was stirred at RT for 0.5 h, followed by addition of 1,2,3,4-tetrahydro-1,8-naphthyridine (324 mg, 1.61 mmol). The reaction mixture was stirred at RT for 16 h. After completion of reaction, water (100 mL) was added and the mixture extracted with EtOAc (3×50 mL). The combined organic layer was washed with brine (50 mL), dried over anhydrous sodium sulfate and concentrated under reduced pressure to obtain a residue, which was purified by Reverse phase HPLC to obtain [4-[4-(2-tert-butyl-4-pyridyl)-2-thienyl]-3-chloro-phenyl]-(3,4-dihydro-2H-1,8-naphthyridin-1-yl)methanone (12 mg) as the HCl salt.

¹H NMR (400 MHz, Methanol-d4) δ (ppm): 8.68 (s, 1H), 8.63 (d, J=6.4 Hz, 1H), 8.32 (s, 1H), 8.25 (d, J=6.1 Hz, 1H), 8.16 (s, 1H), 8.03 (d, J=5.4 Hz, 1H), 7.93 (d, J=7.5 Hz, 1H), 7.73 (d, J=8.1 Hz, 1H), 7.66 (s, 1H), 7.43 (d, J=8.1 Hz, 1H), 7.33-7.25 (m, 1H), 4.02 (t, J=6.1 Hz, 2H), 3.02 (t, J=6.5 Hz, 2H), 2.12 (q, J=6.3 Hz, 2H), 1.58 (s, 9H). LCMS=(M+1) 488.2.

Example 52. Preparation of Compound No. 52

Synthesis of 6-[5-(2-tert-butylpyridin-4-yl)thiophen-3-yl]-7-chloro-2-(propan-2-yl)-1,2,3,4-tetrahydroisoquinolin-1-one

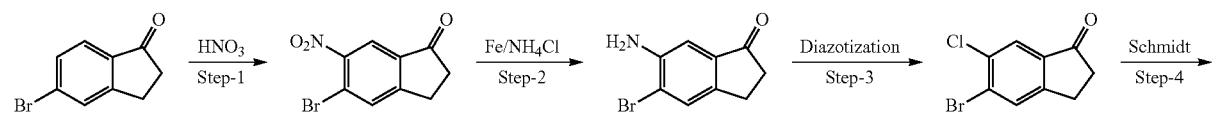

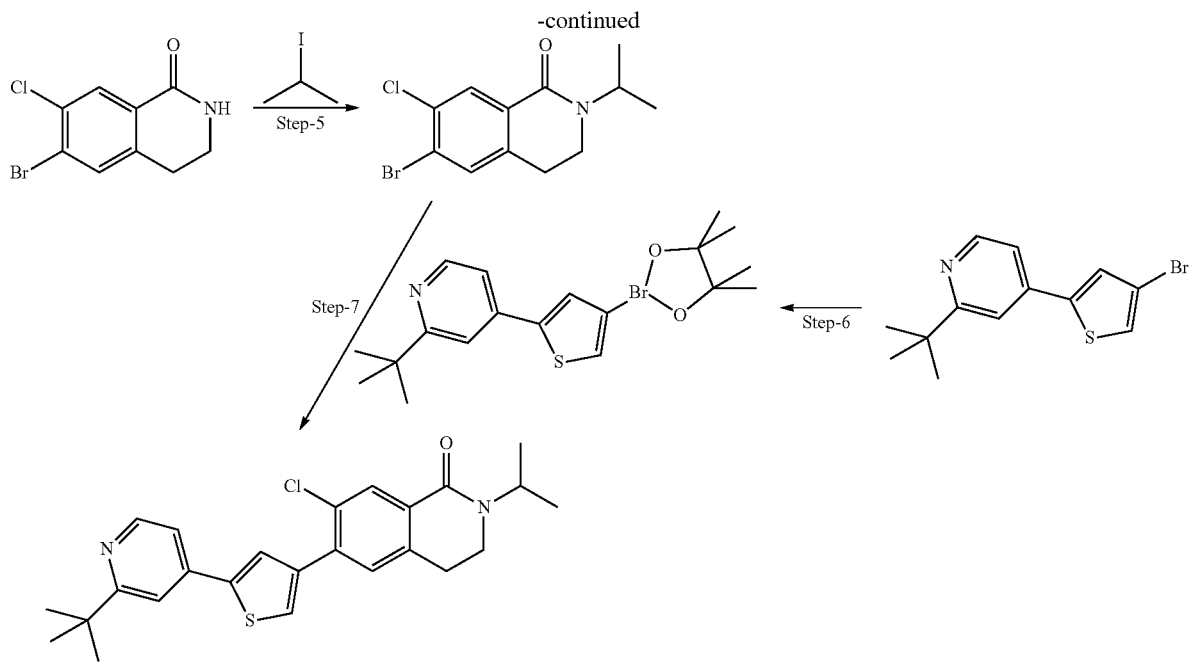

Step-1: Synthesis of 5-bromo-6-nitro-indan-1-one

Fuming nitric acid (25 mL) was cooled to −15° C. and 5-bromoindan-1-one (3.5 g, 0.0165 mol) was then added portionwise. The reaction mixture was stirred at −10° C. under nitrogen atmosphere for 4 h. The reaction was monitored by TLC and LCMS. After completion of reaction, the mixture was poured into ice cold water (100 mL) and extracted with EtOAc (2×200 mL), the organic layer was washed with aq. sodium bicarbonate solution (2×100 mL) and finally brine solution washed (50 mL). The organic layer was dried over anhydrous sodium sulfate and concentrated under reduced pressure to obtain a crude compound that was dissolved in DCM (15 mL) and n-pentane (150 mL) was added. The precipitated compound was filtered and dried under vacuum to obtain 5-bromo-6-nitro-indan-1-one (2.8 g) as a light brown solid.

Step-2: Synthesis of 6-amino-5-bromo-indan-1-one

A mixture of 5-bromo-6-nitro-indan-1-one (2.8 g, 0.0109 mol), iron (1.42 g, 0.0546 mol) and $NH_4Cl$ (0.877 g, 0.0164) in EtOH (20 mL) and water (5 mL) was heated to reflux for 90 min. The reaction was monitored by TLC and LCMS. After completion of reaction, the mixture was filtered through a celite bed, the celite bed washed with hot ethanol (2×25 mL) and the filtrate concentrated under reduced pressure to obtain a crude compound that was diluted with water (50 mL) and extracted with EtOAc (2×200 mL). The extracts were dried over anhydrous sodium sulfate and concentrated under reduced pressure to obtain 6-amino-5-bromo-indan-1-one (1.7 g) as a brown solid.

Step-3: Synthesis of 5-bromo-6-chloro-indan-1-one

To a stirred solution of 6-amino-5-bromo-indan-1-one (500 mg, 2.21 mmol) in conc. HCl (5 mL) at 0° C. under nitrogen atmosphere, was added portionwise sodium nitrite (168 mg, 2.43 mmol) at the same temperature for 30 min, then the reaction mixture was brought to RT and the mixture stirred for 30 min. A solution of copper (I) chloride (307 mg, 3.09 mmol) in conc. HCl (3 mL) was added slowly. The reaction mixture was heated at 60° C. for 50 min. The reaction was monitored by TLC and LCMS. After completion of reaction, the mixture was cooled to RT and diluted with ice cold water (50 mL) and extracted with EtOAc (2×100 mL). The organic layer was dried over anhydrous sodium sulfate and concentrated under reduced pressure to obtain 5-bromo-6-chloro-indan-1-one (370 mg).

Step-4: Synthesis of 6-bromo-7-chloro-3,4-dihydro-2H-isoquinolin-1-one

To a stirred suspension of 5-bromo-6-chloro-indan-1-one (370 mg, 1.507 mmol) in DCM (10 mL) was added methane sulfonic acid (3 mL) at 0° C. under nitrogen atmosphere. Sodium azide (196 mg, 3.014 mmol) was added portionwise and the reaction mixture was stirred at the same temperature for 30 min. The reaction was monitored by TLC and LCMS. After completion of reaction, the mixture was basified with using 20% NaOH solution and extracted with EtOAc (12×50 mL). The organic layer washed with water (2×50 mL), dried over anhydrous sodium sulfate and concentrated under reduced pressure to obtain a crude product which was purified combi-flash chromatography using EtOAc in hexane to obtain 6-bromo-7-chloro-3,4-dihydro-2H-isoquinolin-1-one (200 mg).

Step-5: Synthesis of 6-bromo-7-chloro-2-isopropyl-3,4-dihydroisoquinolin-1-one To a stirred solution of 6-bromo-7-chloro-3,4-dihydro-2H-isoquinolin-1-one (400 mg, 1.538 mmol) in DMF (10 mL) was added NaH (60%) (123 mg, 3.076 mmol) at 0° C. under nitrogen atmosphere and the reaction mixture was stirred at RT for 30 min. Then isopropyl iodide (392 mg, 2.307 mmol) at RT. The reaction mixture was heated at 70° C. for 2 h. The reaction was monitored by TLC and LCMS.

After completion of reaction, the mixture was cooled to RT and quenched with ammonium chloride solution and extracted with EtOAc (2×100 mL). The organic layer was washed with water (2×50 mL) and brine (50 mL) and dried over anhydrous sodium sulfate and concentrated under reduced pressure to obtain 6-bromo-7-chloro-2-isopropyl-3,4-dihydroisoquinolin-1-one (300 mg).

Step-6: Synthesis of 2-tert-butyl-4-[4-(4,4,5,5-tetramethyl-1,3,2-dioxaborolan-2-yl)-2-thienyl]pyridine A stirred solution of 4-(4-bromo-2-thienyl)-2-tert-butylpyridine (1 g, 3.37 mmol), boron bis-pinacolato ester (1.28 g, 5.06 mmol) and potassium tert-butoxide (995 mg, 10.13 mmol) in anhydrous 1,4-dioxane (20 mL), was purged with nitrogen for 15 min and Bis(triphenyl phosphine)palladium (II) dichloride (118 mg, 0.16 mmol) was added and purging continued with nitrogen for 5 min. The reaction mixture was stirred at RT for 10 min and then stirred at 70° C. for 4 h. The reaction was monitored by TLC/1H-NMR & LCMS. After completion of reaction, the mixture was cooled to RT and diluted with water (100 mL) and extracted with EtOAc (3×100 mL) then washed with brine (50 mL), dried over anhydrous sodium sulfate and concentrated under reduced pressure to obtain a crude product which was purified by silica gel (60-120) column chromatography using EtOAc/Hexane (0-20%) to elute to obtain 2-tert-butyl-4-[4-(4,4,5,5-tetramethyl-1,3,2-dioxaborolan-2-yl)-2-thienyl]pyridine pure compound as a light yellow highly viscous (900 mg) oil.

Step-7: Synthesis of 6-[5-(2-tert-butyl-4-pyridyl)-3-thienyl]-7-chloro-2-isopropyl-3,4-dihydroisoquinolin-1-one To a solution of 6-bromo-7-chloro-2-isopropyl-3,4-dihydroisoquinolin-1-one (300 mg, 0.991 mmol) and 2-tert-butyl-4-[4-(4,4,5,5-tetramethyl-1,3,2-dioxaborolan-2-yl)-2-thienyl]pyridine (408 mg, 1.189 mmol) in DMF (5 mL) was added a solution of sodium carbonate (263 mg, 2.478 mmol) in water (5 mL), and purged with nitrogen for 20 min. tetrakis(triphenyl phosphine)palladium (91.6 mg, 0.079 mmol) was added and purging continued with nitrogen for 5 min. The reaction mixture was heated in a reagent bottle at 80° C. overnight. The reaction was monitored by LCMS. After completion of reaction, the mixture was acidified with 6M HCl and extracted with diethyl ether (2×20 mL). The aq layer was basified with saturated sodium carbonate and extracted with EtOAc (2×100 mL). The organic layer was dried over anhydrous sodium sulfate and concentrated under reduced pressure to obtain the crude product which was purified by chromatography to obtain pure compound (110 mg). This was dissolved in ethanolic HCl (10 mL) and concentrated under reduced pressure to obtain 6-[5-(2-tert-butyl-4-pyridyl)-3-thienyl]-7-chloro-2-isopropyl-3,4-dihydroisoquinolin-1-one HCl salt (120 mg) as a light brown solid.

$^1$H NMR (400 MHz, Methanol-d4) δ (ppm): 8.60 (d, J=6.4 Hz, 1H), 8.41 (d, J=1.5 Hz, 1H), 8.28-8.13 (m, 3H), 8.05 (s, 1H), 7.53 (s, 1H), 4.97 (p, J=6.8 Hz, 1H), 3.56 (t, J=6.5 Hz, 2H), 3.03 (t, J=6.5 Hz, 2H), 1.57 (s, 9H), 1.26 (d, J=6.8 Hz, 6H). LCMS=439 (M+1).

Example 53. Preparation of Compound No. 53

Synthesis of 4-[5-(2-tert-butylpyridin-4-yl)thiophen-3-yl]-3-chloro-N-[(4,6-dimethyl-2-oxo-1,2-dihydropyridin-3-yl)methyl]benzamide To a stirred solution of 4-[5-(2-tert-butyl-4-pyridyl)-3-thienyl]-3-chloro-benzoic acid (300 mg, 0.808 mmol) in DMF 10 mL, was added DIPEA (0.6 mL, 3.23 mmol) followed by addition of HATU (614 mg, 1.616 mmol) and stirred at RT for 30 min. Then 3-(amino methyl)-4,6-dimethyl-1H-pyridin-2-one (607 mg, 3.23 mmol) was added at the same temperature. The reaction mixture was stirred at RT overnight. The reaction was monitored by TLC and LCMS. After completion of reaction, the mixture was diluted with water (50 mL) and extracted with EtOAc (2×50 mL), the organic layer was washed with water (2×20 mL) and brine (20 mL) and dried over anhydrous sodium sulfate to obtain a crude compound. This was purified by reverse phase HPLC to obtain 4-[5-(2-tert-butyl-4-pyridyl)-3-thienyl]-3-chloro-N-[(4,6-dimethyl-2-oxo-1H-pyridin-3-yl)methyl]benzamide (90 mg) freebase as a solid.

$^1$H NMR (400 MHz, DMSO-d6) δ (ppm): 8.48 (d, J=5.2 Hz, 1H), 8.08 (m, 2H), 7.95 (s, 1H), 7.82 (d, J=7.9, 1H), 7.62 (m, 2H), 7.42 (d, J=5.3, 1H), 5.90 (s, 1H), 4.25 (s, 2H), 2.10 (s, 3H), 2.08 (s, 3H), 1.40 (s, 9H). LCMS=506.0 (M+1).

Example 54. Preparation of Compound No. 54

Synthesis of 4-[5-(2-tert-butylpyridin-4-yl)thiophen-3-yl]-3-chloro-N-(4-fluorophenyl) benzamide

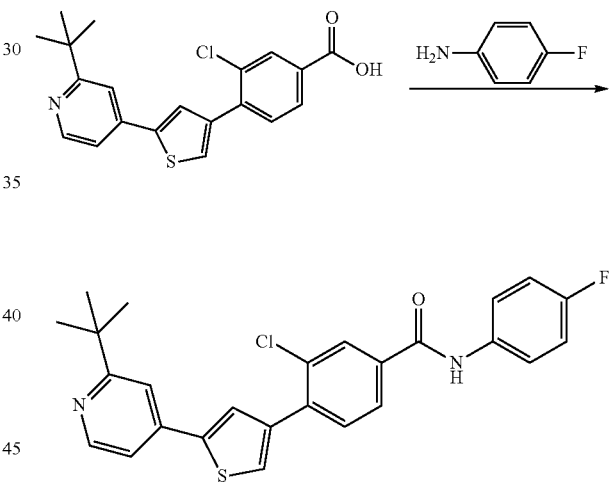

4-[5-(2-tert-Butyl-4-pyridyl)-3-thienyl]-3-chloro-benzoic acid (300 mg, 0.80 mmol) was taken in DMF (10 mL), followed by addition of DIPEA (0.57 mL, 3.22 mmol), HATU (600 mg, 1.61 mmol), under nitrogen atmosphere. The reaction mixture was stirred at RT for 0.5 h, followed by addition of 4-fluoroaniline (358 mg, 3.22 mmol). The reaction mixture was stirred at RT for 16 h. After completion of reaction, water (150 mL) was added and the mixture extracted with EtOAc (2×50 mL). The combined organic layer was washed with brine (50 mL), dried over anhydrous sodium sulfate and concentrated under reduced pressure to obtain the crude product which was purified by reverse phase HPLC to obtain 4-[5-(2-tert-butyl-4-pyridyl)-3-thienyl]-3-chloro-N-(4-fluorophenyl)benzamide (90 mg) as the HCl salt.

$^1$H NMR (400 MHz, DMSO-d6) δ (ppm): 10.52 (s, 1H), 8.68 (d, J=6.0 Hz, 1H), 8.49 (s, 1H), 8.29 (s, 1H), 8.22 (d, J=1.8 Hz, 1H), 8.09-8.02 (m, 2H), 7.88-7.77 (m, 3H), 7.22 (t, J=8.9 Hz, 2H), 1.48 (s, 9H). LCMS=465.2 (M+1).

Example 55. Preparation of Compound Nos. 55, 55a, and 55b

Synthesis of N-(1-{4-[5-(2-tert-butylpyridin-4-yl)thiophen-3-yl]-3-chlorobenzoyl}piperidin-3-yl)-2,2-dimethylpropanamide

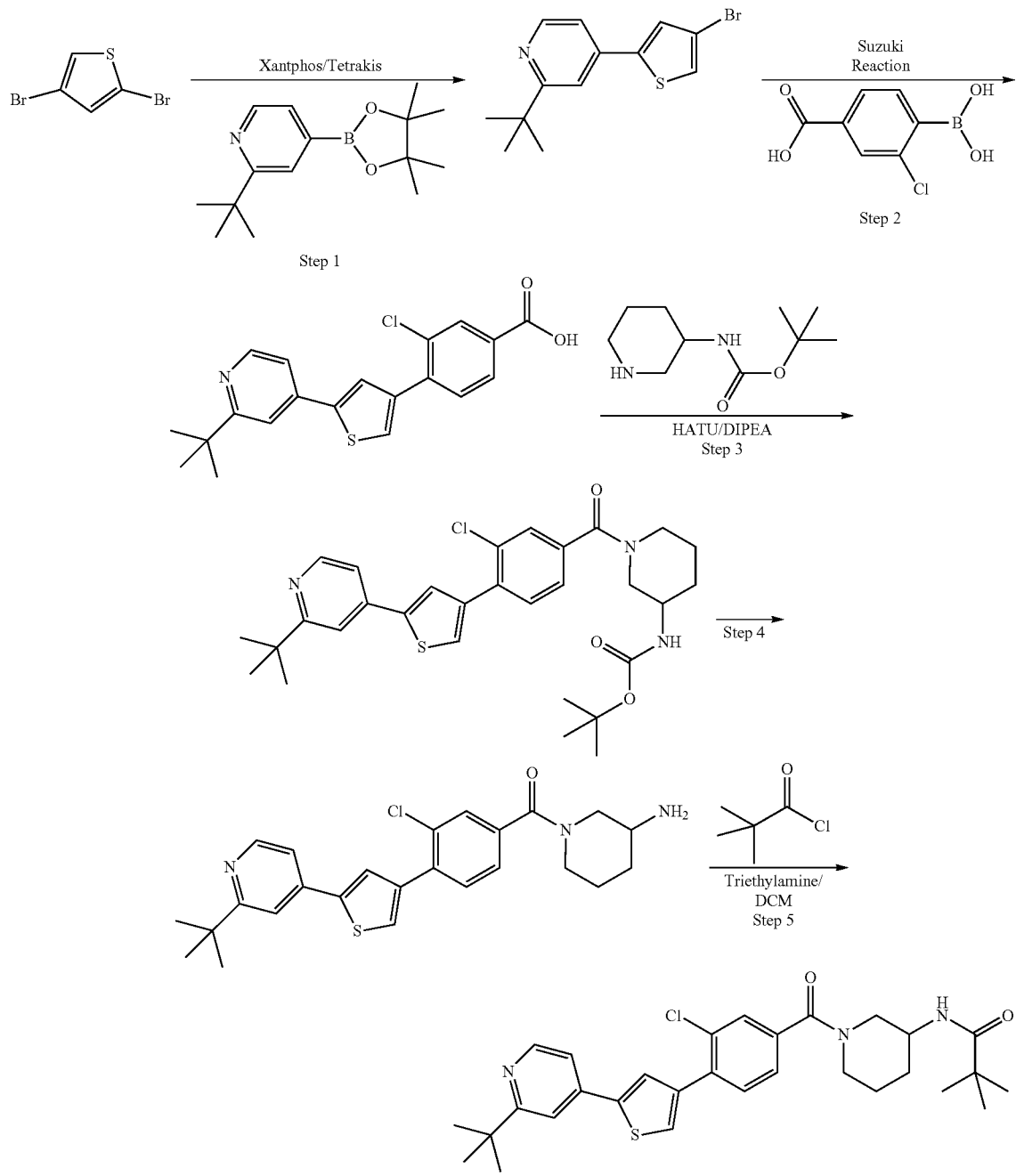

Step-1: Synthesis of 4-(4-bromo-2-thienyl)-2-tert-butyl-pyridine

In a 100 mL glass bottle 2,4 dibromothiophene (600 mg, 2.5 mmol, 1 eq.) along with 2-tert-butyl-4-(4,4,5,5-tetramethyl-1,3,2-dioxaborolan-2-yl)pyridine (652 mg, 1 eq.) and potassium phosphate (1.325 g, 2.5 eq.) were charged in 25 mL of THF. The mixture was purged with nitrogen for 15 min then Xantphos (145 mg, 0.1 eq.) and tetrakis (289 mg, 0.1 eq.) were added, and the mixture repurged for 5 min and the mixture stirred at 60° C. overnight. Progress of the reaction was monitored by TLC & LCMS. When the reaction was completed, the mixture was cooled to RT, water (100 mL) was added and the mixture extracted with EtOAc (3×100 mL). The combined organic layer was washed with brine (50 mL) then dried over anhydrous sodium sulfate, concentrated under reduced pressure to give a viscous compound which was purified by silica gel (60-120) column chromatography using EtOAc/Hexane (0-20%) as eluent system to afford 4-(4-bromo-2-thienyl)-2-tert-butyl-pyridine as a colorless semi-solid (500 mg) in pure form.

Step-2: Synthesis of 4-[5-(2-tert-butyl-4-pyridyl)-3-thienyl]-3-chloro-benzoic acid In a 25 mL glass bottle, 4-(4-bromo-2-thienyl)-2-tert-butyl-pyridine (450 mg, 1.52 mmol, 1 eq.) and 4-borono-3-chloro-benzoic acid (397 mg, 1.98 mmol, 1.3 eq.), were charged in DMF (7 mL) followed by addition of sodium carbonate (404 mg, 2.5 equiv dissolved in water (2.0 mL) and the reaction mixture was purged with nitrogen gas for 5 min. After adding tetrakis (176 mg, 0.152 mmol, 0.1 eq.) the mixture was repurged for 2 min and was stirred at 90° C. overnight. The progress of the reaction was monitored by TLC and LCMS. After completion of reaction, the mixture was allowed to come to RT and diluted with water (50 mL) and extracted with EtOAc:MeOH (90:10), (3×100 mL). The combined organic layer was dried over anhydrous sodium sulfate and concentrated under reduced pressure to afford a semi-solid compound, 3-chloro-4-[5-[3-(1-piperidyl)phenyl]-3-thienyl]benzoic acid (500 mg) which was used as such for the next step of synthesis.

Step-3: Synthesis of tert-butyl N-[1-[4-[5-(2-tert-butyl-4-pyridyl)-3-thienyl]-3-chloro-benzoyl]-3-piperidyl]carbamate In a 100 mL flask, 4-[5-(2-tert-butyl-4-pyridyl)-3-thienyl]-3-chloro-benzoic acid (700 mg, 1.88 mmol, 1 eq.) was dissolved in DMF (10 mL), followed by addition of DIPEA (1.4 mL, 7.54 mmol, 4 eq.) and HATU (1.4 mg, 3.77 mmol, 2 eq.), and the resulting mixture was stirred for 10 min at RT and tert-butyl N-(3-piperidyl)carbamate (1.5 g, 7.54 mmol, 4 eq.) were added and the mixture stirred at RT under nitrogen atmosphere overnight. The progress of the reaction was monitored by TLC and LCMS. After completion of reaction, the mixture was diluted with water (100 mL) and extracted with EtOAc (2×100 mL), washed with water (4×100 mL) then dried over anhydrous sodium sulfate and the combined organic layer was concentrated under reduced pressure to afford N-[1-[4-[5-(2-tert-butyl-4-pyridyl)-3-thienyl]-3-chloro-benzoyl]-3-piperidyl]carbamate (700 mg) as a crude viscous compound which was used as such for the next step of synthesis.

Step-4: Synthesis of (3-amino-1-piperidyl)-[4-[5-(2-tert-butyl-4-pyridyl)-3-thienyl]-3-chloro-phenyl]methanone In a 100 mL flask, tert-butyl N-[1-[4-[5-(2-tert-butyl-4-pyridyl)-3-thienyl]-3-chloro-benzoyl]-3-piperidyl]carbamate (700 mg, 1.26 mmol, 1 eq.) was charged in DCM (15 mL). The reaction mixture was maintained at 0° C. and trifluoroacetic acid (5 mL) was added dropwise and the mixture stirred at RT for 2.5 h. Progress of reaction was monitored by TLC/LCMS. After completion of reaction, the DCM was evaporated under reduced pressure, and the residue basified with saturated aqueous sodium bicarbonate solution and extracted with EtOAc (2×100 mL). The organic layer was washed with brine (100 mL) and dried over anhydrous sodium sulfate. The solution was concentrated under reduced pressure to afford (3-amino-1-piperidyl)-[4-[5-(2-tert-butyl-4-pyridyl)-3-thienyl]-3-chloro-phenyl]methanone as a crude viscous compound (570 mg) which was used as such for the next step of synthesis.

Step-5: Synthesis of N-[1-[4-[5-(2-tert-butyl-4-pyridyl)-3-thienyl]-3-chloro-benzoyl]-3-piperidyl]-2,2-dimethyl-propanamide In a 25 mL flask, (3-amino-1-piperidyl)-[4-[5-(2-tert-butyl-4-pyridyl)-3-thienyl]-3-chloro-phenyl]methanone, (150 mg, 0.33 mmol, 1 eq.) was suspended in 5 mL of DCM then TEA (2 eq.) added and the mixture stirred for 10 min at RT. The mixture was maintained at 0° C. condition and pivaloyl chloride (59.4 mg, 0.49 mmol, 1.5 eq.) was added dropwise and the mixture stirred for 1 h at the same temperature. Progress of the reaction was monitored by TLC & 1H-NMR/LCMS. After maximum conversion of the starting material into product, the mixture was diluted with (100 mL) water and extracted with EtOAc (3×100 mL). The combined organic layer was washed with brine (50 mL) then dried over anhydrous sodium sulfate, concentrated under reduced pressure to give a viscous desired compound which was submitted for reverse phase HPLC for purification to afford N-[1-[4-[5-(2-tert-butyl-4-pyridyl)-3-thienyl]-3-chloro-benzoyl]-3-piperidyl]-2,2-dimethyl-propanamide as the freebase, which was treated with ethanolic HCl to afford its (100 mg-HCl Salt) as an off-white solid. The enantiomers can be prepared from chiral HPLC resolution of the racemate.

$^1$H NMR (400 MHz, Methanol-d4) δ (ppm): 8.60 (d, J=6.4 Hz, 1H), 8.41 (s, 1H), 8.25-8.14 (m, 3H), 7.72-7.60 (m, 2H), 7.48 (s, 1H), 4.39 (m, 1H), 3.82 (s, 1H), 3.63 (s, 1H), 3.06 (t, J=11.5 Hz, 2H), 1.99–1.91 (m, 2H), 1.68 (m, 2H), 1.57 (s, 9H), 1.21 (s, 4H), 1.13 (s, 5H). LCMS −(M+1) 538.1.

Example 56. Preparation of Compound Nos. 56, 56a, and 56b

Synthesis of 1-(1-{4-[5-(2-tert-butylpyridin-4-yl)thiophen-3-yl]-3-chlorobenzoyl}piperidin-3-yl)-3-cyclopropylurea

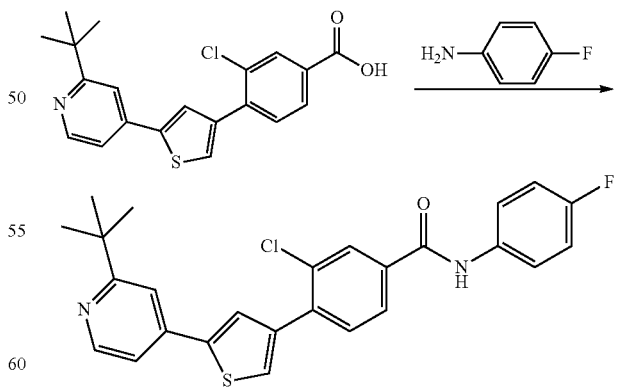

To a stirred solution of (3-amino-1-piperidyl)-[4-[5-(2-tert-butyl-4-pyridyl)-3-thienyl]-3-chloro-phenyl] methanone TFA salt (230 mg, 0.404 mmol) in DCM:DMF (9:1) (10 mL) was added triethylamine (0.22 mL, 1.6197 mmol) at 0° C. under nitrogen atmosphere and the mixture stirred for 5 min at the same temperature. Then isocyanatocyclopropane (50.4 mg, 0.607 mmol) and the mixture stirred for 30 min at RT. The reaction was monitored by TLC and LCMS. After completion of reaction, the mixture was diluted with water (50 mL) and extracted with DCM (12×50 mL), washed with brine solution (2×50 mL). The combined organic layer was dried over anhydrous sodium sulfate and concentrated under reduced pressure to obtain a crude product which was purified by trituration with using n-pentane (2×10 mL) and diethyl ether (10 mL) to obtain 1-[1-[4-[5-(2-tert-butyl-4-pyridyl)-3-thienyl]-3-chloro-benzoyl]-3-piperidyl]-3-cyclopropyl-urea 120 mg as the freebase. 40 mg of pure compound was dissolved in ethanolic HCl (10 mL) and concentrated under reduced pressure to obtain 1-[1-[4-[5-(2-tert-butyl-4-pyridyl)-3-thienyl]-3-chloro-benzoyl]-3-piperidyl]-3-cyclopropyl-urea hydrochloride salt (45 mg) as an off-white solid. The enantiomers can be prepared from chiral HPLC resolution of the racemate.

$^1$H NMR (400 MHz, Methanol-d4) δ (ppm): 8.58 (d, J=6.2 Hz, 1H), 8.32 (s, 1H), 8.15-8.05 (m, 3H), 7.66 (d, J=7.8 Hz, 1H), 7.60 (s, 1H), 7.45 (d, J=8.0 Hz, 1H), 3.82 (m, 1H), 3.69 (m, 2H), 2.42 (m, 1H), 2.00 (m, 1H), 1.85 (m, 1H), 1.65 (m, 3H), 1.55 (s, 9H), 1.36-1.27 (m, 2H), 0.66 (m, 2H), 0.46 (m, 1H), 0.40 (m, 1H). LCMS=537 (M+1).

Example 57. Preparation of Compound No. 57

Synthesis of 1-{4-[5-(2-tert-butylpyridin-4-yl)thiophen-3-yl]-3-chlorobenzoyl}piperidin-4-ol

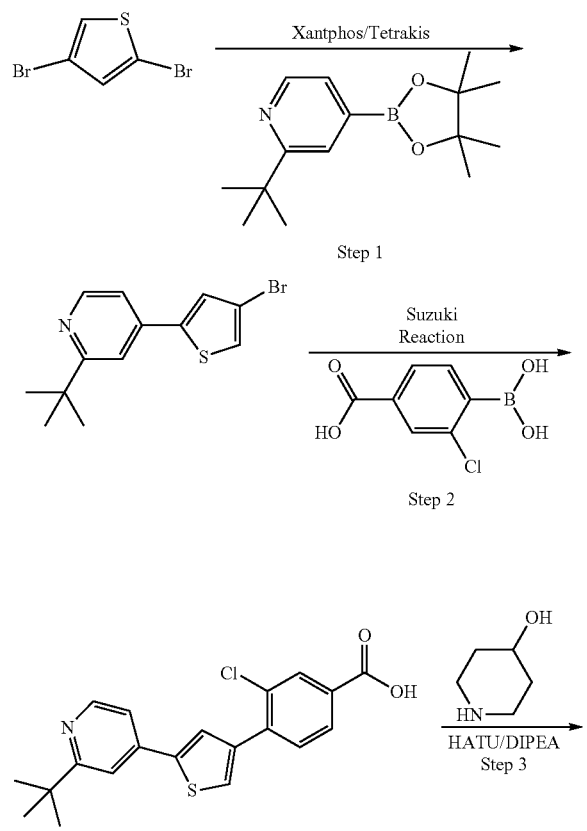

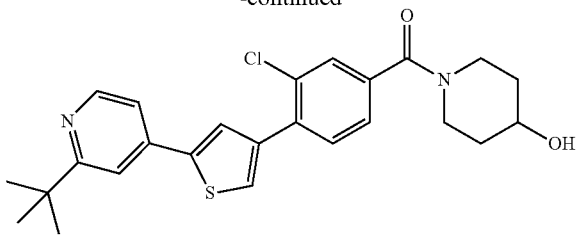

Step-1: Synthesis of 4-(4-bromo-2-thienyl)-2-tert-butyl-pyridine

In a 100 mL glass bottle 2,4 dibromothiophene (600 mg, 2.5 mmol, 1 eq.) along with 2-tert-butyl-4-(4,4,5,5-tetramethyl-1,3,2-dioxaborolan-2-yl)pyridine (652 mg, 1 eq.) and potassium phosphate (1.325 g, 2.5 eq.) were charged in 25 mL of THF. The mixture was purged with nitrogen for 15 min then Xantphos (145 mg, 0.1 eq.) and tetrakis (289 mg, 0.1 eq.) were added, and the mixture repurged for 5 min and the mixture stirred at 60° C. overnight. Progress of the reaction was monitored by TLC & LCMS. When the reaction was completed, the mixture was cooled to RT, water (100 mL) was added and the mixture extracted with EtOAc (3×100 mL). The combined organic layer was washed with brine (50 mL) then dried over anhydrous sodium sulfate, concentrated under reduced pressure to give a viscous compound which was purified by silica gel (60-120) column chromatography using EtOAc/Hexane (0-20%) as eluent system to afford 4-(4-bromo-2-thienyl)-2-tert-butyl-pyridine as a colorless semi-solid (500 mg) in pure form.

Step-2: Synthesis of 4-[5-(2-tert-butyl-4-pyridyl)-3-thienyl]-3-chloro-benzoic acid In a 25 mL glass bottle, 4-(4-bromo-2-thienyl)-2-tert-butyl-pyridine (1 g, 2.69 mmol, 1 eq.) and 4-borono-3-chloro-benzoic acid (700 mg, 3.5 mmol, 1.3 eq.), were charged in DMF (13 mL) followed by addition of sodium carbonate (898 mg, 2.5 equiv dissolved in water (2.0 mL) and the reaction mixture was purged with nitrogen gas for 5 min. After adding tetrakis (311 mg, 0.269 mmol, 0.1 eq.) the mixture was repurged for 2 min and was stirred at 80° C. overnight. The progress of the reaction was monitored by TLC and LCMS. After completion of reaction, the mixture was allowed to come to RT and diluted with water (50 mL) and extracted with EtOAc:MeOH (95:05), (3×100 mL). The combined organic layer was dried over anhydrous sodium sulfate and concentrated under reduced pressure to afford a solid compound, 3-chloro-4-[5-[3-(1-piperidyl)phenyl]-3-thienyl]benzoic acid (700 mg) which was used as such for the next step of synthesis.

Step-3: Synthesis of [4-[5-(2-tert-butyl-4-pyridyl)-3-thienyl]-3-chloro-phenyl]-(4-hydroxy-1-piperidyl)methanone In a 100 mL flask, 4-[5-(2-tert-butyl-4-pyridyl)-3-thienyl]-3-chloro-benzoic acid (150 mg, 0.40 mmol, 1 eq.) was dissolved in DMF (7 mL), followed by addition of DIPEA (0.4 mL, 2.01 mmol, 5 eq.) and HATU (307 mg, 0.80 mmol, 2 eq.), and the resulting mixture was stirred for 10 min at RT and 3-hydroxypiperidine (163 mg, 1.61 mmol, 4 eq.) were added and the mixture stirred at RT under nitrogen atmosphere overnight. The progress of the reaction was monitored by TLC and LCMS. After completion of reaction, the mixture was diluted with water (100 mL) and extracted with EtOAc (2×100 mL), washed with water (4×100 mL) then dried over anhydrous sodium sulfate and the combined organic layer was concentrated under reduced pressure which was submitted to reverse phase HPLC process for its purification to afford [4-[5-(2-tert-butyl-4-pyridyl)-3-thienyl]-3-chloro-phenyl]-(4-hydroxy-1-piperidyl)methanone (130 mg—as freebase) as an off-white solid then it was treated with ethanolic HCl (1.25 M) to obtain its HCl salt (140 mg) as an off-white solid.

$^1$H NMR (400 MHz, Methanol-d4) δ (ppm): 8.61 (d, J=6.4 Hz, 1H), 8.41 (d, J=1.4 Hz, 1H), 8.25-8.14 (m, 3H), 7.68 (d, J=7.9 Hz, 1H), 7.62 (d, J=1.6 Hz, 1H), 7.46 (dd, J=7.9, 1.7 Hz, 1H), 4.18 (s, 1H), 3.93 (dt, J=8.4, 4.4 Hz, 1H), 3.67 (s, 1H), 3.40 (s, 2H), 1.97 (s, 1H), 1.86 (s, 1H), 1.58 (s, 9H), 1.50 (s, 2H). LCMS=455.1 (M+1).

Example 58. Preparation of Compound No. 58

Synthesis of 4-[5-(2-tert-butylpyridin-4-yl)thiophen-3-yl]-3-chloro-N-(pyridin-3-yl)benzamide

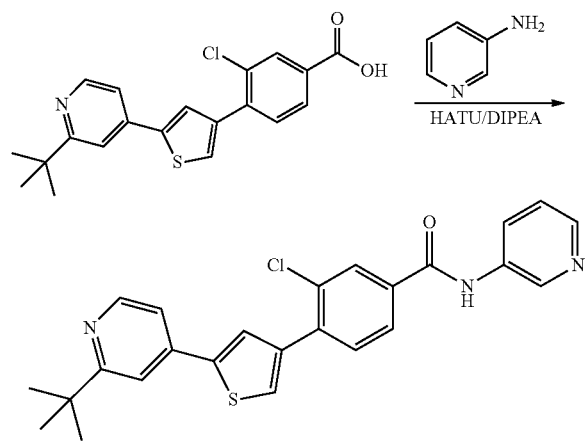

To a stirred solution of 4-[5-(2-tert-butyl-4-pyridyl)-3-thienyl]-3-chloro-benzoic acid (100 mg, 0.269 mmol) in DMF 5 mL, was added DIPEA (34.8 mg, 0.2695 mmol) followed by addition of HATU (204 mg, 0.539 mmol) and the mixture stirred at RT for 30 min. Then pyridine-3-amine (101 mg, 1.07 mmol) was added at the same temperature. The reaction mixture was stirred at RT overnight. The reaction was monitored by TLC and LCMS. After completion of reaction, the mixture was diluted with water (10 mL) and extracted with EtOAc (2×50 mL), the organic layer was washed with water (2×20 mL) and brine (20 mL) and dried over anhydrous sodium sulfate to obtain a crude product which was purified by reverse phase HPLC to obtain 4-[5-(2-tert-butyl-4-pyridyl)-3-thienyl]-3-chloro-N-(3-pyridyl)benzamide (34 mg) as the HCl salt.

$^1$H NMR (400 MHz, Methanol-d4) δ (ppm): 8.91 (d, J=5.2 Hz, 1H), 8.51 (d, J=5.2 Hz, 1H), 8.35 (d, J=5.8 Hz, 1H), 8.31 (d, J=5.2 Hz, 1H), 8.19 (s, 1H), 7.98 (d, J=5.2 Hz, 1H), 7.90 (s, 1H), 7.82 (s, 1H), 7.78 (d, J=5.2 Hz, 1H), 7.70 (s, 1H), 7.59 (d, J=7.9 Hz, 1H), 7.45 (d, J=7.9 Hz, 1H), 1.41 (s, 9H). LCMS=448.1 (M+1).

Example 59. Preparation of Compound No. 59

Synthesis of N-(1-{4-[5-(2-tert-butylpyridin-4-yl)thiophen-3-yl]-3-chlorobenzoyl}piperidin-4-yl)methanesulfonamide

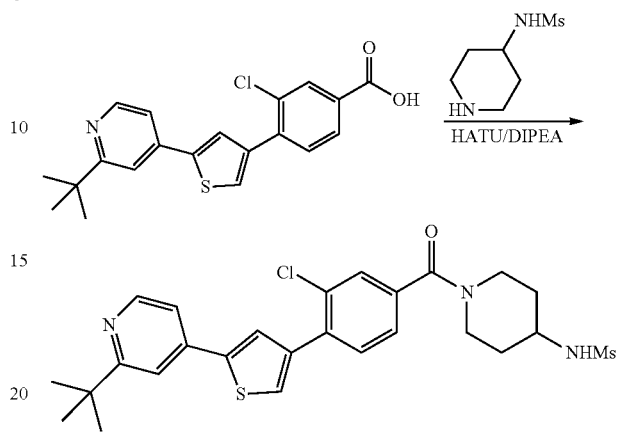

To a solution of 4-[5-(2-tert-butyl-4-pyridyl)-3-thienyl]-3-chloro-benzoic acid (200 mg, 0.5391 mmol) in DMF (7 mL), was added DIPEA (278.7 mg, 2.6954 mmol), followed by the addition of HATU (410 mg, 1.078 mmol). The reaction mixture was stirred for 30 min. N-(4-Piperidyl)methanesulfonamide (480.1 mg, 2.6954 mmol) was added and the reaction mixture was stirred overnight at RT. The reaction was monitored by TLC and LCMS. On completion, the reaction mixture was diluted with water (25 mL) and extracted with EtOAc (3×75 mL). The combined organic layer was washed with brine (50 mL) and water (50 mL), and dried over anhydrous sodium sulfate to obtain a crude product. This compound was purified by reverse phase HPLC to afford N-[1-[4-[5-(2-tert-butyl-4-pyridyl)-3-thienyl]-3-chloro-benzoyl]-4-piperidyl]methanesulfonamide (25 mg) as a white solid.

$^1$H NMR (400 MHz, DMSO-d6) δ (ppm): 8.54 (d, 1H), 8.08 (s, 1H), 7.96 (s, 1H), 7.68 (dd, 1H), 7.67 (s, 1H), 7.58 (d, 1H), 7.52-7.39 (d, 1H), 7.18 (d, 1H), 4.28 (s, 1H), 3.03 (s, 1H), 3.18 (s, 1H), 3.33 (s, 1H), 3.56 (s, 1H), 2.95 (s, 3H), 1.85 (s, 2H), 1.36 (s, 1H), 1.33 (s, 9H), 1.23 (s, 1H). LCMS=532 (M+1).

Example 60. Preparation of Compound No. 60

Synthesis of 4-[5-(2-tert-butyl pyridin-4-yl)thiophen-3-yl]-3-chloro-N-methyl-N-(1,3-oxazol-2-yl)benzamide

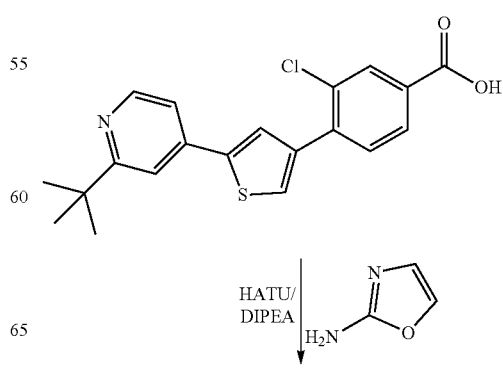

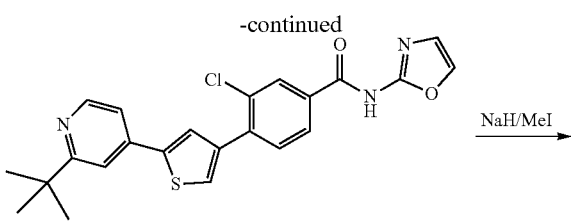

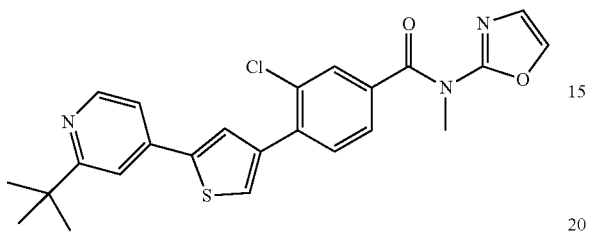

Step-1: Synthesis of 4-[5-(2-tert-butyl-4-pyridyl)-3-thienyl]-3-chloro-N-oxazol-2-yl-benzamide To a stirred solution of 4-[5-(2-tert-butyl-4-pyridyl)-3-thienyl]-3-chloro-benzoic acid (200 mg, 0.538 mmol) in DMF (10 mL) was added DIPEA (0.4 mL, 2.152 mmol) followed by addition of HATU (408 mg, 1.076 mmol), and the mixture stirred at RT for 30 min. Then oxazol-2-amine (171.1 mg, 2.044 mmol) was added at the same temperature. The reaction mixture was stirred at RT overnight. The reaction was monitored by TLC and LCMS. After completion of reaction, the mixture was diluted with water (50 mL) and extracted with EtOAc (2×50 mL). The organic layer was washed with water (2×20 mL) and brine (20 mL) and dried over anhydrous sodium sulfate to obtain a crude product, which was purified by reverse phase HPLC to obtain 4-[5-(2-tert-butyl-4-pyridyl)-3-thienyl]-3-chloro-N-oxazol-2-yl-benzamide (100 mg) freebase as a solid.

Step-2: Synthesis of 4-[5-(2-tert-butyl-4-pyridyl)-3-thienyl]-3-chloro-N-methyl-N-oxazol-2-yl-benzamide To a stirred solution of 4-[5-(2-tert-butyl-4-pyridyl)-3-thienyl]-3-chloro-N-oxazol-2-yl-benzamide (200 mg, 0.456 mmol) in DMF (10 mL), was added sodium hydride (35 mg, 0.913 mmol) at 0° C., and stirred for 30 min. Methyl iodide (96 mg, 0.6849 mmol) was added slowly dropwise and the mixture stirred for 3 h. The reaction was monitored by TLC and LCMS. After completion of reaction, the mixture was diluted with water (50 mL) and extracted with EtOAc (2×50 mL). The organic layer was washed with water (2×20 mL) and brine (20 mL) and dried over anhydrous sodium sulfate to obtain a crude product, which was purified by reverse phase HPLC to obtain 4-[5-(2-tert-butyl-4-pyridyl)-3-thienyl]-3-chloro-N-methyl-N-oxazol-2-yl-benzamide (20 mg) freebase as a solid.

$^1$H NMR (400 MHz, DMSO-d6) δ (ppm): 8.58 (d, J=5.2 Hz, 1H), 8.30 (s, 1H), 8.18 (s, 1H), 7.98 (s, 1H), 7.95 (d, J=5.2 Hz, 1H), 7.80 (s, 1H), 7.58 (d, J=7.9, 1H), 7.48 (s, 1H), 7.38 (d, J=5.3, 1H), 7.06 (s, 1H), 3.38 (s, 3H), 1.40 (s, 9H). LCMS=452.0 (M+1).

Example 61. Preparation of Compound No. 61

Synthesis of 4-[5-(2-tert-butylpyridin-4-yl)thiophen-3-yl]-3-chloro-N-[2-(morpholin-4-yl)-2-oxoethyl]benzamide

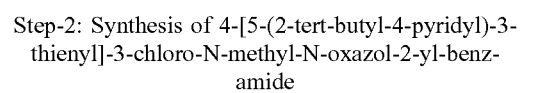

To a stirred solution of 4-[5-(2-tert-butyl-4-pyridyl)-3-thienyl]-3-chloro-benzoic acid (100 mg, 0.269 mmol) in DMF 5 mL, was added DIPEA (34.8 mg, 0.2695 mmol) followed by addition of HATU (204 mg, 0.539 mmol) and the mixture stirred at RT for 30 min. Then 2-amino-1-morpholino-ethanone (101 mg, 1.07 mmol) was added at the same temperature. The reaction mixture was stirred at RT overnight. The reaction was monitored by TLC and LCMS. After completion of reaction, the mixture was diluted with water (10 mL) and extracted with EtOAc (2×50 mL), the organic layer was washed with water (2×20 mL) and brine (20 mL) and dried over anhydrous sodium sulfate to obtain a crude product which was purified by reverse phase HPLC to obtain 4-[5-(2-tert-butyl-4-pyridyl)-3-thienyl]-3-chloro-N-(3-pyridyl) benzamide (36 mg) as the HCl salt.

$^1$H NMR (400 MHz, DMSO-d6) δ (ppm): 8.45 (d, J=5.2 Hz, 1H), 8.06 (d, J=5.2 Hz, 1H), 7.96 (s, 1H), 7.90 (d, J=5.2 Hz, 1H), 7.80 (s, 1H), 7.68 (m, 2H), 7.51 (d, J=5.2 Hz, 1H), 4.25 (s, 2H), 3.65 (m, 4H), 3.58 (s, 4H), 1.41 (s, 9H). LCMS=498.1 (M+1).

Example 62. Preparation of Compound No. 62

Synthesis of 4-[5-(2-tert-butylpyridin-4-yl)thiophen-3-yl]-3-chloro-N-({8-methyl-8-azabicyclo[3.2.1]octan-3-yl}benzamide

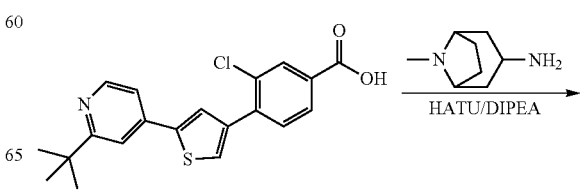

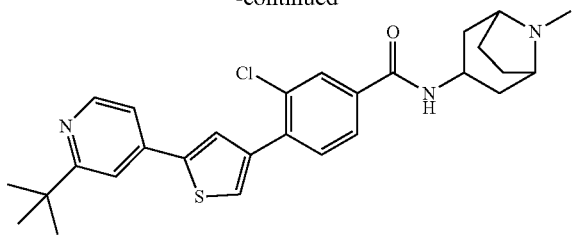

To a stirred solution of 4-[5-(2-tert-butyl-4-pyridyl)-3-thienyl]-3-chloro-benzoic acid (200 mg, 0.537 mmol) in DMF (5 mL), was added DIPEA (0.37 mL, 2.15 mmol) followed by addition of HATU (327 mg, 0.860 mmol) and the mixture stirred at RT for 30 min. Then 8-methyl-8-azabicyclo[3.2.1]octan-3-amine (188 mg, 1.34 mmol) was added at the same temperature. The reaction mixture was stirred at RT overnight. The reaction was monitored by TLC and LCMS. After completion of reaction, the mixture was diluted with water (10 mL) and extracted with EtOAc (2×100 mL). The organic layer was washed with water (2×50 mL) and brine (50 mL) and dried over anhydrous sodium sulfate to obtain a crude product (820 mg). 80 mg of the crude was purified by reverse phase HPLC to obtain 4-[5-(2-tert-butyl-4-pyridyl)-3-thienyl]-3-chloro-N-(8-methyl-8-azabicyclo[3.2.1]octan-3-yl)benzamide (20 mg) freebase as a solid.

$^1$H NMR (400 MHz, DMSO-d6) δ (ppm): 8.54 (d, J=5.1 Hz, 1H), 8.20 (s, 1H), 8.07 (s, 1H), 7.97 (d, J=10.2 Hz, 1H), 7.82 (d, J=7.9 Hz, 1H), 7.77-7.65 (m, 2H), 7.53-7.47 (m, 1H), 2.31 (m, 4H), 2.11 (d, J=14.0 Hz, 3H), 2.03 (s, 3H), 1.92 (m, 2H), 1.36 (s, 9H). LCMS=494 (M+1).

Example 63. Preparation of Compound No. 63

Synthesis of ethyl N-(1-{4-[5-(2-tert-butylpyridin-4-yl)thiophen-3-yl]-3-chlorobenzoyl}piperidin-4-yl)carbamate 4-[5-(2-tert-Butyl-4-pyridyl)-3-thienyl]-3-chloro-benzoic acid (100 mg, 0.26 mmol) was taken in DMF (5.0 mL), followed by addition of DIPEA (0.2 mL, 1.07 mmol), HATU (204 mg, 0.053 mmol), under nitrogen atmosphere. The reaction mixture was stirred at RT for 0.5 h, followed by addition of ethyl N-(4-piperidyl)carbamate (184 mg, 0.10 mmol). The reaction mixture was stirred at RT for 16 h. After completion of reaction, water (150 mL) was added and the mixture extracted with EtOAc (2×50 mL). The combined organic layer was washed with brine (50 mL), dried over anhydrous sodium sulfate and concentrated under reduced pressure to obtain the crude product which was purified by reverse phase HPLC to obtain ethyl N-[1-[4-[5-(2-tert-butyl-4-pyridyl)-3-thienyl]-3-chloro-benzoyl]-4-piperidyl]carbamate (30 mg) as a white solid.

$^1$H NMR (400 MHz, DMSO-d6) δ (ppm): 8.54 (d, J=5.1 Hz, 1H), 8.08 (d, J=1.4 Hz, 1H), 7.68 (dd, J=4.6, 3.2 Hz, 2H), 7.56 (d, J=1.6 Hz, 1H), 7.49 (dd, J=5.2, 1.7 Hz, 1H), 7.41 (dd, J=7.9, 1.6 Hz, 1H), 7.19 (d, J=7.9 Hz, 1H), 4.30 (s, 1H), 3.98 (q, J=7.1 Hz, 2H), 3.58 (s, 2H), 3.18 (s, 2H), 3.00 (s, 2H), 1.83 (s, 18H), 1.76 (s, 18H), 1.36 (s, 9H), 1.16 (t, J=7.1 Hz, 3H). LCMS: −(M+1) 525.9.

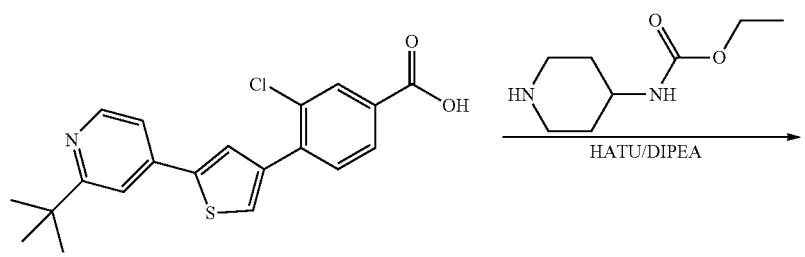

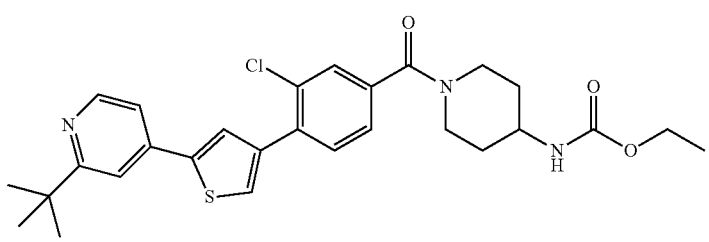

Example 64. Preparation of Compound Nos. 64, 64a, and 64b

Synthesis of tert-butyl N-[1-(3-chloro-4-{5-[2-(morpholin-4-yl)pyridin-4-yl]thiophen-3-yl}benzoyl)piperidin-3-yl]carbamate

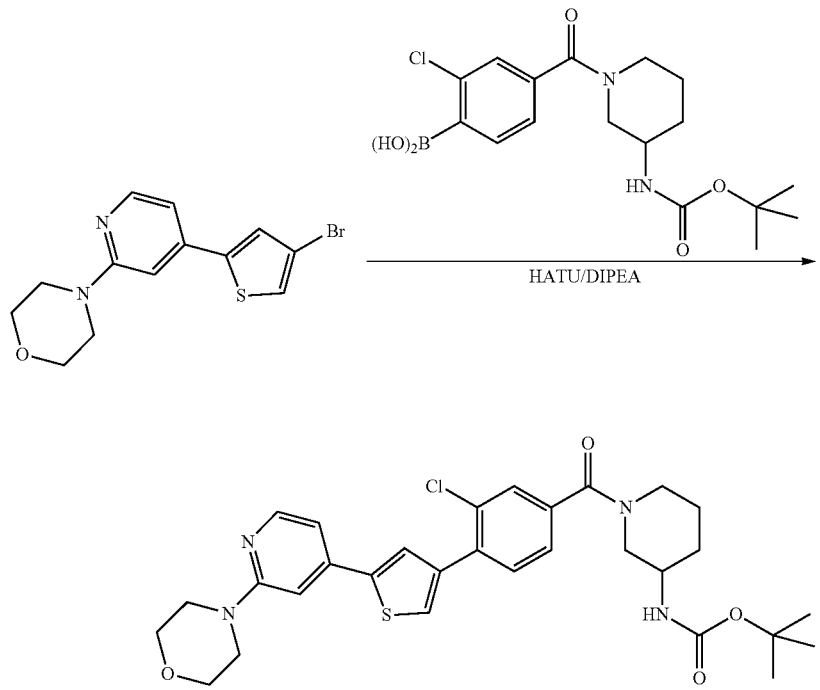

4-[4-(4-Bromo-2-thienyl)-2-pyridyl]morpholine (500 mg, 1.53 mmol), [4-[3-(tert-butoxycarbonylamino)piperidine-1-carbonyl]-2-chloro-phenyl]boronic acid (705 mg, 1.84 mmol), sodium carbonate (407 mg, 3.82 mmol), DMF (10 mL), and water (3 mL) were charged in a 25 mL glass bottle and purged with nitrogen gas for 5 min. After adding tetrakis (176 mg 0.153 mmol), the reaction mixture was heated at 100° C. for 16 h. The reaction was monitored by TLC and LCMS. After completion of reaction, the mixture was diluted with water (50 mL) and extracted with EtOAc (100 mL). The organic layer was washed with brine (50 mL) and water (50 mL) and dried over anhydrous sodium sulfate to obtain a crude product, which was purified by reverse phase chromatography to afford tert-butyl N-[1-[3-chloro-4-[5-(2-morpholino-4-pyridyl)-3-thienyl]benzoyl]-3-piperidyl]carbamate (56 mg) freebase as a white solid. The enantiomers can be prepared from chiral HPLC resolution of the racemate.

$^1$H NMR (400 MHz, DMSO-d6) δ (ppm): 8.15 (d, J=5.2 Hz, 1H), 8.03 (s, 1H), 7.91 (s, 1H), 7.64 (d, J=8.3 Hz, 1H), 7.44 (d, J=7.7 Hz, 1H), 7.10 (s, 1H), 7.03 (s, 1H), 7.00-6.94 (m, 1H), 3.71 (t, J=4.8 Hz, 4H), 3.52 (t, J=4.8 Hz, 4H), 3.05 (s, 2H), 2.78 (s, 2H), 1.84 (s, 1H), 1.32 (s, 9H), 1.21 (s, 2H), 1.12 (s, 2H). LCMS: −(M+1) 583.0.

Example 65. Preparation of Compound Nos. 65, 65a, and 65b

Synthesis of 1-(3-chloro-4-(5-[2-(morpholin-4-yl)pyridin-4-yl]thiophen-3-yl)benzoyl)piperidin-3-amine

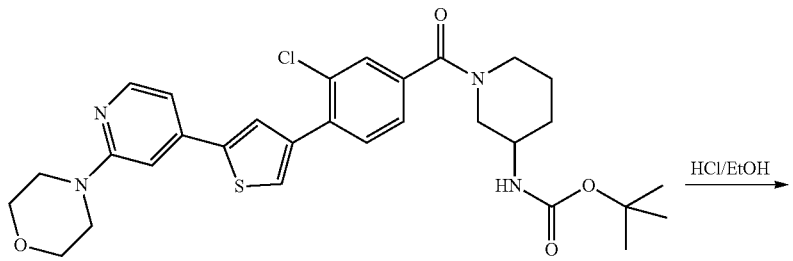

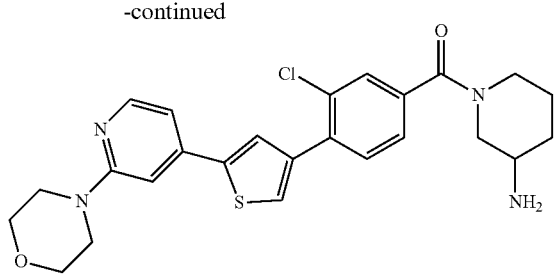

tert-Butyl-N-[1-[3-chloro-4-[5-(2-morpholino-4-pyridyl)-3-thienyl]benzoyl]-3-piperidyl]carbamate (60 mg, 0.10 mmol) was taken in EtOH (4.0 mL) at 0° C., followed by dropwise addition of a 1.25M HCl in EtOH under nitrogen atmosphere. The mixture was stirred at RT for 16 h. Completion of reaction was monitored by TLC and LCMS. After completion of reaction, the mixture was concentrated to get (3-amino-1-piperidyl)-[3-chloro-4-[5-(2-morpholino-4-pyridyl)-3-thienyl]phenyl]methanone as the HCl salt, a light yellow solid. The enantiomers can be prepared from chiral HPLC resolution of the racemate.

$^1$H NMR (400 MHz, DMSO-d6) δ (ppm): 8.40 (s, 1H), 8.33 (s, 1H), 8.27 (s, 1H), 8.15 (s, 1H), 8.06 (s, 1H), 7.68 (d, J=8.6 Hz, 1H), 7.52 (s, 1H), 7.29-7.23 (m, 1H), 4.19 (s, 1H), 3.78 (s, 8H), 3.35 (s, 1H), 3.24 (s, 2H), 3.15 (s, 1H), 2.03 (s, 1H), 1.75 (s, 2H), 1.53 (s, 1H). LCMS: –(M+1) 483.1.

Example 66. Preparation of Compound Nos. 66, 66a, and 66b

Synthesis of 1-{4-[5-(2-tert-butylpyridin-4-yl)-2-methylthiophen-3-yl]-3-chlorobenzoyl}piperidin-3-amine

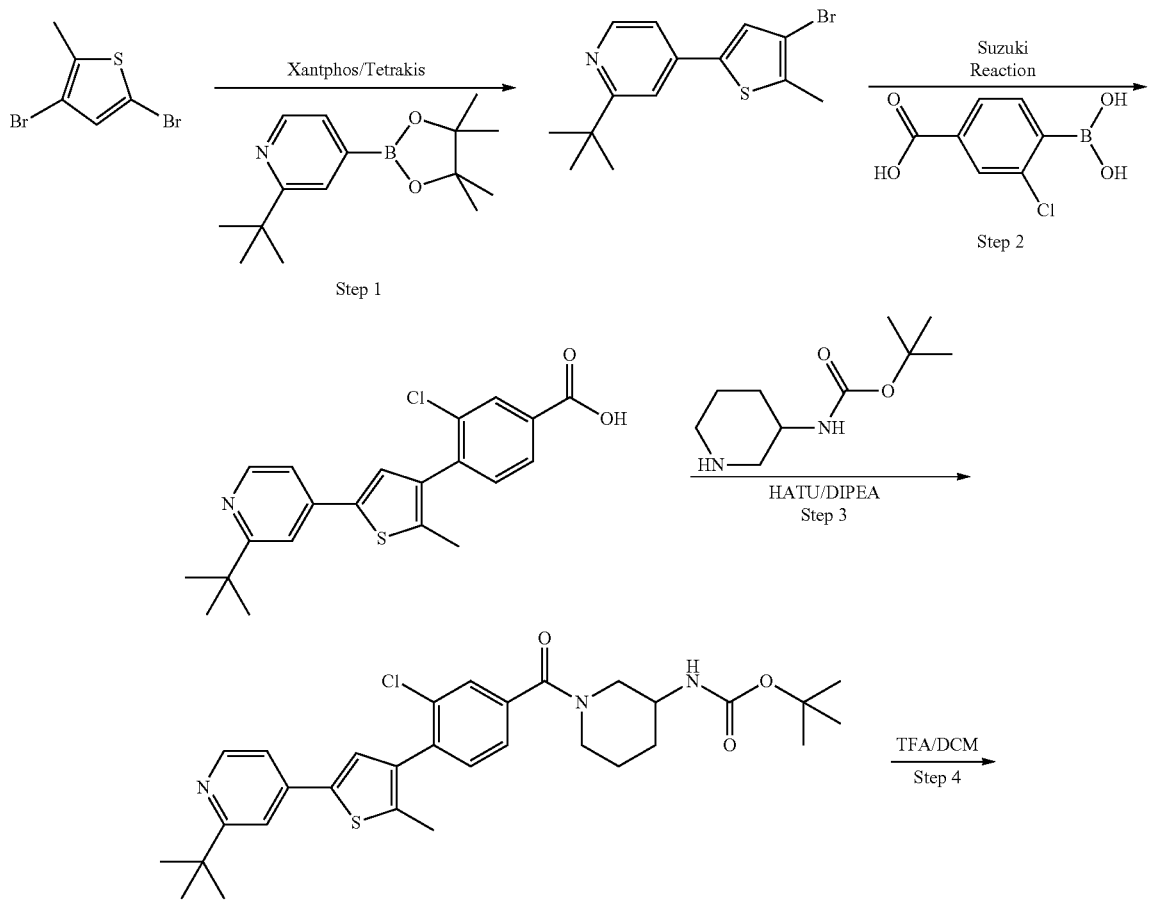

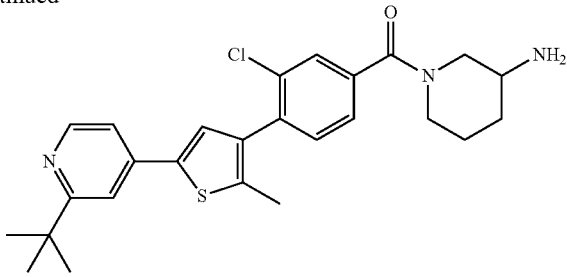

Step-1: Synthesis of 4-(4-bromo-5-methyl-2-thienyl)-2-tert-butyl-pyridine

In a 100 mL glass bottle 3,5-dibromo-2-methyl-thiophene (500 mg, 1.95 mmol, 1 eq.) along with (2-tert-butyl-4-pyridyl)boronic acid (350 mg, 1 eq.) and potassium phosphate (1.03 g, 2.5 eq.) were charged in 15 mL of THF. The mixture was purged with nitrogen for 15 min then Xantphos (90 mg, 0.08 eq.) and tetrakis (180 mg, 0.08 eq.) were added, and the mixture repurged for 5 min and the mixture stirred at 60° C. overnight. Progress of the reaction was monitored by TLC & LCMS. When the reaction was completed, the mixture was cooled to RT, water (100 mL) was added and the mixture extracted with EtOAc (3×100 mL). The combined organic layer was washed with brine (50 mL) then dried over anhydrous sodium sulfate, concentrated under reduced pressure to give a viscous compound which was purified by silica gel (60-120) column chromatography using EtOAc/Hexane (0-20%) as eluent system to afford 4-(4-bromo-5-methyl-2-thienyl)-2-tert-butyl-pyridine as a colorless semi-solid (500 mg) in pure form.

Step-2: Synthesis of 4-[5-(2-tert-butyl-4-pyridyl)-2-methyl-3-thienyl]-3-chloro-benzoic acid In a 25 mL glass bottle, 4-(4-bromo-5-methyl-2-thienyl)-2-tert-butyl-pyridine (350 mg, 1.13 mmol, 1 eq.) and 4-borono-3-chloro-benzoic acid (292 mg, 1.46 mmol, 1.3 eq.), were charged in DMF (7 mL) followed by addition of sodium carbonate (298 mg, 2.5 equiv dissolved in water (1.5 mL) and the reaction mixture was purged with nitrogen gas for 5 min. After adding tetrakis (130 mg, 0.113 mmol, 0.1 eq.) the mixture was repurged for 2 min and was stirred at 90° C. overnight. The progress of the reaction was monitored by TLC and LCMS. After completion of reaction, the mixture was allowed to come to RT and diluted with water (50 mL) and extracted with EtOAc:MeOH (90:10), (3×100 mL). The combined organic layer was dried over anhydrous sodium sulfate and concentrated under reduced pressure to afford a semi-solid compound, 4-[5-(2-tert-butyl-4-pyridyl)-2-methyl-3-thienyl]-3-chloro-benzoic acid (350 mg) which was used as such for the next step of synthesis.

Step-3: Synthesis of tert-butyl N-[1-[4-[5-(2-tert-butyl-4-pyridyl)-2-methyl-3-thienyl]-3-chloro-benzoyl]-3-piperidyl]carbamate In a 100 mL flask, 4-[5-(2-tert-butyl-4-pyridyl)-2-methyl-3-thienyl]-3-chloro-benzoic acid 180 mg, 0.46 mmol, 1 eq.) was dissolved in DMF (8 mL), followed by addition of DIPEA (0.34 mL, 1.87 mmol, 4 eq.) and HATU (355 mg, 0.92 mmol, 2 eq.), and the resulting mixture was stirred for 10 min at RT and tert-butyl N-(3-piperidyl)carbamate (373 mg, 1.87 mmol, 4 eq.) were added and the mixture stirred at RT under nitrogen atmosphere overnight. The progress of the reaction was monitored by TLC and LCMS. After completion of reaction, the mixture was diluted with water (100 mL) and extracted with EtOAc (2×100 mL), washed with water (4×100 mL) then dried over anhydrous sodium sulfate and the combined organic layer was concentrated under reduced pressure to give a viscous compound, to afford tert-butyl N-[1-[4-[5-(2-tert-butyl-4-pyridyl)-2-methyl-3-thienyl]-3-chloro-benzoyl]-3-piperidyl]carbamate (180 mg) as the freebase.

Step-4: Synthesis of (3-amino-1-piperidyl)-[4-[5-(2-tert-butyl-4-pyridyl)-2-methyl-3-thienyl]-3-chloro-phenyl]methanone In a 100 mL flask, tert-butyl N-[1-[4-[5-(2-tert-butyl-4-pyridyl)-2-methyl-3-thienyl]-3-chloro-benzoyl]-3-piperidyl]carbamate (150 mg, 0.31 mmol, 1 eq.) was charged in DCM (10 mL), the reaction mixture was maintained at 0° C. and trifluoroacetic acid (4 mL) was added dropwise and the mixture stirred at RT for 2.5 h. Progress of reaction was monitored by TLC/LCMS. After completion of reaction, the DCM was evaporated under reduced pressure, and the residue basified with saturated aqueous sodium bicarbonate solution and extracted with EtOAc (2×100 mL). The organic layer was washed with brine (100 mL) and dried over anhydrous sodium sulfate. The solution was concentrated under reduced pressure and submitted to reverse phase HPLC process for its purification to afford (3-amino-1-piperidyl)-[4-[5-(2-tert-butyl-4-pyridyl)-2-methyl-3-thienyl]-3-chloro-phenyl]methanone as a greyish solid freebase (56 mg), which was treated with ethanolic HCl to give its respective HCl salt as a yellow-greyish solid (62 mg). The enantiomers can be prepared from chiral HPLC resolution of the racemate.

$^1$H NMR (400 MHz, Methanol-d4) δ (ppm): 8.55 (d, J=6.3 Hz, 1H), 8.08 (d, J=6.4 Hz, 3H), 7.71 (s, 1H), 7.53 (s, 2H), 4.44 (m, 1H), 4.10 (m, 1H), 3.62 (d, J=7.2 Hz, 1H), 3.41 (m, 2H), 2.47 (s, 3H), 2.20 (m, 1H), 1.73 (m, 3H), 1.55 (s, 9H). LCMS: –468.2 (M+1).

Example 67. Preparation of Compound No. 67

Synthesis of 4-[5-(2-tert-butylpyridin-4-yl)-2-methylthiophen-3-yl]-3-chloro-N-phenyl benzamide

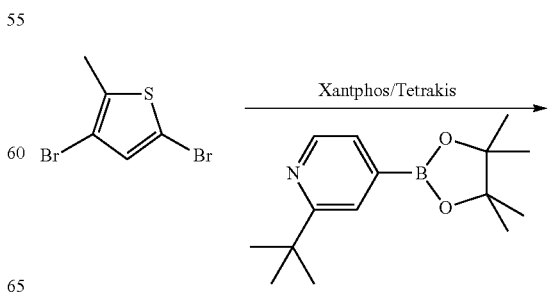

Step 1

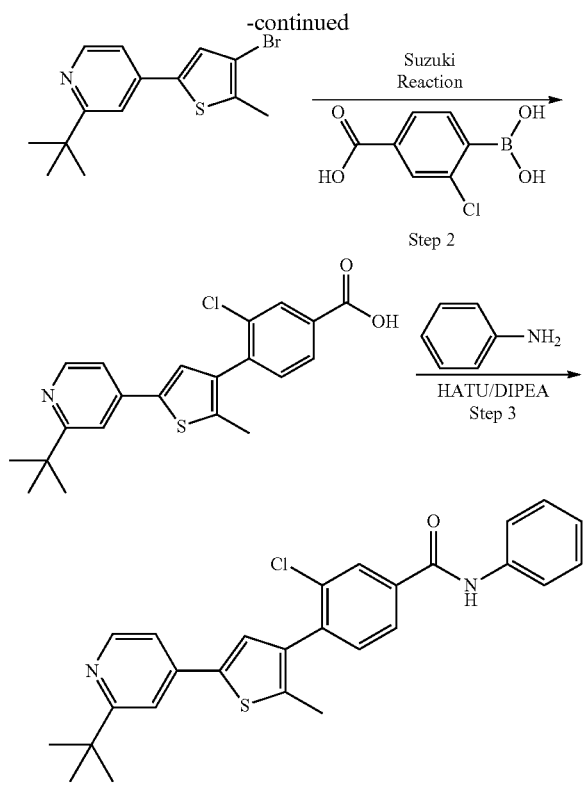

Step-1: Synthesis of 4-(4-bromo-5-methyl-2-thienyl)-2-tert-butyl-pyridine

In a 100 mL glass bottle, 3,5-dibromo-2-methyl-thiophene (500 mg, 1.95 mmol, 1 eq.) along with (2-tert-butyl-4-pyridyl)boronic acid (350 mg, 1 eq.) and potassium phosphate (1.03 g, 2.5 eq.) were charged in 15 mL of THF. The mixture was purged with nitrogen for 15 min then Xantphos (90 mg, 0.08 eq.) and tetrakis (180 mg, 0.08 eq.) were added, and the mixture repurged for 5 min and the mixture stirred at 60° C. overnight. Progress of the reaction was monitored by TLC & LCMS. When the reaction was completed, the mixture was cooled to RT, water (100 mL) was added and the mixture extracted with EtOAc (3×100 mL). The combined organic layer was washed with brine (50 mL) then dried over anhydrous sodium sulfate, concentrated under reduced pressure to give a viscous compound which was purified by silica gel (60-120) column chromatography using EtOAc/Hexane (0-20%) as eluent system to afford 4-(4-bromo-5-methyl-2-thienyl)-2-tert-butyl-pyridine as a colorless semi-solid (500 mg) in pure form.

Step-2: Synthesis of 4-[5-(2-tert-butyl-4-pyridyl)-2-methyl-3-thienyl]-3-chloro-benzoic acid In a 25 mL glass bottle, 4-(4-bromo-5-methyl-2-thienyl)-2-tert-butyl-pyridine (350 mg, 1.13 mmol, 1 eq.) and 4-borono-3-chloro-benzoic acid (292 mg, 1.46 mmol, 1.3 eq.), were charged in DMF (7 mL) followed by addition of sodium carbonate (298 mg, 2.5 equiv dissolved in water (1.5 mL) and the reaction mixture was purged with nitrogen gas for 5 min. After adding tetrakis (130 mg, 0.113 mmol, 0.1 eq.) the mixture was repurged for 2 min and was stirred at 90° C. overnight. The progress of the reaction was monitored by TLC and LCMS. After completion of reaction, the mixture was allowed to come to RT and diluted with water (50 mL) and extracted with EtOAc:MeOH (90:10), (3×100 mL). The combined organic layer was dried over anhydrous sodium sulfate and concentrated under reduced pressure to afford a semi-solid compound, 4-[5-(2-tert-butyl-4-pyridyl)-2-methyl-3-thienyl]-3-chloro-benzoic acid (350 mg) which was used as such for the next step of synthesis.

Step-3: Synthesis of 4-[5-(2-tert-butyl-4-pyridyl)-2-methyl-3-thienyl]-3-chloro-N-phenyl-benzamide In a 100 mL flask, 4-[5-(2-tert-butyl-4-pyridyl)-2-methyl-3-thienyl]-3-chloro-benzoic acid (180 mg, 0.46 mmol, 1 eq.) was dissolved in DMF (8 mL), followed by addition of DIPEA (0.34 mL, 1.87 mmol, 4 eq.) and HATU (355 mg, 0.92 mmol, 2 eq.), and the resulting mixture was stirred for 10 min at RT and aniline (174 mg, 1.87 mmol, 4 eq.) were added and the mixture stirred at RT under nitrogen atmosphere overnight. The progress of the reaction was monitored by TLC and LCMS. After completion of reaction, the mixture was diluted with water (100 mL) and extracted with EtOAc (2×100 mL), washed with water (4×100 mL) then dried over anhydrous sodium sulfate and the combined organic layer was concentrated under reduced pressure to give a viscous compound, which was purified by reverse phase HPLC process to afford 4-[5-(2-tert-butyl-4-pyridyl)-2-methyl-3-thienyl]-3-chloro-N-phenyl-benzamide (56 mg) as the freebase as an off-white solid which was treated with ethanolic HCl to give its respective HCl salt as an off-white solid (61 mg).

$^1$H NMR (400 MHz, Methanol-d4) δ (ppm): 8.54 (d, J=6.4 Hz, 1H), 8.17 (d, J=1.8 Hz, 1H), 8.14-8.10 (m, 2H), 8.10-8.05 (m, 1H), 8.03-7.96 (m, 1H), 7.71 (d, J=8.0 Hz, 2H), 7.57 (d, J=7.9 Hz, 1H), 7.39 (t, J=7.8 Hz, 2H), 7.18 (t, J=7.5 Hz, 1H), 2.48 (s, 3H), 1.55 (s, 9H). LCMS: −(M+1) 461.2.

Example 68. Preparation of Compound Nos. 68a, and 68b

Synthesis of (3S)-1-{4-[4-(2-tert-butylpyridin-4-yl) thiophen-2-yl]-3-chlorobenzoyl}pyrrolidin-3-ol

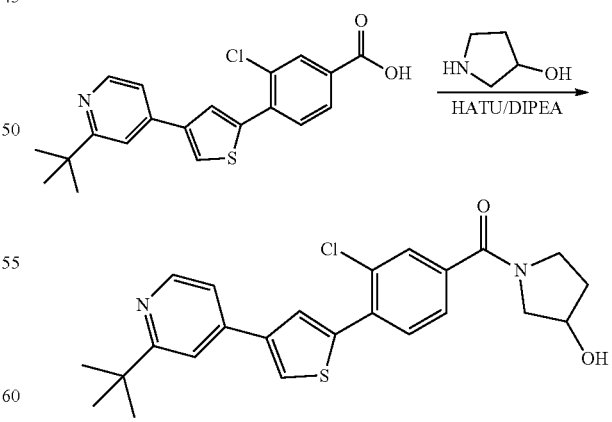

4-[4-(2-tert-Butyl-4-pyridyl)-2-thienyl]-3-chloro-benzoic acid (0.5 g, 1.34 mmol) was taken in DMF (10 mL), followed by addition of DIPEA (0.95 mL, 5.37 mmol), and HATU (1.08 g, 2.68 mmol), under nitrogen atmosphere. The reaction mixture was stirred at RT for 0.5 h, followed by addition of (3S)-pyrrolidin-3-ol (0.467 g, 5.37 mmol). The mixture was stirred at RT for 16 h. After completion of reaction, water (100 mL) was added and the mixture extracted with EtOAc (3×50 mL). The combined organic layer was washed with brine (50 mL), dried over anhydrous sodium sulfate and concentrated under reduced pressure to obtain a residue, which was purified by reverse phase HPLC to obtain Compound 68a [4-[4-(2-tert-butyl-4-pyridyl)-2-thienyl]-3-chloro-phenyl]-[(3S)-3-hydroxypyrrolidin-1-yl]methanone (230 mg) as the HCl salt. Compound 68b, the (3R)-enantiomer, was prepared by using the (3S)-pyrrolidin-3-ol reagent.

$^1$H NMR (400 MHz, Methanol-d4) δ (ppm): 8.62 (d, J=5.7 Hz, 2H), 8.26 (s, 1H), 8.20-8.10 (m, 2H), 7.85-7.73 (m, 2H), 7.59 (t, J=6.8 Hz, 1H), 4.51 (s, 1H), 4.41 (s, 1H), 3.82-3.66 (m, 2H), 3.65-3.51 (m, 1H), 3.42-3.32 (m, 1H), 2.19 (s, 1H), 2.05 (s, 1H), 1.57 (s, 9H). LCMS=441.2 (M+1).

Example 69. Preparation of Compound Nos. 69, 69a, and 69b

Synthesis of tert-butyl N-[(3R)-1-{4-[4-(2-tert-butylpyridin-4-yl)thiophen-2-yl]-3-chlorobenzoyl}piperidin-3-yl]carbamate Step-1: Synthesis of 4-(4-bromo-2-thienyl)-3-chloro-benzoic acid 2,4-Dibromothiophene (10.0 g, 40.84 mmol), 4-borono-3-chloro-benzoic acid (10 mg, 50.2 mmol), sodium carbonate (10.9 g, 104.1 mmol) in water (30 mL), and DMF (100 mL) were charged in a 200 mL glass bottle and purged with nitrogen gas for 10 min. After adding tetrakis (4.8 g, 4.16 mmol), the reaction mixture was heated at 100° C. for 16 h. The reaction was monitored by TLC and LCMS. After completion of reaction, the mixture was diluted with water (50 mL), filtered and dried with washings of ether to afford a white solid 4-(4-bromo-2-thienyl)-3-chloro-benzoic acid (5.0 g) as the freebase.

Step-2: Synthesis of tert-butyl N-[(3R)-1-[4-(4-bromo-2-thienyl)-3-chloro-benzoyl]-3-piperidyl]carbamate 4-(4-Bromo-2-thienyl)-3-chloro-benzoic acid (0.5 g, 1.58 mmol) was taken in DMF (10 mL), followed by addition of DIPEA (3.0 mL, 15.8 mmol), and HATU (2.4 g, 6.3 mmol), under nitrogen atmosphere. The reaction mixture was stirred at RT for 0.5 h, followed by addition of tert-butyl N-[(3R)-3-piperidyl]carbamate (0.63 g, 3.1 mmol). The reaction

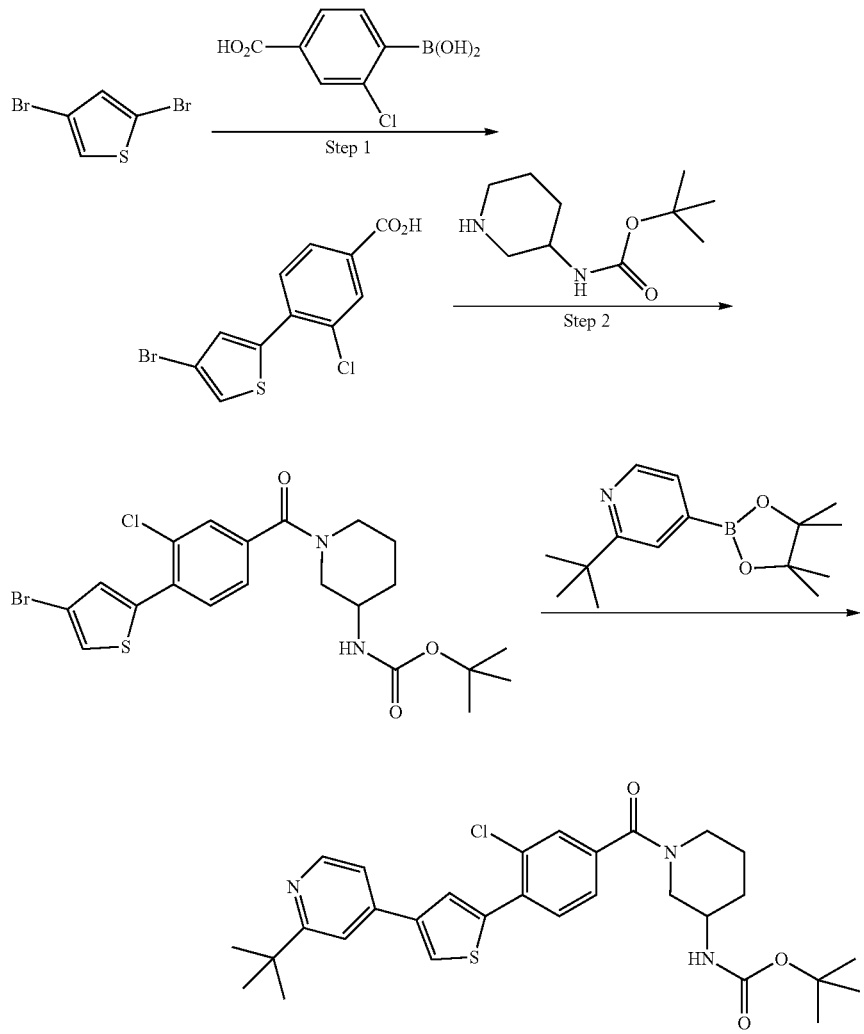

mixture was stirred at RT for 16 h. After completion, water (100 mL) was added and the mixture extracted with EtOAc (3×50 mL). The combined organic layer was washed with brine (50 mL), dried over anhydrous sodium sulfate and concentrated under reduced pressure to obtain crude tert-butyl N-[(3R)-1-[4-(4-bromo-2-thienyl)-3-chloro-benzoyl]-3-piperidyl]carbamate (400 mg) as the freebase.

Step-3: Synthesis of tert-butyl N-[(3R)-1-[4-[4-(2-tert-butyl-4-pyridyl)-2-thienyl]-3-chloro-benzoyl]-3-piperidyl] carbamate tert-Butyl N-[(3R)-1-[4-(4-bromo-2-thienyl)-3-chloro-benzoyl]-3-piperidyl]carbamate (300 mg, 0.70 mmol), 2-tert-butyl-4-(4,4,5,5-tetramethyl-1,3,2-dioxaborolan-2-yl) pyridine (200 mg, 0.77 mmol), sodium carbonate (183 mg, 1.75 mmol) in water (2.0 mL), and DMF (8.0 mL) were charged in a 25 mL glass bottle and purged with nitrogen gas for 10 min. After adding tetrakis (80 mg, 0.07 mmol), the reaction mixture was heated at 100° C. for 16 h. The reaction was monitored by TLC and LCMS. After completion, water (100 mL) was added and the mixture extracted with EtOAc (3×50 mL). The combined organic layer was washed with brine (50 mL), dried over anhydrous sodium sulfate and concentrated under reduced pressure to obtain a residue that was purified by reverse phase HPLC to obtain Compound 69a [tert-butyl N-[(3R)-1-[4-[4-(2-tert-butyl-4-pyridyl)-2-thienyl]-3-chloro-benzoyl]-3-piperidyl]carbamate] as the freebase, an off-white solid. Compound 69b, the (S)-enantiomer, can be prepared from using the (S)-carbamate reagent in Step-2.

$^1$H NMR (400 MHz, DMSO-d6) δ (ppm): 8.54 (d, J=5.1 Hz, 1H), 8.37 (d, J=1.5 Hz, 1H), 8.07 (s, 1H), 7.84 (d, J=8.0 Hz, 1H), 7.76 (s, 1H), 7.64 (s, 1H), 7.57 (dd, J=5.2, 1.7 Hz, 1H), 7.46 (d, J=7.9 Hz, 1H), 7.00 (s, 1H), 4.22 (s, 1H), 3.42 (s, 2H), 3.14 (s, 2H), 2.81 (s, 1H), 1.96 (s, 1H), 1.87 (s, 1H), 1.68 (s, 17H), 1.23 (s, 9H). LCMS: −(M+1) 554.0.

Example 70. Preparation of Compound Nos. 70, 70a, and 70b

Synthesis of tert-butyl N-(1-{4-[5-(2-tert-butylpyridin-4-yl)thiophen-3-yl]-3-chlorobenzoyl}piperidin-3-yl)-N-methylcarbamate

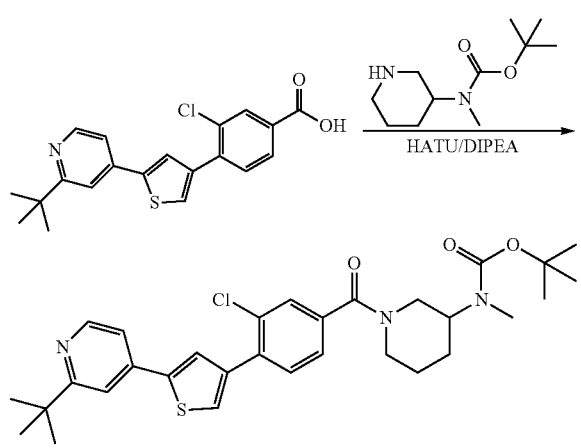

To a stirred solution of 4-[5-(2-tert-butyl-4-pyridyl)-3-thienyl]-3-chloro-benzoic acid (500 mg, 1.347 mmol) in DMF (10 mL), was added DIPEA (0.92 mL, 5.390 mmol) followed by addition of HATU (1.0 g, 2.69 mmol), and the mixture stirred at RT for 30 min. Then tert-butyl N-methyl-N-(3-piperidyl) carbamate (1.1 g, 5.39 mmol) was added at the same temperature. The reaction mixture was stirred at RT overnight. The reaction was monitored by TLC and LCMS. After completion of reaction, the mixture was diluted with water (10 mL) and extracted with EtOAc (2×50 mL). The organic layer was washed with water (2×20 mL) and brine (20 mL), and dried over anhydrous sodium sulfate to obtain a crude product, which was purified by reverse phase HPLC to obtain tert-butyl N-[1-[4-[5-(2-tert-butyl-4-pyridyl)-3-thienyl]-3-chloro-benzoyl]-3-piperidyl]-N-methyl-carbamate (74 mg) freebase as a solid. The enantiomers can be prepared from chiral HPLC resolution of the racemate.

$^1$H NMR (400 MHz, Methanol-d4) δ (ppm): 8.48 (d, J=5.2 Hz, 1H), 7.88 (s, 1H), 7.75 (s, 1H), 7.70-7.57 (m, 3H), 7.51 (dd, J=5.3, 1.8 Hz, 1H), 7.43 (dd, J=7.9, 1.7 Hz, 1H), 3.87 (m, 1H), 3.56 (m, 3H), 2.01 (d, J=19.4 Hz, 3H), 1.87 (m, 2H), 1.76 (m, 2H), 1.47 (m, 1H), 1.41 (s, 18H). LCMS=554 (M+1).

Example 71. Preparation of Compound Nos. 71, 71a, and 71b

Synthesis of tert-butyl 3-{4-[5-(2-tert-butylpyridin-4-yl)thiophen-3-yl]-3-chlorobenzamido}piperidine-1-carboxylate

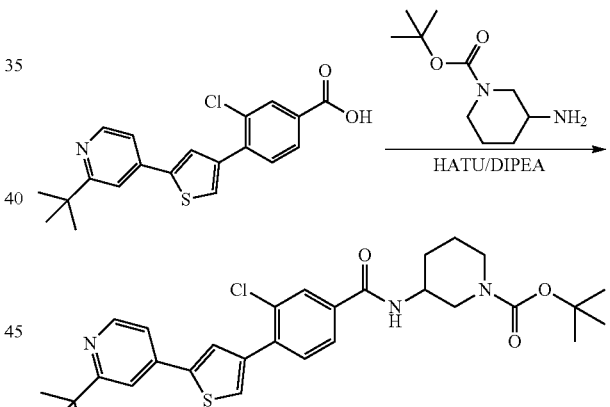

4-[5-(2-tert-Butyl-4-pyridyl)-3-thienyl]-3-chloro-benzoic acid (300 mg, 0.80 mmol) was taken in DMF (10 mL), followed by addition of DIPEA (0.62 mL, 3.22 mmol), and HATU (611 mg, 1.62 mmol), under nitrogen atmosphere. The reaction mixture was stirred at RT for 0.5 h, followed by addition of tert-butyl 3-aminopiperidine-1-carboxylate (640 mg, 3.22 mmol). The reaction mixture was stirred at RT for 16 h. After completion, water (150 mL) was added and the mixture extracted with EtOAc (100 mL). The combined organic layer was washed with brine (50 mL), dried over anhydrous sodium sulfate and concentrated under reduced pressure to obtain a crude product, which was purified by reverse phase HPLC to obtain tert-butyl 3-[[4-[5-(2-tert-butyl-4-pyridyl)-3-thienyl]-3-chloro-benzoyl]amino]piperidine-1-carboxylate (31 mg) freebase as a white solid. The enantiomers can be prepared from chiral HPLC resolution of the racemate.

¹H NMR (400 MHz, DMSO-d6) δ (ppm): 8.54 (d, J=5.1 Hz, 1H), 8.46 (d, J=7.3 Hz, 1H), 8.11-8.03 (m, 2H), 7.90 (d, J=7.8 Hz, 1H), 7.76-7.65 (m, 2H), 7.51 (dd, J=5.1, 1.7 Hz, 1H), 3.89 (s, 2H), 2.84 (s, 2H), 1.86 (s, 2H), 1.78 (s, 2H), 1.5 (t, J=12 Hz, 1H), 1.36 (s, 9H), 1.26 (s, 9H). LCMS: -(M+1) 554.3.

Example 72. Preparation of Compound No. 72

Synthesis of 1-{4-[5-(2-tert-butylpyridin-4-yl)thiophen-3-yl]-3-chlorobenzoyl}piperidin-4-amine

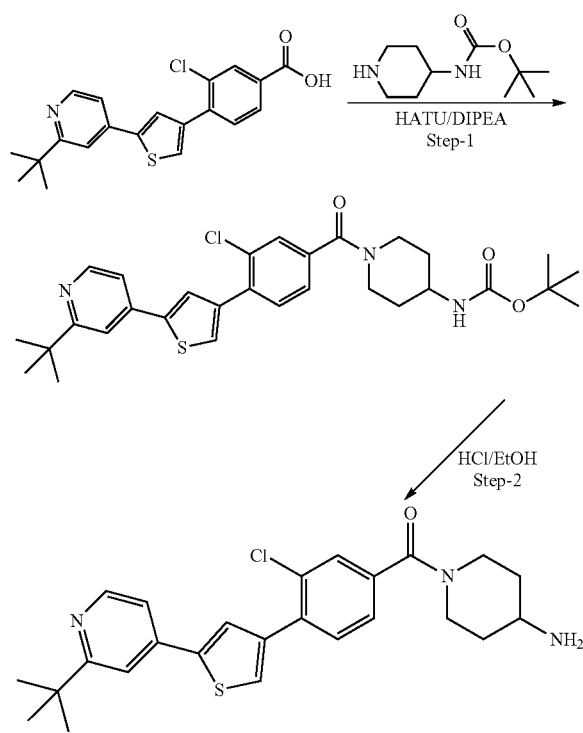

Step-1: Synthesis of tert-butyl N-[1-[4-[5-(2-tert-butyl-4-pyridyl)-3-thienyl]-3-chloro-benzoyl]-4-piperidyl]carbamate To a solution of 4-[5-(2-tert-butyl-4-pyridyl)-3-thienyl]-3-chloro-benzoic acid (300 mg, 0.8086 mmol) in DMF (7 mL), was added DIPEA (418 mg, 3.2344 mmol), followed by HATU (615 mg, 1.6172 mmol), and the reaction mixture was stirred for 30 min at RT. tert-Butyl N-(4-piperidyl) carbamate (809 mg, 4.043 mmol) was added and the reaction mixture was stirred for 16 h at RT. The reaction was monitored by TLC and LCMS. On completion, the reaction mixture was diluted with water (25 mL) and extracted with EtOAc (3×75 mL). The combined organic layer was washed with water (50 mL) and brine (50 mL) and dried over anhydrous sodium sulfate to obtain 500 mg of crude product. The crude compound was purified by reverse phase chromatography to afford tert-butyl N-[1-[4-[5-(2-tert-butyl-4-pyridyl)-3-thienyl]-3-chloro-benzoyl]-4-piperidyl]carbamate (250 mg) as a white solid.

Step-2: Synthesis of (4-amino-1-piperidyl)-[4-[5-(2-tert-butyl-4-pyridyl)-3-thienyl]-3-chloro-phenyl]methanone To a solution of tert-butyl N-[1-[4-[5-(2-tert-butyl-4-pyridyl)-3-thienyl]-3-chloro-benzoyl]-4-piperidyl]carbamate (250 mg, 0.2711 mmol) in EtOH (5 mL), was added 1.2 M ethanolic HCl (5 mL) at 0° C., and the reaction mixture stirred for 16 h at RT. The reaction was monitored by TLC and LCMS. The mixture was concentrated under reduced pressure to obtain (4-amino-1-piperidyl)-[4-[5-(2-tert-butyl-4-pyridyl)-3-thienyl]-3-chloro-phenyl]methanone (170 mg) as a white solid.

¹H NMR (400 MHz, DMSO-d6) δ (ppm): 8.55 (d, J=6.0 Hz, 1H), 8.33 (s, 1H), 8.23 (s, 1H), 8.03-7.95 (m, 2H), 7.67 (d, J=7.9 Hz, 1H), 7.57 (s, 1H), 7.42 (d, J=7.8 Hz, 1H), 4.45 (s, 1H), 3.60 (s, 1H), 3.30 (m, 1H), 3.17 (s, 1H), 2.87 (s, 1H), 2.00 (s, 2H), 1.88 (s, 2H), 1.42 (s, 9H). LCMS=(M+1) 454.2.

Example 73. Preparation of Compound No. 73

Synthesis of 3-(N-[4-[4-(2-tert-butyl-4-pyridyl)-2-thienyl]-3-chloro-benzoyl]-4-fluoro-anilino)propanoic acid

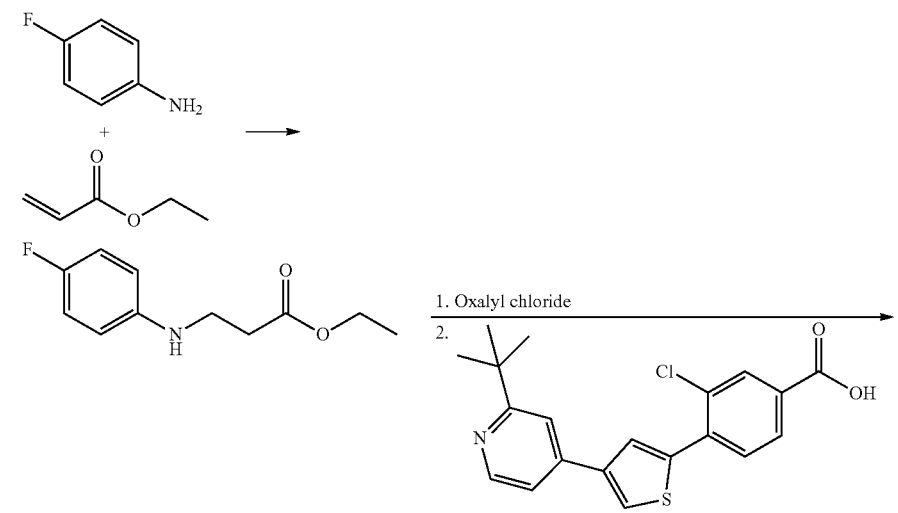

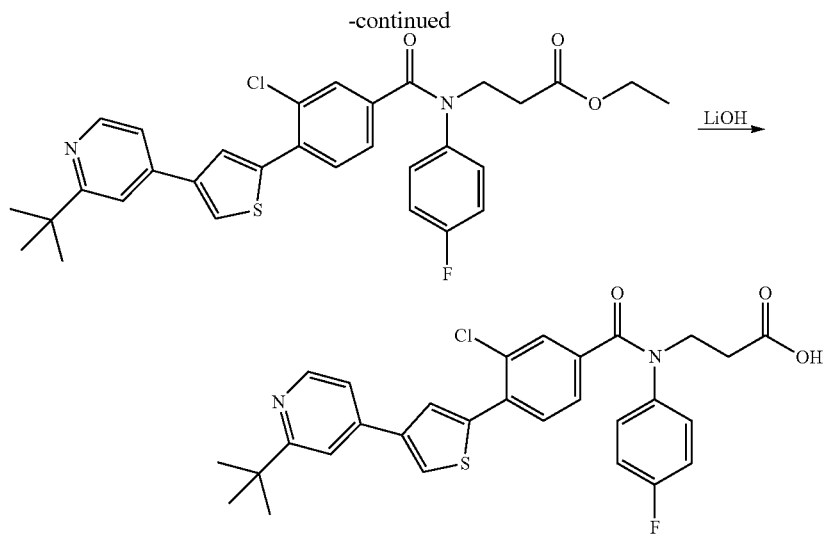

Step-1: Synthesis of ethyl 3-(4-fluoroanilino)propanoate

4-Fluoroaniline (5.0 g, 44.64 mmol) and ethyl prop-2-enoate (4.8 g, 44.64 mmol) were taken in acetic acid (5.0 mL) in a 25 mL microwave vial, then the reaction was stirred at 200° C. for 20 min in a microwave. Completion of reaction was monitored by TLC and LCMS. After completion of reaction, water (200 mL) was added and the mixture extracted with EtOAc (300 mL). The combined organic layer was washed with brine (100 mL), dried over anhydrous sodium sulfate and concentrated under reduced pressure to obtain a crude product, which was purified by chromatography to obtain ethyl 3-(4-fluoroanilino)propanoate compound (2.5 g), as a brown liquid. LCMS: –(M+1) 212.

Step-2: Synthesis of ethyl 3-(N-[4-[4-(2-tert-butyl-4-pyridyl)-2-thienyl]-3-chloro-benzoyl]-4-fluoro-anilino) propanoate 4-[4-(2-tert-Butyl-4-pyridyl)-2-thienyl]-3-chloro-benzoic acid (300 mg, 0.806 mmol) was taken in DCM (5 mL) followed by oxalyl chloride (0.2 mL) at 0° C. and a catalytic amount of DMF. The reaction was stirred at RT for 1 h. After completion of reaction, the mixture was completely evaporated to remove all oxalyl chloride. Separately, ethyl 3-(4-fluoroanilino) propionate prop-2-enoate (188 mg, 0.88 mmol) was taken in DCM (5.0 mL) under nitrogen. Dropwise addition of triethyl amine (0.23 mL, 0.96 mmol) was followed by addition of the above solution of acid chloride in DCM at 0° C. The reaction mixture was stirred RT for 16 h and the reaction was monitored by TLC and LCMS. After completion of reaction, water (100 mL) was added and the mixture extracted with DCM (150 mL). The combined organic layer was washed with brine (25 mL), dried over anhydrous sodium sulfate and concentrated under reduced pressure to obtain crude ethyl 3-(N-[4-[4-(2-tert-butyl-4-pyridyl)-2-thienyl]-3-chloro-benzoyl]-4-fluoro-anilino)propanoate (150 mg), a yellow solid. LCMS: –(M+1) 565.3.

Step-3: Synthesis of 3-(N-[4-[4-(2-tert-butyl-4-pyridyl)-2-thienyl]-3-chloro-benzoyl]-4-fluoro-anilino)propanoic acid Ethyl 3-(N-[4-[4-(2-tert-butyl-4-pyridyl)-2-thienyl]-3-chloro-benzoyl]-4-fluoro-anilino)propanoate (150 mg, 0.265 mmol) was taken in THF:Water (4:2 mL), followed by addition of lithium hydroxide (44 mg, 1.06 mmol) under nitrogen atmosphere. The reaction mixture was stirred at RT for 16 h. After completion of reaction, the mixture was completely concentrated and water (30 mL) was added and washed with DCM (2×50 mL). The aqueous layer was separated and cooled to 0° C. then acidified slowly with 1N HCl to make up to pH=2 and then extracted with EtOAc (3×50 mL). The organic layer was separated and dried over anhydrous sodium sulfate and concentrated under reduced pressure to obtain a crude product, which was purified by HPLC to obtain 3-(N-[4-[4-(2-tert-butyl-4-pyridyl)-2-thienyl]-3-chloro-benzoyl]-4-fluoro-anilino)propanoic acid (10 mg) as the freebase. LCMS: –(M+1) 537.0.

$^1$H NMR (400 MHz, Methanol-d4) δ (ppm): 8.46 (d, J=5.3 Hz, 1H), 8.06 (s, 1H), 7.81 (s, 1H), 7.72 (s, 1H), 7.51 (d, J=4.8 Hz, 3H), 7.27 (s, 3H), 7.08 (t, J=8.4 Hz, 2H), 4.18 (s, 2H), 2.63 (s, 2H), 1.41 (s, 9H).

Example 74. Preparation of Compound Nos. 74, 74a and 74b

Synthesis of (R)-(3-aminopiperidin-1-yl)(4-(4-(2-(tert-butyl)pyridin-4-yl)thiophen-2-yl)-3-chlorophenyl)methanone

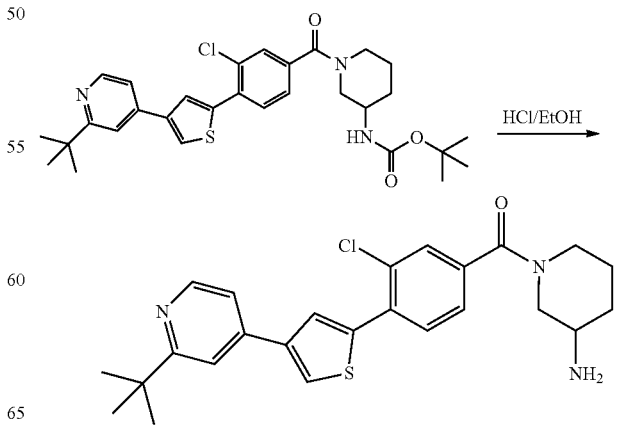

tert-Butyl (R)-(1-(4-(4-(2-(tert-butyl)pyridin-4-yl)thiophen-2-yl)-3-chlorobenzoyl) piperidin-3-yl)carbamate (135 mg, 0.244 mmol) was taken in EtOH (3.0 mL), followed by dropwise addition of 1.25M HCl in EtOH (3.0 mL) under nitrogen atmosphere at 0° C. The reaction mixture was stirred at RT for 16 h. Completion of reaction was monitored by TLC and LCMS. After completion of reaction, the mixture was concentrated to get (R)-(3-aminopiperidin-1-yl)(4-(4-(2-(tert-butyl)pyridin-4-yl)thiophen-2-yl)-3-chlorophenyl)methanone (120 mg) (Compound No. 74a) as the HCl salt light yellow solid. Compound No. 74b, the (S)-enantiomer was prepared using the opposite enantiomeric starting material.

¹H NMR (400 MHz, DMSO-d6) δ (ppm): 8.94 (s, 1H), 8.76 (d, J=6.0 Hz, 1H), 8.44 (s, 1H), 8.30 (s, 2H), 7.91 (d, J=7.9 Hz, 1H), 7.74 (s, 1H), 7.55 (d, J=7.8 Hz, 1H), 4.82 (s, 1H), 4.19 (s, 1H), 3.81 (s, 1H), 3.39 (s, 1H), 3.19 (s, 2H), 2.96 (s, 1H), 2.12 (s, 1H), 1.71 (s, 1H), 1.54 (s, 9H). LCMS: -(M+1) 453.9.

Example 75. Preparation of Compound Nos. 75, 75a, and 75b

Synthesis of 1-{4-[5-(2-tert-butylpyridin-4-yl)thiophen-3-yl]-3-chlorobenzoyl}-N-methylpiperidin-3-amine

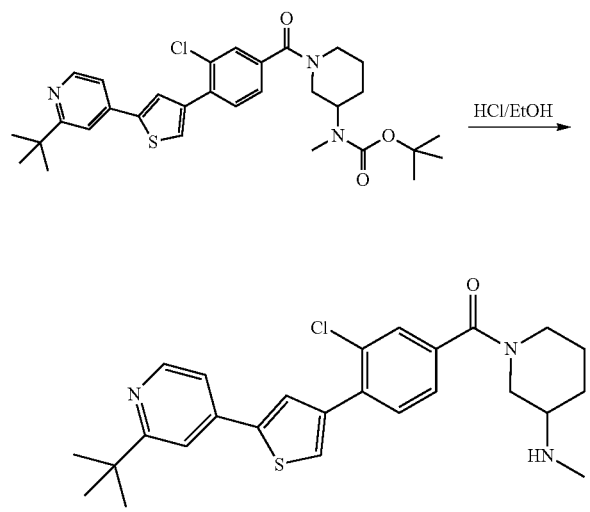

A solution of tert-butyl N-[1-[4-[5-(2-tert-butyl-4-pyridyl)-3-thienyl]-3-chloro-benzoyl]-3-piperidyl]-N-methyl-carbamate (50 mg, 0.0880 mmol) in ethanolic HCl (3 mL) was stirred at RT overnight. The reaction was monitored by LCMS. After completion of reaction, the mixture was concentrated under reduced pressure to obtain [4-[5-(2-tert-butyl-4-pyridyl)-3-thienyl]-3-chloro-phenyl]-[3-(methylamino)-1-piperidyl] methanone (34 mg) as a solid. The enantiomers can be prepared from chiral HPLC resolution of the racemate.

¹H NMR (400 MHz, Methanol-d4) δ (ppm): 8.60 (d, J=6.3 Hz, 1H), 8.36 (s, 1H), 8.15 (d, J=15.3 Hz, 3H), 7.74-7.66 (m, 2H), 7.51 (dd, J=7.8, 1.7 Hz, 1H), 4.3 (s, 1H), 3.64 (m, 2H), 3.38 (m, 2H), 2.80 (s, 3H), 2.22 (s, 1H), 1.80 (m, 2H), 1.74 (s, 1H), 1.56 (s, 9H). LCMS: -468 (M+1).

Example 76. Preparation of Compound No. 76

Synthesis of N-(1-{4-[5-(2-tert-butylpyridin-4-yl)thiophen-3-yl]-3-chlorobenzoyl}piperidin-4-yl)-2,2-dimethylpropanamide

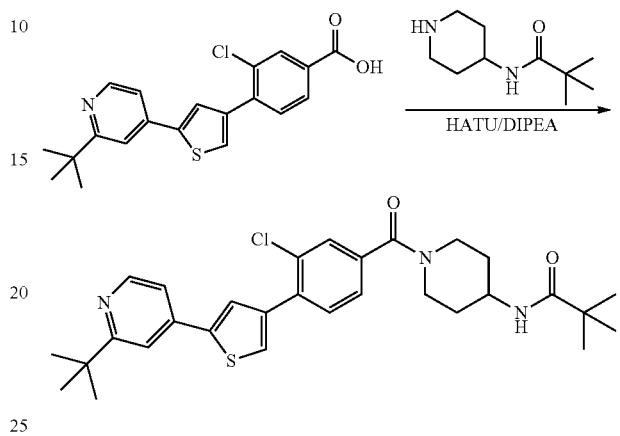

To a solution of 4-[5-(2-tert-butyl-4-pyridyl)-3-thienyl]-3-chloro-benzoic acid (300 mg, 0.8086 mmol) in DMF (10 mL), was added DIPEA (418.1 mg, 3.234 mmol), followed by the addition of HATU (615 mg, 1.6172 mmol), the reaction mixture was stirred for 30 min. 2,2-Dimethyl-N-(4-piperidyl)propanamide (744.7 mg, 4.0431 mmol) was added and the mixture stirred for 16 h at RT. The reaction was monitored by TLC and LCMS. On completion, the reaction mixture was diluted with water (25 mL) and extracted with EtOAc (3×75 mL). The combined organic layer was washed with water (50 mL) and brine (50 mL) and dried over anhydrous sodium sulfate to obtain a crude compound. This crude compound was purified by reverse phase chromatography to afford N-[1-[4-[5-(2-tert-butyl-4-pyridyl)-3-thienyl]-3-chloro-benzoyl]-4-piperidyl]-2,2-dimethyl-propanamide (50 mg) as a white solid.

¹H NMR (400 MHz, DMSO-d6) δ (ppm): 8.54 (d, J=5.0 Hz, 1H), 8.08 (s, 1H), 7.96 (s, 1H), 7.69 (d, J=7.4 Hz, 1H), 7.55 (s, 1H), 7.49 (d, J=5.1 Hz, 1H), 7.41 (d, J=7.8 Hz, 1H), 7.21 (d, J=7.7 Hz, 1H), 4.41 (s, 1H), 3.86 (s, 1H), 3.57 (s, 1H), 3.17 (s, 1H), 2.89 (s, 1H), 1.76 (s, 2H), 1.71 (s, 2H), 1.36 (s, 9H), 1.08 (s, 9H). LCMS: -(M+1) 538.2.

Example 77. Preparation of Compound No. 77

Synthesis of 4-{4-[4-(2-tert-butylpyridin-4-yl)-5-methylthiophen-2-yl]-3-chlorobenzoyl}piperazin-2-one

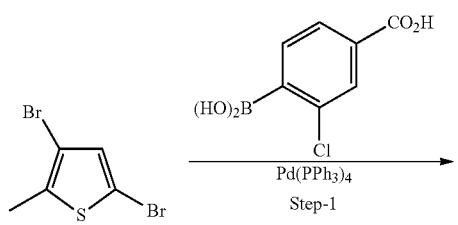

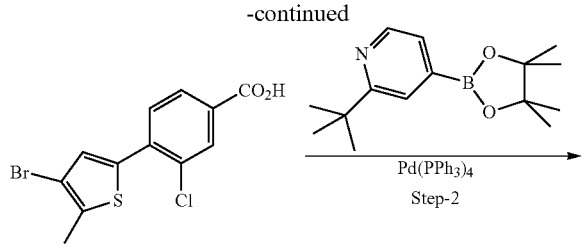

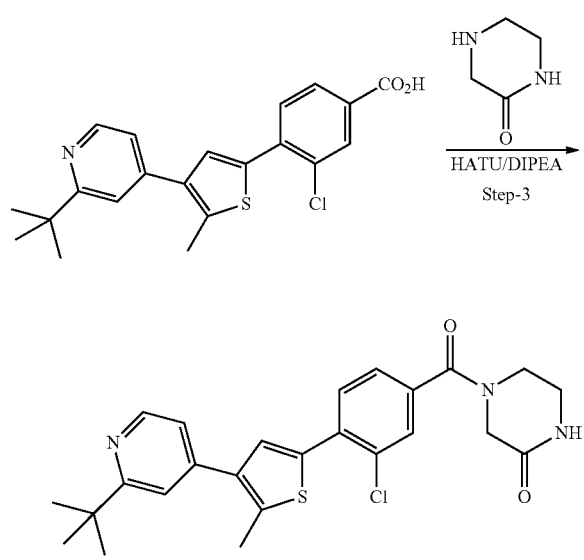

Step-1. Synthesis of 4-(4-bromo-5-methyl-2-thienyl)-3-chloro-benzoic acid 3,5-Dibromo-2-methyl-thiophene (10 g, 39.2 mmol), 4-borono-3-chloro-benzoic acid (9.4 g, 47.0 mmol), and sodium carbonate (10.2 g, 98.0 mmol) in water (10 mL) and DMF (100.0 mL) were charged in a 250 mL glass bottle and purged with nitrogen gas for 20 min. After adding tetrakis (4.5 g, 3.9 mmol), the reaction mixture was heated at 100° C. for 16 h. The reaction was monitored by TLC and LCMS. After completion of reaction, water (200 mL) was added and filtered with washings of ether and hexane obtain 4-(4-bromo-5-methyl-2-thienyl)-3-chloro-benzoic acid (10 gm) as the freebase, a yellow solid. LCMS: −(M+1) 331.0.

Step-2. Synthesis of 4-[4-(2-tert-butyl-4-pyridyl)-5-methyl-2-thienyl]-3-chloro-benzoic acid 4-(4-Bromo-5-methyl-2-thienyl)-3-chloro-benzoic acid (5.0 g, 15.1 mmol), 2-tert-butyl-4-(4,4,5,5-tetramethyl-1,3,2-dioxaborolan-2-yl)pyridine (4.3 g, 16.1 mmol), sodium carbonate (3.9 g, 37.9 mmol) in water (5.0 mL), and DMF (50.0 mL) were charged in a 250 mL glass bottle and purged with nitrogen gas for 15 min. After adding tetrakis (1.7 g, 1.5 mmol), the reaction mixture was heated at 100° C. for 16 h. The reaction was monitored by TLC and LCMS. After completion of reaction, the mixture was cooled to 0° C. and 3N HCl was added dropwise. A yellow precipitate was obtained which was filtered to obtain 4-[4-(2-tert-butyl-4-pyridyl)-5-methyl-2-thienyl]-3-chloro-benzoic acid (4.0 g) as a yellow solid. LCMS: −(M+1) 386.1.

Step-3. Synthesis of 4-[4-[4-(2-tert-butyl-4-pyridyl)-5-methyl-2-thienyl]-3-chloro-benzoyl]piperazin-2-one 4-[4-(2-tert-Butyl-4-pyridyl)-5-methyl-2-thienyl]-3-chloro-benzoic acid (500 mg, 1.29 mmol) was taken in DMF (10 mL), followed by addition of DIPEA (0.9 mL, 5.18 mmol), HATU (980 mg, 2.58 mmol), under nitrogen atmosphere. The reaction mixture was stirred at RT for 0.5 h, followed by addition of piperazin-2-one (510 mg, 5.18 mmol). The reaction mixture was stirred at RT for 16 h. After completion of reaction, water (150 mL) was added and the mixture extracted with EtOAc (2×50 mL). The combined organic layer was washed with brine (50 mL), dried over anhydrous sodium sulfate and concentrated under reduced pressure to obtain the crude product which was purified by reverse phase HPLC to obtain 4-[4-[4-(2-tert-butyl-4-pyridyl)-5-methyl-2-thienyl]-3-chloro-benzoyl]piperazin-2-one (54 mg) as the HCl salt.

$^1$H NMR (400 MHz, Methanol-d4) δ (ppm): 8.69 (d, J=6.3 Hz, 1H), 8.16-8.04 (m, 2H), 7.85-7.75 (m, 2H), 7.73-7.62 (m, 1H), 7.58-7.47 (m, 1H), 4.31 (s, 1H), 4.13 (s, 1H), 3.95 (s, 1H), 3.70 (s, 1H), 3.41 (s, 2H), 2.77 (s, 3H), 1.58 (s, 9H). LCMS: −(M+1) 468.0.

Example 78. Preparation of Compound No. 78

Synthesis of tert-butyl 4-{4-[5-(2-tert-butylpyridin-4-yl)thiophen-3-yl]-3-chlorobenzamido}piperidine-1-carboxylate

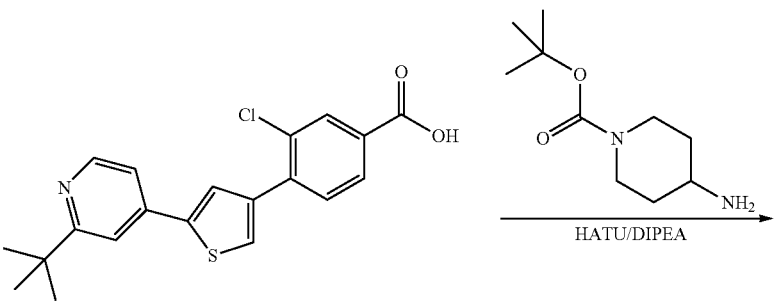

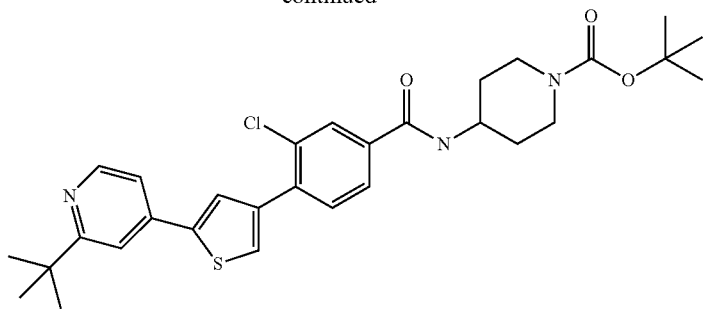

To a solution of 4-[5-(2-tert-butyl-4-pyridyl)-3-thienyl]-3-chloro-benzoic acid (300 mg, 0.8086 mmol) in DMF (10 mL), was added DIPEA (696.8 mg, 5.3908 mmol), followed by the addition of HATU (1025 mg, 2.6954 mmol), the reaction mixture was stirred for 30 min. tert-Butyl 4-aminopiperidine-1-carboxylate (645 mg, 3.22 mmol) was added to the reaction mixture and the mixture stirred the reaction mixture overnight at R.T. The reaction was monitored by TLC and LCMS. On completion, the reaction mixture was diluted with water (30 mL) and extracted with EtOAc (3×50 mL). The combined organic layer was washed with water (50 mL) and brine (50 mL) and dried over anhydrous sodium sulfate to obtain a crude compound. The crude compound was purified by reverse phase HPLC to afford tert-butyl 4-[[4-[5-(2-tert-butyl-4-pyridyl)-3-thienyl]-3-chloro benzoyl]amino]piperidine-1-carboxylate (45 mg) as a white solid.

$^1$H NMR (400 MHz, DMSO-d6) δ (ppm): 8.52 (d, J=8.3 Hz 1H), 8.50 (d, J=8.5 Hz 1H), 8.03 (d, J=9.1 Hz, 2H), 7.87 (s, J=8.0 Hz, 1H), 7.85 (d, J=9.1 Hz 1H),7.71 (d, 1H), 7.65 (s, 1H), 7.49 (d, J=5.1 Hz, 1H), 3.94 (d, J=14.1 Hz, 3H), 2.83 (s, 2H), 1.79 (d, J=11.9 Hz, 3H), 1.39 (s, 10H), 1.34 (s, 9H). LCMS −(M+1) 554.2.

Example 79. Preparation of Compound Nos. 79, 79a and 79b

Synthesis of tert-butyl N-[(3R)-1-{4-[4-(2-tert-butylpyridin-4-yl)-5-methylthiophen-2-yl]-3-chlorobenzoyl}piperidin-3-yl]carbamate

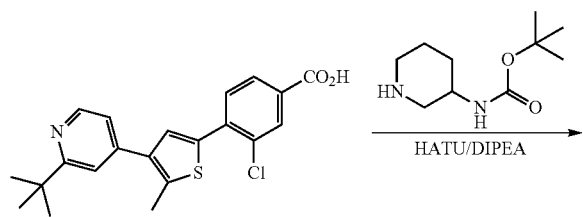
HATU/DIPEA

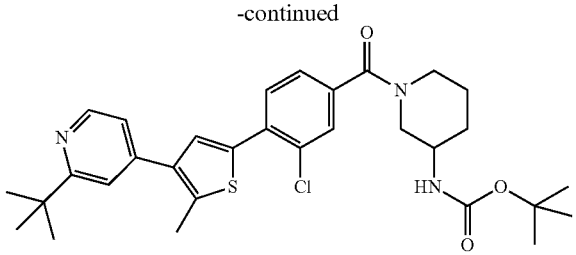

To a stirred solution 4-[4-(2-tert-butyl-4-pyridyl)-5-methyl-2-thienyl]-3-chloro-benzoic acid (500 mg, 1.347 mmol) in DMF (10 mL), was added DIPEA (0.92 mL, 5.390 mmol) followed by addition of HATU (1.0 g, 2.69 mmol) and the mixture stirred at RT for 30 min. Then (R)-tert-butyl N-methyl-N-(3-piperidyl) carbamate (1.1 g, 5.39 mmol) was added at the same temperature. The reaction mixture was stirred at RT overnight. The reaction was monitored by TLC and LCMS. After completion of reaction, the mixture was diluted with water (10 mL) and extracted with EtOAc (2×50 mL), the organic layer was washed with water (2×20 mL) and brine (20 mL) and dried over anhydrous sodium sulfate to obtain a crude product which was purified by reverse phase HPLC to obtain Compound 79a [tert-butyl-(R)—N-[1-[4-[4-(2-tert-butyl-4-pyridyl)-5-methyl-2-thienyl]-3-chloro-benzoyl]-3-piperidyl]carbamate] (174 mg) freebase as a solid. Compound 79b, the (S)-enantiomer, was also prepared using the (S)-tert-butyl N-methyl-N-(3-piperidyl) carbamate reagent.

$^1$H NMR (400 MHz, DMSO-d6) δ (ppm): 8.58 (d, J=5.2 Hz, 1H), 7.88 (s, 1H), 7.62 (s, 2H), 7.52 (s, 1H), 7.42 (d, J=5.3, 1H), 7.36 (d, J=7.9, 1H), 6.98 (s, 1H), 4.2 (s, 1H), 3.42 (s, 2H), 3.08 (s, 2H), 2.75 (s, 1H), 2.58 (s, 3H) 1.80 (s, 3H), 1.41-1.20 (m, 18H). LCMS: −568.1 (M+1).

Example 80. Preparation of Compound Nos. 80, 80a, and 80b

Synthesis of 1-{4-[5-(2-tert-butylpyridin-4-yl)thiophen-3-yl]-3-chlorobenzoyl}-N-[(4-chlorophenyl)methyl]piperidin-3-amine

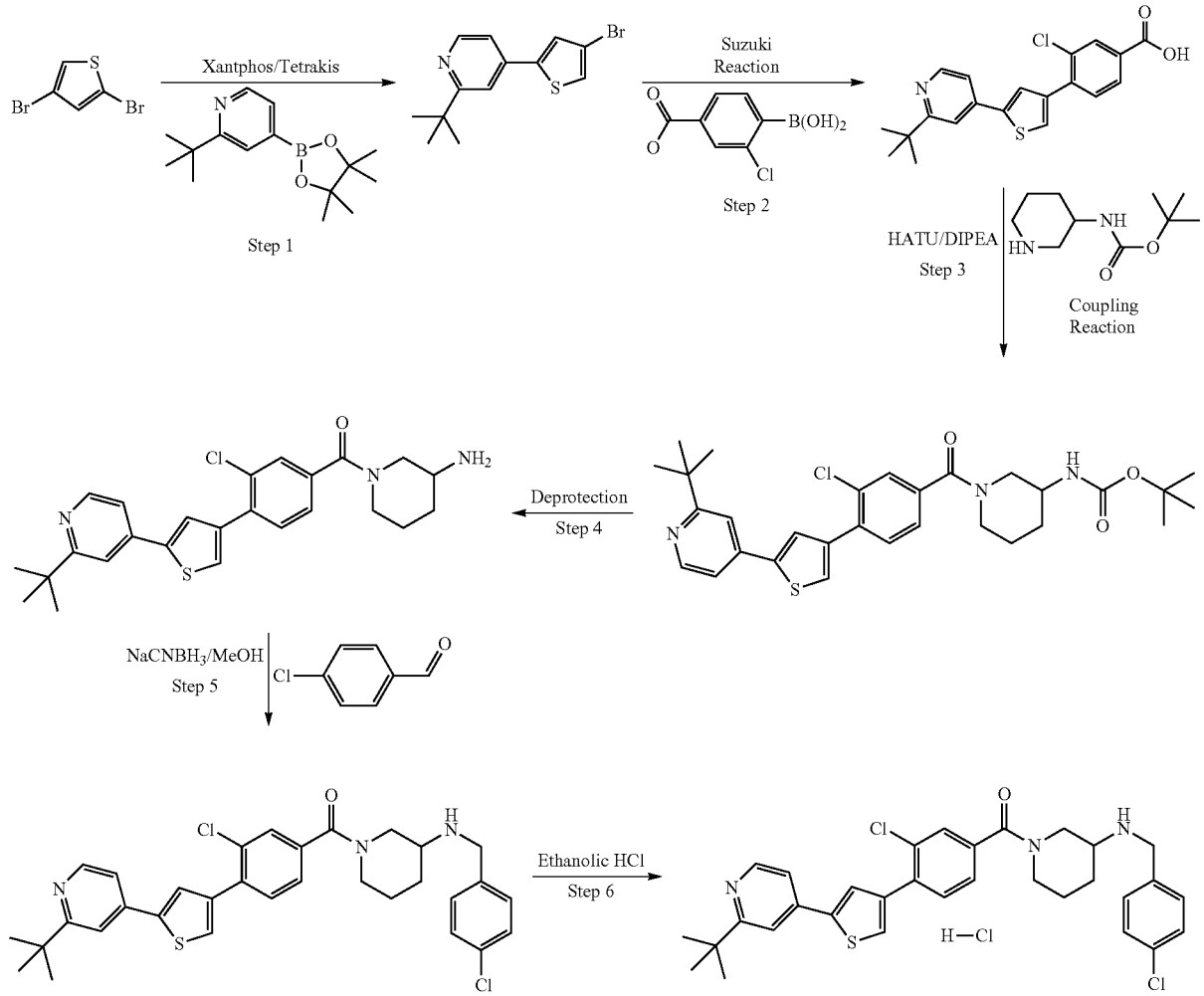

Step-1: Synthesis of 4-(4-bromo-2-thienyl)-2-tert-butyl-pyridine

In a 100 mL glass bottle 2,4 dibromothiophene (600 mg, 2.5 mmol, 1 eq.) along with 2-tert-butyl-4-(4,4,5,5-tetramethyl-1,3,2-dioxaborolan-2-yl)pyridine (652 mg, 1 eq.) and potassium phosphate (1.325 g, 2.5 eq.) were charged in 25 mL of THF. The mixture was purged with nitrogen for 15 min then Xantphos (145 mg, 0.1 eq.) and tetrakis (289 mg, 0.1 eq.) were added, and the mixture repurged for 5 min and the mixture stirred at 60° C. overnight. Progress of the reaction was monitored by TLC & LCMS. When the reaction was completed, the mixture was cooled to RT, water (100 mL) was added and the mixture extracted with EtOAc (3×100 mL). The combined organic layer was washed with brine (50 mL) then dried over anhydrous sodium sulfate, concentrated under reduced pressure to give a viscous compound which was purified by silica gel (60-120) column chromatography using EtOAc/Hexane (0-20%) as eluent system to afford 4-(4-bromo-2-thienyl)-2-tert-butyl-pyridine as a colorless semi-solid (500 mg) in pure form.

Step-2 Synthesis of 4-[5-(2-tert-butyl-4-pyridyl)-3-thienyl]-3-chloro-benzoic acid In a 25 mL glass bottle, 4-(4-bromo-2-thienyl)-2-tert-butyl-pyridine (450 mg, 1.52 mmol, 1 eq.) and 4-borono-3-chloro-benzoic acid (397 mg, 1.98 mmol, 1.3 eq.), were charged in DMF (7 mL) followed by addition of sodium carbonate (404 mg, 2.5 equiv dissolved in water (2.0 mL) and the reaction mixture was purged with nitrogen gas for 5 min. After adding tetrakis (176 mg, 0.152 mmol, 0.1 eq.) the mixture was repurged for 2 min and was stirred at 80° C. overnight. The progress of the reaction was monitored by TLC and LCMS. After completion of reaction, the mixture was allowed to come to RT and diluted with water (50 mL) and extracted with EtOAc:MeOH (90:10), (3×100 mL). The combined organic layer was dried over anhydrous sodium sulfate and concentrated under reduced pressure to afford a solid compound, 3-chloro-4-[5-[3-(1-piperidyl)phenyl]-3-thienyl]benzoic acid (500 mg) which was used as such for the next step of synthesis.

Step-3: Synthesis of tert-butyl N-[1-[4-[5-(2-tert-butyl-4-pyridyl)-3-thienyl]-3-chloro-benzoyl]-3-piperidyl]carbamate In a 100 mL flask, 4-[5-(2-tert-butyl-4-pyridyl)-3-thienyl]-3-chloro-benzoic acid (500 mg, 1.34 mmol, 1 eq.) was dissolved in DMF (13 mL), followed by addition of DIPEA (1.0 mL, 5.4 mmol, 4 eq.) and HATU (1.07 g, 2.69 mmol, 2 eq.), and the resulting mixture was stirred for 10 min at RT and tert-butyl N-(3-piperidyl)carbamate (1.07 g, 5.4 mmol, 4 eq.) were added and the mixture stirred at RT under nitrogen atmosphere overnight. The progress of the reaction was monitored by TLC and LCMS. After completion of reaction, the mixture was diluted with water (100 mL) and extracted with EtOAc (2×100 mL), washed with water (4×100 mL) then dried over anhydrous sodium sulfate and the combined organic layer was concentrated under reduced pressure to afford N-[1-[4-[5-(2-tert-butyl-4-pyridyl)-3-thienyl]-3-chloro-benzoyl]-3-piperidyl]carbamate (700 mg) as a crude viscous compound which was used as such for the next step of synthesis.

Step-4: Synthesis of (3-amino-1-piperidyl)-[4-[5-(2-tert-butyl-4-pyridyl)-3-thienyl]-3-chloro-phenyl]methanone In a 100 mL flask, tert-butyl N-[1-[4-[5-(2-tert-butyl-4-pyridyl)-3-thienyl]-3-chloro-benzoyl]-3-piperidyl]carbamate (700 mg, 1.26 mmol, 1 eq.) was charged in DCM (15 mL), the reaction mixture was maintained at 0° C. and trifluoroacetic acid (5 mL) was added dropwise and the mixture stirred at RT for 2.5 h. Progress of reaction was monitored by TLC/LCMS. After completion of reaction, the DCM was evaporated under reduced pressure, and the residue basified with saturated aqueous sodium bicarbonate solution and extracted with EtOAc (2×100 mL). The organic layer was washed with brine (100 mL) and dried over anhydrous sodium sulfate. The solution was concentrated under reduced pressure to afford (3-amino-1-piperidyl)-[4-[5-(2-tert-butyl-4-pyridyl)-3-thienyl]-3-chloro-phenyl]methanone as a crude viscous compound (570 mg) which was used as such for the next step of synthesis.

Step-5: Synthesis of [4-[5-(2-tert-butyl-4-pyridyl)-3-thienyl]-3-chloro-phenyl]-[3-[(4-chlorophenyl)methylamino]-1-piperidyl]methanone In a 100 mL flask, tert-butyl N-[1-[4-[5-(2-tert-butyl-4-pyridyl)-3-thienyl]-3-chloro-benzoyl]-3-piperidyl]carbamate (230 mg, 0.5 mmol, 1 eq.) was charged in (10 mL) of methanol and the mixture stirred at RT with 4-chlorobenzeldehyde (64 mg, 0.45 mmol, 1 eq.) for 2 h. Then at RT, 3 drops of acetic acid and NaCNBH$_3$ (64 mg, 1.01 mmol, 2 eq.) were added and the mixture stirred for 30 min at RT. Progress of reaction was monitored by TLC/LCMS. After completion of reaction, methanol was evaporated under reduced pressure, and the residue basified with saturated aqueous sodium bicarbonate solution and extracted with EtOAc (2×100 mL). The organic layer was washed with brine (100 mL) and dried over anhydrous sodium sulfate. The solution was concentrated under reduced pressure, to give a viscous compound that was purified by reverse phase chromatography to afford [4-[5-(2-tert-butyl-4-pyridyl)-3-thienyl]-3-chloro-phenyl]-[3-[(4-chlorophenyl)methyl-amino]-1-piperidyl] methanone as a solid free base compound (94 mg).

Step 6: Synthesis of [4-[5-(2-tert-butyl-4-pyridyl)-3-thienyl]-3-chloro-phenyl]-[3-[(4-chlorophenyl)methylamino]-1-piperidyl]methanone hydrochloride In a 250 mL flask, [4-[5-(2-tert-butyl-4-pyridyl)-3-thienyl]-3-chloro-phenyl]-[3-[(4-chlorophenyl)methylamino]-1-piperidyl]methanone (94 mg, 0.163 mmol, 1 eq.) was dissolved in 3 mL of EtOH and at 0° C. treated with 2 mL of ethanolic HCl, then evaporated under reduced pressure and directly lyophilized to get a free flowing solid (100 mg, off-white colored) as its HCl salt. The enantiomers were prepared from chiral HPLC resolution of the racemate, to give Compound 80a [(R)-(4-(5-(2-(tert-butyl)pyridin-4-yl)thiophen-3-yl)-3-chlorophenyl)(3-((4-chlorobenzyl)amino)piperidin-1-yl)methanone] and Compound 80b [(S)-(4-(5-(2-(tert-butyl)pyridin-4-yl)thiophen-3-yl)-3-chlorophenyl)(3-((4-chlorobenzyl)amino)piperidin-1-yl)methanone].
$^1$H NMR (400 MHz, Methanol-d4) δ (ppm): 8.61 (d, J=6.3 Hz, 1H), 8.41 (s, 1H), 8.23-8.14 (m, 3H), 7.75-7.67 (m, 2H), 7.52 (m, J=7.7 Hz, 5H), 4.67 (s, 1H), 4.37 (m, 2H), 3.70 (s, 1H), 3.42 (s, 3H), 2.37 (m, 1H), 1.85 (m, 2H), 1.68 (m, 1H), 1.57 (s, 9H). LCMS=578 (M+1).

Example 81. Preparation of Compound Nos. 81, 81a, and 81b

Synthesis of 1-{4-[5-(2-tert-butylpyridin-4-yl)thiophen-3-yl]-3-chlorobenzoyl}-N-[(3-chlorophenyl)methyl]piperidin-3-amine

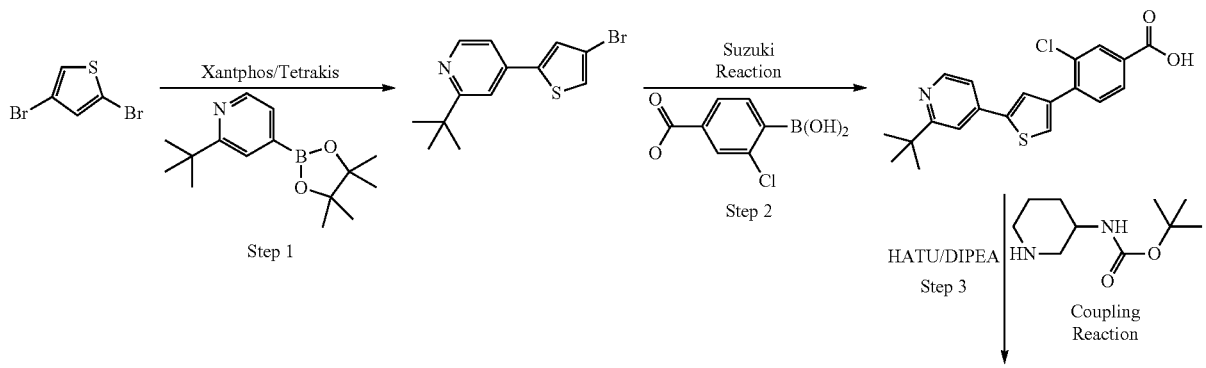

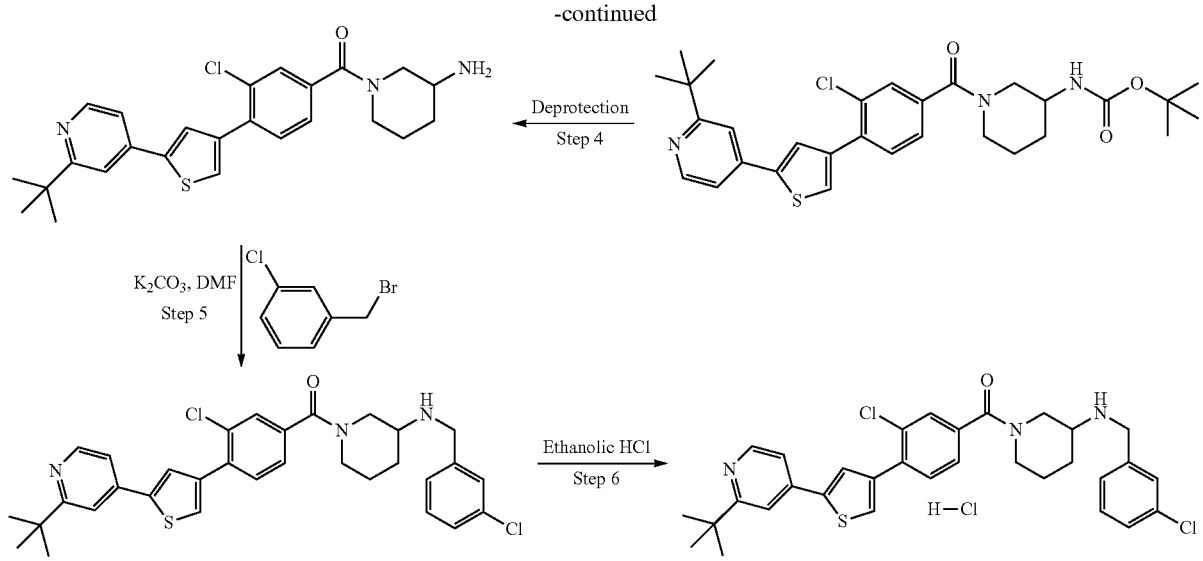

Step-1: Synthesis of 4-(4-bromo-2-thienyl)-2-tert-butyl-pyridine

In a 100 mL glass bottle, 2,4 dibromothiophene (600 mg, 2.5 mmol, 1 eq.) along with 2-tert-butyl-4-(4,4,5,5-tetramethyl-1,3,2-dioxaborolan-2-yl)pyridine (652 mg, 1 eq.) and potassium phosphate (1.325 g, 2.5 eq.) were charged in 25 mL of THF. The mixture was purged with nitrogen for 15 min then Xantphos (145 mg, 0.1 eq.) and tetrakis (289 mg, 0.1 eq.) were added, and the mixture repurged for 5 min and the mixture stirred at 60° C. overnight. Progress of the reaction was monitored by TLC & LCMS. When the reaction was completed, the mixture was cooled to RT, water (100 mL) was added and the mixture extracted with EtOAc (3×100 mL). The combined organic layer was washed with brine (50 mL) then dried over anhydrous sodium sulfate, concentrated under reduced pressure to give a viscous compound which was purified by silica gel (60-120) column chromatography using EtOAc/Hexane (0-20%) as eluent system to afford 4-(4-bromo-2-thienyl)-2-tert-butyl-pyridine as a colorless semi-solid (500 mg) in pure form.

Step-2: Synthesis of 4-[5-(2-tert-butyl-4-pyridyl)-3-thienyl]-3-chloro-benzoic acid In a 25 mL glass bottle, 4-(4-bromo-2-thienyl)-2-tert-butyl-pyridine (450 mg, 1.52 mmol, 1 eq.) and 4-borono-3-chloro-benzoic acid (397 mg, 1.98 mmol, 1.3 eq.), were charged in DMF (7 mL) followed by addition of sodium carbonate (404 mg, 2.5 equiv dissolved in water (2.0 mL) and the reaction mixture was purged with nitrogen gas for 5 min. After adding tetrakis (176 mg, 0.152 mmol, 0.1 eq.) the mixture was repurged for 2 min and was stirred at 80° C. overnight. The progress of the reaction was monitored by TLC and LCMS. After completion of reaction, the mixture was allowed to come to RT and diluted with water (50 mL) and extracted with EtOAc:MeOH (90:10), (3×100 mL). The combined organic layer was dried over anhydrous sodium sulfate and concentrated under reduced pressure to afford a solid compound, 3-chloro-4-[5-[3-(1-piperidyl)phenyl]-3-thienyl]benzoic acid (500 mg) which was used as such for the next step of synthesis.

Step-3: Synthesis of tert-butyl N-[1-[4-[5-(2-tert-butyl-4-pyridyl)-3-thienyl]-3-chloro-benzoyl]-3-piperidyl]carbamate In a 100 mL flask, 4-[5-(2-tert-butyl-4-pyridyl)-3-thienyl]-3-chloro-benzoic acid (500 mg, 1.34 mmol, 1 eq.) was dissolved in DMF (13 mL), followed by addition of DIPEA (1.0 mL, 5.4 mmol, 4 eq.) and HATU (1.07 g, 2.69 mmol, 2 eq.), and the resulting mixture was stirred for 10 min at RT and tert-butyl N-(3-piperidyl)carbamate (1.07 g, 5.4 mmol, 4 eq.) were added and the mixture stirred at RT under nitrogen atmosphere overnight. The progress of the reaction was monitored by TLC and LCMS. After completion of reaction, the mixture was diluted with water (100 mL) and extracted with EtOAc (2×100 mL), washed with water (4×100 mL) then dried over anhydrous sodium sulfate and the combined organic layer was concentrated under reduced pressure to afford N-[1-[4-[5-(2-tert-butyl-4-pyridyl)-3-thienyl]-3-chloro-benzoyl]-3-piperidyl]carbamate (700 mg) as a crude viscous compound which was used as such for the next step of synthesis.

Step-4: Synthesis of (3-amino-1-piperidyl)-[4-[5-(2-tert-butyl-4-pyridyl)-3-thienyl]-3-chloro-phenyl]methanone In a 100 mL flask, tert-butyl N-[1-[4-[5-(2-tert-butyl-4-pyridyl)-3-thienyl]-3-chloro-benzoyl]-3-piperidyl]carbamate (700 mg, 1.26 mmol, 1 eq.) was charged in DCM (15 mL), the reaction mixture was maintained at 0° C. and trifluoroacetic acid (5 mL) was added dropwise and the mixture stirred at RT for 2.5 h. Progress of reaction was monitored by TLC/LCMS. After completion of reaction, the DCM was evaporated under reduced pressure, and the residue basified with saturated aqueous sodium bicarbonate solution and extracted with EtOAc (2×100 mL). The organic layer was washed with brine (100 mL) and dried over anhydrous sodium sulfate. The solution was concentrated under reduced pressure to afford (3-amino-1-piperidyl)-[4-[5-(2-tert-butyl-4-pyridyl)-3-thienyl]-3-chloro-phenyl]methanone as a crude viscous compound (570 mg) which was used as such for the next step of synthesis.

Step-5: Synthesis of [4-[5-(2-tert-butyl-4-pyridyl)-3-thienyl]-3-chloro-phenyl]-[3-[(3-chlorophenyl)methylamino]-1-piperidyl]methanone In a 100 mL flask, tert-butyl N-[1-[4-[5-(2-tert-butyl-4-pyridyl)-3-thienyl]-3-chloro-benzoyl]-3-piperidyl]carbamate (250 mg, 0.55 mmol, 1 eq.) was charged in (8 mL) of DMF and the mixture stirred with potassium carbonate (228 mg, 1.65 mmol, 3 eq.) at RT for 30 min then 3-chlorobenzylbromide (113 mg, 1 eq.), was added and the mixture stirred at RT for 2 h. Progress of reaction was monitored by TLC/LCMS. After maximum conversion of starting material into product, extracted with EtOAc (2×100 mL). Then washed with water (4×100 mL). The organic layer was washed with brine (100 mL) and dried over anhydrous sodium sulfate. The solution was concentrated under reduced pressure, viscous compound and purified by reverse phase chromatography to afford [4-[5-(2-tert-butyl-4-pyridyl)-3-thienyl]-3-chloro-phenyl]-[3-[(3-chlorophenyl)methylamino]-1-piperidyl]methanone as a solid free base compound (47 mg).

Step-6: Synthesis of [4-[5-(2-tert-butyl-4-pyridyl)-3-thienyl]-3-chloro-phenyl]-[3-[(3-chlorophenyl)methylamino]-1-piperidyl]methanone hydrochloride In 250 mL flask, [4-[5-(2-tert-butyl-4-pyridyl)-3-thienyl]-3-chloro-phenyl]-[3-[(3-chlorophenyl)methylamino]-1-piperidyl]methanone (47 mg, 0.081 mmol, 1 eq.) was dissolved in 3 mL of EtOH and at 0° C. treated with 2 mL of ethanolic HCl, then evaporated the EtOH under reduced pressure and directly lyophilized to get free flow solid (50 mg, off-white colored) as its respective HCl salt. The enantiomers can be prepared from chiral HPLC resolution of the racemate.

$^1$H NMR (400 MHz, Methanol-d4) δ (ppm): 8.61 (d, J=6.4 Hz, 1H), 8.41 (d, J=1.4 Hz, 1H), 8.24-8.14 (m, 3H), 7.75-7.67 (m, 2H), 7.64 (s, 1H), 7.51 (d, J=8.8 Hz, 4H), 4.68 (m, 1H), 4.37 (m, 2H), 3.5 (m, 2H), 2.37 (m, 2H), 1.85 (m, 2H), 1.69 (m, 2H), 1.57 (s, 9H). LCMS=578 (M+1).

Example 82. Preparation of Compound Nos. 82, 82a and 82b

Synthesis of (3R)-1-{4-[5-(2-tert-butylpyridin-4-yl)thiophen-3-yl]-3-chlorobenzoyl}pyrrolidin-3-ol

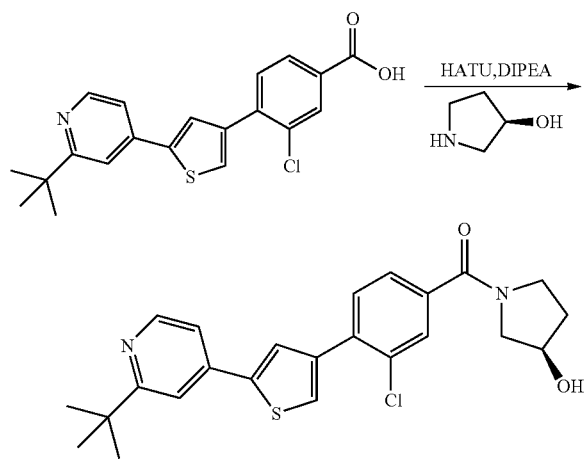

To a stirred solution of 4-[5-(2-tert-butyl-4-pyridyl)-3-thienyl]-3-chloro-benzoic acid (500 mg, 1.34 mmol) in DMF (10 mL), was added DIPEA (0.9 mL, 5.390 mmol) followed by addition of HATU (1.0 g, 2.694 mmol) and the mixture stirred at RT for 30 min. Then (R)-pyrrolidin-3-ol (470 mg, 5.390 mmol) was added at the same temperature. The reaction mixture was stirred at RT overnight. The reaction was monitored by TLC and LCMS. After completion of reaction, the mixture was diluted with water (50 mL) and extracted with EtOAc (2×50 mL), the organic layer was washed with water (2×20 mL) and brine (20 mL) and dried over anhydrous sodium sulfate to obtain a crude product which was purified by reverse phase HPLC to obtain Compound 82a {[4-[5-(2-tert-butyl-4-pyridyl)-3-thienyl]-3-chloro-phenyl]-(3-hydroxypyrrolidin-1-yl)methanone} (132 mg) as a solid. Compound 82b, the (S)-enantiomer, can be prepared by using the (S)-pyrrolidin-3-ol.

$^1$H NMR (400 MHz, DMSO-d6) δ (ppm): 8.7 (d, J=5.2 Hz, 1H), 8.50 (s, 1H), 8.28 (s, 1H), 8.18-8.00 (m, 2H), 7.70 (m, 2H), 7.59 (m, 1H), 4.38-4.20 (m, 1H), 3.6 (m, 2H), 3.4 (m, 1H), 3.2 (m, 1H), 1.95 (m, 1H), 1.80 (m, 1H), 1.41 (s, 9H). LCMS=441.0 (M+1). LCMS=441.0 (M+1).

Example 83. Preparation of Compound Nos. 83, 83a, and 83b

Synthesis of 7-{4-[5-(2-tert-butylpyridin-4-yl)thiophen-3-yl]-3-chlorobenzoyl}-2,7-diazaspiro[4.5]decan-1-one

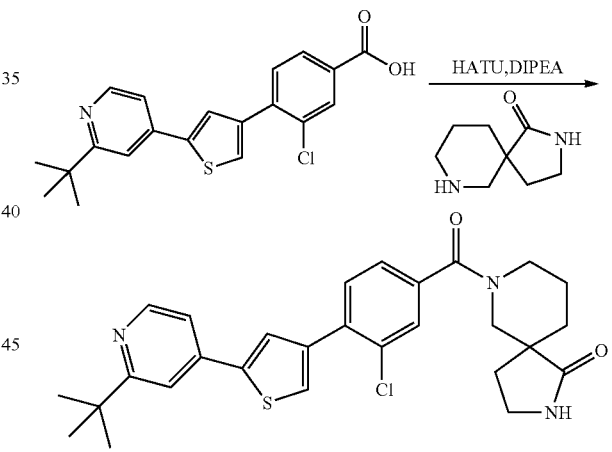

To a stirred solution of 4-[5-(2-tert-butyl-4-pyridyl)-3-thienyl]-3-chloro-benzoic acid (500 mg, 1.34 mmol) in DMF (10 mL), was added DIPEA (0.9 mL, 5.390 mmol) followed by addition of HATU (1.0 g, 2.694 mmol) and the mixture stirred at RT for 30 min. Then 3,9-diazaspiro[4.5]decan-4-one (1.0 g, 5.390 mmol) was added at the same temperature. The reaction mixture was stirred at RT overnight. The reaction was monitored by TLC and LCMS. After completion of reaction, the mixture was diluted with water (50 mL) and extracted with EtOAc (2×50 mL), the organic layer was washed with water (2×20 mL) and brine (20 mL) and dried over anhydrous sodium sulfate to obtain a crude product which was purified by reverse phase HPLC to obtain 9-[4-[5-(2-tert-butyl-4-pyridyl)-3-thienyl]-3-chloro-benzoyl]-3,9-diazaspiro[4.5]decan-4-one (140 mg) as a solid. The enantiomers can be prepared from chiral HPLC resolution of the racemate.

¹H NMR (400 MHz, DMSO-d6) δ (ppm): 8.72 (d, J=5.2 Hz, 1H), 8.48 (s, 1H), 8.24 (s, 1H), 8.18-8.00 (m, 2H), 7.70 (dd, J=5.3, 1.8 Hz, 1H), 7.60 (s, 1H), 7.42 (dd, J=7.9, 1.7 Hz, 1H), 4.20-4.00 (m, 2H), 3.80 (m, 2H), 3.20 (m, 3H), 3.0 (m, 1H), 2.00-1.87 (m, 2H), 1.70 (m, 2H), 1.41 (s, 9H). LCMS=508.1 (M+1).

Example 84. Preparation of Compound Nos. 84, 84a, and 84b

Synthesis of 2-tert-butyl-4-[4-(2-chloro-4-{octahydropyrrolo[1,2-a]piperazine-2-carbonyl}phenyl)thiophen-2-yl]pyridine

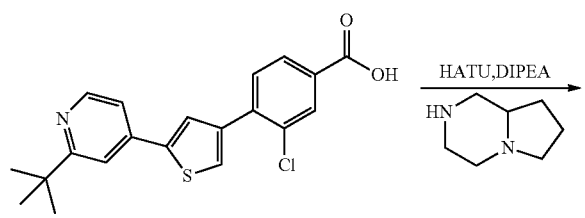

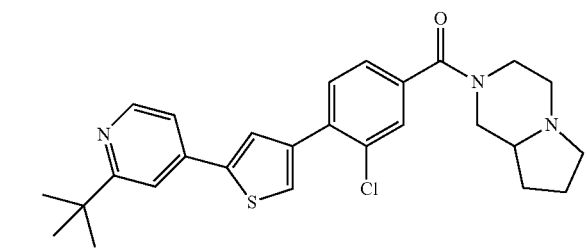

To a stirred solution of 4-[5-(2-tert-butyl-4-pyridyl)-3-thienyl]-3-chloro-benzoic acid (500 mg, 1.34 mmol) in DMF (10 mL), was added DIPEA (0.9 mL, 5.390 mmol) followed by addition of HATU (1.0 g, 2.694 mmol) and the mixture stirred at RT for 30 min. Then 1,2,3,4,6,7,8,8a-octahydropyrrolo[1,2-a]pyrazine (680 mg, 5.390 mmol) was added at the same temperature. The reaction mixture was stirred at RT overnight. The reaction was monitored by TLC and LCMS. After completion of reaction, the mixture was diluted with water (50 mL) and extracted with EtOAc (2×50 mL), the organic layer was washed with water (2×20 mL) and brine (20 mL) and dried over anhydrous sodium sulfate to obtain a crude product which was purified by reverse phase HPLC to obtain 3, 4, 6, 7, 8, 8a-hexahydro-1H-pyrrolo[1,2-a]pyrazin-2-yl-[4-[5-(2-tert-butyl-4-pyridyl)-3-thienyl]-3-chloro-phenyl]methanone (130 mg) as a solid. The enantiomers can be prepared from chiral HPLC resolution of the racemate.

¹H NMR (400 MHz, Dmso-d6) δ (ppm): 8.58 (d. J=5.2 Hz, 1H), 8.04 (s, 1H), 7.98 (s, 1H), 7.70-7.50 (s, 3H), 7.52-7.48 (m, 2H), 3.87 (m, 2H), 3.60 (m, 2H), 3.42 (s, 1H), 3.25 (m, 2H), 3.10 (s, 1H), 2.90 (s, 1H), 1.98 (m, 4H), 1.38 (s, 9H). LCMS=480.2 (M+1).

Example 85. Preparation of Compound Nos. 85, 85a, and 85b

Synthesis of 1-{4-[2-(2-tert-butylpyridin-4-yl)-1H-imidazol-4-yl]-3-chlorobenzoyl}piperidin-3-amine

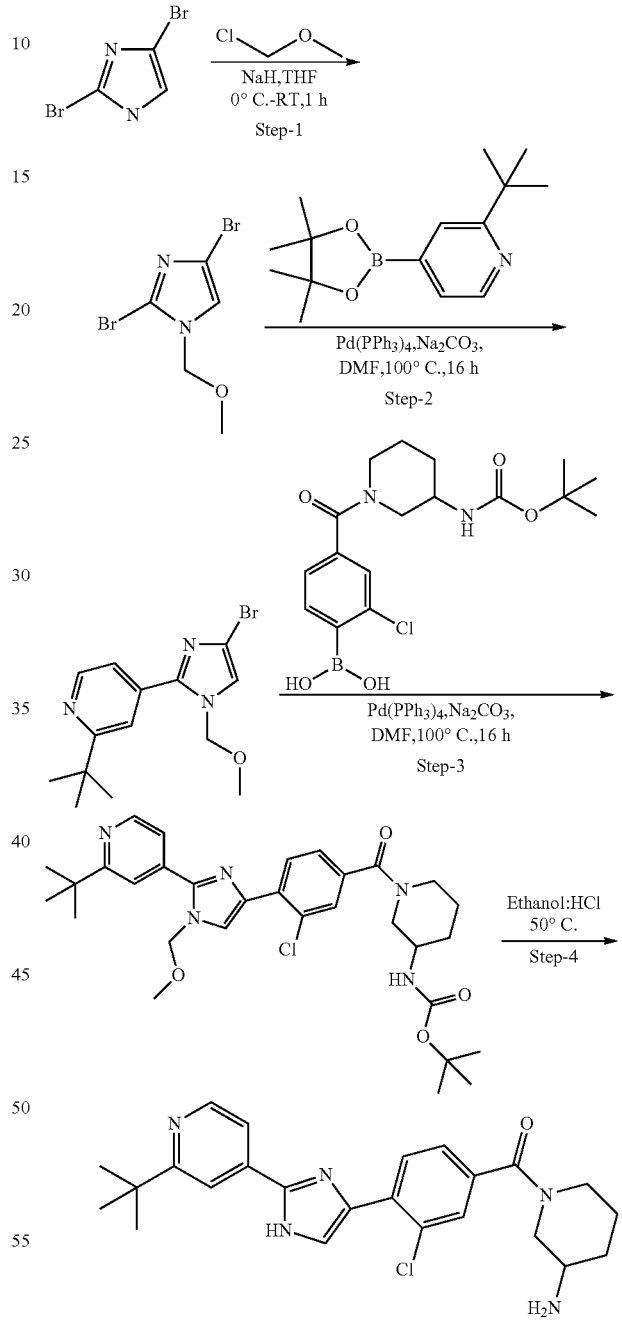

Step-1: Synthesis of 2,4-dibromo-1-(methoxymethyl)imidazole 2,4-Dibromo-1H-imidazole (3.0 g, 13.3 mmol) was taken in THF (25.0 mL) followed by addition of NaH (0.98 g, 20.0 mmol) at 0° C. The reaction mixture was stirred at RT for 15 min followed by addition of chloro(methoxy)methane (1.2 g, 14.6 mmol). The reaction mixture was stirred to RT for 1 h and completion of reaction was monitored by TLC and LCMS. After completion of reaction, ice cooled water (200 mL) was added and the mixture extracted with EtOAc (300 mL). The organic layer was separated, dried over anhydrous sodium sulfate and concentrated under reduced pressure to obtain 2,4-dibromo-1-(methoxymethyl)imidazole (4.0 g) as a crude product.

Step-2: Synthesis of 4-[4-bromo-1-(methoxymethyl) imidazol-2-yl]-2-tert-butyl-pyridine 2,4-Dibromo-1-(methoxymethyl)imidazole (2.0 g, 7.50 mmol), 2-tert-butyl-4-(4,4,5,5-tetramethyl-1,3,2-dioxaborolan-2-yl)pyridine (1.6 g, 6.00 mmol), sodium carbonate (2.0 g, 18.8 mmol) in water (5.0 mL), and dioxane (20.0 mL) were charged in a 100 mL glass bottle and purged with nitrogen gas for 15 min. Tetrakis (0.866 g, 0.80 mmol) and Xantphos (0.463 g, 0.86 mmol) were added then the reaction mixture was heated at 80° C. for 16 h. Completion of reaction was monitored by TLC and LCMS. After completion of reaction, the mixture was diluted with water (150 mL) and extracted with EtOAc (200 mL). The organic layer was separated and washed with brine (100 mL) and dried over anhydrous sodium sulfate to obtain crude 4-[4-bromo-1-(methoxymethyl)imidazol-2-yl]-2-tert-butyl-pyridine (3.0 g) as the freebase.

Step-3: Synthesis of tert-butyl N-[1-[4-[2-(2-tert-butyl-4-pyridyl)-1-(methoxymethyl) imidazol-4-yl]-3-chloro-benzoyl]-3-piperidyl] carbamate 4-[4-Bromo-1-(methoxymethyl)imidazol-2-yl]-2-tert-butyl-pyridine (500 mg, 1.54 mmol), [4-[3-(tert-butoxycarbonylamino)piperidine-1-carbonyl]-2-chloro-phenyl]boronic acid (1.18 g, 3.08 mmol), and sodium carbonate (405 mg, 3.85 mmol) in water (1.0 mL), DMF (5.0 mL) were charged in a 25.0 mL glass bottle and purged with nitrogen gas for 15 min. After addition of tetrakis (178 mg, 0.015 mmol), the reaction mixture was heated at 100° C. for 16 h. Completion of reaction was monitored by TLC and LCMS. After completion of reaction, the mixture was diluted with water (100 mL) and extracted with EtOAc (150 mL). The organic layer was separated and washed with brine (50 mL), dried over anhydrous sodium sulfate and concentrated under reduced pressure. The crude product was purified by reverse phase HPLC to obtain tert-butyl N-[1-[4-[2-(2-tert-butyl-4-pyridyl)-1-(methoxymethyl) imidazol-4-yl]-3-chloro-benzoyl]-3-piperidyl] carbamate (200 mg) as freebase.

Step-4: Synthesis of (3-amino-1-piperidyl)-[4-[2-(2-tert-butyl-4-pyridyl)-1H-imidazol-4-yl]-3-chloro-phenyl]methanone tert-Butyl N-[1-[4-[2-(2-tert-butyl-4-pyridyl)-1-(methoxymethyl)imidazol-4-yl]-3-chloro-benzoyl]-3-piperidyl]carbamate (200 mg, 0.34 mmol) was taken in 1.25M HCl in EtOH (5.0 mL) under nitrogen atmosphere. The reaction mixture was stirred at 50° C. for 2 h. Completion of reaction was monitored by TLC and LCMS. After completion of reaction, the mixture was concentrated under reduced pressure to obtain the crude product which was purified by reverse phase HPLC method to obtain (3-amino-1-piperidyl)-[4-[2-(2-tert-butyl-4-pyridyl)-1H-imidazol-4-yl]-3-chloro-phenyl]methanone (15 mg) as the HCl salt, a yellow solid. The enantiomers can be prepared from chiral HPLC resolution of the racemate.

$^1$H NMR (400 MHz, Methanol-d4) δ (ppm): 8.74 (d, J=6.3 Hz, 1H), 8.57 (s, 1H), 8.43 (d, J=6.4 Hz, 1H), 8.27-8.17 (m, 2H), 7.68 (d, J=1.7 Hz, 1H), 7.53 (d, J=8.4 Hz, 1H), 4.41 (s, 1H), 3.64 (s, 1H), 3.39 (s, 1H), 2.18 (s, 1H), 1.84 (s, 1H), 1.73 (d, J=15.5 Hz, 2H), 1.60 (s, 9H), 1.29 (s, 2H).

Example 86. Preparation of Compound No. 86

Synthesis of 1-{4-[4-(2-tert-butylpyridin-4-yl)thiophen-2-yl]-3-chlorobenzoyl}piperidin-4-ol

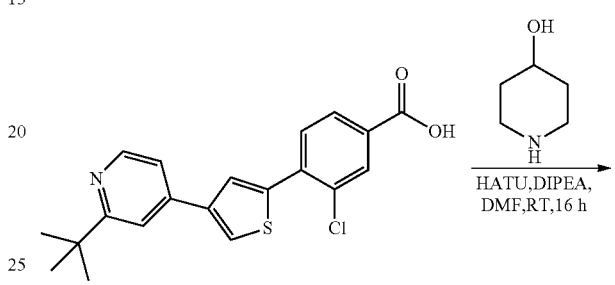

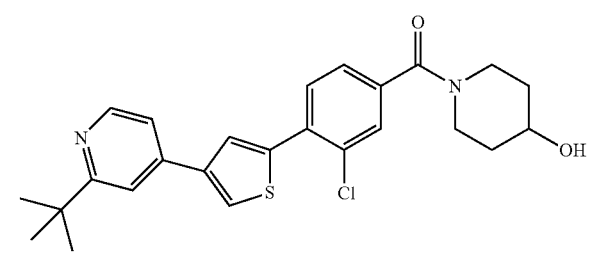

4-[4-(2-tert-Butyl-4-pyridyl)-2-thienyl]-3-chloro-benzoic acid (300 mg, 0.80 mmol) was taken in DMF (6.0 mL), followed by addition of DIPEA (0.60 mL, 3.22 mmol), HATU (612 mg, 1.61 mmol), under nitrogen atmosphere. The reaction mixture was stirred at RT for 0.5 h, followed by addition of piperidin-4-ol (322 mg, 3.22 mmol). The reaction mixture was stirred at RT for 16 h. After completion of reaction, water (50 mL) was added and the mixture extracted with EtOAc (2×50 mL). The combined organic layer was washed with brine (50 mL), dried over anhydrous sodium sulfate and concentrated under reduced pressure to obtain the crude product which was purified by reverse phase HPLC to obtain [4-[4-(2-tert-butyl-4-pyridyl)-2-thienyl]-3-chloro-phenyl]-(4-hydroxy-1-piperidyl)methanone (40 mg) as the freebase.

$^1$H NMR (400 MHz, Methanol-d4) δ (ppm): 8.70-8.60 (m, 2H), 8.31 (s, 1H), 8.24 (d, J=6.4 Hz, 1H), 8.14 (d, J=1.6 Hz, 1H), 7.82 (d, J=8.0 Hz, 1H), 7.64 (d, J=1.7 Hz, 1H), 7.47 (dd, J=7.9, 1.7 Hz, 1H), 4.18 (s, 1H), 3.93 (dt, J=8.4, 4.5 Hz, 1H), 3.67 (s, 1H), 3.40 (s, 2H), 1.97 (s, 1H), 1.86 (s, 1H), 1.58 (s, 9H), 1.51 (s, 2H). LCMS: -(M+1) 454.0.

Example 87. Preparation of Compound Nos. 87, 87a and 87b

Synthesis of (3S)-1-{4-[4-(2-tert-butylpyridin-4-yl)-5-methylthiophen-2-yl]-3-chlorobenzoyl}piperidin-3-amine

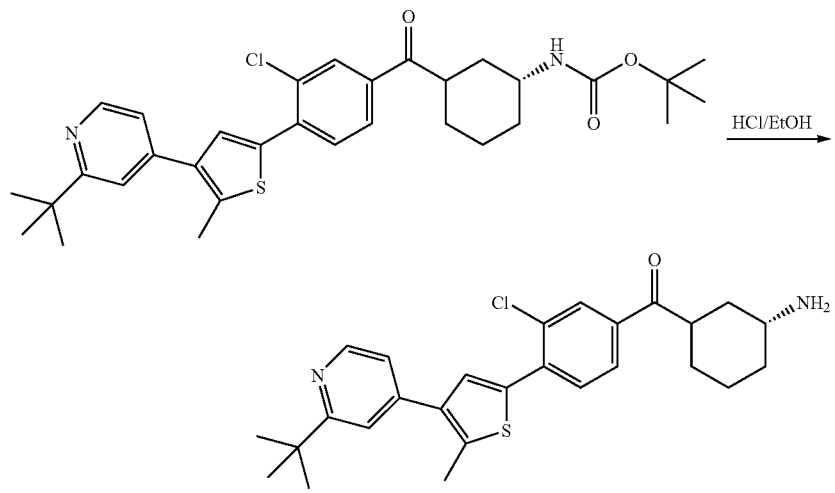

tert-Butyl N-[(1S)-3-[4-[4-(2-tert-butyl-4-pyridyl)-5-methyl-2-thienyl]-3-chloro-benzoyl]cyclohexyl]carbamate (40 mg, 0.074 mmol) was taken in EtOH (3.0 mL) at 0° C., followed by dropwise addition of 1.25M HCl in EtOH (3.0 mL) under nitrogen atmosphere. The reaction mixture was stirred at RT for 16 h. Completion of reaction was monitored by TLC and LCMS. After completion of reaction, the mixture was concentrated to obtain Compound 87a {[(3S)-3-aminocyclohexyl]-[4-[4-(2-tert-butyl-4-pyridyl)-5-methyl-2-thienyl]-3-chloro-phenyl]methanone} (30 mg) as the HCl salt white solid. Compound 87b, the (R)-enantiomer, was prepared using the opposite (R)-enantiomeric starting material.

$^1$H NMR (400 MHz, DMSO-d6) δ (ppm): 8.70 (d, J=7.7 Hz, 1H), 7.98 (m, 2H), 7.82 (m, 2H), 7.62 (s, 1H), 7.48 (d, J=7.7 Hz, 1H), 4.18 (s, 1H), 3.28 (m, 3H), 2.64 (s, 3H), 2.02 (s, 2H), 1.78 (s, 1H), 1.60 (s, 1H), 1.41 (s, 10H). LCMS= (M+1) 468.1.

Example 88. Preparation of Compound No. 88

Synthesis of 1-{4-[4-(2-tert-butylpyridin-4-yl)thiophen-2-yl]-3-chlorobenzoyl}piperidine-4-carboxylic acid

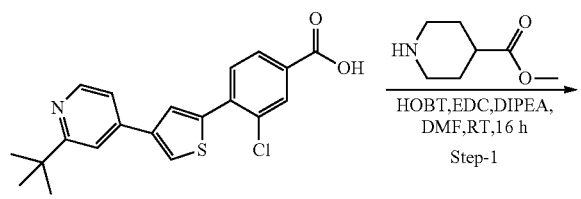

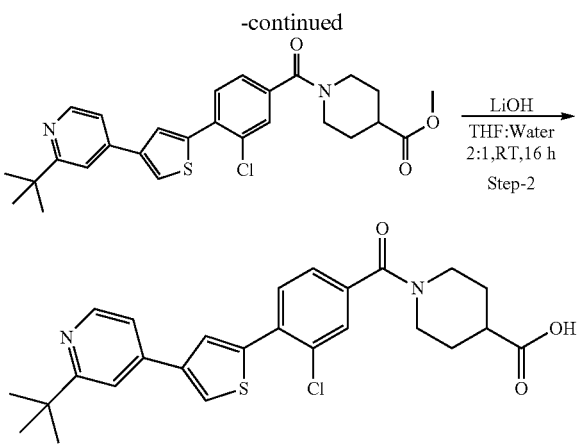

Step-1: Synthesis of methyl 1-[4-[4-(2-tert-butyl-4-pyridyl)-2-thienyl]-3-chloro-benzoyl]piperidine-4-carboxylate 4-[4-(2-tert-Butyl-4-pyridyl)-2-thienyl]-3-chloro-benzoic acid (500 mg, 1.34 mmol) was taken in DMF (5 mL), followed by addition of DIPEA (1 mL, 5.36 mmol), HOBT (308 mg, 2.01 mmol), and EDC (385 mg, 2.01 mmol) under nitrogen atmosphere. The reaction mixture was stirred at RT for 0.5 h, followed by addition of methyl piperidine-4-carboxylate (760 mg, 5.33 mmol). The reaction mixture was stirred at RT for 16 h. After completion of reaction, water (100 mL) was added and the mixture extracted with EtOAc (3×50 mL). The combined organic layer was washed with brine (50 mL), dried over anhydrous sodium sulfate and concentrated under reduced pressure to obtain a crude product, which was purified by Reverse phase HPLC to obtain methyl 1-[4-[4-(2-tert-butyl-4-pyridyl)-2-thienyl]-3-chloro-benzoyl]piperidine-4-carboxylate (150 mg) as the freebase.

Step-2: Synthesis of 1-[4-[4-(2-tert-butyl-4-pyridyl)-2-thienyl]-3-chloro-benzoyl] piperidine-4-carboxylic acid Methyl 1-[4-[4-(2-tert-butyl-4-pyridyl)-2-thienyl]-3-chloro-benzoyl]piperidine-4-carboxylate (150 mg, 0.30 mmol) was taken in THF:Water (4:2 mL), followed by addition of lithium hydroxide (37 mg, 0.90 mmol), under nitrogen atmosphere. The reaction mixture was stirred at RT for 16 h. After completion of reaction, the mixture was concentrated and water (30 mL) was added and the mixture extracted with DCM (2×50 mL). The aqueous layer was separated and cooled to 0° C. then acidified slowly with 1 N HCl to make up to pH=2 and extracted with EtOAc (3×50 mL). The organic layer was separated and dried over anhydrous sodium sulfate and concentrated under reduced pressure to obtain a crude product, which was purified by Reverse phase HPLC to obtain 1-[4-[4-(2-tert-butyl-4-pyridyl)-2-thienyl]-3-chloro-benzoyl]piperidine-4-carboxylic acid (10 mg) as the freebase.

$^1$H NMR (400 MHz, DMSO-d6) δ (ppm): 8.54 (d, J=5.1 Hz, 1H), 8.37 (s, 1H), 8.08 (s, 1H), 7.85 (d, J=8.0 Hz, 1H), 7.77 (s, 1H), 7.65-7.55 (m, 2H), 7.45 (d, J=7.9 Hz, 1H), 4.29 (s, 1H), 3.56 (s, 1H), 3.16 (s, 2H), 2.99 (s, 1H), 1.91 (s, 1H), 1.82 (s, 1H), 1.54 (d, J=12.9 Hz, 2H), 1.37 (s, 9H). LCMS= (M+1) 483.2.

Example 89. Preparation of Compound Nos. 89, 89a, and 89b

Synthesis of 1-{4-[4-(2-tert-butylpyridin-4-yl)thiophen-2-yl]-3-chlorobenzoyl}piperidin-3-ol

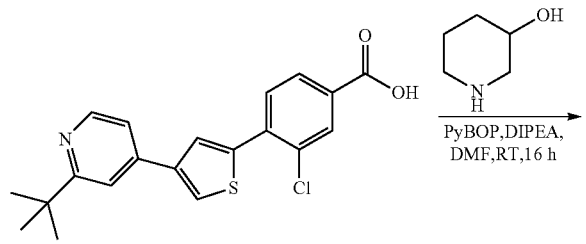

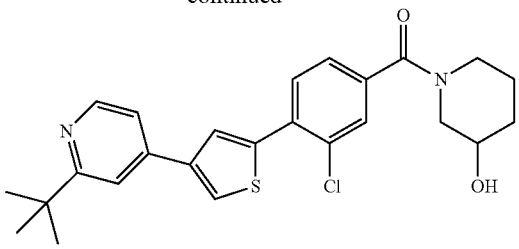

4-[4-(2-tert-Butyl-4-pyridyl)-2-thienyl]-3-chloro-benzoic acid (300 mg, 0.80 mmol) was taken in DMF (6 mL), followed by addition of DIPEA (0.60 mL, 3.22 mmol), PyBOP (838 mg, 1.61 mmol), under nitrogen atmosphere. The reaction mixture was stirred at RT for 0.5 h, followed by addition of piperidin-3-ol (322 mg, 3.22 mmol). The reaction mixture was stirred at RT for 16 h. After completion of reaction, water (50 mL) was added and the mixture extracted with EtOAc (2×50 mL). The combined organic layer was washed with brine (50 mL), dried over anhydrous sodium sulfate and concentrated under reduced pressure to obtain a crude product, which was purified by Reverse phase HPLC to obtain [4-[4-(2-tert-butyl-4-pyridyl)-2-thienyl]-3-chloro-phenyl]-(3-hydroxy-1-piperidyl)methanone (16 mg) as the HCl salt. The enantiomers were prepared from chiral HPLC resolution of the racemate, to give Compound 89a [(R)-(4-(4-(2-(tert-butyl)pyridin-4-yl)thiophen-2-yl)-3-chlorophenyl)(3-hydroxypiperidin-1-yl)methanone], and Compound 89b [(S)-(4-(4-(2-(tert-butyl)pyridin-4-yl)thiophen-2-yl)-3-chlorophenyl)(3-hydroxypiperidin-1-yl)methanone].

$^1$H NMR (400 MHz, Methanol-d4) δ (ppm): 8.72-8.60 (m, 2H), 8.33 (s, 1H), 8.26 (d, J=6.6 Hz, 1H), 8.15 (s, 1H), 7.81 (d, J=8.0 Hz, 1H), 7.67 (d, J=11.4 Hz, 1H), 7.49 (s, 1H), 4.11 (d, J=11.6 Hz, 1H), 3.72 (s, 2H), 3.55 (d, J=13.1 Hz, 1H), 1.96 (s, 2H), 1.82 (s, 1H), 1.59 (s, 9H), 1.54 (s, 1H), 1.29 (s, 1H). LCMS: –(M+1) 455.3.

Example 90. Preparation of Compound Nos. 90, 90a, and 90b

Synthesis of tert-butyl N-[(3R)-1-{4-[5-(2-tert-butylpyridin-4-yl)thiophen-3-yl]-3-chlorobenzoyl}pyrrolidin-3-yl]carbamate

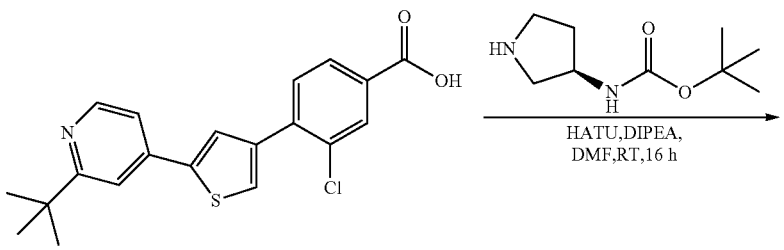

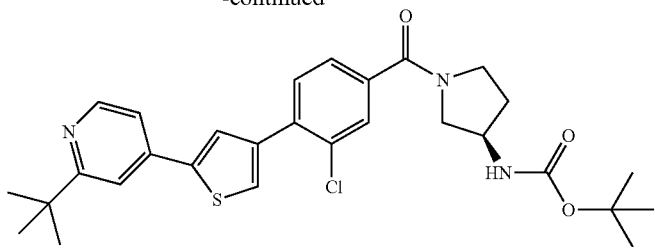

4-[4-(2-tert-Butyl-4-pyridyl)-2-thienyl]-3-chloro-benzoic acid (300 mg, 0.80 mmol) was taken in DMF (5 mL), followed by addition of DIPEA (0.6 mL, 3.22 mmol), HATU (612 mg, 1.61 mmol), under nitrogen atmosphere. The reaction mixture was stirred at RT for 0.5 h, followed by addition of tert-butyl N-[(3R)-pyrrolidin-3-yl]carbamate (600 mg, 3.22 mmol). The reaction mixture was stirred at RT for 16 h. After completion of reaction, water (100 mL) was added and the mixture extracted with EtOAc (3×50 mL). The combined organic layer was washed with brine (50 mL), dried over anhydrous sodium sulfate and concentrated under reduced pressure to obtain a crude product, which was purified by reverse phase HPLC to obtain Compound 90a {tert-butyl N-[(3R)-1-[4-[5-(2-tert-butyl-4-pyridyl)-3-thienyl]-3-chloro-benzoyl]pyrrolidin-3-yl]carbamate} (10 mg) as the freebase. Compound 90b, the (S)-enantiomer, can be prepared by using the (S)-carbamate reagent.

$^1$H NMR (400 MHz, DMSO-d6) δ (ppm): 8.54 (d, J=5.1 Hz, 1H), 8.38 (d, J=1.5 Hz, 1H), 8.09 (s, 1H), 7.86 (dd, J=8.1, 3.9 Hz, 1a), 7.79-7.67 (m, 2H), 7.61-7.52 (m, 2H), 7.23 (s, 1H), 4.12 (s, 1H), 3.60 (dd, J=23.0, 6.8 Hz, 1H), 3.42 (s, 1H), 3.24 (s, 1H), 2.03 (dd, J=13.1, 6.7 Hz, 1H), 1.79 (s, 1H), 1.68 (s, 1H), 1.33 (s, 18H). LCMS=(M+1) 540.2.

Example 91. Preparation of Compound Nos. 91, 91a, and 91b

Synthesis of (3R)-1-{4-[4-(2-tert-butylpyridin-4-yl)thiophen-2-yl]-3-chlorobenzoyl}piperidine-3-carboxylic acid

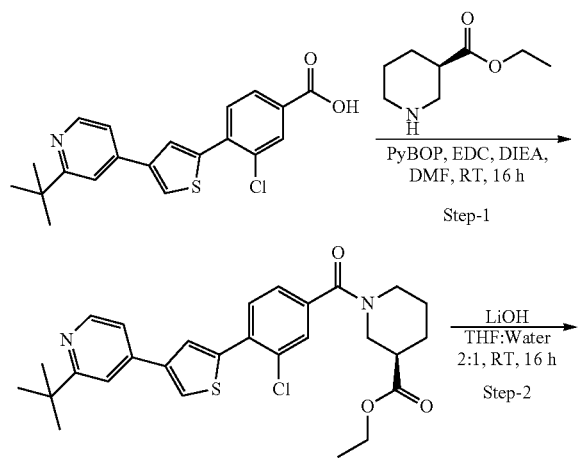

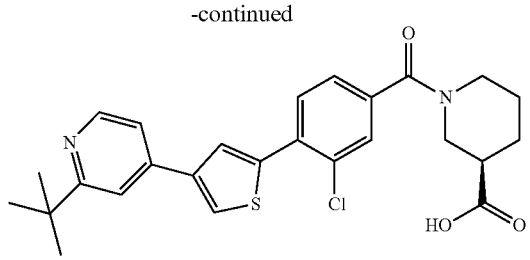

Step-1: Synthesis of ethyl (3R)-1-[4-[4-(2-tert-butyl-4-pyridyl)-2-thienyl]-3-chloro-benzoyl]piperidine-3-carboxylate 4-[4-(2-tert-Butyl-4-pyridyl)-2-thienyl]-3-chloro-benzoic acid (300 mg, 0.80 mmol) was taken in DMF (5 mL), followed by addition of DIPEA (0.6 mL, 3.22 mmol), HATU (612 mg, 1.61 mmol), under nitrogen atmosphere. The reaction mixture was stirred at RT for 0.5 h, followed by addition of ethyl (3R)-piperidine-3-carboxylate (506 mg, 3.22 mmol). The reaction mixture was stirred at RT for 16 h. After completion of reaction, water (100 mL) was added and the mixture extracted with EtOAc (3×50 mL). The combined organic layer was washed with brine (50 mL), dried over anhydrous sodium sulfate and concentrated under reduced pressure to obtain a crude product, which was purified by Reverse phase HPLC to obtain ethyl (3R)-1-[4-[4-(2-tert-butyl-4-pyridyl)-2-thienyl]-3-chloro-benzoyl]piperidine-3-carboxylate (150 mg) as the freebase.

Step-2: Synthesis of (3R)-1-[4-[4-(2-tert-butyl-4-pyridyl)-2-thienyl]-3-chloro-benzoyl]piperidine-3-carboxylic acid Ethyl (3R)-1-[4-[4-(2-tert-butyl-4-pyridyl)-2-thienyl]-3-chloro-benzoyl]piperidine-3-carboxylate (150 mg, 0.29 mmol) was taken in THF:Water (4:2 mL), followed by addition of lithium hydroxide (61 mg, 1.46 mmol), under nitrogen atmosphere. The reaction mixture was stirred at RT for 16 h. After completion of reaction, the mixture was completely concentrated and water (30 mL) was added and the mixture extracted with DCM (2×50 mL). Then aqueous layer was separated and cooled to 0° C. then acidified slowly with 1 N HCl to make up to pH=2 and extracted with EtOAc (3×50 mL). The organic layer was separated and dried over anhydrous sodium sulfate and concentrated under reduced pressure to obtain a crude product, which was purified by Reverse phase HPLC to obtain Compound 91a ((3R)-1-[4-[4-(2-tert-butyl-4-pyridyl)-2-thienyl]-3-chloro-benzoyl]piperidine-3-carboxylic acid) (18 mg) as the freebase. Compound 91b, the (S)-enantiomer, can be prepared by using the (S)-carboxylate reagent in Step-1.

¹H NMR (400 MHz, DMSO-d6) δ (ppm): 8.54 (d, J=5.1 Hz, 1H), 8.37 (s, 1H), 8.08 (s, 1H), 7.85 (d, J=8.0 Hz, 1H), 7.77 (s, 1H), 7.65-7.55 (m, 2H), 7.45 (d, J=7.9 Hz, 1H), 4.29 (s, 1H), 3.59 (s, 1H), 3.45 (s, 2H), 3.25 (s, 1H), 3.16 (s, 1H), 2.39 (s, 1H), 1.88 (s, 1H), 1.58 (s, 1H), 1.25 (s, 1H), 1.37 (s, 9H). LCMS=(M+1) 483.3.

Example 92. Preparation of Compound No. 92

Synthesis of 2-tert-butyl-4-[5-(2-chloro-4-{3H,4H,5H,6H,7H-imidazo[4,5-c]pyridine-5-carbonyl}phenyl)thiophen-3-yl]pyridine

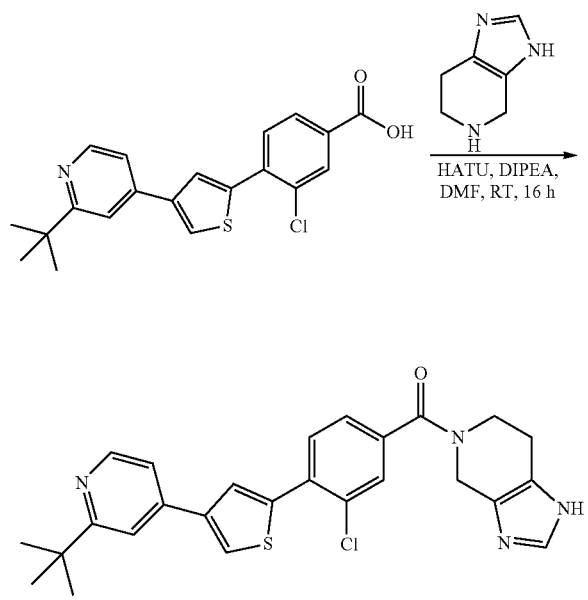

4-[4-(2-tert-Butyl-4-pyridyl)-2-thienyl]-3-chloro-benzoic acid (300 mg, 0.80 mmol) was taken in DMF (6 mL), followed by addition of DIPEA (0.60 mL, 3.22 mmol), HATU (600 mg, 1.61 mmol), under nitrogen atmosphere. The reaction mixture was stirred at RT for 0.5 h, followed by addition of 4,5,6,7-tetrahydro-3H-imidazo[4,5-c]pyridine (508 mg, 3.22 mmol). The reaction mixture was stirred at RT for 16 h. After completion of reaction, water (50 mL) was added and the mixture extracted with EtOAc (2×50 mL). The combined organic layer was washed with brine (50 mL), dried over anhydrous sodium sulfate and concentrated under reduced pressure to obtain a crude product, which was purified by Reverse phase HPLC to obtain [4-[4-(2-tert-butyl-4-pyridyl)-2-thienyl]-3-chloro-phenyl]-(1,4,6,7-tetrahydroimidazo[4, 5-c]pyridin-5-yl)methanone (20 mg) as the HCl salt.

¹H NMR (400 MHz, Methanol-d4) δ (ppm): 8.84 (s, 1H), 8.72 (d, J=1.4 Hz, 1H), 8.65 (d, J=6.3 Hz, 1H), 8.36-8.24 (m, 2H), 8.19 (d, J=1.6 Hz, 1H), 7.88 (d, J=8.0 Hz, 1H), 7.76 (s, 1H), 7.61-7.53 (m, 1H), 4.11 (s, 2H), 3.84 (s, 2H), 2.92 (s, 2H), 1.59 (s, 9H). LCMS: -(M+1) 477.3.

Example 93. Preparation of Compound No. 93

Synthesis of 4-{4-[4-(2-tert-butylpyridin-4-yl)thiophen-2-yl]-3-chlorobenzoyl}piperazin-2-one

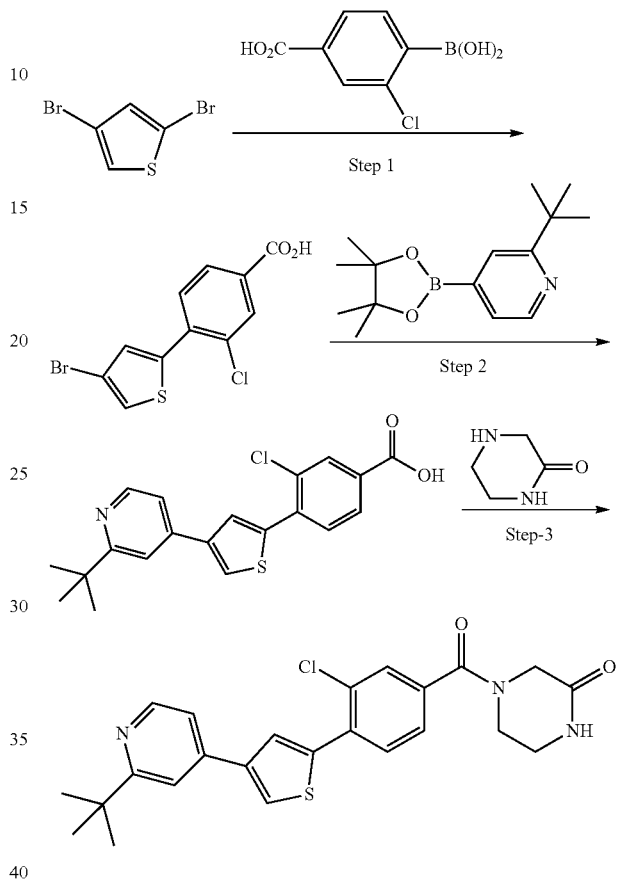

Step-1: Synthesis of 4-(4-bromo-2-thienyl)-3-chloro-benzoic acid 2,4-Dibromothiophene (10 g, 41.84 mmol), 4-borono-3-chloro-benzoic acid (10 g, 50.02 mmol), and sodium carbonate (10.9 g, 104.1 mmol) in water (15 mL), DMF (100 mL) were charged in a 250 mL glass bottle and purged with nitrogen gas for 20 min. After adding tetrakis (4.8 g, 4.16 mmol), the reaction mixture was heated at 100° C. for 16 h. The reaction was monitored by TLC and LCMS. After completion of reaction, water (200 mL) was added and filtered with washings of ether and hexane obtain 4-(4-bromo-2-thienyl)-3-chloro-benzoic acid (5 g) as the free-base, a white solid.

Step-2: Synthesis of 4-[4-(2-tert-butyl-4-pyridyl)-2-thienyl]-3-chloro-benzoic acid 4-(4-Bromo-2-thienyl)-3-chloro-benzoic acid (2 g, 6.30 mmol), 2-tert-butyl-4-(4,4,5,5-tetramethyl-1,3,2-dioxaborolan-2-yl)pyridine (1.81 g, 6.94 mmol), and sodium carbonate (1.65 g, 15.7 mmol) in water (5 mL), DMF (20 mL) were charged in a 100 mL glass bottle and purged with nitrogen gas for 15 min. After adding tetrakis (0.720 g, 0.63 mmol), the reaction mixture was heated at 100° C. for 16 h. The reaction was monitored by TLC and LCMS. After completion of reaction, the mixture was cooled to 0° C. and 3M HCl was added dropwise to make pH=2. The brown precipitate obtained was filtered with washings of hexane and EtOAc to obtain 4-[4-(2-tert-butyl-4-pyridyl)-2-thienyl]-3-chloro-benzoic acid (2 g) as the freebase, an off-white solid.

Step-3: Synthesis of 4-[4-[4-(2-tert-butyl-4-pyridyl)-2-thienyl]-3-chloro-benzoyl]piperazin-2-one 4-[4-(2-tert-Butyl-4-pyridyl)-2-thienyl]-3-chloro-benzoic acid (500 mg, 1.34 mmol) was taken in DMF (10 mL), followed by addition of DIPEA (0.96 mL, 5.38 mmol), HATU (994 mg, 2.68 mmol), under nitrogen atmosphere. The reaction mixture was stirred at RT for 0.5 h, followed by addition of piperazin-2-one (536 mg, 5.36 mmol). The reaction mixture was stirred at RT for 16 h. After completion of reaction, water (150 mL) was added and the mixture extracted with EtOAc (2×50 mL). The combined organic layer was washed with brine (50 mL), dried over anhydrous sodium sulfate and concentrated under reduced pressure to obtain a crude product, which was purified by Reverse phase HPLC to obtain 4-[4-[4-(2-tert-butyl-4-pyridyl)-2-thienyl]-3-chloro-benzoyl]piperazin-2-one (35 mg) as the freebase.

$^1$H NMR (400 MHz, DMSO-d6) δ (ppm): 8.54 (d, J=5.1 Hz, 1H), 8.39 (d, J=1.5 Hz, 1H), 8.17 (s, 1H), 8.10 (s, 1H), 7.89 (d, J=8.0 Hz, 1H), 7.77 (s, 1H), 7.55 (dd, J=23.5, 6.3 Hz, 2H), 4.09 (s, 1H), 3.96 (s, 1H), 3.78 (s, 1H), 3.54 (s, 1H), 3.25 (s, 2H), 1.37 (s, 9H). LCMS=(M+1) 454.0.

Example 94. Preparation of Compound Nos. 94, 94a, and 94b

Synthesis of 1-[1-{4-[4-(2-tert-butylpyridin-4-yl)thiophen-2-yl]-3-chlorobenzoyl}piperidin-3-yl]imidazolidin-2-one

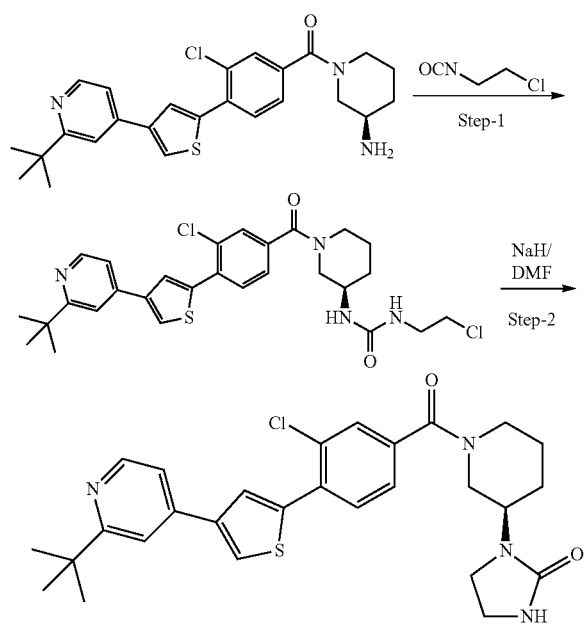

Step-1: Synthesis of 1-[1-[4-[5-(2-tert-butyl-4-pyridyl)-2-thienyl]-3-chloro-benzoyl]-3-piperidyl]-3-(2-chloroethyl)urea To a stirred solution of (3-amino-1-piperidyl)-[4-[5-(2-tert-butyl-4-pyridyl)-2-thienyl]-3-chloro-phenyl]methanone (500 mg, 1.098 mmol) in DCM (10 mL) was added triethylamine (0.46 mL, 3.29 mmol) at 0° C. and stirred for 5 min. Then 1-chloro-2-isocyanato-ethane (174 mg, 1.648 mmol) was added and the mixture stirred for RT for 1 h. The reaction was monitored by LCMS. After completion of reaction, the mixture was quenched with water and extracted with DCM (2×50 mL), the organic layer washed with water (20 mL). The organic layer was dried over anhydrous sodium sulfate and concentrated under reduced pressure to obtain 1-[1-[4-[5-(2-tert-butyl-4-pyridyl)-2-thienyl]-3-chloro-benzoyl]-3-piperidyl]-3-(2-chloroethyl) urea (500 mg) used in the next step.

Step-2: Synthesis of 1-[1-[4-[5-(2-tert-butyl-4-pyridyl)-2-thienyl]-3-chloro-benzoyl]-3-piperidyl] imidazolidin-2-one To a stirred solution of (1-[1-[4-[5-(2-tert-butyl-4-pyridyl)-2-thienyl]-3-chloro-benzoyl]-3-piperidyl]-3-(2-chloroethyl) urea (500 mg, 0.893 mmol) in DMF (10 mL) was added NaH (60% mineral oil) (71 mg, 1.876 mmol) at 0° C. and stirred for 5 min at RT. The reaction mixture was heated at 70° C. for 3 h. The reaction was monitored by LCMS. After completion of reaction, the mixture was quenched with water and extracted with EtOAc (2×50 mL), the organic layer washed with water (20 mL) and brine solution. The organic layer was dried over anhydrous sodium sulfate and concentrated under reduced pressure to obtain a crude product, which was purified by chromatography to obtain 1-[1-[4-[5-(2-tert-butyl-4-pyridyl)-2-thienyl]-3-chloro-benzoyl]-3-piperidyl]imidazolidin-2-one (150 mg) as the freebase. The enantiomers can be prepared from chiral HPLC resolution of the racemate.

$^1$H NMR (400 MHz, Methanol-d4) δ (ppm): 8.49 (d, J=5.2 Hz, 1H), 8.11 (d, J=1.6 Hz, 1H), 7.90 (s, 1H), 7.82-7.72 (m, 2H), 7.66-7.51 (m, 2H), 7.46 (s, 1H), 4.57 (m, 1H), 3.74 (m, 2H), 3.55 (m, 2H), 3.42 (m, 3H), 3.01 (m, 2H), 1.81 (t, J=10.5 Hz, 2H), 1.67 (m, 1H), 1.43 (s, 9H). LCMS=523 (M+1).

Example 95. Preparation of Compound Nos. 95, 95a, and 95b

Synthesis of 1-{4-[4-(2-tert-butylpyridin-4-yl)thiophen-2-yl]-3-chlorobenzoyl}-3-methylpiperidin-3-amine

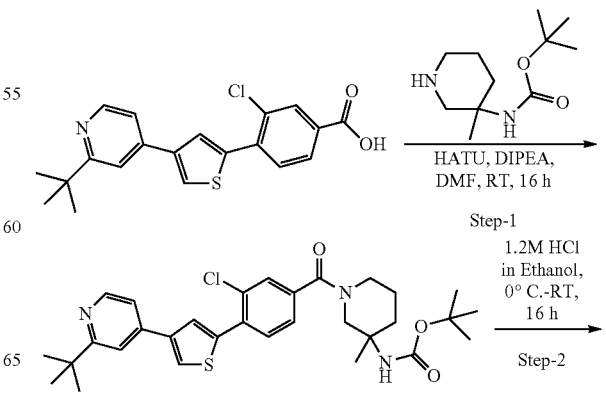

-continued

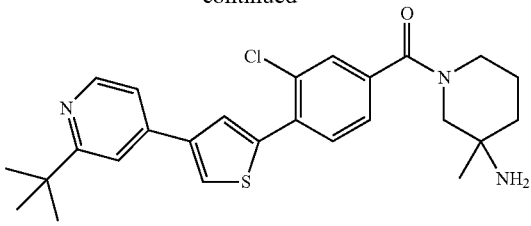

Step-1: Synthesis of tert-butyl N-[1-[4-[4-(2-tert-butyl-4-pyridyl)-2-thienyl]-3-chloro-benzoyl]-3-methyl-3-piperidyl]carbamate To a solution of 4-[4-(2-tert-butyl-4-pyridyl)-2-thienyl]-3-chloro-benzoic acid (300 mg, 0.8086 mmol) in DMF (10 mL), was added DIPEA (418 mg, 3.2344 mmol), followed by the addition of HATU (615 mg, 1.6172 mmol). The reaction mixture was stirred for 30 min at RT. tert-Butyl N-(3-methyl-3-piperidyl)carbamate (433 mg, 2.022 mmol) was added and the reaction mixture stirred for 16 h at RT. The reaction was monitored by TLC and LCMS. On completion, the reaction mixture was diluted with water (50 mL) and extracted with EtOAc (2×100 mL). The combined organic layer was washed with water (2×50 mL) and brine (2×50 mL) and dried over anhydrous sodium sulfate to obtain 500 mg of crude product. The crude compound was purified by reverse phase combi-flash to afford tert-butyl N-[1-[4-[4-(2-tert-butyl-4-pyridyl)-2-thienyl]-3-chloro-benzoyl]-3-methyl-3-piperidyl]carbamate (300 mg) as a white solid.

Step-2: Synthesis of (3-amino-3-methyl-1-piperidyl)-[4-[4-(2-tert-butyl-4-pyridyl)-2-thienyl]-3-chloro-phenyl] methanone To a solution of tert-butyl N-[1-[4-[4-(2-tert-butyl-4-pyridyl)-2-thienyl]-3-chloro-benzoyl]-3-methyl-3-piperidyl]carbamate (300 mg, 0.529 mmol) in EtOH (5 mL), was added 1.2M ethanolic HCl (5 mL) at 0° C. The reaction mixture was stirred for 16 h at RT. The reaction was monitored by TLC and LCMS. The reaction mixture was concentrated under reduced pressure to obtain (3-amino-3-methyl-1-piperidyl)-[4-[4-(2-tert-butyl-4-pyridyl)-2-thienyl]-3-chloro-phenyl] methanone (50 mg) as a white solid. The enantiomers were prepared by chiral HPLC resolution of the racemate, to give Compound 95a [(R)-(3-amino-3-methylpiperidin-1-yl)(4-(4-(2-(tert-butyl)pyridin-4-yl)thiophen-2-yl)-3-chlorophenyl)methanone] and Compound 95b [(R)-(3-amino-3-methylpiperidin-1-yl)(4-(4-(2-(tert-butyl)pyridin-4-yl)thiophen-2-yl)-3-chlorophenyl)methanone].

$^1$H NMR (400 MHz, Methanol-d4) δ (ppm): 8.70 (s, 1H), 8.64 (d, J=6.1 Hz, 1H), 8.32 (s, 1H), 8.26 (d, J=6.1 Hz, 1H), 8.17 (s, 1H), 7.85 (d, J=7.8 Hz, 1H), 7.76 (s, 1H), 7.55 (d, J=7.6 Hz, 1H), 3.59 (d, J=13.5 Hz, 2H), 1.93 (s, 2H), 1.77 (s, 2H), 1.59 (s, 9H), 1.43 (s, 2H), 1.30 (s, 3H). LCMS=468.2 (M+1).

Example 96. Preparation of Compound Nos. 96, 96a and 96b

Synthesis of (3R)-1-{4-[4-(2-tert-butylpyridin-4-yl)thiophen-2-yl]-3-chlorobenzoyl}pyrrolidin-3-amine

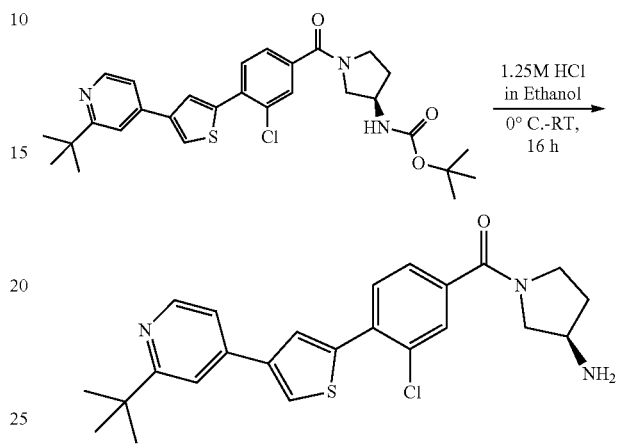

tert-Butyl N-[(3R)-1-[4-[4-(2-tert-butyl-4-pyridyl)-2-thienyl]-3-chloro-benzoyl]pyrrolidin-3-yl]carbamate (135 mg, 0.244 mmol) was taken in EtOH (3 mL) at 0° C., followed by dropwise addition of 1.25 M HCl in EtOH (3 mL) under nitrogen atmosphere. The reaction mixture was stirred at RT for 16 h. The reaction was monitored by TLC and LCMS. After completion of reaction, the mixture was concentrated to obtain a crude product, which was purified by reverse phase HPLC method to obtain Compound 96a [(3R)-3-aminopyrrolidin-1-yl]-[4-[4-(2-tert-butyl-4-pyridyl)-2-thienyl]-3-chloro-phenyl]methanone as (25 mg) HCl salt, an off-white solid. Compound 96b, the (S)-enantiomeric product was prepared using the (S)-enantiomeric starting material.

$^1$H NMR (400 MHz, Methanol-d4) δ (ppm): 8.71 (d, J=1.6 Hz, 1H), 8.65 (d, J=6.4 Hz, 1H), 8.35-8.24 (m, 2H), 8.18 (s, 1H), 7.86 (d, J=8.0 Hz, 1H), 7.80 (s, 1H), 7.64 (d, J=7.6 Hz, 1H), 4.06-3.95 (m, 2H), 3.76 (s, 2H), 3.59 (s, 1H), 2.45 (s, 1H), 2.15 (s, 1H), 1.59 (s, 9H). LCMS=(M+1) 440.1.

Example 97. Preparation of Compound No. 97

Synthesis of 1-{4-[4-(2-tert-butylpyridin-4-yl)thiophen-2-yl]-3-chlorobenzoyl}-1,2,3,4-tetrahydro-1,5-naphthyridine

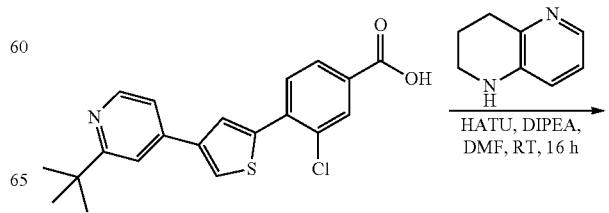

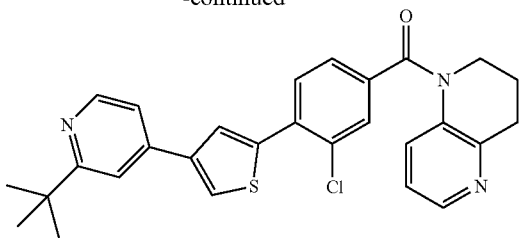

To a stirred solution of 4-[4-(2-tert-butyl-4-pyridyl)-2-thienyl]-3-chloro-benzoic acid (300 mg, 0.80 mmol) in DMF (5 mL), added the DIPEA (0.6 mL, 3.22 mmol), HATU (612 mg, 1.61 mmol), under nitrogen atmosphere. The reaction mixture was stirred at RT for 0.5 h, followed by addition of 1,2,3,4-tetrahydro-1,5-naphthyridine (324 mg, 1.61 mmol). The reaction mixture was stirred at RT for 16 h. After completion of reaction, water (100 mL) was added and the mixture extracted with EtOAc (3×50 mL). The combined organic layer was washed with brine (50 mL), dried over anhydrous sodium sulfate and concentrated under reduced pressure to obtain a residue, which was purified by Reverse phase HPLC to obtain (100 mg) as [4-[4-(2-tert-butyl-4-pyridyl)-2-thienyl]-3-chloro-phenyl]-(3,4-dihydro-2H-1,5-naphthyridin-1-yl)methanone (6 mg) as the formate salt.

$^1$H NMR (400 MHz, Methanol-d4) δ (ppm): 8.49 (d, J=5.2 Hz, 1H), 8.24 (d, J=4.7 Hz, 1H), 8.12 (d, J=1.6 Hz, 1H), 7.91 (d, J=1.6 Hz, 1H), 7.77-7.66 (m, 2H), 7.71 (s, 1H), 7.62 (s, 1H), 7.54 (dd, J=5.3, 1.7 Hz, 1H), 7.44 (d, J=7.8 Hz, 1H), 7.13 (dd, J=8.3, 4.8 Hz, 1H), 3.92 (t, J=6.0 Hz, 2H), 3.08 (t, J=6.8 Hz, 2H), 2.12-2.19 (m, 2H), 1.43 (s, 9H). LCMS=(M+1) 488.2.

Example 98. Preparation of Compound No. 98

Synthesis of 1-{4-[2-(2-tert-butylpyridin-4-yl)-1H-imidazol-4-yl]-3-chlorobenzoyl}piperidin-4-ol

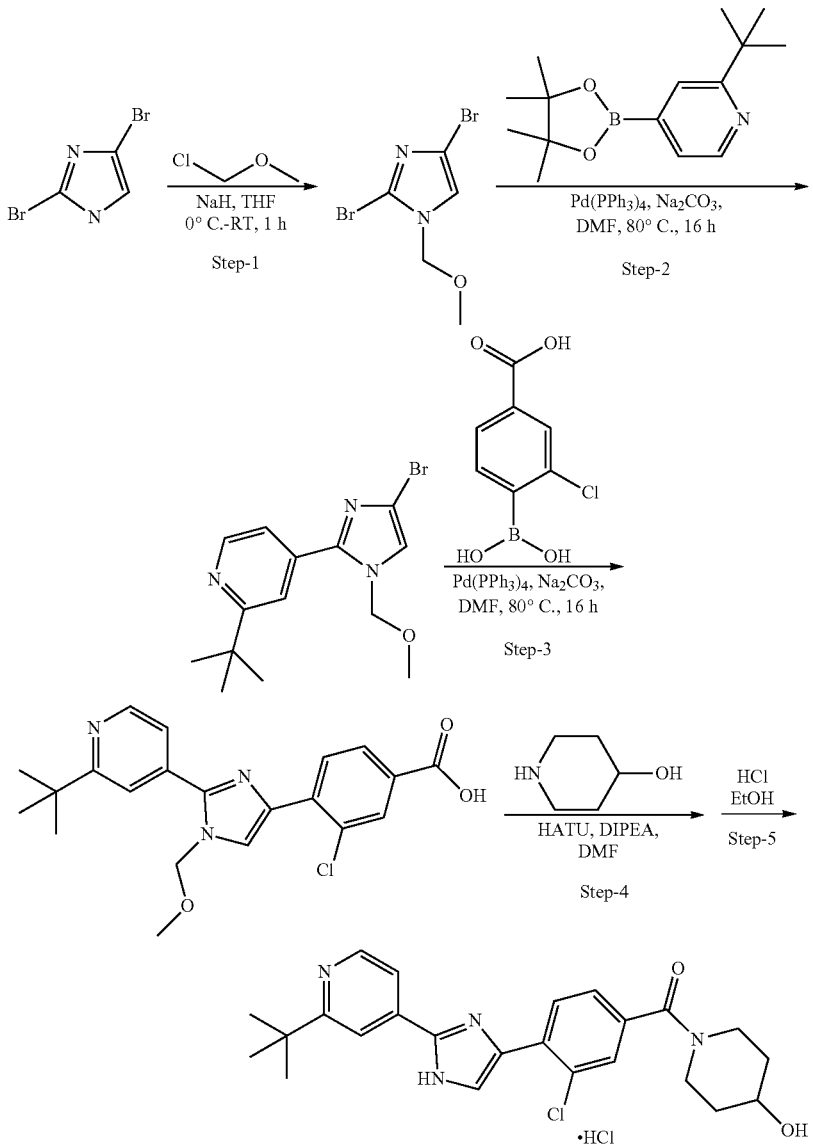

Step-1: Synthesis of 2,4-dibromo-1-(methoxymethyl)imidazole 2,4-Dibromo-1H-imidazole (5 g, 22.124 mmol) was taken in THF (30 mL) followed by addition of NaH (0.76 g, 33.186 mmol) at 0° C. The reaction was stirred at RT for 15 min, followed by addition of chloro (methoxy)methane (2 g, 24.34 mmol). The reaction mixture was stirred at RT for 1 h and monitored by TLC and LCMS. After completion of reaction, ice cooled water (200 mL) was added and the mixture extracted with EtOAc (300 mL). The organic layer was separated, dried over anhydrous sodium sulfate and concentrated under reduced pressure to obtain 2,4-dibromo-1-(methoxymethyl)imidazole (5.5 g) as a crude product, used as is.

Step-2: Synthesis of 4-[4-bromo-1-(methoxymethyl)imidazol-2-yl]-2-tert-butyl-pyridine 2,4-Dibromo-1-(methoxymethyl)imidazole (3 g, 11.2 mmol), 2-tert-butyl-4-(4,4,5,5-tetramethyl-1,3,2-dioxaborolan-2-yl)pyridine (3.5 g, 13.4 mmol), sodium carbonate (2.5 g, 28 mmol) in water (5 mL), and dioxane (25 mL) were charged in a 100 mL glass bottle and purged with nitrogen gas for 15 min. Tetrakis (1.3 g, 1.12 mmol) and Xantphos (0.637 g, 1.12 mmol) were added, then the reaction mixture was heated at 80° C. for 16 h. The reaction was monitored by TLC and LCMS. After completion of reaction, the mixture was diluted with water (150 mL) and extracted with EtOAc (200 mL). The organic layer was separated and washed with brine (100 mL) and dried over anhydrous sodium sulfate and concentrated under reduced pressure to obtain crude 4-[4-bromo-1-(methoxymethyl)imidazol-2-yl]-2-tert-butyl-pyridine (3 g) as the freebase.

Step-3: Synthesis of 4-[2-(2-tert-butyl-4-pyridyl)-1-(methoxymethyl)imidazol-4-yl]-3-chloro-benzoic acid 4-[4-Bromo-1-(methoxymethyl)imidazol-2-yl]-2-tert-butyl-pyridine (1000 mg, 3.096 mmol), 4-borono-3-chloro-benzoic acid (700 mg, 3.7 mmol), and sodium carbonate (800 mg, 7.8 mmol) in water (5 mL), DMF (20 mL) were charged in a 100 mL glass bottle and purged with nitrogen gas for 15 min. After addition of tetrakis (400 mg, 0.309 mmol), the reaction mixture was heated at 80° C. for 16 h. The reaction was monitored by TLC and LCMS. After completion of reaction, the mixture was diluted with water (50 mL) and extracted with EtOAc (3×100 mL). The organic layer was separated and washed with brine (2×50 mL), dried over anhydrous sodium sulfate and concentrated under reduced pressure to obtain crude 4-[2-(2-tert-butyl-4-pyridyl)-1-(methoxymethyl)imidazol-4-yl]-3-chloro-benzoic acid (1000 mg) as the freebase.

Step-4: Synthesis of [4-[2-(2-tert-butyl-4-pyridyl)-1-(methoxymethyl)imidazol-4-yl]-3-chloro-phenyl]-(4-hydroxy-1-piperidyl)methanone To a solution of 4-[2-(2-tert-butyl-4-pyridyl)-1-(methoxymethyl)imidazol-4-yl]-3-chloro-benzoic acid (500 mg, 1.253 mmol) in DMF (10 mL), was added DIPEA (648 mg, 5.012 mmol), followed by the addition of HATU (953 mg, 2.506 mmol). The reaction mixture was stirred for 30 min at RT. Piperidin-4-ol (632.7 mg, 6.264 mmol) was added and the reaction mixture stirred for 16 h at RT. The reaction was monitored by TLC and LCMS. On completion, the reaction mixture was diluted with water (30 mL) and extracted with EtOAc (2×100 mL). The combined organic layer was washed with water (2×50 mL) and brine (2×50 mL) and dried over anhydrous sodium sulfate to obtain 500 mg of crude compound. The crude compound was purified by reverse phase chromatography to afford [4-[2-(2-tert-butyl-4-pyridyl)-1-(methoxymethyl) imidazol-4-yl]-3-chloro-phenyl]-(4-hydroxy-1-piperidyl)methanone (300 mg) as a white solid.

Step-5: Synthesis of [4-[2-(2-tert-butyl-4-pyridyl)-1H-imidazol-4-yl]-3-chloro-phenyl]-(4-hydroxy-1-piperidyl) methanone

[4-[2-(2-tert-Butyl-4-pyridyl)-1-(methoxymethyl) imidazol-4-yl]-3-chloro-phenyl]-(4-hydroxy-1-piperidyl)methanone (300 mg, 0.623 mmol) was taken in 1.25M HCl in EtOH (15 mL) under nitrogen atmosphere. The reaction mixture was stirred at 80° C. for 3 h The reaction was monitored by TLC and LCMS. After completion of reaction, the mixture was concentrated under reduced pressure to obtain a crude product, which was purified by Reverse phase chromatography to obtain [4-[2-(2-tert-butyl-4-pyridyl)-1H-imidazol-4-yl]-3-chloro-phenyl]-(4-hydroxy-1-piperidyl) methanone (80 mg) as the HCl salt, a yellow solid.

$^1$H NMR (400 MHz, DMSO-d6) δ (ppm): 8.57 (d, J=5.1 Hz, 1H), 8.17 (s, 1H), 7.99 (s, 2H), 7.74 (dd, J=5.2, 1.6 Hz, 1H), 7.49 (s, 1H), 7.41 (dd, J=8.0, 1.7 Hz, 1H), 4.79 (d, J=3.8 Hz, 1H), 4.00 (s, 1H), 3.75 (s, 2H), 3.52 (s, 1H), 3.18 (s, 2H), 1.79 (s, 2H), 1.34 (s, 9H). LCMS=(M+1) 439.2.

Example 99. Preparation of Compound Nos. 99, 99a, and 99b

Synthesis of 2-tert-butyl-4-{5-[2-chloro-4-(3-methoxypiperidine-1-carbonyl)phenyl]thiophen-3-yl}pyridine

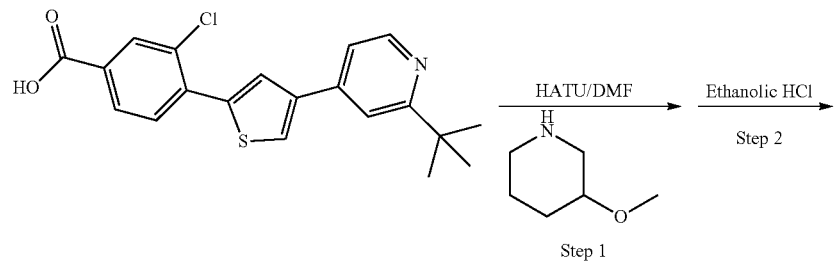

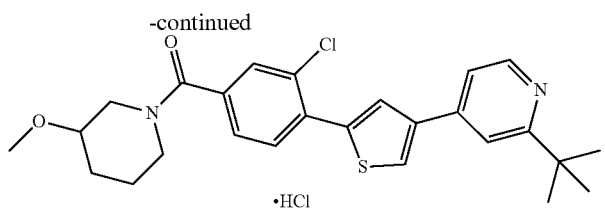

·HCl

Step-1: Synthesis of [4-[4-(2-tert-butyl-4-pyridyl)-2-thienyl]-3-chloro-phenyl]-(3-methoxy-1-piperidyl)methanone In a 100 mL flask, 4-[4-(2-tert-butyl-4-pyridyl)-2-thienyl]-3-chloro-benzoic acid (220 mg, 0.59 mmol, 1 equiv) was dissolved in DMF (8 mL), followed by addition of DIPEA (0.54 mL, 2.96 mmol, 5 equiv) and HATU (450 mg, 1.18 mmol, 2 equiv) and the resulting mixture was stirred for 10 min at RT. 3-Methoxypiperidinehydrochloride (317 mg, 2.07 mmol, 3.5 equiv) was added and the mixture stirred at RT under nitrogen atmosphere overnight. The progress of the reaction was monitored by TLC and LCMS. After completion of reaction, the mixture was diluted with water (100 mL) and extracted with EtOAc (2×100 mL), washed with water (4×100 mL) then dried by anhydrous sodium sulfate, and the combined organic layer concentrated under reduced pressure. The crude product was purified by reverse phase chromatography to afford [4-[4-(2-tert-butyl-4-pyridyl)-2-thienyl]-3-chloro-phenyl]-(3-methoxy-1-piperidyl)methanone (38 mg), an off-white solid.

Step-2: Synthesis of [4-[4-(2-tert-butyl-4-pyridyl)-2-thienyl]-3-chloro-phenyl]-(3-methoxy-1-piperidyl)methanone hydrochloride In 250 mL flask, [4-[4-(2-tert-butyl-4-pyridyl)-2-thienyl]-3-chloro-phenyl]-(3-methoxy-1-piperidyl)methanone (38 mg, 0.081 mmol, 1 equiv) was dissolved in 3 mL of EtOH and at 0° C. treated with 2 mL of ethanolic HCl. The ethanol was removed under reduced pressure and directly lyophilized to the product (40 mg, off-white colored) as its respective HCl salt. The enantiomers can be prepared from chiral HPLC resolution of the racemate.

$^1$H NMR (400 MHz, Methanol-d4) δ (ppm): 8.72-8.62 (m, 2H), 8.35-8.23 (m, 2H), 8.18-8.13 (m, 1H), 7.82 (d, J=8.0 Hz, 1H), 7.65 (d, J=19.6 Hz, 1H), 7.49 (d, J=9.4 Hz, 1H), 4.14-4.03 (m, 1H), 3.56 (d, J=12.2 Hz, 1H), 3.44 (m, 2H), 3.38 (s, 3H), 3.23 (m, 2H), 1.86 (d, J=8.8 Hz, 1H), 1.82 (s, 2H), 1.59 (s, 9H). LCMS=469.2 (M+1).

Example 100. Preparation of Compound No. 100

Synthesis of 1-{4-[4-(2-tert-butylpyridin-4-yl)thiophen-2-yl]-3-chlorobenzoyl}-4-methylpiperidin-4-ol

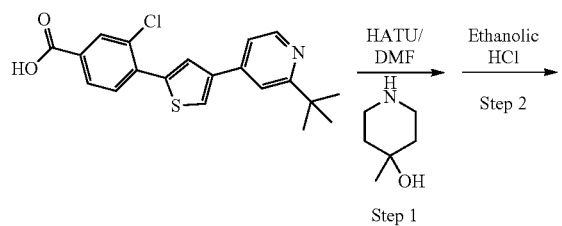

Step 1

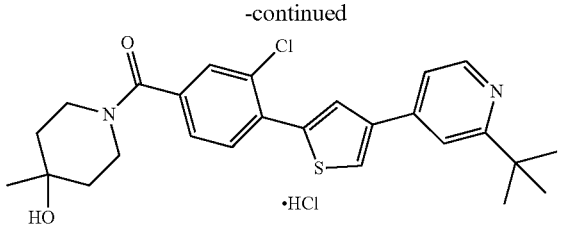

·HCl

Step-1: Synthesis of [4-[4-(2-tert-butyl-4-pyridyl)-2-thienyl]-3-chloro-phenyl]-(4-hydroxy-4-methyl-1-piperidyl)methanone In a 100 mL flask, 4-[4-(2-tert-butyl-4-pyridyl)-2-thienyl]-3-chloro-benzoic acid (210 mg, 0.55 mmol, 1 equiv) was dissolved in DMF (8 mL), followed by addition of DIPEA (0.52 mL, 2.82 mmol, 5 equiv) and HATU (430 mg, 1.13 mmol, 2 equiv) and the resulting mixture stirred for 10 min at RT. 4-Methylpiperidine-4-ol (227 mg, 1.98 mmol, 3.5 equiv) was added and the mixture stirred at RT under nitrogen atmosphere overnight. The progress of the reaction was monitored by TLC and LCMS. After completion of reaction, the mixture was diluted with water (100 mL) and extracted with EtOAc (2×100 mL), washed with water (4×100 mL) then dried over anhydrous sodium sulfate. The organic layer was concentrated under reduced pressure to afford [4-[4-(2-tert-butyl-4-pyridyl)-2-thienyl]-3-chloro-phenyl]-(4-hydroxy-4-methyl-1-piperidyl)methanone (60 mg) as a solid, an off-white compound.

Step-2: Synthesis of [4-[4-(2-tert-butyl-4-pyridyl)-2-thienyl]-3-chloro-phenyl]-(4-hydroxy-4-methyl-1-piperidyl)methanone hydrochloride In 250 mL flask, [4-[4-(2-tert-butyl-4-pyridyl)-2-thienyl]-3-chloro-phenyl]-(4-hydroxy-4-methyl-1-piperidyl)methanone (60 mg, 0.127 mmol, 1 equiv) was dissolved in 3 mL of EtOH and at 0° C. treated with 2 mL of ethanolic HCl, then the EtOH was evaporated under reduced pressure and directly lyophilized to get the product (63 mg, off-white colored) as its respective HCl salt.

$^1$H NMR (400 MHz, Methanol-d4) δ (ppm): 8.72-8.61 (m, 2H), 8.35-8.23 (m, 2H), 8.15 (d, J=1.6 Hz, 1H), 7.81 (d, J=8.0 Hz, 1H), 7.64 (d, J=1.6 Hz, 1H), 7.46 (dd, J=8.0, 1.7 Hz, 1H), 4.26 (d, J=13.2 Hz, 1H), 3.50 (m, 2H), 3.39 (m, 2H), 1.70 (m, 2H), 1.59 (s, 9H), 1.55 (m, 2H), 1.28 (s, 3H). LCMS=469.3 (M+1).

Example 101. Preparation of Compound Nos. 101, 101a, and 101b

Synthesis of [4-[4-(2-tert-butyl-4-pyridyl)-2-thienyl]-3-chloro-phenyl]-[(3S)-3-hydroxy-3-methyl-1-piperidyl] methanone hydrochloride

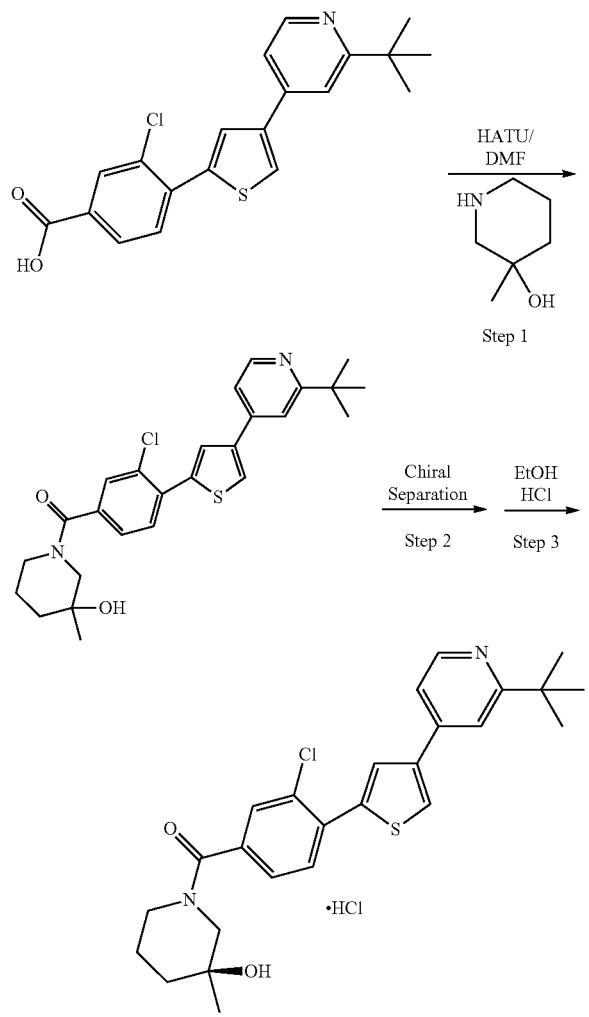

Step-1: Synthesis of [4-[4-(2-tert-butyl-4-pyridyl)-2-thienyl]-3-chloro-phenyl]-(3-hydroxy-3-methyl-1-piperidyl)methanone In a 100 mL flask was placed, 4-[4-(2-tert-butyl-4-pyridyl)-2-thienyl]-3-chloro-benzoic acid (250 mg, 0.67 mmol, 1 equiv) in DMF (8 mL), followed by addition of DIPEA (0.5 mL, 2.72 mmol, 4 equiv) and HATU (510 mg, 1.34 mmol, 2 equiv) and the resulting mixture was stirred for 10 min at RT. tert-Butyl 3-methylpiperidine-3-ol (234 mg, 2.02 mmol, 3 equiv) was added and the mixture stirred at RT under nitrogen atmosphere overnight. Progress of the reaction was monitored by TLC and LCMS. After completion of reaction, the mixture was diluted with water (100 mL) and extracted with EtOAc (2×100 mL), washed with water (4×100 mL) then dried over anhydrous sodium sulfate. The combined organic layer was concentrated under reduced pressure to give a viscous compound, which was purified by reverse phase chromatography to afford [4-[4-(2-tert-butyl-4-pyridyl)-2-thienyl]-3-chloro-phenyl]-(3-hydroxy-3-methyl-1-piperidyl)methanone (170 mg), an off-white solid. LCMS: –469.3 (M+1).

Step-2: Synthesis of [4-[4-(2-tert-butyl-4-pyridyl)-2-thienyl]-3-chloro-phenyl]-[(3S)-3-hydroxy-3-methyl-1-piperidyl]methanone The racemic mixture of [4-[4-(2-tert-butyl-4-pyridyl)-2-thienyl]-3-chloro-phenyl]-(3-hydroxy-3-methyl-1-piperidyl)methanone (170 mg) was separated by chiral HPLC to afford [4-[4-(2-tert-butyl-4-pyridyl)-2-thienyl]-3-chloro-phenyl]-[(3S)-3-hydroxy-3-methyl-1-piperidyl]methanone (50 mg, an off white solid).

Step-3: Synthesis of [4-[4-(2-tert-butyl-4-pyridyl)-2-thienyl]-3-chloro-phenyl]-[(3S)-3-hydroxy-3-methyl-1-piperidyl] methanone hydrochloride In a 250 mL flask was placed [4-[4-(2-tert-butyl-4-pyridyl)-2-thienyl]-3-chloro-phenyl]-[(3S)-3-hydroxy-3-methyl-1-piperidyl] methanone (50 mg, 0.106 mmol, 1 equiv) dissolved in 3 mL of EtOH and at 0° C. treated with 2 mL of ethanolic HCl, then evaporated under reduced pressure and directly lyophilized to get Compound 101a [[4-[4-(2-tert-butyl-4-pyridyl)-2-thienyl]-3-chloro-phenyl]-[(3S)-3-hydroxy-3-methyl-1-piperidyl] methanone hydrochloride], a free flowing solid (53 mg, off white color). LCMS: –469.3 (M+1). Compound 101b, the (R) enantiomer, was also prepared by isolation at Step-2, and treated accordingly in Step-3.

$^1$H NMR (400 MHz, Methanol-d4) δ (ppm): 8.72-8.60 (m, 2H), 8.33 (s, 1H), 8.26 (d, J=6.5 Hz, 1H), 8.18-8.12 (m, 1H), 7.79 (d, J=8.6 Hz, 1H), 7.68 (d, J=13.9 Hz, 1H), 7.52 (d, J=9.2 Hz, 1H), 4.29 (m, 0.5H), 4.02 (m, J=12.8 Hz, 0.5H), 3.51-3.41 (m, J=13.4 Hz, 2H), 3.29-3.18 (dd, J=31.0, 17.5 Hz, 2H), 1.94 (m, 1H), 1.75 (m, 1H), 1.65 (m, 1H), 1.59 (s, 9H), 1.29 (s, 3H).

Example 102. Preparation of Compound No. 102

Synthesis of [3-chloro-4-[5-(2-isopentylpyrazol-3-yl)-3-thienyl]phenyl]-morpholino-methanone

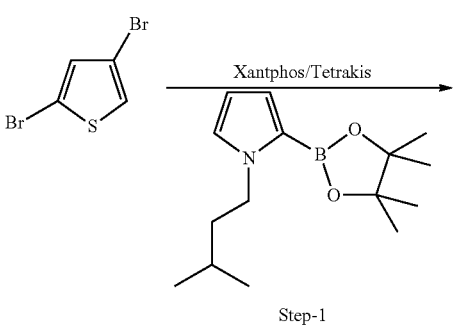

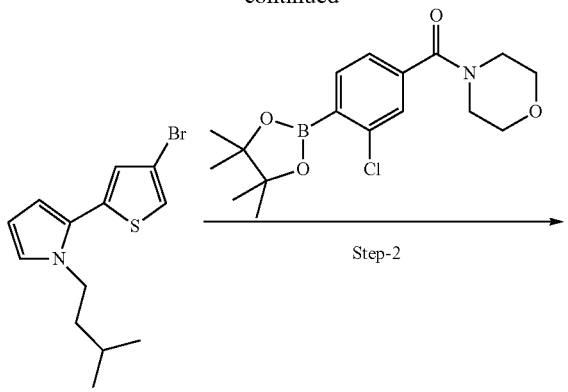

Step-1: Synthesis of 5-(4-bromo-2-thienyl)-1-isopentyl-pyrazole

In a 100 mL glass bottle were placed 1-isopentyl-5-(4,4,5,5-tetramethyl-1,3,2-dioxaborolan-2-yl)pyrazole (500 mg, 1.8925 mmol), 2,4-dibromothiophene (542.5 mg, 2.271 mmol), sodium carbonate (497 mg 4.7313 mmol), DMF (20 mL), and water (5 mL), and the mixture purged with nitrogen for 5 min. Pd(PPh$_3$)$_4$ (218.6 mg 0.1893 mmol) and Xantphos (109.5 mg, 0.1893 mmol) were added and the reaction mixture was heated at 80° C. overnight. The reaction mixture was monitored by TLC and LCMS. After completion of reaction, the mixture was diluted with water (75 mL) and extracted with EtOAc (3×150 mL). The organic layer was washed with water (2×75 mL) and brine (150 mL), dried over anhydrous sodium sulfate and concentrated under reduced pressure to obtain 5-(4-bromo-2-thienyl)-1-isopentyl-pyrazole (800 mg) as a brown crude solid, used as-is. LCMS: −299.1 (M+1).

Step-2: Synthesis of [3-chloro-4-[5-(2-isopentylpyrazol-3-yl)-3-thienyl]phenyl]-morpholino-methanone 5-(4-Bromo-2-thienyl)-1-isopentyl-pyrazole (400 mg, 1.3423 mmol), [2-chloro-4-(morpholine-4-carbonyl)phenyl]boronic acid (433.3 mg, 1.6107 mmol), sodium carbonate (352.4 mg 3.3558 mmol), DMF (10 mL), and water (3 mL) were charged in a 25 mL glass bottle and the mixture purged with nitrogen for 5 min. After adding Pd(PPh$_3$)$_4$ (155 mg 0.1342 mmol), the reaction mixture was heated at 80° C. overnight. The reaction was monitored by TLC and LCMS. After completion of reaction, the mixture was diluted with water (30 mL) and extracted with EtOAc (3×100 mL). The organic layer was washed with water (2×50 mL), brine (100 mL), dried over anhydrous sodium sulfate and concentrated under reduced pressure to obtain a crude product, which was purified by reverse phase HPLC to afford [3-chloro-4-[5-(2-isopentylpyrazol-3-yl)-3-thienyl]phenyl]-morpholino-methanone (65 mg), as the HCl salt. LCMS: −(M+1) 444.1.

$^1$H NMR (400 MHz, DMSO-d6) δ (ppm): 7.93 (d, J=1.4 Hz, 1H), 7.67-7.60 (m, 2H), 7.58 (d, J=1.4 Hz, 1H), 7.51 (d, J=1.9 Hz, 1H), 7.46 (dd, J=7.9, 1.7 Hz, 1H), 6.51 (d, J=1.9 Hz, 1H), 4.29 (t, J=7.5 Hz, 2H), 3.62 (s, 8H), 1.64 (q, J=7.2 Hz, 2H), 1.52 (m, J=13.3, 6.6 Hz, 1H), 0.84 (d, J=6.5 Hz, 6H).

Example 103. Preparation of Compound No. 103

Synthesis of [3-chloro-4-[5-(2-isopentylpyrazol-3-yl)-3-thienyl]phenyl]-(4,4-difluoro-1-piperidyl)methanone

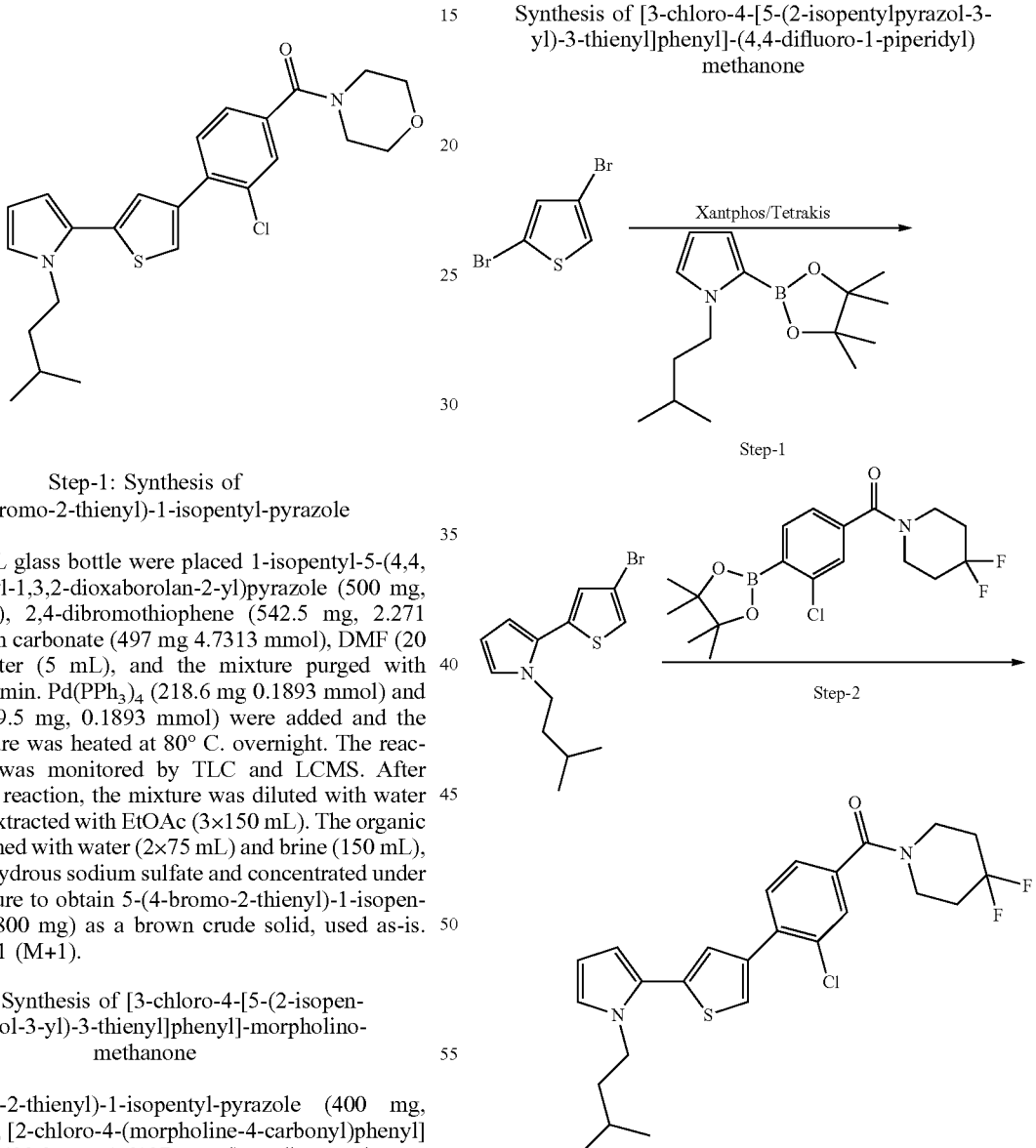

Synthesis of 5-(4-bromo-2-thienyl)-1-isopentyl-pyrazole

In a 100 mL flask were placed 1-isopentyl-5-(4,4,5,5-tetramethyl-1,3,2-dioxaborolan-2-yl)pyrazole (500 mg, 1.8925 mmol), 2,4-dibromothiophene (542.5 mg, 2.271 mmol), sodium carbonate (497 mg, 4.7313 mmol), DMF (20 mL), and water (5 mL), and the mixture purged with nitrogen for 5 min. After adding Pd(PPh₃)₄ (218.6 mg 0.1893 mmol) and Xantphos (109.5 mg, 0.1893 mmol), the reaction mixture was heated at 80° C. overnight. The reaction was monitored by TLC and LCMS. After completion of reaction, the reaction mixture was diluted with water (75 mL) and extracted with EtOAc (3×150 mL). The organic layer was washed with water (2×75 mL) and brine (150 mL), and dried over anhydrous sodium sulfate to obtain 5-(4-bromo-2-thienyl)-1-isopentyl-pyrazole (800 mg) as a brown crude product, used as-is. LCMS: −299.1 (M+1).

Step-2: Synthesis of [3-chloro-4-[5-(2-isopentylpyrazol-3-yl)-3-thienyl]phenyl]-(4,4-difluoro-1-piperidyl)methanone 5-(4-Bromo-2-thienyl)-1-isopentyl-pyrazole (400 mg, 1.3423 mmol), [2-chloro-4-(4,4-difluoropiperidine-1-carbonyl)phenyl]boronic acid (488 mg, 1.6107 mmol), sodium carbonate (352.4 mg 3.3558 mmol), DMF (10 mL), and water (3 mL) were charged in a 25 mL glass bottle and purged with nitrogen for 5 min. After adding Pd(PPh₃)₄ (155 mg 0.1342 mmol), the reaction mixture was heated at 80° C. overnight. The reaction was monitored by TLC and LCMS. After completion of reaction, the mixture was diluted with water (25 mL) and extracted with EtOAc (3×75 mL). The organic layer was washed with brine (2×50 mL) and water (2×50 mL), dried over anhydrous sodium sulfate to obtain a crude product, which was purified by reverse phase HPLC to afford [3-chloro-4-[5-(2-isopentylpyrazol-3-yl)-3-thienyl]phenyl]-(4,4-difluoro-1-piperidyl)methanone (80 mg) as a white solid. LCMS: −(M+1) 478.2.

¹H NMR (400 MHz, DMSO-d6) δ (ppm): 7.93 (s, 1H), 7.71-7.62 (m, 2H), 7.51 (s, 1H), 7.43 (d, 2H), 6.52 (s, 1H), 4.29 (t, 2H), 3.72 (s, 2H), 3.42-3.54 (m, 2H), 2.07 (s, 4H), 1.64 (q, 2H), 1.52 (dq, 1H), 0.84 (d, 6H).

Example 104. Preparation of Compound Nos. 104, 104a, and 104b

Synthesis of [3-chloro-4-[4-(2-isopentylpyrazol-3-yl)-2-thienyl]phenyl]-(3-hydroxy-1-piperidyl)methanone

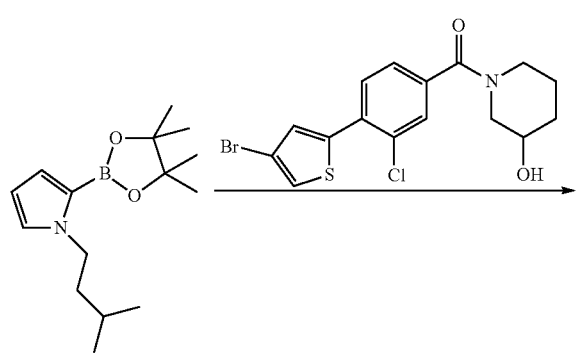

-continued

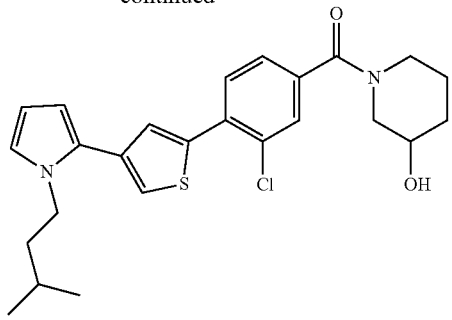

In a 25 mL glass bottle, 1-isopentyl-5-(4,4,5,5-tetramethyl-1,3,2-dioxaborolan-2-yl)pyrazole (250 mg, 0.9463 mmol), [4-(4-bromo-2-thienyl)-3-chloro-phenyl]-(3-hydroxy-1-piperidyl)methanone (453.1 mg, 1.1355 mmol), sodium carbonate (248.4 mg 2.3658 mmol), DMF (10 mL), and water (2 mL) were charged and the mixture purged with nitrogen for 5 min. After adding Pd(PPh₃)₄ (109.3 mg 0.0946 mmol), the reaction mixture was heated at 80° C. overnight. The reaction was monitored by TLC and LCMS. After completion of reaction, the mixture was diluted with water (25 mL) and extracted with EtOAc (3×75 mL). The organic layer was washed with water (2×50 mL) and brine (100 mL) and dried over anhydrous sodium sulfate to obtain a crude product, which was purified by reverse phase HPLC to afford [3-chloro-4-[4-(2-isopentylpyrazol-3-yl)-2-thienyl]phenyl]-(3-hydroxy-1-piperidyl)methanone (110 mg) as a white solid. LCMS: −458 (M+1).

¹H NMR (400 MHz, DMSO-d6) δ (ppm): 7.82 (s, 1H), 7.73 (d, J=8.0 Hz, 1H), 7.64-7.54 (m, 2H), 7.46 (s, 1H), 7.40 (s, 1H), 6.44 (s, 1H), 4.21 (t, J=7.3 Hz, 2H), 3.55 (s, 2H), 3.41 (s, 1H), 3.40-3.28 (m, 1H), 3.08 (s, 1H), 2.96 (s, 1H), 1.63 (s, 3H), 1.55 (t, J=7.2 Hz, 2H), 1.40 (q, J=6.6 Hz, 1H), 0.75 (d, J=6.5 Hz, 6H).

Example P1. Preparation of Compound Nos. 2.1 to 2.152

Compound nos. 2.1 to 2.152 and can be prepared using conditions analogous to those in both the General Methods and Examples provided above.

Example B1. Effect of Compounds on SREBP2 Cleavage and Cell Viability in HEPG2 Cells Average SREBP2 cleavage in HEPG2 cells was measured in the presence of compounds disclosed in Table 1. HepG2 cells were seeded at 500,000 cells per well in 6-well plates in DMEM supplemented with 10% FBS. After 2 days, cells were treated with compounds (20 μM) for 1 day in DMEM without FBS. Western blots were normalized with respect to actin.

For viability measurements, HepG2 cells were seeded at 5,000 cells per well in 96-well plates in DMEM supplemented with 10% FBS. After 1 day in culture, cells were treated with compounds (20 μM) for 3 days in DMEM without FBS. Viability was measured by MTS. Treatment with compounds was carried out in medium without FBS, and viability was measured by MTS. The results are shown in Table B1.

TABLE B1

| | (20 µM) | |
|---|---|---|
| Compound No. | Average SREBP2 cleavage (% Inhibition, n = 3) | Average Viability (% Inhibition, n = 3) |
| 2 | 73.85 | 30.73 |
| 3 | 12.18 | 19.52 |

Example B2. Effect of Compounds on SREBP2 Cleavage and Cytotoxicity

Dose response effects were measured of Compounds on the transcriptional activity of a Luciferase reporter driven by a SREBP-2 specific promoter in HepG2_LSSprom cells.

Cell Culture

HepG2_LSSprom cells (SwitchGear Genomics, cat# C711010L) were cultured in DMEM with 10% of fetal bovine serum (FBS), supplemented with Puromycin (1 µg/mL), 1% Penicillin/Streptomycin (Pen-Strep), 37° C., humidified, 95% air and 5% $CO_2$. Culture media was refreshed every 2 or 3 days. Cells were used between passage number 6-12.

Drug Treatments

For luminescence assays, cells were plated out at 20,000 cells/well in white 96 well plates in DMEM plus 10% FBS and 1% Pen-Strep without puromycin. After 1 day, cells were treated with Compound by diluting the drug in culture medium without FBS to a final concentration of 0.625, 1.25, 2.5, 3.75, 5 and 10 µM. Drug was prepared by dilutions of 10 mM stock aliquots. As control was used culture medium without FBS plus DMSO. Treatments with Compound were maintained for 6 h, or 24 h, until the luciferase assay was carried out.

For cytotoxicity assays, cells were plated out at 20,000 cells/well in transparent 96 well plates in DMEM plus 10% FBS and 1% Pen-Strep without puromycin. After 1 day, cells were treated with Compound by diluting in culture medium without FBS to a final concentration of 0.625, 1.25, 2.5, 3.75, 5 and 10 µM. Compound was prepared by dilutions of 10 mM stock aliquots. As a negative control culture medium was used without FBS plus DMSO. As maximum LDH release control (Lysis control) a lysis buffer provided by the kit manufacturer was used. Treatments with Compound were maintained for 6 h, or 24 h, in cell culture medium without serum until the cytotoxicity assay was started.

Luciferase Assay

After 6 h of treatments with Compound, the luciferase assay was performed. Briefly, the assay solution (buffer+ substrate) was prepare just prior to use. To each well 100 µL of assay solution was added. The 96-well plate was then gently mix for 2 min and incubated for 30 min at RT protected from light. The luminescence was read using a Synergy 4 (Biotek) equipment recording luminescence with sensibility set up at 150.

Cytotoxicity Assay

The cytotoxicity assay was performed according to the manufacturer's instructions. As maximum LDH release control (Lysis control) 3 wells per plate were treated with 10 µL of lysis buffer 45 min before the treatment was over. Briefly, after the 6 h, or 24 h, of treatment, 50 µL of media from each well was transferred to a new 96-well plate. To the transferred media, 50 µL of reconstituted substrate mix was added. The plates were covered from light and incubated at RT for 10 min. Then, 50 µL of stop solution was added to each well. The plates were then read using a Synergy 4 (Biotek) equipment recording the absorbance at 490 nm.

Analysis of the Data

Five independent experiments were carried out for both luciferase and cytotoxicity assay. In each experiment, three wells were use per condition and the results are represented as means±SEM.

For luciferase assay, Vehicle (no treatment) was taken as 100% of luciferase activity. This value represents the SREBP-2 transcriptional activity for the vehicle condition and was taken as 100% of SREBP-2 cleaved. The percentage for each treatment was calculated normalizing against the vehicle control. The graphics were made using the GraphPad Prism ver. 6.05 software. Half of maximal inhibitory concentration (IC50) of the effect of Compound on SREBP was obtain by nonlinear fit regression of mean normalized values vs. Compound concentration using the log(inhibitor) vs. response–Variable slope (four parameters) tool.

For cytotoxicity assay, Lysis control was taken as 100%/o of LDH release. The vehicle values were taken as basal LDH release and were subtracted to all the treatments (including vehicle itself) having this value as 0% of LDH release. The LDH release for the treatments was calculated respect to the 100% of LDH release of Lysis control normalized against vehicle. All the negatives values were taken as 0% of cytotoxicity. The graphics were made using the Graph Prism ver. 6.05 software.

The results are shown in Table B2.

TABLE B2

| Cpd No. | SREBP2 Cleavage (5 µM) (% Inh) | SREBP2 Cleavage ($IC_{50}$ µM) 6 h | SREBP2 Cleavage ($IC_{50}$ µM) 24 h | Cytotoxicity (5 µM) % | Cytotoxicity ($IC_{50}$ µM) 6 h | Cytotoxicity ($IC_{50}$ µM) 24 h |
|---|---|---|---|---|---|---|
| 4 | 48 | | | 1 | | |
| 5 | 71 | | | 4 | | |
| 6 | 41 | | | 0 | | |
| 7 | | | >1 | | | >3 |
| 8 | | | >3 | | | >3 |
| 9 | 52 | | | 1 | | |
| 10 | | | >3 | | | |
| 11 | | <1 | 0.3 | | >10 | |
| 12 | | >10 | 0.5 | | >10 | |
| 13 | | >10 | 0.54 | | >10 | |
| 14 | | 3.17 | | | | |
| 15 | | >5 | | | | |
| 16 | | | 0.81 | | | >3 |
| 17 | | >3 | >3 | | | |

TABLE B2-continued

| Cpd No. | SREBP2 Cleavage (5 μM) (% Inh) | SREBP2 Cleavage (IC$_{50}$ μM) 6 h | SREBP2 Cleavage (IC$_{50}$ μM) 24 h | Cytotoxicity (5 μM) % | Cytotoxicity (IC$_{50}$ μM) 6 h | Cytotoxicity (IC$_{50}$ μM) 24 h |
|---|---|---|---|---|---|---|
| 18 | | >3 | >3 | | | |
| 19 | | | 0.25 | | | >3 |
| 19a | | | 0.069 | | | >10 |
| 19b | | | 0.22 | | | >10 |
| 20 | | | >3 | | | |
| 21 | | | >1 | | | >3 |
| 21a | | | 0.71 | | | >10 |
| 21b | | | >3 | | | >10 |
| 22 | | | 0.82 | | | >3 |
| 23 | | | 0.48 | | | >10 |
| 24 | | | >3, 2.7 | | | >10 |
| 25 | | | 0.62 | | | >10 |
| 26 | | | >3 | | | >10 |
| 27 | | | 0.68 | | | >10 |
| 28 | | | >3 | | | >10 |
| 29 | | | 1.4 | | | >10 |
| 30 | | | 2.5 | | | >10 |
| 31 | | | 0.99 | | | >10 |
| 32 | | | 0.81 | | | >10 |
| 33 | | | 0.21 | | | >10 |
| 34 | | | 0.85 | | | >10 |
| 35 | | | 2.4 | | | >10 |
| 36 | | | 0.49 | | | >10 |
| 37 | | | 0.91 | | | >10 |
| 38 | | | 2.1 | | | >10 |
| 39 | | | 6.2 | | | >10 |
| 40 | | | 0.15 | | | >10 |
| 41 | | | 0.39 | | | >10 |
| 42 | | | 0.84 | | | >10 |
| 43 | | | 3.8 | | | >10 |
| 44 | | | 0.44 | | | >10 |
| 45 | | | 1.8 | | | >10 |
| 46 | | | 1.3 | | | >10 |
| 47 | | | 0.33 | | | >10 |
| 48 | | | 0.26 | | | >10 |
| 48a | | | 0.31 | | | >10 |
| 48b | | | 0.12 | | | >10 |
| 49 | | | >1 | | | >10 |
| 50 | | | 1.3 | | | >10 |
| 52 | | | 1.7 | | | >10 |
| 53 | | | 3.9 | | | >10 |
| 54 | | | 0.54 | | | >10 |
| 55 | | | 0.36 | | | >10 |
| 56 | | | 1 | | | >10 |
| 57 | | | 0.55 | | | >10 |
| 58 | | | 1.4 | | | >10 |
| 59 | | | 1.6 | | | >10 |
| 60 | | | 3.5 | | | >10 |
| 61 | | | 1.5 | | | >10 |
| 62 | | | >3 | | | >10 |
| 63 | | | 2.1 | | | >10 |
| 64 | | | 0.4 | | | >10 |
| 65 | | | 2.4 | | | >10 |
| 66 | | | >10 | | | >10 |
| 67 | | | 4.7 | | | >10 |
| 68a | | | 0.15 | | | >10 |
| 68b | | | 0.06 | | | >10 |
| 69 | | | 0.015 | | | >10 |
| 70 | | | 0.08 | | | >10 |
| 71 | | | 0.34 | | | >10 |
| 72 | | | >10 | | | >10 |
| 73 | | | >3 | | | >10 |
| 74a | | | 0.74 | | | >10 |
| 74b | | | 0.51 | | | >10 |
| 75 | | | 3.2 | | | >10 |
| 76 | | | 1.6 | | | >10 |
| 77 | | | 2.3 | | | >10 |
| 78 | | | 0.2 | | | >10 |
| 79a | | | 0.29 | | | >10 |
| 79b | | | 0.52 | | | >10 |
| 80 | | | 0.06 | | | >10 |
| 80a | | | 0.095 | | | >10 |
| 80b | | | 0.04 | | | >10 |
| 81 | | | 0.14 | | | >10 |
| 82 | | | 0.5 | | | >10 |

TABLE B2-continued

| Cpd No. | SREBP2 Cleavage (5 µM) (% Inh) | SREBP2 Cleavage (IC$_{50}$ µM) 6 h | SREBP2 Cleavage (IC$_{50}$ µM) 24 h | Cytotoxicity (5 µM) % | Cytotoxicity (IC$_{50}$ µM) 6 h | Cytotoxicity (IC$_{50}$ µM) 24 h |
|---|---|---|---|---|---|---|
| 83 | | | 0.47 | | | >10 |
| 84 | | | >3 | | | >10 |
| 85 | | | >3 | | | >10 |
| 86 | | | 0.06 | | | >10 |
| 87a | | | >10 | | | >10 |
| 87b | | | >10 | | | >10 |
| 88 | | | 2.8 | | | >10 |
| 89 | | | 0.037 | | | >10 |
| 89a | | | 0.03 | | | >10 |
| 89b | | | 0.02 | | | >10 |
| 90 | | | 0.37 | | | >10 |
| 91 | | | 0.72 | | | >10 |
| 92 | | | 0.74 | | | >10 |
| 93 | | | 0.41 | | | >10 |
| 94 | | | 0.52 | | | >10 |
| 95 | | | 0.42 | | | >10 |
| 95a | | | 0.26 | | | >10 |
| 95b | | | 0.65 | | | >10 |
| 96a | | | 1.4 | | | >10 |
| 96b | | | 0.6 | | | >10 |
| 97 | | | 0.17 | | | >3 |
| 98 | | | 0.99 | | | >10 |
| 99 | | | 0.051 | | | >10 |
| 100 | | | 0.74 | | | >10 |
| 101a | | | 0.15 | | | >10 |
| 101b | | | 0.025 | | | >10 |
| 102 | | | 0.44 | | | >10 |
| 103 | | | 0.69 | | | >10 |
| 104 | | | 0.13 | | | >10 |

Example B3. Effect of Compounds on a Human LnCap Xenograft

LnCap cells are inoculated in male nude mice. Animals are randomized into 3 treatment groups (n=10 per group) when tumor size reaches 100 mm$^3$. One group is treated by oral gavage with the vehicle solution twice a day; and another group is treated at 40 mg/kg/po/bid of Compound. Tumor volume is measured by caliper measurements twice a week during the course of the experiment (4 weeks).

Example B4. Effect of Compounds in Various Cell Lines

Cytotoxicity and IC$_{50}$ Determination

Cell plating: Cells are cultured in medium with 10% regular FBS. Cells are harvested respectively during the logarithmic growth period and counted using Countstar. Cells are split to two sets: one set is cultured in medium+5% regular FBS and the other set is cultured in medium+5% LDFBS (lipid reduced FBS). Cell concentrations are adjusted to 2.22×104 cells/mL with respective culture medium for 3-day CTG assay. (The cell density is optimized before actual study; cell density used in the test may vary for different cell lines). For each serum condition, 90 µL cell suspensions are added to two 96-well plates (plate A and B) with the final cell density of 2×10$^3$ cells/well for 3-day CTG assay (The cell density is optimized before actual study; cell density used in the test may vary for different cell lines). 10 µL of culture medium is added to each well of plate A group for T0 reading. All plates are incubated (A and B groups) overnight in humidified incubator at 37° C. with 5% CO$_2$.

Day 0: T0 reading: For plate A group, CellTiter-Glo® Reagent is added at equal volume of cell culture medium present in each well (e.g., add 100 µL of reagent to 100 µL of medium containing cells for a 96-well plate). Contents are mixed for 2 min on an orbital shaker to facilitate cell lysis. The plate is allowed to incubate at RT for 10 min to stabilize luminescent signal. Note: Uneven luminescent signal within standard plates can be caused by temperature gradients, uneven seeding of cells or edge effects in multiwall plates. A Backseal black sticker is affixed to the bottom of each plate. Luminescence is recorded (T0) using EnVision Multi Label Reader.

Day 0: compound treatment: Test compounds and positive controls are dissolved with PBS as stock solution at the concentration indicated at Test Article Dilution map. A 500× solution is prepared in DMSO, then diluted with appropriate culture media (1:50) into 10× working solutions. 10 µL (10×) drug solutions are dispensed in each well (triplicate for each drug concentration) of the plate B group according to plate inoculation map. The test plates are incubated for 3 days in the humidified incubator at 37° C. with 5% CO$_2$.

Day 3: Plate B group reading. CellTiter-Glo® Reagent is added at equal volume of cell culture medium present in each well (e.g., add 100 µL of reagent to 100 µL of medium containing cells for a 96-well plate). The contents are mixed for 2 min on an orbital shaker to induce cell lysis. The plate is allowed to incubate at RT for 10 min to stabilize luminescent signal. Note: Uneven luminescent signal within standard plates can be caused by temperature gradients, uneven seeding of cells or edge effects in multiwall plates. A Backseal black sticker is affixed to the bottom of each plate. Luminescence is recorded using EnVision Multi Label Reader. IC$_{50}$ values are calculated for each Compound for each cell line.

Example B5. Effect of Compounds on a Human In-Vivo MDA-MB-453 Xenograft

Cell line: Human breast cancer cell line MD-MB-453 is purchased from ATCC (Manassas, Va.). Cells are grown at atmospheric $CO_2$ in L-15 media containing 10% fetal bovine serum, penicillin streptomycin, L-glutamine, and sodium pyruvate. Cells are spun down and resuspended at a concentration of 6.0E07 cells/mL in serum-free medium without additives, then combined 1:1 with MATRIGEL® (Trevigen, Gaithersburg, Md.).

Surgical implantation of DHT pellets: One week after castration, the animals are anesthetized with a mixture of isoflurane and oxygen and the surgical area sterilized using iodine and alcohol. Each animal is implanted with 12.5 mg 5α-DHT 60-day slow release pellets (Innovative Research of America, Sarasota, Fla.) on the lateral side of the neck between the ear and the shoulder. The skin is closed with a 6-0 silk suture.

Injection of orthotopic cells: Two days after pellet implantation, the mice are inoculated by injection underneath the nipple of the number 4 mammary fat pad with 200 µL (6.0E06 cells) per mouse of the freshly prepared MD-MB-453:MATRIGEL® mixture. All procedures are carried out in HEPA-filtered laminar-flow hoods.

Study design: When the tumors reach a mean volume of approximately 100 mm$^3$, sixty animals with established tumors and moderate body weights are randomized into 6 treatment groups (Group 1-6, n=10 mice each). Group 1 is treated once daily with vehicle (20% HPBCD). Groups 2 to 5 are treated once daily with Compound with (respectively) 1, 3, 10, or 30 mg/kg. Group 6 is treated twice daily (at intervals of ~8-10 h) with Compound at 10 mg/kg. All treatments are administered as oral gavage (PO) at a dose volume of 5 mL/kg. Doses are administered starting on the staging day and continued for 42 days (Days 0-41).

Tumor volume is measured by caliper measurements twice a week during the course of the experiment (4 weeks).

Example B6. Effect of Compounds on an In-Vivo LnCAP Human Prostate Adenocarcinoma Xenograft Experimental Animals:

Ninety-five male Beige Severe Combined Immune Deficiency (SCID) mice are purchased from Charles River (Hollister, Calif.) as 6- to 7-week-old mice. Following arrival, animals are weighed using an electronic balance (Ohaus SCOUT® PRO, Parsippany, N.J.), given a clinical examination to ensure that the animals are in good condition, and housed 5 per cage. The animals are maintained in a HEPA-filtered environment in a Modular Animal Caging System (MACS) full-ventilation rodent housing system (Alternative Design, Arkansas). Animal room controls are set to maintain temperature and relative humidity at 22° C.±4° C. and 50%±20%, respectively. Housing rooms are on a 12:12 light/dark cycle. Cages are autoclaved. Water is autoclaved and supplied ad libitum to each cage via water bottles. Irradiated 2016 Teklad Global 16% Protein Rodent Diet and SaniChip irradiated bedding 7090A are obtained from Harlan Teklad (Hayward, Calif.).

Compound Formulation:

Dose suspensions of compounds are formulated in 20% HPCD at 5.0, 15.0, 50.0, and 150 mg/mL (for administration at 1, 3, 10, and 30 mg/kg (mg/kg), respectively). Specifically, vehicle is dispensed into a vial containing a measured amount of test article powder and the vial is vortexed and sonicated until the test article is suspended completely, approximately 5-15 min. The vial contents then are brought to the required volume with additional vehicle, and the solution is vortexed and sonicated for an additional 2-5 min. The dosing suspensions (compounds in 20% HPCD) are prepared freshly and used within one h of formulation.

Cell Line:

Human prostate adenoma cancer cell line LnCaP is purchased from ATCC (Manassas, Va.). Cells are grown in 1640 RPMI containing 100% fetal bovine serum. Cells are spun down and resuspended at a concentration of 5.0E07 cells/mL in serum-free medium without additives, then combined 1:1 with MATRIGEL® (Trevigen, Gaithersburg, Md.).

Injection of Cells:

At approximately 5 weeks before the projected initiation of dosing, each mouse is implanted, under isoflurane anesthesia, by injection into the left flank with 200 µL (5.0E06 cells) per mouse of the freshly prepared LnCaP:MATRIGEL® mixture (50:50). All procedures are carried out in HEPA-filtered laminar-flow hoods.

Study Design:

Study design and treatments of all groups are shown in Table B6.

TABLE B6

Study Design

| | | Treatment Phase (Days 0-39) | | |
|---|---|---|---|---|
| Group | Agent | Dose (mg/kg, PO) | Frequency | n |
| 1 | Vehicle | 0 | QD | 10 |
| 2 | Compound | 1 | QD | 10 |
| 3 | Compound | 3 | QD | 10 |
| 4 | Compound | 10 | QD | 10 |
| 5 | Compound | 30 | QD | 10 |
| 6 | Compound | 10 | BID | 10 |

When the tumors reach a mean volume of approximately 100 mm$^3$, sixty animals with established tumors and moderate body weights are randomized into 6 treatment groups (Group 1-6, n=10 mice each). Group 1 is treated once daily with vehicle. Groups 2 to 5 are treated once daily with the compound to be tested at 1, 3, 10, or 30 mg/kg. Group 6 is treated twice daily (at intervals of ~8-10 hr) with the compound at 10 mg/kg. All treatments are administered as oral gavage (PO) at a dose volume of 5 mL/kg. Doses are administered starting on the staging day and continued for 40 days (Days 0-39).

Body weights are measured twice per week using an electronic balance (Ohaus SCOUT® PRO). Tumor sizes are measured twice per week using microcalipers (Mitutoyo, Aurora, Ill.) to measure the perpendicular minor dimension (W) and major dimension (L). Tumor volume (mm$^3$) is calculated using the formula L×W×H/2.

At 1 h after the final dose administration on Day 39, animals are subjected to terminal cardiocentesis and euthanized. For each animal, blood is collected as $K_2$EDTA plasma, split into 2 aliquots (minimum 50 µL each), and frozen at −80° C. One aliquot from each animal is assessed for compound exposure, the remaining aliquot is retained at −80° C. At necropsy, terminal body weights are recorded, and tumors excised, weighed, and split in two. Separate halves of each specimen are flash-frozen on dry ice and stored at −80° C. or drop-fixed in 10% neutral buffered formalin (NBF) pending further analyses.

Statistical Analysis:

Descriptive and inferential analyses are performed using the corresponding functions of Excel 2010 (Microsoft, Redmond, Wash.). Inferential analysis consisted of t-test comparisons (two-tailed, heteroscedasticity assumed) to data from the vehicle-dosed (Group-1) animals. Values of p≤0.05 are considered statistically significant.

Example B7. Effect of Compounds in a Mouse Liver Steatosis Model

Male C57BL/6J mice (n=40), 8 weeks old, are fed a high fat/cholesterol/cholic acid diet ("Paigen" diet) for up to 21 days, and compounds are dosed once daily at both 5 mg/kg and 20 mg/kg. Parameters to be determined include plasma biochemistry (ALT, AST, triglycerides, total cholesterol, fatty acids, IL-6), liver biochemistry (triglycerides, total cholesterol, fatty acids, 15 gene expression by RT-qPCR to assess lipid metabolism, cholesterol metabolism, SREBP proteolysis, ER stress, oxidative stress, inflammation, and fibrosis), and liver histology (H/E, Red Oil with quantification). Changes in liver weight, cholesterol, triglycerides, fatty acids, and enzymes are assessed.

The invention claimed is:
1. A compound of Formula (IIa):

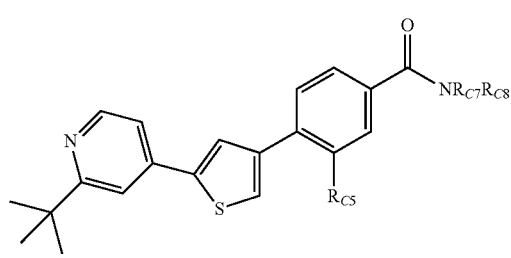

IIa or a pharmaceutically acceptable salt thereof, wherein:
$R_{C5}$ is halogen;
each $R_{C7}$ and $R_{C8}$ is independently hydrogen, R1, or —SO$_2$R$_{C12}$; or $R_{C7}$ and $R_{C8}$ are taken together with the N to which they are attached to form a C3-C8 heterocycle optionally substituted with one or more R1 or R3;
R1 is C1-C6 linear or branched alkyl, C2-C6 linear or branched alkenyl, C2-C6 linear or branched alkynyl, C3-C6 cycloalkyl, C3-C6 cycloalkylmethyl, C3-C6 cycloalkenyl, aryl, or heteroaryl; each optionally substituted with one or more R3;
R3 is halogen, —CN, —OH, —O(Alkyl), =O, —NO$_2$, —SH, —S(Alkyl), —S(O)(Alkyl), —S(O)$_2$(Alkyl), —CH$_2$OCH$_3$, —OBn, —CO$_2$H, —CO$_2$(Alkyl), —NR10R11, —CONR10R11, or —S(O)$_2$NR10R11;
R10 and R11 are independently hydrogen, C1-C6 linear or branched alkyl, —C(O)R$_{C12}$, —C(O)$_2$R$_{C12}$, —C(O)N(R$_{C12}$)$_2$, —SO$_2$R$_{C12}$, or are taken together with the N to which they are attached to form a C3-C8 heterocyclyl; and
$R_{C12}$ is hydrogen, a linear or branched C1-C6 alkyl, a linear or branched C2-C6 alkenyl, a linear or branched C2-C6 alkynyl, or aryl; wherein each alkyl, alkenyl, alkynyl, or aryl group is optionally substituted with one or more halogen atoms, one or more —NH$_2$ groups, or one or more —OH groups.

2. The compound of claim 1, or the pharmaceutically acceptable salt thereof, wherein
(a) $R_{C5}$ is chloro; or
(b) $R_{C7}$ and $R_{C8}$ are taken together with the N to which they are attached to form a C3-C8 heterocycle, wherein the C3-C8 heterocycle is selected from the group consisting of pyrrolidinyl, piperidinyl, piperazinyl, and morpholinyl, each optionally substituted with one or more R1 or R3.

3. A compound of Formula (IIb):

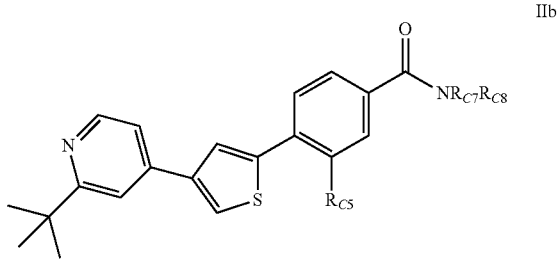

IIb or a pharmaceutically acceptable salt thereof, wherein;
$R_{C5}$ is halogen;
each $R_{C7}$ and $R_{C8}$ is independently hydrogen, R1, or —SO$_2$R$_{C12}$; or $R_{C7}$ and $R_{C8}$ are taken together with the N to which they are attached to form a C3-C8 heterocycle optionally substituted with one or more R1 or R3 ;
R1 is C1-C6 linear or branched alkyl, C2-C6 linear or branched alkenyl, C2-C6 linear or branched alkynyl, C3-C6 cycloalkyl, C3-C6 cycloalkylmethyl, C3-C6 cycloalkenyl, aryl, or heteroaryl; each optionally substituted with one or more R3;
R3 is halogen, —CN, —OH, —O(Alkyl), =O, —NO$_2$, —SH, —S(Alkyl), —S(O)(Alkyl), —S(O)$_2$(Alkyl), —CH$_2$OCH$_3$, —OBn, —CO$_2$H, —CO$_2$(Alkyl), —NR10R11, —CONR10R11, or —S(O)$_2$NR10R11;
R10 and R11 are independently hydrogen, C1-C6 linear or branched alkyl, —C(O)R$_{C12}$, —C(O)$_2$R$_{C12}$, —C(O)N(R$_{C12}$)$_2$, —SO$_2$R$_{C12}$, or are taken together with the N to which they are attached to form a C3-C8 heterocyclyl; and
$R_{C12}$ is hydrogen, a linear or branched C1-C6 alkyl, a linear or branched C2-C6 alkenyl, a linear or branched C2-C6 alkynyl, or aryl; wherein each alkyl, alkenyl, alkynyl, or aryl group is optionally substituted with one or more halogen atoms, one or more —NH$_2$ groups, or one or more —OH groups.

4. The compound of claim 3, or the pharmaceutically acceptable salt thereof, wherein:
(a) $R_{C5}$ is chloro; or
(b) $R_{C7}$ and $R_{C8}$ are taken together with the N to which they are attached to form a C3-C8 heterocycle, wherein the C3-C8 heterocycle is selected from the group consisting of pyrrolidinyl, piperidinyl, piperazinyl, and morpholinyl, each optionally substituted with one or more R1 or R3.

5. A compound, or a pharmaceutically acceptable salt thereof, selected from the group consisting of:
N-methyl-4-[2-(2-propylpyridin-4-yl)-1,3-thiazol-4-yl]benzamide;
N,N-dimethyl-4-[2-(2-propylpyridin-4-yl)-1,3-thiazol-4-yl]benzamide;
4-[2-(2-propylpyridin-4-yl)-1,3-thiazol-4-yl]benzamide;
4-{4-[2-chloro-4-(piperidine-1-carbonyl)phenyl]-1,3-thiazol-2-yl}-1H-indole;
2-tert-butyl-4-{4-[2-chloro-4-(piperidine-1-carbonyl)phenyl]-1,3-thiazol-2-yl}pyridine;
3-chloro-4-[2-(1H-indol-4-yl)-1,3-thiazol-4-yl]-N,N-dimethylbenzamide;

4-{4-[5-(2-tert-butylpyridin-4-yl)thiophen-3-yl]-3-chlorobenzoyl}piperazin-2-one;
4-[5-(2-tert-butylpyridin-4-yl)thiophen-3-yl]-3-chloro-N-cyclobutylbenzamide;
3-chloro-N,N-dimethyl-4-{2-[2-(piperidin-1-yl)pyridin-4-yl]-1,3-thiazol-4-yl}benzamide;
1-{4-[5-(2-tert-butylpyridin-4-yl)thiophen-3-yl]-3-chlorobenzoyl}-4-methylpiperazine;
2-tert-butyl-4-{4-[2-chloro-4-(piperidine-1-carbonyl)phenyl]thiophen-2-yl}pyridine;
2-tert-butyl-4-{4-[2-chloro-4-(3,3-difluoropyrrolidine-1-carbonyl)phenyl]thiophen-2-yl}pyridine;
2-tert-butyl-4-{4-[2-chloro-4-(4,4-difluoropiperidine-1-carbonyl)phenyl]thiophen-2-yl}pyridine;
4-[5-(2-tert-butylpyridin-4-yl)thiophen-3-yl]-3-chloro-N-cyclopropylbenzamide;
N-tert-butyl-4-[5-(2-tert-butylpyridin-4-yl)thiophen-3-yl]-3-chlorobenzamide;
2-tert-butyl-4-{4-[2-chloro-4-(piperidine-1-carbonyl)phenyl]-5-methylthiophen-2-yl}pyridine;
4-(3-chloro-4-{2-[2-(piperidin-1-yl)pyridin-4-yl]-1,3-thiazol-4-yl}benzoyl)morpholine;
3-chloro-N-(2-hydroxypropyl)-4-{2-[2-(piperidin-1-yl)pyridin-4-yl]-1,3-thiazol-4-yl}benzamide;
tert-butyl N-(1-{4-[5-(2-tert-butylpyridin-4-yl)thiophen-3-yl]-3-chlorobenzoyl}piperidin-3-yl)carbamate;
tert-butyl N-[(3R)-1-{4-[5-(2-tert-butylpyridin-4-yl)thiophen-3-yl]-3-chlorobenzoyl}piperidin-3-yl]carbamate;
tert-butyl N-[(3S)-1-{4-[5-(2-tert-butylpyridin-4-yl)thiophen-3-yl]-3-chlorobenzoyl}piperidin-3-yl]carbamate;
4-{4-[5-(2-tert-butylpyridin-4-yl)thiophen-3-yl]-3-chlorobenzoyl}-1$\lambda^6$,4-thiomorpholine-1, 1-dione;
1-{4-[5-(2-tert-butylpyridin-4-yl)thiophen-3-yl]-3-chlorobenzoyl}piperidin-3-amine;
(3R)-1-{4-[5-(2-tert-butylpyridin-4-yl)thiophen-3-yl]-3-chlorobenzoyl}piperidin-3-amine;
(3S)-1-{4-[5-(2-tert-butylpyridin-4-yl)thiophen-3-yl]-3-chlorobenzoyl}piperidin-3-amine;
4-{4-[5-(2-tert-butylpyridin-4-yl)thiophen-3-yl]-3-chlorobenzoyl}morpholine;
4-[5-(2-tert-butylpyridin-4-yl)thiophen-3-yl]-3-chloro-N-phenylbenzamide;
2-tert-butyl-4-{4-[2-chloro-4-(4,4-difluoropiperidine-1-carbonyl)phenyl]-1H-imidazol-2-yl}pyridine;
2-tert-butyl-4-{4-[2-chloro-4-(piperidine-1-carbonyl)phenyl]-1H-imidazol-2-yl}pyridine;
6-[5-(2-tert-butylpyridin-4-yl)thiophen-3-yl]-2-methyl-1,2,3,4-tetrahydroisoquinolin-1-one;
tert-butyl 4-{4-[5-(2-tert-butylpyridin-4-yl)thiophen-3-yl]-3-chlorobenzoyl}piperazine-1-carboxylate;
1-{4-[5-(2-tert-butylpyridin-4-yl)thiophen-3-yl]-3-chlorobenzoyl}piperazine;
1-(4-{4-[5-(2-tert-butylpyridin-4-yl)thiophen-3-yl]-3-chlorobenzoyl}piperazin-1-yl)ethan-1-one;
1-{4-[5-(2-tert-butylpyridin-4-yl)thiophen-3-yl]-3-chlorobenzoyl}-4-methanesulfonylpiperazine;
N-(1-{4-[5-(2-tert-butylpyridin-4-yl)thiophen-3-yl]-3-chlorobenzoyl}piperidin-3-yl)methanesulfonamide;
N-(1-{4-[5-(2-tert-butylpyridin-4-yl)thiophen-3-yl]-3-chlorobenzoyl}piperidin-3-yl)acetamide;
4-[5-(2-tert-butylpyridin-4-yl)thiophen-3-yl]-3-chloro-N,N-bis(propan-2-yl)benzamide;
1-(1-{4-[5-(2-tert-butylpyridin-4-yl)thiophen-3-yl]-3-chlorobenzoyl}piperidin-3-yl)pyrrolidin-2-one;
6-[5-(2-tert-butylpyridin-4-yl)thiophen-3-yl]-2-(propan-2-yl)-1,2,3,4-tetrahydroisoquinolin-1-one;
2-(1-{4-[5-(2-tert-butylpyridin-4-yl)thiophen-3-yl]-3-chlorobenzoyl}piperidin-3-yl)-1$\lambda^6$,2-thiazolidine-1, 1-dione;
tert-butyl N-(1-{4-[5-(2-tert-butylpyridin-4-yl)thiophen-3-yl]-3-chlorobenzoyl}piperidin-4-yl)carbamate;
N-(1-{4-[5-(2-tert-butylpyridin-4-yl)thiophen-3-yl]-3-chlorobenzoyl}piperidin-4-yl)acetamide;
4-{4-[5-(2-tert-butylpyridin-4-yl)thiophen-3-yl]-3-chlorobenzoyl}-1-ethylpiperazin-2-one;
2-tert-butyl-4-{5-[2-chloro-4-(4,4-difluoropiperidine-1-carbonyl)phenyl]thiophen-3-yl}pyridine;
4-[5-(2-tert-butylpyridin-4-yl)thiophen-3-yl]-3-chloro-N-methyl-N-phenylbenzamide;
4-{4-[4-(azetidine-1-carbonyl)-2-chlorophenyl]thiophen-2-yl}-2-tert-butylpyridine;
6-{4-[5-(2-tert-butylpyridin-4-yl)thiophen-3-yl]-3-chlorobenzoyl}-2-oxa-6-azaspiro[3.3]heptane;
ethyl N-(1-{4-[5-(2-tert-butylpyridin-4-yl)thiophen-3-yl]-3-chlorobenzoyl}piperidin-3-yl)carbamate;
ethyl 4-{4-[5-(2-tert-butylpyridin-4-yl)thiophen-3-yl]-3-chlorobenzoyl}piperazine-1-carboxylate;
1-(4-{4-[5-(2-tert-butylpyridin-4-yl)thiophen-3-yl]-3-chlorobenzoyl}piperazin-1-yl)-2,2-dimethylpropan-1-one;
N-[2-(1-{4-[5-(2-tert-butylpyridin-4-yl)thiophen-3-yl]-3-chlorophenyl}-N-ethylformamido)ethyl] acetamide;
1-{4-[5-(2-tert-butylpyridin-4-yl)thiophen-3-yl]-3-chlorobenzoyl}piperidin-3-ol;
(3R)-1-{4-[5-(2-tert-butylpyridin-4-yl)thiophen-3-yl]-3-chlorobenzoyl}piperidin-3-ol;
(3S)-1-{4-[5-(2-tert-butylpyridin-4-yl)thiophen-3-yl]-3-chlorobenzoyl}piperidin-3-ol;
4-[5-(2-tert-butylpyridin-4-yl)thiophen-3-yl]-3-chloro-N-(3-hydroxyphenyl)benzamide;
(2S,6R)-4-{4-[5-(2-tert-butylpyridin-4-yl)thiophen-3-yl]-3-chlorobenzoyl}-2,6-dimethylmorpholine;
1-{4-[4-(2-tert-butylpyridin-4-yl)thiophen-2-yl]-3-chlorobenzoyl}-1,2,3,4-tetrahydro-1,8-naphthyridine;
6-[5-(2-tert-butylpyridin-4-yl)thiophen-3-yl]-7-chloro-2-(propan-2-yl)-1,2,3,4-tetrahydroisoquinolin-1-one;
4-[5-(2-tert-butylpyridin-4-yl)thiophen-3-yl]-3-chloro-N-[(4,6-dimethyl-2-oxo-1,2-dihydropyridin-3-yl)methyl]benzamide;
4-[5-(2-tert-butylpyridin-4-yl)thiophen-3-yl]-3-chloro-N-(4-fluorophenyl)benzamide
N-(1-{4-[5-(2-tert-butylpyridin-4-yl)thiophen-3-yl]-3-chlorobenzoyl}piperidin-3-yl)-2,2-dimethylpropanamide;
1-(1-{4-[5-(2-tert-butylpyridin-4-yl)thiophen-3-yl]-3-chlorobenzoyl}piperidin-3-yl)-3-cyclopropylurea;
1-{4-[5-(2-tert-butylpyridin-4-yl)thiophen-3-yl]-3-chlorobenzoyl}piperidin-4-ol;
4-[5-(2-tert-butylpyridin-4-yl)thiophen-3-yl]-3-chloro-N-(pyridin-3-yl)benzamide;
N-(1-{4-[5-(2-tert-butylpyridin-4-yl)thiophen-3-yl]-3-chlorobenzoyl}piperidin-4-yl)methanesulfonamide;
4-[5-(2-tert-butylpyridin-4-yl)thiophen-3-yl]-3-chloro-N-methyl-N-(1,3-oxazol-2-yl)benzamide;
4-[5-(2-tert-butylpyridin-4-yl)thiophen-3-yl]-3-chloro-N-[2-(morpholin-4-yl)-2-oxoethyl]benzamide;
4-[5-(2-tert-butylpyridin-4-yl)thiophen-3-yl]-3-chloro-N-{8-methyl-8-azabicyclo[3.2.1]octan-3-yl}benzamide;
ethyl N-(1-{4-[5-(2-tert-butylpyridin-4-yl)thiophen-3-yl]-3-chlorobenzoyl}piperidin-4-yl)carbamate;
tert-butyl N-[1-(3-chloro-4-{5-[2-(morpholin-4-yl)pyridin-4-yl]thiophen-3-yl}benzoyl)piperidin-3-yl]carbamate;

1-(3-chloro-4-{5-[2-(morpholin-4-yl)pyridin-4-yl]thiophen-3-yl}benzoyl)piperidin-3-amine;
1-{4-[5-(2-tert-butylpyridin-4-yl)-2-methylthiophen-3-yl]-3-chlorobenzoyl}piperidin-3-amine;
4-[5-(2-tert-butylpyridin-4-yl)-2-methylthiophen-3-yl]-3-chloro-N-phenylbenzamide;
(3S)-1-{4-[4-(2-tert-butylpyridin-4-yl)thiophen-2-yl]-3-chlorobenzoyl}pyrrolidin-3-ol;
(3R)-1-{4-[4-(2-tert-butylpyridin-4-yl)thiophen-2-yl]-3-chlorobenzoyl}pyrrolidin-3-ol;
tert-butyl N-[(3R)-1-{4-[4-(2-tert-butylpyridin-4-yl)thiophen-2-yl]-3-chlorobenzoyl}piperidin-3-yl]carbamate;
tert-butyl N-(1-{4-[5-(2-tert-butylpyridin-4-yl)thiophen-3-yl]-3-chlorobenzoyl}piperidin-3-yl)-N-methylcarbamate;
tert-butyl 3-{4-[5-(2-tert-butylpyridin-4-yl)thiophen-3-yl]-3-chlorobenzamido}piperidine-1-carboxylate;
1-{4-[5-(2-tert-butylpyridin-4-yl)thiophen-3-yl]-3-chlorobenzoyl}piperidin-4-amine;
6-[5-(2-tert-butylpyridin-4-yl)thiophen-3-yl]-5-chloro-N-phenylpyridine-3-carboxamide;
(3R)-1-{4-[4-(2-tert-butylpyridin-4-yl)thiophen-2-yl]-3-chlorobenzoyl}piperidin-3-amine;
(3S)-1-{4-[4-(2-tert-butylpyridin-4-yl)thiophen-2-yl]-3-chlorobenzoyl}piperidin-3-amine;
1-{4-[5-(2-tert-butylpyridin-4-yl)thiophen-3-yl]-3-chlorobenzoyl}-N-methylpiperidin-3-amine;
N-(1-{4-[5-(2-tert-butylpyridin-4-yl)thiophen-3-yl]-3-chlorobenzoyl}piperidin-4-yl)-2,2-dimethylpropanamide;
4-{4-[4-(2-tert-butylpyridin-4-yl)-5-methylthiophen-2-yl]-3-chlorobenzoyl}piperazin-2-one;
tert-butyl 4-{4-[5-(2-tert-butylpyridin-4-yl)thiophen-3-yl]-3-chlorobenzamido}piperidine-1-carboxylate;
tert-butyl N-[(3R)-1-{4-[4-(2-tert-butylpyridin-4-yl)-5-methylthiophen-2-yl]-3-chlorobenzoyl}piperidin-3-yl]carbamate;
tert-butyl N-[(3S)-1-{4-[4-(2-tert-butylpyridin-4-yl)-5-methylthiophen-2-yl]-3-chlorobenzoyl}piperidin-3-yl]carbamate;
1-{4-[5-(2-tert-butylpyridin-4-yl)thiophen-3-yl]-3-chlorobenzoyl}-N-[(4-chlorophenyl)methyl]piperidin-3-amine;
(3R)-1-{4-[5-(2-tert-butylpyridin-4-yl)thiophen-3-yl]-3-chlorobenzoyl}-N-[(4-chlorophenyl)methyl]piperidin-3-amine;
(3R)-1-{4-[4-(2-tert-butylpyridin-4-yl)thiophen-2-yl]-3-chlorobenzoyl}-N-[(4-chlorophenyl)methyl]piperidin-3-amine;
1-{4-[5-(2-tert-butylpyridin-4-yl)thiophen-3-yl]-3-chlorobenzoyl}-N-[(3-chlorophenyl)methyl]piperidin-3-amine;
(3R)-1-{4-[5-(2-tert-butylpyridin-4-yl)thiophen-3-yl]-3-chlorobenzoyl}pyrrolidin-3-ol;
7-{4-[5-(2-tert-butylpyridin-4-yl)thiophen-3-yl]-3-chlorobenzoyl}-2,7-diazaspiro[4.5]decan-1-one;
2-tert-butyl-4-[4-(2-chloro-4-{octahydropyrrolo [1,2-a]piperazine-2-carbonyl}phenyl)thiophen-2-yl]pyridine;
1-{4-[2-(2-tert-butylpyridin-4-yl)-1H-imidazol-4-yl]-3-chlorobenzoyl}piperidin-3-amine;
1-{4-[4-(2-tert-butylpyridin-4-yl)thiophen-2-yl]-3-chlorobenzoyl}piperidin-4-ol;
(3S)-1-{4-[4-(2-tert-butylpyridin-4-yl)-5-methylthiophen-2-yl]-3-chlorobenzoyl}piperidin-3-amine;
(3R)-1-{4-[4-(2-tert-butylpyridin-4-yl)-5-methylthiophen-2-yl]-3-chlorobenzoyl}piperidin-3-amine;
1-{4-[4-(2-tert-butylpyridin-4-yl)thiophen-2-yl]-3-chlorobenzoyl}piperidine-4-carboxylic acid;
1-{4-[4-(2-tert-butylpyridin-4-yl)thiophen-2-yl]-3-chlorobenzoyl}piperidin-3-ol;
(3R)-1-{4-[4-(2-tert-butylpyridin-4-yl)thiophen-2-yl]-3-chlorobenzoyl}piperidin-3-ol;
(3S)-1-{4-[4-(2-tert-butylpyridin-4-yl)thiophen-2-yl]-3-chlorobenzoyl}piperidin-3-ol;
tert-butyl N-[(3R)-1-{4-[5-(2-tert-butylpyridin-4-yl)thiophen-3-yl]-3-chlorobenzoyl}pyrrolidin-3-yl]carbamate;
(3R)-1-{4-[4-(2-tert-butylpyridin-4-yl)thiophen-2-yl]-3-chlorobenzoyl}piperidine-3-carboxylic acid;
2-tert-butyl-4-[5-(2-chloro-4-{3H,4H, 5H,6H,7H-imidazo[4, 5-c]pyridine-5-carbonyl}phenyl)thiophen-3-yl]pyridine;
4-{4-[4-(2-tert-butylpyridin-4-yl)thiophen-2-yl]-3-chlorobenzoyl}piperazin-2-one;
1-[(3R)-1-{4-[4-(2-tert-butylpyridin-4-yl)thiophen-2-yl]-3-chlorobenzoyl}piperidin-3-yl]imidazolidin-2-one;
1-{4-[4-(2-tert-butylpyridin-4-yl)thiophen-2-yl]-3-chlorobenzoyl}-3-methylpiperidin-3-amine;
(3R)-1-{4-[4-(2-tert-butylpyridin-4-yl)thiophen-2-yl]-3-chlorobenzoyl}-3-methylpiperidin-3-amine;
(3S)-1-{4-[4-(2-tert-butylpyridin-4-yl)thiophen-2-yl]-3-chlorobenzoyl}-3-methylpiperidin-3-amine;
(3R)-1-{4-[4-(2-tert-butylpyridin-4-yl)thiophen-2-yl]-3-chlorobenzoyl}pyrrolidin-3-amine;
(3S)-1-{4-[4-(2-tert-butylpyridin-4-yl)thiophen-2-yl]-3-chlorobenzoyl}pyrrolidin-3-amine;
1-{4-[4-(2-tert-butylpyridin-4-yl)thiophen-2-yl]-3-chlorobenzoyl}-1,2,3,4-tetrahydro-1,5-naphthyridine;
1-{4-[2-(2-tert-butylpyridin-4-yl)-1H-imidazol-4-yl]-3-chlorobenzoyl}piperidin-4-ol;
2-tert-butyl-4-{5-[2-chloro-4-(3-methoxypiperidine-1-carbonyl)phenyl]thiophen-3-yl}pyridine;
1-{4-[4-(2-tert-butylpyridin-4-yl)thiophen-2-yl]-3-chlorobenzoyl}-4-methylpiperidin-4-ol;
(3R)-1-{4-[4-(2-tert-butylpyridin-4-yl)thiophen-2-yl]-3-chlorobenzoyl}-3-methylpiperidin-3-ol;
(3S)-1-{4-[4-(2-tert-butylpyridin-4-yl)thiophen-2-yl]-3-chlorobenzoyl}-3-methylpiperidin-3-ol;
4-(3-chloro-4-{5-[1-(3-methylbutyl)-1H-pyrazol-5-yl]thiophen-3-yl}benzoyl)morpholine;
1-(3-chloro-4-{5-[1-(3-methylbutyl)-1H-pyrazol-5-yl]thiophen-3-yl}benzoyl)-4,4-difluoropiperidine;
1-(3-chloro-4-{4-[1-(3-methylbutyl)-1H-pyrazol-5-yl]thiophen-2-yl}benzoyl)piperidin-3-ol; and
3-(1-{4-[4-(2-tert-butylpyridin-4-yl)thiophen-2-yl]-3-chlorophenyl}-N-(4-fluorophenyl)formamido)propanoic acid.

6. A compound, or a pharmaceutically acceptable salt thereof, selected from the group consisting of:
piperidin-1-yl(4-(5-(2-propylpyridin-4-yl)thiophen-3-yl)phenyl)methanone;
piperidin-1-yl(3-(5-(2-propylpyridin-4-yl)thiophen-3-yl)phenyl)methanone;
(4-(5-(1-isobutyl-1H-pyrazol-5-yl)thiophen-3-yl)phenyl)(piperidin-1-yl)methanone;
(3-chloro-4-(5-(2-propylpyridin-4-yl)thiophen-3-yl)phenyl)(piperidin-1-yl)methanone;
(4-(4-(2-tert-butylpyridin-4-yl)thiophen-2-yl)-3-chlorophenyl)(piperidin-1-yl)methanone;
(3-chloro-4-(5-(1,2-dimethyl-1H-pyrrolo[2,3-b]pyridin-4-yl)thiophen-3-yl)phenyl) (piperidin-1-yl)methanone;
(3-chloro-4-(5-(1-propyl-1H-pyrrolo[2,3-b]pyridin-4-yl)thiophen-3-yl)phenyl)(piperidin-1-yl)methanone;

(3-chloro-4-(5-(2,3-dimethyl-3H-imidazo[4,5-b]pyridin-7-yl)thiophen-3-yl)phenyl) (piperidin-1-yl)methanone;
(3-chloro-4-(5-(3-propyl-3H-imidazo[4,5-b]pyridin-7-yl)thiophen-3-yl)phenyl)(piperidin-1-yl)methanone;
(4-(5-(3H-imidazo[4,5-b]pyridin-7-yl)thiophen-3-yl)-3-chlorophenyl)(piperidin-1-yl)methanone;
(3-chloro-4-(5-(1,2-dipropyl-1H-pyrrolo[2,3-b]pyridin-4-yl)thiophen-3-yl)phenyl) (piperidin-1-yl)methanone;
(4-(5-(6-(butylamino)-2-isobutylpyrimidin-4-yl)thiophen-3-yl)-3-chlorophenyl) (piperidin-1-yl)methanone;
(3-chloro-4-(5-(6-(dibutylamino)-2-isobutylpyrimidin-4-yl)thiophen-3-yl)phenyl) (piperidin-1-yl)methanone;
(4-(5-(6-amino-2-isobutylpyrimidin-4-yl)thiophen-3-yl)-3-chlorophenyl)(piperidin-1-yl)methanone;
(4-(5-(2-aminopyrimidin-4-yl)thiophen-3-yl)-3-chlorophenyl)(piperidin-1-yl)methanone;
(3-chloro-4-(5-(2-(propylamino)pyrimidin-4-yl)thiophen-3-yl)phenyl)(piperidin-1-yl) methanone;
(4-(5-(2-(butyl(propyl)amino)pyrimidin-4-yl)thiophen-3-yl)-3-chlorophenyl)(piperidin-1-yl)methanone;
(3-chloro-4-(5-(2-propylthiazol-4-yl)thiophen-3-yl)phenyl)(piperidin-1-yl)methanone;
(3-chloro-4-(5-(5-propyl-1,2,4-thiadiazol-3-yl)thiophen-3-yl)phenyl)(piperidin-1-yl) methanone;
(3-chloro-4-(5-(5-propyl-1,2,4-oxadiazol-3-yl)thiophen-3-yl)phenyl)(piperidin-1-yl) methanone;
(3-chloro-4-(5-(2-propylthiazol-5-yl)thiophen-3-yl)phenyl)(piperidin-1-yl)methanone;
(3-chloro-4-(5-(5-propyl-1,3,4-thiadiazol-2-yl)thiophen-3-yl)phenyl)(piperidin-1-yl) methanone;
(3-chloro-4-(5-(5-propyl-1,3,4-oxadiazol-2-yl)thiophen-3-yl)phenyl)(piperidin-1-yl) methanone;
5-(4-(2-chloro-4-(piperidine-1-carbonyl)phenyl)thiophen-2-yl)-isobutylpyridin-2(1H)-one;
(3-chloro-4-(5-(2-morpholinopyridin-4-yl)thiophen-3-yl)phenyl)(4,4-difluoropiperidin-1-yl)methanone;
(2-bromo-3-chloro-4-(5-(2-isobutylpyridin-4-yl)thiophen-3-yl)phenyl)(piperidin-1-yl) methanone;
(3,5-dichloro-4-(5-(2-isobutylpyridin-4-yl)thiophen-3-yl)phenyl)(piperidin-1-yl) methanone;
(4-(5-(2-isobutylpyridin-4-yl)thiophen-3-yl)-2-(trifluoromethyl)phenyl)(piperidin-1-yl) methanone;
(2-cyclopropyl-4-(5-(2-isobutylpyridin-4-yl)thiophen-3-yl)phenyl)(piperidin-1-yl) methanone;
(4-(5-(2-isobutylpyridin-4-yl)thiophen-3-yl)-2-methylphenyl)(piperidin-1-yl)methanone;
(4-(5-(2-isobutylpyridin-4-yl)thiophen-3-yl)-2-isopropylphenyl)(piperidin-1-yl) methanone;
(2-ethynyl-4-(5-(2-isobutylpyridin-4-yl)thiophen-3-yl)phenyl)(piperidin-1-yl)methanone;
(2-bromo-3-ethynyl-4-(5-(2-isobutylpyridin-4-yl)thiophen-3-yl)phenyl)(piperidin-1-yl) methanone;
(2-bromo-6-chloro-4-(5-(2-isobutylpyridin-4-yl)thiophen-3-yl)phenyl)(piperidin-1-yl) methanone;
(2-chloro-4-(5-(2-isobutylpyridin-4-yl)thiophen-3-yl)-6-methylphenyl)(piperidin-1-yl) methanone;
(4-(4-(2-tert-butylpyridin-4-yl)-1-methyl-1H-imidazol-2-yl)-3-chlorophenyl)(piperidin-1-yl)methanone;
(3-chloro-4-(5-(2-isobutylpyridin-4-yl)thiophen-3-yl)phenyl)(piperidin-1-yl)methanone;
(2-bromo-4-(2-(2-isobutylpyridin-4-yl)-1-methyl-1H-imidazol-4-yl)phenyl)(piperidin-1-yl)methanone;
(2-bromo-3-chloro-4-(2-(2-isobutylpyridin-4-yl)-1H-imidazol-4-yl)phenyl)(piperidin-1-yl)methanone;
(2-bromo-5-chloro-4-(2-(2-isobutylpyridin-4-yl)-1-methyl-1H-imidazol-4-yl)phenyl) (piperidin-1-yl) methanone;
(4-(4-(2-tert-butylpyridin-4-yl)oxazol-2-yl)-3-chlorophenyl)(piperidin-1-yl)methanone;
(4-(2-(2-tert-butylpyridin-4-yl)oxazol-4-yl)-3-chlorophenyl)(piperidin-1-yl)methanone;
(3-chloro-4-(5-(2-(dimethylamino)pyridin-4-yl)thiophen-3-yl)phenyl)(piperidin-1-yl) methanone;
(3,5-dichloro-4-(5-(2-propylpyridin-4-yl)thiophen-3-yl)phenyl)(piperidin-1-yl) methanone;
N-(4-(4-(2-chloro-4-(piperidine-1-carbonyl)phenyl)thiophen-2-yl)pyridin-2-yl) methanesulfonamide;
(3-chloro-4-(5-(2-(3,3,3-trifluoropropyl)pyridin-4-yl)thiophen-3-yl)phenyl)(piperidin-1-yl)methanone;
(3-chloro-4-(1-methyl-2-(2-(3,3,3-trifluoropropyl)pyridin-4-yl)-1H-imidazol-4-yl)phenyl) (piperidin-1-yl) methanone;
(2-hydroxy-4-(5-(2-propylpyridin-4-yl)thiophen-3-yl)phenyl)(piperidin-1-yl)methanone;
(4-(5-(2-tert-butylpyridin-4-yl)thiophen-3-yl)-2-hydroxyphenyl)(piperidin-1-yl) methanone;
(2-methoxy-4-(5-(2-propylpyridin-4-yl)thiophen-3-yl)phenyl)(piperidin-1-yl)methanone;
(4-(5-(2-isobutylpyridin-4-yl)thiophen-3-yl)-2-methoxyphenyl)(piperidin-1-yl) methanone;
(4-(5-(2-tert-butylpyridin-4-yl)thiophen-3-yl)-2-methoxyphenyl)(piperidin-1-yl) methanone;
(4-(5-(2-isobutylpyridin-4-yl)thiophen-3-yl)-3-(trifluoromethyl)phenyl)(piperidin-1-yl) methanone;
(3-chloro-4-(5-(2-neopentylpyridin-4-yl)thiophen-3-yl)phenyl)(piperidin-1-yl) methanone;
(3-chloro-4-(5-(2-isobutylpyridin-4-yl)thiophen-3-yl)-5-(trifluoromethyl)phenyl) (piperidin-1-yl)methanone;
(2,3-dichloro-4-(5-(2-isobutylpyridin-4-yl)thiophen-3-yl)phenyl)(piperidin-1-yl) methanone;
(4-(2-(2-isobutylpyridin-4-yl)-1-methyl-1H-imidazol-4-yl)-2-methoxyphenyl)(piperidin-1-yl)methanone;
(2-methoxy-4-(1-methyl-2-(2-propylpyridin-4-yl)-1H-imidazol-4-yl)phenyl)(piperidin-1-yl)methanone;
(4-(2-(2-tert-butylpyridin-4-yl)-1-methyl-1H-imidazol-4-yl)-2-methoxyphenyl)(piperidin-1-yl)methanone;
(4-(5-(2-benzylpyridin-4-yl)thiophen-3-yl)-3-chlorophenyl)(piperidin-1-yl)methanone;
(4-(5-(2-aminopyridin-4-yl)thiophen-3-yl)-3-chlorophenyl)(piperidin-1-yl)methanone;
N-(4-(4-(2-chloro-4-(piperidine-1-carbonyl)phenyl)-1-methyl-1H-imidazol-2-yl)pyridin-2-yl)methanesulfonamide;
(2-hydroxy-4-(5-(2-isobutylpyridin-4-yl)thiophen-3-yl)phenyl)(piperidin-1-yl) methanone;
(3-chloro-4-(5-(2-(3,3,3-trifluoropropyl)pyridin-4-yl)furan-3-yl)phenyl)(piperidin-1-yl) methanone;
(2-methoxy-4-(5-(2-neopentylpyridin-4-yl)thiophen-3-yl)phenyl)(piperidin-1-yl) methanone;
N-(4-(4-(2-chloro-4-(piperidine-1-carbonyl)phenyl)thiophen-2-yl)pyridin-2-yl)-1, 1, 1-trifluoromethanesulfonamide;
1-(4-(4-(4-(2-chloro-4-(4,4-difluoropiperidine-1-carbonyl)phenyl)thiophen-2-yl)pyridin-2-yl)piperazin-1-yl)ethanone;
(3-chloro-4-(5-(1-isopentyl-1H-pyrazol-5-yl)thiophen-3-yl)phenyl)(piperidin-1-yl) methanone;
(3-chloro-4-(5-(1-isopentyl-1H-pyrazol-5-yl)furan-3-yl)phenyl)(piperidin-1-yl) methanone;
(3-chloro-4-(5-(2-(cyclohexylmethyl)pyridin-4-yl)thiophen-3-yl)phenyl)(piperidin-1-yl)methanone;

(3-chloro-4-(5-(naphthalen-1-yl)thiophen-3-yl)phenyl)(piperidin-1-yl)methanone;
(4-(5-(1H-indol-6-yl)thiophen-3-yl)-3-chlorophenyl)(piperidin-1-yl)methanone;
(4-(5-(1H-indol-4-yl)thiophen-3-yl)-3-chlorophenyl)(4,4-difluoropiperidin-1-yl) methanone;
(4-(5-(1H-benzo[d]imidazol-4-yl)thiophen-3-yl)-3-chlorophenyl)(4,4-difluoropiperidin-1-yl)methanone;
(3-chloro-4-(5-(isoquinolin-4-yl)thiophen-3-yl)phenyl)(piperidin-1-yl)methanone;
(3-chloro-4-(5-(2-(4-methylpiperazin-1-yl)pyridin-4-yl)thiophen-3-yl)phenyl)(piperidin-1-yl)methanone;
(3-chloro-4-(5-(3,5-dimethylisoxazol-4-yl)thiophen-3-yl)phenyl)(piperidin-1-yl) methanone;
(3-chloro-4-(5-(1-isopentyl-1H-pyrazol-5-yl)thiophen-3-yl)phenyl)(4,4-difluoropiperidin-1-yl)methanone;
(3-chloro-4-(5-(1-ethyl-1H-indol-4-yl)thiophen-3-yl)phenyl)(4,4-difluoropiperidin-1-yl) methanone;
(4-(5-(1H-indol-4-yl)thiophen-3-yl)-3-chlorophenyl)(piperidin-1-yl)methanone;
(3-chloro-4-(5-(1-ethyl-1H-benzo[d]imidazol-4-yl)thiophen-3-yl)phenyl)(4,4-difluoropiperidin-1-yl)methanone;
(3-chloro-4-(5-(2,3-dihydrobenzofuran-5-yl)thiophen-3-yl)phenyl)(piperidin-1-yl) methanone;
(3-chloro-4-(5-(2-(hydroxymethyl)pyridin-4-yl)thiophen-3-yl)phenyl)(piperidin-1-yl) methanone;
(3-chloro-4-(5-(3-(hydroxymethyl)pyridin-4-yl)thiophen-3-yl)phenyl)(piperidin-1-yl) methanone;
(3-chloro-4-(5-(2-(piperidin-1-yl)pyridin-4-yl)thiophen-3-yl)phenyl)(piperidin-1-yl) methanone;
(3-chloro-4-(5-(3-methylpyridin-4-yl)thiophen-3-yl)phenyl)(piperidin-1-yl)methanone;
(4-(5-(1H-pyrrolo[2,3-b]pyridin-4-yl)thiophen-3-yl)-3-chlorophenyl)(piperidin-1-yl) methanone;
(3-chloro-4-(5-(2-(piperidin-1-yl)pyridin-4-yl)thiophen-3-yl)phenyl)(4,4-difluoropiperidin-1-yl)methanone;
(3-chloro-4-(5-(5-fluoro-1H-pyrrolo[2, 3-b]pyridin-4-yl)thiophen-3-yl)phenyl)(piperidin-1-yl)methanone;
(4-(5-(benzo[b]thiophen-3-yl)thiophen-3-yl)-3-chlorophenyl)(piperidin-1-yl)methanone;
(3-chloro-4-(5-(3-(pyrrolidin-1-ylmethyl)pyridin-4-yl)thiophen-3-yl)phenyl)(piperidin-1-yl)methanone;
(3-chloro-4-(5-(2-(cyclopentylamino)pyridin-4-yl)thiophen-3-yl)phenyl)(piperidin-1-yl) methanone;
(4-(5-(1H-indol-3-yl)thiophen-3-yl)-3-chlorophenyl)(piperidin-1-yl)methanone;
(3-chloro-4-(5-(quinolin-4-yl)thiophen-3-yl)phenyl)(piperidin-1-yl)methanone;
(3-chloro-4-(5-(2-chloropyridin-4-yl)thiophen-3-yl)phenyl)(piperidin-1-yl)methanone;
(2-bromo-4-(5-(2-tert-butylpyridin-4-yl)thiophen-3-yl)-3-chlorophenyl)(piperidin-1-yl) methanone;
(2-bromo-4-(2-(2-propylpyridin-4-yl)-1H-imidazol-4-yl)phenyl)(piperidin-1-yl) methanone;
(2-bromo-4-(5-(2-tert-butylpyridin-4-yl)furan-3-yl)-3-chlorophenyl)(piperidin-1-yl) methanone;
(2-bromo-4-(5-(2-tert-butylpyridin-4-yl)-1H-pyrrol-3-yl)-3-chlorophenyl)(piperidin-1-yl) methanone;
(4-(2-(2-tert-butylpyridin-4-yl)-1H-imidazol-4-yl)-3-fluorophenyl)(piperidin-1-yl) methanone;
(4-(4-(2-tert-butylpyridin-4-yl)-1H-imidazol-2-yl)-3-chlorophenyl)(piperidin-1-yl) methanone;
(2-bromo-4-(2-(2-(piperidin-1-yl)pyridin-4-yl)-1H-imidazol-4-yl)phenyl)(piperidin-1-yl) methanone;
(4-(2-(2-tert-butylpyridin-4-yl)-1-methyl-1H-imidazol-4-yl)-3-chlorophenyl)(piperidin-1-yl)methanone;
(4-(5-(2-tert-butylpyridin-4-yl)-1H-pyrrol-3-yl)-3-chlorophenyl)(piperidin-1-yl) methanone;
(4-(4-(2-tert-butylpyridin-4-yl)furan-2-yl)-3-chlorophenyl)(piperidin-1-yl)methanone;
(4-(4-(2-tert-butylpyridin-4-yl)-1H-pyrrol-2-yl)-3-chlorophenyl)(piperidin-1-yl) methanone;
(4-(4-(2-tert-butylpyridin-4-yl)-1-methyl-1H-pyrrol-2-yl)-3-chlorophenyl)(piperidin-1-yl) methanone;
(4-(4-(2-tert-butylpyridin-4-yl)thiazol-2-yl)-3-chlorophenyl)(piperidin-1-yl)methanone;
(4-(5-(2-tert-butylpyridin-4-yl)isothiazol-3-yl)-3-chlorophenyl)(piperidin-1-yl) methanone;
(4-(5-(2-tert-butylpyridin-4-yl)isoxazol-3-yl)-3-chlorophenyl)(piperidin-1-yl)methanone;
(4-(5-(2-tert-butylpyridin-4-yl)-1H-pyrazol-3-yl)-3-chlorophenyl)(piperidin-1-yl) methanone;
(4-(3-(2-tert-butylpyridin-4-yl)isothiazol-5-yl)-3-chlorophenyl)(piperidin-1-yl) methanone;
(4-(3-(2-tert-butylpyridin-4-yl)isoxazol-5-yl)-3-chlorophenyl)(piperidin-1-yl)methanone;
(4-(3-(2-tert-butylpyridin-4-yl)-1H-pyrazol-5-yl)-3-chlorophenyl)(piperidin-1-yl) methanone;
(4-(3-(2-tert-butylpyridin-4-yl)-1-methyl-1H-pyrazol-5-yl)-3-chlorophenyl)(piperidin-1-yl)methanone;
(3-chloro-4-(5-(2-isobutylpyridin-4-yl)-1H-pyrrol-3-yl)phenyl)(piperidin-1-yl) methanone;
(3-fluoro-4-(5-(2-propylpyridin-4-yl)thiophen-3-yl)phenyl)(piperidin-1-yl)methanone;
(3-chloro-4-(2-(2-isobutylpyridin-4-yl)-1H-imidazol-4-yl)phenyl)(piperidin-1-yl) methanone;
(3-chloro-4-(2-(2-isobutylpyridin-4-yl)oxazol-4-yl)phenyl)(piperidin-1-yl)methanone;
(3-chloro-4-(2-(2-isobutylpyridin-4-yl)thiazol-4-yl)phenyl)(piperidin-1-yl)methanone;
(3-(5-(2-isobutylpyridin-4-yl)thiophen-3-yl)phenyl)(piperidin-1-yl)methanone;
(2-bromo-4-(5-(2-isobutylpyridin-4-yl)thiophen-3-yl)phenyl)(piperidin-1-yl)methanone;
(2-bromo-4-(2-(2-isobutylpyridin-4-yl)-1H-imidazol-4-yl)phenyl)(piperidin-1-yl) methanone;
(4-(5-(2-butylpyridin-4-yl)thiophen-3-yl)-3-chlorophenyl)(piperidin-1-yl)methanone;
(3-chloro-4-(5-(2-(methoxymethyl)pyridin-4-yl)thiophen-3-yl)phenyl)(piperidin-1-yl) methanone;
(3-chloro-4-(5-(4,6-dipropylpyridin-2-yl)thiophen-3-yl)phenyl)(piperidin-1-yl) methanone;
piperidin-1-yl(4-(5-(4-propylpyridin-2-yl)thiophen-3-yl)phenyl)methanone;
(4-(5-(2, 6-dipropylpyridin-3-yl)thiophen-3-yl)phenyl)(piperidin-1-yl)methanone;
(4-(5-(2-(cyclohexylmethyl)pyridin-4-yl)thiophen-3-yl)phenyl)(piperidin-1-yl) methanone;
(4-(5-(2-isobutylpyridin-4-yl)thiophen-3-yl)-3-methoxyphenyl)(piperidin-1-yl) methanone;
(3-chloro-4-(5-(2-((trifluoromethylsulfonyl)methyl)pyridin-4-yl)thiophen-3-yl)phenyl) (piperidin-1-yl)methanone;
(3-chloro-4-(1-methyl-2-(1H-pyrrolo[2, 3-b]pyridin-4-yl)-1H-imidazol-4-yl)phenyl) (piperidin-1-yl)methanone;
(3-chloro-4-(5-(2-propyl-3H-imidazo[4, 5-b]pyridin-7-yl)thiophen-3-yl)phenyl)(piperidin-1-yl)methanone;
4-(4-(2-chloro-4-(piperidine-1-carbonyl)phenyl)thiophen-2-yl)-N-cyclopropyl picolinamide;
4-(4-(2-chloro-4-(piperidine-1-carbonyl)phenyl)thiophen-2-yl)-N-cyclohexyl picolinamide;

(4-(2-(1H-indol-4-yl)-1-methyl-1H-imidazol-4-yl)-3-chlorophenyl)(piperidin-1-yl) methanone;
(3-chloro-4-(4-(2-(piperidin-1-yl)pyridin-4-yl)thiophen-2-yl)phenyl)(4,4-difluoro piperidin-1-yl)methanone;
(3-chloro-4-(4-(2-(piperidin-1-yl)pyridin-4-yl)thiophen-2-yl)phenyl)(piperidin-1-yl) methanone;
(2-bromo-4-(2-(2-tert-butylpyridin-4-yl)-1H-imidazol-4-yl)phenyl)(piperidin-1-yl) methanone;
(2-chloro-4-(2-(2-propylpyridin-4-yl)-1H-imidazol-4-yl)phenyl)(piperidin-1-yl) methanone;
(2-bromo-5-chloro-4-(2-(2-propylpyridin-4-yl)-1H-imidazol-4-yl)phenyl)(piperidin-1-yl) methanone;
(3-chloro-4-(5-(2-isobutylpyridin-4-yl)thiophen-3-yl)phenyl)(4,4-difluoropiperidin-1-yl) methanone;
(3-chloro-4-(5-(2-cyclopropylpyridin-4-yl)thiophen-3-yl)phenyl)(piperidin-1-yl) methanone;
piperidin-1-yl(4-(5-(2-propylpyridin-4-yl)thiophen-3-yl)-3-(trifluoromethyl)phenyl) methanone;
(3-chloro-4-(5-(2-propylpyridin-4-yl)thiophen-3-yl)phenyl)(3,3-difluoropyrrolidin-1-yl) methanone;
(3-chloro-4-(2-(2-propylpyridin-4-yl)-1H-imidazol-4-yl)phenyl)(piperidin-1-yl) methanone;
(2-bromo-4-(5-(2-propylpyridin-4-yl)thiophen-3-yl)phenyl)(piperidin-1-yl)methanone;
(4-(5-(2-isobutylpyridin-4-yl)thiophen-3-yl)phenyl)(piperidin-1-yl)methanone;
5-(5-(2-isobutylpyridin-4-yl)thiophen-3-yl)-2-(piperidine-1-carbonyl)benzonitrile;
piperidin-1-yl(4-(5-(6-propylpyridin-3-yl)thiophen-3-yl)phenyl)methanone;
(4-(5-(2-pentylpyridin-4-yl)thiophen-3-yl)phenyl)(piperidin-1-yl)methanone; and
(2-bromo-4-(1-methyl-2-(2-propylpyridin-4-yl)-1H-imidazol-4-yl)phenyl)(piperidin-1-yl) methanone.

7. A pharmaceutical composition comprising a compound of claim 1, or a pharmaceutically acceptable salt thereof, and a pharmaceutically acceptable vehicle.

8. (4-(4-(2-tert-butylpyridin-4-yl)thiophen-2-yl)-3-chlorophenyl)(piperidin-1-yl)methanone:

9. A pharmaceutical composition comprising (4-(4-(2-tert-butylpyridin-4-yl)thiophen-2-yl)-3-chlorophenyl)(piperidin-1-yl)methanone:

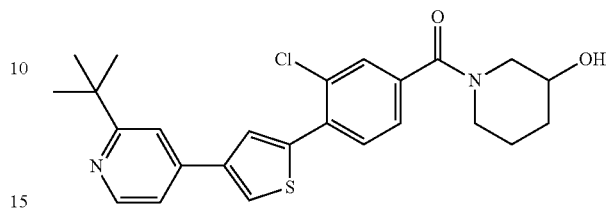

or a pharmaceutically acceptable salt thereof, and a pharmaceutically acceptable vehicle.

10. The pharmaceutical composition of claim 7, wherein:

(a) $R_{C5}$ is chloro; or (b) $R_{C7}$ and $R_{C8}$ are taken together with the N to which they are attached to form a C3-C8 heterocycle, wherein the C3-C8 heterocycle is selected from the group consisting of pyrrolidinyl, piperidinyl, piperazinyl, and morpholinyl, each optionally substituted with one or more R1 or R3.

11. A pharmaceutical composition comprising a compound of claim 3, or a pharmaceutically acceptable salt thereof, and a pharmaceutically acceptable vehicle.

12. The pharmaceutical composition of claim 11, wherein:

(a) $R_{C5}$ is chloro; or (b) $R_{C7}$ and $R_{C8}$ are taken together with the N to which they are attached to form a C3-C8 heterocycle, wherein the C3-C8 heterocycle is selected from the group consisting of pyrrolidinyl, piperidinyl, piperazinyl, and morpholinyl, each optionally substituted with one or more R1 or R3.

13. A pharmaceutical composition comprising a compound of claim 5.

14. A pharmaceutical composition comprising a compound of claim 6.

* * * * *